US012643910B2

(12) United States Patent
Pinkerton et al.

(10) Patent No.: US 12,643,910 B2
(45) Date of Patent: Jun. 2, 2026

(54) SUBSTITUTED PYRAZOLO[3,4-B]PYRIDINES AS ECTONUCLEOTIDE PYROPHOSPHATASE/PHOSPHODIESTERASE 1 (ENPP1) MODULATORS

(71) Applicant: SANFORD BURNHAM PREBYS MEDICAL DISCOVERY INSTITUTE, La Jolla, CA (US)

(72) Inventors: Anthony Pinkerton, La Jolla, CA (US); Eduard Sergienko, La Jolla, CA (US); Yohei Kiyotsuka, Tokyo (JP); Katsuji Kagechika, Tokyo (JP); Yasunobu Kurosaki, Tokyo (JP); Yoshikazu Arai, Tokyo (JP); Masatoshi Nagamochi, Tokyo (JP); Koutaro Ishibashi, Tokyo (JP)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 918 days.

(21) Appl. No.: 17/788,262

(22) PCT Filed: Dec. 23, 2020

(86) PCT No.: PCT/US2020/066857
§ 371 (c)(1),
(2) Date: Jun. 22, 2022

(87) PCT Pub. No.: WO2021/133915
PCT Pub. Date: Jul. 1, 2021

(65) Prior Publication Data

US 2023/0121698 A1 Apr. 20, 2023

Related U.S. Application Data

(60) Provisional application No. 62/953,066, filed on Dec. 23, 2019.

(51) Int. Cl.

| | |
|---|---|
| ***A61K 31/4353*** | (2006.01) |
| ***A61P 19/02*** | (2006.01) |
| ***A61P 19/06*** | (2006.01) |
| ***C07D 471/04*** | (2006.01) |
| ***C07D 473/34*** | (2006.01) |
| ***C07D 487/04*** | (2006.01) |
| ***C07D 495/04*** | (2006.01) |
| ***C07D 498/04*** | (2006.01) |

(52) U.S. Cl.
CPC ............ *C07D 495/04* (2013.01); *A61P 19/02* (2018.01); *A61P 19/06* (2018.01); *C07D 471/04* (2013.01); *C07D 473/34* (2013.01); *C07D 487/04* (2013.01); *C07D 498/04* (2013.01)

(58) Field of Classification Search
CPC .......................... A61K 31/4353; C07D 471/04
USPC .......................................... 514/303; 546/119
See application file for complete search history.

(56) References Cited

U.S. PATENT DOCUMENTS

| | | | |
|---|---|---|---|
| 4,923,872 A | 5/1990 | Kostlan et al. | |
| 10,351,561 B2 * | 7/2019 | Kehler | A61K 31/4745 |
| 10,377,759 B2 | 8/2019 | Yamamoto et al. | |
| 2006/0063751 A1 | 3/2006 | Aquila et al. | |
| 2007/0249587 A1 | 10/2007 | Yonetoku et al. | |
| 2007/0275984 A1 | 11/2007 | Imogai et al. | |
| 2010/0063047 A1 | 3/2010 | Borchardt et al. | |
| 2010/0168141 A1 | 7/2010 | Evans et al. | |
| 2017/0355700 A1 | 12/2017 | Hagen et al. | |
| 2019/0282703 A1 | 9/2019 | Gallatin et al. | |

FOREIGN PATENT DOCUMENTS

| | | | |
|---|---|---|---|
| CN | 1829712 | A | 9/2006 |
| CN | 105153154 | A | 12/2015 |
| KR | 10-2013-0112248 | A | 10/2013 |
| WO | WO-2006030031 | A1 | 3/2006 |
| WO | WO-2009023978 | A1 | 2/2009 |
| WO | WO-2009029617 | A1 | 3/2009 |
| WO | 2009/097446 | A1 | 8/2009 |
| WO | WO-2010118367 | A2 | 10/2010 |
| WO | WO-2011025940 | A1 | 3/2011 |
| WO | WO-2016011394 | A1 | 1/2016 |
| WO | 2016/209749 | A1 | 12/2016 |

(Continued)

OTHER PUBLICATIONS

Jordan, V. C. Nature Reviews: Drug Discovery, Feb. 2003, 205.*
Noell, et al. Journal of Organic Chemistry, 23, 1958, 1547-1550.*
Vippagunta, et al. Advanced Drug Delivery Reviews, 48, 2001, 18.*
Chemical Abstracts Service. CAS Registry: 1328807-35-7. Benzenesulfonamide, 44[(1-(2-fluorophenyl)-1H-pyrazolo[3,4-c]pyrimidin-4-yljamino]methyl]—(ACI): pp. 1-2. STN Entry Date Sep. 6, 2011.
Chemical Abstracts Service. CAS Registry: 1328871-40-4.
Chemical Abstracts Service. CAS Registry: 1360307-91-0.

(Continued)

*Primary Examiner* — Douglas M Willis
(74) *Attorney, Agent, or Firm* — Dickinson Wright PLLC

(57) ABSTRACT

Provided herein are small molecule modulators of ecto-nucleotide pyrophosphatase/phosphodiesterase 1 (ENPP1), compositions comprising the compounds of Formula (XI), and methods of using the compounds and compositions comprising the compounds Formula (XI)

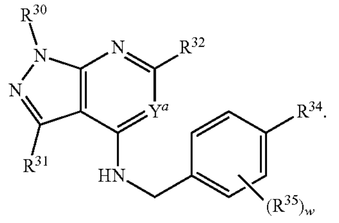

16 Claims, No Drawings

(56) References Cited

FOREIGN PATENT DOCUMENTS

| | | | |
|---|---|---|---|
| WO | WO-2016208595 A1 | 12/2016 |
| WO | WO-2018115067 A1 | 6/2018 |
| WO | WO-2019046778 A1 | 3/2019 |
| WO | WO-2021133915 A1 | 7/2021 |

OTHER PUBLICATIONS

Chemical Abstracts Service. CAS Registry: 1377972-16-1.
Chemical Abstracts Service. CAS Registry: 2331048-51-0.
Chemical Abstracts Service. CAS Registry: 2341604-88-2.
Chemical Abstracts Service. CAS Registry: 2341604-92-8.
Chemical Abstracts Service. CAS Registry: 2348018-35-7.
Cho. Recent Advances in Oral Prodrug Discovery. Annual Reports in Medicinal Chemistry 41:395-407 (2006).
Nogrady. Chapter 4: Pro Drugs and Soft Drugs. In: Medicinal Chemistry: A Biochemical approach. New York: Oxford University Press, p. 388-392 (1985).
PCT/US2020/066857 International Search Report and Written Opinion dated Apr. 12, 2021.
Rooseboom et al. Enzyme-catalyzed activation of anticancer prodrugs. Pharmacological Reviews 56:53-102 (2004).
Silverman. Chapter 8: Prodrugs and Drug Delivery Systems. The Organic Chemistry of Drug Design and Drug Action, Academic Press, Inc., San Diego (pp. 352-401) (1992).

* cited by examiner

SUBSTITUTED PYRAZOLO[3,4-B]PYRIDINES AS ECTONUCLEOTIDE PYROPHOSPHATASE/PHOSPHODIESTERASE 1 (ENPP1) MODULATORS

CROSS REFERENCE

This application claims the benefit of U.S. Application No. 62/953,066, filed Dec. 23, 2019, which is hereby incorporated by reference in its entirety.

FIELD OF THE INVENTION

Described herein are ectonucleotide pyrophosphatase/phosphodiesterase 1 (ENPP1) modulators, methods of making such compounds, pharmaceutical compositions and medicaments comprising such compounds, and methods of using such compounds in the treatment of conditions, diseases, or disorders in which ENPP1 is involved.

SUMMARY OF THE INVENTION

Described herein are compounds and compositions, and methods of using these compounds and compositions, as modulators of ectonucleotide pyrophosphatase/phosphodiesterase 1 (ENPP1), and for treating disorders associated with ectonucleotide pyrophosphatase/phosphodiesterase 1 (ENPP1), such as pseudogout.

In one aspect, presented herein is a compound having the structure of Formula (I), or a pharmaceutically acceptable salt or solvate thereof:

Formula (I)

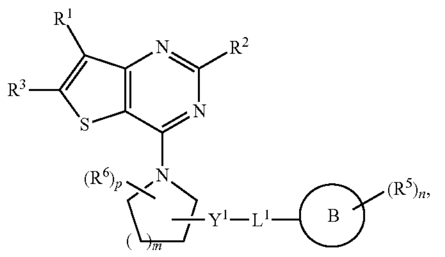

wherein:

ring B is aryl or a 5 or 6-membered heteroaryl;

n is 0, 1, 2, or 3;

m is 1 or 2;

p is 0, 1, 2, or 3;

$Y^1$ is —$NR^4$— or —O—;

$L^1$ is —$Y^2$-$L^2$- or —$Y^2$-$L^2$-$L^3$-;

$Y^2$ is bond or —C(═O)—;

$L^2$ is bond or an optionally substituted $C_1$-$C_6$ alkylene, $C_1$-$C_6$ heteroalkylene, $C_2$-$C_6$ alkenylene, $C_2$-$C_6$ alkynylene, or $C_3$-$C_6$ cycloalkylene, each optionally substituted with one, two, or three $R^7$;

$L^3$ is $C_3$-$C_6$ cycloalkylene, optionally substituted with one, two, or three $R^7$;

$R^1$ is H, halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^8$;

$R^2$ is H, halogen, —CN, —OH, —$OR^{1B}$, —$SR^{1B}$, —$N(R^{1A})_2$, —$NR^{1A}S(═O)_2(C_1$-$C_4$alkyl), —$S(═O)_2N(R^{1A})_2$, —OC(═O)($C_1$-$C_4$alkyl), —$CO_2H$, —$CO_2(C_1$-$C_4$alkyl), —C(═O)$N(R^{1A})_2$, —$NR^{1A}C$(═O)($C_1$-$C_4$alkyl), —$NR^{1A}C$(═O)O($C_1$-$C_4$alkyl), —OC(═O)$N(R^{1A})_2$, —$NR^{1A}C$(═O)$N(R^{1A})_2$, —S($C_1$-$C_4$alkyl), —S(═O)($C_1$-$C_4$alkyl), —$S(═O)_2(C_1$-$C_4$alkyl), $C_1$-$C_6$alkyl, $C_2$-$C_4$alkenyl, $C_2$-$C_4$alkynyl, $C_1$-$C_4$fluoroalkyl, $C_1$-$C_4$fluoroalkoxy, —$C_{1-6}$alkyl-OH, —$C_{1-6}$heteroalkyl-OH, $C_{1-6}$alkyl-C(═O)OH, —$C_{1-6}$heteroalkyl-C(═O)OH, monocyclic $C_2$-$C_6$heterocycloalkyl, phenyl, or monocyclic 5-6 membered heteroaryl; wherein alkyl, alkenyl, alkynyl, aryl, and heteroaryl are each optionally substituted with one, two, or three $R^9$;

$R^3$ is H, halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^9$ $R^4$ is H, $C_1$-$C_6$alkyl, or $C_3$-$C_6$cycloalkyl;

each $R^5$ is independently halogen, —CN, —OH, —$OR^{1B}$, —SH, —$SR^{1B}$, —S(═O)$R^{1B}$, —$NO_2$, —$N(R^{1A})_2$, —$S(═O)_2R^{1B}$, —$NHS(═O)_2R^{1B}$, —$S(═O)_2N(R^{1A})_2$, —C(═O)$R^{1B}$, —OC(═O)$R^{1B}$, —C(═O)$OR^{1A}$, —OC(═O)$OR^{1A}$, —C(═O)$N(R^{1A})_2$, —OC(═O)$N(R^{1A})_2$, —$NR^{1A}C$(═O)$N(R^{1A})_2$, —$NR^{1A}C$(═O)$R^{1B}$, —$NR^{1A}C$(═O)$OR^{1A}$, $C_1$-$C_6$ alkyl, $C_1$-$C_6$ haloalkyl, $C_1$-$C_6$ hydroxyalkyl, $C_1$-$C_6$ heteroalkyl, or cycloalkyl;

each $R^6$ is independently halogen, —CN, —OH, —$OR^{1B}$, —SH, —$SR^{1B}$, $N(R^{1A})_2$, $C_1$-$C_4$alkyl, $C_2$-$C_4$alkenyl, $C_2$-$C_4$alkynyl, $C_1$-$C_4$fluoroalkyl, $C_1$-$C_4$fluoroalkoxy, or $C_1$-$C_4$heteroalkyl;

each $R^7$, $R^8$ and $R^9$ is independently halogen, —CN, —OH, —$OR^{1B}$, —SH, —$SR^{1B}$, —$N(R^{1A})_2$, —C(═O)$OR^{1A}$ oxo (═O), $C_1$-$C_4$alkyl, or $C_1$-$C_4$fluoroalkyl;

each $R^{1A}$ is independently hydrogen, $C_1$-$C_6$ alkyl, cycloalkyl, heterocycloalkyl, aryl, or heteroaryl; and each $R^{1B}$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl.

In some embodiments presented herein, the compound of Formula (I) has the structure of Formula (II), or a pharmaceutically acceptable salt or solvate thereof:

Formula (II)

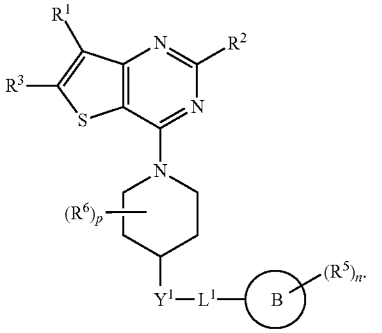

In some embodiments presented herein, the compound of Formula (I) has the structure of Formula (III), or a pharmaceutically acceptable salt or solvate thereof:

Formula (III)

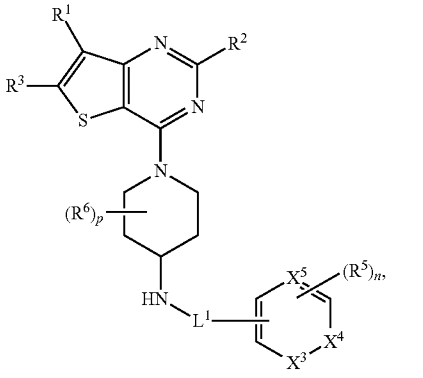

wherein: $X^3$, $X^4$, and $X^5$ are each independently CH or N.

In some embodiments presented herein, the compound of Formula (I) has the structure of Formula (IV), or a pharmaceutically acceptable salt or solvate thereof:

Formula (IV)

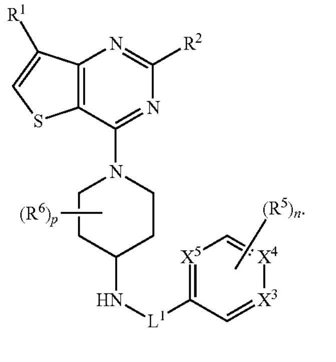

In another aspect, presented herein is a compound having the structure of Formula (V), or a pharmaceutically acceptable salt or solvate thereof:

Formula (V)

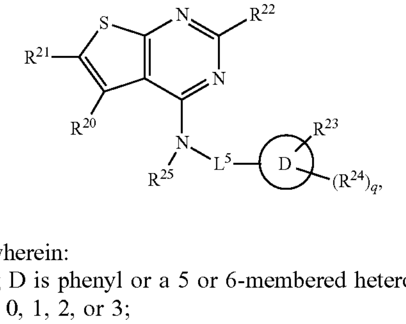

wherein:

ring D is phenyl or a 5 or 6-membered heteroaryl;

q is 0, 1, 2, or 3;

$L^5$ is an optionally substituted $C_1$-$C_3$ alkylene, optionally substituted with one, two, or three $R^{26}$;

$R^{20}$ is H, halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^{27}$.

$R^{21}$ is H, halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^{28}$.

$R^{22}$ is H, halogen, —CN, —OH, —$OR^{1B}$, —$SR^{1B}$, —$N(R^{1A})_2$, —$NR^{1A}S(=O)_2(C_1$-$C_4$alkyl), —$S(=O)_2N(R^{1A})_2$, —OC(=O)($C_1$-$C_4$alkyl), —$CO_2H$, —$CO_2(C_1$-$C_4$alkyl), —C(=O)$N(R^{1A})_2$, —$NR^{1A}C(=O)(C_1$-$C_4$alkyl), —$NR^{1A}C(=O)O(C_1$-$C_4$alkyl), —OC(=O)$N(R^{1A})_2$, —$NR^{1A}C(=O)N(R^{1A})_2$, —S($C_1$-$C_4$alkyl), —S(=O)($C_1$-$C_4$alkyl), —$S(=O)_2(C_1$-$C_4$alkyl), $C_1$-$C_6$alkyl, $C_2$-$C_4$alkenyl, $C_2$-$C_4$alkynyl, $C_1$-$C_4$fluoroalkyl, $C_1$-$C_4$fluoroalkoxy, —$C_{1\text{-}6}$alkyl-OH, —$C_{1\text{-}6}$heteroalkyl-OH, $C_{1\text{-}6}$alkyl-C(=O)OH, —$C_{1\text{-}6}$heteroalkyl-C(=O)OH, monocyclic $C_2$-$C_6$heterocycloalkyl, phenyl, or monocyclic 5-6 membered heteroaryl; wherein alkyl, alkenyl, alkynyl, aryl, and heteroaryl are each optionally substituted with one, two, or three $R^{29}$;

$R^{23}$ is H, halogen, —CN, —OH, —$OR^{1B}$, —SH, —$SR^{1B}$, —S(=O)$R^{1B}$, —$NO_2$, —$N(R^{1A})_2$, —$S(=O)_2R^{1B}$, —$NHS(=O)_2R^{1B}$, —$S(=O)_2N(R^{1A})_2$, —C(=O)$R^{1B}$, —OC(=O)$R^{1B}$, —C(=O)$OR^{1A}$, —OC(=O)$OR^{1A}$, —C(=O)$N(R^{1A})_2$, —OC(=O)$N(R^{1A})_2$, —$NR^{1A}C(=O)N(R^{1A})_2$, —$NR^{1A}C(=O)R^{1B}$, —$NR^{1A}C(=O)OR^{1A}$, $C_1$-$C_6$ alkyl, $C_2$-$C_4$alkynyl, $C_1$-$C_6$ haloalkyl, $C_1$-$C_6$ hydroxyalkyl, $C_1$-$C_6$heteroalkyl, or cycloalkyl each $R^{24}$ is independently halogen, —CN, —OH, —$OR^{1B}$, —SH, —$SR^{1B}$, —S(=O)$R^{1B}$, —$NO_2$, —$N(R^{1A})_2$, —$S(=O)_2R^{1B}$, —$NHS(=O)_2R^{1B}$, —$S(=O)_2N(R^{1A})_2$, —C(=O)$R^{1B}$, —OC(=O)$R^{1B}$, —C(=O)$OR^{1A}$, —OC(=O)$OR^{1A}$, —C(=O)$N(R^{1A})_2$, —OC(=O)$N(R^{1A})_2$, —$NR^{1A}C(=O)N(R^{1A})_2$, —$NR^{1A}C(=O)R^{1B}$, —$NR^{1A}C(=O)OR^{1A}$, $C_1$-$C_6$ alkyl, $C_2$-$C_4$alkynyl, $C_1$-$C_6$ haloalkyl, $C_1$-$C_6$ hydroxyalkyl, $C_1$-$C_6$ heteroalkyl, or cycloalkyl;

$R^{25}$ is H, $C_{1\text{-}6}$alkyl, or $C_1$-$C_6$cycloalkyl;

each $R^{26}$ is halogen or $C_1$-$C_6$ alkyl;

each $R^{27}$, $R^{28}$ and $R^{29}$ is independently halogen, —CN, —OH, —$OR^{1B}$, —SH, —$SR^{1B}$, —$N(R^{1A})_2$, —C(=O)$OR^{1A}$ oxo (=O), $C_1$-$C_4$alkyl, or $C_1$-$C_4$fluoroalkyl;

each $R^{1A}$ is independently hydrogen, $C_1$-$C_6$ alkyl, cycloalkyl, heterocycloalkyl, aryl, benzyl, or heteroaryl; and each $R^{1B}$ is independently H, $C_1$-$C_6$ alkyl, $C_2$-$C_6$ alkenyl, $C_2$-$C_6$ alkynyl, $C_1$-$C_6$heteroalkyl, cycloalkyl, heterocycloalkyl, aryl, or heteroaryl.

In some embodiments presented herein, the compound of Formula (V) has the structure of Formula (VI), or a pharmaceutically acceptable salt or solvate thereof:

Formula (VI)

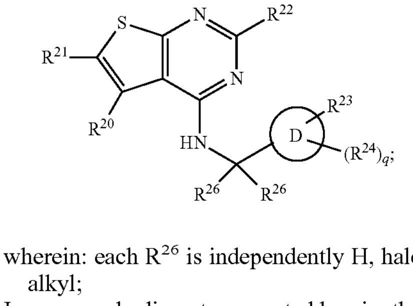

wherein: each $R^{26}$ is independently H, halogen, or $C_1$-$C_4$ alkyl;

In some embodiments presented herein, the compound of Formula (V) has the structure of Formula (VII), or a pharmaceutically acceptable salt or solvate thereof:

Formula (VII)

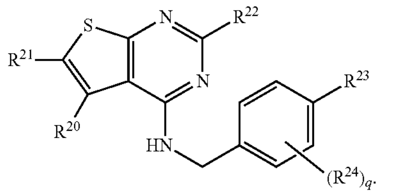

In some embodiments presented herein, the compound of Formula (V) has the structure of Formula (VIII), or a pharmaceutically acceptable salt or solvate thereof:

Formula (VIII)

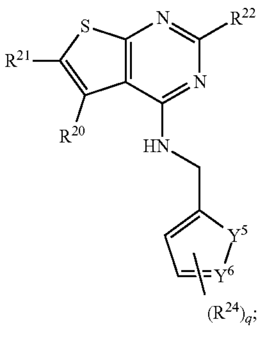

wherein: $Y^3$ is O or S; and $Y^4$ is CH.

In another aspect, presented herein is a compound having the structure of Formula (IX), or a pharmaceutically acceptable salt or solvate thereof:

Formula (IX)

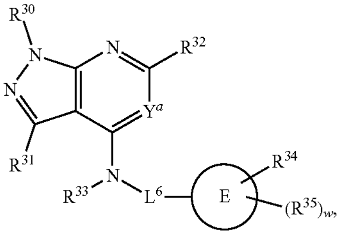

wherein:

$Y^a$ is CH or N;

ring E is phenyl or a 5 or 6-membered heteroaryl;

w is 0, 1, 2, or 3;

$L^6$ is an optionally substituted $C_1$-$C_3$ alkylene, optionally substituted with one, two, or three $R^{36}$;

$R^{30}$ is —$C_1$-$C_6$alkyl, —$C_3$-$C_6$ cycloalkyl, —$C_3$-$C_6$ heterocycloalkyl, phenyl, or monocyclic heteroaryl, wherein alkyl, alkenyl, alkynyl, aryl, and heteroaryl are each optionally substituted with one, two, or three $R^{37}$;

$R^{31}$ is H, halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^{38}$;

$R^{32}$ is H, halogen, —CN, —OH, —$OR^{1B}$, —$SR^{1B}$, —$N(R^{1A})_2$, —$NR^{1A}S(=O)_2(C_1$-$C_4$alkyl), —$S(=O)_2N(R^{1A})_2$, —$OC(=O)(C_1$-$C_4$alkyl), —$CO_2H$, —$CO_2(C_1$-$C_4$alkyl), —$C(=O)N(R^{1A})_2$, —$NR^{1A}C(=O)(C_1$-$C_4$alkyl), —$NR^{1A}C(=O)O(C_1$-$C_4$alkyl), —$OC(=O)N(R^{1A})_2$, —$NR^{1A}C(=O)N(R^{1A})_2$, —$S(C_1$-$C_4$alkyl), —$S(=O)(C_1$-$C_4$alkyl), —$S(=O)_2(C_1$-$C_4$alkyl), $C_1$-$C_6$alkyl, $C_2$-$C_4$alkenyl, $C_2$-$C_4$alkynyl, $C_1$-$C_4$fluoroalkyl, $C_1$-$C_4$fluoroalkoxy, —$C_{1\text{-}6}$alkyl-OH, —$C_{1\text{-}6}$heteroalkyl-OH, $C_{1\text{-}6}$alkyl-C(=O)OH, —$C_{1\text{-}6}$heteroalkyl-C(=O)OH, monocyclic $C_2$-$C_6$heterocycloalkyl, phenyl, or monocyclic 5-6 membered heteroaryl; wherein alkyl, alkenyl, alkynyl, aryl, and heteroaryl are each optionally substituted with one, two, or three $R^{39}$;

$R^{33}$ is H, $C_1$-$C_6$alkyl, or $C_1$-$C_6$ cycloalkyl;

$R^{34}$ is H, halogen, —CN, —OH, —$OR^{1B}$, —SH, —$SR^{1B}$, —$S(=O)R^{1B}$, —$NO_2$, —$N(R^{1A})_2$, —$S(=O)_2R^{1B}$, —$NHS(=O)_2R^{1B}$, —$S(=O)_2N(R^{1A})_2$, —$C(=O)R^{1B}$, —$OC(=O)R^{1B}$, —$C(=O)OR^{1A}$, —$OC(=O)OR^{1A}$, —$C(=O)N(R^{1A})_2$, —$OC(=O)N(R^{1A})_2$, —$NR^{1A}C(=O)N(R^{1A})_2$, —$NR^{1A}C(=O)R^{1B}$, —$NR^{1A}C(=O)OR^{1A}$, $C_1$-$C_6$ alkyl, $C_2$-$C_4$alkynyl, $C_1$-$C_6$ haloalkyl, $C_1$-$C_6$ hydroxyalkyl, $C_1$-$C_6$ heteroalkyl, or cycloalkyl; each $R^{35}$ is independently halogen, —CN, —OH, —$OR^{1B}$, —SH, —$SR^{1B}$, —$S(=O)R^{1B}$, —$NO_2$, —$N(R^{1A})_2$, —$S(=O)_2R^{1B}$, —$NHS(=O)_2R^{1B}$, —$S(=O)_2N(R^{1A})_2$, —$C(=O)R^{1B}$, —$OC(=O)R^{1B}$, —$C(=O)OR^{1A}$, —$OC(=O)OR^{1A}$, —$C(=O)N(R^{1A})_2$, —$OC(=O)N(R^{1A})_2$, —$NR^{1A}C(=O)N(R^{1A})_2$, —$NR^{1A}C(=O)R^{1B}$, —$NR^{1A}C(=O)OR^{1A}$, $C_1$-$C_6$ alkyl, $C_2$-$C_4$alkynyl, $C_1$-$C_6$ haloalkyl, $C_1$-$C_6$ hydroxyalkyl, $C_1$-$C_6$ heteroalkyl, or cycloalkyl;

each $R^{36}$ is halogen or $C_1$-$C_6$ alkyl;

each $R^{37}$, $R^{38}$ and $R^{39}$ is independently halogen, —CN, —OH, —$OR^{1B}$, —SH, —$SR^{1B}$, —$N(R^{1A})_2$, —$C(=O)OR^{1A}$, oxo (=O), $C_1$-$C_4$alkyl, or $C_1$-$C_4$fluoroalkyl;

each $R^{1A}$ is independently hydrogen, $C_1$-$C_6$ alkyl, cycloalkyl, heterocycloalkyl, aryl, benzyl, or heteroaryl; and each $R^{1B}$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl.

In some embodiments presented herein, the compound of Formula (IX) has the structure of Formula (X), or a pharmaceutically acceptable salt or solvate thereof:

Formula (X)

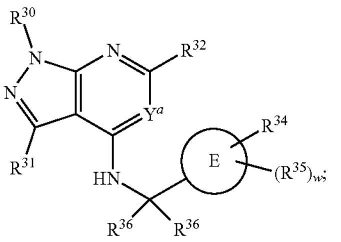

wherein: each $R^{36}$ is independently H, halogen, or $C_1$-$C_4$ alkyl.

In some embodiments presented herein, the compound of Formula (IX) has the structure of Formula (XI), or a pharmaceutically acceptable salt or solvate thereof:

Formula (XI)

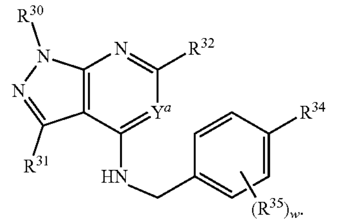

In some embodiments presented herein, the compound of Formula (IX) has the structure of Formula (XII), or a pharmaceutically acceptable salt or solvate thereof:

Formula (XII)

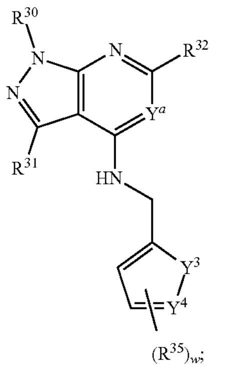

wherein: $Y^3$ is O or S; and $Y^4$ is CH.

In another aspect, provided herein is a pharmaceutical composition comprising a compound having the structure of Formula (I), (II), (III), (IV), (V), (VI), (VII), (VIII), (IX), (X), (XI), or (XII), or a pharmaceutically acceptable salt thereof; and a pharmaceutically acceptable excipient.

In another aspect, provided herein is a method of treating a disease or condition by modulation of the ENPP1 in a subject in need thereof, which method comprises administering to the subject a therapeutically effective amount of a compound of Formula (I), (II), (III), (IV), (V), (VI), (VII), (VIII), (IX), (X), (XI), or (XII), or a pharmaceutically acceptable salt thereof. In some embodiments, the disease or condition is a pseudogout.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Pseudogout (or "false gout") is a form of arthritis that results from deposits of calcium pyrophosphate crystals and is sometimes known as calcium pyrophosphate dihydrate crystal deposition disease (CPPD). CPPD is a form of arthritis that causes pain, stiffness, tenderness, redness, warmth, and swelling (inflammation) in some joints. It usually affects one joint at a time, but sometimes it may affect several joints at once. The symptoms are similar to the symptoms of other diseases, especially gout (which is why this form of arthritis had the old name of pseudogout—"false gout"). Some symptoms of CPPD may appear to be symptoms of rheumatoid arthritis or osteoarthritis. CPPD commonly affects the knee or wrist. Less often, it can involve the hips, shoulders, elbows, knuckles, toes, or ankles. Symptoms include sudden intense joint pain; swollen joint that is warm and tender to the touch; red skin involving the affected joint. Less often, CPPD may cause persistent swelling, warmth, and pain in several joints, and can even mimic rheumatoid arthritis. This condition results from the abnormal formation of calcium pyrophosphate dihydrate (CPPD) crystals in the cartilage or the joint fluid (synovial fluid), which can lead to a sudden attack of arthritis, similar to gout. The cause of abnormal deposits of CPPD crystals in cartilage is often unknown. CPPD crystals may be seen associated with some underlying disorders such as injury to the joint, hyperparathyroidism, hypomagnesemia, hypophosphatasia, hypothyroidism, and hemochromatosis. The abnormal formation of CPPD crystals may also be a hereditary trait.

CPPD affects both men and women. It occurs more frequently in people as they age, commonly affecting people over age 60. People who have a thyroid condition, kidney failure, or disorders that affect calcium, phosphate, or iron metabolism have an increased risk for CPPD. The condition is also commonly present in people who have osteoarthritis. "Attacks" of osteoarthritis associated with pain, swelling, and redness of the joint may in fact, in certain cases, be due to CPPD. CPPD in young patients is unusual.

The treatment of CPPD is similar to the treatment of acute gout attacks with anti-inflammatory medication. Anti-inflammatory drugs are usually continued until the CPPD attack completely resolves. Otherwise colchicine is usually prescribed for CPPD attacks. At low doses, it can be prescribed for a longer period of time to reduce the risk of recurrent attacks of CPPD. Nonsteroidal anti-inflammatory drugs (NSAIDS), especially if colchicine cannot be prescribed, are used to treat CPPD attacks. Certain patients cannot take these medications, such as those who have poor kidney function, bleeding disorders, heart disease, and certain other health complications. Corticosteroids may be prescribed for people who cannot take NSAIDs or colchicine.

Ectonucleotide pyrophosphatase/phosphodiesterase family member 1 is an enzyme that in humans is encoded by the ENPP1 gene. This gene is a member of the ecto-nucleotide pyrophosphatase/phosphodiesterase (ENPP) family. The encoded protein is a type II transmembrane glycoprotein comprising two identical disulfide-bonded subunits. This protein has broad specificity and cleaves a variety of substrates, including phosphodiester bonds of nucleotides and nucleotide sugars. This protein may function to hydrolyze nucleoside 5' triphosphates to their corresponding monophosphates and may also hydrolyze diadenosine polyphosphates. Mutations in this gene have been associated with Generalized arterial calcification of infancy, ossification of the posterior longitudinal ligament of the spine (OPLL), Hypophosphatemic rickets autosomal recessive 2 ($ARHR^2$), and insulin resistance.

The ENPP1 gene provides instructions for making a protein called ectonucleotide pyrophosphatase/phosphodiesterase 1 (ENPP1). The ENPP1 protein helps break down a molecule called adenosine triphosphate (ATP), specifically when it is found outside the cell (extracellular). Extracellular ATP is quickly broken down into other molecules called adenosine monophosphate (AMP) and pyrophosphate. Pyrophosphate is important in preventing the accumulation of abnormal deposits of calcium (calcification) and other minerals (mineralization) in the body.

In some embodiments, the compounds described herein are modulators of ENPP1. In some embodiments, the compounds described herein are used to treat an ENPP1 related disorder. In some embodiments, the ENPP1-mediated disorder is pseudogout or calcium pyrophosphate dihydrate crystal deposition disease (CPPD).

In another aspect the disclosure provides methods for treating pseudogout, by administering to a subject in need thereof, an effective amount of a compound having the structure of Formula (I), (II), (III), (IV), (V), (VI), (VII), (VIII), (IX), (X), (XI), or (XII), or a pharmaceutically acceptable salt or solvate thereof.

Compounds

In one aspect, provided herein is a compound having the structure of Formula (I), or a pharmaceutically acceptable salt or solvate, thereof:

Formula (I)

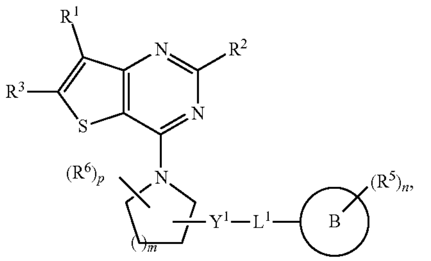

wherein:

ring B is aryl or a 5 or 6-membered heteroaryl;

n is 0, 1, 2, or 3;

m is 1 or 2;

p is 0, 1, 2, or 3;

$Y^1$ is —$NR^4$— or —O—;

$L^1$ is —$Y^2$-$L^2$- or —$Y^2$-$L^2$-$L^3$-;

$Y^2$ is bond or —C(═O)—;

$L^2$ is bond or an optionally substituted $C_1$-$C_6$ alkylene, $C_1$-$C_6$ heteroalkylene, $C_2$-$C_6$ alkenylene, $C_2$-$C_6$ alkenylene, or $C_3$-$C_6$ cycloalkylene, each optionally substituted with one, two, or three $R^7$;

$L^3$ is $C_3$-$C_6$ cycloalkylene, optionally substituted with one, two, or three $R^7$;

$R^1$ is H, halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^1$;

$R^2$ is H, halogen, —CN, —OH, —$OR^{1B}$, —$SR^{1B}$, —$N(R^{1A})_2$, —$NR^{1A}S(=O)_2(C_1$-$C_4$alkyl), —$S(=O)_2N(R^{1A})_2$, —OC(═O)($C_1$-$C_4$alkyl), —$CO_2H$, —$CO_2$($C_1$-$C_4$alkyl), —C(═O)$N(R^{1A})_2$, —$NR^{1A}$C(═O)($C_1$-$C_4$alkyl), —$NR^{1A}$C(═O)O($C_1$-$C_4$alkyl), —OC(═O)$N(R^{1A})_2$, —$NR^{1A}$C(═O)$N(R^{1A})_2$, —S($C_1$-$C_4$alkyl), —S(═O)($C_1$-$C_4$alkyl), —$S(=O)_2$($C_1$-$C_4$alkyl), $C_1$-$C_6$alkyl, $C_2$-$C_4$alkenyl, $C_2$-$C_4$alkynyl, $C_1$-$C_4$fluoroalkyl, $C_1$-$C_4$fluoroalkoxy, —$C_{1-6}$alkyl-OH, —$C_{1-6}$heteroalkyl-OH, $C_{1-6}$alkyl-C(═O)OH, —$C_{1-6}$heteroalkyl-C(═O)OH, monocyclic $C_2$-$C_6$heterocycloalkyl, phenyl, or monocyclic 5-6 membered heteroaryl; wherein alkyl, alkenyl, alkynyl, aryl, and heteroaryl are each optionally substituted with one, two, or three $R^9$;

$R^3$ is H, halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^9$;

$R^4$ is H, $C_1$-$C_6$alkyl, or $C_3$-$C_6$cycloalkyl;

each $R^5$ is independently halogen, —CN, —OH, —$OR^{1B}$, —SH, —$SR^{1B}$, —S(═O)$R^{1B}$, —$NO_2$, —$N(R^{1A})_2$, —$S(=O)_2R^{1B}$, —$NHS(=O)_2R^{1B}$, —$S(=O)_2N(R^{1A})_2$, —C(═O)$R^{1B}$, —OC(═O)$R^{1B}$, —C(═O)$OR^{1A}$, —OC(═O)$OR^{1A}$, —C(═O)$N(R^{1A})_2$, —OC(═O)$N(R^{1A})_2$, —$NR^{1A}$C(═O)$N(R^{1A})_2$, —$NR^{1A}$C(═O)$R^{1B}$, —$NR^{1A}$C(═O)$OR^{1A}$, $C_1$-$C_6$alkyl, $C_1$-$C_6$ haloalkyl, $C_1$-$C_6$ hydroxyalkyl, $C_1$-$C_6$ heteroalkyl, or cycloalkyl;

each $R^6$ is independently halogen, —CN, —OH, —$OR^{1B}$, —SH, —$SR^{1B}$, $N(R^{1A})_2$, $C_1$-$C_4$alkyl, $C_2$-$C_4$alkenyl, $C_2$-$C_4$alkynyl, $C_1$-$C_4$fluoroalkyl, $C_1$-$C_4$fluoroalkoxy, or $C_1$-$C_4$heteroalkyl;

each $R^7$, $R^8$ and $R^9$ is independently halogen, —CN, —OH, —$OR^{1B}$, —SH, —$SR^{1B}$, —$N(R^{1A})_2$, —C(═O)$OR^{1A}$, oxo (═O), $C_1$-$C_4$alkyl, or $C_1$-$C_4$fluoroalkyl;

each $R^{1A}$ is independently hydrogen, $C_1$-$C_6$ alkyl, cycloalkyl, heterocycloalkyl, aryl, benzyl, or heteroaryl; and each $R^{1B}$ is independently H, $C_1$-$C_6$ alkyl, $C_2$-$C_6$ alkenyl, $C_2$-$C_6$ alkynyl, $C_1$-$C_6$heteroalkyl, cycloalkyl, heterocycloalkyl, aryl, or heteroaryl.

In some embodiments of Formula (I), or a pharmaceutically acceptable salt or solvate thereof, $R^1$ is halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^8$. In some embodiments, $R^1$ is halogen, —$C_1$-$C_6$alkyl, $C_2$-$C_6$alkenyl, phenyl, or monocyclic heteroaryl. In some embodiments, $R^1$ is phenyl. In some embodiments, $R^1$ is monocyclic heteroaryl. In some embodiments, $R^1$ is halogen or —$C_1$-$C_6$alkyl. In some embodiments, $R^1$ is —Br, —Cl, —I, or —F. In some embodiments, $R^1$ is —Br. In some embodiments, $R^1$ is —Cl. In some embodiments, $R^1$ is —$CH_3$, —$CH_2CH_3$, or —$CH(CH_3)_2$. In some embodiments, $R^1$ is —$CH_3$. In some embodiments, $R^1$ is H.

In some embodiments of Formula (I), or a pharmaceutically acceptable salt or solvate thereof, $R^3$ is H, halogen, —$C_1$-$C_6$alkyl, —$C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^9$. In some embodiments, $R^3$ is phenyl. In some embodiments, $R^3$ is halogen. In some embodiments, $R^3$ is —Cl, —Br, —I, or —F. In some embodiments, $R^3$ is —Cl. In some embodiments, $R^3$ is —Br. In some embodiments, $R^3$ is —I. In some embodiments, $R^3$ is —$C_1$-$C_6$alkyl. In some embodiments, $R^3$ is —$CH_3$, —$CH_2CH_3$, or —$CH(CH_3)_2$. In some embodiments, $R^3$ is —$CH_3$. In some embodiments, $R^3$ is H.

In some embodiments of Formula (I), or a pharmaceutically acceptable salt or solvate thereof, $R^3$ is hydrogen; and $R^1$ is halogen, $C_1$-$C_6$ alkyl, or phenyl. In some embodiments, $R^3$ is hydrogen; and $R^1$ is —Br, —Cl, or —I. In some embodiments, $R^3$ is hydrogen; and $R^1$ is —$CH_3$. In some embodiments, $R^3$ is hydrogen; and $R^1$ is phenyl.

In some embodiments of Formula (I), or a pharmaceutically acceptable salt or solvate thereof, $R^4$ is H or $C_1$-$C_6$alkyl. In some embodiments, $R^4$ is $C_1$-$C_6$alkyl. In some embodiments, $R^4$ is —$CH_3$. In some embodiments, $R^4$ is H.

In some embodiments of Formula (I), or a pharmaceutically acceptable salt or solvate thereof, each $R^6$ is independently halogen, —CN, —OH, —$OR^{1B}$, —SH, —$SR^{1B}$, $N(R^{1A})_2$, $C_1$-$C_4$alkyl, $C_2$-$C_4$alkenyl, $C_2$-$C_4$alkynyl, $C_1$-$C_4$fluoroalkyl, $C_1$-$C_4$fluoroalkoxy, or $C_1$-$C_4$heteroalkyl. In some embodiments, each Riis independently halogen or $C_1$-$C_4$alkyl. In some embodiments, each $R^6$ is independently —Cl, —Br, —F, —I, —$CH_3$, or —$CH_2CH_3$. In some embodiments, each $R^6$ is independently —$CH_3$.

In some embodiments of Formula (I), or a pharmaceutically acceptable salt or solvate thereof, p is 1, 2, or 3. In some embodiments, p is 1. In some embodiments, p is 2. In some embodiments, p is 0.

In some embodiments of Formula (I), or a pharmaceutically acceptable salt or solvate thereof, m is 1. In some embodiments, m is 2.

In some embodiments of Formula (I), the compound has the structure of Formula (II), or a pharmaceutically acceptable salt or solvate thereof:

Formula (II)

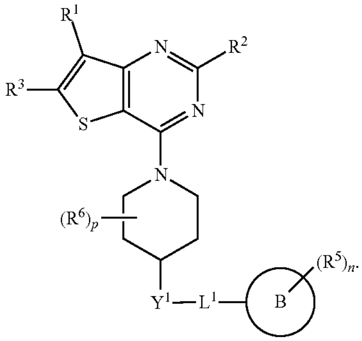

In some embodiments of Formula (I) or (II), or a pharmaceutically acceptable salt or solvate thereof, $Y^1$ is —$NR^4$—, wherein $R^4$ is H or $C_1$-$C_4$alkyl. In some embodiment, $R^4$ is H. In some embodiments, $R^4$ is $C_1$-$C_4$alkyl. In some embodiments, $R^4$ is —$CH_3$. In some embodiments of Formula (I) or (II), $Y^1$ is —NH—.

In some embodiments, ring B aryl. In some embodiments, ring B is a monocyclic or bicyclic aryl. In some embodiments, the aryl is phenyl. In some embodiments of Formula (I) or (II), or a pharmaceutically acceptable salt or solvate thereof, ring B is phenyl.

In some embodiments of Formula (I) or (II), or a pharmaceutically acceptable salt or solvate thereof, ring B is a 6-membered heteroaryl. In some embodiments, ring B is pyridinyl, pyrimidinyl, pyrazinyl, or pyridazinyl. In some embodiments, ring B is pyridinyl.

In some embodiments of Formula (I) or (II), or a pharmaceutically acceptable salt or solvate thereof,

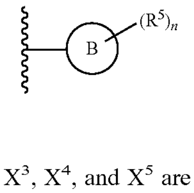 is 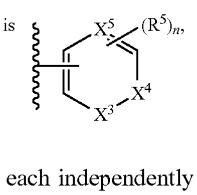

wherein: $X^3$, $X^4$, and $X^5$ are each independently CH or N.

In some embodiments of Formula (I) or (II), or a pharmaceutically acceptable salt or solvate thereof, $X^3$ is N; and $X^4$ and $X^5$ are each CH. In some embodiments, $X^3$ and $X^4$ are N; and $X^5$ is CH. In some embodiments, $X^3$ is CH; and $X^4$ and $X^5$ are each N. In some embodiments, $X^3$ and $X^5$ are each N; and $X^4$ is CH. In some embodiments, $X^3$, $X^4$ and $X^5$ are each CH. In some embodiments, $X^3$, $X^4$ and $X^5$ are each N.

In some embodiments, the compound of Formula (I) has the structure of Formula (III), or a pharmaceutically acceptable salt or solvate thereof:

Formula (III)

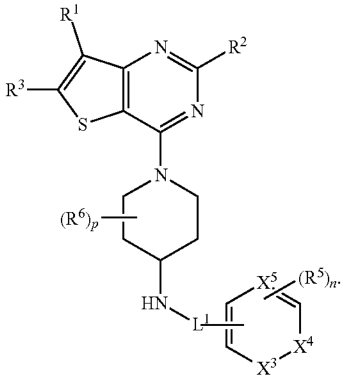

In some embodiments of Formula (I), (II), or (III), or a pharmaceutically acceptable salt or solvate thereof, $L^1$ is $Y^2$-$L^2$, wherein $Y^2$ is bond or —C(═O)—; and $L^2$ is $C_1$-$C_5$ alkylene, $C_2$-$C_6$ alkenylene, or $C_1$-$C_6$ heteroalkylene, optionally substituted with one, two, or three $R^7$, wherein $R^7$ is $C_1$-$C_6$alkyl. In some embodiments, $Y^2$ is bond. In some embodiments, $Y^2$ is —C(═O)—. In some embodiments, $L^2$ is $C_1$-$C_6$ heteroalkylene, optionally substituted with 1 or 2 —$CH_3$. In some embodiments, $L^2$ is $C_2$-$C_6$ alkynylene, optionally substituted with 1 or 2 —$CH_3$. In some embodiments, $L^2$ is $C_2$-$C_5$ alkylene or $C_2$-$C_6$ alkenylene, optionally substituted with 1 or 2 —$CH_3$. In some embodiments, $L^2$ is —$CH_2$—, —$CH_2CH_2$—, —$CH_2CH_2CH_2$—, —$CH_2(CH_2)_2CH_2$—, —$CH_2(CH_2)_3CH_2$—, —$CH(CH_3)CH_2CH_2$—, —$CH_2CH(CH_3)CH_2$—, —$C(CH_3)_2CH_2CH_2$—, —$CH_2C(CH_3)_2CH_2$—, —$CH_2CH$═$CH$—, or —$CH(CH_3)CH$═$CH$—. In some embodiments, $L^2$ is —$CH_2CH_2$—, —$CH_2CH_2CH_2$—, —$CH_2(CH_2)_2CH_2$—, or —$CH_2CH$═$CH$—. In some embodiments, $L^2$ is —$C(CH_3)_2CH_2CH_2$— or —$CH(CH_3)CH_2CH_2$—. In some embodiments, $L^2$ is —$CH_2CH_2CH_2$—. In some embodiments, $L^2$ is —$CH_2(CH_2)_2CH_2$—. In some embodiments, $L^2$ is —$CH_2CH$═$CH$—. In some embodiments, $L^2$ is —$CH(CH_3)CH$═$CH$—.

In some embodiments of Formula (I), (II), or (III), or a pharmaceutically acceptable salt or solvate thereof, $L^1$ is $Y^2$-$L^2$, wherein $Y^2$ is bond or —C(═O)—; and $L^2$ is cyclopropylene. In some embodiments, $Y^2$ is —C(═O)—; and $L^2$ is cycloproylene, cyclobutylene, cyclopentylene, or cyclohexene. In some embodiments, $L^2$ s cyclopropylene.

In some embodiments of Formula (I), (II), or (III), or a pharmaceutically acceptable salt or solvate thereof, $L^1$ is —$Y^2$-$L^2$-$L^3$-, wherein $Y^2$ is bond or —C(═O)—; $L^2$ is $C_2$-$C_5$alkylene or $C_2$-$C_6$ heteroalkylene, optionally substituted with 1 or 2 —$CH_3$; and $L^3$ is $C_3$-$C_6$cyclopropylene. In some embodiments, $L^1$ is —$Y^2$-$L^2$-$L^3$-, wherein $Y^2$ is bond or —C(═O)—; $L^2$ is $C_2$-$C_5$alkylene, optionally substituted with 1 or 2 —$CH_3$; and $L^3$ is $C_3$-$C_6$cyclopropylene. In some embodiments, $L^1$ is —$Y^2$-$L^2$-$L^3$-, wherein $Y^2$ is bond or —C(═O)—; $L^2$ is —$CH_2$—; and $L^3$ is $C_3$-$C_6$cyclopropylene. In some embodiments, $L^1$ is —$Y^2$-$L^2$-$L^3$-, wherein $Y^2$ is bond or —C(═O)—; $L^2$ is —$CH_2$—; and $L^3$ is cyclopropylene.

In some embodiments of Formula (I), (II), or (III), or a pharmaceutically acceptable salt or solvate thereof, $Y^2$ is bond. In some embodiments, $Y^2$ is —C(═O)—.

In some embodiments, the compound of Formula (I) has the structure of Formula (IV), or a pharmaceutically acceptable salt or solvate thereof:

Formula (IV)

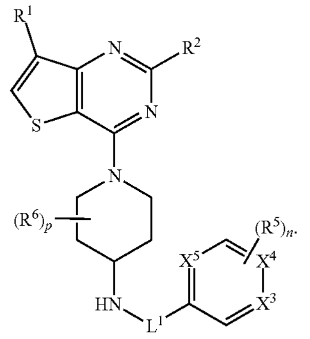

In some embodiments of Formula (IV), or a pharmaceutically acceptable salt or solvate thereof $X^3$ is N; and $X^4$ and $X^5$ are each CH. In some embodiments, $X^4$ is N; and $X^3$ and $X^5$ are each CH. In some embodiments, $X^5$ is N; and $X^3$ and $X^4$ are each CH. In some embodiments, $X^3$, $X^4$, and $X^5$ are each CH. In some embodiments, $X^3$, $X^4$, and $X^5$ are each N.

In some embodiments of Formula (I), (II), (III), or (IV), or a pharmaceutically acceptable salt or solvate thereof, each R is independently halogen, —CN, —ORB, —$C_1$-$C_6$ alkyl, $C_1$-$C_6$ haloalkyl, $C_1$-$C_6$ hydroxyalkyl, or $C_1$-$C_6$ heteroalkyl. In some embodiments, each $R^5$ is independently —Br, —Cl, —F, —CN, —$CF_3$, —$CH_3$, or —$OCH_3$. In some embodiments, each $R^5$ is independently —Br, —Cl, —F, or —I. In some embodiments, each R is independently —Cl or —F. In some embodiments, each R is independently —I. In some embodiments, each $R^5$ is independently —F. In some embodiments, each $R^5$ is independently —CN, —$CF_3$, —$CH_3$, or —$OCH_3$. In some embodiments, each $R^5$ is independently —CN. In some embodiments, each R is independently —$CF_3$. In some embodiments, each $R^5$ is independently —$CH_3$. In some embodiments, each $R^5$ is independently —$OCH_3$.

In some embodiments of Formula (I), (II), (III), or (VI), or a pharmaceutically acceptable salt or solvate thereof, n is 1 or 2. In some embodiments, n is 1. In some embodiments, n is 0.

In some embodiments of Formula (I), (II), (III), or (IV), or a pharmaceutically acceptable salt or solvate thereof, is

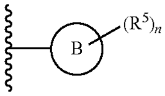 is 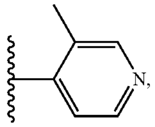 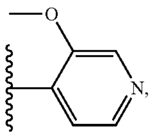

-continued

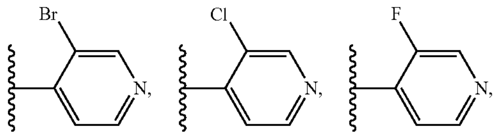

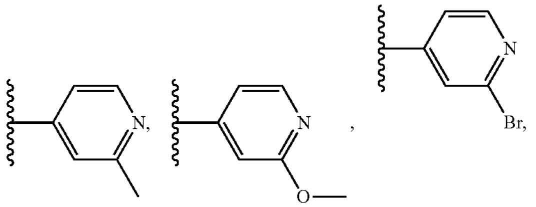

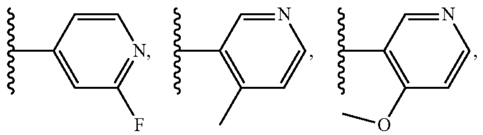

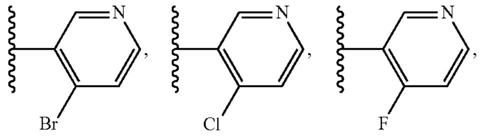

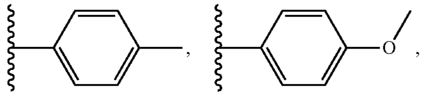

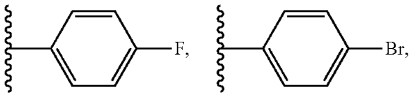 or

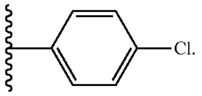

In some embodiments,

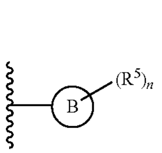 is 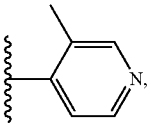 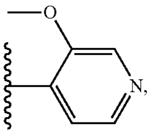 or

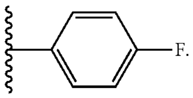

In some embodiments,

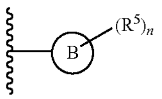 is 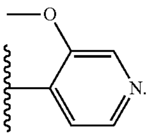

In some embodiments,

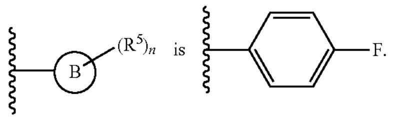

In some embodiments,

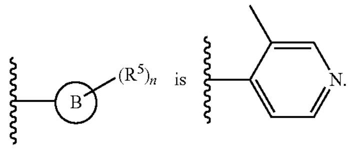

In some embodiments of Formula (I), (II), (III), or (IV), or a pharmaceutically acceptable salt or solvate thereof, $R^2$ is halogen, —CN, —OH, —$OR^{1B}$, —$SR^{1B}$, —$N(R^{1A})_2$, —$NR^{1A}S(=O)_2(C_1$-$C_4$alkyl), —$S(=O)_2N(R^{1A})_2$, —OC(=O)($C_1$-$C_4$alkyl), —$CO_2H$, —$CO_2(C_1$-$C_4$alkyl), —C(=O)$N(R^{1A})_2$, —$NR^{1A}C(=O)(C_1$-$C_4$alkyl), —$NR^{1A}C$(=O)O($C_1$-$C_4$alkyl), —OC(=O)$N(R^{1A})_2$, —$NR^{1A}C(=O)N(R^{1A})_2$, —S($C_1$-$C_4$alkyl), —S(=O)($C_1$-$C_4$alkyl), —$S(=O)_2(C_1$-$C_4$alkyl), $C_1$-$C_6$alkyl, $C_2$-$C_4$alkenyl, $C_2$-$C_4$alkynyl, $C_1$-$C_4$fluoroalkyl, $C_1$-$C_4$fluoroalkoxy, —$C_{1-6}$alkyl-OH, —$C_{1-6}$heteroalkyl-OH, monocyclic $C_2$-$C_6$heterocycloalkyl, phenyl, or monocyclic 5-6 membered heteroaryl; wherein alkyl, alkenyl, alkynyl, aryl, and heteroaryl are each optionally substituted with one, two, or three $R^9$, wherein each $R^9$ is independently halogen, —OH, —$OR^{1B}$, —SH, —$SR^{1B}$, —$N(R^{1A})_2$, $C_1$-$C_4$alkyl, or $C_1$-$C_4$fluoroalkyl.

In some embodiments of Formula (I), (II), (III), or (IV), or a pharmaceutically acceptable salt or solvate thereof, $R^2$ is halogen, —CN, —OH, —$OR^{1B}$, —$SR^{1B}$, —$N(R^{1A})_2$, —$C_1$-$C_6$alkyl, $C_1$-$C_4$fluoroalkyl, —$C_{1-6}$alkyl-OH, or —$C_{1-6}$heteroalkyl-OH. In some embodiments, $R^2$ is —Br, —Cl, —F, —CN, —$NH_2$, —$NHCH_3$, —$NHCH_2CH_3$, —$N(CH_3)_2$, —$OCH_3$, —$CF_3$, —$CH_3$, —$CH_2CH_3$, or —NH$(CH_2)_2$OH. In some embodiments, $R^2$ is —Br, —Cl, —F, or —CN. In some embodiments, $R^2$ is —$NH_2$, —$NHCH_3$, —$NHCH_2CH_3$, —$N(CH_3)_2$, —$NH(CH_2)_2CH_3$, —$NH(CH_2)_3CH_3$, —$NH(CH_2)_4CH_3$, —$NH(CH_2)_3CH(CH_3)_2$, or —$NH(CH_2)_2OH$. In some embodiments, $R^2$ is —$NH(CH_2)_2OH$. In some embodiments, $R^2$ is —NH($C_3$-$C_6$cycloalkyl). In some embodiments, $R^2$ is —NH-cyclopropyl, —NH-cyclobutyl, or —NH-cyclohexyl. In some embodiments, $R^2$ is —NH-benzyl. In some embodiments, $R^2$ is —$SH_2$, —$SCH_3$, or —$SCH_2CH_3$. In some embodiments, $R^2$ is —OH, —$OCH_3$, or —$OCH_2CH_3$, —$OCH_2CH_2CH_3$, —$OCH_2CH_2CH(CH_3)_2$. In some embodiments, $R^2$ is —$OCH_3$, —$CF_3$, —$CH_3$, or —$CH_2CH_3$.

In some embodiments of Formula (I), (II), (III), or (IV), or a pharmaceutically acceptable salt or solvate thereof, $R^2$ is $C_2$-$C_6$heterocycloalkyl, optionally substituted with one, two, or three $R^9$. In some embodiments, $R^2$ is piperazine, piperdine, or morpholino. In some embodiments, $R^2$ is piperazine. In some embodiments, $R^2$ is piperdine. In some embodiments, $R^2$ is morpholine.

In some embodiments of Formula (I), (II), (III), or (IV), or a pharmaceutically acceptable salt or solvate thereof, $R^2$ is H.

In some embodiments of Formula (I), (II), (III), or (IV), or a pharmaceutically acceptable salt or solvate thereof, $R^2$ is phenyl or a monocyclic heteroaryl, optionally substituted with one, two, or three $R^9$, wherein each $R^9$ is independently halogen, —OH, —$OR^{1B}$, —SH, —$SR^{1B}$, —$N(R^{1A})_2$, $C_1$-$C_4$alkyl, or $C_1$-$C_4$fluoroalkyl. In some embodiments, $R^2$ is phenyl. In some embodiments, $R^2$ is a monocyclic heteroaryl. In some embodiments, the monocyclic heteroaryl is 2-pyridyl, 3-pyridyl, or 4-pyridyl. In some embodiments, the monocyclic heteroaryl is 2-pyridyl. In some embodiments, the monocyclic heteroaryl is 3-pyridyl. In some embodiments, the monocyclic heteroaryl is 4-pyridyl.

In another aspect, provided herein is a compound having the structure of Formula (V), or a pharmaceutically acceptable salt or solvate, thereof:

Formula (V)

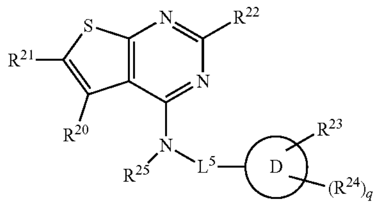

wherein:

ring D is phenyl or a 5 or 6-membered heteroaryl;

q is 0, 1, 2, or 3;

$L^5$ is an optionally substituted $C_1$-$C_3$ alkylene, optionally substituted with one, two, or three $R^{26}$;

$R^{20}$ is H, halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^{27}$.

$R^{21}$ is H, halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^{28}$.

$R^{22}$ is H, halogen, —CN, —OH, —$OR^{1B}$, —$SR^{1B}$, —$N(R^{1A})_2$, —$NR^{1A}S(=O)_2(C_1$-$C_4$alkyl), —$S(=O)_2N(R^{1A})_2$, —OC(=O)($C_1$-$C_4$alkyl), —$CO_2H$, —$CO_2(C_1$-$C_4$alkyl), —C(=O)$N(R^{1A})_2$, —$NR^{1A}C(=O)(C_1$-$C_4$alkyl), —$NR^{1A}C(=O)O(C_1$-$C_4$alkyl), —OC(=O)$N(R^{1A})_2$, —$NR^{1A}C(=O)N(R^{1A})_2$, —S($C_1$-$C_4$alkyl), —S(=O)($C_1$-$C_4$alkyl), —$S(=O)_2(C_1$-$C_4$alkyl), $C_1$-$C_6$alkyl, $C_2$-$C_4$alkenyl, $C_2$-$C_4$alkynyl, $C_1$-$C_4$fluoroalkyl, $C_1$-$C_4$fluoroalkoxy, —$C_{1-6}$alkyl-OH, —$C_{1-6}$heteroalkyl-OH, $C_{1-6}$alkyl-C(=O)OH, —$C_{1-6}$heteroalkyl-C(=O)OH, monocyclic $C_2$-$C_6$heterocycloalkyl, phenyl, or monocyclic 5-6 membered heteroaryl; wherein alkyl, alkenyl, alkynyl, aryl, and heteroaryl are each optionally substituted with one, two, or three $R^{29}$;

$R^{23}$ is H, halogen, —CN, —OH, —$OR^{1B}$, —SH, —$SR^{1B}$, —S(=O)$R^{1B}$, —$NO_2$, —$N(R^{1A})_2$, —$S(=O)_2R^{1B}$, —$NHS(=O)_2R^{1B}$, —$S(=O)_2N(R^{1A})_2$, —C(=O)$R^{1B}$, —OC(=O)$R^{1B}$, —C(=O)$OR^{1A}$, —OC(=O)$OR^{1A}$, —C(=O)$N(R^{1A})_2$, —OC(=O)$N(R^{1A})_2$, —$NR^{1A}C(=O)N(R^{1A})_2$, —$NR^{1A}C(=O)R^{1B}$, —$NR^{1A}C(=O)OR^{1A}$, $C_1$-$C_6$alkyl, $C_2$-$C_4$alkynyl, $C_1$-$C_6$ haloalkyl, $C_1$-$C_6$ hydroxyalkyl, $C_1$-$C_6$heteroalkyl, or cycloalkyl each $R^{24}$ is independently halogen, —CN, —OH, —$OR^{1B}$, —SH, —$SR^{1B}$, —S(═O)$R^{1B}$, —$NO_2$, —$N(R^{1A})_2$, —$S(═O)_2R^{1B}$, —$NHS(═O)_2R^{1B}$, —$S(═O)_2N(R^{1A})_2$, —C(═O)$R^{1B}$, —OC(═O)$R^{1B}$, —C(═O)$OR^{1A}$, —OC(═O)$OR^{1A}$, —C(═O)$N(R^{1A})_2$, —OC(═O)$N(R^{1A})_2$, —$NR^{1A}C(═O)N(R^{1A})_2$, —$NR^{1A}C(═O)R^{1B}$, —$NR^{1A}C(═O)OR^{1A}$, $C_1$-$C_6$alkyl, $C_2$-$C_4$alkynyl, $C_1$-$C_6$ haloalkyl, $C_1$-$C_6$ hydroxyalkyl, $C_1$-$C_6$ heteroalkyl, or cycloalkyl;

$R^{25}$ is H, $C_1$-$C_6$alkyl, or $C_1$-$C_6$cycloalkyl;

each $R^{26}$ is independently H, halogen or $C_1$-$C_6$ alkyl;

each $R^{27}$, $R^{28}$ and $R^{29}$ is independently halogen, —CN, —OH, —$OR^{1B}$, —SH, —$SR^{1B}$, —$N(R^{1A})_2$, —C(═O)$OR^{1A}$, oxo (═O), $C_1$-$C_4$alkyl, or $C_1$-$C_4$fluoroalkyl;

each $R^{1A}$ is independently hydrogen, $C_1$-$C_6$ alkyl, cycloalkyl, heterocycloalkyl, aryl, benzyl, or heteroaryl; and each $R^{1B}$ is independently H, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl.

In some embodiments of Formula (V), or a pharmaceutically acceptable salt or solvate thereof, $R^{21}$ is H, halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^{28}$. In some embodiments, $R^{21}$ is —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^{28}$. In some embodiments, $R^{21}$ is —$C_1$-$C_6$alkyl, phenyl, or monocyclic heteroaryl, each optionally substituted with one, two, or three halogens. In some embodiments, $R^{21}$ is phenyl, optionally substituted with one, two, or three —Cl, —Br, or —F. In some embodiments, $R^{21}$ is monocyclic heteroaryl. In some embodiments, the monocyclic heteroaryl is 2-pyridyl, 3-pyridyl, or 4-pyridyl. In some embodiments, $R^{21}$ is unsubstituted phenyl. In some embodiments, $R^{21}$ is unsubstituted 2-pyridyl, 3-pyridyl, or 4-pyridyl. In some embodiments, $R^{21}$ is halogen or —$C_1$-$C_6$alkyl. In some embodiments, $R^{21}$ is —$CH_3$, —$CH_2CH_3$, or —$CH(CH_3)_2$. In some embodiments, $R^{21}$ is —$CH_3$. In some embodiments, $R^{21}$ is —Cl, —Br, —I, or —F. In some embodiments, $R^{21}$ is H.

In some embodiments of Formula (V), or a pharmaceutically acceptable salt or solvate thereof, $R^{25}$ is H or $C_1$-$C_6$alkyl. In some embodiments, $R^{25}$ is $C_1$-$C_6$alkyl. In some embodiments, $R^{25}$ is —$CH_3$ or —$CH_2CH_3$. In some embodiments, $R^{25}$ is H.

In some embodiments of Formula (V), or a pharmaceutically acceptable salt or solvate thereof, $R^{21}$ is H; and $R^{25}$ is H.

In some embodiments of Formula (V), or a pharmaceutically acceptable salt or solvate thereof, $L^5$ is an optionally substituted $C_1$-$C_3$ alkylene, optionally substituted with one, two, or three $R^{26}$, wherein each $R^{26}$ is independently halogen or $C_1$-$C_6$alkyl. In some embodiments, $L^5$ is unsubstituted $C_1$-$C_3$ alkylene. In some embodiments, $L^5$ is —$CH_2$—, —$CH_2CH_2$—, or —$CH_2CH_2CH_2$—. In some embodiments, $L^5$ is —$CH_2$—.

In some embodiments, the compound of Formula (V) has the structure of Formula (VI), or a pharmaceutically acceptable salt or solvate thereof:

Formula (VI)

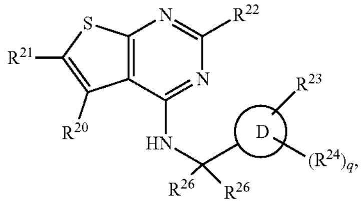

wherein, each $R^{26}$ is independently H, halogen, or $C_1$-$C_4$ alkyl.

In some embodiments of Formula (VI), or a pharmaceutically acceptable salt or solvate thereof, each $R^{26}$ is independently halogen or $C_1$-$C_4$ alkyl. In some embodiments, each $R^{26}$ is independently H or $C_1$-$C_4$ alkyl. In some embodiments, each $R^{26}$ is independently H, —$CH_3$, —$CH_2CH_3$, or —$CH(CH_3)_2$. In some embodiments, each $R^{26}$ is independently H or —$CH_3$. In some embodiments, each $R^{26}$ is H.

In some embodiments of Formula (V) or (VI), or a pharmaceutically acceptable salt or solvate thereof, $R^{20}$ is halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^{27}$. In some embodiments, $R^{20}$ is phenyl or a monocyclic heteroaryl optionally substituted with one, two or three $R^{27}$, wherein $R^{27}$ is halogen or $C_1$-$C_4$ alkyl. In some embodiments, the monocyclic heteroaryl is 2-pyridyl, 3-pyridyl, or 4-pyridyl. In some embodiments, $R^2$ is phenyl, 2-pyridyl, 3-pyridyl, or 4-pyridyl, optionally substituted with one, two, or three —Cl, —Br, or —F. In some embodiments, $R^2$ is phenyl. In some embodiments, $R^{20}$ is 2-pyridyl. In some embodiments, $R^{2'}$ is halogen or —$C_1$-$C_6$alkyl. In some embodiments, $R^{20}$ is —$CH_3$, —$CH_2CH_3$, or —$CH(CH_3)_2$. In some embodiments, $R^{20}$ is —$CH_3$. In some embodiments, $R^{20}$ is —Cl, —Br, —I, or —F. In some embodiments, $R^{21}$ is H.

In some embodiments of Formula (V) or (VI), or a pharmaceutically acceptable salt or solvate thereof, $R^{20}$ is an unsubstituted phenyl.

In some embodiments of Formula (V) or (VI), or a pharmaceutically acceptable salt or solvate thereof, ring D is phenyl. In some embodiments, ring D is a 6-membered heteroaryl. In some embodiments, ring D is pyridinyl, pyrimidinyl, pyrazinyl, or pyridazinyl. In some embodiments, ring D is pyridinyl.

In some embodiments of Formula (V) or (VI), or a pharmaceutically acceptable salt or solvate thereof,

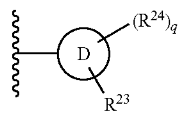

is

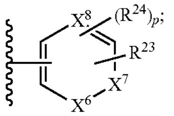

wherein: $X^6$, $X^7$ and $X^8$ are each independently CH or N.

In some embodiments of Formula (V) or (VI), or a pharmaceutically acceptable salt thereof, $X^6$ is N; and $X^7$ and $X^8$ are each independently CH. In some embodiments, $X^6$ and $X^7$ are independently N; and $X^8$ is CH. In some embodiments, $X^6$ is CH; and $X^7$ and $X^8$ are each independently N.

In some embodiments of Formula (V) or (VI), or a pharmaceutically acceptable salt or solvate thereof,

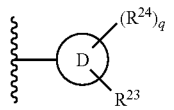
is
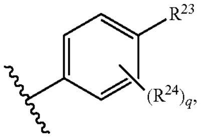
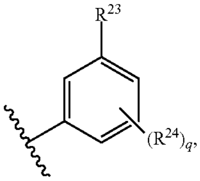
or
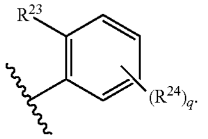

In some embodiments of Formula (V) or (VI), or a pharmaceutically acceptable salt or solvate thereof,

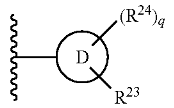
is
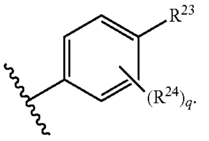

In some embodiments, the compound of Formula (V) has the structure of Formula (VII), or a pharmaceutically acceptable salt or solvate thereof:

Formula (VII)

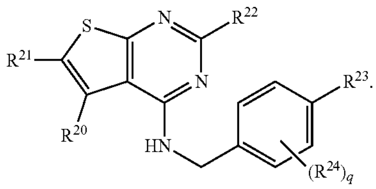

In some embodiments of Formula (V), (VI), or (VII), or a pharmaceutically acceptable salt or solvate thereof, $R^{23}$ is halogen, —CN, —OH, —$OR^{1B}$, —SH, —$SR^{1B}$, —S(═O)$R^{1B}$, —$NO_2$, —$N(R^{1A})_2$, —$S(═O)_2R^{1B}$, —$S(═)_2N(R^{1A})_2$, —C(═O)$R^{1B}$, —$C_1$-$C_6$ alkyl, or $C_1$-$C_6$ haloalkyl. In some embodiments, $R^{23}$ is halogen, $C_1$-$C_6$ alkyl, or $C_1$-$C_6$ haloalkyl. In some embodiments, $R^{23}$ is —Cl, —F, —Br, —CN, —$CH_3$, —$CF_3$, —SH, —$NH_2$, or —$OCH_3$. In some embodiments, $R^{23}$ is —F. In some embodiments, $R^{23}$ is —Cl. In some embodiments, $R^{23}$ is —Br. In some embodiments, $R^{23}$ is —$CF_3$. In some embodiments, $R^{23}$ is —$CH_3$. In some embodiments, $R^{23}$ is —$OCH_3$.

In some embodiments of Formula (V), (VI), or (VII), or a pharmaceutically acceptable salt or solvate thereof, $R^{23}$ is —$S(═O)_2N(R^{1A})_2$, wherein each $R^{1A}$ is independently H or —$C_1$-$C_3$ alkyl. In some embodiments, $R^{23}$ is —$S(═O)_2NH_2$.

In some embodiments of Formula (V), (VI), or (VII), or a pharmaceutically acceptable salt or solvate thereof, $R^{24}$ is halogen, —CN, —OH, —$OR^{1B}$, —$NO_2$, —$N(R^{1A})_2$, $C_1$-$C_6$ alkyl, $C_1$-$C_6$ haloalkyl, or $C_1$-$C_6$ hydroxyalkyl. In some embodiments, $R^{23}$ is —Br, —Cl, —F, —CN, —$CF_3$, —$CH_3$, or —$OCH_3$. In some embodiments, $R^{23}$ is —Br, —Cl, or —F. In some embodiments, $R^{23}$ is —$CH_3$, or —$OCH_3$.

In some embodiments of Formula (V), (VI), or (VII), or a pharmaceutically acceptable salt or solvate thereof, each $R^{24}$ is independently halogen, —CN, —OH, —$OR^{1B}$, —SH, —$SR^{1B}$, —S(═O)$R^{1B}$, —$NO_2$, —$N(R^{1A})_2$, —$S(═O)_2R^{1B}$, —$S(═)_2N(R^{1A})_2$, —C(═O)$R^{1B}$, —$C_1$-$C_6$ alkyl, or $C_1$-$C_6$ haloalkyl. In some embodiments, each $R^{24}$ is independently halogen, $C_1$-$C_6$ alkyl, or $C_1$-$C_6$ haloalkyl. In some embodiments, each $R^{24}$ is independently —Cl, —F, —Br, —CN, —$CH_3$, —$CF_3$, —SH, —$NH_2$, or —$OCH_3$. In some embodiments, each $R^{24}$ is —F. In some embodiments, each $R^{24}$ is —Cl. In some embodiments, each $R^{24}$ is —Br. In some embodiments, each $R^{24}$ is —$CF_3$. In some embodiments, each $R^{24}$ is —$CH_3$. In some embodiments, each $R^{24}$ is —$OCH_3$.

In some embodiments of Formula (V), (VI), or (VII), or a pharmaceutically acceptable salt or solvate thereof, q is 1 and $R^{24}$ is —$S(═O)_2N(R^{1A})_2$, wherein each $R^{1A}$ is independently H or —$C_1$-$C_3$ alkyl. In some embodiments, q is 1 and $R^{24}$ is —$S(═O)_2NH_2$.

In some embodiments of Formula (V), (VI), or (VII), or a pharmaceutically acceptable salt or solvate thereof, each $R^{24}$ is independently halogen, —CN, —OH, —$NO_2$, —$N(R^{1A})_2$, $C_1$-$C_6$ alkyl, $C_1$-$C_6$ haloalkyl, or $C_1$-$C_6$ hydroxyalkyl. In some embodiments, each $R^{24}$ is independently —Br, —Cl, —F, —CN, —$CF_3$, —$CH_3$, or —$OCH_3$. In some embodiments, each $R^{24}$ is independently —Br, —Cl, or —F. In some embodiments, each $R^{24}$ is independently —$CH_3$, or —$OCH_3$.

In some embodiments of Formula (V), (VI), or (VII), or a pharmaceutically acceptable salt or solvate thereof, q is 1 or 2. In some embodiments, q is 1. In some embodiments, q is 0.

In some embodiments of Formula (V), (VI), or (VII), or a pharmaceutically acceptable salt or solvate thereof,

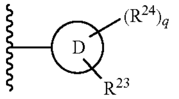
is
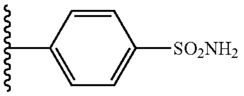
,
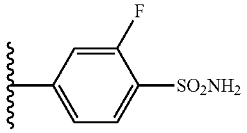
,
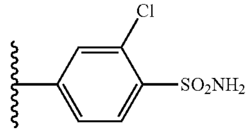
,
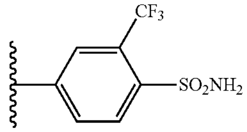
,
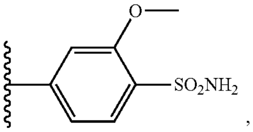
,
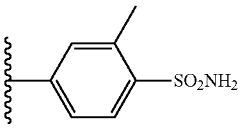
,
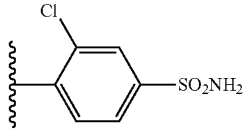
,
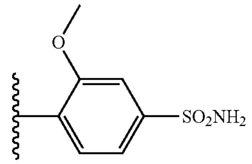
,
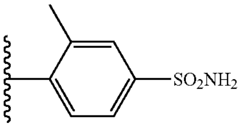
,
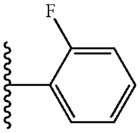
,
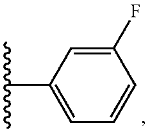
,
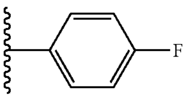
, -continued

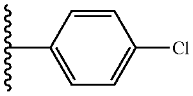, 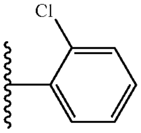, 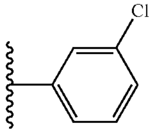,

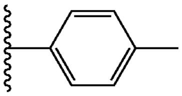, 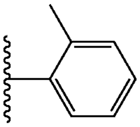, 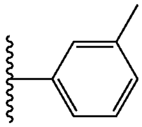,

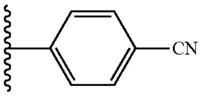, 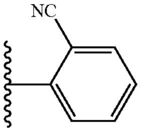, 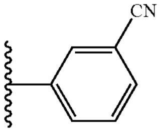,

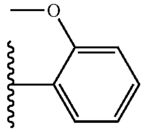, 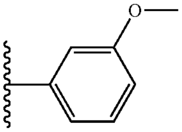, or

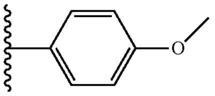.

In some embodiments of Formula (V), (VI), or (VII), or a pharmaceutically acceptable salt or solvate thereof

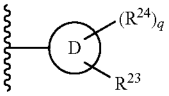 is 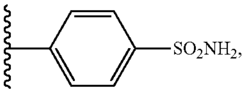

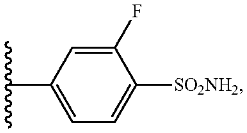 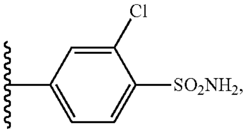

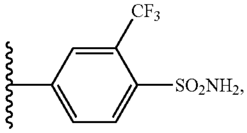 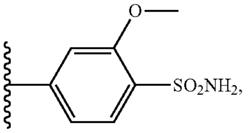

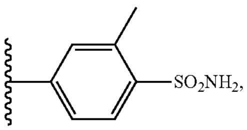 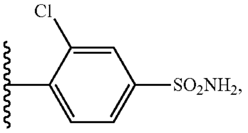

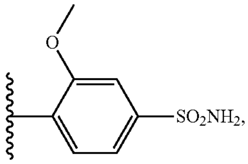 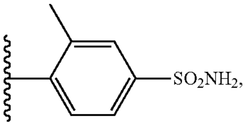

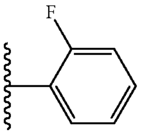 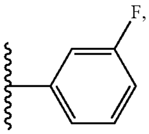 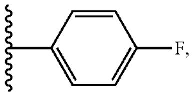

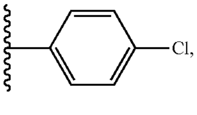 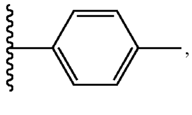

-continued

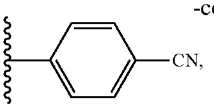 or 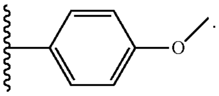

In some embodiments of Formula (V), (VI), or (VII), or a pharmaceutically acceptable salt or solvate thereof,

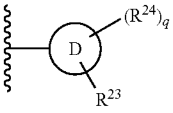 is 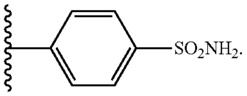

In some embodiments of Formula (V), (VI), or (VII), or a pharmaceutically acceptable salt or solvate thereof, ring D is a 5-membered heteroaryl. In some embodiments, ring D is oxazole, thiazole, pyrrole, furan, or thiophene. In some embodiments, ring D is furan or thiophene. In some embodiments, ring D is furan. In some embodiments, ring D is thiophene.

In some embodiments of Formula (V), or (VI), or a pharmaceutically acceptable salt or solvate thereof,

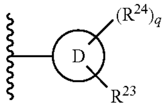 is 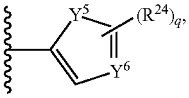

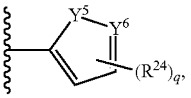 or 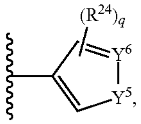

wherein $Y^5$ is O, S, or $NR^{1C}$; $Y^6$ is O, S, N, or CH; and $R^{1C}$ is H or $C_1$-$C_6$ alkyl.

In some embodiments of Formula (V), or (VI), or a pharmaceutically acceptable salt or solvate thereof,

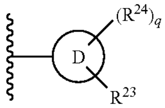 is 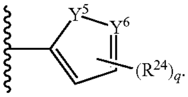

In some embodiments, $Y^5$ is O; and $Y^6$ is CH. In some embodiments, $Y^5$ is S; and $Y^6$ is CH. In some embodiments, $Y^5$ is $NR^{1C}$; $Y^6$ is CH; and $R^{1C}$ is H or —$CH_3$. In some embodiments, $Y^5$ is $NR^{1C}$; $Y^6$ is N; and $R^{1C}$ is H or —$CH_3$. In some embodiments, $Y^5$ is $NR^{1C}$; $Y^6$ is O; and $R^{1C}$ is H or —$CH_3$. In some embodiments, $Y^5$ is $NR^{1C}$; $Y^6$ is S; and $R^{1C}$ is H or —$CH_3$.

In some embodiments of Formula (V), or (VI), or a pharmaceutically acceptable salt or solvate thereof,

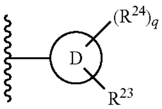 is 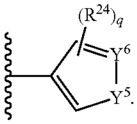

In some embodiments, $Y^5$ is O; and $Y^6$ is CH. In some embodiments, $Y^5$ is S; and $Y^6$ is CH. In some embodiments, $Y^5$ is $NR^{1C}$; $Y^6$ is CH; and $R^{1C}$ is H or —$CH_3$. In some embodiments, $Y^5$ is $NR^{1C}$; $Y^6$ is N; and $R^{1C}$ is H or —$CH_3$. In some embodiments, $Y^5$ is $NR^{1C}$; $Y^6$ is O; and $R^{1C}$ is H or —$CH_3$. In some embodiments, $Y^5$ is $NR^{1C}$; $Y^6$ is S; and $R^{1C}$ is H or —$CH_3$.

In some embodiments, the compound of Formula (V) has the structure of Formula (VIII), or a pharmaceutically acceptable salt or solvate thereof:

Formula (VIII)

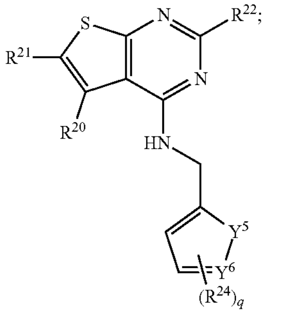

wherein:

$Y^5$ is O or S; and $Y^6$ is CH.

In some embodiments of Formula (VIII), or a pharmaceutically acceptable salt or solvate thereof, $Y^5$ is S. In some embodiments, $Y^5$ is O.

In some embodiments of Formula (VIII), or a pharmaceutically acceptable salt or solvate thereof, each $R^{24}$ is independently halogen, —CN, —$OR^{1B}$, —$S(=O)_2N(R^{1A})_2$, —$C_1$-$C_6$ alkyl, or $C_1$-$C_6$ haloalkyl. In some embodiments, each $R^{24}$ is independently —Cl, —F, —Br, —CN, —$CH_3$, —$CF_3$, or —$OCH_3$.

In some embodiments of Formula (VIII), or a pharmaceutically acceptable salt or solvate thereof, each $R^{24}$ is independently —$S(=O)_2N(R^{1A})_2$, wherein $R^{1A}$ is H or —$C_1$-$C_3$ alkyl. In some embodiments, each $R^{24}$ is independently —$S(=O)_2NH_2$.

In some embodiments of Formula (VIII), or a pharmaceutically acceptable salt or solvate thereof, q is 1. In some embodiments, q is 0.

In some embodiments of Formula (V), (VI), (VII), or (VIII), or a pharmaceutically acceptable salt or solvate thereof, $R^{22}$ is halogen, —CN, —OH, —$OR^{1B}$, —$SR^{1B}$, —$N(R^{1A})_2$, —$NR^{1A}S(=O)_2(C_1$-$C_4$alkyl), —$S(=O)_2N(R^{1A})_2$, —$OC(=O)(C_1$-$C_4$alkyl), —$CO_2H$, —$CO_2(C_1$-$C_4$alkyl), —$C(=O)N(R^{1A})_2$, —$NR^{1A}C(=O)(C_1$-$C_4$alkyl), —$NR^{1A}C(=O)O(C_1$-$C_4$alkyl), —$OC(=O)N(R^{1A})_2$, —$NR^{1A}C(=O)N(R^{1A})_2$, —$S(C_1$-$C_4$alkyl), —$S(=O)(C_1$-$C_4$alkyl), —$S(=O)_2(C_1$-$C_4$alkyl), $C_1$-$C_6$alkyl, $C_2$-$C_4$alkenyl, $C_2$-$C_4$alkynyl, $C_1$-$C_4$fluoroalkyl, $C_1$-$C_4$fluoroalkoxy, —$C_1$-$C_6$alkyl-OH, —$C_1$-$C_6$heteroalkyl-OH, monocyclic $C_2$-$C_6$heterocycloalkyl, phenyl, or monocyclic 5-6 membered heteroaryl; wherein alkyl, alkenyl, alkynyl, aryl, and heteroaryl are each optionally substituted with one, two, or three $R^{29}$, wherein each $R^{29}$ is independently halogen, —CN, —OH, —$OR^{1B}$, —SH, —$SR^{1B}$, $N(R^{1A})_2$, $C_1$-$C_4$alkyl, or $C_1$-$C_4$fluoroalkyl.

In some embodiments of Formula (V), (VI), (VII), or (VIII), or a pharmaceutically acceptable salt or solvate thereof, $R^{22}$ is halogen, —CN, —OH, —$OR^{1B}$, —$SR^{1B}$, —$N(R^{1A})_2$, —$C_1$-$C_6$alkyl, $C_1$-$C_4$fluoroalkyl, —$C_{1-6}$alkyl-OH, or —$C_{1-6}$heteroalkyl-OH. In some embodiments, $R^{22}$ is —Br, —Cl, —F, —CN, —$NH_2$, —$NHCH_3$, —$NHCH_2CH_3$, —$N(CH_3)_2$, —$OCH_3$, —$CF_3$, —$CH_3$, —$CH_2CH_3$, or —$NH(CH_2)_2OH$. In some embodiments, $R^{22}$ is —Br, —Cl, —F, or —CN. In some embodiments, $R^{22}$ is —$NH_2$, —$NHCH_3$, —$NHCH_2CH_3$, —$N(CH_3)_2$, —$NH(CH_2)_2CH_3$, —$NH(CH_2)_3CH_3$, —$NH(CH_2)_4CH_3$, —$NH(CH_2)_3CH(CH_3)_2$, or —$NH(CH_2)_2OH$. In some embodiments, $R^{22}$ is —$NH(CH_2)_2OH$. In some embodiments, $R^{22}$ is —$NH(C_3$-$C_6$cycloalkyl). In some embodiments, $R^{22}$ is —NH-cyclopropyl, —NH-cyclobutyl, or —NH-cyclohexyl. In some embodiments, $R^{22}$ is —NH-benzyl. In some embodiments, $R^{22}$ is —$SH_2$, —$SCH_3$, or —$SCH_2CH_3$. In some embodiments, $R^{22}$ is —OH, —$OCH_3$, or —$OCH_2CH_3$, —$OCH_2CH_2CH_3$, —$OCH_2CH_2CH(CH_3)_2$. In some embodiments, $R^{22}$ is —$OCH_3$, —$CF_3$, —$CH_3$, or —$CH_2CH_3$.

In some embodiments of Formula (V), (VI), (VII), or (VIII), or a pharmaceutically acceptable salt or solvate thereof, $R^{22}$ is halogen, —CN, —OH, —$OR^{1B}$, —$N(R^{1A})_2$, —$C_1$-$C_6$alkyl, $C_1$-$C_4$fluoroalkyl, —$C_1$-$C_6$alkyl-OH, or —$C_1$-$C_6$heteroalkyl-OH. In some embodiments, $R^{32}$ is —$OR^{1B}$, —$N(R^{1A})_2$, —$C_1$-$C_6$alkyl, or —$C_1$-$C_6$alkyl-OH. In some embodiments, $R^{22}$ is —$NH_2$, —$NHCH_3$, —$NHCH_2CH_3$, —$N(CH_3)_2$, —$OCH_3$, —$CH_3$, —$CH_2CH_3$, or —$NH(CH_2)_2OH$. In some embodiments, $R^{22}$ is —$NH(CH_2)_2OH$. In some embodiments, $R^{22}$ is H. In some embodiments, $R^{22}$ is —Br or —Cl.

In some embodiments of Formula (V), (VI), (VII), or (VIII), or a pharmaceutically acceptable salt or solvate thereof, $R^{22}$ is $C_2$-$C_6$heterocycloalkyl, optionally substituted with one, two, or three $R^{29}$. In some embodiments, $R^{22}$ is piperazine, piperidine, or morpholino. In some embodiments, $R^{22}$ is piperazine. In some embodiments, $R^{22}$ is piperidine. In some embodiments, $R^{22}$ is morpholine.

In some embodiments of Formula (V), (VI), (VII), or (VIII), or a pharmaceutically acceptable salt or solvate thereof, $R^{22}$ is benzyl, phenyl, or a 6-membered heteroaryl, each of which is optionally substituted with one, two, or three $R^{29}$, wherein each $R^{29}$ is independently halogen, —CN, —OH, —$OR^{1B}$, —SH, —$SR^{1B}$, $N(R^{1A})_2$, $C_1$-$C_4$alkyl, or $C_1$-$C_4$fluoroalkyl. In some embodiments, $R^{22}$ is phenyl. In some embodiments, $R^{22}$ is a 6-membered heteroaryl. In some embodiments, the 6-membered heteroaryl is 2-pyridyl, 3-pyridyl, or 4-pyridyl. In some embodiments, $R^{22}$ is heteroaryl is 2-pyridyl. In some embodiments, $R^{22}$ is heteroaryl is 3-pyridyl. In some embodiments, $R^{22}$ is heteroaryl is 4-pyridyl.

In another aspect, provided herein is a compound having the structure of Formula (IX), or a pharmaceutically acceptable salt or solvate, thereof:

Formula (IX)

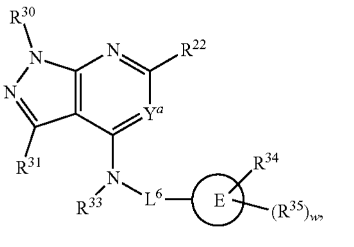

wherein:

$Y^a$ is CH or N;

ring E is phenyl or a 5 or 6-membered heteroaryl;

w is 0, 1, 2, or 3;

$L^6$ is an optionally substituted $C_1$-$C_3$ alkylene, optionally substituted with one, two, or three $R^{36}$;

$R^{30}$ is —$C_1$-$C_6$alkyl, —$C_3$-$C_6$ cycloalkyl, —$C_3$-$C_6$ heterocycloalkyl, phenyl, or monocyclic heteroaryl, wherein alkyl, alkenyl, alkynyl, aryl, and heteroaryl are each optionally substituted with one, two, or three $R^{37}$;

$R^{31}$ is H, halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^{38}$;

$R^{32}$ is H, halogen, —CN, —OH, —$OR^{1B}$, —$SR^{1B}$, —$N(R^{1A})_2$, —$NR^{1A}S(=O)_2(C_1$-$C_4$alkyl), —$S(=O)_2N(R^{1A})_2$, —OC(=O)($C_1$-$C_4$alkyl), —$CO_2H$, —$CO_2(C_1$-$C_4$alkyl), —$C(=O)N(R^{1A})_2$, —$NR^{1A}C(=O)(C_1$-$C_4$alkyl), —$NR^{1A}C(=O)O(C_1$-$C_4$alkyl), —$OC(=O)N(R^{1A})_2$, —$NR^{1A}C(=O)N(R^{1A})_2$, —S($C_1$-$C_4$alkyl), —S(=O)($C_1$-$C_4$alkyl), —$S(=O)_2(C_1$-$C_4$alkyl), $C_1$-$C_6$alkyl, $C_2$-$C_4$alkenyl, $C_2$-$C_4$alkynyl, $C_1$-$C_4$fluoroalkyl, $C_1$-$C_4$fluoroalkoxy, —$C_{1-6}$alkyl-OH, —$C_{1-6}$heteroalkyl-OH, $C_{1-6}$alkyl-C(=O)OH, —$C_{1-6}$heteroalkyl-C(=O)OH, monocyclic $C_2$-$C_6$heterocycloalkyl, phenyl, or monocyclic 5-6 membered heteroaryl; wherein alkyl, alkenyl, alkynyl, aryl, and heteroaryl are each optionally substituted with one, two, or three $R^{39}$;

$R^{33}$ is H, $C_1$-$C_6$alkyl, or $C_1$-$C_6$ cycloalkyl;

$R^{34}$ is H, halogen, —CN, —OH, —$OR^{1B}$, —SH, —$SR^{1B}$, —$S(=O)R^{1B}$, —$NO_2$, —$N(R^{1A})_2$, —$S(=O)_2R^{1B}$, —$NHS(=O)_2R^{1B}$, —$S(=O)_2N(R^{1A})_2$, —$C(=O)R^{1B}$, —$OC(=O)R^{1B}$, —$C(=O)OR^{1A}$, —$OC(=O)OR^{1A}$, —$C(=O)N(R^{1A})_2$, —$OC(=O)N(R^{1A})_2$, —$NR^{1A}C(=O)N(R^{1A})_2$, —$NR^{1A}C(=O)R^{1B}$, —$NR^{1A}C(=O)OR^{1A}$, $C_1$-$C_6$ alkyl, $C_2$-$C_4$alkynyl, $C_1$-$C_6$ haloalkyl, $C_1$-$C_6$ hydroxyalkyl, $C_1$-$C_6$ heteroalkyl, or cycloalkyl;

each $R^{36}$ is independently H, halogen or $C_1$-$C_6$ alkyl;

each $R^{35}$ is independently halogen, —CN, —OH, —$OR^{1B}$, —SH, —$SR^{1B}$, —$S(=O)R^{1B}$, —$NO_2$, —$N(R^{1A})_2$, —$S(=O)_2R^{1B}$, —$NHS(=O)_2R^{1B}$, —$S(=O)_2N(R^{1A})_2$, —$C(=O)R^{1B}$, —$OC(=O)R^{1B}$, —$C(=O)OR^{1A}$, —$OC(=O)OR^{1A}$, —$C(=O)N(R^{1A})_2$, —$OC(=O)N(R^{1A})_2$, —$NR^{1A}C(=O)N(R^{1A})_2$, —$NR^{1A}C(=O)R^{1B}$, —$NR^{1A}C(=O)OR^{1A}$, $C_1$-$C_6$alkyl, $C_2$-$C_4$alkynyl, $C_1$-$C_6$ haloalkyl, $C_1$-$C_6$ hydroxyalkyl, $C_1$-$C_6$ heteroalkyl, or cycloalkyl;

each $R^{37}$, $R^{38}$ and $R^{39}$ is independently halogen, —CN, —OH, —$OR^{1B}$, —SH, —$SR^{1B}$, —$N(R^{1A})_2$, —$C(=O)OR^{1A}$, oxo (=O), $C_1$-$C_4$alkyl, or $C_1$-$C_4$fluoroalkyl;

each $R^{1A}$ is independently hydrogen, $C_1$-$C_6$ alkyl, cycloalkyl, heterocycloalkyl, aryl, benzyl, or heteroaryl; and each $R^{1B}$ is independently H, $C_1$-$C_6$ alkyl, $C_2$-$C_6$ alkenyl, $C_2$-$C_6$ alkynyl, $C_1$-$C_6$heteroalkyl, cycloalkyl, heterocycloalkyl, aryl, or heteroaryl.

In some embodiments of Formula (IX), or a pharmaceutically acceptable salt or solvate thereof, $R^{30}$ is —$C_1$-$C_6$alkyl, —$C_3$-$C_6$ cycloalkyl, or —$C_3$-$C_6$ heterocycloalkyl, each optionally substituted with one, two, or three $R^{37}$. In some embodiments, $R^{30}$ is phenyl, or monocyclic heteroaryl, optionally substituted with one, two, or three $R^{37}$. In some embodiments, $R^{30}$ is $C_3$-$C_6$ cycloalkyl or —$C_3$-$C_6$ heterocycloalkyl. In some embodiments, $R^{30}$ is cyclopropyl, cyclopentyl, cyclohexyl, or piperidyl. In some embodiments, $R^{30}$ is phenyl. In some embodiments, $R^{30}$ is $C_1$-$C_6$ alkyl. In some embodiments, $R^{30}$ is —$CH_3$, —$CH_2CH_3$, or —$CH(CH_3)_2$. In some embodiments, $R^{30}$ is —$CH_3$.

In some embodiments of Formula (IX), or a pharmaceutically acceptable salt or solvate thereof, $R^{31}$ is halogen, —CN, —OH, —$OR^{1B}$, —$SR^{1B}$, —$N(R^{1A})_2$, —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, wherein alkyl, alkenyl, alkynyl, aryl, and heteroaryl are each optionally substituted with one, two, or three $R^{38}$. In some embodiments, $R^{31}$ is —$C_1$-$C_6$alkyl, $C_2$-$C_6$alkenyl, $C_2$-$C_6$alkynyl, $C_1$-$C_4$fluoroalkyl, $C_1$-$C_4$fluoroalkoxy, $C_1$-$C_6$heteroalkyl, phenyl, or monocyclic heteroaryl, each of which is optionally substituted with one, two or three halogen or $C_1$-$C_6$alkyl. In some embodiments, $R^{31}$ is phenyl, or monocyclic heteroaryl, optionally substituted with one, two, or three $R^{38}$. In some embodiments, $R^{31}$ is $C_3$-$C_6$ cycloalkyl or —$C_3$-$C_6$ heterocycloalkyl. In some embodiments, $R^{31}$ is cyclopropyl, cyclopentyl, cyclohexyl, or piperidyl. In some embodiments, $R^{31}$ is phenyl. In some embodiments, $R^{31}$ is halogen or $C_1$-$C_6$ alkyl. In some embodiments, $R^{31}$ is —Br, —Cl, —I, or —F. In some embodiments, $R^{31}$ is —Br or —Cl. In some embodiments, $R^{31}$ is —$CH_3$, —$CH_2CH_3$, or —$CH(CH_3)_2$. In some embodiments, $R^{31}$ is —$CH_3$. In some embodiments, $R^{31}$ is H.

In some embodiments of Formula (IX), or a pharmaceutically acceptable salt or solvate thereof, $R^{33}$ is H or $C_1$-$C_6$alkyl. In some embodiments, $R^{33}$ is —$CH_3$. In some embodiments, $R^{33}$ is H.

In some embodiments of Formula (IX), or a pharmaceutically acceptable salt or solvate thereof, $R^{31}$ is H; and $R^{33}$ is H.

In some embodiments of Formula (IX), or a pharmaceutically acceptable salt or solvate thereof, $R^{30}$ is —$C_1$-$C_6$alkyl; and $R^{31}$ and $R^{33}$ are H. In some embodiments, $R^{30}$ is —$CH_3$; and $R^{31}$ and $R^{33}$ are H.

In some embodiments of Formula (IX), or a pharmaceutically acceptable salt or solvate thereof, $L^6$ is an optionally substituted $C_1$-$C_3$ alkylene, optionally substituted with one, two, or three $R^{36}$, wherein each $R^{36}$ is independently halogen or $C_{1-6}$alkyl. In some embodiments, $L^6$ is unsubstituted $C_1$-$C_3$ alkylene. In some embodiments, $L^6$ is —$CH_2$—, —$CH_2CH_2$—, or —$CH_2CH_2CH_2$—. In some embodiments, $L^6$ is —$CH_2$—.

In some embodiments, the compound of Formula (IX) has the structure of Formula (X), or a pharmaceutically acceptable salt or solvate thereof:

Formula (X)

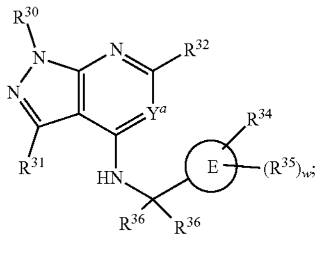

wherein:

each $R^{36}$ is independently H, halogen, or $C_1$-$C_4$ alkyl.

In some embodiments of Formula (X), or a pharmaceutically acceptable salt or solvate thereof, each $R^{36}$ is independently halogen or $C_1$-$C_4$ alkyl. In some embodiments, each $R^{36}$ is independently H or $C_1$-$C_4$ alkyl. In some embodiments, each $R^{36}$ is independently H, —$CH_3$, —$CH_2CH_3$, or —$CH(CH_3)_2$. In some embodiments, each $R^{36}$ is independently H or —$CH_3$. In some embodiments, each $R^{36}$ is H.

In some embodiments of Formula (IX) or (X), or a pharmaceutically acceptable salt or solvate thereof, ring E is phenyl. In some embodiments, ring E is a 6-membered heteroaryl. In some embodiments, the 6-membered heteroaryl is pyridinyl, pyrimidinyl, pyrazinyl, or pyridazinyl. In some embodiments, the 6-membered heteroaryl is pyridinyl.

In some embodiments of Formula (IX) or (X), or a pharmaceutically acceptable salt or solvate thereof,

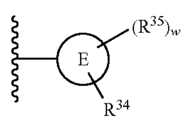
is
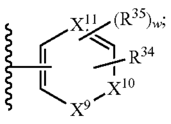

wherein $X^9$, $X^{10}$ and $X^{11}$ are each independently CH or N.

In some embodiments of Formula (IX) or (X), or a pharmaceutically acceptable salt or solvate thereof, $X^{11}$ is N; and $X^9$ and $X^{10}$ are each independently CH. In some embodiments, $X^{11}$ and $X^9$ are each independently N; and $X^{10}$ is CH. In some embodiments, $X^{11}$ is CH; and $X^9$ and $X^{10}$ are each independently N.

In some embodiments of Formula (IX) or (X), or a pharmaceutically acceptable salt or solvate thereof,

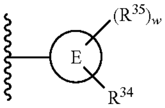
is
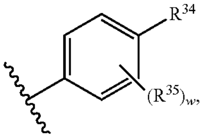
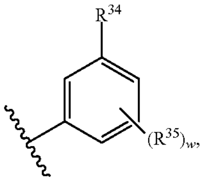
or
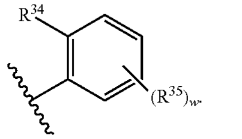

In some embodiments of Formula (IX) or (X), or a pharmaceutically acceptable salt or solvate thereof,

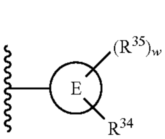
is
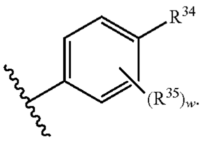

In some embodiments, the compound of Formula (IX) has the structure of Formula (XI), or a pharmaceutically acceptable salt or solvate thereof:

Formula (XI)

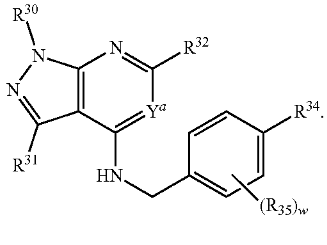

In some embodiments of Formula (XI), or a pharmaceutically acceptable salt or solvate thereof, $R^{34}$ is halogen, —CN, —OH, —$OR^{1B}$, —SH, —$SR^{1B}$, —S(=O)$R^{1B}$, —$NO_2$, —$N(R^{1A})_2$, —$S(=O)_2R^{1B}$, —$S(=O)_2N(R^{1A})_2$, —C(=O)$R^{1B}$, —$C_1$-$C_6$ alkyl, or $C_1$-$C_6$ haloalkyl. In some embodiments, $R^{34}$ is —CN, —$OR^{1B}$, halogen, $C_1$-$C_6$ alkyl, or $C_1$-$C_6$ haloalkyl. In some embodiments, $R^{34}$ is —Cl, —F, —Br, —CN, —$CH_3$, —$CF_3$, —SH, —$NH_2$, or —$OCH_3$. In some embodiments, $R^{34}$ is —F. In some embodiments, $R^{34}$ is —Cl. In some embodiments, $R^{34}$ is —Br. In some embodiments, $R^{34}$ is —$CF_3$. In some embodiments, $R^{34}$ is —$CH_3$. In some embodiments, $R^{34}$ is —$OCH_3$.

In some embodiments of Formula (XI), or a pharmaceutically acceptable salt or solvate thereof, $R^{34}$ is —$S(=O)_2N(R^{1A})_2$, wherein each $R^{1A}$ is independently H or —$C_1$-$C_3$ alkyl. In some embodiments, $R^{34}$ is —$S(=O)_2NH_2$.

In some embodiments of Formula (XI), or a pharmaceutically acceptable salt or solvate thereof, each $R^{34}$ is independently halogen, —CN, —OH, —$OR^{1B}$, —$NO_2$, —$N(R^{1A})_2$, $C_1$-$C_6$ alkyl, $C_1$-$C_6$ haloalkyl, or $C_1$-$C_6$ hydroxyalkyl. In some embodiments, each $R^{35}$ is independently —Br, —Cl, —F, —CN, —$CF_3$, —$CH_3$, or —$OCH_3$. In some embodiments, each $R^{35}$ is independently —Br, —Cl, or —F. In some embodiments, each $R^{35}$ is independently —$CH_3$, or —$OCH_3$.

In some embodiments of Formula (XI), or a pharmaceutically acceptable salt or solvate thereof, w is 1 or 2. In some embodiments, w is 1. In some embodiments, w is 0.

In some embodiments of Formula (XI), or a pharmaceutically acceptable salt or solvate thereof,

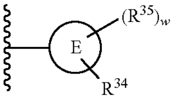
is
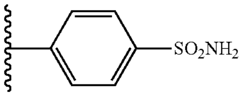
,
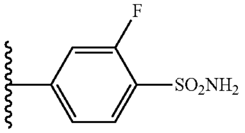
,
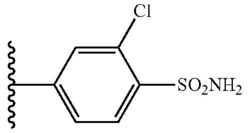
,
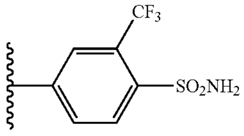
,
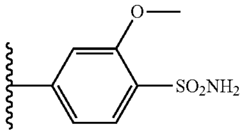
,
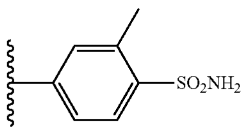
,
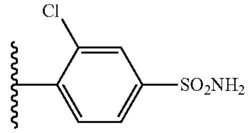
,
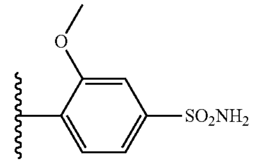
,
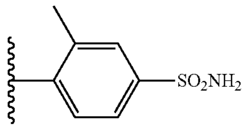
,
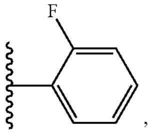
,
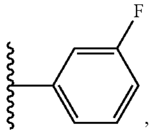
,
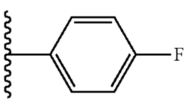
,
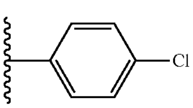
,
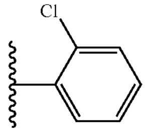
,
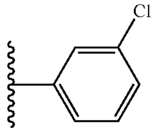
, -continued

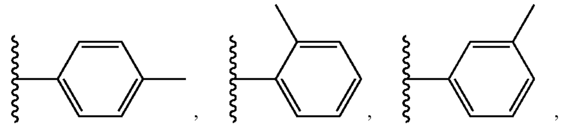

, , ,

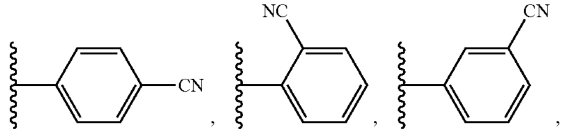

, , ,

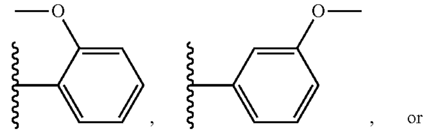

, , or

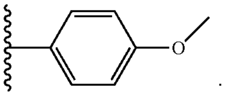

.

In some embodiments of Formula (XI), or a pharmaceutically acceptable salt or solvate thereof

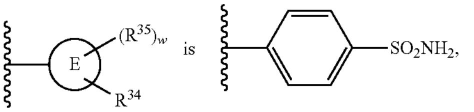

is ,

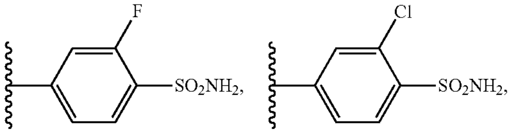

, ,

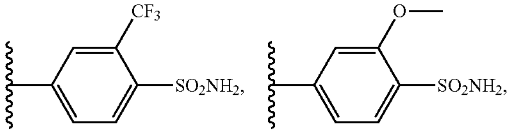

, ,

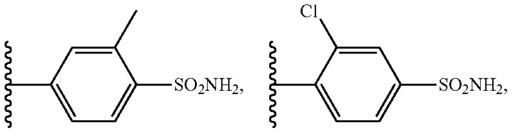

, ,

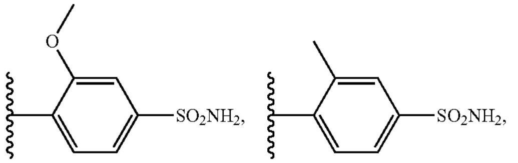

, ,

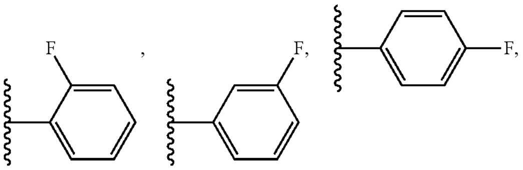

, , ,

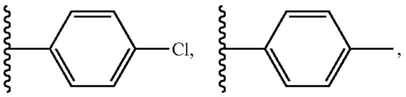

, ,

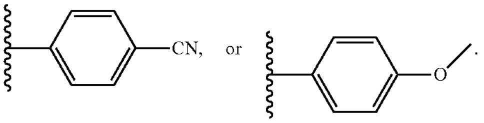

, or .

In some embodiments of Formula (XI), or a pharmaceutically acceptable salt or solvate thereof,

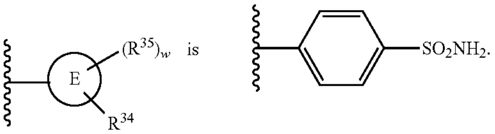

is .

In some embodiments of Formula (IX) or (X), or a pharmaceutically acceptable salt or solvate thereof, ring E is a 5-membered heteroaryl. In some embodiments, the 5-membered heteroaryl is oxazole, thiazole, pyrrole, furan, or thiophene. In some embodiments, the 5-membered heteroaryl is furan or thiophene. In some embodiments, the 5-membered heteroaryl is furan. In some embodiments, the 5-membered heteroaryl is thiophene.

In some embodiments of Formula (IX) or (X), or a pharmaceutically acceptable salt or solvate thereof,

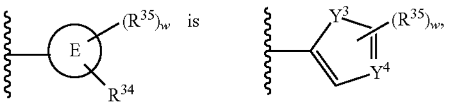

is ,

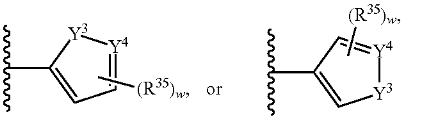

, or wherein $Y^3$ is O, S, or $NR^{1C}$; $Y^4$ is O, S, N, or CH; and $R^{1C}$ is hydrogen or $C_1$-$C_6$ alkyl.

In some embodiments of Formula (IX) or (X), or a pharmaceutically acceptable salt or solvate thereof,

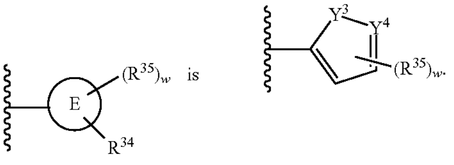

is .

In some embodiments, $Y^3$ is O; and $Y^4$ is CH. In some embodiments, $Y^3$ is S; and $Y^4$ is CH. In some embodiments, $Y^3$ is $NR^{1C}$; $Y^4$ is CH; and $R^{1C}$ is H or —$CH_3$. In some embodiments, $Y^3$ is $NR^{1C}$; $Y^4$ is N; and $R^{1C}$ is H or —$CH_3$. In some embodiments, $Y^3$ is $NR^{1C}$; $Y^4$ is O; and $R^{1C}$ is H or —$CH_3$. In some embodiments, $Y^3$ is $NR^{1C}$; $Y^4$ is S; and $R^{1C}$ is H or —$CH_3$.

In some embodiments of Formula (IX) or (X), or a pharmaceutically acceptable salt or solvate thereof,

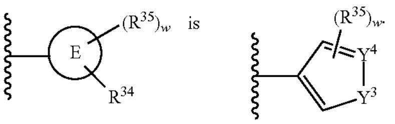

is .

In some embodiments, $Y^3$ is O; and $Y^4$ is CH. In some embodiments, $Y^3$ is S; and $Y^4$ is CH. In some embodiments, $Y^3$ is $NR^{1C}$; $Y^4$ is CH; and $R^{1C}$ is H or —$CH_3$. In some embodiments, $Y^3$ is $NR^{1C}$; $Y^4$ is N; and $R^{1C}$ is H or —$CH_3$.

In some embodiments, $Y^3$ is $NR^{1C}$; $Y^4$ is O; and $R^{1C}$ is H or —$CH_3$. In some embodiments, $Y^3$ is $NR^{1C}$; $Y^4$ is S; and $R^{1C}$ is H or —$CH_3$.

In some embodiments, the compound of Formula (IX) has the structure of Formula (XII), or a pharmaceutically acceptable salt or solvate thereof:

Formula (XII)

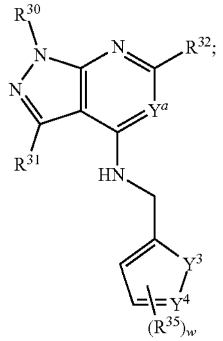

wherein:

$Y^3$ is O or S; and $Y^4$ is CH.

In some embodiments of Formula (XII), or a pharmaceutically acceptable salt or solvate thereof, $Y^3$ is S. In some embodiments, $Y^3$ is O.

In some embodiments of Formula (XII), or a pharmaceutically acceptable salt or solvate thereof, each $R^{35}$ is independently halogen, —CN, —$S(=O)_2N(R^{1A})_2$, —$C_1$-$C_6$ alkyl, or $C_1$-$C_6$ haloalkyl. In some embodiments, $R^{35}$ is —Cl, —F, —Br, —CN, —$CH_3$, —$CF_3$, or —$OCH_3$.

In some embodiments of Formula (XII), or a pharmaceutically acceptable salt or solvate thereof, each $R^{35}$ is independently —$S(=O)_2N(R^{1A})_2$, wherein $R^{1A}$ is H or —$C_1$-$C_3$ alkyl. In some embodiments, each $R^{35}$ is independently —$S(=O)_2NH_2$.

In some embodiments of Formula (XII), or a pharmaceutically acceptable salt or solvate thereof, w is 0. In some embodiments, w is 1.

In some embodiments of Formula (IX), (X), (XI), or (XII), or a pharmaceutically acceptable salt or solvate thereof, $R^{32}$ is halogen, —CN, —OH, —$OR^{1B}$, —$SR^{1B}$, —$N(R^{1A})_2$, —$NR^{1A}S(=O)_2(C_1$-$C_4$alkyl), —$S(=O)_2N(R^{1A})_2$, —$OC(=O)(C_1$-$C_4$alkyl), —$CO_2H$, —$CO_2(C_1$-$C_4$alkyl), —$C(=O)N(R^{1A})_2$, —$NR^{1A}C(=O)(C_1$-$C_4$alkyl), —$NR^{1A}C(=O)O(C_1$-$C_4$alkyl), —$OC(=O)N(R^{1A})_2$, —$NR^{1A}C(=O)N(R^{1A})_2$, —$S(C_1$-$C_4$alkyl), —$S(=O)(C_1$-$C_4$alkyl), —$S(=O)_2(C_1$-$C_4$alkyl), $C_1$-$C_6$alkyl, $C_2$-$C_4$alkenyl, $C_2$-$C_4$alkynyl, $C_1$-$C_4$fluoroalkyl, $C_1$-$C_4$fluoroalkoxy, —$C_{1-6}$alkyl-OH, —$C_{1-6}$heteroalkyl-OH, monocyclic $C_2$-$C_6$heterocycloalkyl, phenyl, or monocyclic 5-6 membered heteroaryl; wherein alkyl, alkenyl, alkynyl, aryl, and heteroaryl are each optionally substituted with one, two, or three $R^{39}$, wherein each $R^{39}$ is independently halogen, —CN, —OH, —$OR^{1B}$, —SH, —$SR^{1B}$, $N(R^{1A})_2$, $C_1$-$C_4$alkyl, or $C_1$-$C_4$fluoroalkyl.

In some embodiments of Formula (IX), (X), (XI), or (XII), or a pharmaceutically acceptable salt or solvate thereof, $R^{32}$ is halogen, —CN, —OH, —$OR^{1B}$, —$SR^{1B}$, —$N(R^{1A})_2$, —$C_1$-$C_6$alkyl, $C_1$-$C_4$fluoroalkyl, —$C_{1-6}$alkyl-OH, or —$C_{1-6}$heteroalkyl-OH. In some embodiments, $R^{32}$ is —Br, —Cl, —F, —CN, —$NH_2$, —$NHCH_3$, —$NHCH_2CH_3$, —$N(CH_3)_2$, —$OCH_3$, —$CF_3$, —$CH_3$, —$CH_2CH_3$, or —$NH(CH_2)_2OH$. In some embodiments, $R^{32}$ is —Br, —Cl, —F, or —CN. In some embodiments, $R^{32}$ is —$NH_2$, —$NHCH_3$, —$NHCH_2CH_3$, —$N(CH_3)_2$, —$NH(CH_2)_2CH_3$, —$NH(CH_2)_3CH_3$, —$NH(CH_2)_4CH_3$, —$NH(CH_2)_3CH(CH_3)_2$, or —$NH(CH_2)_2OH$. In some embodiments, $R^{32}$ is —$NH(CH_2)_2OH$. In some embodiments, $R^{32}$ is —$NH(C_3$-$C_6$cycloalkyl). In some embodiments, $R^{32}$ is —NH-cyclopropyl, —NH-cyclobutyl, or —NH-cyclohexyl. In some embodiments, $R^{32}$ is —NH-benzyl. In some embodiments, $R^{32}$ is —$SH_2$, —$SCH_3$, or —$SCH_2CH_3$. In some embodiments, $R^{32}$ is —OH, —$OCH_3$, or —$OCH_2CH_3$, —$OCH_2CH_2CH_3$, —$OCH_2CH_2CH(CH_3)_2$. In some embodiments, $R^{32}$ is —$OCH_3$, —$CF_3$, —$CH_3$, or —$CH_2CH_3$.

In some embodiments of Formula (IX), (X), (XI), or (XII), or a pharmaceutically acceptable salt or solvate thereof, $R^{32}$ is halogen, —CN, —OH, —$OR^{1B}$, —$N(R^{1A})_2$, —$C_1$-$C_6$alkyl, $C_1$-$C_4$fluoroalkyl, —$C_{1-6}$alkyl-OH, or —$C_{1-6}$heteroalkyl-OH. In some embodiments, $R^{32}$ is —$OR^{1B}$, —$N(R^{1A})_2$, —$C_1$-$C_6$alkyl, or —$C_{1-6}$alkyl-OH. In some embodiments, $R^{32}$ is —$NH_2$, —$NHCH_3$, —$NHCH_2CH_3$, —$N(CH_3)_2$, —$OCH_3$, —$CH_3$, —$CH_2CH_3$, or —$NH(CH_2)_2OH$. In some embodiments, $R^{32}$ is —$NH(CH_2)_2OH$. In some embodiments, $R^{32}$ is H. In some embodiments, $R^{32}$ is —Br or —Cl.

In some embodiments of Formula (IX), (X), (XI), or (XII), or a pharmaceutically acceptable salt or solvate thereof, $R^{32}$ is $C_2$-$C_6$heterocycloalkyl, optionally substituted with one, two, or three $R^{39}$. In some embodiments, $R^{32}$ is piperazine, piperidine, or morpholino. In some embodiments, $R_2$ is piperazine. In some embodiments, $R^{32}$ is piperidine. In some embodiments, $R^{32}$ is morpholine.

In some embodiments of Formula (IX), (X), (XI), or (XII), or a pharmaceutically acceptable salt or solvate thereof, $R^{32}$ is phenyl or a 6-membered heteroaryl, each of which is optionally substituted with one, two, or three $R^{39}$, wherein each $R^{39}$ is independently halogen, —CN, —OH, —$OR^{1B}$, —SH, —$SR^{1B}$, $N(R^{1A})_2$, $C_1$-$C_4$alkyl, or $C_1$-$C_4$fluoroalkyl. In some embodiments, $R^{32}$ is phenyl. In some embodiments, $R^{32}$ is a 6-membered heteroaryl. In some embodiments, the 6-membered heteroaryl is 2-pyridyl, 3-pyridyl, or 4-pyridyl. In some embodiments, $R^{32}$ is heteroaryl is 2-pyridyl In some embodiments of Formula (IX), (X), (XI), or (XII), or a pharmaceutically acceptable salt or solvate thereof, $Y^a$ is N.

In some embodiments of Formula (IX), (X), (XI), or (XII), or a pharmaceutically acceptable salt or solvate thereof, $Y^a$ is CH.

In some embodiments, each $R^{26}$ and $R^{36}$ is independently H, halogen or —$C_1$-$C_4$alkyl. In some embodiments, each $R^{26}$ and $R^{36}$ is independently halogen or —$C_1$-$C_4$alkyl. In some embodiments, each $R^{26}$ and $R^{36}$ is independently H or halogen. In some embodiments, each $R^{26}$ and $R^{36}$ is independently H, —Br, —Cl, —I, or —F. In some embodiments, each $R^{26}$ and $R^{36}$ is independently H or —$C_1$-$C_4$alkyl. In some embodiments, each $R^{26}$ and $R^{36}$ is independently H.

In some embodiments, each $R^7$, $R^8$, $R^9$, $R^{27}$, $R^{28}$, $R^{29}$, $R^{37}$, $R^{38}$, and $R^{39}$ is independently halogen, —CN, —OH, —$OR^{1B}$, —SH, —$SR^{1B}$, —$N(R^{1A})_2$, —$C(=O)OR^{1A}$, oxo (=O), $C_1$-$C_4$alkyl, or $C_1$-$C_4$fluoroalkyl. In some embodiments, each $R^7$, $R^8$, $R^9$, $R^{27}$, $R^{28}$, $R^{29}$, $R^{37}$, $R^{38}$, and $R^{39}$ is independently halogen, —CN, —OH, —$OR^{1B}$, —SH, —$SR^{1B}$, $N(R^{1A})_2$, $C_1$-$C_4$alkyl, or $C_1$-$C_4$fluoroalkyl. In some embodiments, each $R^7$, $R^8$, $R^9$, $R^{27}$, $R^{28}$, $R^{29}$, $R^{37}$, $R^{38}$, and $R^{39}$ is independently —Cl, —Br, —I, or —F. In some embodiments, each $R^7$, $R^8$, $R^9$, $R^{27}$, $R^{28}$, $R^{29}$, $R^{37}$, $R^{38}$, and $R^{39}$ is independently —Cl or —Br. In some embodiments, each $R^7$, $R^8$, $R^9$, $R^{27}$, $R^{28}$, $R^{29}$, $R^{37}$, $R^{38}$, and $R^{39}$ is independently CN, —OH, —$OR^{1B}$, —SH, —$SR^{1B}$, wherein $R^{1B}$ is $C_1$-$C_6$ alkyl or $C_2$-$C_6$ alkenyl. In some embodiments, each $R^7$, $R^8$, $R^9$, $R^{27}$, $R^{28}$, $R^{29}$, $R^{37}$, $R^{38}$, and $R^{39}$ is independently —CN, —OH, —$OCH_3$, —SH, or —$SCH_3$. In some embodiments, each $R^7$, $R^8$, $R^9$, $R^{27}$, $R^{28}$, $R^{29}$, $R^{37}$, $R^{38}$, and $R^{39}$ is $N(R^{1A})_2$, wherein $R^{1A}$ is H or $C_1$-$C_6$ alkyl. In some embodiments, each $R^7$, $R^8$, $R^9$, $R^{27}$, $R^{28}$, $R^{29}$, $R^{37}$, $R^{38}$, and $R^{39}$ is independently —$NH_2$. In some embodiments, each $R^7$, $R^8$, $R^9$, $R^{27}$, $R^{28}$, $R^{29}$, $R^{37}$, $R^{38}$, and $R^{39}$ is independently $C_1$-$C_4$alkyl, or $C_1$-$C_4$fluoroalkyl.

In some embodiments, $R^{1A}$ is independently hydrogen, $C_1$-$C_6$ alkyl, cycloalkyl, heterocycloalkyl, aryl, benzyl, or heteroaryl. In some embodiments, each $R^{1A}$ is independently H or $C_1$-$C_6$ alkyl. each $R^{1A}$ is independently $C_1$-$C_6$ alkyl. each $R^{1A}$ is independently —$CH_3$, —$CH_2CH_3$, or —$CH(CH_3)_2$. In some embodiments, each $R^{1A}$ is independently H. In some embodiments, each $R^{1A}$ is independently cycloalkyl or heterocycloalkyl. In some embodiments, the cycloalkyl is cyclopentyl, cyclobutyl, cyclohexyl, or cycloheptyl.

In some embodiments, each $R^{1B}$ is independently H, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl. In some embodiments, each $R^{1B}$ is independently $C_1$-$C_6$ alkyl. In some embodiments, each $R^{1B}$ is —$CH_3$, —$CH_2CH_3$, or —$CH(CH_3)_2$. In some embodiments, each $R^{1B}$ is independently $C_1$-$C_6$ heteroalkyl. In some embodiments, each $R^{1B}$ is independently aryl. In some embodiments, each $R^{1B}$ is independently phenyl. In some embodiments, each $R^{1B}$ is independently cycloalkyl or heterocycloalkyl. In some embodiments, the cycloalkyl is cyclopentyl, cyclobutyl, cyclohexyl, or cycloheptyl.

In some embodiments of the compound of Formula (I), (II), (III), (IV), (V), (VI), (VII), (VIII), (IX), (X), (XI), or (XII), or a pharmaceutically acceptable salt or solvate thereof, non-limiting examples of compounds described herein are presented in Table 1 through Table 3.

TABLE 1

| Cmpd. | Structure |
|---|---|
| 1 | 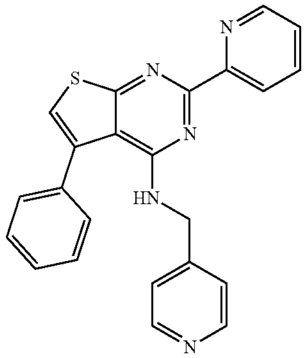 [SMILES: c1ccc(-c2csc3nc(-c4ccccn4)nc(NCc4ccncc4)c23)cc1] |
| 1.1 | 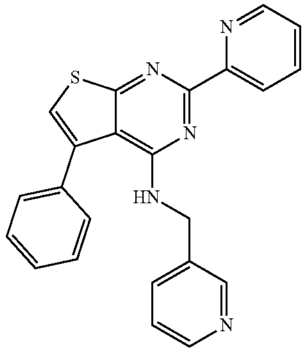 [SMILES: c1ccc(-c2csc3nc(-c4ccccn4)nc(NCc4cccnc4)c23)cc1] |

TABLE 1-continued

| Cmpd. | Structure |
|---|---|
| 1.2 | 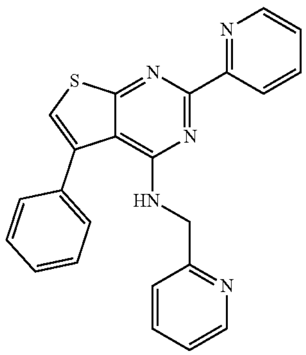 [SMILES: c1ccc(-c2csc3nc(-c4ccccn4)nc(NCc4ccccn4)c23)cc1] |
| 1.3 | 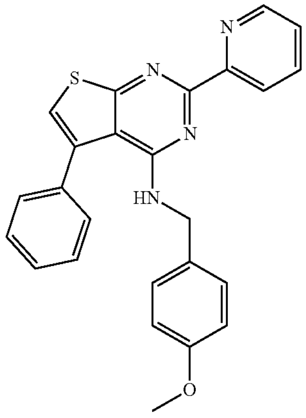 [SMILES: COc1ccc(CNc2nc(-c3ccccn3)nc3scc(-c4ccccc4)c23)cc1] |
| 1.4 | 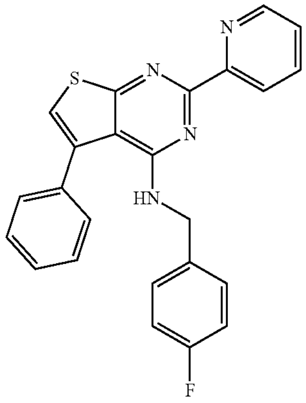 [SMILES: Fc1ccc(CNc2nc(-c3ccccn3)nc3scc(-c4ccccc4)c23)cc1] |
| 1.5 | 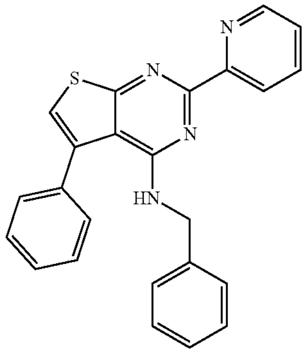 [SMILES: c1ccc(CNc2nc(-c3ccccn3)nc3scc(-c4ccccc4)c23)cc1] |

TABLE 1-continued
| Cmpd. | Structure |
|---|---|
| 1.6 | 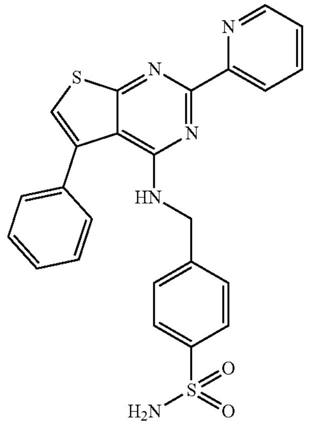 [SMILES: NS(=O)(=O)c1ccc(CNc2nc(-c3ccccn3)nc3scc(-c4ccccc4)c23)cc1] |
| 1.7 | 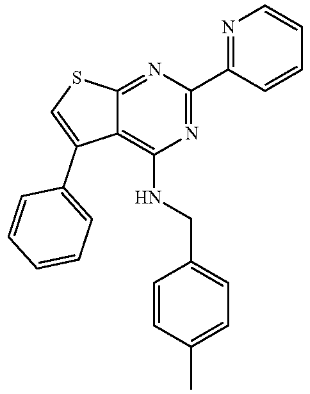 [SMILES: Cc1ccc(CNc2nc(-c3ccccn3)nc3scc(-c4ccccc4)c23)cc1] |
| 1.8 | 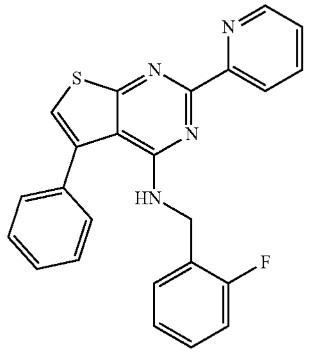 [SMILES: Fc1ccccc1CNc1nc(-c2ccccn2)nc2scc(-c3ccccc3)c12] |
| 1.9 | 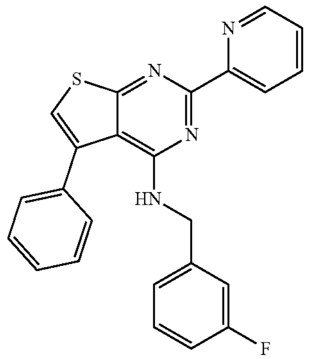 [SMILES: Fc1cccc(CNc2nc(-c3ccccn3)nc3scc(-c4ccccc4)c23)c1] |
TABLE 1-continued
| Cmpd. | Structure |
|---|---|
| 1.10 | 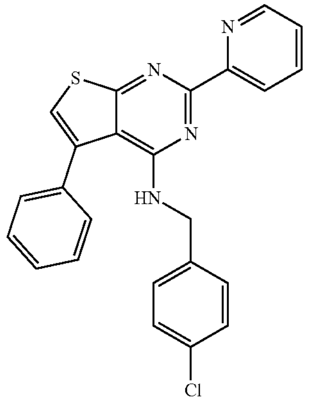 [SMILES: Clc1ccc(CNc2nc(-c3ccccn3)nc3scc(-c4ccccc4)c23)cc1] |
| 1.11 | 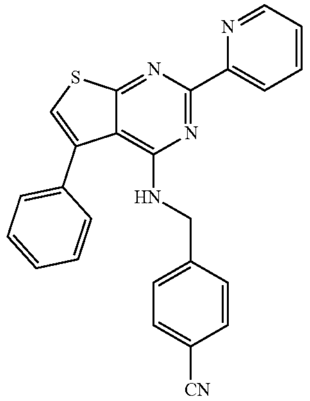 [SMILES: N#Cc1ccc(CNc2nc(-c3ccccn3)nc3scc(-c4ccccc4)c23)cc1] |
| 1.12 | 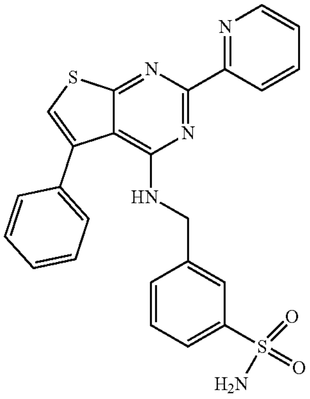 [SMILES: NS(=O)(=O)c1cccc(CNc2nc(-c3ccccn3)nc3scc(-c4ccccc4)c23)c1] |
| 1.13 | 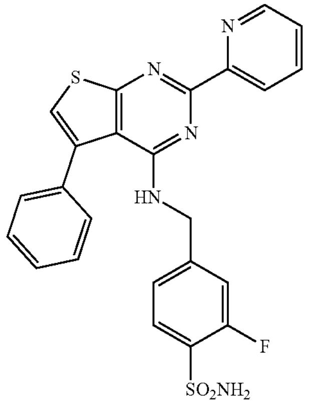 [SMILES: NS(=O)(=O)c1ccc(CNc2nc(-c3ccccn3)nc3scc(-c4ccccc4)c23)cc1F] |

TABLE 1-continued
| Cmpd. | Structure |
| --- | --- |
| 1.14 | 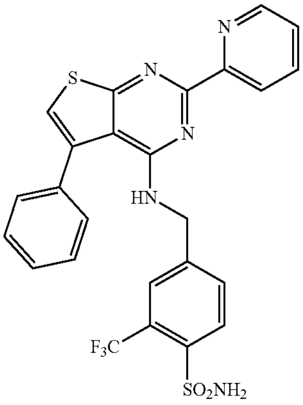 [SMILES: NS(=O)(=O)c1ccc(CNc2nc(-c3ccccn3)nc3scc(-c4ccccc4)c23)cc1C(F)(F)F] |
| 1.15 | 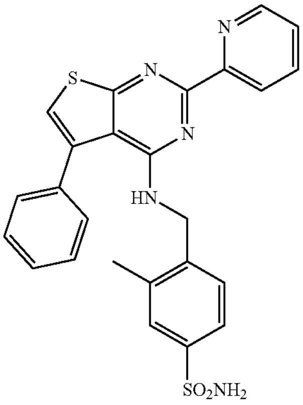 [SMILES: Cc1cc(S(N)(=O)=O)ccc1CNc1nc(-c2ccccn2)nc2scc(-c3ccccc3)c12] |
| 1.16 | 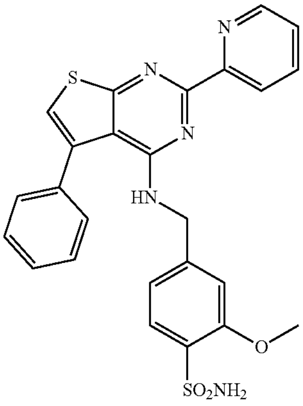 [SMILES: COc1cc(CNc2nc(-c3ccccn3)nc3scc(-c4ccccc4)c23)ccc1S(N)(=O)=O] |
| 1.17 | 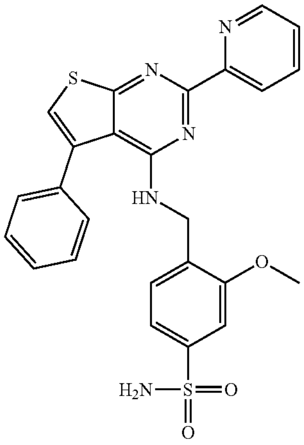 [SMILES: COc1cc(S(N)(=O)=O)ccc1CNc1nc(-c2ccccn2)nc2scc(-c3ccccc3)c12] |
| 1.18 | 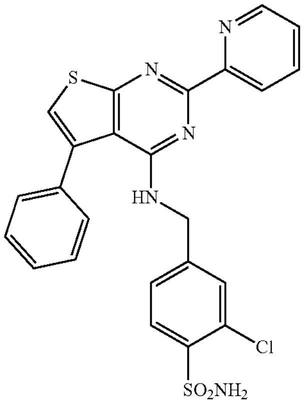 [SMILES: NS(=O)(=O)c1ccc(CNc2nc(-c3ccccn3)nc3scc(-c4ccccc4)c23)cc1Cl] |
| 1.19 | 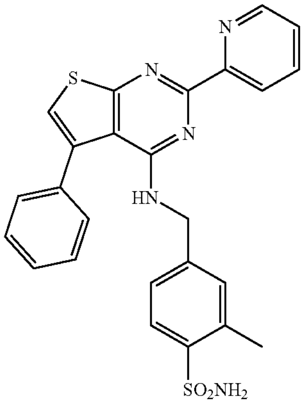 [SMILES: Cc1cc(CNc2nc(-c3ccccn3)nc3scc(-c4ccccc4)c23)ccc1S(N)(=O)=O] |

TABLE 1-continued
| Cmpd. | Structure |
| --- | --- |
| 1.20 | 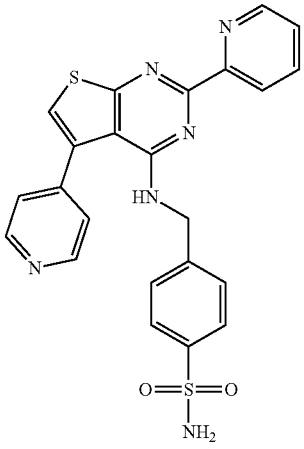 [SMILES: NS(=O)(=O)c1ccc(CNc2nc(-c3ccccn3)nc3scc(-c4ccncc4)c23)cc1] |
| 1.21 | 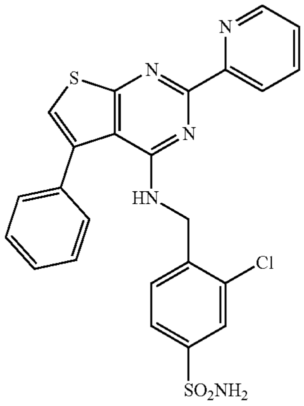 [SMILES: NS(=O)(=O)c1ccc(CNc2nc(-c3ccccn3)nc3scc(-c4ccccc4)c23)c(Cl)c1] |
| 1.22 | 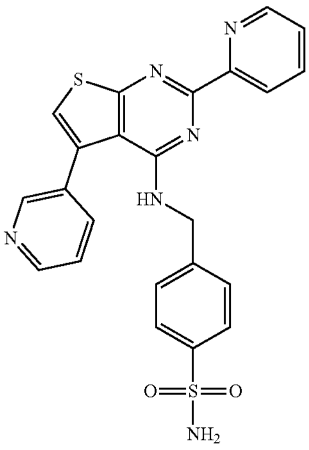 [SMILES: NS(=O)(=O)c1ccc(CNc2nc(-c3ccccn3)nc3scc(-c4cccnc4)c23)cc1] |
| 1.23 | 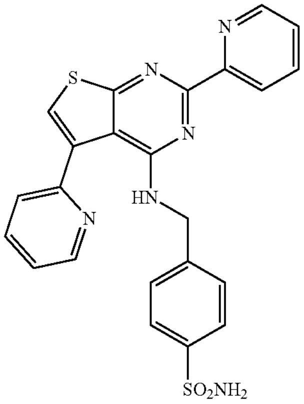 [SMILES: NS(=O)(=O)c1ccc(CNc2nc(-c3ccccn3)nc3scc(-c4ccccn4)c23)cc1] |
| 1.24 | 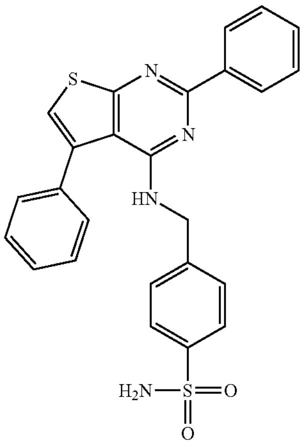 [SMILES: NS(=O)(=O)c1ccc(CNc2nc(-c3ccccc3)nc3scc(-c4ccccc4)c23)cc1] |
| 1.25 | 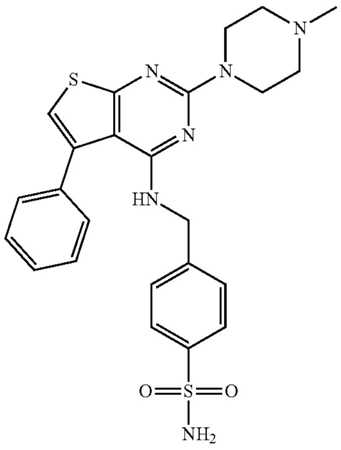 [SMILES: CN1CCN(c2nc(NCc3ccc(S(N)(=O)=O)cc3)c3c(-c4ccccc4)csc3n2)CC1] |

TABLE 1-continued
| Cmpd. | Structure |
| --- | --- |
| 1.26 | 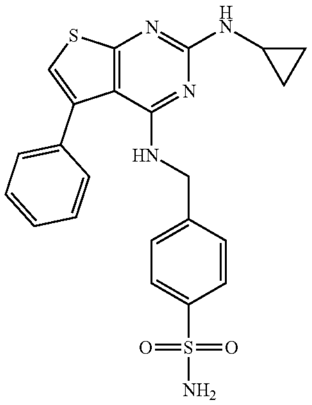 [SMILES: NS(=O)(=O)c1ccc(CNc2nc(NC3CC3)nc3scc(-c4ccccc4)c23)cc1] |
| 1.27 | 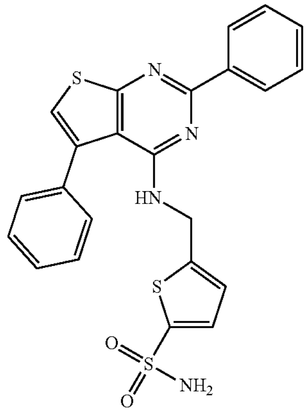 [SMILES: NS(=O)(=O)c1ccc(CNc2nc(-c3ccccc3)nc3scc(-c4ccccc4)c23)s1] |
| 1.28 | 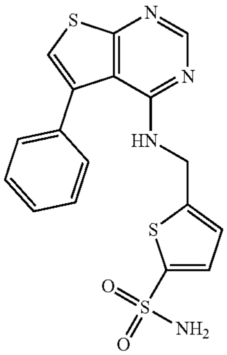 [SMILES: NS(=O)(=O)c1ccc(CNc2ncnc3scc(-c4ccccc4)c23)s1] |
| 1.29 | 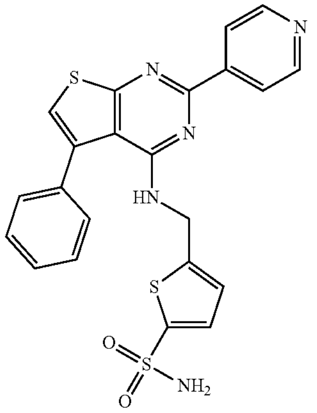 [SMILES: NS(=O)(=O)c1ccc(CNc2nc(-c3ccncc3)nc3scc(-c4ccccc4)c23)s1] |
TABLE 1-continued
| Cmpd. | Structure |
| --- | --- |
| 1.30 | 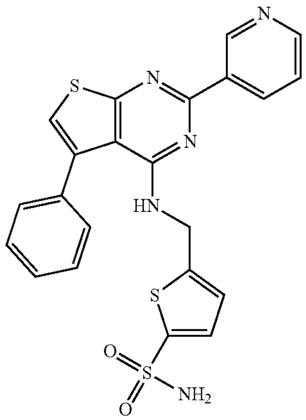 [SMILES: NS(=O)(=O)c1ccc(CNc2nc(-c3cccnc3)nc3scc(-c4ccccc4)c23)s1] |
| 1.31 | 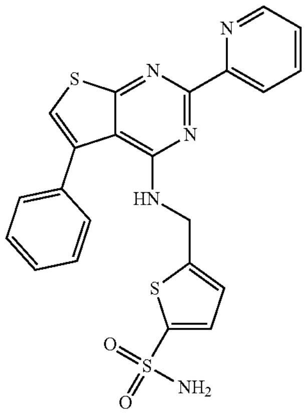 [SMILES: NS(=O)(=O)c1ccc(CNc2nc(-c3ccccn3)nc3scc(-c4ccccc4)c23)s1] |
| 1.32 | 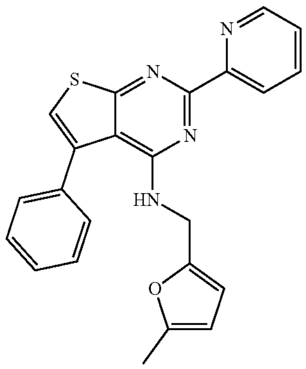 [SMILES: Cc1ccc(CNc2nc(-c3ccccn3)nc3scc(-c4ccccc4)c23)o1] |
| 1.33 | 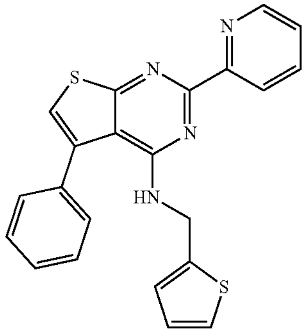 [SMILES: c1ccc(-c2csc3nc(-c4ccccn4)nc(NCc4cccs4)c23)cc1] |

TABLE 1-continued
| Cmpd. | Structure |
| --- | --- |
| 1.34 | 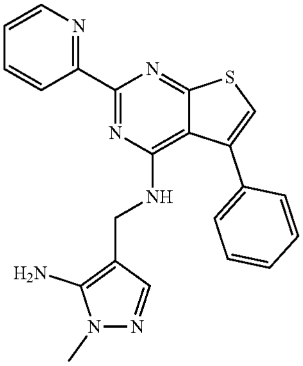 [SMILES: Cn1ncc(CNc2nc(-c3ccccn3)nc3scc(-c4ccccc4)c23)c1N] |
| 1.35 | 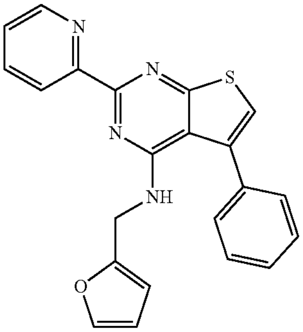 [SMILES: c1ccc(-c2csc3nc(-c4ccccn4)nc(NCc4ccco4)c23)cc1] |
| 1.36 | 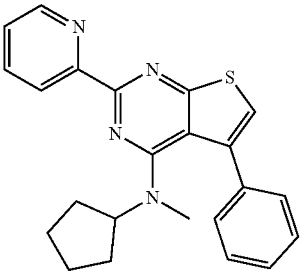 [SMILES: CN(c1nc(-c2ccccn2)nc2scc(-c3ccccc3)c12)C1CCCC1] |
| 1.37 | 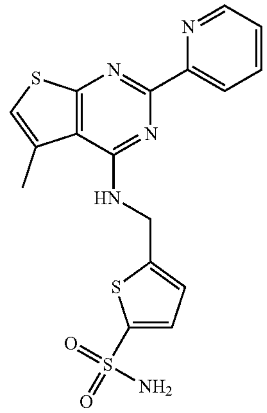 [SMILES: Cc1csc2nc(-c3ccccn3)nc(NCc3ccc(S(N)(=O)=O)s3)c12] |
TABLE 1-continued
| Cmpd. | Structure |
| --- | --- |
| 1.38 | 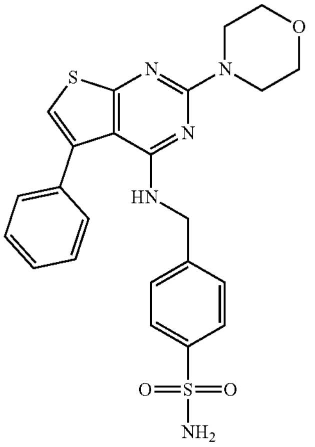 [SMILES: NS(=O)(=O)c1ccc(CNc2nc(N3CCOCC3)nc3scc(-c4ccccc4)c23)cc1] |
| 1.39 | 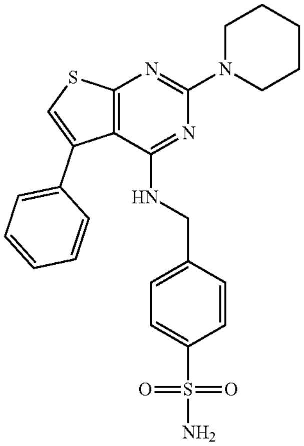 [SMILES: NS(=O)(=O)c1ccc(CNc2nc(N3CCCCC3)nc3scc(-c4ccccc4)c23)cc1] |
| 1.40 | 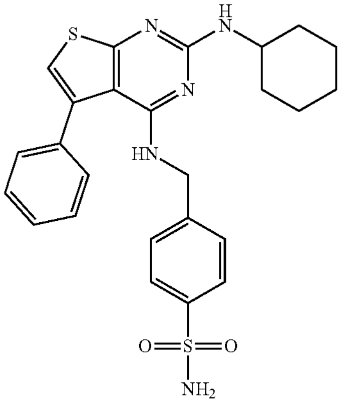 [SMILES: NS(=O)(=O)c1ccc(CNc2nc(NC3CCCCC3)nc3scc(-c4ccccc4)c23)cc1] |

TABLE 1-continued
| Cmpd. | Structure |
| --- | --- |
| 1.41 | 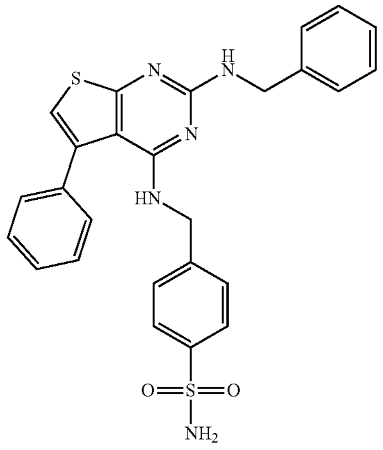 [SMILES: NS(=O)(=O)c1ccc(CNc2nc(NCc3ccccc3)nc3scc(-c4ccccc4)c23)cc1] |
| 1.42 | 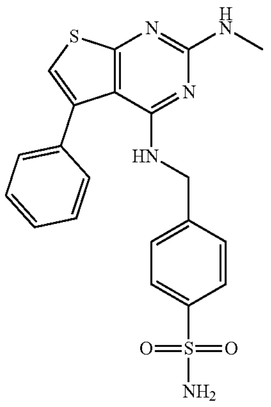 [SMILES: CNc1nc(NCc2ccc(S(N)(=O)=O)cc2)c2c(-c3ccccc3)csc2n1] |
| 1.43 | 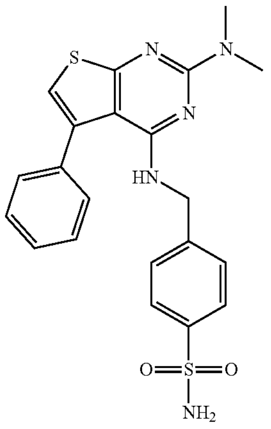 [SMILES: CN(C)c1nc(NCc2ccc(S(N)(=O)=O)cc2)c2c(-c3ccccc3)csc2n1] |
| 1.44 | 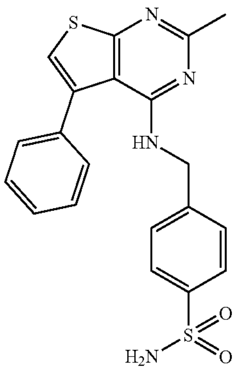 [SMILES: Cc1nc(NCc2ccc(S(N)(=O)=O)cc2)c2c(-c3ccccc3)csc2n1] |
| 1.45 | 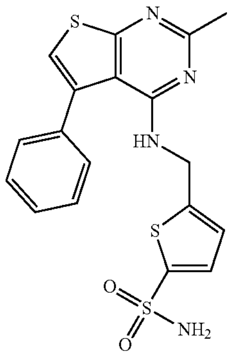 [SMILES: Cc1nc(NCc2ccc(S(N)(=O)=O)s2)c2c(-c3ccccc3)csc2n1] |
| 1.46 | 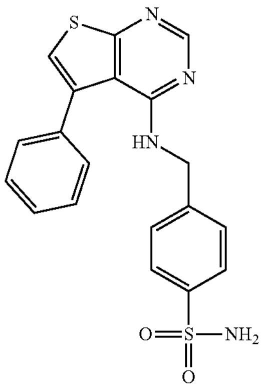 [SMILES: NS(=O)(=O)c1ccc(CNc2ncnc3scc(-c4ccccc4)c23)cc1] |
| 1.47 | 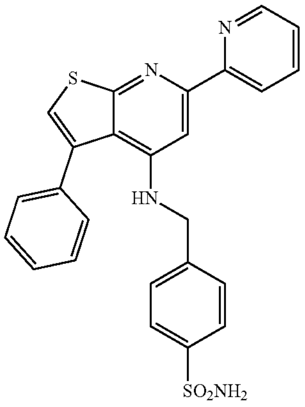 [SMILES: NS(=O)(=O)c1ccc(CNc2cc(-c3ccccn3)nc3scc(-c4ccccc4)c23)cc1] |

TABLE 1-continued
| Cmpd. | Structure |
|---|---|
| 1.48 | 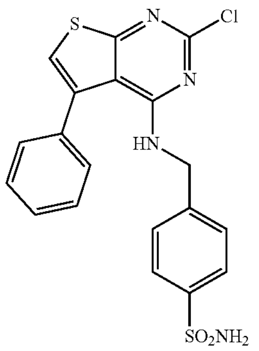 [SMILES: NS(=O)(=O)c1ccc(CNc2nc(Cl)nc3scc(-c4ccccc4)c23)cc1] |
| 1.49 | 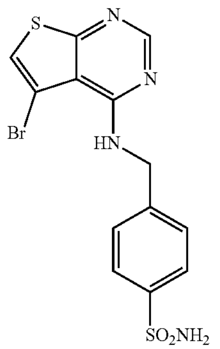 [SMILES: NS(=O)(=O)c1ccc(CNc2ncnc3scc(Br)c23)cc1] |
| 1.50 | 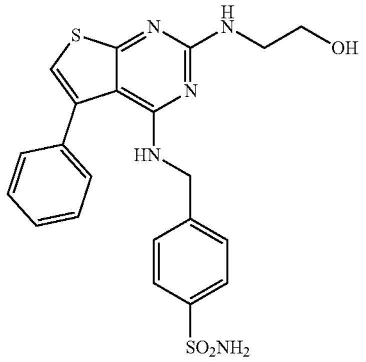 [SMILES: NS(=O)(=O)c1ccc(CNc2nc(NCCO)nc3scc(-c4ccccc4)c23)cc1] |
| 1.51 | 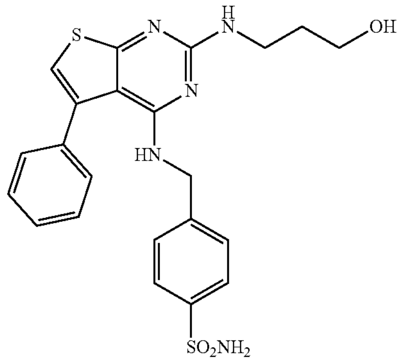 [SMILES: NS(=O)(=O)c1ccc(CNc2nc(NCCCO)nc3scc(-c4ccccc4)c23)cc1] |
TABLE 1-continued
| Cmpd. | Structure |
|---|---|
| 1.52 | 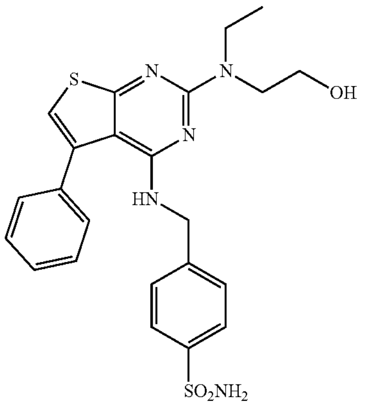 [SMILES: CCN(CCO)c1nc(NCc2ccc(S(N)(=O)=O)cc2)c2c(-c3ccccc3)csc2n1] |
| 1.53 | 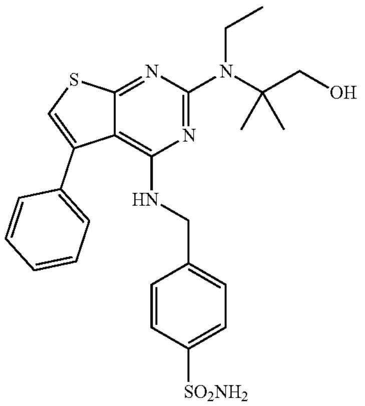 [SMILES: CCN(c1nc(NCc2ccc(S(N)(=O)=O)cc2)c2c(-c3ccccc3)csc2n1)C(C)(C)CO] |
| 1.54 | 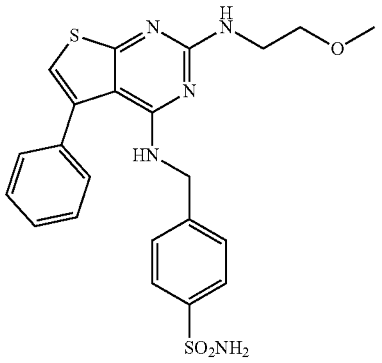 [SMILES: COCCNc1nc(NCc2ccc(S(N)(=O)=O)cc2)c2c(-c3ccccc3)csc2n1] |
| 1.55 | 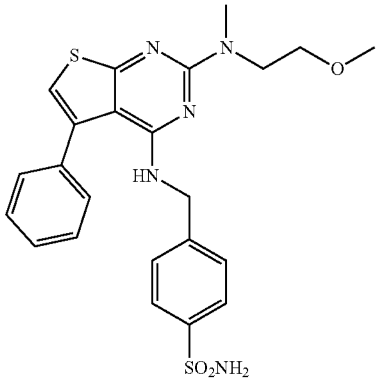 [SMILES: COCCN(C)c1nc(NCc2ccc(S(N)(=O)=O)cc2)c2c(-c3ccccc3)csc2n1] |

TABLE 1-continued
| Cmpd. | Structure |
| --- | --- |
| 1.56 | 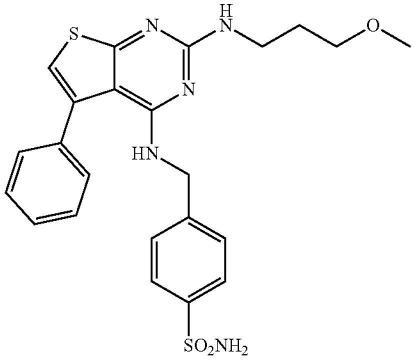 [SMILES: COCCCNc1nc(NCc2ccc(S(N)(=O)=O)cc2)c2c(-c3ccccc3)csc2n1] |
| 1.57 | 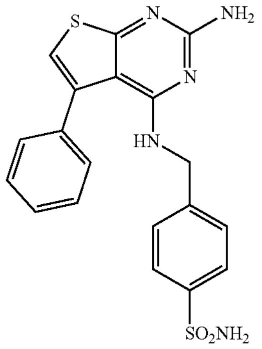 [SMILES: Nc1nc(NCc2ccc(S(N)(=O)=O)cc2)c2c(-c3ccccc3)csc2n1] |
| 1.58 | 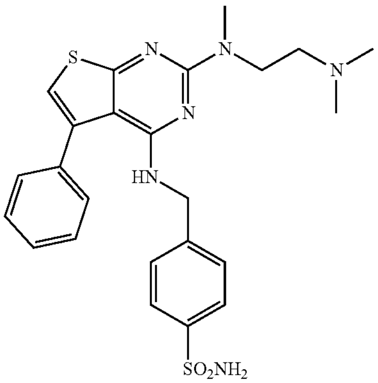 [SMILES: CN(C)CCN(C)c1nc(NCc2ccc(S(N)(=O)=O)cc2)c2c(-c3ccccc3)csc2n1] |
| 1.59 | 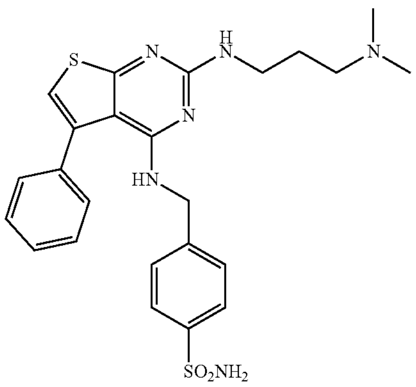 [SMILES: CN(C)CCCNc1nc(NCc2ccc(S(N)(=O)=O)cc2)c2c(-c3ccccc3)csc2n1] |
TABLE 1-continued
| Cmpd. | Structure |
| --- | --- |
| 1.60 | 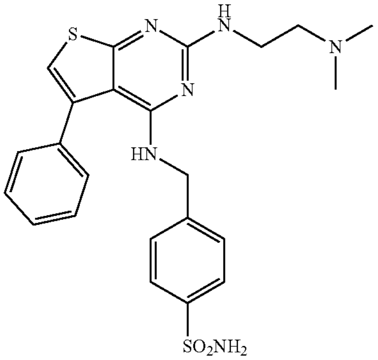 [SMILES: CN(C)CCNc1nc(NCc2ccc(S(N)(=O)=O)cc2)c2c(-c3ccccc3)csc2n1] |
| 1.61 | 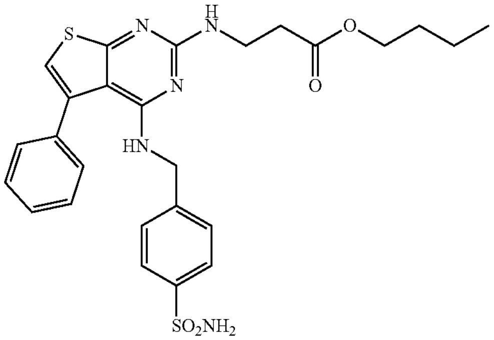 [SMILES: CCCCOC(=O)CCNc1nc(NCc2ccc(S(N)(=O)=O)cc2)c2c(-c3ccccc3)csc2n1] |
| 1.62 | 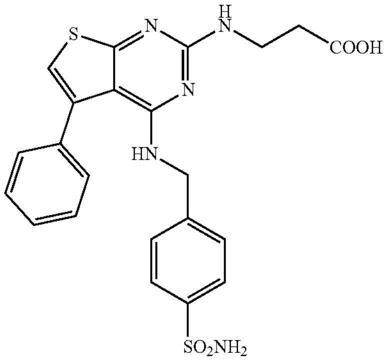 [SMILES: NS(=O)(=O)c1ccc(CNc2nc(NCCC(=O)O)nc3scc(-c4ccccc4)c23)cc1] |
| 1.63 | 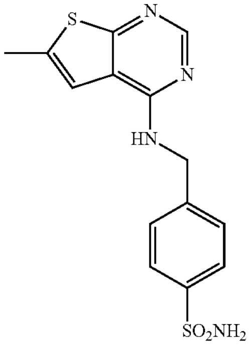 [SMILES: Cc1cc2c(NCc3ccc(S(N)(=O)=O)cc3)ncnc2s1] |

TABLE 1-continued
| Cmpd. | Structure |
|---|---|
| 1.64 | 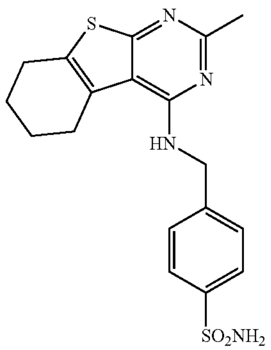 [SMILES: Cc1nc(NCc2ccc(S(N)(=O)=O)cc2)c2c3c(sc2n1)CCCC3] |
| 1.65 | 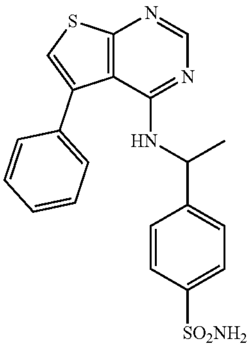 [SMILES: CC(Nc1ncnc2scc(-c3ccccc3)c12)c1ccc(S(N)(=O)=O)cc1] |
| 1.66 | 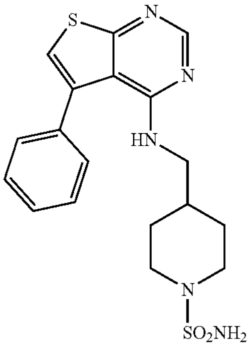 [SMILES: NS(=O)(=O)N1CCC(CNc2ncnc3scc(-c4ccccc4)c23)CC1] |
| 1.67 | 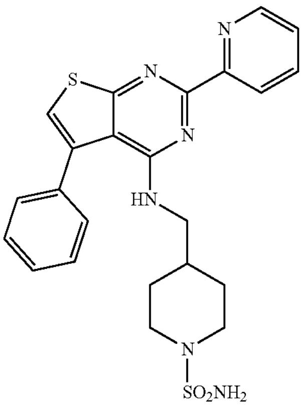 [SMILES: NS(=O)(=O)N1CCC(CNc2nc(-c3ccccn3)nc3scc(-c4ccccc4)c23)CC1] |
TABLE 1-continued
| Cmpd. | Structure |
|---|---|
| 1.68 | 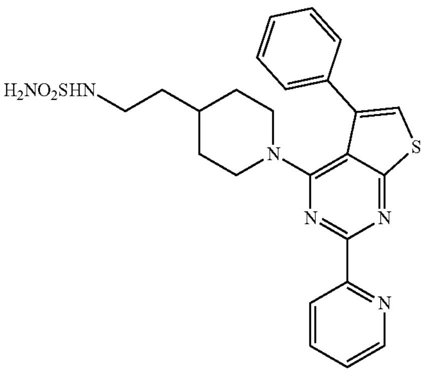 |
| 1.69 | 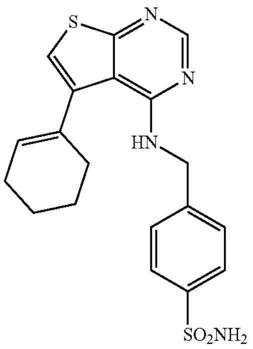 [SMILES: NS(=O)(=O)c1ccc(CNc2ncnc3scc(C4=CCCCC4)c23)cc1] |
| 1.70 | 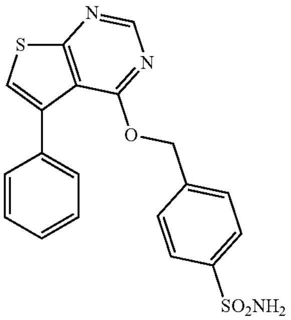 [SMILES: NS(=O)(=O)c1ccc(COc2ncnc3scc(-c4ccccc4)c23)cc1] |

TABLE 2
| Cmpd. | Structure |
| --- | --- |
| 2.0 | 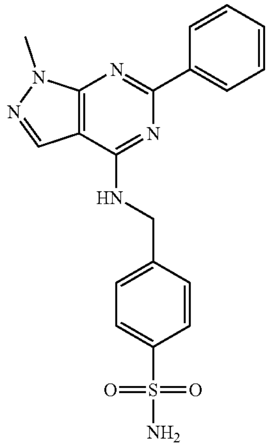 [SMILES: Cn1ncc2c(NCc3ccc(S(N)(=O)=O)cc3)nc(-c3ccccc3)nc21] |
| 2.1 | 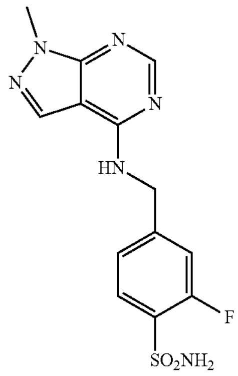 [SMILES: Cn1ncc2c(NCc3ccc(S(N)(=O)=O)c(F)c3)ncnc21] |
| 2.2 | 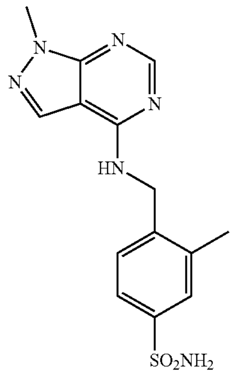 |
| 2.3 | 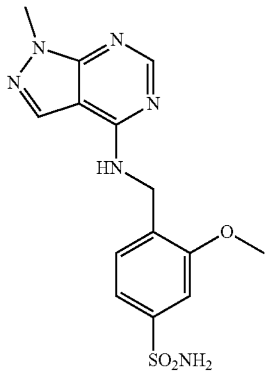 [SMILES: COc1cc(S(N)(=O)=O)ccc1CNc1ncnc2c1cnn2C] |
TABLE 2-continued
| Cmpd. | Structure |
| --- | --- |
| 2.4 | 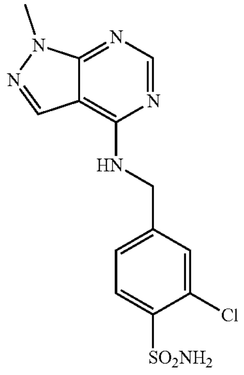 [SMILES: Cn1ncc2c(NCc3ccc(S(N)(=O)=O)c(Cl)c3)ncnc21] |
| 2.5 | 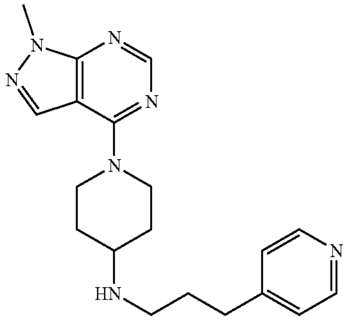 [SMILES: Cn1ncc2c(N3CCC(NCCCc4ccncc4)CC3)ncnc21] |
| 2.6 | 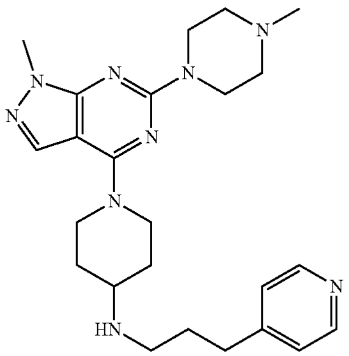 [SMILES: CN1CCN(c2nc(N3CCC(NCCCc4ccncc4)CC3)c3cnn(C)c3n2)CC1] |
| 2.7 | 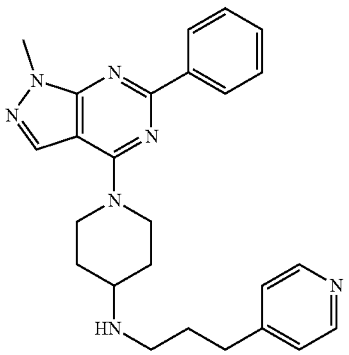 [SMILES: Cn1ncc2c(N3CCC(NCCCc4ccncc4)CC3)nc(-c3ccccc3)nc21] |

TABLE 2-continued
| Cmpd. | Structure |
|---|---|
| 2.8 | 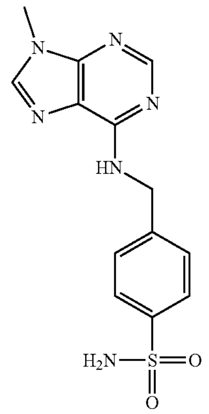 [SMILES: Cn1cnc2c(NCc3ccc(S(N)(=O)=O)cc3)ncnc21] |
| 2.9 | 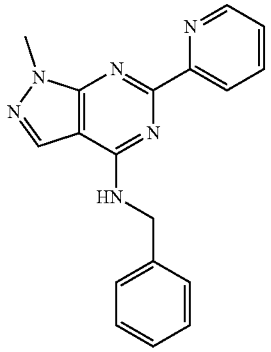 |
| 2.10 | 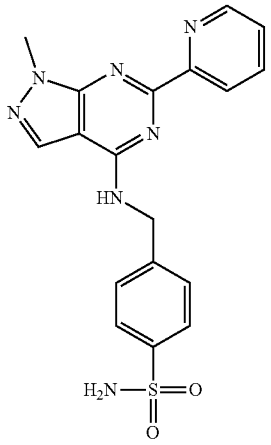 [SMILES: Cn1ncc2c(NCc3ccc(S(N)(=O)=O)cc3)nc(-c3ccccn3)nc21] |
TABLE 2-continued
| Cmpd. | Structure |
|---|---|
| 2.11 | 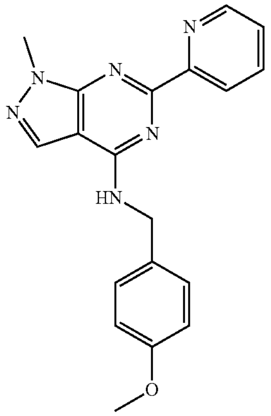 [SMILES: COc1ccc(CNc2nc(-c3ccccn3)nc3c2cnn3C)cc1] |
| 2.12 | 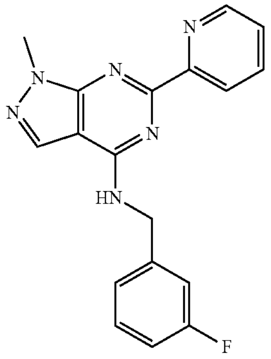 [SMILES: Cn1ncc2c(NCc3cccc(F)c3)nc(-c3ccccn3)nc21] |
| 2.13 | 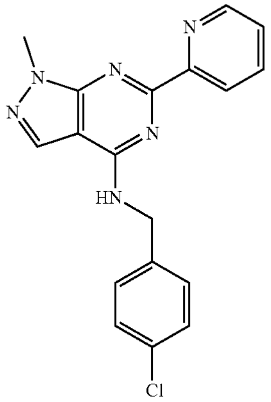 [SMILES: Cn1ncc2c(NCc3ccc(Cl)cc3)nc(-c3ccccn3)nc21] |
| 2.14 | 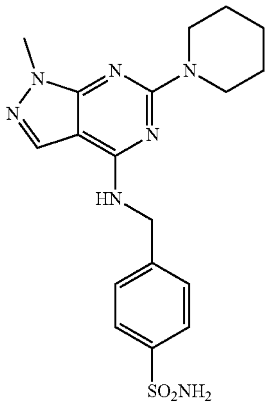 [SMILES: Cn1ncc2c(NCc3ccc(S(N)(=O)=O)cc3)nc(N3CCCCC3)nc21] |

TABLE 2-continued
| Cmpd. | Structure |
| --- | --- |
| 2.15 | 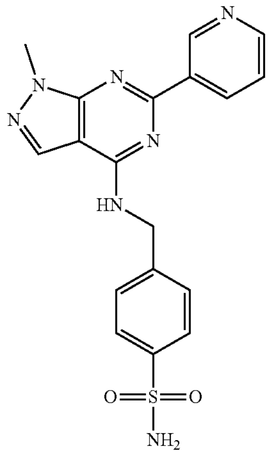 [SMILES: Cn1ncc2c(NCc3ccc(S(N)(=O)=O)cc3)nc(-c3cccnc3)nc21] |
| 2.16 | 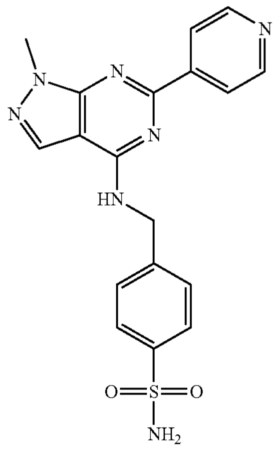 [SMILES: Cn1ncc2c(NCc3ccc(S(N)(=O)=O)cc3)nc(-c3ccncc3)nc21] |
| 2.17 | 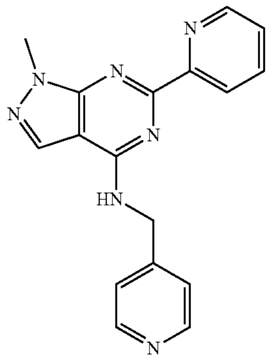 [SMILES: Cn1ncc2c(NCc3ccncc3)nc(-c3ccccn3)nc21] |
TABLE 2-continued
| Cmpd. | Structure |
| --- | --- |
| 2.18 | 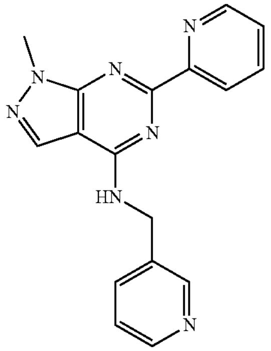 [SMILES: Cn1ncc2c(NCc3cccnc3)nc(-c3ccccn3)nc21] |
| 2.19 | 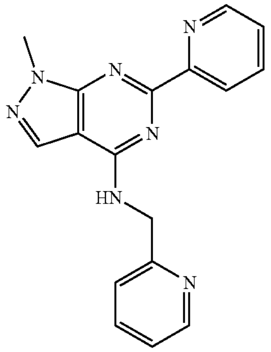 [SMILES: Cn1ncc2c(NCc3ccccn3)nc(-c3ccccn3)nc21] |
| 2.20 | 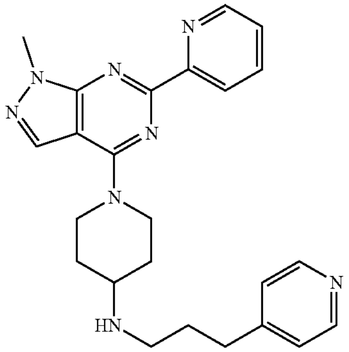 |
| 2.21 | 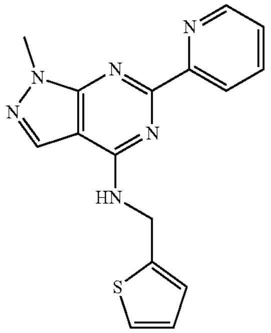 |

TABLE 2-continued
| Cmpd. | Structure |
| --- | --- |
| 2.22 | 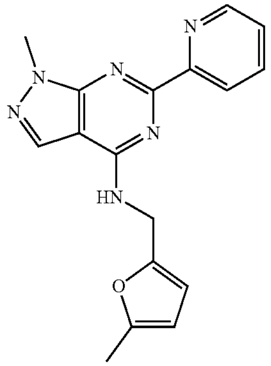 [SMILES: Cc1ccc(CNc2nc(-c3ccccn3)nc3c2cnn3C)o1] |
| 2.23 | 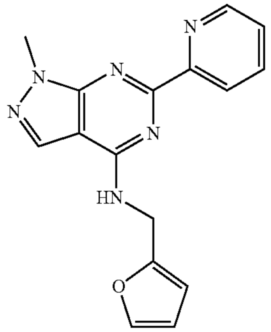 |
| 2.24 | 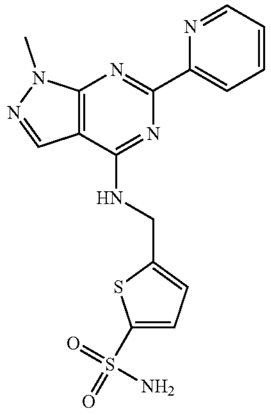 [SMILES: Cn1ncc2c(NCc3ccc(S(N)(=O)=O)s3)nc(-c3ccccn3)nc21] |
| 2.25 | 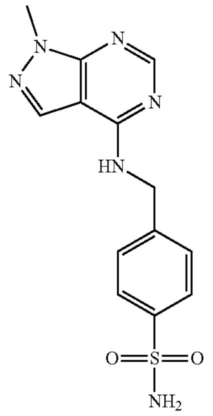 |
TABLE 2-continued
| Cmpd. | Structure |
| --- | --- |
| 2.26 | 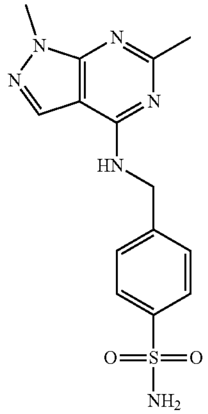 |
| 2.27 | 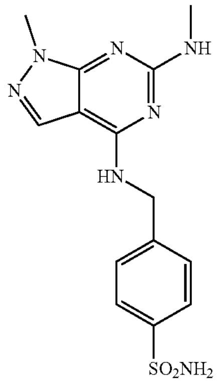 [SMILES: CNc1nc(NCc2ccc(S(N)(=O)=O)cc2)c2cnn(C)c2n1] |
| 2.28 | 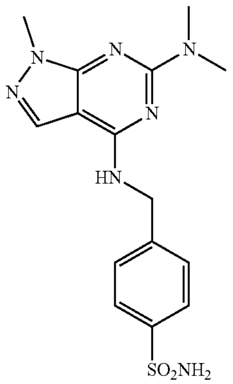 [SMILES: CN(C)c1nc(NCc2ccc(S(N)(=O)=O)cc2)c2cnn(C)c2n1] |
| 2.29 | 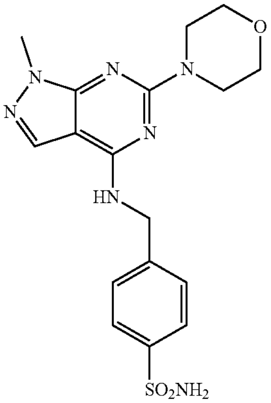 [SMILES: Cn1ncc2c(NCc3ccc(S(N)(=O)=O)cc3)nc(N3CCOCC3)nc21] |

TABLE 2-continued
| Cmpd. | Structure |
|---|---|
| 2.30 | 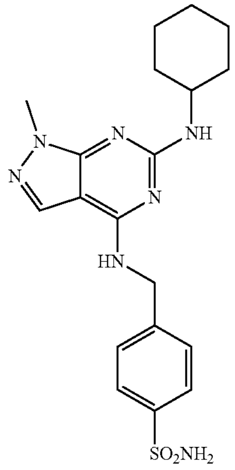 [SMILES: Cn1ncc2c(NCc3ccc(S(N)(=O)=O)cc3)nc(NC3CCCCC3)nc21] |
| 2.31 | 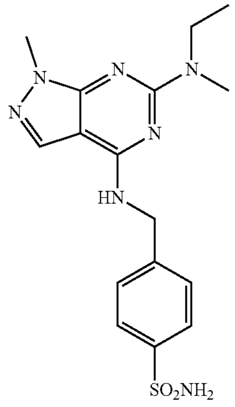 [SMILES: CCN(C)c1nc(NCc2ccc(S(N)(=O)=O)cc2)c2cnn(C)c2n1] |
| 2.32 | 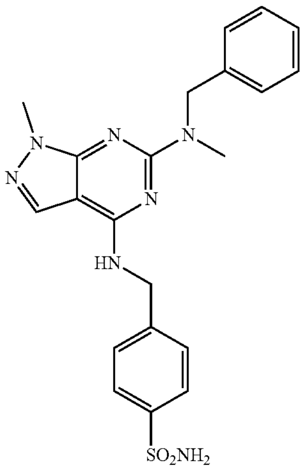 [SMILES: CN(Cc1ccccc1)c1nc(NCc2ccc(S(N)(=O)=O)cc2)c2cnn(C)c2n1] |
| 2.34 | 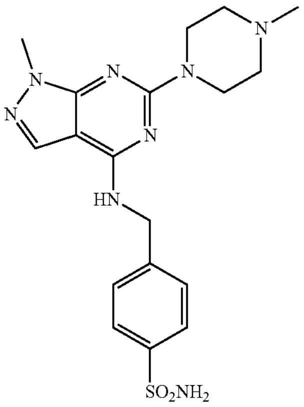 [SMILES: CN1CCN(c2nc(NCc3ccc(S(N)(=O)=O)cc3)c3cnn(C)c3n2)CC1] |
| 2.35 | 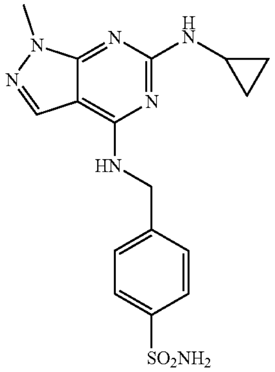 [SMILES: Cn1ncc2c(NCc3ccc(S(N)(=O)=O)cc3)nc(NC3CC3)nc21] |
| 2.36 | 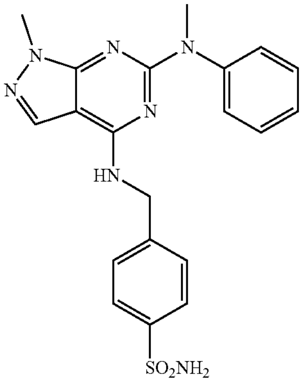 [SMILES: CN(c1ccccc1)c1nc(NCc2ccc(S(N)(=O)=O)cc2)c2cnn(C)c2n1] |
| 2.37 | 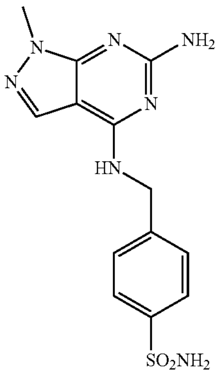 |

TABLE 2-continued
| Cmpd. | Structure |
| --- | --- |
| 2.38 | 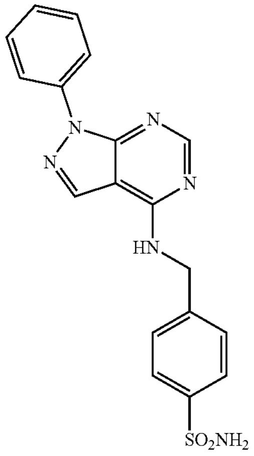 [SMILES: NS(=O)(=O)c1ccc(CNc2ncnc3c2cnn3-c2ccccc2)cc1] |
| 2.39 | 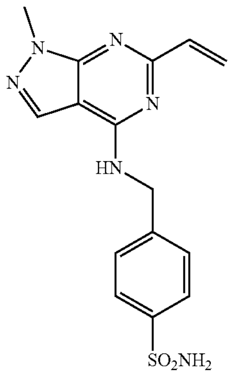 [SMILES: C=Cc1nc(NCc2ccc(S(N)(=O)=O)cc2)c2cnn(C)c2n1] |
| 2.40 | 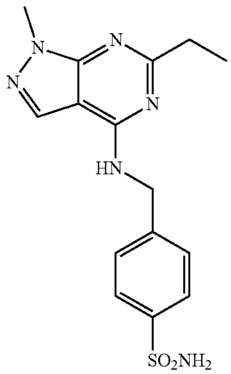 [SMILES: CCc1nc(NCc2ccc(S(N)(=O)=O)cc2)c2cnn(C)c2n1] |
| 2.41 | 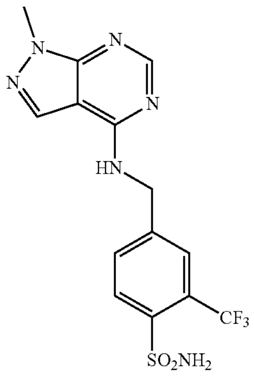 |
TABLE 2-continued
| Cmpd. | Structure |
| --- | --- |
| 2.42 | 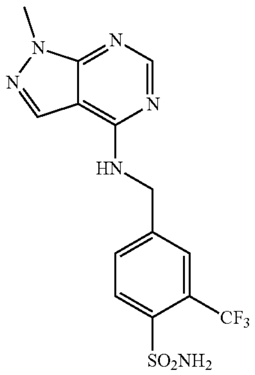 |
| 2.43 | 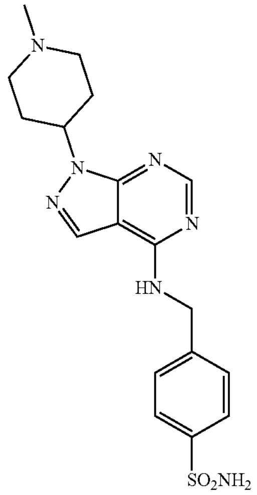 [SMILES: CN1CCC(n2ncc3c(NCc4ccc(S(N)(=O)=O)cc4)ncnc32)CC1] |
| 2.44 | 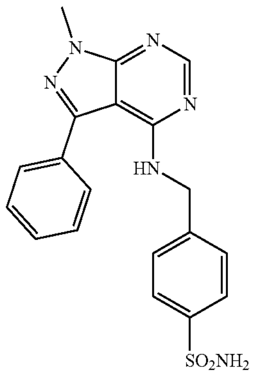 [SMILES: Cn1nc(-c2ccccc2)c2c(NCc3ccc(S(N)(=O)=O)cc3)ncnc21] |

TABLE 2-continued
| Cmpd. | Structure |
| --- | --- |
| 2.45 | 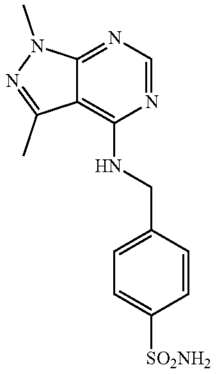 [SMILES: Cc1nn(C)c2ncnc(NCc3ccc(S(N)(=O)=O)cc3)c12] |
| 2.46 | 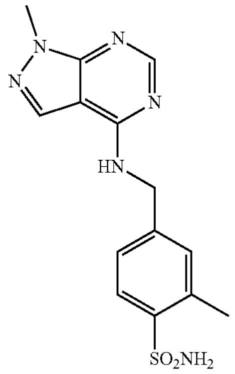 |
| 2.47 | 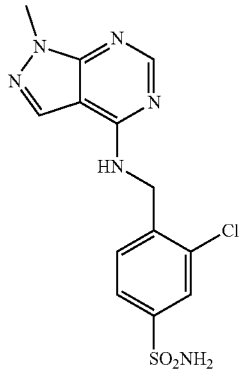 [SMILES: Cn1ncc2c(NCc3ccc(S(N)(=O)=O)cc3Cl)ncnc21] |
| 2.48 | 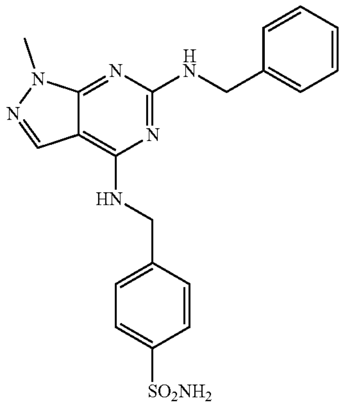 [SMILES: Cn1ncc2c(NCc3ccc(S(N)(=O)=O)cc3)nc(NCc3ccccc3)nc21] |
TABLE 2-continued
| Cmpd. | Structure |
| --- | --- |
| 2.49 | 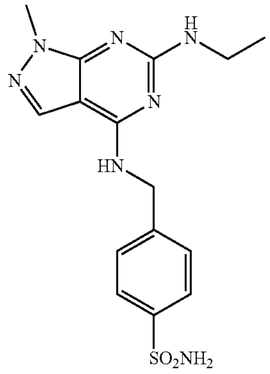 |
| 2.50 | 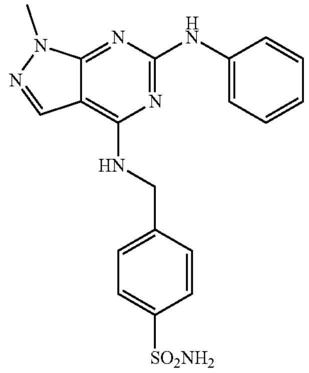 [SMILES: Cn1ncc2c(NCc3ccc(S(N)(=O)=O)cc3)nc(Nc3ccccc3)nc21] |
| 2.51 | 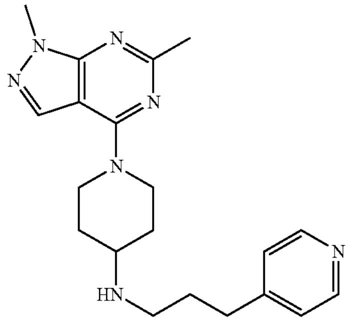 [SMILES: Cc1nc(N2CCC(NCCCc3ccncc3)CC2)c2cnn(C)c2n1] |
| 2.52 | 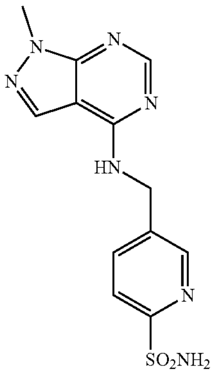 |

TABLE 2-continued
| Cmpd. | Structure |
| --- | --- |
| 2.53 | 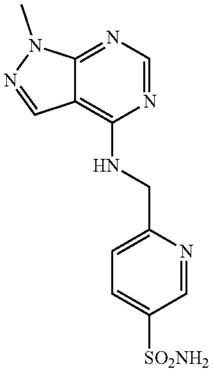 |
| 2.54 | 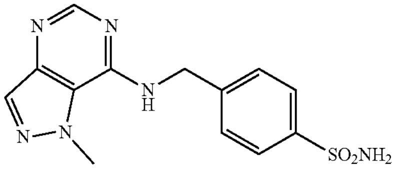 [SMILES: Cn1ncc2ncnc(NCc3ccc(S(N)(=O)=O)cc3)c21] |
| 2.55 | 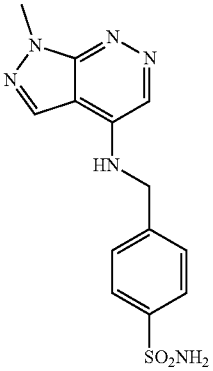 |
| 2.56 | 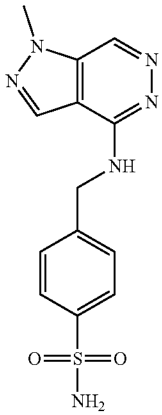 [SMILES: Cn1ncc2c(NCc3ccc(S(N)(=O)=O)cc3)nncc21] |
TABLE 2-continued
| Cmpd. | Structure |
| --- | --- |
| 2.57 | 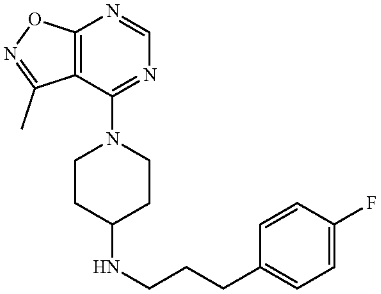 [SMILES: Cc1noc2ncnc(N3CCC(NCCCc4ccc(F)cc4)CC3)c12] |
| 2.58 | 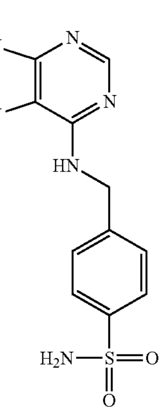 |
| 2.59 | 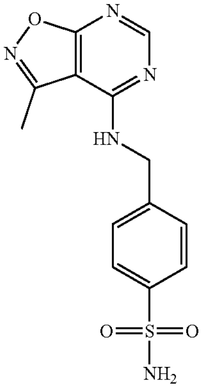 |
| 2.60 | 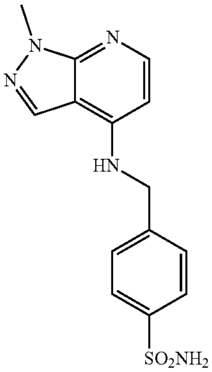 |

TABLE 2-continued
| Cmpd. | Structure |
|---|---|
| 2.61 | 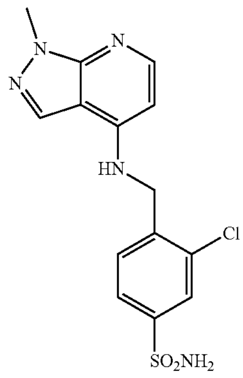 |
| 2.62 | 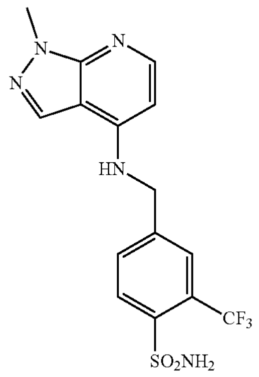 [SMILES: Cn1ncc2c(NCc3ccc(S(N)(=O)=O)c(C(F)(F)F)c3)ccnc21] |
| 2.63 | 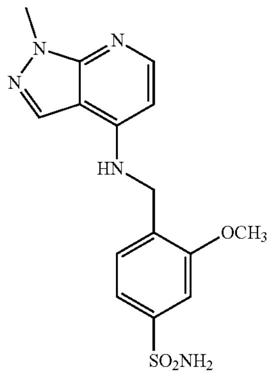 [SMILES: COc1cc(S(N)(=O)=O)ccc1CNc1ccnc2c1cnn2C] |
| 2.64 | 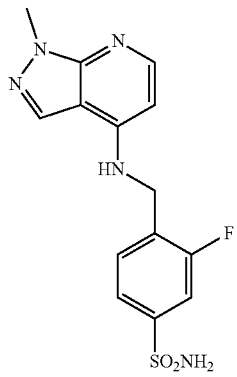 [SMILES: Cn1ncc2c(NCc3ccc(S(N)(=O)=O)cc3F)ccnc21] |
TABLE 2-continued
| Cmpd. | Structure |
|---|---|
| 2.65 | 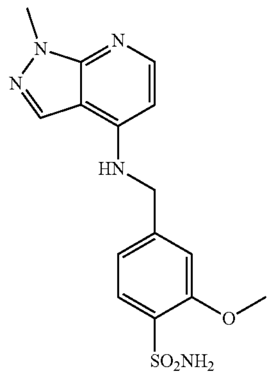 |
| 2.66 | 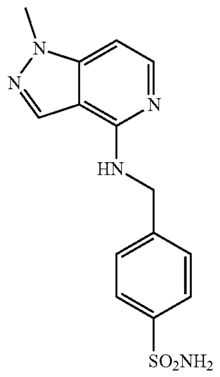 |
| 2.67 | 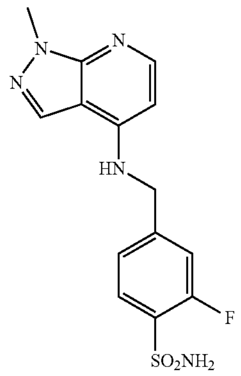 |
| 2.68 | 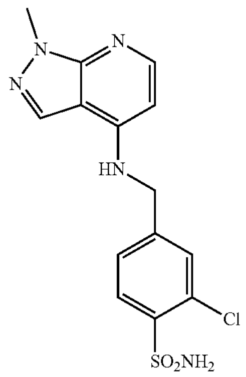 [SMILES: Cn1ncc2c(NCc3ccc(S(N)(=O)=O)c(Cl)c3)ccnc21] |

TABLE 2-continued
| Cmpd. | Structure |
| --- | --- |
| 2.69 | 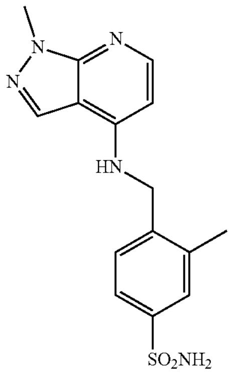 [SMILES: Cc1cc(S(N)(=O)=O)ccc1CNc1ccnc2c1cnn2C] |
| 2.70 | 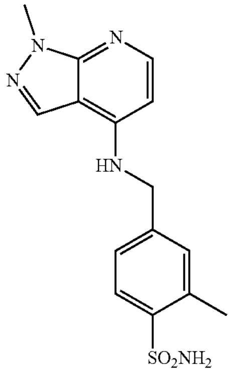 [SMILES: Cc1cc(CNc2ccnc3c2cnn3C)ccc1S(N)(=O)=O] |
| 2.71 | 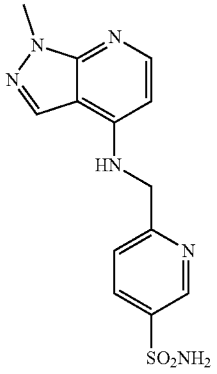 |
| 2.72 | 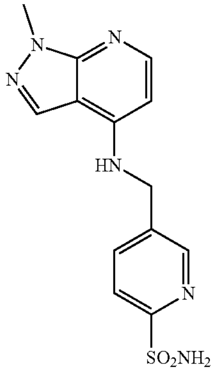 |
TABLE 2-continued
| Cmpd. | Structure |
| --- | --- |
| 2.73 | 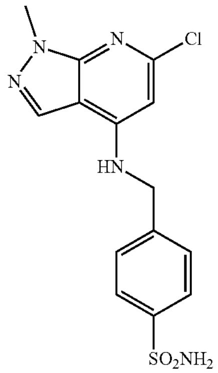 [SMILES: Cn1ncc2c(NCc3ccc(S(N)(=O)=O)cc3)cc(Cl)nc21] |
| 2.74 | 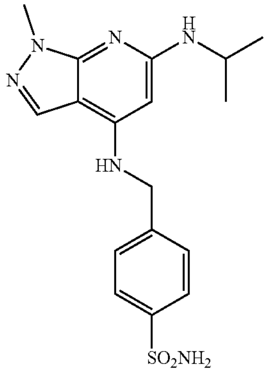 [SMILES: CC(C)Nc1cc(NCc2ccc(S(N)(=O)=O)cc2)c2cnn(C)c2n1] |
| 2.75 | 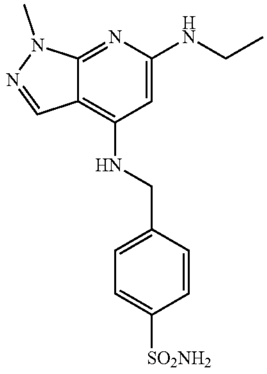 [SMILES: CCNc1cc(NCc2ccc(S(N)(=O)=O)cc2)c2cnn(C)c2n1] |
| 2.76 | 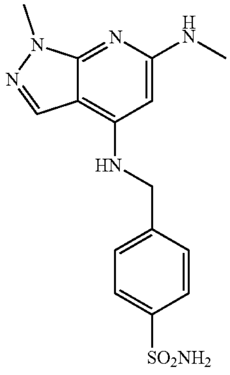 [SMILES: CNc1cc(NCc2ccc(S(N)(=O)=O)cc2)c2cnn(C)c2n1] |

TABLE 2-continued
| Cmpd. | Structure |
| --- | --- |
| 2.77 | 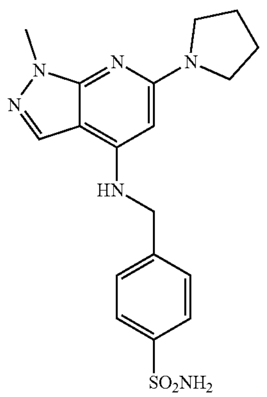 [SMILES: Cn1ncc2c(NCc3ccc(S(N)(=O)=O)cc3)cc(N3CCCC3)nc21] |
| 2.78 | 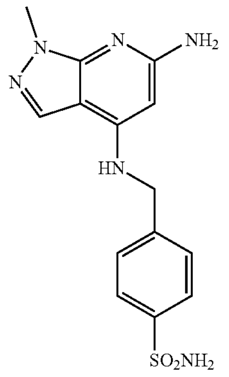 [SMILES: Cn1ncc2c(NCc3ccc(S(N)(=O)=O)cc3)cc(N)nc21] |
| 2.79 | 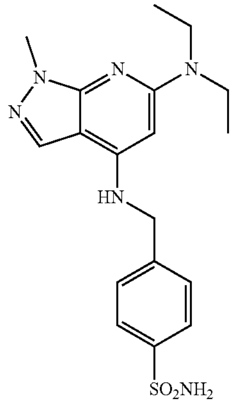 [SMILES: CCN(CC)c1cc(NCc2ccc(S(N)(=O)=O)cc2)c2cnn(C)c2n1] |
| 2.80 | 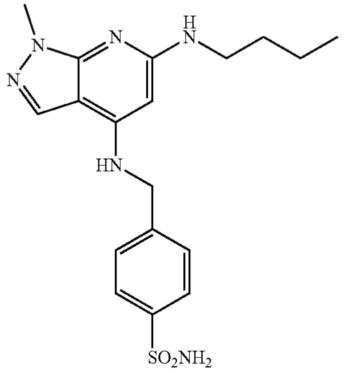 [SMILES: CCCCNc1cc(NCc2ccc(S(N)(=O)=O)cc2)c2cnn(C)c2n1] |
| 2.81 | 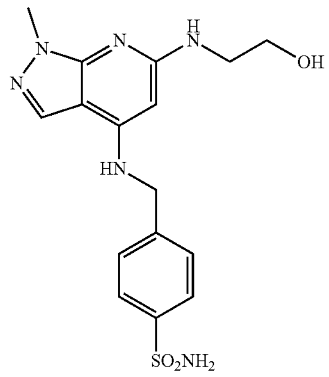 [SMILES: Cn1ncc2c(NCc3ccc(S(N)(=O)=O)cc3)cc(NCCO)nc21] |
| 2.82 | 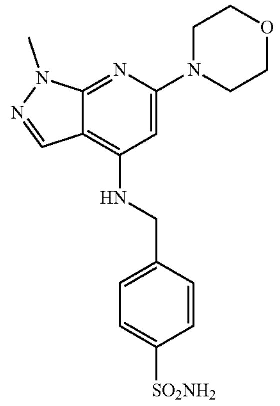 [SMILES: Cn1ncc2c(NCc3ccc(S(N)(=O)=O)cc3)cc(N3CCOCC3)nc21] |
| 2.83 | 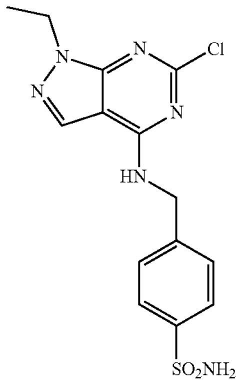 [SMILES: CCn1ncc2c(NCc3ccc(S(N)(=O)=O)cc3)nc(Cl)nc21] |
| 2.84 | 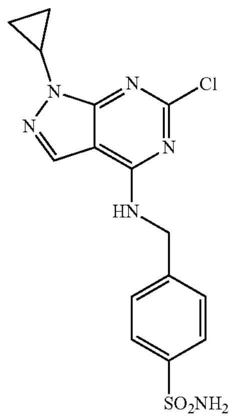 [SMILES: NS(=O)(=O)c1ccc(CNc2nc(Cl)nc3c2cnn3C2CC2)cc1] |

TABLE 2-continued
| Cmpd. | Structure |
| --- | --- |
| 2.85 | 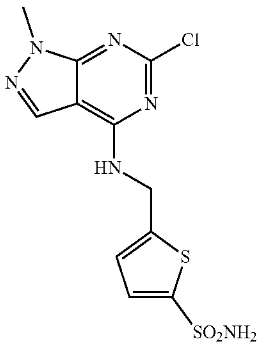 [SMILES: Cn1ncc2c(NCc3ccc(S(N)(=O)=O)s3)nc(Cl)nc21] |
| 2.86 | 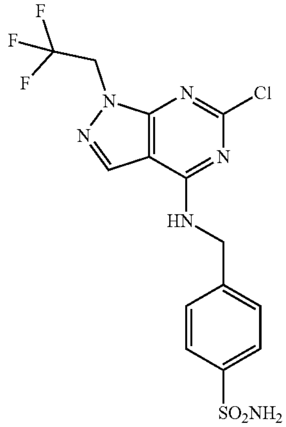 [SMILES: NS(=O)(=O)c1ccc(CNc2nc(Cl)nc3c2cnn3CC(F)(F)F)cc1] |
| 2.87 | 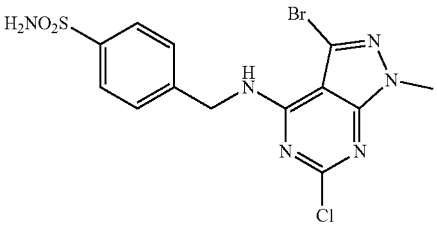 [SMILES: Cn1nc(Br)c2c(NCc3ccc(S(N)(=O)=O)cc3)nc(Cl)nc21] |
| 2.88 | 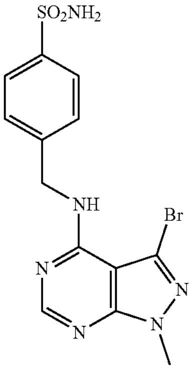 [SMILES: Cn1nc(Br)c2c(NCc3ccc(S(N)(=O)=O)cc3)ncnc21] |
| 2.89 | 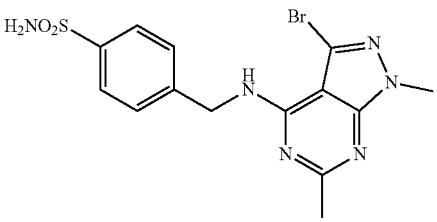 [SMILES: Cc1nc(NCc2ccc(S(N)(=O)=O)cc2)c2c(Br)nn(C)c2n1] |
TABLE 2-continued
| Cmpd. | Structure |
| --- | --- |
| 2.90 | 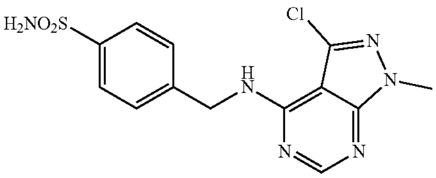 [SMILES: Cn1nc(Cl)c2c(NCc3ccc(S(N)(=O)=O)cc3)ncnc21] |
| 2.91 | 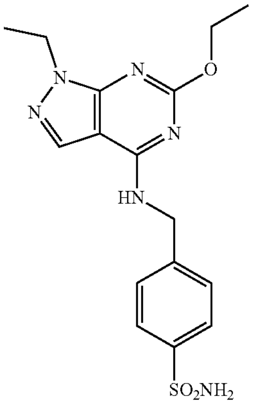 [SMILES: CCOc1nc(NCc2ccc(S(N)(=O)=O)cc2)c2cnn(CC)c2n1] |
| 2.92 | 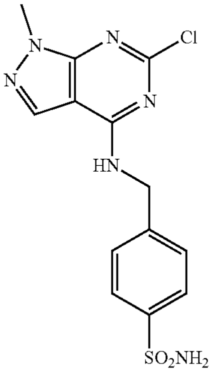 [SMILES: Cn1ncc2c(NCc3ccc(S(N)(=O)=O)cc3)nc(Cl)nc21] |
| 2.93 | 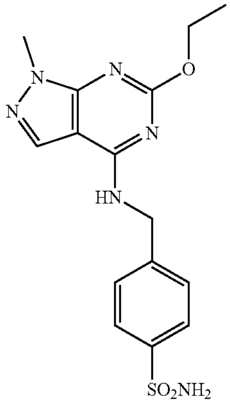 |

TABLE 2-continued
| Cmpd. | Structure |
|---|---|
| 2.94 | 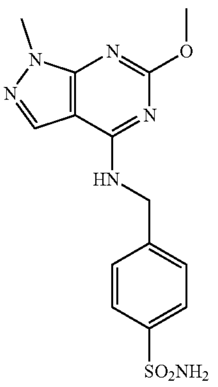 |
| 2.95 | 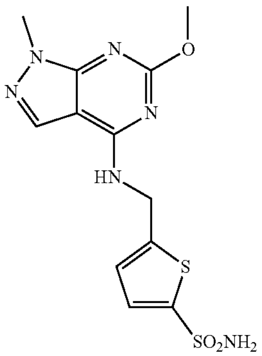 [SMILES: COc1nc(NCc2ccc(S(N)(=O)=O)s2)c2cnn(C)c2n1] |
| 2.96 | 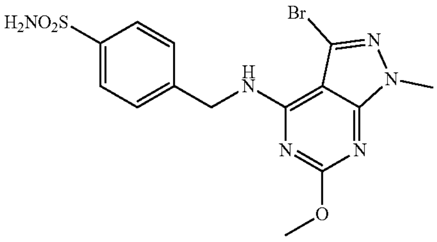 [SMILES: COc1nc(NCc2ccc(S(N)(=O)=O)cc2)c2c(Br)nn(C)c2n1] |
| 2.97 | 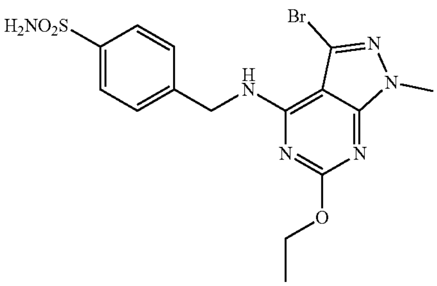 [SMILES: CCOc1nc(NCc2ccc(S(N)(=O)=O)cc2)c2c(Br)nn(C)c2n1] |
TABLE 2-continued
| Cmpd. | Structure |
|---|---|
| 2.98 | 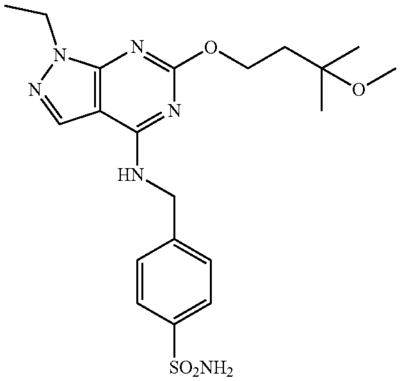 [SMILES: CCn1ncc2c(NCc3ccc(S(N)(=O)=O)cc3)nc(OCCC(C)(C)OC)nc21] |
| 2.99 | 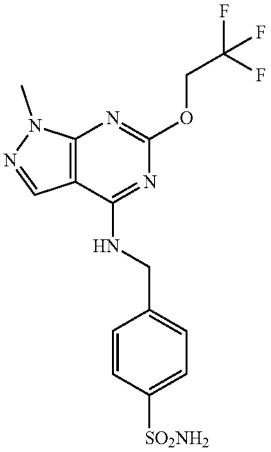 [SMILES: Cn1ncc2c(NCc3ccc(S(N)(=O)=O)cc3)nc(OCC(F)(F)F)nc21] |
| 2.100 | 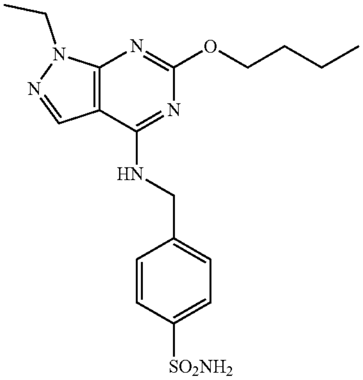 [SMILES: CCCCOc1nc(NCc2ccc(S(N)(=O)=O)cc2)c2cnn(CC)c2n1] |
| 2.101 | 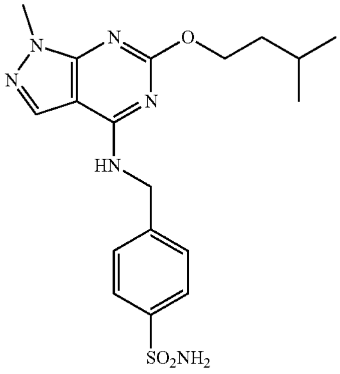 [SMILES: CC(C)CCOc1nc(NCc2ccc(S(N)(=O)=O)cc2)c2cnn(C)c2n1] |

TABLE 2-continued
| Cmpd. | Structure |
|---|---|
| 2.102 | 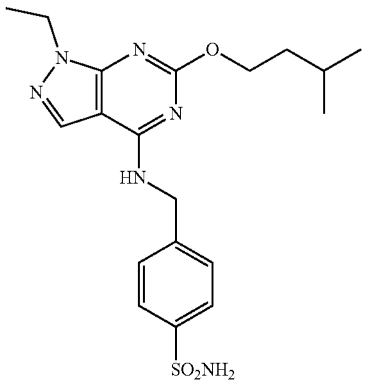 [SMILES: CCn1ncc2c(NCc3ccc(S(N)(=O)=O)cc3)nc(OCCC(C)C)nc21] |
| 2.103 | 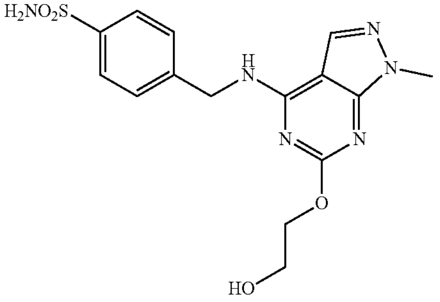 [SMILES: Cn1ncc2c(NCc3ccc(S(N)(=O)=O)cc3)nc(OCCO)nc21] |
| 2.104 | 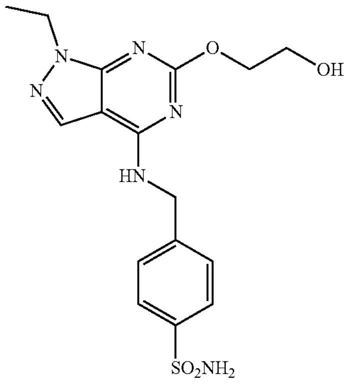 [SMILES: CCn1ncc2c(NCc3ccc(S(N)(=O)=O)cc3)nc(OCCO)nc21] |
| 2.105 | 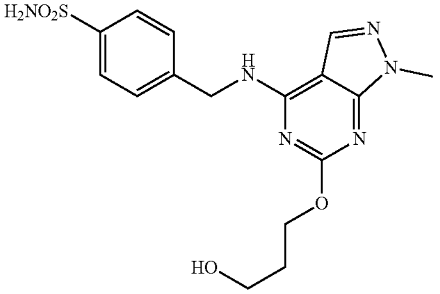 [SMILES: Cn1ncc2c(NCc3ccc(S(N)(=O)=O)cc3)nc(OCCCO)nc21] |
TABLE 2-continued
| Cmpd. | Structure |
|---|---|
| 2.106 | 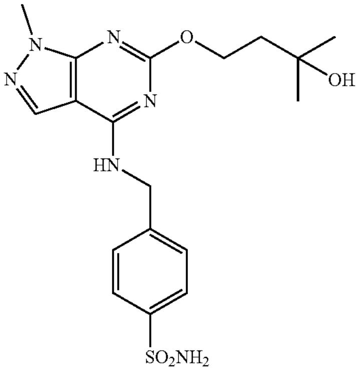 [SMILES: Cn1ncc2c(NCc3ccc(S(N)(=O)=O)cc3)nc(OCCC(C)(C)O)nc21] |
| 2.107 | 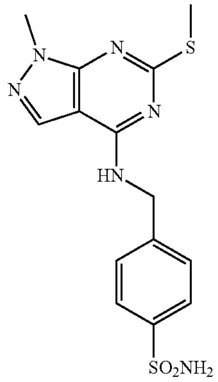 |
| 2.108 | 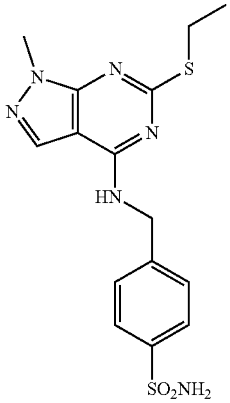 |
| 2.109 | 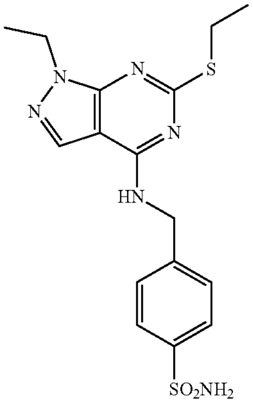 |

TABLE 2-continued
| Cmpd. | Structure |
|---|---|
| 2.110 | 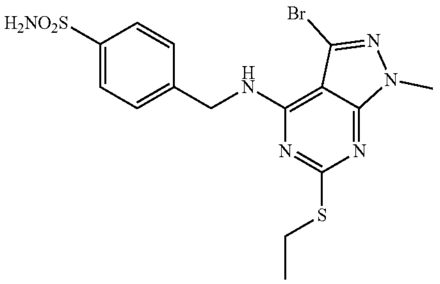 |
| 2.111 | 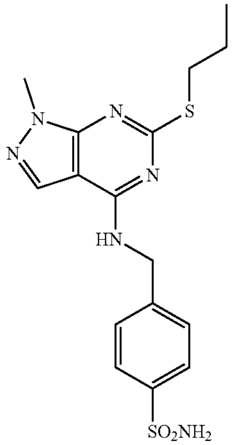 [SMILES: CCCSc1nc(NCc2ccc(S(N)(=O)=O)cc2)c2cnn(C)c2n1] |
| 2.112 | 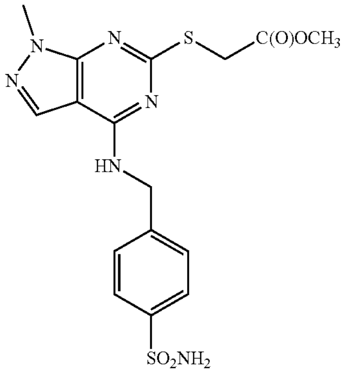 |
| 2.113 | 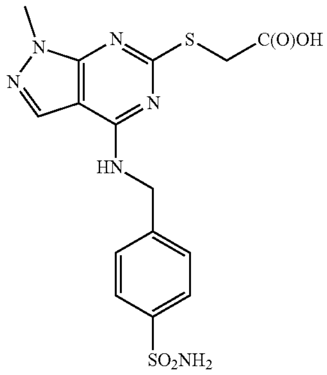 |
TABLE 2-continued
| Cmpd. | Structure |
|---|---|
| 2.114 | 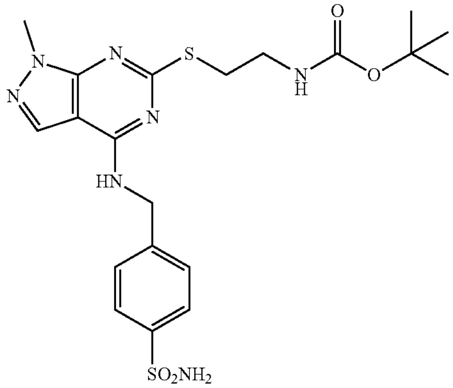 [SMILES: Cn1ncc2c(NCc3ccc(S(N)(=O)=O)cc3)nc(SCCNC(=O)OC(C)(C)C)nc21] |
| 2.115 | 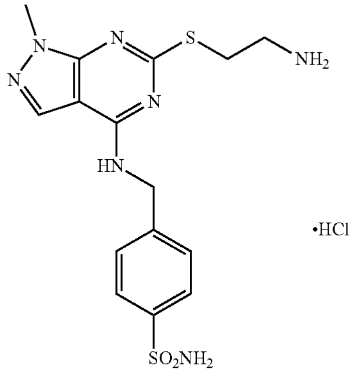 [SMILES: Cn1ncc2c(NCc3ccc(S(N)(=O)=O)cc3)nc(SCCN)nc21 ; Cl] •HCl |
| 2.116 | 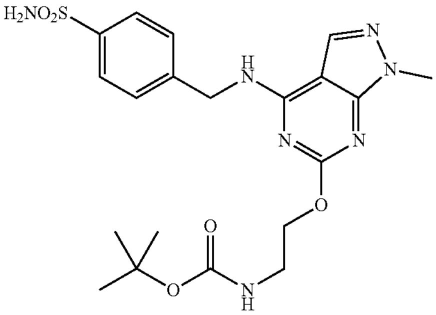 [SMILES: Cn1ncc2c(NCc3ccc(S(N)(=O)=O)cc3)nc(OCCNC(=O)OC(C)(C)C)nc21] |
| 2.117 | 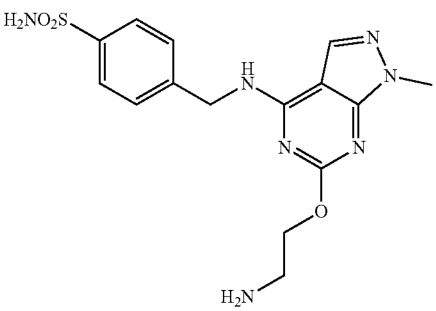 [SMILES: Cn1ncc2c(NCc3ccc(S(N)(=O)=O)cc3)nc(OCCN)nc21] |

TABLE 2-continued
| Cmpd. | Structure |
| --- | --- |
| 2.118 | 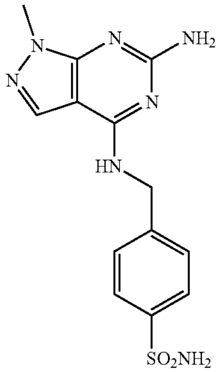 [SMILES: Cn1ncc2c(NCc3ccc(S(N)(=O)=O)cc3)nc(N)nc21] |
| 2.119 | 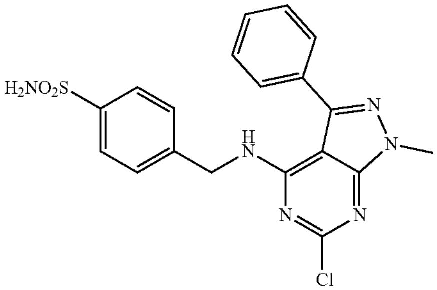 [SMILES: Cn1nc(-c2ccccc2)c2c(NCc3ccc(S(N)(=O)=O)cc3)nc(Cl)nc21] |
| 2.120 | 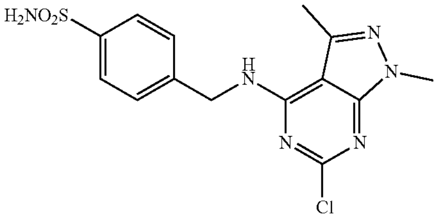 [SMILES: Cc1nn(C)c2nc(Cl)nc(NCc3ccc(S(N)(=O)=O)cc3)c12] |
| 2.121 | 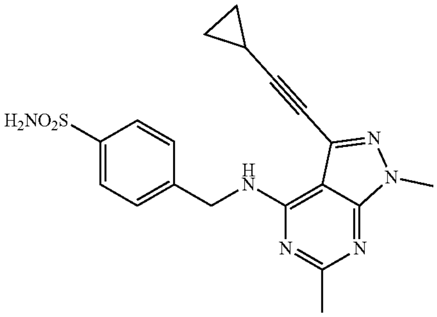 [SMILES: Cc1nc(NCc2ccc(S(N)(=O)=O)cc2)c2c(C#CC3CC3)nn(C)c2n1] |
| 2.122 | 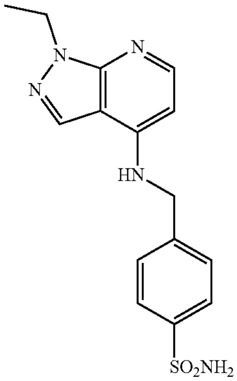 [SMILES: CCn1ncc2c(NCc3ccc(S(N)(=O)=O)cc3)ccnc21] |
TABLE 2-continued
| Cmpd. | Structure |
| --- | --- |
| 2.123 | 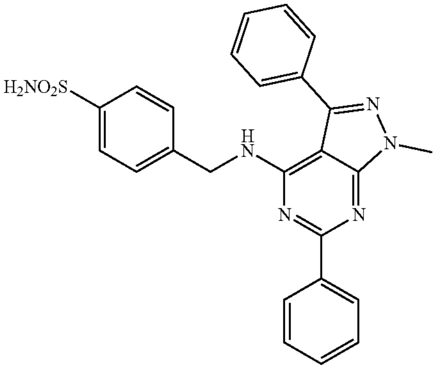 [SMILES: Cn1nc(-c2ccccc2)c2c(NCc3ccc(S(N)(=O)=O)cc3)nc(-c3ccccc3)nc21] |
| 2.124 | 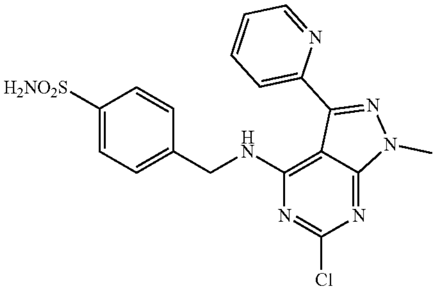 [SMILES: Cn1nc(-c2ccccn2)c2c(NCc3ccc(S(N)(=O)=O)cc3)nc(Cl)nc21] |
| 2.125 | 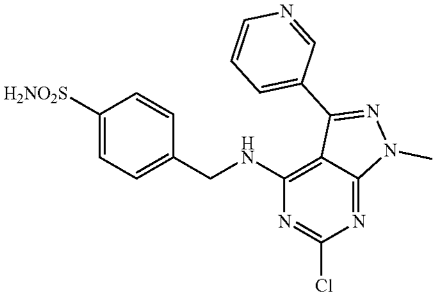 [SMILES: Cn1nc(-c2cccnc2)c2c(NCc3ccc(S(N)(=O)=O)cc3)nc(Cl)nc21] |
| 2.126 | 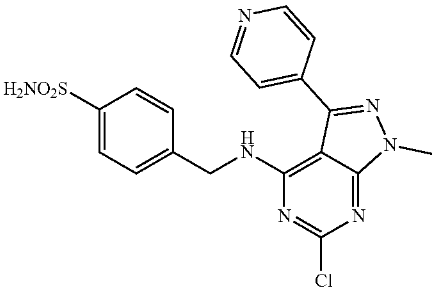 [SMILES: Cn1nc(-c2ccncc2)c2c(NCc3ccc(S(N)(=O)=O)cc3)nc(Cl)nc21] |
| 2.127 | 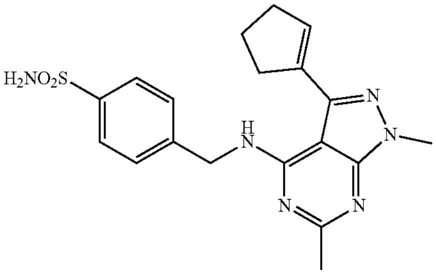 [SMILES: Cc1nc(NCc2ccc(S(N)(=O)=O)cc2)c2c(C3=CCCC3)nn(C)c2n1] |

TABLE 2-continued
| Cmpd. | Structure |
|---|---|
| 2.128 | 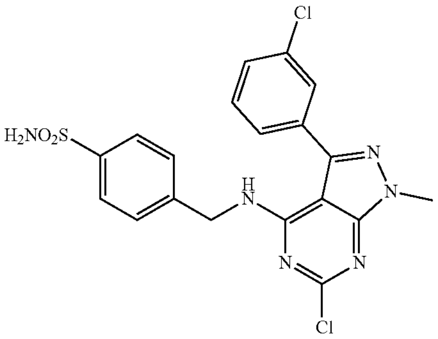 [SMILES: Cn1nc(-c2cccc(Cl)c2)c2c(NCc3ccc(S(N)(=O)=O)cc3)nc(Cl)nc21] |
| 2.129 | 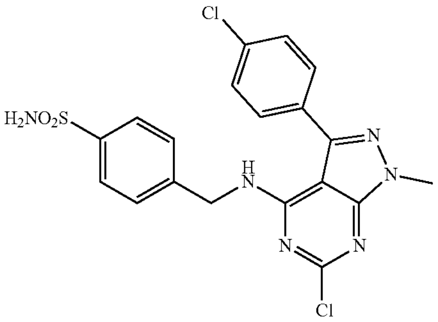 [SMILES: Cn1nc(-c2ccc(Cl)cc2)c2c(NCc3ccc(S(N)(=O)=O)cc3)nc(Cl)nc21] |
| 2.130 | 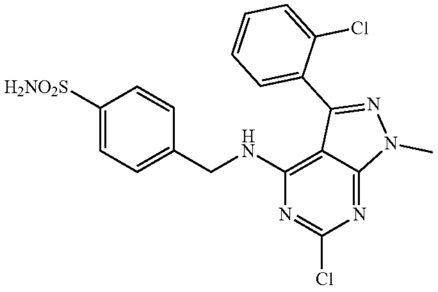 [SMILES: Cn1nc(-c2ccccc2Cl)c2c(NCc3ccc(S(N)(=O)=O)cc3)nc(Cl)nc21] |
| 2.131 | 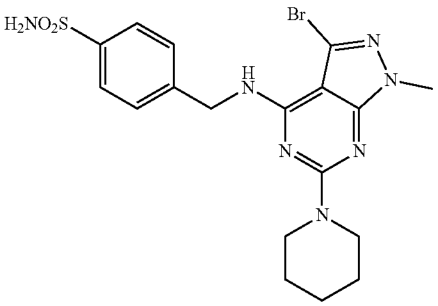 [SMILES: Cn1nc(Br)c2c(NCc3ccc(S(N)(=O)=O)cc3)nc(N3CCCCC3)nc21] |
TABLE 2-continued
| Cmpd. | Structure |
|---|---|
| 2.132 | 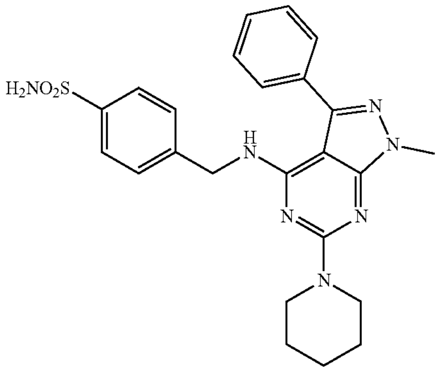 [SMILES: Cn1nc(-c2ccccc2)c2c(NCc3ccc(S(N)(=O)=O)cc3)nc(N3CCCCC3)nc21] |
| 2.133 | 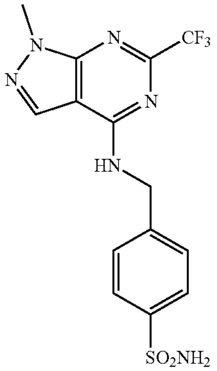 [SMILES: Cn1ncc2c(NCc3ccc(S(N)(=O)=O)cc3)nc(C(F)(F)F)nc21] |
| 2.134 | 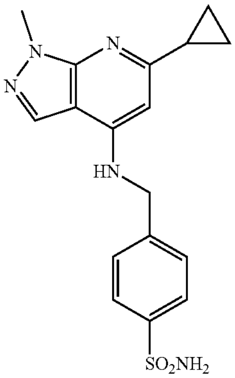 [SMILES: Cn1ncc2c(NCc3ccc(S(N)(=O)=O)cc3)cc(C3CC3)nc21] |
| 2.135 | 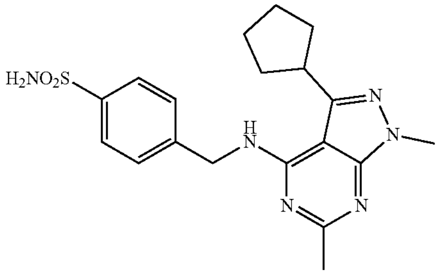 [SMILES: Cc1nc(NCc2ccc(S(N)(=O)=O)cc2)c2c(C3CCCC3)nn(C)c2n1] |
| 2.136 | 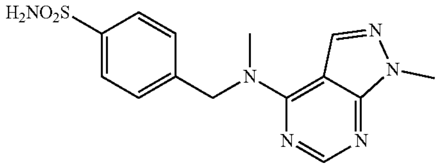 [SMILES: CN(Cc1ccc(S(N)(=O)=O)cc1)c1ncnc2c1cnn2C] |

TABLE 2-continued
| Cmpd. | Structure |
|---|---|
| 2.137 | 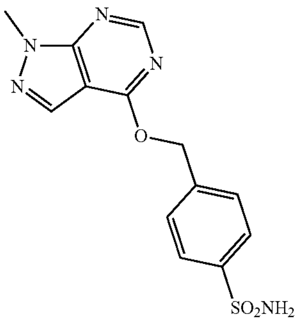 [SMILES: Cn1ncc2c(OCc3ccc(S(N)(=O)=O)cc3)ncnc21] |
| 2.139 | 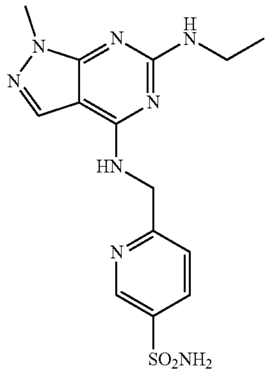 [SMILES: CCNc1nc(NCc2ccc(S(N)(=O)=O)cn2)c2cnn(C)c2n1] |
| 2.140 | 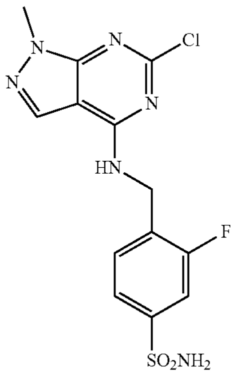 [SMILES: Cn1ncc2c(NCc3ccc(S(N)(=O)=O)cc3F)nc(Cl)nc21] |
| 2.141 | 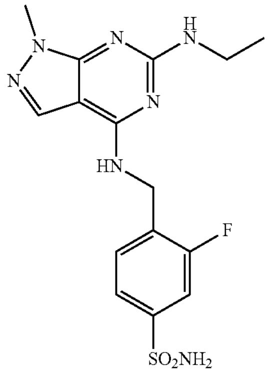 |
TABLE 2-continued
| Cmpd. | Structure |
|---|---|
| 2.142 | 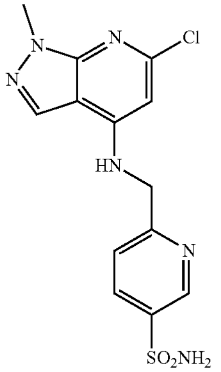 [SMILES: Cn1ncc2c(NCc3ccc(S(N)(=O)=O)cn3)cc(Cl)nc21] |
| 2.143 | 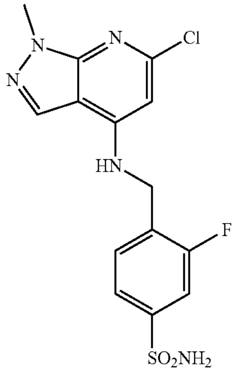 |
| 2.144 | 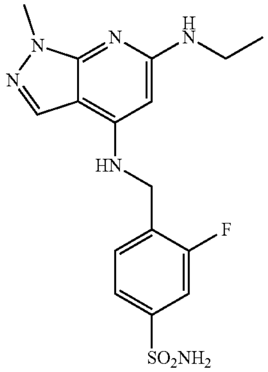 [SMILES: CCNc1cc(NCc2ccc(S(N)(=O)=O)cc2F)c2cnn(C)c2n1] |
TABLE 3
| Cmpd. | Structure |
|---|---|
| 3.0 | 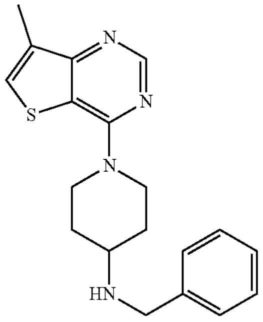 [SMILES: Cc1csc2c(N3CCC(NCc4ccccc4)CC3)ncnc12] |

TABLE 3-continued
| Cmpd. | Structure |
|---|---|
| 3.1 | 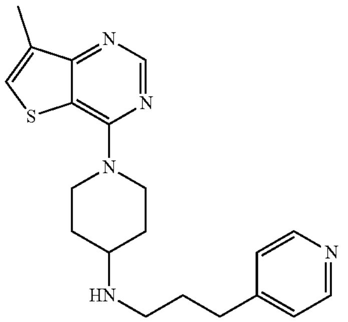 [SMILES: Cc1csc2c(N3CCC(NCCCc4ccncc4)CC3)ncnc12] |
| 3.2 | 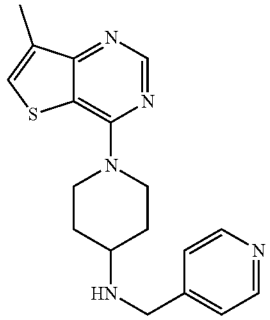 [SMILES: Cc1csc2c(N3CCC(NCc4ccncc4)CC3)ncnc12] |
| 3.3 | 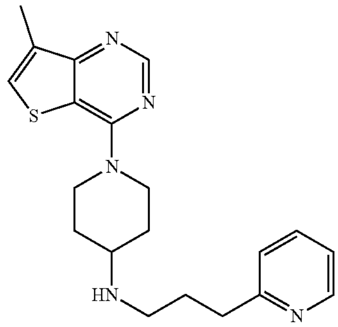 [SMILES: Cc1csc2c(N3CCC(NCCCc4ccccn4)CC3)ncnc12] |
| 3.4 | 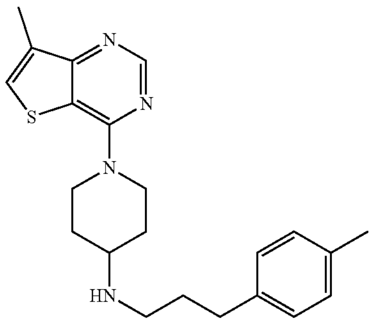 [SMILES: Cc1ccc(CCCNC2CCN(c3ncnc4c(C)csc34)CC2)cc1] |
TABLE 3-continued
| Cmpd. | Structure |
|---|---|
| 3.5 | 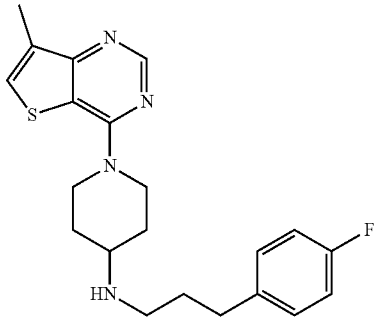 [SMILES: Cc1csc2c(N3CCC(NCCCc4ccc(F)cc4)CC3)ncnc12] |
| 3.6 | 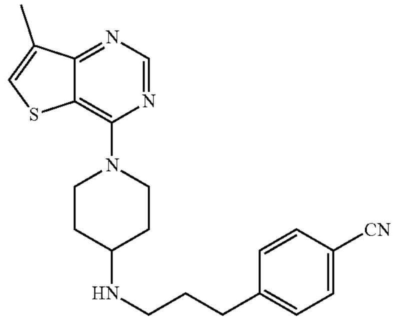 [SMILES: Cc1csc2c(N3CCC(NCCCc4ccc(C#N)cc4)CC3)ncnc12] |
| 3.7 | 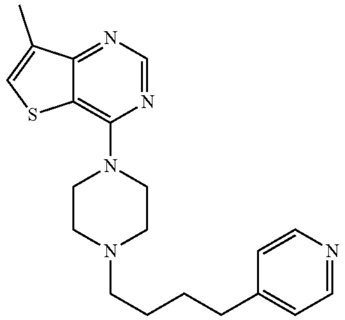 [SMILES: Cc1csc2c(N3CCN(CCCCc4ccncc4)CC3)ncnc12] |
| 3.8 | 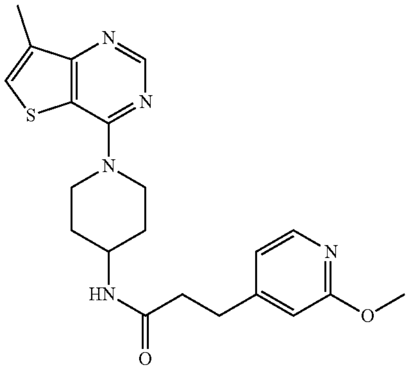 [SMILES: COc1cc(CCC(=O)NC2CCN(c3ncnc4c(C)csc34)CC2)ccn1] |

TABLE 3-continued
| Cmpd. | Structure |
| --- | --- |
| 3.9 | 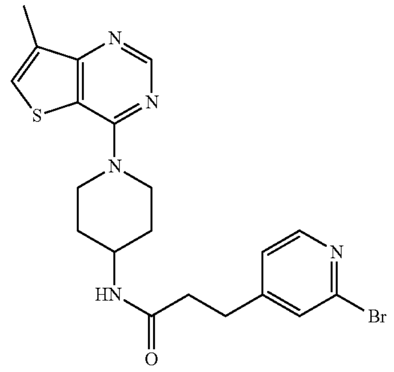 [SMILES: Cc1csc2c(N3CCC(NC(=O)CCc4ccnc(Br)c4)CC3)ncnc12] |
| 3.10 | 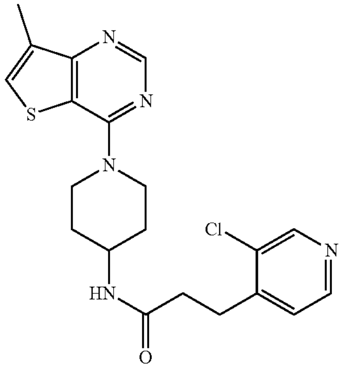 |
| 3.11 | 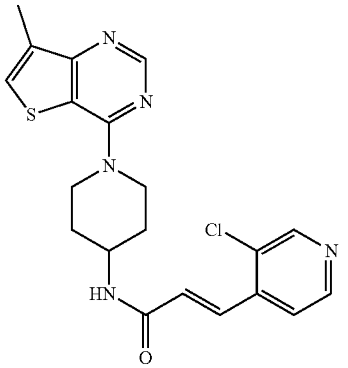 |
| 3.12 | 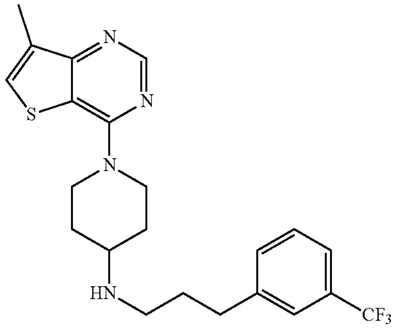 |
TABLE 3-continued
| Cmpd. | Structure |
| --- | --- |
| 3.13 | 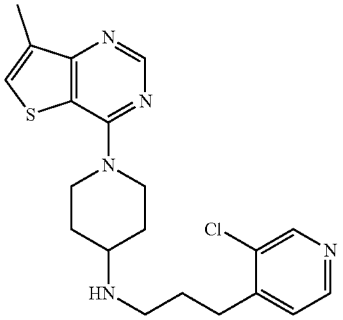 [SMILES: Cc1csc2c(N3CCC(NCCCc4ccncc4Cl)CC3)ncnc12] |
| 3.14 | 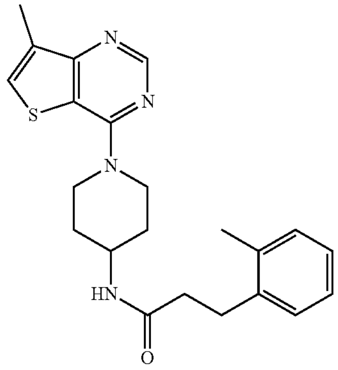 [SMILES: Cc1ccccc1CCC(=O)NC1CCN(c2ncnc3c(C)csc23)CC1] |
| 3.15 | 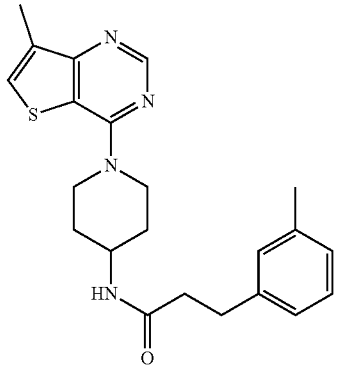 [SMILES: Cc1cccc(CCC(=O)NC2CCN(c3ncnc4c(C)csc34)CC2)c1] |
| 3.16 | 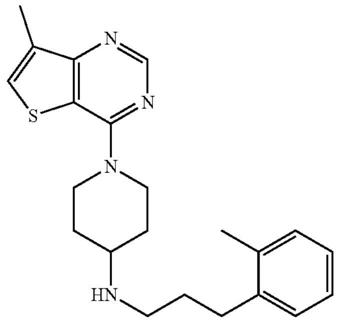 [SMILES: Cc1ccccc1CCCNC1CCN(c2ncnc3c(C)csc23)CC1] |

TABLE 3-continued
| Cmpd. | Structure |
|---|---|
| 3.17 | 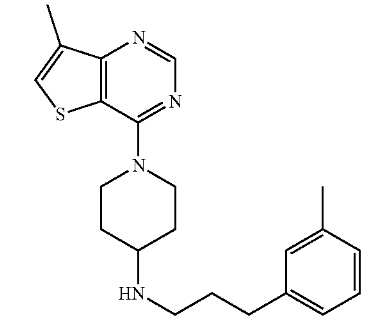 [SMILES: Cc1cccc(CCCNC2CCN(c3ncnc4c(C)csc34)CC2)c1] |
| 3.18 | 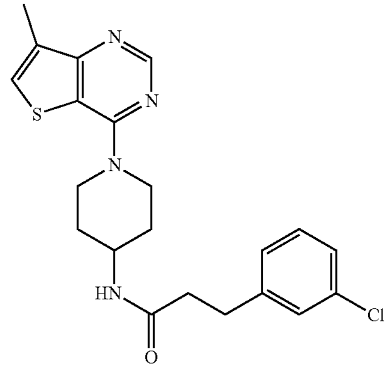 [SMILES: Cc1csc2c(N3CCC(NC(=O)CCc4cccc(Cl)c4)CC3)ncnc12] |
| 3.19 | 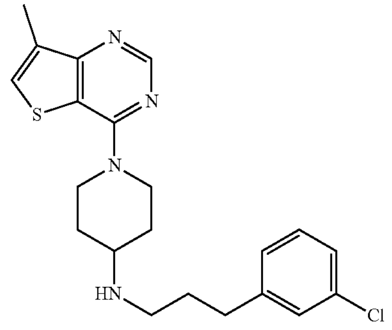 [SMILES: Cc1csc2c(N3CCC(NCCCc4cccc(Cl)c4)CC3)ncnc12] |
| 3.20 | 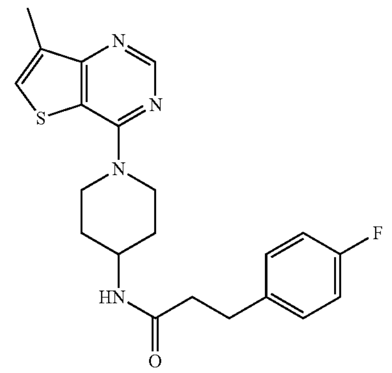 [SMILES: Cc1csc2c(N3CCC(NC(=O)CCc4ccc(F)cc4)CC3)ncnc12] |
TABLE 3-continued
| Cmpd. | Structure |
|---|---|
| 3.22 | 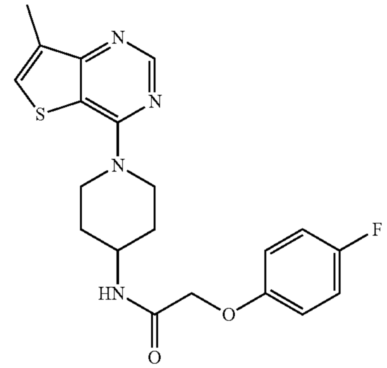 [SMILES: Cc1csc2c(N3CCC(NC(=O)COc4ccc(F)cc4)CC3)ncnc12] |
| 3.23 | 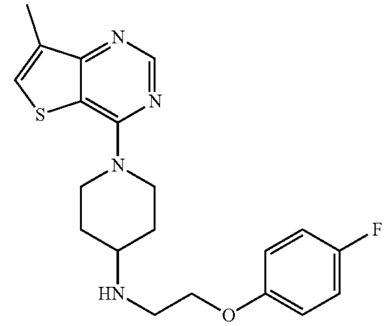 [SMILES: Cc1csc2c(N3CCC(NCCOc4ccc(F)cc4)CC3)ncnc12] |
| 3.24 | 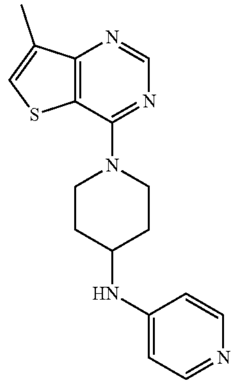 [SMILES: Cc1csc2c(N3CCC(Nc4ccncc4)CC3)ncnc12] |
| 3.25 | 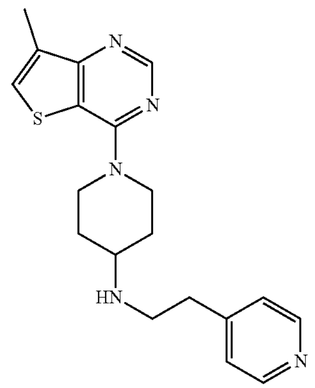 [SMILES: Cc1csc2c(N3CCC(NCCc4ccncc4)CC3)ncnc12] |

TABLE 3-continued
| Cmpd. | Structure |
|---|---|
| 3.26 | 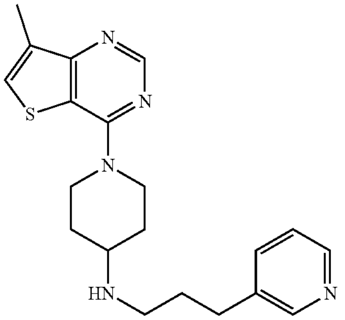 [SMILES: Cc1csc2c(N3CCC(NCCCc4cccnc4)CC3)ncnc12] |
| 3.27 | 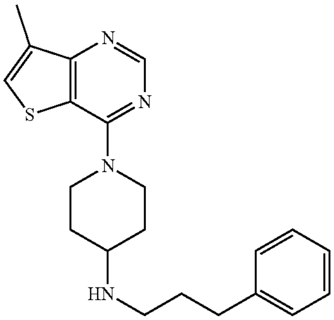 |
| 3.28 | 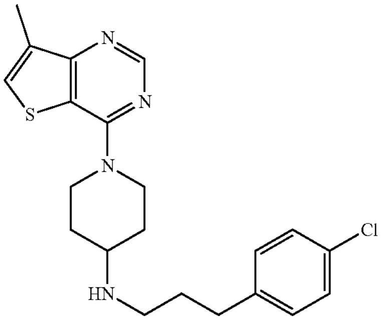 [SMILES: Cc1csc2c(N3CCC(NCCCc4ccc(Cl)cc4)CC3)ncnc12] |
| 3.29 | 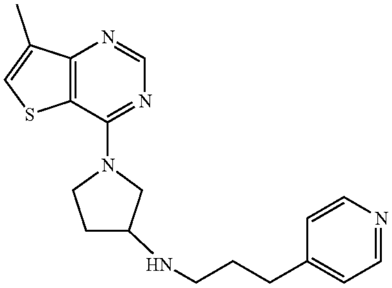 [SMILES: Cc1csc2c(N3CCC(NCCCc4ccncc4)C3)ncnc12] |
| 3.30 | 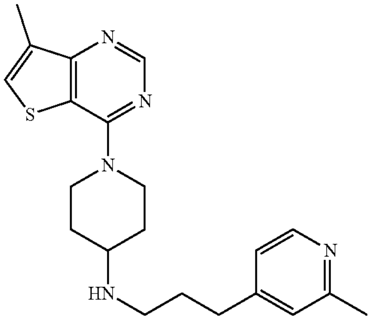 [SMILES: Cc1cc(CCCNC2CCN(c3ncnc4c(C)csc34)CC2)ccn1] |
TABLE 3-continued
| Cmpd. | Structure |
|---|---|
| 3.31 | 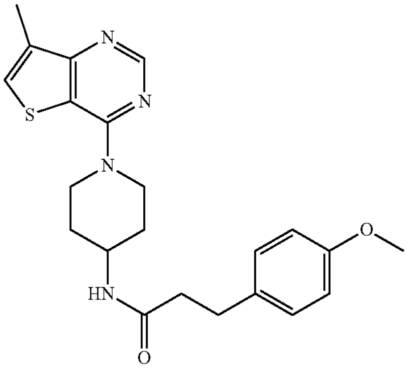 [SMILES: COc1ccc(CCC(=O)NC2CCN(c3ncnc4c(C)csc34)CC2)cc1] |
| 3.32 | 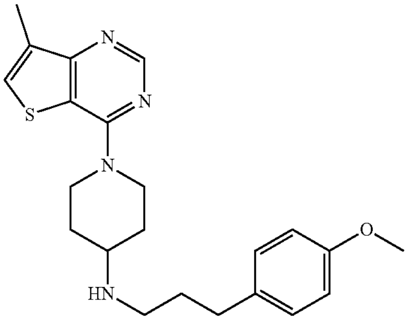 [SMILES: COc1ccc(CCCNC2CCN(c3ncnc4c(C)csc34)CC2)cc1] |
| 3.33 | 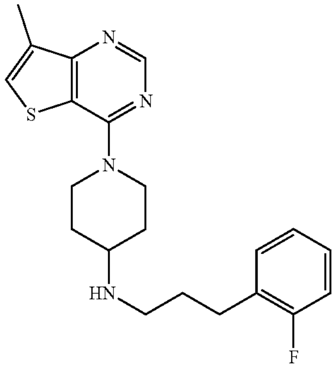 [SMILES: Cc1csc2c(N3CCC(NCCCc4ccccc4F)CC3)ncnc12] |
| 3.34 | 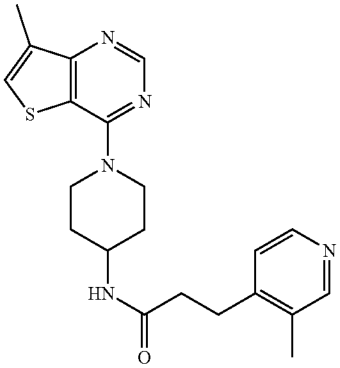 [SMILES: Cc1cnccc1CCC(=O)NC1CCN(c2ncnc3c(C)csc23)CC1] |

TABLE 3-continued
| Cmpd. | Structure |
|---|---|
| 3.35 | 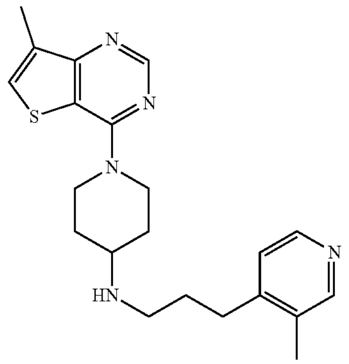 [SMILES: Cc1cnccc1CCCNC1CCN(c2ncnc3c(C)csc23)CC1] |
| 3.36 | 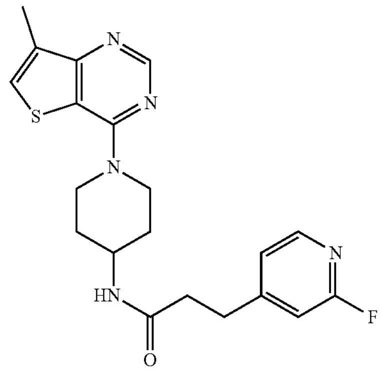 [SMILES: Cc1csc2c(N3CCC(NC(=O)CCc4ccnc(F)c4)CC3)ncnc12] |
| 3.37 | 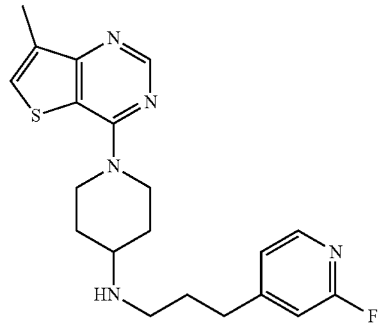 [SMILES: Cc1csc2c(N3CCC(NCCCc4ccnc(F)c4)CC3)ncnc12] |
| 3.38 | 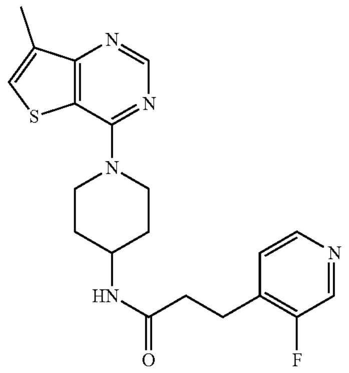 [SMILES: Cc1csc2c(N3CCC(NC(=O)CCc4ccncc4F)CC3)ncnc12] |
TABLE 3-continued
| Cmpd. | Structure |
|---|---|
| 3.39 | 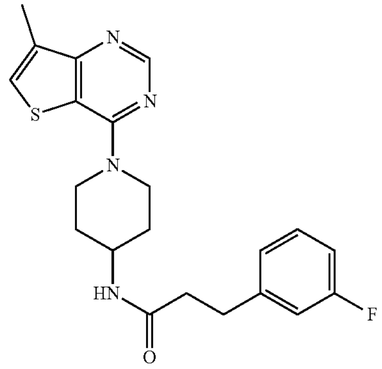 |
| 3.40 | 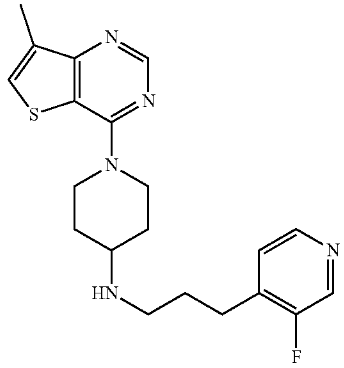 [SMILES: Cc1csc2c(N3CCC(NCCCc4ccncc4F)CC3)ncnc12] |
| 3.41 | 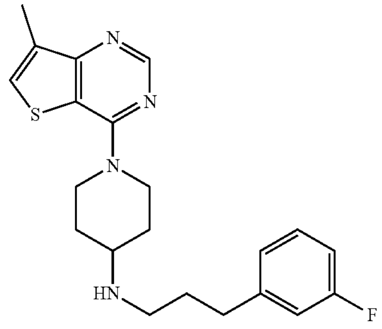 |
| 3.42 | 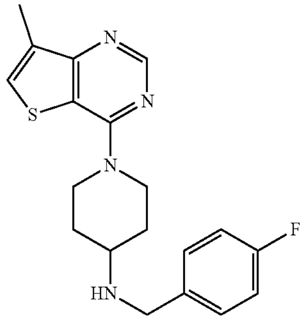 [SMILES: Cc1csc2c(N3CCC(NCc4ccc(F)cc4)CC3)ncnc12] |

TABLE 3-continued
| Cmpd. | Structure |
| --- | --- |
| 3.43 | 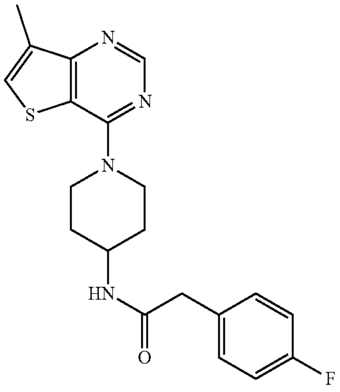 [SMILES: Cc1csc2c(N3CCC(NC(=O)Cc4ccc(F)cc4)CC3)ncnc12] |
| 3.44 | 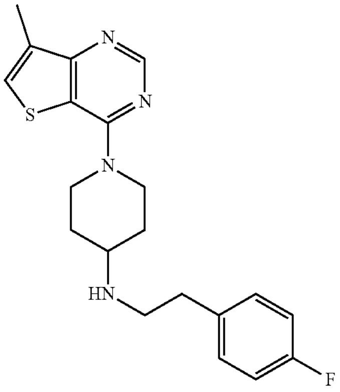 [SMILES: Cc1csc2c(N3CCC(NCCc4ccc(F)cc4)CC3)ncnc12] |
| 3.45 | 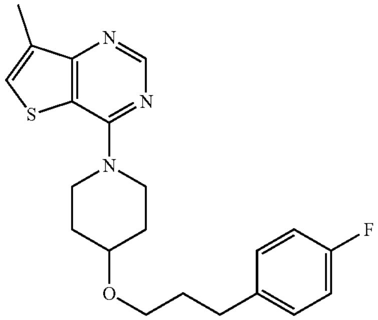 [SMILES: Cc1csc2c(N3CCC(OCCCc4ccc(F)cc4)CC3)ncnc12] |
| 3.46 | 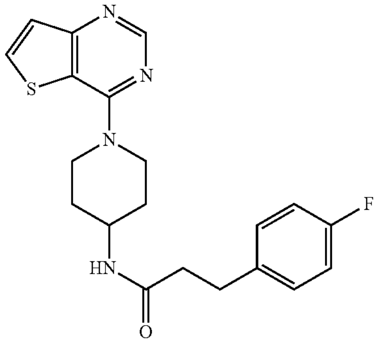 [SMILES: O=C(CCc1ccc(F)cc1)NC1CCN(c2ncnc3ccsc23)CC1] |
TABLE 3-continued
| Cmpd. | Structure |
| --- | --- |
| 3.47 | 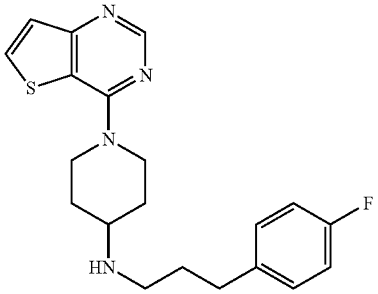 [SMILES: Fc1ccc(CCCNC2CCN(c3ncnc4ccsc34)CC2)cc1] |
| 3.48 | 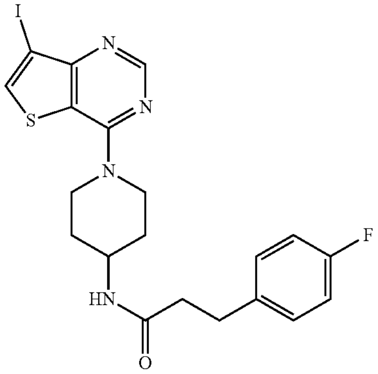 [SMILES: O=C(CCc1ccc(F)cc1)NC1CCN(c2ncnc3c(I)csc23)CC1] |
| 3.50 | 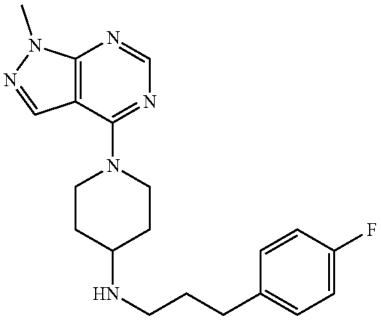 [SMILES: Cn1ncc2c(N3CCC(NCCCc4ccc(F)cc4)CC3)ncnc21] |
| 3.51 | 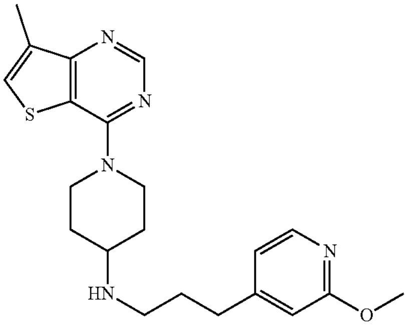 [SMILES: COc1cc(CCCNC2CCN(c3ncnc4c(C)csc34)CC2)ccn1] |

TABLE 3-continued
| Cmpd. | Structure |
| --- | --- |
| 3.52 | 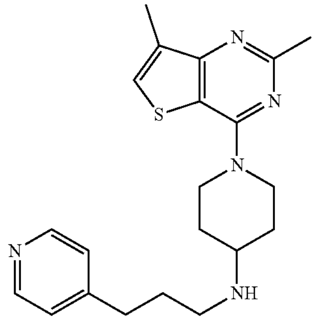 [SMILES: Cc1nc(N2CCC(NCCCc3ccncc3)CC2)c2scc(C)c2n1] |
| 3.53 | 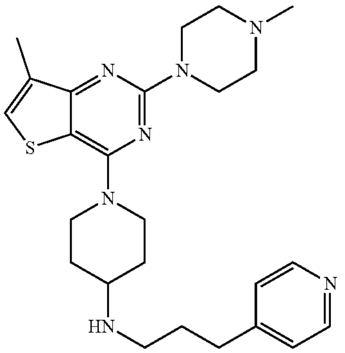 [SMILES: Cc1csc2c(N3CCC(NCCCc4ccncc4)CC3)nc(N3CCN(C)CC3)nc12] |
| 3.54 | 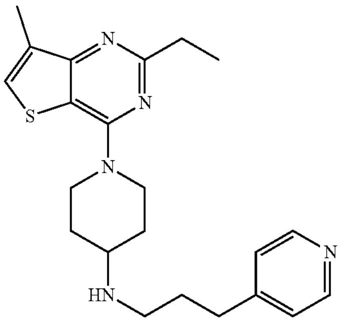 [SMILES: CCc1nc(N2CCC(NCCCc3ccncc3)CC2)c2scc(C)c2n1] |
| 3.55 | 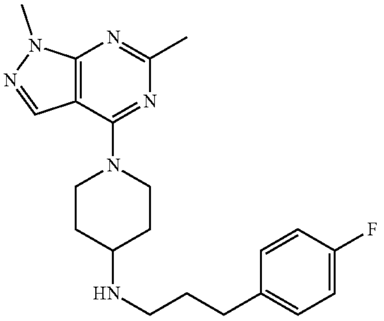 [SMILES: Cc1nc(N2CCC(NCCCc3ccc(F)cc3)CC2)c2cnn(C)c2n1] |
| 3.56 | 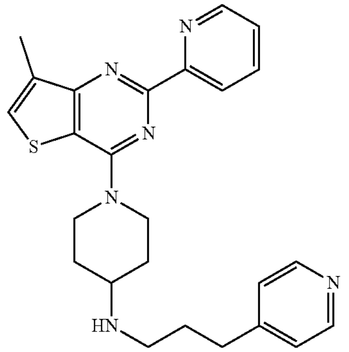 [SMILES: Cc1csc2c(N3CCC(NCCCc4ccncc4)CC3)nc(-c3ccccn3)nc12] |
| 3.57 | 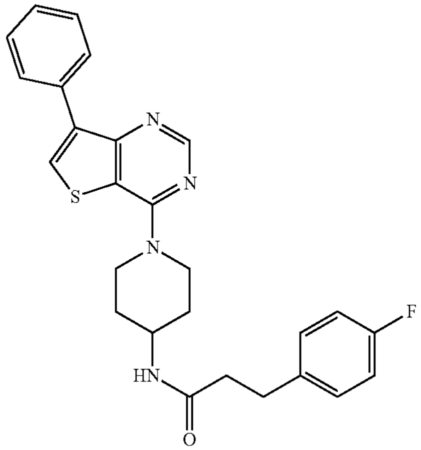 [SMILES: O=C(CCc1ccc(F)cc1)NC1CCN(c2ncnc3c(-c4ccccc4)csc23)CC1] |
| 3.58 | 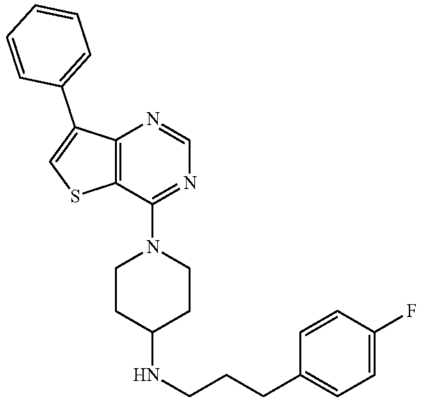 [SMILES: Fc1ccc(CCCNC2CCN(c3ncnc4c(-c5ccccc5)csc34)CC2)cc1] |
| 3.59 | 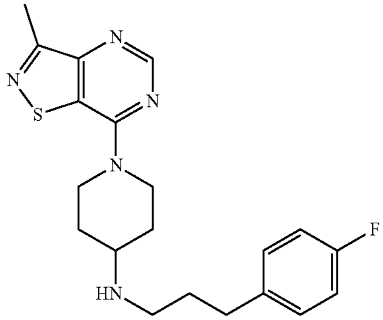 [SMILES: Cc1nsc2c(N3CCC(NCCCc4ccc(F)cc4)CC3)ncnc12] |

TABLE 3-continued
| Cmpd. | Structure |
| --- | --- |
| 3.60 | 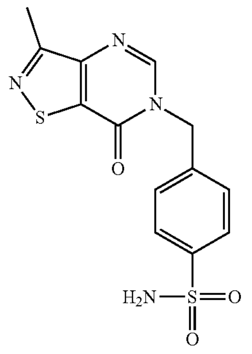 [SMILES: Cc1nsc2c(=O)n(Cc3ccc(S(N)(=O)=O)cc3)cnc12] |
| 3.61 | 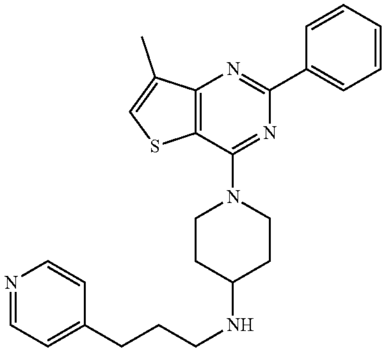 [SMILES: Cc1csc2c(N3CCC(NCCCc4ccncc4)CC3)nc(-c3ccccc3)nc12] |
| 3.62 | 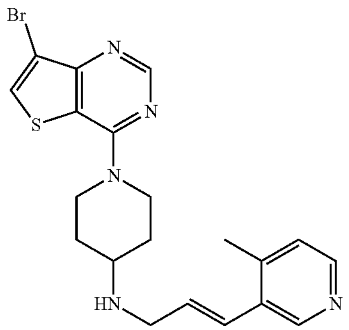 [SMILES: Cc1ccncc1/C=C/CNC1CCN(c2ncnc3c(Br)csc23)CC1] |
| 3.63 | 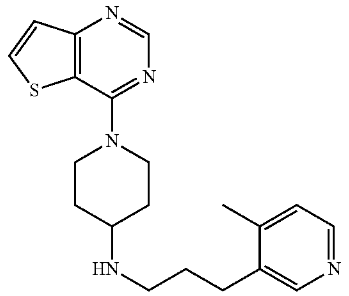 [SMILES: Cc1ccncc1CCCNC1CCN(c2ncnc3ccsc23)CC1] |
TABLE 3-continued
| Cmpd. | Structure |
| --- | --- |
| 3.64 | 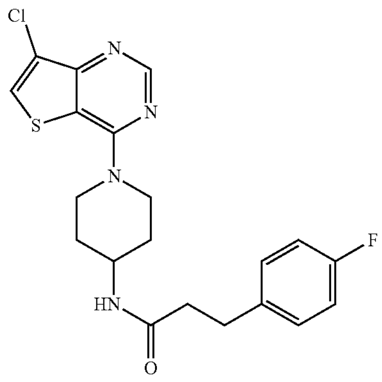 [SMILES: O=C(CCc1ccc(F)cc1)NC1CCN(c2ncnc3c(Cl)csc23)CC1] |
| 3.65 | 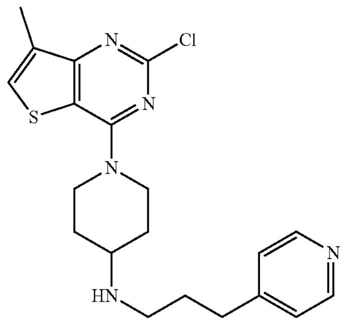 |
| 3.66 | 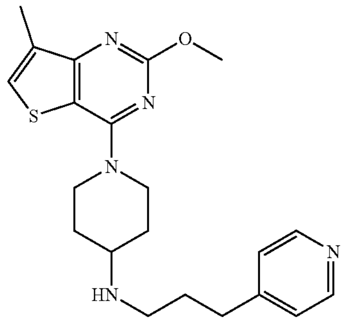 |
| 3.67 | 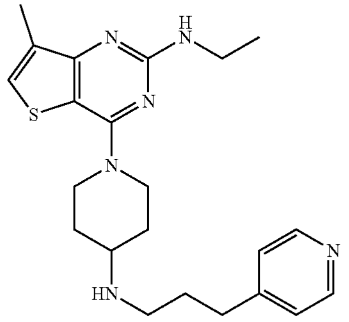 |

TABLE 3-continued
| Cmpd. | Structure |
|---|---|
| 3.68 | 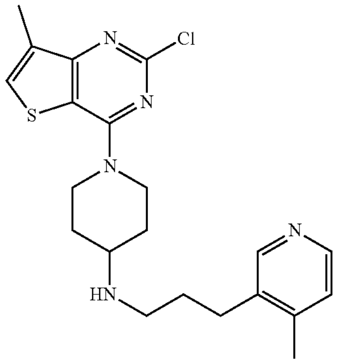 [SMILES: Cc1ccncc1CCCNC1CCN(c2nc(Cl)nc3c(C)csc23)CC1] |
| 3.69 | 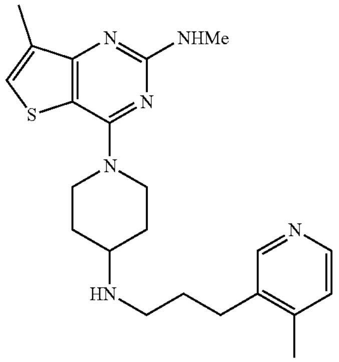 [SMILES: CNc1nc(N2CCC(NCCCc3cnccc3C)CC2)c2scc(C)c2n1] |
| 3.70 | 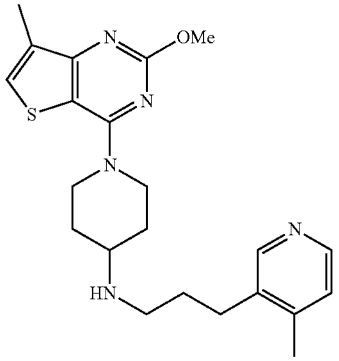 [SMILES: COc1nc(N2CCC(NCCCc3cnccc3C)CC2)c2scc(C)c2n1] |
| 3.71 | 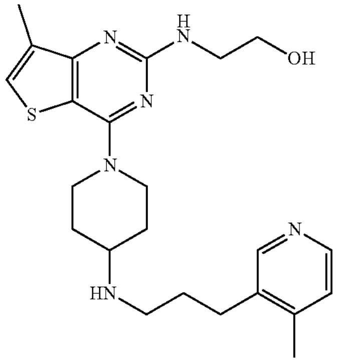 [SMILES: Cc1ccncc1CCCNC1CCN(c2nc(NCCO)nc3c(C)csc23)CC1] |
TABLE 3-continued
| Cmpd. | Structure |
|---|---|
| 3.72 | 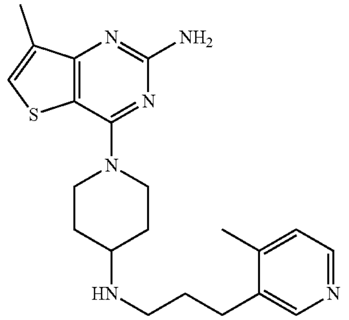 [SMILES: Cc1ccncc1CCCNC1CCN(c2nc(N)nc3c(C)csc23)CC1] |
| 3.73 | 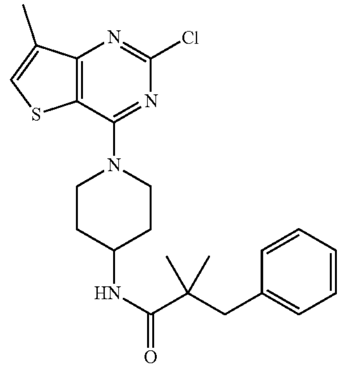 [SMILES: Cc1csc2c(N3CCC(NC(=O)C(C)(C)Cc4ccccc4)CC3)nc(Cl)nc12] |
| 3.74 | 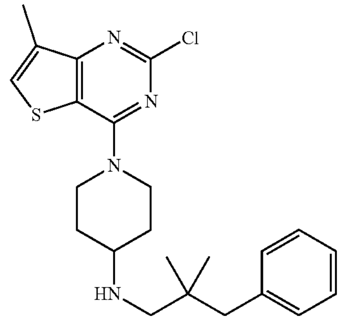 [SMILES: Cc1csc2c(N3CCC(NCC(C)(C)Cc4ccccc4)CC3)nc(Cl)nc12] |
| 3.75 | 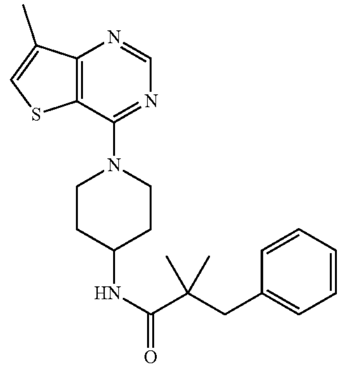 [SMILES: Cc1csc2c(N3CCC(NC(=O)C(C)(C)Cc4ccccc4)CC3)ncnc12] |

TABLE 3-continued
| Cmpd. | Structure |
| --- | --- |
| 3.76 | 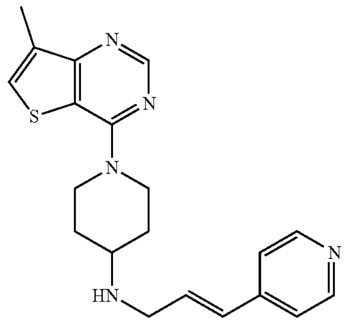 [SMILES: Cc1csc2c(N3CCC(NC/C=C/c4ccncc4)CC3)ncnc12] |
| 3.77 | 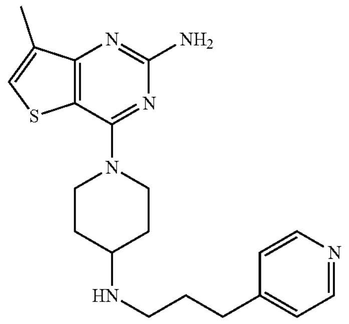 [SMILES: Cc1csc2c(N3CCC(NCCCc4ccncc4)CC3)nc(N)nc12] |
| 3.78 | 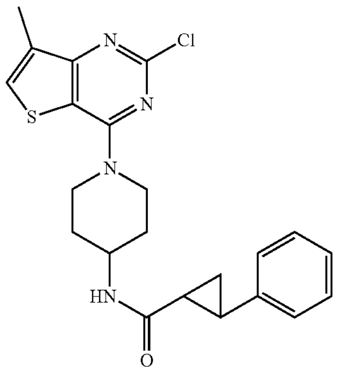 [SMILES: Cc1csc2c(N3CCC(NC(=O)C4CC4c4ccccc4)CC3)nc(Cl)nc12] |
| 3.79 | 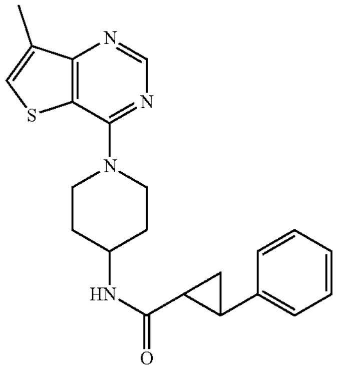 [SMILES: Cc1csc2c(N3CCC(NC(=O)C4CC4c4ccccc4)CC3)ncnc12] |
TABLE 3-continued
| Cmpd. | Structure |
| --- | --- |
| 3.80 | 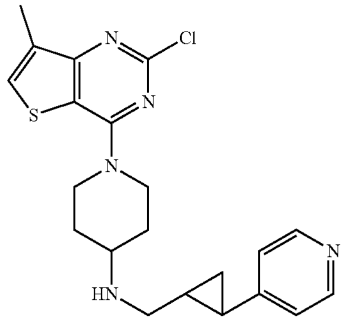 |
| 3.81 | 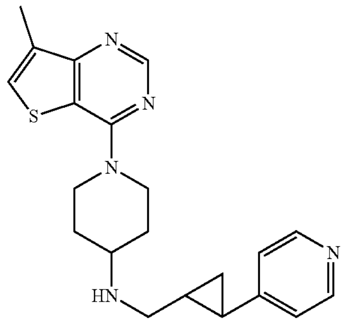 [SMILES: Cc1csc2c(N3CCC(NCC4CC4c4ccncc4)CC3)ncnc12] |
| 3.82 | 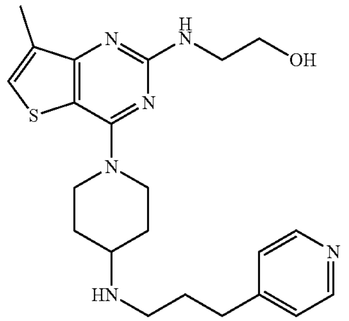 [SMILES: Cc1csc2c(N3CCC(NCCCc4ccncc4)CC3)nc(NCCO)nc12] |
| 3.83 | 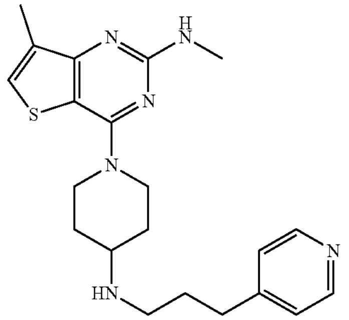 [SMILES: CNc1nc(N2CCC(NCCCc3ccncc3)CC2)c2scc(C)c2n1] |

TABLE 3-continued
| Cmpd. | Structure |
|---|---|
| 3.84 | 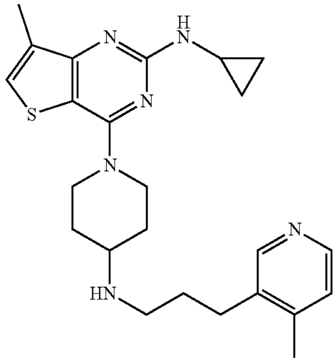 [SMILES: Cc1ccncc1CCCNC1CCN(c2nc(NC3CC3)nc3c(C)csc23)CC1] |
| 3.85 | 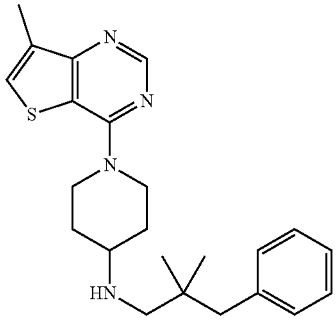 [SMILES: Cc1csc2c(N3CCC(NCC(C)(C)Cc4ccccc4)CC3)ncnc12] |
| 3.86 | 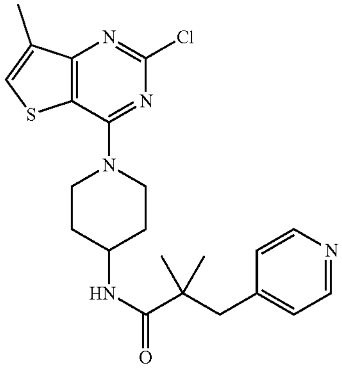 [SMILES: Cc1csc2c(N3CCC(NC(=O)C(C)(C)Cc4ccncc4)CC3)nc(Cl)nc12] |
| 3.87 | 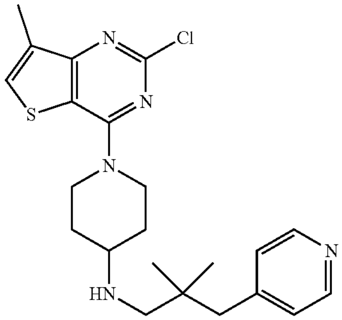 [SMILES: Cc1csc2c(N3CCC(NCC(C)(C)Cc4ccncc4)CC3)nc(Cl)nc12] |
TABLE 3-continued
| Cmpd. | Structure |
|---|---|
| 3.88 | 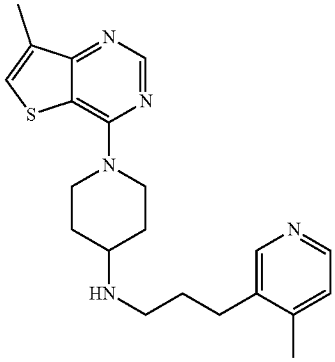 [SMILES: Cc1ccncc1CCCNC1CCN(c2ncnc3c(C)csc23)CC1] |
| 3.89 | 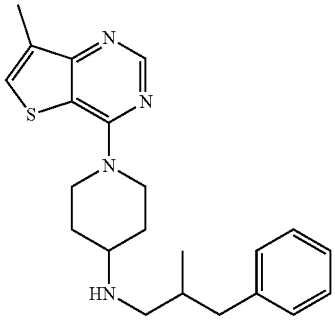 [SMILES: Cc1csc2c(N3CCC(NCC(C)Cc4ccccc4)CC3)ncnc12] |
| 3.90 | 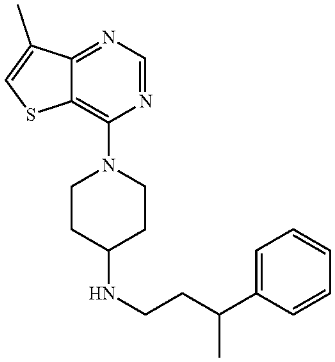 [SMILES: Cc1csc2c(N3CCC(NCCC(C)c4ccccc4)CC3)ncnc12] |
| 3.91 | 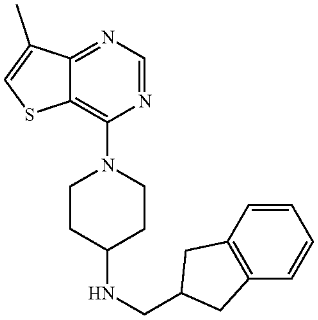 [SMILES: Cc1csc2c(N3CCC(NCC4Cc5ccccc5C4)CC3)ncnc12] |

TABLE 3-continued
| Cmpd. | Structure |
|---|---|
| 3.92 | 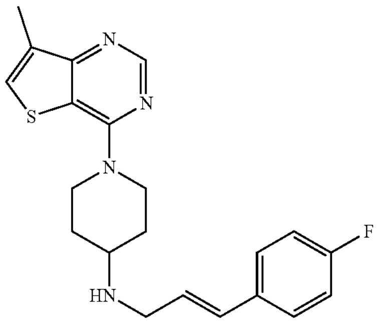 [SMILES: Cc1csc2c(N3CCC(NC/C=C/c4ccc(F)cc4)CC3)ncnc12] |
| 3.93 | 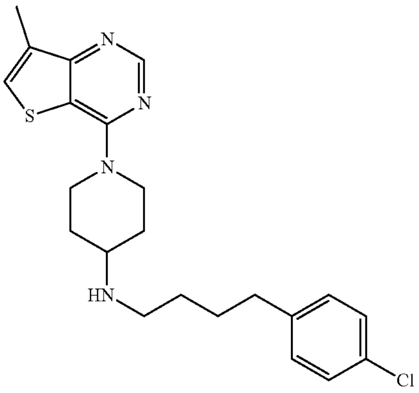 [SMILES: Cc1csc2c(N3CCC(NCCCCc4ccc(Cl)cc4)CC3)ncnc12] |
| 3.94 | 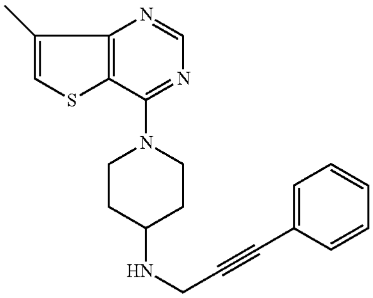 [SMILES: Cc1csc2c(N3CCC(NCC#Cc4ccccc4)CC3)ncnc12] |
| 3.95 | 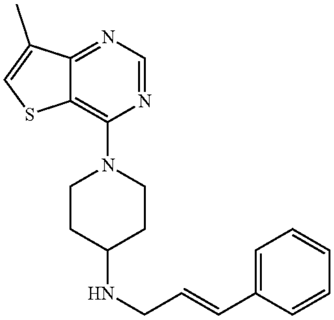 [SMILES: Cc1csc2c(N3CCC(NC/C=C/c4ccccc4)CC3)ncnc12] |
| 3.96 | 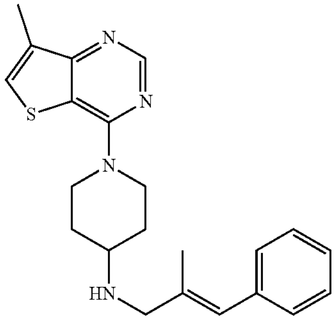 [SMILES: C/C(=C\c1ccccc1)CNC1CCN(c2ncnc3c(C)csc23)CC1] |
| 3.97 | 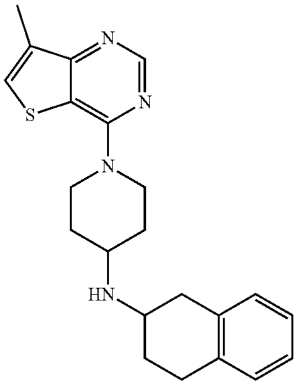 [SMILES: Cc1csc2c(N3CCC(NC4CCc5ccccc5C4)CC3)ncnc12] |
| 3.98 | 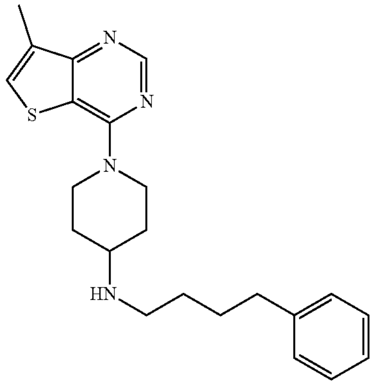 [SMILES: Cc1csc2c(N3CCC(NCCCCc4ccccc4)CC3)ncnc12] |
| 3.99 | 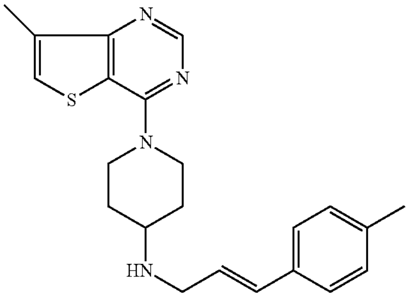 |

TABLE 3-continued
| Cmpd. | Structure |
| --- | --- |
| 3.100 | 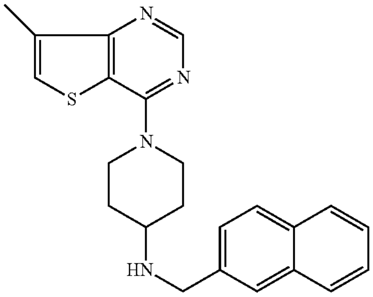 [SMILES: Cc1csc2c(N3CCC(NCc4ccc5ccccc5c4)CC3)ncnc12] |
| 3.101 | 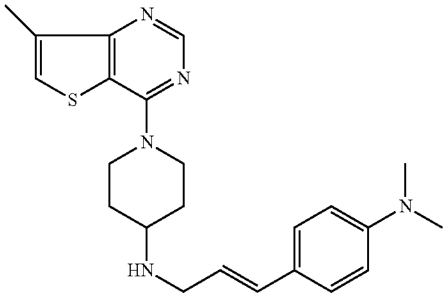 |
| 3.102 | 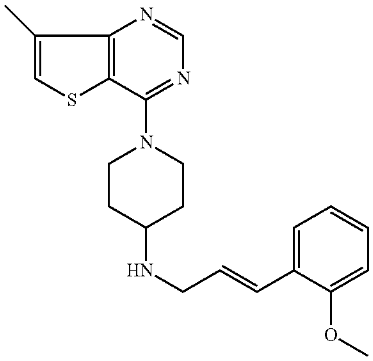 |
| 3.103 | 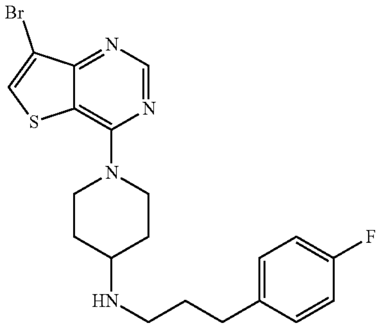 [SMILES: Fc1ccc(CCCNC2CCN(c3ncnc4c(Br)csc34)CC2)cc1] |
TABLE 3-continued
| Cmpd. | Structure |
| --- | --- |
| 3.104 | 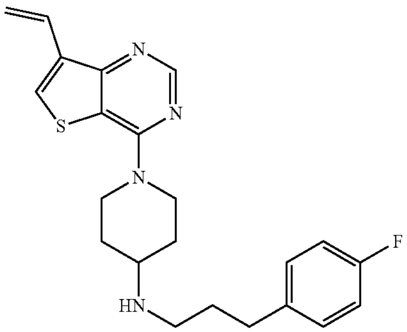 [SMILES: C=Cc1csc2c(N3CCC(NCCCc4ccc(F)cc4)CC3)ncnc12] |
| 3.105 | 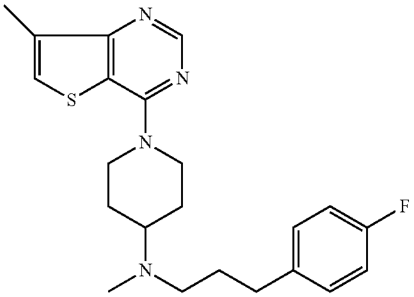 [SMILES: Cc1csc2c(N3CCC(N(C)CCCc4ccc(F)cc4)CC3)ncnc12] |
| 3.106 | 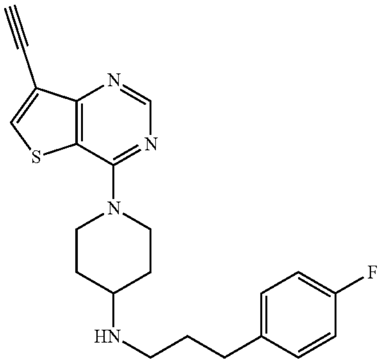 [SMILES: C#Cc1csc2c(N3CCC(NCCCc4ccc(F)cc4)CC3)ncnc12] |
| 3.107 | 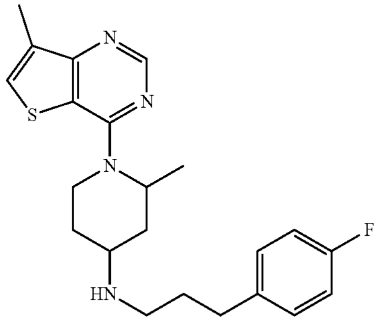 [SMILES: Cc1csc2c(N3CCC(NCCCc4ccc(F)cc4)CC3C)ncnc12] |

TABLE 3-continued
| Cmpd. | Structure |
| --- | --- |
| 3.108 | 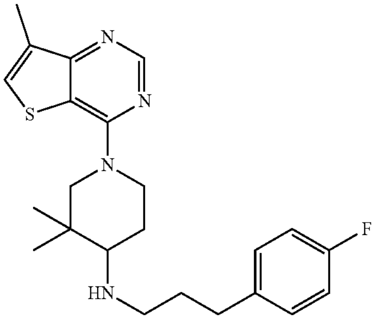 [SMILES: Cc1csc2c(N3CCC(NCCCc4ccc(F)cc4)C(C)(C)C3)ncnc12] |
| 3.109 | 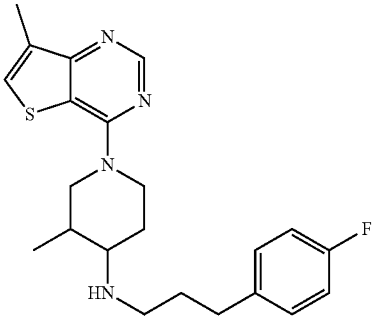 [SMILES: Cc1csc2c(N3CCC(NCCCc4ccc(F)cc4)C(C)C3)ncnc12] |
| 3.110 | 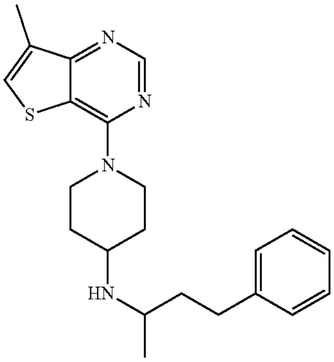 [SMILES: Cc1csc2c(N3CCC(NC(C)CCc4ccccc4)CC3)ncnc12] |
| 3.111 | 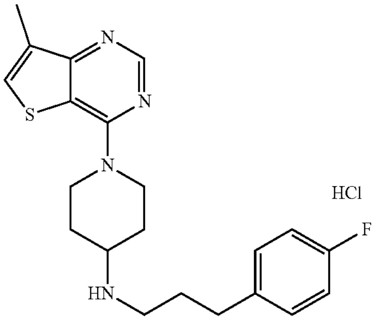 [SMILES: Cc1csc2c(N3CCC(NCCCc4ccc(F)cc4)CC3)ncnc12 ; Cl] HCl |
TABLE 3-continued
| Cmpd. | Structure |
| --- | --- |
| 3.112 | 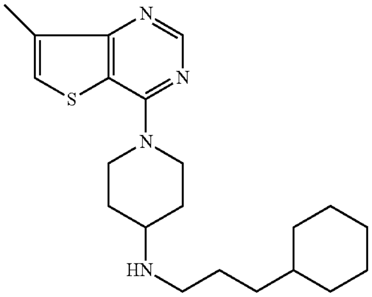 [SMILES: Cc1csc2c(N3CCC(NCCCC4CCCCC4)CC3)ncnc12] |
| 3.113 | 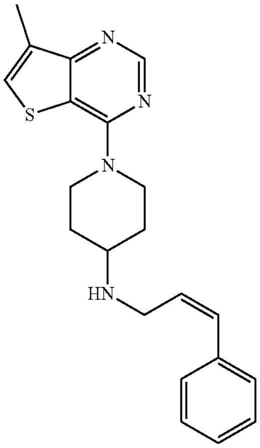 [SMILES: Cc1csc2c(N3CCC(NC/C=C\c4ccccc4)CC3)ncnc12] |
| 3.114 | 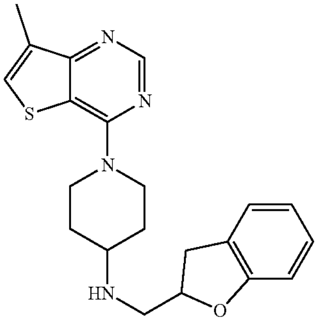 [SMILES: Cc1csc2c(N3CCC(NCC4Cc5ccccc5O4)CC3)ncnc12] |
| 3.115 | 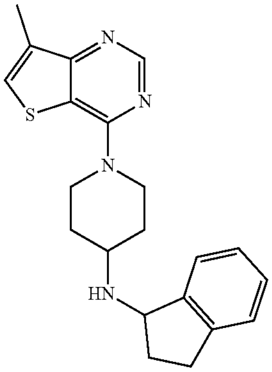 [SMILES: Cc1csc2c(N3CCC(NC4CCc5ccccc54)CC3)ncnc12] |

TABLE 3-continued

| Cmpd. | Structure |
| --- | --- |
| 3.116 | 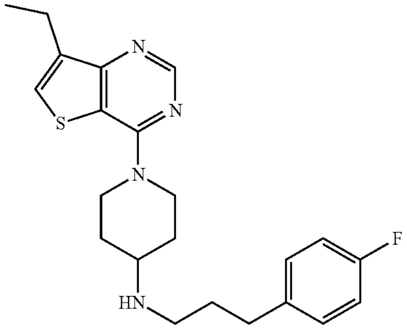 [SMILES: CCc1csc2c(N3CCC(NCCCc4ccc(F)cc4)CC3)ncnc12] |

Further Forms of Compounds

In another aspect, the compound having the structure of Formula (I), (II), (III), (IV), (V), (VI), (VII), (VIII), (IX), (X), (XI), or (XII), possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design prodrugs of the compound is possible. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews*, 56:53-102, 2004; Aesop Cho, "Recent Advances in Oral Prodrug Discovery", *Annual Reports in Medicinal Chemistry*, Vol. 41, 395-407, 2006; T. Higuchi and V. Stella, *Pro-drugs as Novel Delivery Systems*, Vol. 14 of the A.C.S. Symposium Series).

In some cases, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^{2}H$, $^{3}H$, $^{13}C$, $^{14}C$, $^{5}N$, $^{18}O$, $^{17}O$, $^{35}S$, $^{18}F$, and $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I), (II), (III), (IV), (V), (VI), (VII), (VIII), (IX), (X), (XI), or (XII) with an acid. Pharmaceutically acceptable salts are also obtained by reacting a compound of Formula (I), (II), (III), (IV), (V), (VI), (VII), (VIII), (IX), (X), (XI), or (XII) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g., lithium, sodium, or potassium), an alkaline earth ion (e.g., magnesium or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of the Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, Fisher Scientific (Fisher Chemicals), and Acros Organics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure).

It will be understood that the reactions shown above are illustrative.

In one aspect, compounds are synthesized as described in the Examples section.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Oxo" refers to the =O substituent.

"Thioxo" refers to the =S substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_7$ alkyl, $C_1$-$C_7$ alkyl, $C_1$-$C_6$ alkyl, $C_1$-$C_7$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl, ethyl, s-butyl, or 1-ethyl-propyl. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is $—CH_2—$, $—CH_2CH_2—$, or $—CH_2CH_2CH_2—$. In some embodiments, the alkylene is $—CH_2—$. In some embodiments, the alkylene is $—CH_2CH_2—$. In some embodiments, the alkylene is $—CH_2CH_2CH_2—$.

The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkylene" refers to an alkyl radical as described above where one or more carbon atoms of the alkyl is replaced with a 0, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to $—OCH_2OMe$, $—OCH_2CH_2OMe$, or $—OCH_2CH_2OCH_2CH_2NH_2$. Representative heteroalkylene groups include, but are not limited to $—OCH_2CH_2O—$, $—OCH_2CH_2OCH_2CH_2O—$, or $—OCH_2CH_2OCH_2CH_2OCH_2CH_2O—$.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthalenyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to $—CO_2H$. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

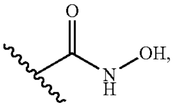, 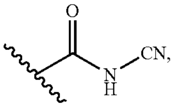, 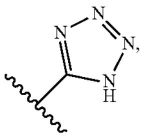, 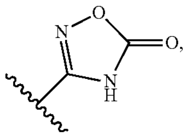, 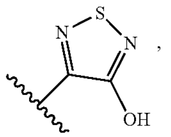, 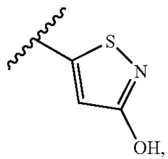, 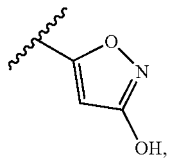, 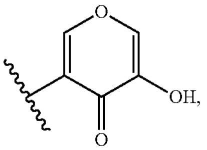, and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. In some embodiments, a cycloalkyl is a $C_3$-$C_6$ cycloalkyl. In some embodiments, a cycloalkyl is a 3- to 6-membered cycloalkyl. Representative cycloalkyls include, but are not limited to, cycloakyls having from three to ten carbon atoms, from three to eight carbon atoms, from three to six carbon atoms, or from three to five carbon atoms. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. Polycyclic radicals include, for example, adamantyl, norbornyl, decalinyl, and 3,4-dihydronaphthalen-1(2H)-one. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 13 carbon atoms and from one to 6 heteroatoms selected from the group consisting of nitrogen, oxygen, and sulfur. In some embodiments, the heterocycloalkyl is a $C_2$-$C_7$ heterocycloalkyl. In some embodiments, the heterocycloalkyl is a $C_2$-$C_6$ heterocycloalkyl. In some embodiments, the heterocycloalkyl is a $C_2$-$C_5$ heterocycloalkyl. In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 3- to 5-membered heterocycloalkyl. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

Heteroaryl" refers to an aryl group that includes one or more ring heteroatoms selected from nitrogen, oxygen and sulfur. The heteroaryl is monocyclic or bicyclic. In some embodiments, the heteroaryl is a 5- or 6-membered heteroaryl. In some embodiments, the heteroaryl is a 5-membered heteroaryl. In some embodiments, the heteroaryl is a 6-membered heteroaryl. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2H$, —$CO_2$alkyl, nitro, and amino, including mono- and di-substituted amino groups (e.g., —$NH_2$, —NHR, —$N(R)_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2H$, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, optional substituents are independently selected from fluoro, chloro, —$CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (II), (III), (IV), (V), (VI), (VII), (VIII), (IX), (X), (XI), or (XII) and a co-agent, are both administered to a patient simultaneously in the form of a single entity or dosage. The term "non-fixed combination" means that the active ingredients, e.g. a compound of Formula (I), (II), (III), (IV), (V), (VI), (VII), (VIII), (IX), (X), (XI), or (XII) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

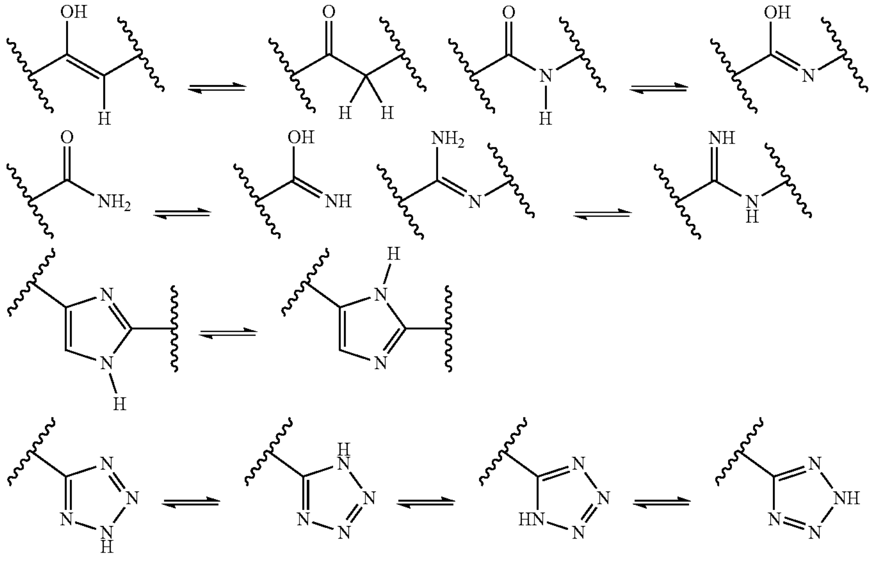

Administration and Pharmaceutical Composition

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), (II), (III), (IV), (V), (VI), (VII), (VIII), (IX), (X), (XI), or (XII) with other chemical components (i.e., pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I), (II), (III), (IV), (V), (VI), (VII), (VIII), (IX), (X), (XI), or (XII) are administered orally.

In some embodiments, the compounds of Formula (I), (II), (III), (IV), (V), (VI), (VII), (VIII), (IX), (X), (XI), or (XII) are administered topically. In such embodiments, the compound of Formula (I), (II), (III), (IV), (V), (VI), (VII), (VIII), (IX), (X), (XI), or (XII) is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds of Formula (I), (II), (III), (IV), (V), (VI), (VII), (VIII), (IX), (X), (XI), or (XII) are administered topically to the skin.

In another aspect, the compounds of Formula (I), (II), (III), (IV), (V), (VI), (VII), (VIII), (IX), (X), (XI), or (XII) are administered by inhalation.

In another aspect, the compounds of Formula (I), (II), (III), (IV), (V), (VI), (VII), (VIII), (IX), (X), (XI), or (XII) are formulated for intranasal administration. Such formulations include nasal sprays, nasal mists, and the like.

In another aspect, the compounds of Formula (I), (II), (III), (IV), (V), (VI), (VII), (VIII), (IX), (X), (XI), or (XII) are formulated as eye drops.

In any of the aforementioned aspects are further embodiments in which the effective amount of the compound of Formula (I), (II), (III), (IV), (V), (VI), (VII), (VIII), (IX), (X), (XI), or (XII) is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain embodiments, a compound as described herein is administered in a local rather than systemic manner.

In some embodiments, the compound described herein is administered topically. In some embodiments, the compound described herein is administered systemically.

In some embodiments, the pharmaceutical formulation is in the form of a tablet. In other embodiments, pharmaceutical formulations of the compounds of Formula (I), (II), (III), (IV), (V), (VI), (VII), (VIII), (IX), (X), (XI), or (XII) are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound of Formula (I), (II), (III), (IV), (V), (VI), (VII), (VIII), (IX), (X), (XI), or (XII) is formulated for use as an aerosol, a mist or a powder.

For buccal or sublingual administration, the compositions may take the form of tablets, lozenges, or gels formulated in a conventional manner.

In some embodiments, compounds of Formula (I), (II), (III), (IV), (V), (VI), (VII), (VIII), (IX), (X), (XI), or (XII) are prepared as transdermal dosage forms.

In one aspect, a compound of Formula (I), (II), (III), (IV), (V), (VI), (VII), (VIII), (IX), (X), (XI), or (XII) is formulated into a pharmaceutical composition suitable for intramuscular, subcutaneous, or intravenous injection.

In some embodiments, the compounds described herein may be administered topically and can be formulated into a variety of topically administrable compositions, such as solutions, suspensions, lotions, gels, pastes, medicated sticks, balms, creams or ointments.

In some embodiments, the compounds of Formula (I), (II), (III), (IV), (V), (VI), (VII), (VIII), (IX), (X), (XI), or (XII) are formulated in rectal compositions such as enemas, rectal gels, rectal foams, rectal aerosols, suppositories, jelly suppositories, or retention enemas Methods of Dosing and Treatment Regimens In one embodiment, the compounds of Formula (I), (II), (III), (IV), (V), (VI), (VII), (VIII), (IX), (X), (XI), or (XII) are used in the preparation of medicaments for the treatment of diseases or conditions described herein. In addition, a method for treating any of the diseases or conditions described herein in a subject in need of such treatment, involves administration of pharmaceutical compositions that include at least one compound of Formula (I), (II), (III), (IV), (V), (VI), (VII), (VIII), (IX), (X), (XI), or (XII) or a pharmaceutically acceptable salt, active metabolite, prodrug, or solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Combination Treatments

In certain instances, it is appropriate to administer at least one compound of Formula (I), (II), (III), (IV), (V), (VI), (VII), (VIII), (IX), (X), (XI), or (XII) in combination with another therapeutic agent.

In one specific embodiment, a compound of Formula (I), (II), (III), (IV), (V), (VI), (VII), (VIII), (IX), (X), (XI), or (XII) is co-administered with a second therapeutic agent, wherein the compound of Formula (I), (II), (III), (IV), (V), (VI), (VII), (VIII), (IX), (X), (XI), or (XII) and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

EXAMPLES

The following examples are intended to illustrate but not limit the disclosed embodiments.

All reactions were performed in oven-dried glassware under an atmosphere of argon with magnetic stirring. All solvents and chemicals used were purchased from Sigma-Aldrich or Acros, and were used as received without further purification. Purity of compounds was established by liquid chromatography-mass spectroscopy (HPLC-MS) and was >95% for all tested compounds. Silica gel column chromatography was carried out using prepacked silica cartridges from RediSep (ISCO Ltd.) and eluted using an Isco Companion system. $^{1}H$- and $^{13}C$-NMR spectra were obtained on a Jeol 400 spectrometer at 400 MHz and 100 MHz, respectively. Chemical shifts are reported in δ (ppm) relative to residual solvent peaks or TMS as internal standards. Coupling constants are reported in Hz. High-resolution ESI-TOF mass spectra were acquired from the Mass Spectrometry Core at The Sanford-Burnham Medical Research Institute (Orlando, Florida). HPLC-MS analyses were performed on a Shimadzu 2010EV LCMS using the following conditions: Kromisil C18 column (reverse phase, 4.6 mm×50 mm); a linear gradient from 10% acetonitrile and 90% water to 95% acetonitrile and 5% water over 4.5 min; flow rate of 1 mL/min; UV photodiode array detection from 200 to 300 nm.

Example 1

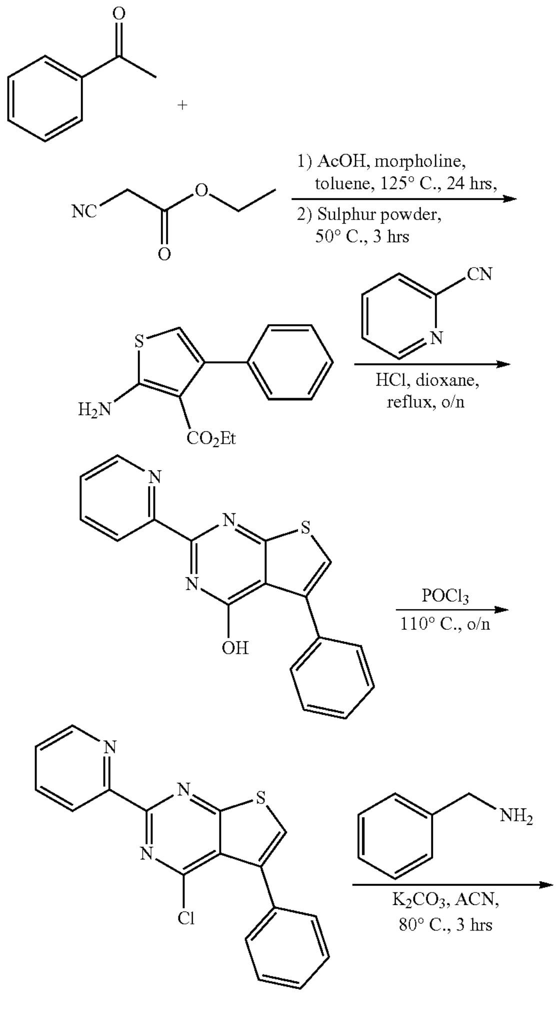

-continued

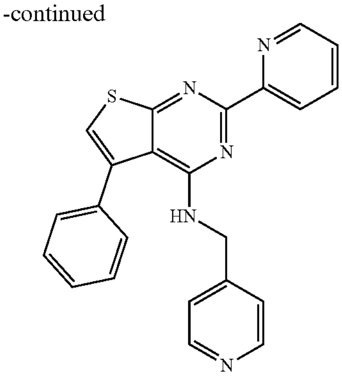

5-Phenyl-2-(pyridin-2-yl)-N-(pyridin-4-ylmethyl) thieno[2,3-d]pyrimidin-4-amine

Step 1: To a solution of acetophenone (1.20 g, 10.0 mmol) and ethyl 2-cyanoacetate (2.48 g, 22.0 mmol) in toluene (40 mL) were added morpholine (1.31 g, 15.0 mmol) and AcOH (1.20 g, 20.0 mmol). The resulting mixture was stirred at 125° C. for 24 hrs with Dean stark apparatus. The mixture was then concentrated in vacuum to give a residue, which was dissolved in EtOH (40 mL). Then sulphur powder (480 mg, 15.0 mmol) and diethyl-amine (730 mg, 10.0 mmol) were added into the reaction mixture, which was heated to 50° C. for 3 hrs. The reaction was monitored by LCMS. The hot solution was filtered to remove sulphur powder, concentrated in vacuum and purified by silica gel column (PE/EA=100/1 to 20/1) to afford ethyl 2-amino-4-phenylthiophene-3-carboxylate (2.12 g, yield: 86%) as a white solid.

Step 2: To a solution of ethyl 2-amino-4-phenylthiophene-3-carboxylate (247 mg, 1.0 mmol) and picolinonitrile (208 mg, 2.0 mmol) in dioxane (10 mL) was added HCl/dioxane (10 mL, >2 M). The resulting mixture was stirred at 100° C. overnight. The reaction was monitored by LCMS. Then the reaction mixture was concentrated in vacuum to give a residue, which was purified by reverse phase column (5-95% ACN in $H_2O$, 40 mins) to afford 5-phenyl-2-(pyridin-2-yl)thieno[2,3-d]pyrimidin-4-ol (238 mg, yield: 78%) as a yellow solid. $^1$HNMR (400 MHz, DMSO-$d_6$): δ=11.82 (s, 1H), 8.78 (d, J=4.4 Hz, 1H), 8.41 (d, J=8.0 Hz, 1H), 8.11-8.06 (m, 1H), 7.69-7.66 (m, 1H), 7.62 (s, 1H), 7.60-7.57 (m, 2H), 7.44-7.37 (m, 3H).

Step 3: A mixture of 5-phenyl-2-(pyridin-2-yl)thieno[2,3-d]pyrimidin-4-ol (238 mg, 0.78 mmol) in $POCl_3$ (5 mL) was stirred at 110° C. overnight. The reaction was monitored by LCMS and TLC. Then the reaction mixture was concentrated in vacuum to give a residue, which was purified by silica gel column (DCM/MeOH=100/1 to 20/1) to afford 4-chloro-5-phenyl-2-(pyridin-2-yl)thieno[2,3-d]pyrimidine (126 mg, yield: 50%) as a yellow solid.

Step 4: To a solution of 4-chloro-5-phenyl-2-(pyridin-2-yl)thieno[2,3-d]pyrimidine (100 mg, 0.31 mmol) in ACN (20 mL) was added phenylmethanamine (66.8 mg, 0.62 mmol), followed by $K_2CO_3$ (128 mg, 0.93 mmol). Then the resulting mixture was stirred at 80° C. for 3 hrs. The reaction was monitored by LCMS. Then $K_2CO_3$ was filtered off, and the filtrate was concentrated in vacuum to give a residue, which was purified by prep-HPLC with $NH_4OH$ as additive to afford 5-phenyl-2-(pyridin-2-yl)-N-(pyridin-4-ylmethyl) thieno[2,3-d]pyrimidin-4-amine (48.6 mg, yield: 40%) as a yellow solid. $^1$HNMR (400 MHz, DMSO-$d_6$): δ=8.74 (s, 1H), 8.49-8.47 (m, 2H), 8.27 (s, 1H), 7.93 (s, 1H), 7.61-7.58 (m, 3H), 7.55-7.47 (m, 4H), 7.34 (d, J=7.2 Hz, 2H), 6.13 (s, 1H), 4.77 (d, J=5.2 Hz, 2H). MS: m/z 396.0 (M+H$^+$).

Example 1.1

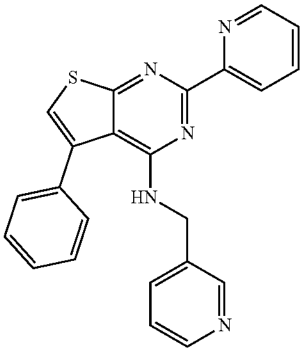 [SMILES: c1ccc(-c2csc3nc(-c4ccccn4)nc(NCc4cccnc4)c23)cc1]

5-Phenyl-2-(pyridin-2-yl)-N-(pyridin-3-ylmethyl) thieno[2,3-d]pyrimidin-4-amine

The title compound was prepared using general procedure of 5-phenyl-2-(pyridin-2-yl)-N-(pyridin-4-ylmethyl)thieno [2,3-d]pyrimidin-4-amine (Example 1). $^1$HNMR (400 MHz, DMSO-$d_6$): δ=8.77 (s, 1H), 8.59 (s, 1H), 8.44 (d, J=3.6 Hz, 1H), 8.39 (s, 1H), 7.97 (s, 1H), 7.76 (d, J=7.6 Hz, 1H), 7.60 (s, 1H), 7.55-7.46 (m, 6H), 7.35-7.32 (m, 1H), 6.05 (s, 1H), 4.76 (d, J=4.8 Hz, 2H). MS: m/z 396.0 (M+H$^+$).

Example 1.2

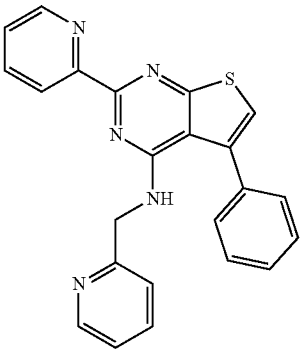 [SMILES: c1ccc(-c2csc3nc(-c4ccccn4)nc(NCc4ccccn4)c23)cc1]

(5-Phenyl-2-pyridin-2-yl-thieno[2,3-d]pyrimidin-4-yl)-pyridin-2-ylmethyl-amine

The title compound was prepared using general procedure of (4-methyl-benzyl)-(5-phenyl-2-pyridin-2-yl-thieno[2,3-d]pyrimidin-4-yl)-amine (Example 1.7). $^1$HNMR (400 MHz, DMSO-$d_6$): δ=8.74 (d, J=4.4 Hz, 1H), 8.41 (d, J=8.0 Hz, 1H), 8.27 (d, J=4.8 Hz, 1H), 7.98-7.91 (m, 1H), 7.77-7.71 (m, 1H), 7.58 (s, 1H), 7.57-7.53 (m, 5H), 7.52-7.47 (m, 1H), 7.41 (d, J=8.4 Hz, 1H), 7.28-7.22 (m, 1H), 6.77 (t, J=4.4 Hz, 1H), 4.81 (d, J=4.0 Hz, 2H). MS: m/z 396.1 (M+H$^+$).

Example 1.3

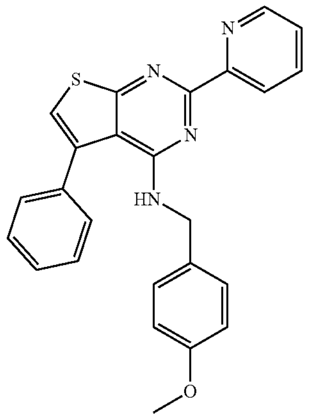 [SMILES: COc1ccc(CNc2nc(-c3ccccn3)nc3scc(-c4ccccc4)c23)cc1]

N-(4-Methoxybenzyl)-5-phenyl-2-(pyridin-2-yl) thieno[2,3-d]pyrimidin-4-amine

The title compound was prepared using general procedure of 5-phenyl-2-(pyridin-2-yl)-N-(pyridin-4-ylmethyl)thieno [2,3-d]pyrimidin-4-amine (Example 1). $^{1}$HNMR (400 MHz, DMSO-$d_6$): δ=8.74 (d, J=3.6 Hz, 1H), 8.41 (d, J=8.0 Hz, 1H), 7.94-7.93 (m, 1H), 7.58 (s, 1H), 7.54-7.45 (m, 6H), 7.21 (d, J=8.8 Hz, 2H), 6.85 (d, J=8.8 Hz, 2H), 5.71 (t, J=9.2 Hz, 1H), 4.65 (d, J=5.2 Hz, 2H), 3.72 (s, 3H). MS: m/z 425.0 ($M+H^+$).

Example 1.4

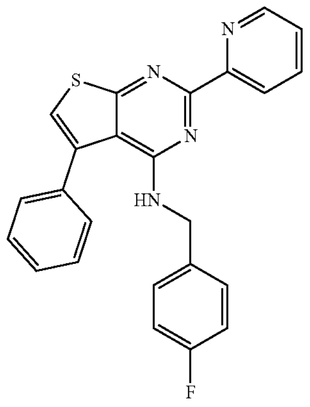 [SMILES: Fc1ccc(CNc2nc(-c3ccccn3)nc3scc(-c4ccccc4)c23)cc1]

N-(4-Fluorobenzyl)-5-phenyl-2-(pyridin-2-yl)thieno [2,3-d]pyrimidin-4-amine

The title compound was prepared using general procedure of 5-phenyl-2-(pyridin-2-yl)-N-(pyridin-4-ylmethyl)thieno [2,3-d]pyrimidin-4-amine (Example 1). $^{1}$HNMR (400 MHz, DMSO-$d_6$): δ=8.74-8.72 (m, 1H), 8.37 (d, J=8.0 Hz, 1H), 7.96-7.91 (m, 1H), 7.59 (s, 1H), 7.55-7.46 (m, 6H), 7.38-7.34 (m, 2H), 7.15-7.11 (m, 2H), 5.84 (t, J=5.6 Hz, 1H), 4.71 (d, J=5.2 Hz, 2H). MS: m/z 413.0 ($M+H^+$).

Example 1.5

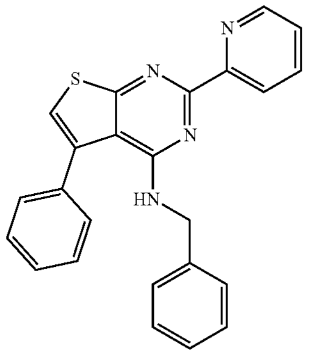 [SMILES: c1ccc(CNc2nc(-c3ccccn3)nc3scc(-c4ccccc4)c23)cc1]

N-Benzyl-5-phenyl-2-(pyridin-2-yl)thieno[2,3-d] pyrimidin-4-amine

The title compound was prepared using general procedure of 5-phenyl-2-(pyridin-2-yl)-N-(pyridin-4-ylmethyl)thieno [2,3-d]pyrimidin-4-amine (Example 1). $^{1}$HNMR (400 MHz, DMSO-$d_6$): δ=8.74-8.72 (m, 1H), 8.37 (d, J=8.0 Hz, 1H), 7.95-7.91 (m, 1H), 7.59 (s, 1H), 7.56-7.53 (m, 2H), 7.51-7.45 (m, 4H), 7.33-7.27 (m, 4H), 7.23-7.22 (m, 1H), 5.82 (t, J=5.6 Hz, 1H), 4.73 (d, J=4.8 Hz, 2H). MS: m/z 395.1 ($M+H^+$).

Example 1.6

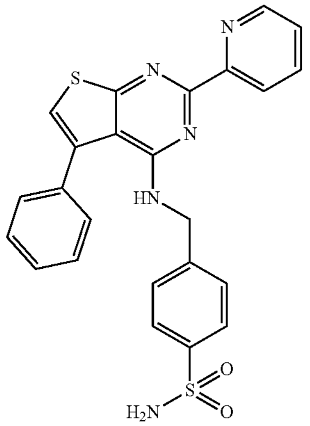 [SMILES: NS(=O)(=O)c1ccc(CNc2nc(-c3ccccn3)nc3scc(-c4ccccc4)c23)cc1]

4-(((5-Phenyl-2-(pyridin-2-yl)thieno[2,3-d]pyrimidin-4-yl)amino)methyl)benzenesulfonamide The title compound was prepared using general procedure of 5-phenyl-2-(pyridin-2-yl)-N-(pyridin-4-ylmethyl)thieno [2,3-d]pyrimidin-4-amine (Example 1). $^{1}$HNMR (400 MHz, DMSO-$d_6$): δ=8.73-8.71 (m, 1H), 8.30 (d, J=8.0 Hz, 1H), 7.94-7.90 (m, 1H), 7.75 (d, J=8.0 Hz, 2H), 7.61 (s, 1H), 7.59-7.58 (m, 2H), 7.57-7.46 (m, 6H), 7.30 (s, 2H), 6.05 (t, J=5.6 Hz, 1H), 4.80 (d, J=6.0 Hz, 2H). MS: m/z 474.0 ($M+H^+$).

Example 1.7

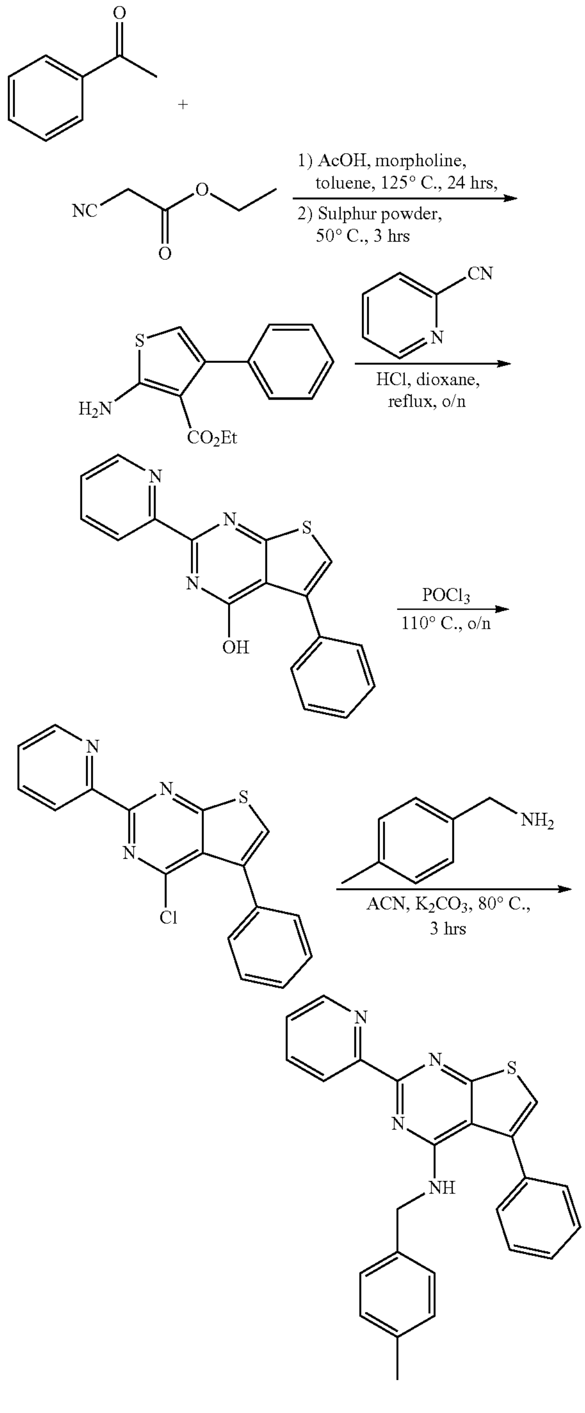

(4-Methyl-benzyl)-(5-phenyl-2-pyridin-2-yl-thieno [2,3-d]pyrimidin-4-yl)-amine

Step 1: To a solution of 1-phenyl-ethanone (12 g, 100 mmol) in toluene was added cyano-acetic acid ethyl ester (24.8 g, 220 mmol), morpholine (13.05 g, 150 mmol) and acetiacid (12.0 g, 200 mmol). The reaction mixture was refluxed for 24 hrs using a Dean start apparatus. Cooled to room temperature, the reaction mixture was quenched with water (50 mL) and extracted with EA (300 mL). The organic layer was dried over $Na_2SO_4$ and concentrated. The residue was dissolved with EtOH (50 mL). Then sulphur powder (4.8 g, 150 mmol) and diethylamine (7.3 g, 100 mmol) were added into the solution, which was heated to 50° C. for 3 hrs. The hot solution was filtered to removed unreacted sulphur and the filtrate was concentrated in vacuum to give a residue, which was purified by silica gel column (PE/EA=10/1) to afford 2-amino-4-phenyl-thiophene-3-carboxylic acid ethyl ester (19.7 g, yield: 79.8%) as a yellow solid. $^1$HNMR (400 MHz, DMSO-$d_6$): δ=7.38 (s, 2H), 7.28-7.25 (m, 5H), 6.15 (s, 1H), 4.00-3.90 (m, 2H), 0.89 (t, J=9.2 Hz, 3H).

Step 2: To a solution of 2-amino-4-phenyl-thiophene-3-carboxylic acid ethyl ester (4.0 g, 16.19 mmol) in HCl/dioxane (50 ml) was added pyridine-2-carbonitrile (2.02 g, 19.43 mmol). The mixture was stirred at 100° C. overnight. The reaction was monitored by TLC and LCMS. Then the mixture was concentrated in vacuum to give a residue, which was purified by silica gel column (PE/EA=1/1) to afford 5-phenyl-2-pyridin-2-yl-thieno[2,3-d]pyrimidin-4-ol (4.0 g, yield: 81.6%) as a yellow solid. $^1$HNMR (400 MHz, DMSO-$d_6$): δ=11.82 (s, 1H), 8.78 (d, J=4.8 Hz, 1H), 8.41 (d, J=8.0 Hz, 1H), 8.12-8.03 (m, 1H), 7.70-7.65 (m, 1H), 7.62 (s, 1H), 7.58 (dd, J=6.4, 2.4 Hz, 2H), 7.44-7.35 (m, 3H).

Step 3: A solution of 5-phenyl-2-pyridin-2-yl-thieno[2,3-d]pyrimidin-4-ol (4.0 g, 13.11 mmol) in $POCl_3$ (20 mL) was stirred at 110° C. overnight. The remaining phosphorus oxychloride was removed in vacuum and the residue diluted with DCM (100 mL). The mixture washed with saturated aqueous $NaHCO_3$ solution (50 mL), brine (50 mL), dried over $Na_2SO_4$ and concentrated to dryness in vacuum. The residue was purified by silica gel column (PE/EA=1/1) to give 4-chloro-5-phenyl-2-pyridin-2-yl-thieno[2,3-d]pyrimidine (2.0 g, yield: 47.3%) as a yellow solid.

Step 4: To a solution of 4-chloro-5-phenyl-2-pyridin-2-yl-thieno[2,3-d]pyrimidine (100 mg, 0.31 mmol) in ACN (30 ml) was added 4-methyl-benzylamine (74.64 mg, 0.62 mmol) and $K_2CO_3$ (127.7 mg, 0.93 mmol). The mixture was stirred at 80° C. for 3 hrs. The reaction was monitored by LCMS, then The mixture was concentrated in vacuum to give a residue, which was purified by prep-HPLC to give (4-methyl-benzyl)-(5-phenyl-2-pyridin-2-yl-thieno[2,3-d] pyrimidin-4-yl)-amine (70.2 mg, yield: 57%) as a yellow solid. $^1$HNMR (400 MHz, DMSO-$d_6$): δ=8.73 (d, J=3.6 Hz, 1H), 8.39 (d, J=7.6 Hz, 1H), 7.96-7.91 (m, 1H), 7.58 (s, 1H), 7.56-7.45 (m, 6H), 7.15 (d, J=8.0 Hz, 2H), 7.10 (d, J=8.0 Hz, 2H), 5.76 (t, J=5.6 Hz, 1H), 4.68 (d, J=5.2 Hz, 2H), 2.25 (s, 3H). MS: m/z 409.1 (M+H$^+$).

Example 1.8

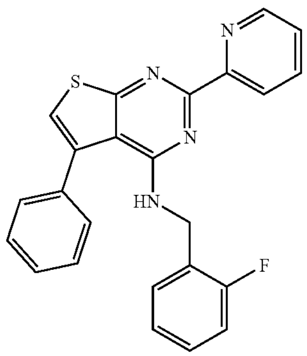 [SMILES: Fc1ccccc1CNc1nc(-c2ccccn2)nc2scc(-c3ccccc3)c12]

(2-Fluoro-benzyl)-(5-phenyl-2-pyridin-2-yl-thieno[2,3-d]pyrimidin-4-yl)-amine

The title compound was prepared using general procedure of (4-methyl-benzyl)-(5-phenyl-2-pyridin-2-yl-thieno[2,3-d]pyrimidin-4-yl)-amine (Example 1.7). $^1$HNMR (400 MHz, DMSO-$d_6$): δ=8.73 (d, J=4.8 Hz, 1H), 8.37 (d, J=8.0 Hz, 1H), 7.99-7.88 (m, 1H), 7.59 (s, 1H), 7.56-7.46 (m, 6H), 7.41 (t, J=9.2 Hz, 1H), 7.34-7.26 (m, 1H), 7.22-7.08 (m, 2H), 5.85 (t, J=5.6 Hz, 1H), 4.77 (d, J=5.6 Hz, 2H). MS: m/z 413.1 ($M+H^+$).

Example 1.9

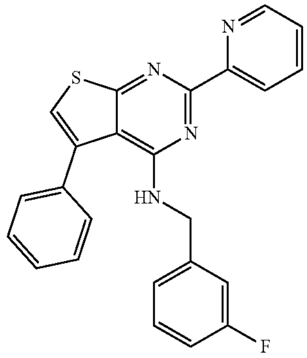 [SMILES: Fc1cccc(CNc2nc(-c3ccccn3)nc3scc(-c4ccccc4)c23)c1]

(3-Fluoro-benzyl)-(5-phenyl-2-pyridin-2-yl-thieno[2,3-d]pyrimidin-4-yl)-amine

The title compound was prepared using general procedure of (4-methyl-benzyl)-(5-phenyl-2-pyridin-2-yl-thieno[2,3-d]pyrimidin-4-yl)-amine (Example 1.7). $^1$HNMR (400 MHz, DMSO-$d_6$): δ=8.72 (d, J=4.0 Hz, 1H), 8.35 (d, J=8.0 Hz, 1H), 7.96-7.89 (m, 1H), 7.59 (s, 1H), 7.58-7.54 (m, 2H), 7.53-7.45 (m, 4H), 7.38-7.31 (m, 1H), 7.19-7.13 (m, 2H), 7.08-7.02 (m, 1H), 5.92 (t, J=5.6 Hz, 1H), 4.74 (d, J=5.6 Hz, 2H) MS: m/z 413.1 ($M+H^+$).

Example 1.10

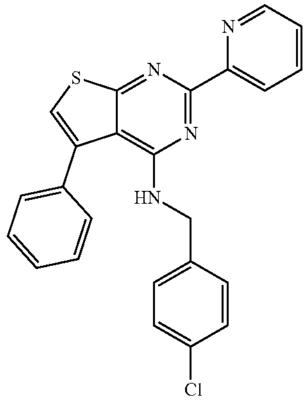

(4-Chloro-benzyl)-(5-phenyl-2-pyridin-2-yl-thieno[2,3-d]pyrimidin-4-yl)-amine

The title compound was prepared using general procedure of (4-methyl-benzyl)-(5-phenyl-2-pyridin-2-yl-thieno[2,3-d]pyrimidin-4-yl)-amine (Example 1.7). $^1$HNMR (400 MHz, DMSO-$d_6$): δ=8.72 (d, J=4.0 Hz, 1H), 8.34 (d, J=8.0 Hz, 1H), 7.95-7.89 (m, 1H), 7.59 (s, 1H), 7.56-7.46 (m, 6H), 7.38-7.34 (m, 4H), 5.92 (t, J=5.6 Hz, 1H), 4.72 (d, J=5.6 Hz, 2H) MS: m/z 428.8 ($M+H^+$).

Example 1.11

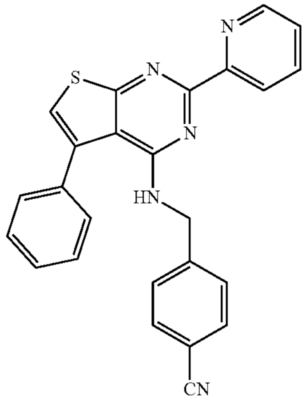

4-[(5-Phenyl-2-pyridin-2-yl-thieno[2,3-d]pyrimidin-4-ylamino)-methyl]-benzonitrile The title compound was prepared using general procedure of (4-methyl-benzyl)-(5-phenyl-2-pyridin-2-yl-thieno[2,3-d]pyrimidin-4-yl)-amine (Example 1.7). $^1$HNMR (400 MHz, DMSO-$d_6$): δ=8.71 (d, J=4.4 Hz, 1H), 8.26 (d, J=8.0 Hz, 1H), 7.94-7.87 (m, 1H), 7.77 (d, J=8.4 Hz, 2H), 7.60 (s, 1H), 7.58-7.45 (m, 8H), 6.09 (t, J=5.6 Hz, 1H), 4.82 (d, J=5.6 Hz, 2H) MS: m/z 420.0 ($M+H^+$).

Example 1.12

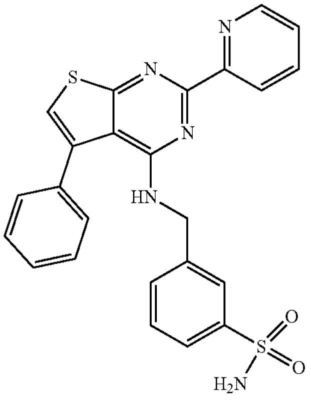 [SMILES: NS(=O)(=O)c1cccc(CNc2nc(-c3ccccn3)nc3scc(-c4ccccc4)c23)c1]

3-[(5-Phenyl-2-pyridin-2-yl-thieno[2,3-d]pyrimidin-4-ylamino)-methyl]-benzenesulfonamide The title compound was prepared using general procedure of (4-methyl-benzyl)-(5-phenyl-2-pyridin-2-yl-thieno[2,3-d]pyrimidin-4-yl)-amine (Example 1.7). $^1$HNMR (400 MHz, DMSO-$d_6$): δ=8.71 (d, J=4.0 Hz, 1H), 8.31 (d, J=7.6 Hz, 1H), 7.95-7.88 (m, 1H), 7.87 (s, 1H), 7.70 (d, J=7.6 Hz, 1H), 7.60 (s, 1H), 7.59-7.44 (m, 8H), 7.34 (s, 2H), 6.12 (t, J=6.0 Hz, 1H), 4.82 (d, J=5.6 Hz, 2H). MS: m/z 474.0 ($M+H^+$).

Example 1.13

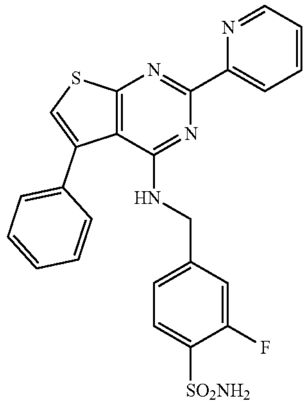

2-Fluoro-4-(((5-phenyl-2-(pyridin-2-yl)thieno[2,3-d]pyrimidin-4-yl)amino)methyl)benzenesulfonamide The title compound was prepared using general procedure of 2-chloro-4-(((5-phenyl-2-(pyridin-2-yl)thieno[2,3-d]pyrimidin-4-yl)amino)methyl)benzenesulfonamide (Example 1.18). $^1$HNMR (400 MHz, $CDCl_3$): δ=8.77-8.76 (m, 1H), 8.27 (d, J=8 Hz, 1H), 7.77-7.71 (m, 2H), 7.41 (d, J=10 Hz, 5H), 7.31-7.28 (m, 1H), 7.13 (s, 1H), 7.07-7.02 (m, 2H), 5.37-5.34 (m, 1H), 5.00 (brs, 2H), 4.74 (d, J=6 Hz, 2H). MS: m/z 492.1 ($M+H^+$).

Example 1.14

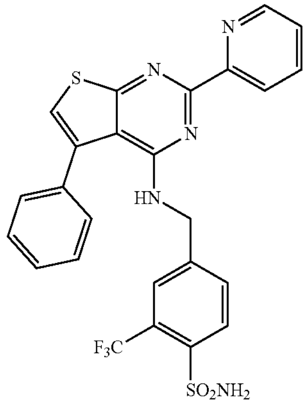 [SMILES: NS(=O)(=O)c1ccc(CNc2nc(-c3ccccn3)nc3scc(-c4ccccc4)c23)cc1C(F)(F)F]

4-(((5-Phenyl-2-(pyridin-2-yl)thieno[2,3-d]pyrimidin-4-yl)amino)methyl)-2-(trifluoromethyl)benzenesulfonamide The title compound was prepared using general procedure of 3-methyl-4-(((1-methyl-1H-pyrazolo[3,4-d]pyrimidin-4-yl)amino)methyl)benzenesulfonamide (Example 2.2). $^1$HNMR (400 MHz, DMSO-$d_6$): δ=8.72 (s, 1H), 8.27 (d, J=7.6 Hz, 1H), 8.08 (d, J=8.4 Hz, 1H), 8.00 (s, 1H), 7.89-7.85 (m, 2H), 7.62-7.46 (m, 9H), 6.27 (s, 1H), 4.83-4.82 (m, 2H). MS: m/z 542.1 ($M+H^+$).

Example 1.15

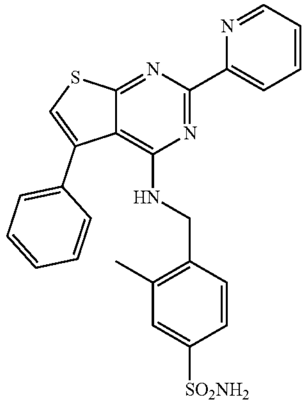 [SMILES: Cc1cc(S(N)(=O)=O)ccc1CNc1nc(-c2ccccn2)nc2scc(-c3ccccc3)c12]

3-Methyl-4-(((5-phenyl-2-(pyridin-2-yl)thieno[2,3-d]pyrimidin-4-yl)amino)methyl)-benzenesulfonamide The title compound was prepared using general procedure of 3-methyl-4-(((1-methyl-1H-pyrazolo[3,4-d]pyrimidin-4-yl)amino)methyl)benzenesulfonamide (Example 2.2). $^1$HNMR (400 MHz, DMSO-$d_6$): δ=8.73 (s, 1H), 8.32 (d, J=8.0 Hz, 1H), 7.93-7.92 (m, 1H), 7.60-7.43 (m, 10H), 7.23 (s, 2H), 5.81 (s, 1H), 4.75-4.74 (m, 2H), 2.32 (s, 3H). MS: m/z 488.1 ($M+H^+$).

Example 1.16

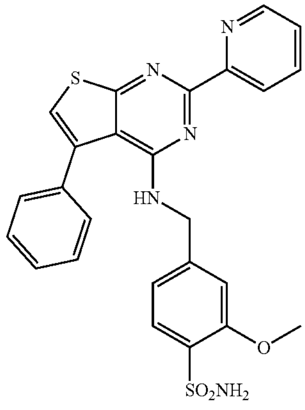 [SMILES: COc1cc(CNc2nc(-c3ccccn3)nc3scc(-c4ccccc4)c23)ccc1S(N)(=O)=O]

2-Methoxy-4-(((5-phenyl-2-(pyridin-2-yl)thieno[2,3-d]pyrimidin-4-yl)amino)methyl)benzenesulfonamide The title compound was prepared using general procedure of 3-methyl-4-(((1-methyl-1H-pyrazolo[3,4-d]pyrimidin-4-yl)amino)methyl)benzenesulfonamide (Example 2.2). $^{1}$HNMR (400 MHz, DMSO-$d_6$): δ=8.74 (s, 1H), 8.41 (d, J=8.0 Hz, 1H), 7.96 (s, 1H), 7.57-7.49 (m, 9H), 7.36-7.31 (m, 3H), 5.85 (s, 1H), 4.71-4.70 (m, 2H), 3.74 (s, 3H). MS: m/z 504.1 (M+$H^+$).

Example 1.17

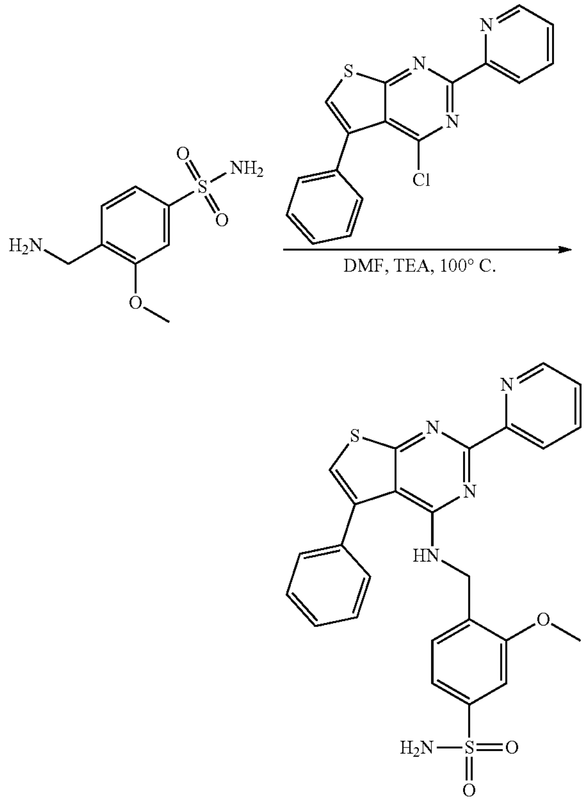

3-Methoxy-4-(((5-phenyl-2-(pyridin-2-yl)thieno[2,3-d]pyrimidin-4-yl)amino)methyl)-benzenesulfonamide To a solution of 4-chloro-5-phenyl-2-(pyridin-2-yl)thieno[2,3-d]pyrimidine (113 mg, 0.35 mmol) and 4-(aminomethyl)-3-methoxybenzenesulfonamide (100 mg, 0.46 mmol) in DMF (2 mL) was added TEA (106 mg, 1.05 mmol). The reaction was stirred at 100° C. for 3 hrs. The DMF was removed under reduced pressure. The residue was purified by perp-HPLC to give 3-methoxy-4-(((5-phenyl-2-(pyridin-2-yl)thieno[2,3-d]pyrimidin-4-yl)amino)methyl)benzenesulfonamide (7.5 mg, yield: 2.8%) as a white solid. $^{1}$HNMR (400 MHz, DMSO-$d_6$): δ=8.75 (s, 1H), 8.41 (d, J=8.0 Hz, 1H), 7.96 (t, J=8.0 Hz, 1H), 7.51-7.31 (m, 7H), 7.36-7.31 (m, 2H), 5.58 (t, J=4.8 Hz, 1H), 4.71 (d, J=5.2 Hz, 2H), 3.74 (s, 3H). MS: m/z 504.1 (M+$H^+$).

Example 1.18

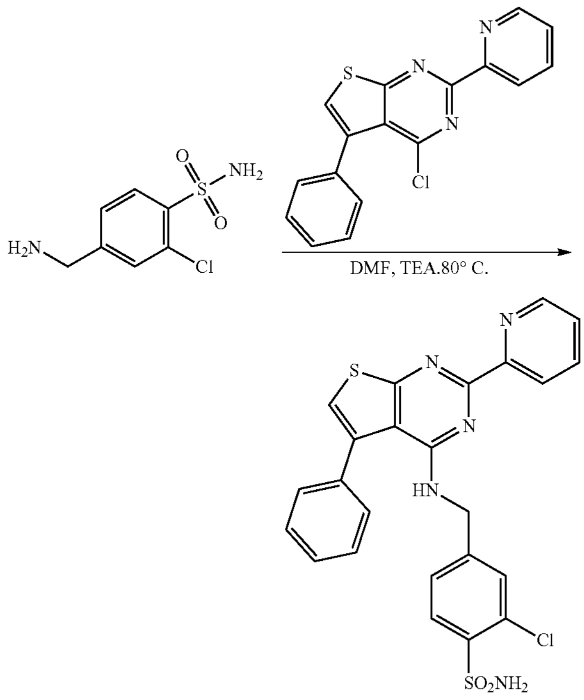

2-Chloro-4-(((5-phenyl-2-(pyridin-2-yl)thieno[2,3-d]pyrimidin-4-yl)amino)methyl)-benzenesulfonamide A solution of 4-(aminomethyl)-2-chlorobenzenesulfonamide (60 mg, 0.27 mmol), TEA (46 mg, 0.46 mmol) and 4-chloro-5-phenyl-2-(pyridin-2-yl)thieno[2,3-d]pyrimidine (73 mg, 0.23 mmol) in DMF (3 mL) was stirred at 80° C. overnight. The DMF was removed under reduced pressure. The residue was purified by prep-HPLC ($NH_4HCO_3$) to give 2-chloro-4-(((5-phenyl-2-(pyridin-2-yl)thieno[2,3-d]pyrimidin-4-yl)amino)methyl)benzenesulfonamide (7.1 mg, yield: 6.1%) as a yellow solid. $^{1}$HNMR (400 MHz, DMSO-$d_6$): δ=8.74-8.72 (m, 1H), 8.32-8.30 (m, 1H), 7.94-7.88 (m, 2H), 7.69 (s, 1H), 7.61-7.47 (m, 10H), 6.16-6.15 (m, 1H), 4.77 (d, J=5.6 Hz, 2H). MS: m/z 508.0 (M+$H^+$).

Example 1.19

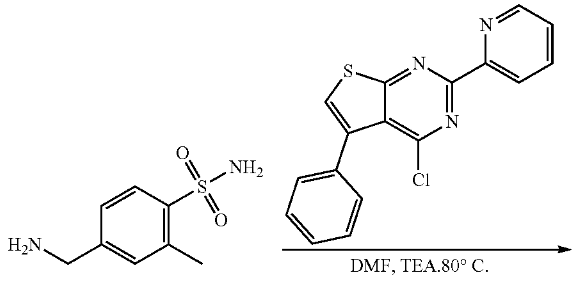

-continued

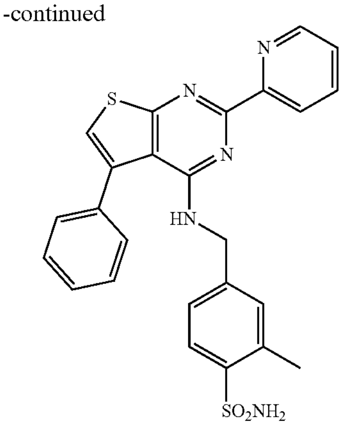

2-Methyl-4-(((5-phenyl-2-(pyridin-2-yl)thieno[2,3-d]pyrimidin-4-yl)amino)methyl)-benzenesulfonamide The title compound was prepared using general procedure of 2-chloro-4-(((5-phenyl-2-(pyridin-2-yl)thieno[2,3-d]pyrimidin-4-yl)amino)methyl)benzenesulfonamide (Example 1.18). $^1$HNMR (400 MHz, DMSO-$d_6$): δ=8.74-8.72 (m, 1H), 8.34 (d, J=8.0 Hz, 1H), 7.95-7.93 (m, 1H), 7.76 (d, J=8.0 Hz, 1H), 7.66-7.33 (m, 7H), 7.47-7.27 (m, 4H), 5.97 (t, J=6.0 Hz, 1H), 7.74 (d, J=5.6 Hz, 2H), 2.56 (s, 3H). MS: m/z 488.1 (M+H$^+$).

Example 1.20

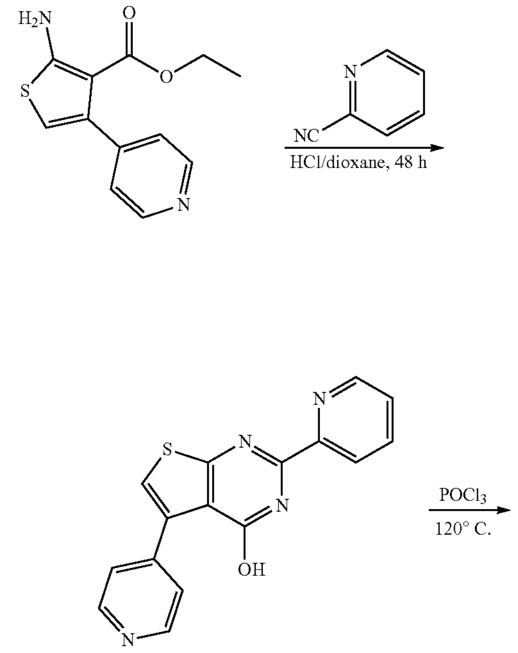

-continued

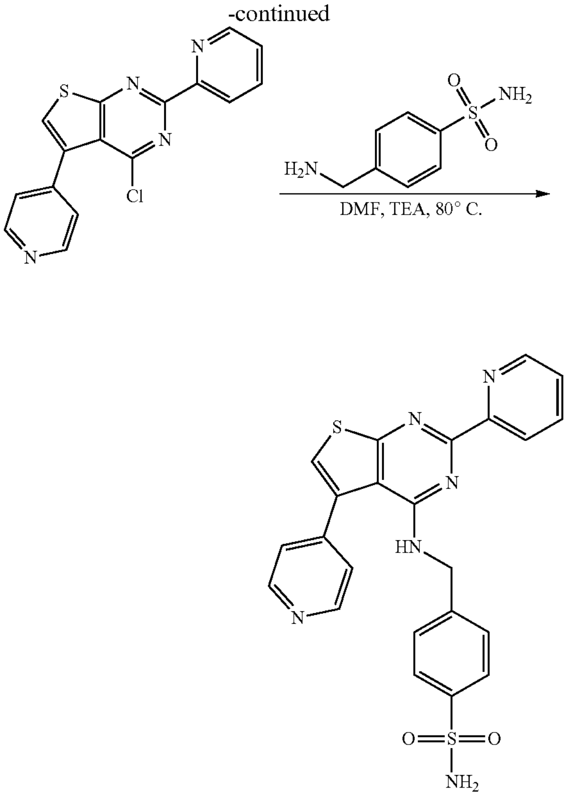

4-(((2-(Pyridin-2-yl)-5-(pyridin-4-yl)thieno[2,3-d]pyrimidin-4-yl)amino)methyl)-benzenesulfonamide Step 1: A solution of ethyl 2-amino-4-(pyridin-4-yl)thiophene-3-carboxylate (500 mg, 2 mmol) and picolinonitrile (315 mg, 3 mmol) in HCl/dioxane (15 mL) was stirred at 90° C. for 2 days. The reaction mixture was filtered and the pad was dried to give 2-(pyridin-2-yl)-5-(pyridin-4-yl)thieno[2,3-d]pyrimidin-4-ol (200 mg, yield: 32.4%) as a gray solid. MS: m/z 307.3 (M+H$^+$).

Step 2: A solution of 2-(pyridin-2-yl)-5-(pyridin-4-yl)thieno[2,3-d]pyrimidin-4-ol (150 mg, 0.49 mmol) in $POCl_3$ (3 mL) was stirred at 120° C. for 2 hrs. The $POCl_3$ was removed under reduced pressure. The residue was washed with saturated aqueous $NaHCO_3$ solution (80 mL) and the aqueous phase was extracted with EA (100 mL). The organic layer was dried over $Na_2SO_4$ and concentrated to give 4-chloro-2-(pyridin-2-yl)-5-(pyridin-4-yl)thieno[2,3-d]pyrimidine (200 mg, crude) as a gray solid. MS: m/z 325.2 (M+H$^+$).

Step 3: A solution of 4-chloro-2-(pyridin-2-yl)-5-(pyridin-4-yl)thieno[2,3-d]pyrimidine (150 mg, 0.46 mmol), 4-(aminomethyl)benzenesulfonamide (103 mg, 0.46 mmol) and TEA (140 mg, 1.38 mmol) in DMF (5 mL) was stirred at 80° C. overnight. The DMF was removed under reduced pressure. The residue was purified by prep-HPLC ($NH_4HCO_3$) to give 4-(((2-(pyridin-2-yl)-5-(pyridin-4-yl)thieno[2,3-d]pyrimidin-4-yl)amino)methyl)benzenesulfonamide (0.7 mg, yield: 0.3%) as a brown solid. $^1$HNMR (400 MHz, DMSO-$d_6$): δ=8.73-8.69 (m, 3H), 8.28 (d, J=8.0 Hz, 1H), 7.93-7.89 (m, 1H), 7.80-7.75 (m, 3H), 7.61-7.57 (m, 4H), 7.49-7.46 (m, 1H), 7.27 (s, 2H), 6.65-6.62 (m, 1H), 4.82 (d, J=5.6 Hz, 2H). MS: m/z 475.1 (M+H$^+$).

Example 1.21

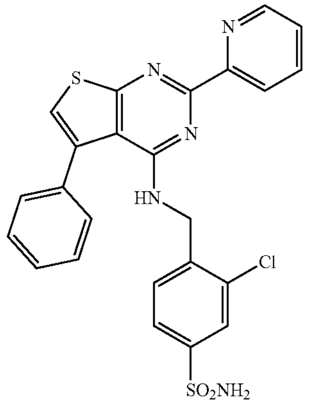 [SMILES: NS(=O)(=O)c1ccc(CNc2nc(-c3ccccn3)nc3scc(-c4ccccc4)c23)c(Cl)c1]

3-Chloro-4-(((5-phenyl-2-(pyridin-2-yl)thieno[2,3-d]pyrimidin-4-yl)amino)methyl)-benzenesulfonamide The title compound was prepared using general procedure of 2-chloro-4-(((5-phenyl-2-(pyridin-2-yl)thieno[2,3-d]pyrimidin-4-yl)amino)methyl)benzenesulfonamide (Example 1.18). $^{1}$HNMR (400 MHz, DMSO-$d_6$): δ=8.74 (s, 1H), 8.29 (d, J=8.0 Hz, 1H), 7.92 (s, 1H), 7.83 (s, 1H), 7.76 (d, J=8.0 Hz, 1H), 7.69 (d, J=8.0 Hz, 1H), 7.62-7.44 (m, 9H), 6.11 (s, 1H), 4.82 (d, J=4.4 Hz, 2H). MS: m/z 508.1 (M+H$^+$).

Example 1.22

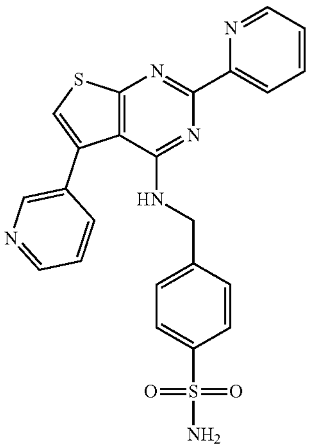 [SMILES: NS(=O)(=O)c1ccc(CNc2nc(-c3ccccn3)nc3scc(-c4cccnc4)c23)cc1]

4-(((2-(Pyridin-2-yl)-5-(pyridin-3-yl)thieno[2,3-d]pyrimidin-4-yl)amino)methyl)-benzenesulfonamide The title compound was prepared using general procedure of 4-(((2-(pyridin-2-yl)-5-(pyridin-4-yl)thieno[2,3-d]pyrimidin-4-yl)amino)methyl)benzenesulfonamide (Example 1.20). $^{1}$HNMR (400 MHz, DMSO-$d_6$): δ=8.79 (s, 1H), 8.79-8.71 (m, 1H), 8.66-8.65 (m, 1H), 8.27 (d, J=8.0 Hz, 1H), 7.97 (d, J=8.0 Hz, 1H), 7.91 (d, J=2.0 Hz, 1H), 7.77-7.72 (m, 3H), 7.58-7.47 (m, 4H), 7.27 (s, 2H), 6.56 (s, 1H), 4.80 (d, J=5.6 Hz, 2H). MS: m/z 475.1 (M+H$^+$).

Example 1.23

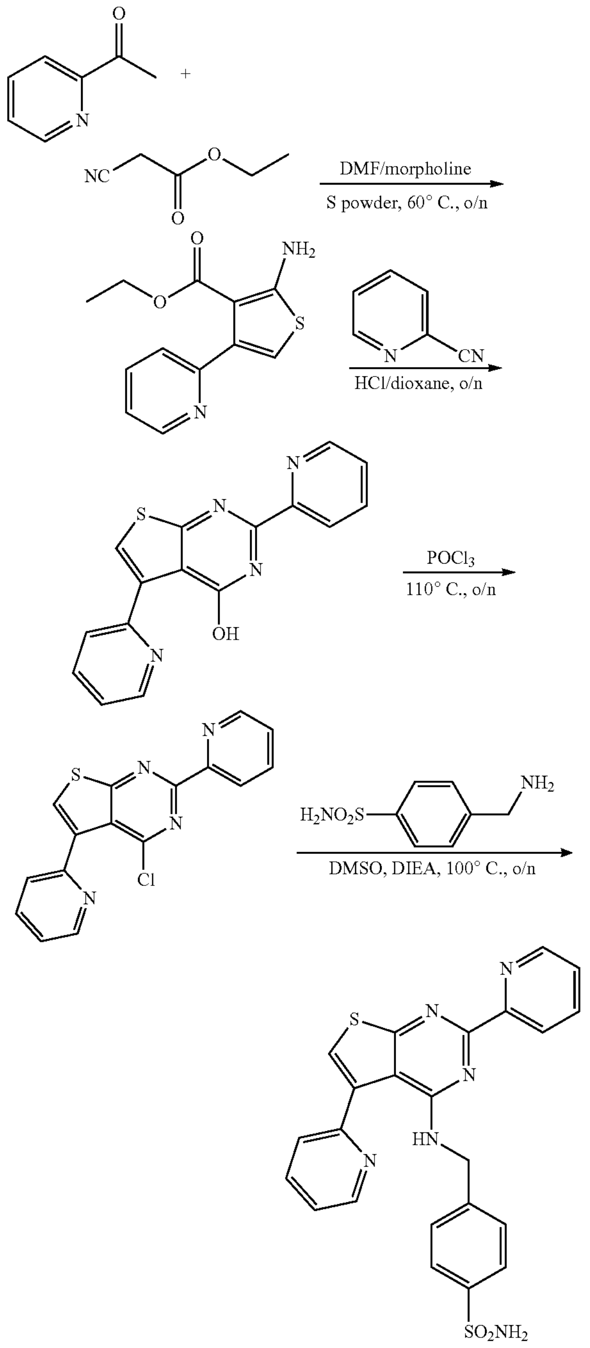

4-(((2,5-Di(pyridin-2-yl)thieno[2,3-d]pyrimidin-4-yl)amino)methyl)benzenesulfonamide Step 1: To a solution of 1-(pyridin-2-yl)ethanone (1.2 g, 10 mmol) in DMF (40 mL) was added ethyl 2-cyanoacetate (2.33 mL, 22 mmol), morpholine (1.3 mL, 5.7 mmol) and S powder (480 mg, 15 mmol). The mixture was stirred at 60° C. overnight under $N_2$ atmosphere (balloon). The reaction mixture was concentrated and the residue was purified by silica gel column (PE/EA=7/1) to give ethyl 2-amino-4-(pyridin-2-yl)thiophene-3-carboxylate (1.8 g, yield: 73%) as a brown oil.

Step 2: To a solution of ethyl 2-amino-4-(pyridin-2-yl) thiophene-3-carboxylate (100 mg, 0.28 mmol) in dioxane (5 mL) was added picolinonitrile (35 mg, 0.34 mmol) and HCl/dioxane (5 mL). The reaction mixture was stirred at 100° C. overnight. The mixture was concentrated in vacuum to give a crude product, which was purified by silica gel column (DCM/MeOH=10/1) to give 4-chloro-2,5-di(pyridin-2-yl)thieno[2,3-d]pyrimidine (20 mg, yield: 23%) as a yellow solid.

Step 3: A solution of 4-chloro-2,5-di(pyridin-2-yl)thieno [2,3-d]pyrimidine (100 mg, 0.31 mmol), 4-(aminomethyl) benzenesulfonamide (76 mg, 0.33 mmol) and DIEA (80 mg, 0.62 mmol) in DMSO (10 mL) was stirred at 100° C. overnight. The mixture was purified by prep-HPLC to give 4-(((2,5-di(pyridin-2-yl)thieno[2,3-d]pyrimidin-4-yl)amino) methyl)benzenesulfonamide (6.8 mg, yield: 4.6%) as a yellow solid. $^1$HNMR (400 MHz, DMSO-$d_6$): δ=11.57 (t, J=5.2 Hz, 1H), 8.74-8.72 (m, 1H), 8.49-8.48 (m, 1H), 8.40 (s, 1H), 8.36 (d, J=5.6 Hz, 1H), 8.16 (d, J=4.2 Hz, 1H), 8.05-8.01 (m, 1H), 8.00-7.91 (m, 1H), 7.81 (d, J=4.2 Hz, 2H), 7.69 (d, J=4.2 Hz, 2H), 7.51-7.45 (m, 2H), 7.32 (s, 2H), 4.99 (d, J=2.6 Hz, 2H). MS: m/z 475.0 (M+$H^+$).

Example 1.24

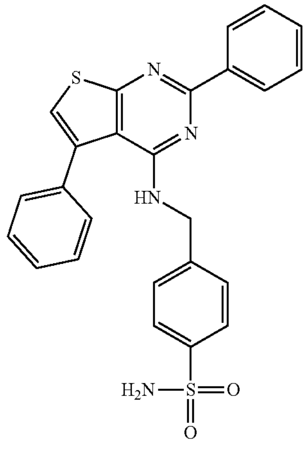 [SMILES: NS(=O)(=O)c1ccc(CNc2nc(-c3ccccc3)nc3scc(-c4ccccc4)c23)cc1]

4-(((2,5-Diphenylthieno[2,3-d]pyrimidin-4-yl) amino)methyl)benzenesulfonamide

The title compound was prepared using general procedure of 5-(((5-methyl-2-(pyridin-2-yl)thieno[2,3-d]pyrimidin-4-yl)amino)methyl)thiophene-2-sulfonamide (Example 1.37). $^1$HNMR (400 MHz, DMSO-$d_6$): δ=8.21-8.19 (m, 2H), 8.10 (brs, 3H), 7.78 (d, J=4 Hz, 2H), 7.63-7.61 (m, 2H), 7.41-7.32 (m, 8H), 7.21 (s, 1H), 4.01 (s, 2H). MS: m/z 472.7 (M+$H^+$).

Example 1.25

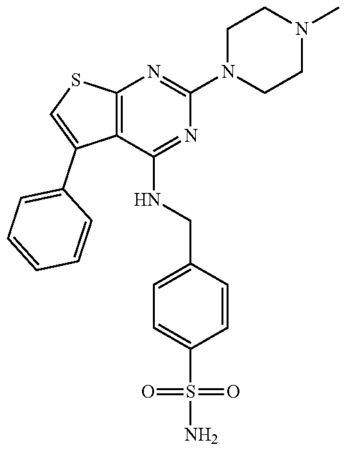 [SMILES: CN1CCN(c2nc(NCc3ccc(S(N)(=O)=O)cc3)c3c(-c4ccccc4)csc3n2)CC1]

4-(((2-(4-Methylpiperazin-1-yl)-5-phenylthieno[2,3-d]pyrimidin-4-yl)amino)methyl)-benzenesulfonamide The title compound was prepared using general procedure of 4-(((2-morpholino-5-phenylthieno[2,3-d]pyrimidin-4-yl) amino)methyl)benzenesulfonamide (Example 1.38). $^1$HNMR (400 MHz, DMSO-$d_6$): δ=11.19 (s, 1H), 7.76 (d, J=8.4 Hz, 2H), 7.54-7.49 (m, 5H), 7.47-7.44 (m, 2H), 7.42-7.37 (m, 2H), 7.12 (s, 1H), 6.18 (s, 1H), 4.61 (d, J=6.4 Hz, 4H), 3.38-3.31 (m, 4H), 2.88-2.86 (m, 2H), 2.71 (d, J=4.4 Hz, 3H). MS: m/z 494.8 (M+$H^+$).

Example 1.26

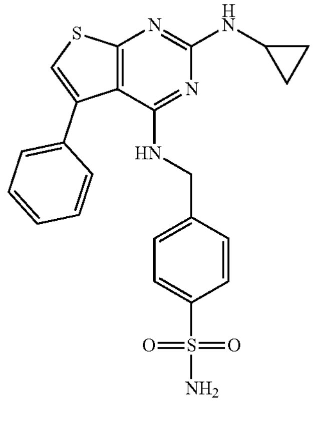 [SMILES: NS(=O)(=O)c1ccc(CNc2nc(NC3CC3)nc3scc(-c4ccccc4)c23)cc1]

4-(((2-(Cyclopropylamino)-5-phenylthieno[2,3-d] pyrimidin-4-yl)amino)methyl)-benzenesulfonamide The title compound was prepared using general procedure of 4-(((2-morpholino-5-phenylthieno[2,3-d]pyrimidin-4-yl) amino)methyl)benzenesulfonamide (Example 1.38). $^1$HNMR (400 MHz, DMSO-$d_6$): δ=7.73 (d, J=8 Hz, 2H), 7.47-7.42 (m, 5H), 7.41-7.38 (m, 2H), 7.32 (brs, 2H), 7.02-6.99 (m, 1H), 6.90 (m, 1H), 5.55 (brs, 1H), 4.59 (d, J=4

Hz, 2H), 2.70-2.64 (m, 1H), 0.62-0.59 (m, 2H), 0.43-0.40 (m, 2H). MS: m/z 452.1 ($M+H^+$).

Example 1.27

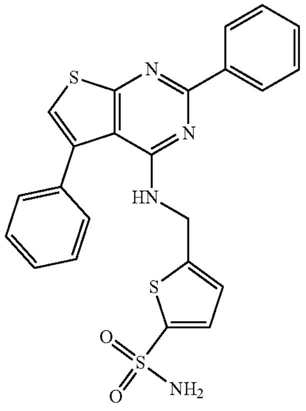 [SMILES: NS(=O)(=O)c1ccc(CNc2nc(-c3ccccc3)nc3scc(-c4ccccc4)c23)s1]

5-(((2,5-Diphenylthieno[2,3-d]pyrimidin-4-yl)amino)methyl)thiophene-2-sulfonamide The title compound was prepared using general procedure of 5-(((5-methyl-2-(pyridin-2-yl)thieno[2,3-d]pyrimidin-4-yl)amino)methyl)thiophene-2-sulfonamide (Example 1.37). $^1$HNMR (400 MHz, DMSO-$d_6$): δ=8.38-8.35 (m, 2H), 8.07 (brs, 3H), 7.63-7.61 (m, 2H), 7.45-7.42 (m, 3H), 7.36-7.30 (m, 4H), 7.21 (s, 1H), 6.97 (d, J=4 Hz, 1H), 4.12 (s, 2H). MS: m/z 478.7 ($M+H^+$).

Example 1.28

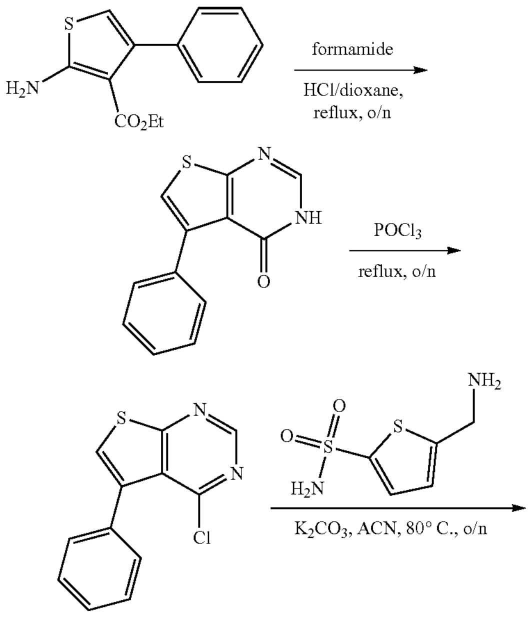

-continued

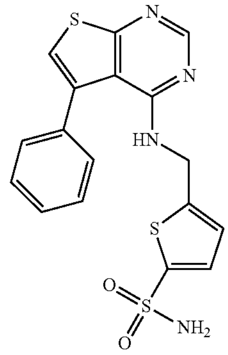

5-(((5-Phenylthieno[2,3-d]pyrimidin-4-yl)amino)methyl)thiophene-2-sulfonamide

Step 1: A mixture of ethyl 2-amino-4-phenylthiophene-3-carboxylate (500 mg, 2.02 mmol) in formamide (4 mL) was stirred at 200° C. for 2 hrs under microwave irradiation. The reaction was monitored by LCMS. Then the reaction mixture was concentrated in vacuum to give a residue, which was purified by reverse phase column (5-95% ACN in $H_2O$, 40 mins) to afford 5-phenylthieno[2,3-d]pyrimidin-4(3H)-one (408 mg, yield: 88%) as a white solid. $^1$HNMR (400 MHz, DMSO-d6): δ=12.48 (brs, 1H), 8.15 (s, 1H), 7.55-7.52 (m, 3H), 7.41-7.35 (m, 3H).

Step 2: A mixture of 5-phenylthieno[2,3-d]pyrimidin-4(3H)-one (408 mg, 1.79 mmol) in $POCl_3$ (10 mL) was stirred at 110° C. overnight. The reaction was monitored by LCMS. Then the reaction mixture was concentrated in vacuum to give a residue, which was purified by silica gel column (DCM/MeOH=100/1 to 30/1) to afford 4-chloro-5-phenylthieno[2,3-d]pyrimidine (186 mg, yield: 42%) as a yellow solid.

Step 3: To a solution of 4-chloro-5-phenyl-thieno[2,3-d]pyrimidine (93 mg, 0.38 mmol) in ACN (20 mL) was added 5-(aminomethyl)thiophene-2-sulfonamide (172 mg, 0.76 mmol), followed by $K_2CO_3$ (157 mg, 1.14 mmol). Then the resulting mixture was stirred at 80° C. overnight. The reaction was monitored by LCMS. Then $K_2CO_3$ was filtered off, and the filtrate was concentrated in vacuum to give a residue, which was purified by prep-HPLC with $NH_4HCO_3$ as additive to afford 5-(((5-phenylthieno[2,3-d]pyrimidin-4-yl)amino)methyl)thiophene-2-sulfonamide (15.0 mg, yield: 10%) as a white solid. $^1$HNMR (400 MHz, DMSO-$d_6$): δ=8.22 (brs, 1H), 8.13 (brs, 2H), 7.55-7.53 (m, 2H), 7.31-7.24 (m, 5H), 7.00 (d, J=4 Hz, 1H), 4.15 (s, 2H). MS: m/z 402.7 ($M+H^+$).

Example 1.29

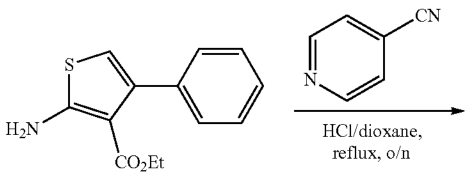

-continued

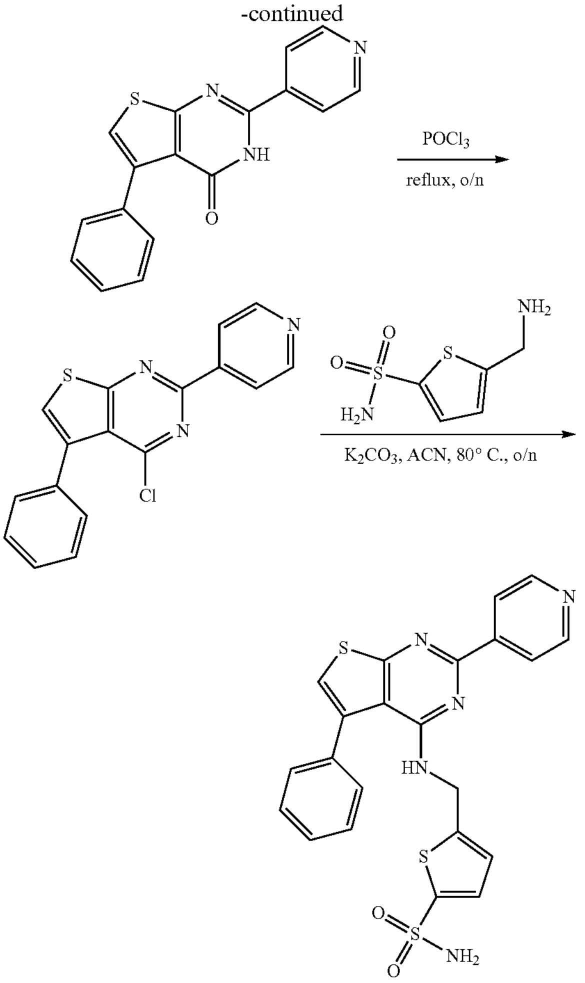

5-(((5-Phenyl-2-(pyridin-4-yl)thieno[2,3-d]pyrimidin-4-yl)amino)methyl)thiophene-2-sulfonamide Step 1: To a solution of ethyl 2-amino-4-phenylthiophene-3-carboxylate (1.0 g, 4.04 mmol) and isonicotinonitrile (842 mg, 8.08 mmol) in dioxane (10 mL) was added HCl/dioxane (10 mL). The resulting mixture was stirred at 100° C. overnight. The reaction was monitored by LCMS. Then the reaction mixture was concentrated in vacuum to give a residue, which was purified by silica gel column (DCM/MeOH=30/1) to afford 5-phenyl-2-(pyridin-4-yl)thieno[2,3-d]pyrimidin-4(3H)-one (882 mg, yield: 72%) as a yellow solid.

Step 2: A mixture of 5-phenyl-2-(pyridin-4-yl)thieno[2,3-d]pyrimidin-4(3H)-one (882 mg, 2.89 mmol) in $POCl_3$ (6 mL) was stirred at 110° C. overnight. The reaction was monitored by LCMS. Then the reaction mixture was concentrated in vacuum to give a residue, which was purified by silica gel column (DCM/MeOH=100/1 to 30/1) to afford 4-chloro-5-phenyl-2-(pyridin-4-yl)thieno[2,3-d]pyrimidine (706 mg, yield: 75%) as a yellow solid.

Step 3: To a solution of 4-chloro-5-phenyl-2-(pyridin-4-yl)thieno[2,3-d]pyrimidine (100 mg, 0.31 mmol) in ACN (20 mL) was added 5-(aminomethyl)thiophene-2-sulfonamide (106 mg, 0.46 mmol), followed by $K_2CO_3$ (128 mg, 0.93 mmol). Then the resulting mixture was stirred at 80° C. overnight. The reaction was monitored by LCMS. Then $K_2CO_3$ was filtered off, and the filtrate was concentrated in vacuum to give a residue, which was purified by prep-HPLC with $NH_4HCO_3$ as additive to afford 5-(((5-phenyl-2-(pyridin-4-yl)thieno[2,3-d]pyrimidin-4-yl)amino)methyl)thiophene-2-sulfonamide (12.4 mg, yield: 8%) as a yellow solid. $^1$HNMR (400 MHz, DMSO-$d_6$): δ=8.69 (d, J=4 Hz, 2H), 8.20 (d, J=4 Hz, 2H), 8.07 (brs, 2H), 7.63-7.60 (m, 2H), 7.36-7.30 (m, 5H), 6.98 (d, J=4 Hz, 1H), 4.12 (s, 2H). MS: m/z 480.0 (M+H$^+$).

Example 1.30

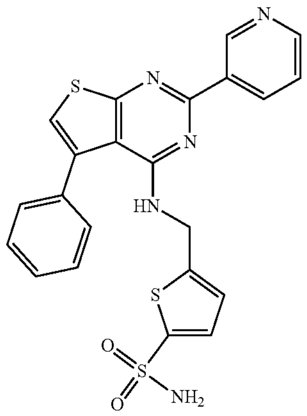 [SMILES: NS(=O)(=O)c1ccc(CNc2nc(-c3cccnc3)nc3scc(-c4ccccc4)c23)s1]

5-(((5-Phenyl-2-(pyridin-3-yl)thieno[2,3-d]pyrimidin-4-yl)amino)methyl)thiophene-2-sulfonamide The title compound was prepared using general procedure of 5-(((5-methyl-2-(pyridin-2-yl)thieno[2,3-d]pyrimidin-4-yl)amino)methyl)thiophene-2-sulfonamide (Example 1.37). $^1$HNMR (400 MHz, DMSO-$d_6$): δ=9.40-9.38 (m, 1H), 8.62-8.59 (m, 2H), 8.01 (brs, 3H), 7.63-7.60 (m, 2H), 7.50-7.46 (m, 1H), 7.36-7.30 (m, 5H), 6.98 (d, J=4 Hz, 1H), 4.13 (s, 2H). MS: m/z 479.7 (M+H$^+$).

Example 1.31

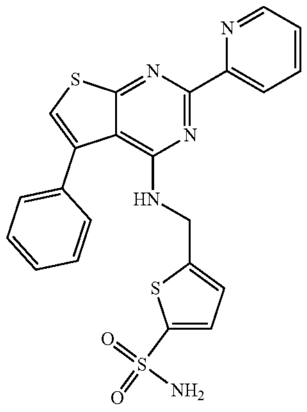 [SMILES: NS(=O)(=O)c1ccc(CNc2nc(-c3ccccn3)nc3scc(-c4ccccc4)c23)s1]

5-(((5-Phenyl-2-(pyridin-2-yl)thieno[2,3-d]pyrimidin-4-yl)amino)methyl)thiophene-2-sulfonamide The title compound was prepared using general procedure of 5-phenyl-2-(pyridin-2-yl)-N-(pyridin-4-ylmethyl)thieno

[2,3-d]pyrimidin-4-amine (Example 1). $^1$HNMR (400 MHz, DMSO-$d_6$): δ=8.69 (d, J=4.4 Hz, 1H), 8.36 (d, J=8.0 Hz, 1H), 8.01 (s, 2H), 7.92 (t, J=7.6 Hz, 1H), 7.62-7.57 (m, 3H), 7.45 (t, J=4.8 Hz, 1H), 7.37-7.31 (m, 4H), 6.97 (d, J=3.6 Hz, 1H), 4.13 (s, 2H). MS: m/z 480.0 (M+$H^+$).

Example 1.32

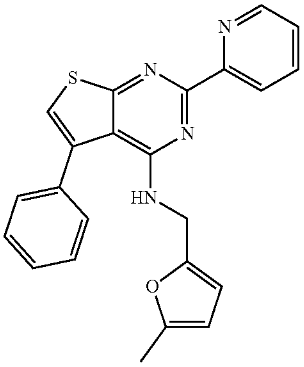 [SMILES: Cc1ccc(CNc2nc(-c3ccccn3)nc3scc(-c4ccccc4)c23)o1]

N-((5-methylfuran-2-yl)methyl)-5-phenyl-2-(pyridin-2-yl)thieno[2,3-d]pyrimidin-4-amine The title compound was prepared using general procedure of (4-methyl-benzyl)-(5-phenyl-2-pyridin-2-yl-thieno[2,3-d]pyrimidin-4-yl)-amine (Example 1.7). $^1$HNMR (400 MHz, DMSO-$d_6$): δ=8.75-8.73 (m, 1H), 8.46 (d, J=8.0 Hz, 1H), 7.99-7.94 (m, 1H), 7.60 (s, 1H), 7.54-7.48 (m, 6H), 6.14 (d, J=2.8 Hz, 1H), 5.98-5.93 (m, 1H), 5.65 (t, J=5.2 Hz, 1H), 4.67 (d, J=8.8 Hz, 2H), 2.20 (s, 3H). MS: m/z 399.1 (M+$H^+$).

Example 1.33

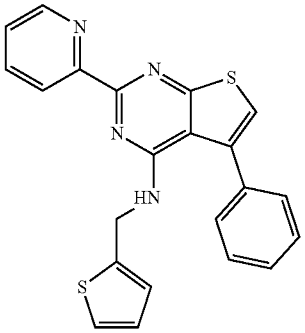 [SMILES: c1ccc(-c2csc3nc(-c4ccccn4)nc(NCc4cccs4)c23)cc1]

(5-Phenyl-2-pyridin-2-yl-thieno[2,3-d]pyrimidin-4-yl)-thiophen-2-ylmethyl-amine

The title compound was prepared using general procedure of (4-methyl-benzyl)-(5-phenyl-2-pyridin-2-yl-thieno[2,3-d]pyrimidin-4-yl)-amine (Example 1.7). $^1$HNMR (400 MHz, DMSO-$d_6$): δ=8.74 (d, J=4.0 Hz, 1H), 8.48 (d, J=8.0 Hz, 1H), 8.00-7.92 (m, 1H), 7.60 (s, 1H), 7.55-7.45 (m, 6H), 7.38-7.34 (m, 1H), 7.03 (d, J=2.4 Hz, 1H), 6.96-6.90 (m, 1H), 5.97 (t, J=5.6 Hz, 1H), 4.92 (d, J=5.2 Hz, 2H). MS: m/z 401.0 (M+$H^+$).

Example 1.34

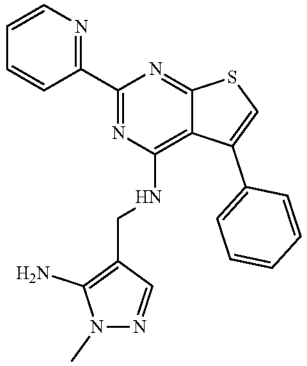 [SMILES: Cn1ncc(CNc2nc(-c3ccccn3)nc3scc(-c4ccccc4)c23)c1N]

(5-Amino-1-methyl-1H-pyrazol-4-ylmethyl)-(5-phenyl-2-pyridin-2-yl-thieno[2,3-d]pyrimidin-4-yl)-amine The title compound was prepared using general procedure of (4-methyl-benzyl)-(5-phenyl-2-pyridin-2-yl-thieno[2,3-d]pyrimidin-4-yl)-amine (Example 1.7). $^1$HNMR (400 MHz, DMSO-$d_6$): δ=8.76 (d, J=4.0 Hz, 1H), 8.51 (d, J=8.0 Hz, 1H), 8.00-7.95 (m, 1H), 7.56 (s, 1H), 7.55-7.46 (m, 6H), 6.96 (s, 1H), 5.65 (t, J=5.6 Hz, 1H), 5.52 (s, 2H), 4.35 (d, J=5.6 Hz, 2H), 3.45 (s, 3H). MS: m/z 414.1 (M+$H^+$).

Example 1.35

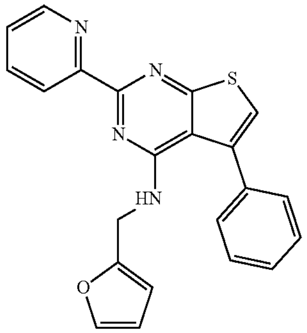 [SMILES: c1ccc(-c2csc3nc(-c4ccccn4)nc(NCc4ccco4)c23)cc1]

Furan-2-ylmethyl-(5-phenyl-2-pyridin-2-yl-thieno[2,3-d]pyrimidin-4-yl)-amine

The title compound was prepared using general procedure of (4-methyl-benzyl)-(5-phenyl-2-pyridin-2-yl-thieno[2,3-d]pyrimidin-4-yl)-amine (Example 1.7). $^1$HNMR (400 MHz, DMSO-$d_6$): δ=8.74 (d, J=5.2 Hz, 1H), 8.44 (d, J=8.0 Hz, 1H), 7.99-7.93 (m, 1H), 7.60 (s, 1H), 7.56-7.54 (m, 1H), 7.53-7.47 (m, 6H), 6.39-6.35 (m, 1H), 6.28 (d, J=3.2 Hz, 1H), 5.73 (t, J=5.2 Hz, 1H), 4.74 (d, J=5.2 Hz, 2H). MS: m/z 385.0 (M+$H^+$).

Example 1.36

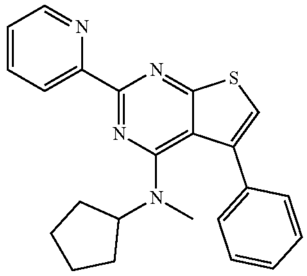 [SMILES: CN(c1nc(-c2ccccn2)nc2scc(-c3ccccc3)c12)C1CCCC1]

Cyclopentyl-methyl-(5-phenyl-2-pyridin-2-yl-thieno[2,3-d]pyrimidin-4-yl)-amine

The title compound was prepared using general procedure of (4-methyl-benzyl)-(5-phenyl-2-pyridin-2-yl-thieno[2,3-d]pyrimidin-4-yl)-amine (Example 1.7). $^{1}$HNMR (400 MHz, DMSO-$d_6$): δ=8.74 (d, J=4.0 Hz, 1H), 8.43 (d, J=8.0 Hz, 1H), 8.01-7.94 (m, 1H), 7.69 (s, 1H), 7.54-7.45 (m, 5H), 7.44-7.38 (m, 1H), 4.58-4.49 (m, 1H), 2.43 (s, 3H), 1.61-1.33 (m, 8H). MS: m/z 387.1 (M+H$^{+}$).

Example 1.37

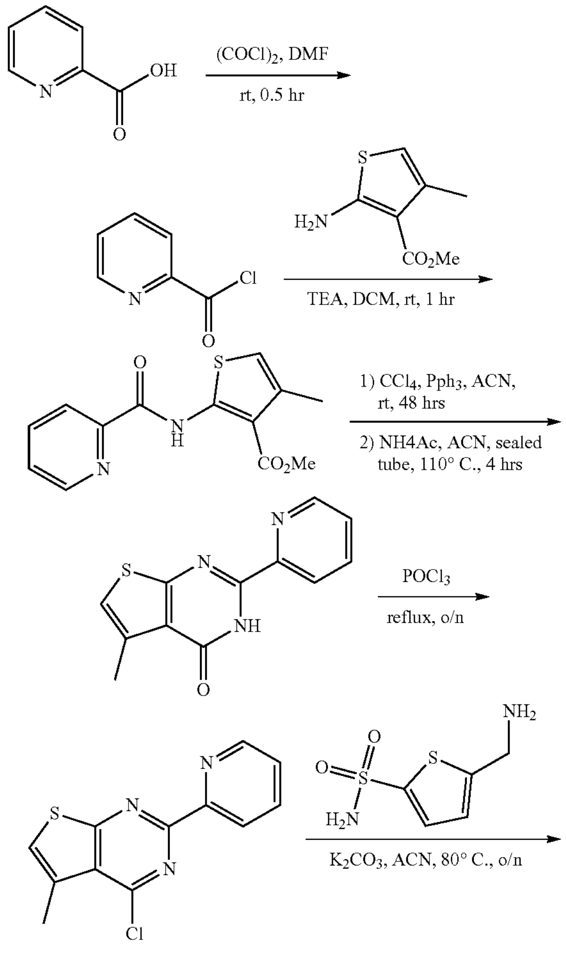

-continued

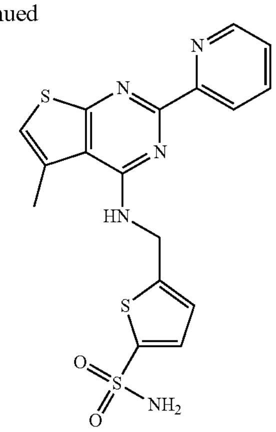

5-(((5-Methyl-2-(pyridin-2-yl)thieno[2,3-d]pyrimidin-4-yl)amino)methyl)thiophene-2-sulfonamide Step 1 and Step 2: To a solution of picolinic acid (1.23 g, 10.0 mmol) in $(COCl)_2$ (10 mL) was added 2 drops of DMF. The resulting mixture was stirred at room temperature for 0.5 hr. Then the mixture was concentrated in vacuum to give picolinoyl chloride as a white solid, which was dissolved in dry DCM (40 mL). Then methyl 2-amino-4-methylthiophene-3-carboxylate (2.05 g, 12.0 mmol) was added, followed by TEA (3.03 g, 30.0 mmol). The resulting mixture was stirred at room temperature for 1 hr. The reaction was monitored by LCMS and TLC. Then the reaction mixture was concentrated in vacuum to give a residue, which was purified by silica gel column (DMC) to afford methyl 4-methyl-2-(picolinamido)thiophene-3-carboxylate (2.54 g, yield: 92%) as a brown solid.

Step 3: To a mixture of methyl 4-methyl-2-(picolinamido)thiophene-3-carboxylate (1.38 g, 5.0 mmol) and triphenylphosphine (3.93 g, 15.0 mmol) in ACN (30 mL) was added $CCl_4$ (2.31 g, 15.0 mmol). The resulting mixture was stirred at room temperature for 48 hrs. Then the reaction was treated with NH4Ac (excess) and heated at 110° C. overnight in a sealed tube vial. The reaction was monitored by LCMS. Then the reaction mixture was concentrated in vacuum to give a residue, which was purified by reverse phase column (5-95% ACN in $H_2O$, 60 mins) to afford 5-methyl-2-(pyridin-2-yl)thieno[2,3-d]pyrimidin-4(3H)-one (924 mg, yield: 76%) as a yellow solid. $^{1}$HNMR (400 MHz, DMSO-$d_6$): δ=11.75 (s, 1H), 8.76-8.75 (m, 1H), 8.36 (d, J=8.4 Hz, 1H), 8.08-8.04 (m, 1H), 7.67-7.63 (m, 1H), 7.25 (s, 1H), 3.32 (s, 3H).

Step 4: A mixture of 5-methyl-2-(pyridin-2-yl)thieno[2,3-d]pyrimidin-4(3H)-one (924 mg, 3.80 mmol) in $POCl_3$ (8 mL) was stirred at 110° C. overnight. The reaction was monitored by LCMS and TLC. Then the reaction mixture was concentrated in vacuum to give a residue, which was purified by silica gel column (DCM/MeOH=30/1) to afford 4-chloro-5-methyl-2-(pyridin-2-yl)thieno[2,3-d]pyrimidine (910 mg, yield: 92%) as a brown solid.

Step 5: To a solution of 4-chloro-5-methyl-2-(pyridin-2-yl)thieno[2,3-d]pyrimidine (200 mg, 0.76 mmol) in ACN (20 mL) was added 5-(aminomethyl)thiophene-2-sulfonamide (262 mg, 1.15 mmol), followed by $K_2CO_3$ (309 mg, 2.24 mmol). Then the resulting mixture was stirred at 80° C. overnight. The reaction was monitored by LCMS. Then $K_2CO_3$ was filtered off, and the filtrate was concentrated in vacuum to give a residue, which was purified by prep-HPLC with $NH_4OH$ as additive to afford 5-(((5-Methyl-2-(pyridin-2-yl)thieno[2,3-d]pyrimidin-4-yl)amino)methyl)thiophene-2-sulfonamide (23.0 mg, yield: 7%) as a yellow solid. $^1$HNMR (400 MHz, DMSO-$d_6$): δ=8.67 (d, J=4.4 Hz, 1H), 8.33 (d, J=7.6 Hz, 1H), 7.99-7.92 (m, 2H), 7.92-7.89 (m, 1H), 7.76 (d, J=3.6 Hz, 1H), 7.45-7.42 (m, 1H), 7.01 (d, J=3.6 Hz, 2H), 4.15 (s, 2H), 2.58 (s, 3H). MS: m/z 418.0 (M+$H^+$).

Example 1.38

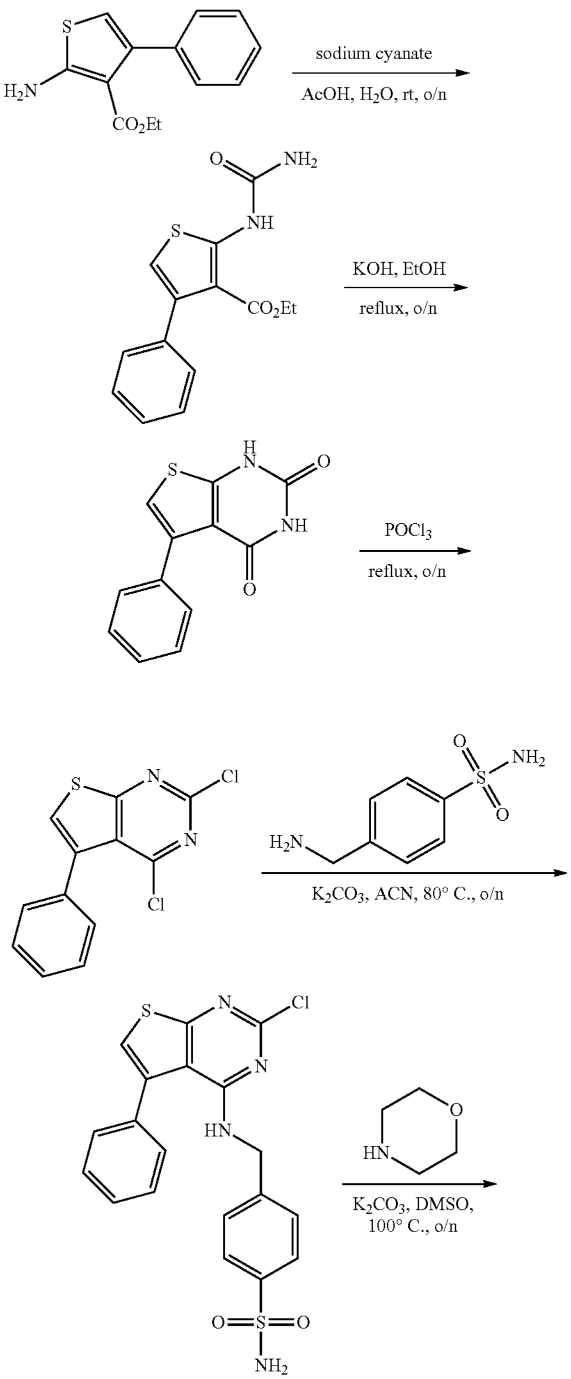

-continued

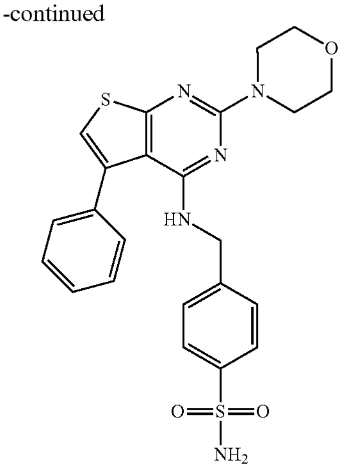

4-(((2-Morpholino-5-phenylthieno[2,3-d]pyrimidin-4-yl)amino)methyl)-benzenesulfonamide Step 1: To a solution of ethyl 2-amino-4-phenylthiophene-3-carboxylate (494 mg, 2.0 mmol) in acetic acid (10 mL) was added a water solution of sodium cyanate (260 mg, 4.0 mmol). The resulting mixture was stirred at room temperature overnight. The reaction was monitored by LCMS and TLC. Then the reaction mixture was concentrated in vacuum to give a residue, which was purified by silica gel column (DCM/MeOH=30/1) to afford ethyl 4-phenyl-2-ureidothiophene-3-carboxylate (312 mg, yield: 54%) as a white solid. $^1$HNMR (400 MHz, DMSO-$d_6$): δ=10.21 (s, 1H), 7.33-7.31 (m, 5H), 7.28-7.25 (m, 2H), 6.67 (s, 1H), 4.03-3.98 (m, 2H), 0.87-0.84 (m, 3H).

Step 2: To a solution of ethyl 4-phenyl-2-ureidothiophene-3-carboxylate (312 mg, 1.07 mmol) in ethanol (30 mL) was added KOH (180 mg, 3.21 mmol). The resulting mixture was stirred at 80° C. overnight. The reaction was monitored by LCMS. Then the white solid precipitated from the mixture was filtered and dried in air to afford 5-phenylthieno[2,3-d]pyrimidine-2,4(1H,3H)-dione (204 mg, yield: 78%) as a white solid.

Step 3: A mixture of 5-phenylthieno[2,3-d]pyrimidine-2,4(1H,3H)-dione (400 mg, 1.64 mmol) in $POCl_3$ (10 mL) was stirred at 110° C. overnight. The reaction was monitored by LCMS. Then the reaction mixture was concentrated in vacuum to give a residue, which was purified by silica gel column (DCM) to afford 2,4-dichloro-5-phenylthieno[2,3-d]pyrimidine (404 mg, yield: 70%) as a colorless oil.

Step 4: To a solution of 2,4-dichloro-5-phenylthieno[2,3-d]pyrimidine (340 mg, 1.21 mmol) in ACN (20 mL) was added 4-(aminomethyl)benzenesulfonamide (538 mg, 2.42 mmol), followed by DIEA (626 mg, 4.84 mmol). Then the resulting mixture was stirred at room temperature overnight. The reaction was monitored by LCMS. Then the solid precipitated from the mixture was filtered, washed with ACN (30 mL) and dried in air to afford 4-(((2-chloro-5-phenylthieno[2,3-d]pyrimidin-4-yl)amino)methyl)benzenesulfonamide (420 mg, yield: 81%) as a white solid.

Step 5: To a solution of 4-(((2-chloro-5-phenylthieno[2,3-d]pyrimidin-4-yl)amino)methyl)benzenesulfonamide (50 mg, 0.12 mmol) and morpholine (21 mg, 0.24 mmol) in DMSO (5 mL) was added $K_2CO_3$ (50 mg, 0.36 mmol). Then the resulting mixture was stirred at room temperature overnight. The reaction was monitored by LCMS. Then $K_2CO_3$ was filtered off, and the filtrate was concentrated in vacuum to give a residue, which was purified by prep-HPLC with $NH_4HCO_3$ as additive to afford 4-(((2-morpholino-5-phenylthieno[2,3-d]pyrimidin-4-yl)amino)methyl)benzenesulfonamide (15.2 mg, yield: 27%) as a white solid. $^1$HNMR (400 MHz, DMSO-$d_6$): δ=7.73 (d, J=8.4 Hz, 2H), 7.50-7.48 (m, 4H), 7.47-7.43 (m, 1H), 7.40-7.38 (d, J=8.4 Hz, 2H), 7.32 (s, 2H), 6.98 (s, 1H), 5.77 (t, J=5.6 Hz, 1H), 4.58 (d, J=5.6 Hz, 2H), 3.61-3.58 (m, 8H). MS: m/z 482.1 (M+H$^+$).

Example 1.39

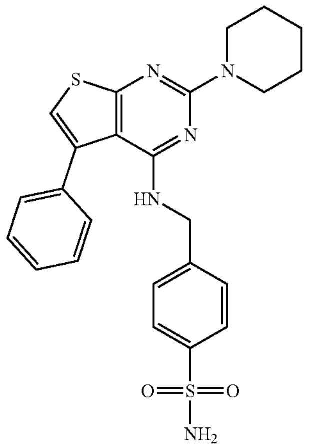 [SMILES: NS(=O)(=O)c1ccc(CNc2nc(N3CCCCC3)nc3scc(-c4ccccc4)c23)cc1]

4-(((5-Phenyl-2-(piperidin-1-yl)thieno[2,3-d]pyrimidin-4-yl)amino)methyl)-benzenesulfonamide The title compound was prepared using general procedure of 4-(((2-morpholino-5-phenylthieno[2,3-d]pyrimidin-4-yl)amino)methyl)benzenesulfonamide (Example 1.38). $^1$HNMR (400 MHz, DMSO-d6): δ=7.73 (d, J=8.4 Hz, 2H), 7.49-7.45 (m, 4H), 7.44-7.41 (m, 1H), 7.38 (d, J=8.4 Hz, 2H), 7.30 (s, 1H), 7.14 (s, 1H), 6.91 (s, 1H), 5.68 (t, J=5.6 Hz, 1H), 4.56 (d, J=5.6 Hz, 2H), 3.65 (t, J=5.6 Hz, 4H), 1.59-1.55 (m, 2H), 1.42-1.41 (m, 4H). MS: m/z 480.1 (M+H$^+$).

Example 1.40

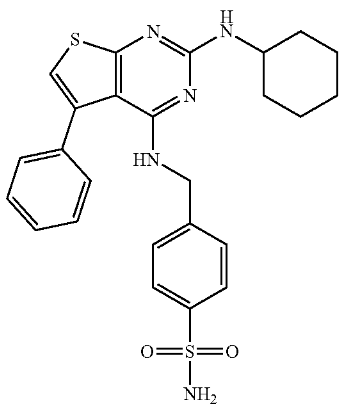 [SMILES: NS(=O)(=O)c1ccc(CNc2nc(NC3CCCCC3)nc3scc(-c4ccccc4)c23)cc1]

4-(((2-(Cyclohexylamino)-5-phenylthieno[2,3-d]pyrimidin-4-yl)amino)methyl)-benzenesulfonamide The title compound was prepared using general procedure of 4-(((2-morpholino-5-phenylthieno[2,3-d]pyrimidin-4-yl)amino)methyl)benzenesulfonamide (Example 1.38). $^1$HNMR (400 MHz, DMSO-$d_6$): δ=7.43 (d, J=8.4 Hz, 2H), 7.48-7.43 (m, 5H), 7.37 (d, J=8.0 Hz, 2H), 7.32 (s, 2H), 6.85 (s, 1H), 6.63-6.62 (m, 1H), 5.80-5.40 (m, 1H), 4.57 (d, J=5.2 Hz, 2H), 3.80 (brs, 1H), 1.80-1.55 (m, 5H), 1.16-1.06 (m, 5H). MS: m/z 493.8 (M+H$^+$).

Example 1.41

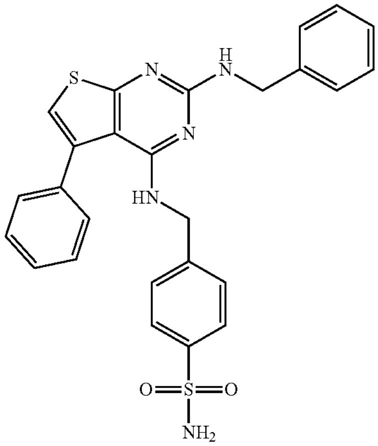 [SMILES: NS(=O)(=O)c1ccc(CNc2nc(NCc3ccccc3)nc3scc(-c4ccccc4)c23)cc1]

4-(((2-(Benzylamino)-5-phenylthieno[2,3-d]pyrimidin-4-yl)amino)methyl)-benzenesulfonamide The title compound was prepared using general procedure of 4-(((2-morpholino-5-phenylthieno[2,3-d]pyrimidin-4-yl)amino)methyl)benzenesulfonamide (Example 1.38). $^1$HNMR (400 MHz, DMSO-$d_6$): δ=8.25 (brs, 0.5H), 7.72 (d, J=6.8 Hz, 2H), 7.48-7.43 (m, 5H), 7.34-7.22 (m, 10H), 7.05 (s, 1H), 6.40 (brs, 0.5H), 4.60-4.59 (m, 2H), 4.50-4.49 (m, 2H). MS: m/z 501.8 (M+H$^+$).

Example 1.42

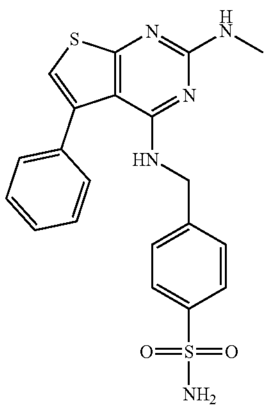 [SMILES: CNc1nc(NCc2ccc(S(N)(=O)=O)cc2)c2c(-c3ccccc3)csc2n1]

4-(((2-(Methylamino)-5-phenylthieno[2,3-d]pyrimidin-4-yl)amino)methyl)-benzenesulfonamide The title compound was prepared using general procedure of 4-(((2-morpholino-5-phenylthieno[2,3-d]pyrimidin-4-yl)amino)methyl)benzenesulfonamide (Example 1.38). $^1$HNMR (400 MHz, DMSO-$d_6$): δ=7.74 (d, J=8 Hz, 2H), 7.48-7.43 (m, 5H), 7.40-7.37 (m, 2H), 7.26 (brs, 2H), 6.87 (s, 1H), 6.73-6.69 (m, 1H), 5.53 (brs, 1H), 4.59 (d, J=4 Hz, 2H), 2.75 (d, J=4 Hz, 3H), MS: m/z 425.8 (M+H$^+$).

Example 1.43

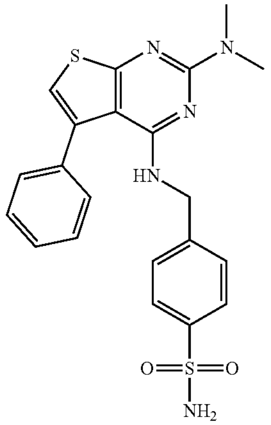 [SMILES: CN(C)c1nc(NCc2ccc(S(N)(=O)=O)cc2)c2c(-c3ccccc3)csc2n1]

4-(((2-(Dimethylamino)-5-phenylthieno[2,3-d]pyrimidin-4-yl)amino)methyl)-benzenesulfonamide The title compound was prepared using general procedure of 4-(((2-morpholino-5-phenylthieno[2,3-d]pyrimidin-4-yl)amino)methyl)benzenesulfonamide (Example 1.38). $^1$HNMR (400 MHz, DMSO-$d_6$): δ=7.74 (d, J=8.4 Hz, 2H), 7.49-7.46 (m, 4H), 7.45-7.42 (m, 1H), 7.39 (d, J=8.0 Hz, 2H), 7.29 (brs, 2H), 6.90 (s, 1H), 5.68-5.65 (m, 1H), 4.59 (d, J=4 Hz, 2H), 3.03 (s, 6H). MS: m/z 440.1 (M+H$^+$).

Example 1.44

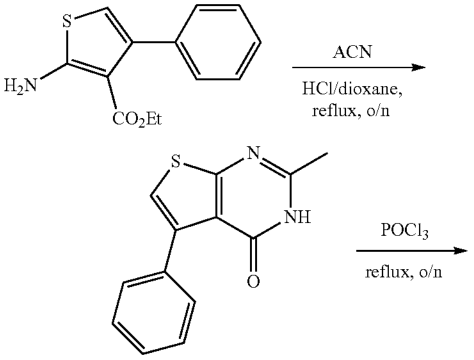

-continued

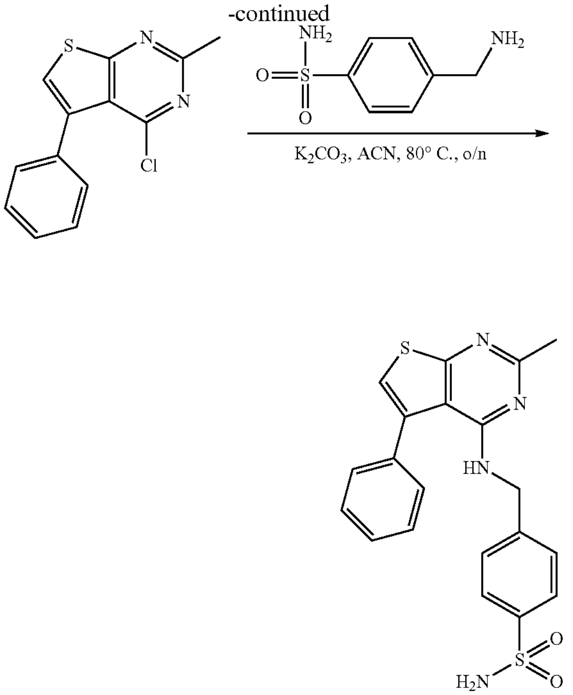

4-(((2-Methyl-5-phenylthieno[2,3-d]pyrimidin-4-yl)amino)methyl)benzenesulfonamide Step 1: To a solution of ethyl 2-amino-4-phenylthiophene-3-carboxylate (1.0 g, 4.04 mmol) and acetonitrile (332 mg, 8.08 mmol) in dioxane (5 mL) was added HCl/dioxane (10 mL). The resulting mixture was stirred at 100° C. overnight. The reaction was monitored by LCMS. Then the reaction mixture was concentrated in vacuum to give a residue, which was purified by reverse phase column (10-80% ACN in $H_2O$, 60 mins) to afford 2-methyl-5-phenylthieno[2,3-d]pyrimidin-4(3H)-one (542 mg, yield: 55%) as a yellow solid.

Step 2: A mixture of 2-methyl-5-phenylthieno[2,3-d]pyrimidin-4(3H)-one (542 mg, 2.24 mmol) in $POCl_3$ (8 mL) was stirred at 110° C. overnight. The reaction was monitored by LCMS. Then the reaction mixture was concentrated in vacuum to give a residue, which was purified by silica gel column (DCM/MeOH=100/1 to 30/1) to afford 4-chloro-2-methyl-5-phenylthieno[2,3-d]pyrimidine (446 mg, yield: 77%) as a yellow solid.

Step 3: To a solution of 4-chloro-2-methyl-5-phenylthieno[2,3-d]pyrimidine (100 mg, 0.38 mmol) in ACN (20 mL) was added 4-(aminomethyl)benzenesulfonamide (171 mg, 0.77 mmol), followed by $K_2CO_3$ (159 mg, 1.15 mmol). Then the resulting mixture was stirred at 80° C. overnight. The reaction was monitored by LCMS. Then $K_2CO_3$ was filtered off, and the filtrate was concentrated in vacuum to give a residue, which was purified by prep-HPLC with $NH_4OH$ as additive to afford 4-(((2-methyl-5-phenylthieno[2,3-d]pyrimidin-4-yl)amino)methyl)benzenesulfonamide (41.6 mg, yield: 26%) as a white solid. $^1$HNMR (400 MHz, DMSO-$d_6$): δ=7.75-7.73 (d, J=8 Hz, 2H), 7.52-7.44 (m, 5H), 7.45-7.42 (m, 3H), 7.32 (s, 2H), 5.79-5.76 (m, 1H), 4.35 (d, J=5.6 Hz, 2H), 2.46 (s, 3H). MS: m/z 411.1 (M+H$^+$).

Example 1.45

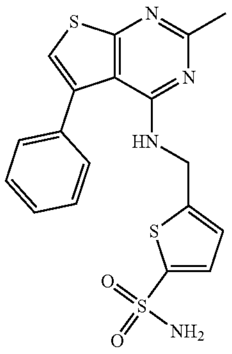 [SMILES: Cc1nc(NCc2ccc(S(N)(=O)=O)s2)c2c(-c3ccccc3)csc2n1]

5-(((2-Methyl-5-phenylthieno[2,3-d]pyrimidin-4-yl)amino)methyl)thiophene-2-sulfonamide The title compound was prepared using general procedure of 4-(((2-methyl-5-phenylthieno[2,3-d]pyrimidin-4-yl)amino)methyl)benzenesulfonamide (Example 1.44). $^1$HNMR (400 MHz, DMSO-$d_6$): δ=8.05 (brs, 2H), 7.56 (m, 2H), 7.34-7.26 (m, 5H), 7.14-7.08 (m, 1H), 7.00 (d, J=8 Hz, 1H), 4.17 (s, 2H), 2.43 (s, 3H). MS: m/z 417.0 (M+H$^+$).

Example 1.46

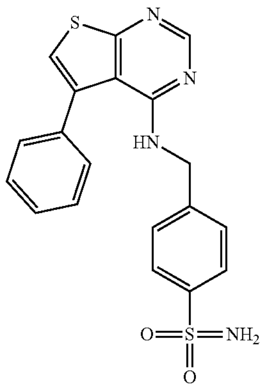

4-(((5-Phenylthieno[2,3-d]pyrimidin-4-yl)amino)methyl)benzenesulfonamide

The title compound was prepared using general procedure of 5-(((5-phenylthieno[2,3-d]pyrimidin-4-yl)amino)methyl)thiophene-2-sulfonamide (Example 1.28). $^1$HNMR (400 MHz, DMSO-$d_6$): δ=8.41 (brs, 1H), 7.75-7.73 (m, 2H), 7.55-7.46 (m, 6H), 7.39-7.37 (d, J=8 Hz, 2H), 7.32 (brs, 2H), 5.94-5.91 (m, 1H), 4.68-4.66 (d, J=8 Hz, 2H). MS: m/z 397.1 (M+H$^+$).

Example 1.47

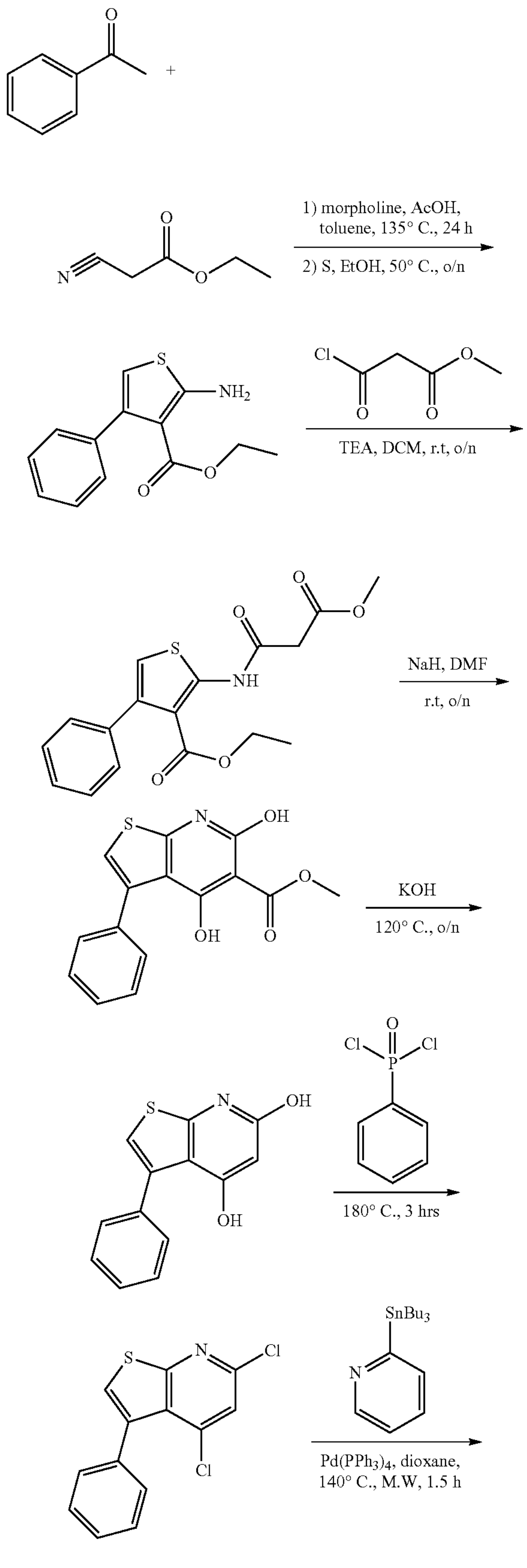

-continued

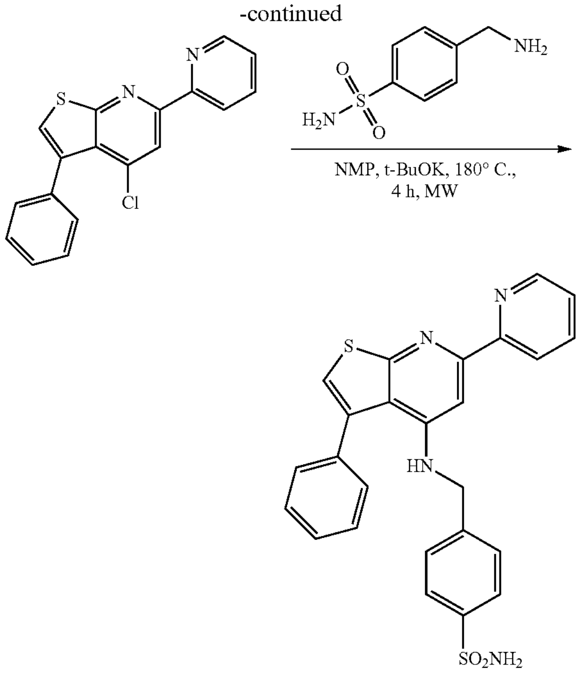

4-(((3-Phenyl-6-(pyridin-2-yl)thieno[2,3-b]pyridin-4-yl)amino)methyl)benzenesulfonamide Step 1: To a solution of acetophenone (12 g, 100 mmol) and ethyl 2-cyanoacetate (24.8 g, 220 mmol) in toluene (200 mL) was added morpholine (13.1 g, 150 mmol) and AcOH (12 g, 200 mmol). The mixture was stirred at 130° C. for 24 hrs with Dean stark apparatus. Then the mixture was concentrated to give a residue, which was dissolved in EtOH (200 mL). S (4.8 g, 150 mmol) and diethylamine (3.3 g) was added into the mixture. The mixture was stirred at 50° C. for 3 hrs. The resulting solution was purified by silica gel column (PE/EA=20/1) to give ethyl 2-amino-4-phenylthiophene-3-carboxylate (11.3 g, yield: 46%) as a yellow solid.

Step 2: To a solution of ethyl 2-amino-4-phenylthiophene-3-carboxylate (2 g, 8.1 mmol) in DCM (100 mL) was added methyl 3-chloro-3-oxopropanoate (1.32 g, 9.7 mmol) and TEA (1 mL). The mixture was stirred at room temperature for 10 mins. The resulting solution was purified by silica gel column (DCM) to give ethyl 2-(3-methoxy-3-oxopropanamido)-4-phenylthiophene-3-carboxylate (2.8 g, yield: 100%) as a yellow oil.

Step 3: To a solution of ethyl 2-(3-methoxy-3-oxopropanamido)-4-phenylthiophene-3-carboxylate (2.8 g, 8.1 mmol) in DMF (20 mL) was added NaH (1.1 g, 48.6 mmol) at 0° C. The mixture was stirred at room temperature overnight. The resulting solution was added $H_2O$ (100 mL) and acidified with HCl to PH=1. The suspension was filtered. The cake was dried to give methyl 4,6-dihydroxy-3-phenylthieno[2,3-b]pyridine-5-carboxylate (2.0 g, yield: 87%) as a yellow solid.

Step 4: To a solution of methyl 4,6-dihydroxy-3-phenylthieno[2,3-b]pyridine-5-carboxylate (2.0 g, 6.9 mmol) in KOH solution (100 mL, 2 M) was stirred at 120° C. overnight. The resulting solution was acidified with HCl (100 mL) to pH=5. The suspension was filtered and rinsed with $H_2O$ (1 mL) to give 3-phenylthieno[2,3-b]pyridine-4,6-diol (1.7 g, crude) as a yellow solid.

Step 5: To a solution of 3-phenylthieno[2,3-b]pyridine-4,6-diol (1.0 g, 4.1 mmol) in phenylphosphonic dichloride (15 mL) was stirred at 180° C. for 3 hrs. The resulting solution was added DCM (100 mL), quenched with saturated aqueous $NaHCO_3$ and extracted with DCM (60 mL×3). The combined organic layers were concentrated and the residue was purified by silica gel column (DCM) to give 4,6-dichloro-3-phenylthieno[2,3-b]pyridine (430 mg, yield: 39%) as a brown solid.

Step 6: To a solution of 4,6-dichloro-3-phenylthieno[2,3-b]pyridine (150 mg, 0.5 mmol) in dioxane (5 mL) was added 2-(tributylstannyl)pyridine (276 mg, 0.75 mmol) and $Pd(PPh_3)_4$ (57 mg, 0.05 mmol). The mixture was stirred at 140° C. for 1.5 hrs. The resulting solution was added saturated aqueous KF solution and stirred for 30 mins. The solution was extracted with EA (60 mL×3). The combined organic layers were concentrated to give 4-chloro-3-phenyl-6-(pyridin-2-yl)thieno[2,3-b]pyridine (67 mg, yield: 42%) as a yellow solid. $^1$HNMR (400 MHz, DMSO-d6): δ=8.74 (d, J=4.4 Hz, 1H), 8.49 (d, J=8.4 Hz, 1H), 8.44 (s, 1H), 8.02 (t, J=1.6 Hz, 1H), 7.98 (s, 1H), 7.54-7.51 (m, 1H), 7.49-7.44 (m, 5H).

Step 7: To a solution of 4-chloro-3-phenyl-6-(pyridin-2-yl)thieno[2,3-b]pyridine (67 mg, 0.2 mmol) in NMP (5 mL) was added 4-(aminomethyl)benzenesulfonamide (154 mg, 0.8 mmol) and t-BuOK (1.3 mg, 0.12 mmol). The mixture was stirred at 200° C. for 4 hrs. The resulting solution was concentrated and purified by prep-HPLC to give 4-(((3-phenyl-6-(pyridin-2-yl)thieno[2,3-b]pyridin-4-yl)amino)methyl)benzenesulfonamide (3.5 mg, yield: 4%) as a yellow solid. $^1$HNMR (400 MHz, DMSO-$d_6$): δ=8.63 (t, J=4.0 Hz, 1H), 8.40 (d, J=8.0 Hz, 1H), 7.91 (t, J=2.0 Hz, 1H), 7.74 (t, J=8.4 Hz, 2H), 7.57-7.54 (m, 3H), 7.51-7.41 (m, 5H), 7.37 (d, J=8.4 Hz, 2H), 7.32 (s, 2H), 5.16 (t, J=4.0 Hz, 1H), 4.50 (d, J=5.6 Hz, 2H). MS: m/z 473.0 (M+H$^+$).

Example 1.48

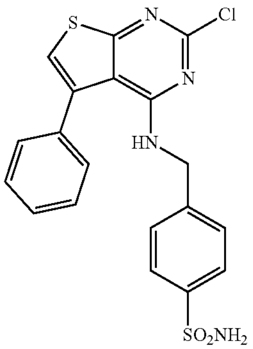 [SMILES: NS(=O)(=O)c1ccc(CNc2nc(Cl)nc3scc(-c4ccccc4)c23)cc1]

4-((2-Chloro-5-phenylthieno[2,3-d]pyrimidin-4-yl)aminomethyl)benzenesulfonamide

To a suspension of 2,4-dichloro-5-phenylthieno[2,3-d]pyrimidine (136 mg) and homosulfamine hydrochloride (130 mg) in 2-propanol (5 mL) was added N,N-diisopropylethylamine (0.2 mL) at room temperature. The resulting mixture was stirred at 90° C. for 3 hours and then cooled to room temperature. The precipitate was collected and washed with methanol, then dried under reduced pressure, to give the title compound as a pale-yellow solid (200 mg, yield 96%). $^1$H-NMR (DMSO-$D_6$) δ: 7.76 (2H, d, J=8.5 Hz), 7.56 (1H, s), 7.54-7.45 (5H, m), 7.41 (2H, d, J=8.5 Hz), 7.34 (2H, s), 6.33 (1H, t, J=5.8 Hz), 4.64 (2H, d, J=6.1 Hz). MS: m/z 431.0 (M+H$^+$).

Example 1.49

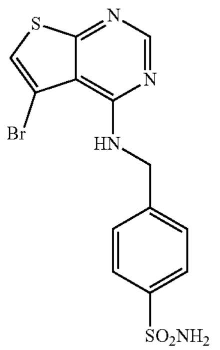 [SMILES: NS(=O)(=O)c1ccc(CNc2ncnc3scc(Br)c23)cc1]

4-((5-Bromothieno[2,3-d]pyrimidin-4-yl)aminomethyl)benzenesulfonamide

The title compound was prepared according to the general procedure of Example 1.48 using 5-bromo-4-chlorothieno[2,3-d]pyrimidine and homosulfamine hydrochloride. $^1$H-NMR (DMSO-$D_6$) δ: 8.37 (1H, s), 7.85-7.84 (2H, m), 7.77 (2H, d, J=7.9 Hz), 7.52 (2H, d, J=8.5 Hz), 7.31 (2H, s), 4.88 (2H, d, J=6.1 Hz). MS: m/z 399.0 (M+H$^+$).

Example 1.50

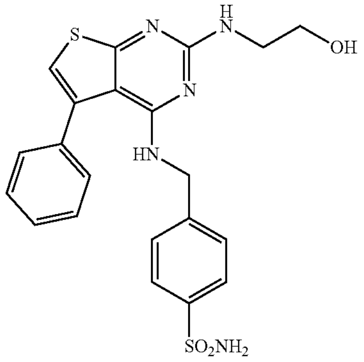 [SMILES: NS(=O)(=O)c1ccc(CNc2nc(NCCO)nc3scc(-c4ccccc4)c23)cc1]

4-((2-(2-Hydroxyethylamino)-5-phenylthieno[2,3-d]pyrimidin-4-yl)aminomethyl)-benzenesulfonamide To a mixture of 4-((2-chloro-5-phenylthieno[2,3-d]pyrimidin-4-yl)aminomethyl)benzenesulfonamide (40 mg) obtained in Example 1.48 in n-butanol (1.5 mL) was added 2-aminoethanol (0.02 mL). After stirring at 200° C. for 3 hours by microwave, the resulting mixture was concentrated under reduced pressure. The residue was purified by automated flash chromatography using 1-5% methanol in dichloromethane as eluent, to give the title compound as a colorless solid (37 mg, yield 88%). $^1$H-NMR (DMSO-$D_6$) δ: 7.74 (2H, d, J=8.5 Hz), 7.47 (4H, d, J=4.3 Hz), 7.43-7.41 (1H, m), 7.38 (2H, d, J=7.9 Hz), 7.31 (2H, s), 6.88 (1H, s), 6.65-6.63 (1H, br m), 5.54 (1H, br s), 4.63 (1H, br s), 4.58 (2H, d, J=6.1 Hz), 3.48-3.45 (2H, br m), 3.31-3.30 (2H, br m). MS: m/z 456.1 (M+H$^+$).

Example 1.51

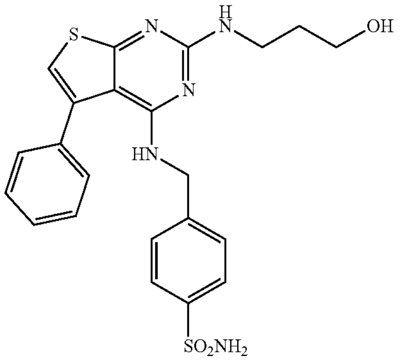 [SMILES: NS(=O)(=O)c1ccc(CNc2nc(NCCCO)nc3scc(-c4ccccc4)c23)cc1]

4-((2-(3-Hydroxypropyl)amino-5-phenylthieno[2,3-d]pyrimidin-4-yl)aminomethyl)-benzenesulfonamide The title compound was prepared according to the general procedure of Example 1.50 using 4-((2-chloro-5-phenylthieno[2,3-d]pyrimidin-4-yl)aminomethyl)benzenesulfonamide obtained in Example 1.48 and 3-amino-1-propanol. $^1$H-NMR (DMSO-$D_6$) δ: 7.74 (2H, d, J=7.9 Hz), 7.47 (5H, d, J=3.0 Hz), 7.44-7.41 (1H, m), 7.38 (2H, d, J=8.5 Hz), 7.26 (1H, br s), 6.86 (1H, s), 6.74-6.73 (1H, br m), 5.51 (1H, br s), 4.58 (2H, d, J=6.1 Hz), 4.46 (1H, br s), 3.43 (2H, br m), 3.27 (2H, br m), 1.62 (2H, br m). MS: m/z 470.2 (M+H$^+$).

Example 1.52

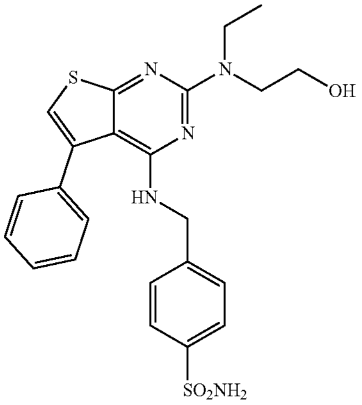 [SMILES: CCN(CCO)c1nc(NCc2ccc(S(N)(=O)=O)cc2)c2c(-c3ccccc3)csc2n1]

4-((2-(N-Ethyl-N-(2-hydroxyethyl)amino)-5-phenylthieno[2,3-d]pyrimidin-4-yl)aminomethyl)-benzenesulfonamide The title compound was prepared according to the general procedure of Example 1.50 using 4-((2-chloro-5-phenylthieno[2,3-d]pyrimidin-4-yl)aminomethyl)benzenesulfonamide obtained in Example 1.48 and 2-(ethylamino)ethanol. $^{1}$H-NMR (DMSO-$D_6$) δ: 7.75 (2H, d, J=8.5 Hz), 7.49 (4H, d, J=4.3 Hz), 7.46-7.42 (1H, m), 7.39 (2H, d, J=8.5 Hz), 7.31 (2H, s), 6.89 (1H, s), 5.67 (1H, br s), 4.65 (1H, br s), 4.56 (2H, d, J=5.5 Hz), 3.52 (6H, br m), 1.58 (3H, br m). MS: m/z 484.1 (M+$H^+$).

Example 1.53

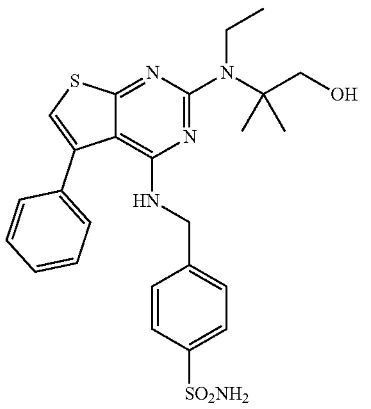 [SMILES: CCN(c1nc(NCc2ccc(S(N)(=O)=O)cc2)c2c(-c3ccccc3)csc2n1)C(C)(C)CO]

4-((2-(N-Ethyl-N-(1-hydroxy-2-methylpropan-2-yl) amino)-5-phenylthieno[2,3-d]pyrimidin-4-yl)aminomethyl)benzenesulfonamide The title compound was prepared according to the general procedure of Example 1.50 using 4-((2-chloro-5-phenylthieno[2,3-d]pyrimidin-4-yl)aminomethyl)benzenesulfonamide obtained in Example 1.48 and 1-ethylamino-2-methyl-2-propanol. $^{1}$H-NMR (DMSO-$D_6$) δ: 7.74 (2H, d, J=7.9 Hz), 7.52-7.43 (6H, m), 7.37 (2H, d, J=7.9 Hz), 7.32 (2H, s), 6.90 (1H, s), 5.65 (1H, br s), 4.59-4.56 (2H, br m), 3.65-3.62 (2H, br m), 3.47 (2H, br m), 1.16-1.06 (9H, br m). MS: m/z 512.2 (M+$H^+$).

Example 1.54

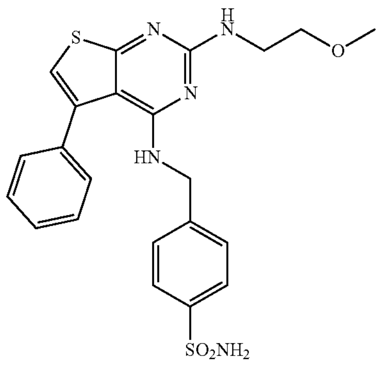 [SMILES: COCCNc1nc(NCc2ccc(S(N)(=O)=O)cc2)c2c(-c3ccccc3)csc2n1]

4-((2-(2-Methoxyethyl)amino-5-phenylthieno[2,3-d] pyrimidin-4-yl)aminomethyl)-benzenesulfonamide The title compound was prepared according to the general procedure of Example 1.50 using 4-((2-chloro-5-phenylthieno[2,3-d]pyrimidin-4-yl)aminomethyl)-benzenesulfonamide obtained in Example 1.48 and 2-methoxyethylamine. $^{1}$H-NMR (DMSO-$D_6$) δ: 7.74 (2H, d, J=7.9 Hz), 7.48 (4H, d, J=3.0 Hz), 7.45-7.42 (2H, m), 7.38 (2H, d, J=8.5 Hz), 7.31 (2H, s), 6.88 (1H, s), 6.73 (1H, br s), 5.55 (1H, br s), 4.58 (2H, d, J=5.5 Hz), 3.37 (3H, br m), 3.21 (3H, br m). MS: m/z 470.1 (M+$H^+$).

Example 1.55

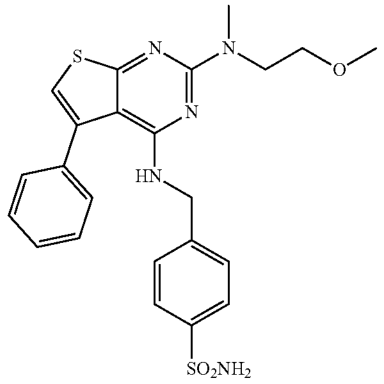 [SMILES: COCCN(C)c1nc(NCc2ccc(S(N)(=O)=O)cc2)c2c(-c3ccccc3)csc2n1]

4-((2-(N-Methyl-N-(2-methoxyethyl)amino)-5-phenylthieno[2,3-d]pyrimidin-4-yl)aminomethyl)benzenesulfonamide The title compound was prepared according to the general procedure of Example 1.50 using 4-((2-chloro-5-phenylthieno[2,3-d]pyrimidin-4-yl)aminomethyl)-benzenesulfonamide obtained in Example 1.48 and N-(2-methoxyethyl) methylamine. $^{1}$H-NMR (DMSO-$D_6$) δ: 7.74 (2H, d, J=8.5 Hz), 7.48-7.47 (4H, m), 7.44-7.42 (1H, m), 7.37 (2H, d, J=8.5 Hz), 7.32 (2H, s), 6.88 (1H, s), 6.57 (1H, br s), 5.55 (1H, br s), 4.59 (2H, d, J=5.5 Hz), 2.36 (2H, br m), 2.16 (7H, br m). MS: m/z 484.2 (M+$H^+$).

Example 1.56

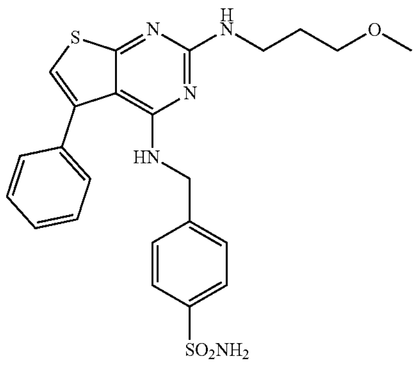 [SMILES: COCCCNc1nc(NCc2ccc(S(N)(=O)=O)cc2)c2c(-c3ccccc3)csc2n1]

4-((2-(3-Methoxypropyl)amino-5-phenylthieno[2,3-d]pyrimidin-4-yl)aminomethyl)-benzenesulfonamide The title compound was prepared according to the general procedure of Example 1.50 using 4-((2-chloro-5-phenylthieno[2,3-d]pyrimidin-4-yl)aminomethyl)-benzenesulfonamide obtained in Example 1.48 and 3-methoxypropylamine. $^{1}$H-NMR (DMSO-$D_6$) δ: 7.74 (2H, d, J=8.5 Hz), 7.47 (4H, d, J=3.0 Hz), 7.43-7.42 (1H, m), 7.38 (2H, d, J=8.5 Hz), 7.19 (1H, br s), 6.87 (1H, s), 6.80-6.77 (1H, br m), 5.53-5.43 (1H, m), 4.58 (2H, d, J=10.0 Hz), 3.36 (3H, s), 3.25 (2H, br m), 3.21 (3H, s), 1.67-1.60 (2H, br m). MS: m/z 484.1 (M+H$^{+}$).

Example 1.57

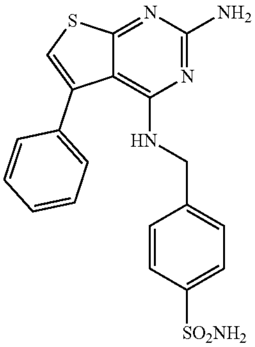 [SMILES: Nc1nc(NCc2ccc(S(N)(=O)=O)cc2)c2c(-c3ccccc3)csc2n1]

4-((2-Amino-5-phenylthieno[2,3-d]pyrimidin-4-yl) aminomethyl)benzenesulfonamide

The title compound was prepared according to the general procedure of Example 1.50 using 4-((2-chloro-5-phenylthieno[2,3-d]pyrimidin-4-yl)aminomethyl)benzenesulfonamide obtained in Example 1.48 and 10% ammonia solution. $^{1}$H-NMR (DMSO-$D_6$) δ: 7.74 (2H, d, J=8.5 Hz), 7.46 (4H, d, J=6.4 Hz), 7.43-7.40 (1H, m), 7.38 (2H, d, J=8.5 Hz), 7.31 (2H, s), 6.87 (1H, s), 6.30 (2H, br m), 5.45 (1H, t, J=10.0 Hz), 4.58 (2H, d, J=5.5 Hz). MS: m/z 412.1 (M+H$^{+}$).

Example 1.58

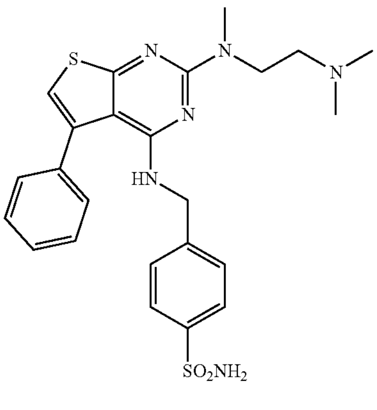 [SMILES: CN(C)CCN(C)c1nc(NCc2ccc(S(N)(=O)=O)cc2)c2c(-c3ccccc3)csc2n1]

4-((2-((N-2-(Dimethylamino)ethyl)-N-methylamino)-5-phenylthieno[2,3-d]pyrimidin-4-yl)aminomethyl)benzenesulfonamide The title compound was prepared according to the general procedure of Example 1.50 using 4-((2-chloro-5-phenylthieno[2,3-d]pyrimidin-4-yl)aminomethyl)-benzenesulfonamide obtained in Example 1.48 and N,N,N'-trimethylethylenediamine. $^{1}$H-NMR (DMSO-$D_6$) δ: 7.74 (2H, d, J=8.5 Hz), 7.48 (4H, d, J=4.3 Hz), 7.46-7.43 (1H, m), 7.37 (2H, d, J=8.5 Hz), 7.31 (2H, s), 6.90 (1H, s), 5.66 (1H, t, J=5.5 Hz), 4.60 (2H, d, J=5.5 Hz), 3.59 (2H, br m), 3.04 (3H, s), 2.36 (2H, br m), 2.15 (6H, br m). MS: m/z 497.2 (M+H$^{+}$).

Example 1.59

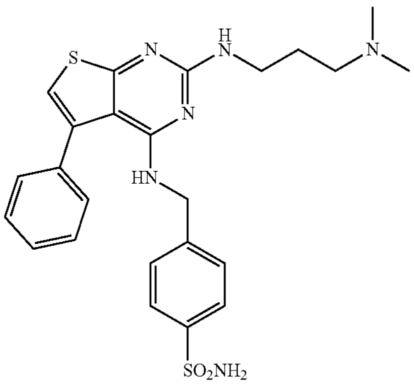 [SMILES: CN(C)CCCNc1nc(NCc2ccc(S(N)(=O)=O)cc2)c2c(-c3ccccc3)csc2n1]

4-((2-(3-Dimethylaminopropyl)amino-5-phenylthieno[2,3-d]pyrimidin-4-yl)aminomethyl)-benzenesulfonamide The title compound was prepared according to the general procedure of Example 1.50 using 4-((2-chloro-5-phenylthieno[2,3-d]pyrimidin-4-yl)aminomethyl)-benzenesulfonamide obtained in Example 1.48 and N,N-dimethyl-1,3-propanediamine. $^{1}$H-NMR (DMSO-$D_6$) δ: 7.74 (2H, d, J=7.9 Hz), 7.49 (4H, d, J=7.9 Hz), 7.45-7.40 (1H, m), 7.38 (2H, d, J=8.5 Hz), 7.32 (2H, s), 6.85 (1H, s), 6.81-6.79 (1H, br m), 5.55 (1H, br s), 4.58 (2H, d, J=5.5 Hz), 3.27-3.24 (2H, br m), 2.30-2.20 (2H, br m), 2.14 (6H, s), 1.65-1.60 (2H, br m). MS: m/z 497.2 (M+H$^{+}$).

Example 1.60

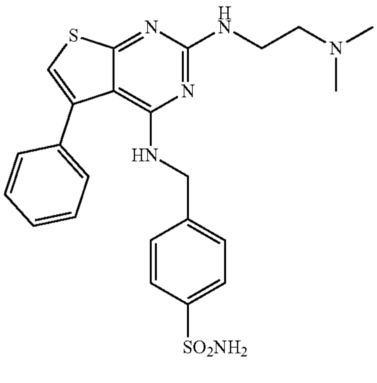 [SMILES: CN(C)CCNc1nc(NCc2ccc(S(N)(=O)=O)cc2)c2c(-c3ccccc3)csc2n1]

4-((2-(2-Dimethylamino)ethylamino-5-phenylthieno [2,3-d]pyrimidin-4-yl)aminomethyl)-benzenesulfonamide The title compound was prepared according to the general procedure of Example 1.50 using 4-((2-chloro-5-phenylthieno[2,3-d]pyrimidin-4-yl)aminomethyl)-benzenesulfonamide obtained in Example 1.48 and N,N-dimethylethylenediamine. $^1$H-NMR (DMSO-$D_6$) δ: 7.74 (2H, d, J=8.5 Hz), 7.50 (4H, d, J=4.3 Hz), 7.47-7.43 (1H, m), 7.38 (2H, d, J=7.9 Hz), 7.31 (2H, s), 6.91 (1H, s), 5.72 (1H, t, J=5.5 Hz), 4.57 (2H, d, J=5.5 Hz), 3.63 (2H, br m), 3.35-3.33 (3H, br m), 3.17 (3H, br m), 3.05 (3H, br m). MS: m/z 483.2 (M+H$^+$).

Example 1.61

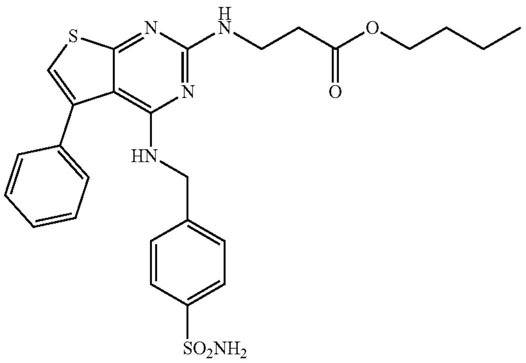 [SMILES: CCCCOC(=O)CCNc1nc(NCc2ccc(S(N)(=O)=O)cc2)c2c(-c3ccccc3)csc2n1]

4-((2-(2-Butoxycarbonyl)ethylamino-5-phenylthieno [2,3-d]pyrimidin-4-yl)aminomethyl)-benzenesulfonamide The title compound was prepared according to the general procedure of Example 1.50 using 4-((2-chloro-5-phenylthieno[2,3-d]pyrimidin-4-yl)aminomethyl)-benzenesulfonamide obtained in Example 1.48, tert-butyl 3-aminopropanoate hydrochloride and N,N-diisopropylethylamine in n-butanol. MS: m/z 540.2 (M+H$^+$).

Example 1.62

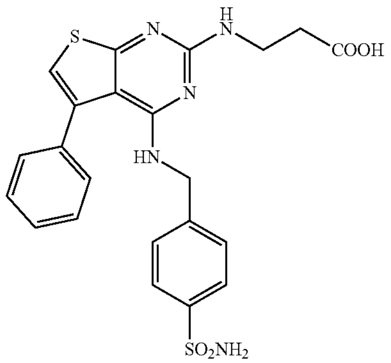 [SMILES: NS(=O)(=O)c1ccc(CNc2nc(NCCC(=O)O)nc3scc(-c4ccccc4)c23)cc1]

4-((2-(2-Carboxy)ethylamino-5-phenylthieno[2,3-d] pyrimidin-4-yl)aminomethyl)-benzenesulfonamide To a solution of 4-((2-(2-Butoxycarbonyl)ethylamino-5-phenylthieno[2,3-d]pyrimidin-4-yl)aminomethyl)benzenesulfonamide obtained in Example 1.61 (12 mg) in tetrahydrofuran (0.8 mL) was added 1 mol/L sodium hydroxide solution (0.4 mL) at room temperature. After stirring overnight, 1 mol/L hydrochloric acid (0.4 mL) was added to the mixture and the resulting mixture was extracted with ethyl acetate. The combined organic layer was washed with water, and dried under reduced pressure. The residue was washed with methanol twice, to give the title compound as a pale-yellow solid (6 mg, yield 56%). $^1$H-NMR (DMSO-$D_6$) δ: 12.20 (1H, br s), 7.74 (2H, d, J=8.5 Hz), 7.49-7.45 (4H, m), 7.43-7.42 (1H, m), 7.38 (2H, d, J=8.5 Hz), 7.31 (2H, s), 6.89 (1H, s), 6.79-6.76 (1H, br m), 5.52 (1H, br s), 4.58 (2H, d, J=6.1 Hz), 3.44-3.42 (2H, m), 2.48-2.40 (2H, m). MS: m/z 484.1 (M+H$^+$).

Example 1.63

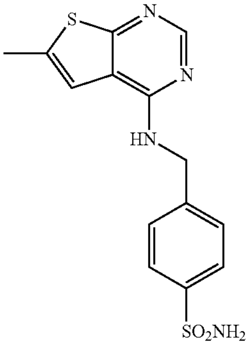 [SMILES: Cc1cc2c(NCc3ccc(S(N)(=O)=O)cc3)ncnc2s1]

4-((6-Methylthieno[2,3-d]pyrimidin-4-yl)aminomethyl)benzenesulfonamide

The title compound was prepared according to the general procedure of Example 1.48 using 4-chloro-6-methylthieno [2,3-d]pyrimidine and homosulfamine hydrochloride. $^1$H-NMR (DMSO-$D_6$) δ: 8.44 (1H, t, J=5.8 Hz), 8.25 (1H, s), 7.76 (2H, d, J=8.5 Hz), 7.49 (2H, d, J=8.5 Hz), 7.32 (1H, s), 7.30 (2H, s), 4.77 (2H, d, J=5.8 Hz), 2.54 (3H, s). MS: m/z 335 (M+H$^+$).

Example 1.64

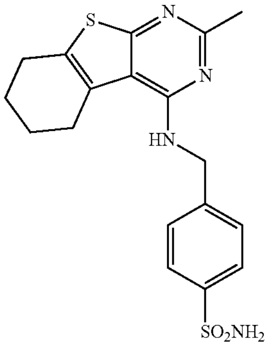 [SMILES: Cc1nc(NCc2ccc(S(N)(=O)=O)cc2)c2c3c(sc2n1)CCCC3]

4-((2-Methyl-5,6,7,8-tetrahydro[1]benzothieno[2,3-d]pyrimidin-4-yl)aminomethyl)-benzenesulfonamide The title compound was prepared according to the general procedure of Example 1.48 using 4-chloro-2-methyl-5,6,7, 8-tetrahydro[1]benzothieno[2,3-d]pyrimidine and homosulfamine hydrochloride. $^1$H-NMR (DMSO-$D_6$) δ: 7.75 (2H, d, J=8.5 Hz), 7.53 (2H, d, J=8.5 Hz), 7.17 (2H, s), 7.03 (1H, t, J=6.1 Hz), 4.76 (2H, d, J=6.1 Hz), 3.00-2.94 (2H, br m), 2.77-2.71 (2H, br m), 2.35 (3H, s), 1.88-1.79 (4H, br m). MS: m/z 389 (M+H$^+$).

Example 1.65

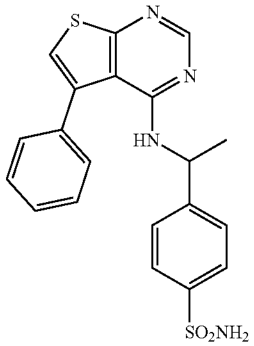 [SMILES: CC(Nc1ncnc2scc(-c3ccccc3)c12)c1ccc(S(N)(=O)=O)cc1]

4-(1-(5-Phenylthieno[2,3-d]pyrimidin-4-yl)aminoethyl)benzenesulfonamide

The title compound was prepared according to the general procedure of Example 1.48 using 4-chloro-5-phenylthieno[2,3-d]pyrimidine and 4-(1-aminoethyl)benzenesulfonamide. MS: m/z 411 (M+H$^+$).

Example 1.66

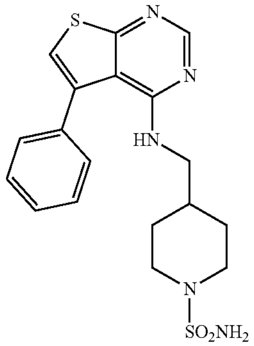 [SMILES: NS(=O)(=O)N1CCC(CNc2ncnc3scc(-c4ccccc4)c23)CC1]

4-(5-Phenylthieno[2,3-d]pyrimidin-4-yl)aminomethyl-1-piperidinesulfonamide

The title compound was prepared according to the general procedure of Example 1.48 using 4-chloro-5-phenylthieno[2,3-d]pyrimidine and 4-aminomethyl-1-piperidinesulfonamide hydrochloride. MS: m/z 404 (M+H$^+$).

Example 1.67

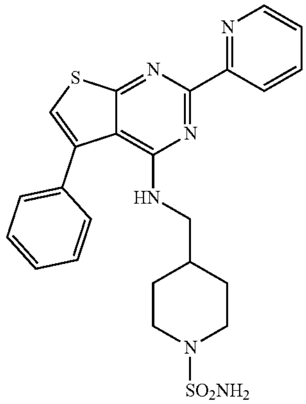 [SMILES: NS(=O)(=O)N1CCC(CNc2nc(-c3ccccn3)nc3scc(-c4ccccc4)c23)CC1]

4-((5-Phenyl-2-(2-pyridyl)thieno[2,3-d]pyrimidin-4-yl)aminomethyl)-1-piperidinesulfonamide The title compound was prepared according to the general procedure of Example 1.48 using 4-chloro-5-phenyl-2-(2-pyridyl)thieno[2,3-d]pyrimidine and 4-aminomethyl-1-piperidinesulfonamide hydrochloride. $^1$H-NMR (DMSO-$D_6$) δ: 8.73 (1H, d, J=4.3 Hz), 8.41 (1H, d, J=8.0 Hz), 7.99-7.93 (1H, m), 7.61-7.47 (7H, m), 6.70 (2H, s), 5.31 (1H, t, J=5.2 Hz), 3.46-3.39 (4H, m), 2.45-2.36 (2H, m), 1.63-1.37 (3H, m), 1.22-1.08 (2H, m). MS: m/z 481 (M+H$^+$).

Example 1.68

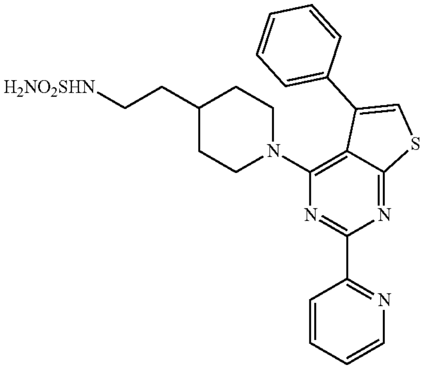

N-(2-(1-(5-Phenyl-2-(2-pyridyl)thieno[2,3-d]pyrimidin-4-yl)-4-piperidyl)ethyl)sulfamide The title compound was prepared according to the general procedure of Example 1.48 using 4-chloro-5-phenyl-2-(2-pyridyl)thieno[2,3-d]pyrimidine and N-(2-(4-piperidyl)ethyl)sulfamide hydrochloride. $^1$H-NMR (DMSO-$D_6$) δ: 8.72-8.78 (1H, m), 8.45 (1H, d, J=7.9 Hz), 7.98 (1H, td, J=7.6, 1.8 Hz), 7.74 (1H, s), 7.46-7.53 (5H, m), 7.39-7.46 (1H, m), 6.44 (2H, s), 6.37 (1H, t, J=6.1 Hz), 3.80-3.90 (2H, m), 2.73-2.82 (2H, m), 2.56-2.67 (2H, m), 1.32-1.44 (3H, m), 1.20-1.27 (2H, m), 0.59-0.71 (2H, m). MS: m/z 495.1 (M+H$^+$).

Example 1.69

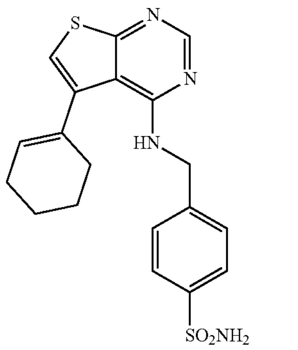 [SMILES: NS(=O)(=O)c1ccc(CNc2ncnc3scc(C4=CCCCC4)c23)cc1]

4-((5-(1-Cyclohexenyl)thieno[2,3-d]pyrimidin-4-yl) aminomethyl)benzenesulfonamide To a mixture of 4-((5-bromothieno[2,3-d]pyrimidin-4-yl) aminomethyl)benzenesulfonamide (150 mg) obtained in Example 1.49, 2-(1-cyclohexenyl)-4,4,5,5-tetramethyl-1,3,2-dioxaborolane (94 mg) and tripotassium phosphate (160 mg) in 1,4-dioxane (1.5 mL) and water (0.4 mL) was added chloro-(2-dicyclohexylphosphino-2',4',6'-triisopropyl-1,1'-biphenyl)[2-(2-aminoethyl)phenyl]palladium(II) (28 mg). After stirring at 120° C. for 3 hours by microwave, the resulting mixture was diluted with ethyl acetate and filtered on a Celite pad. The filtrate was concentrated under reduced pressure. The residue was purified by automated flash chromatography ($NH_2$-modified silica gel) using 0-15% methanol in dichloromethane as eluent, followed by automated flash chromatography (Diol-modified silica gel) using 0-2% methanol in dichloromethane as eluent, to give the title compound as a pale-yellow amorphous (125 mg, yield 83%). $^1$H-NMR (DMSO-$D_6$) δ: 8.36 (1H, s), 7.78 (2H, d, J=7.9 Hz), 7.52 (2H, d, J=7.9 Hz), 7.37 (1H, s), 7.33 (2H, s), 6.63 (1H, t, J=5.8 Hz), 5.87-5.83 (1H, br m), 4.82 (2H, d, J=5.8 Hz), 2.32-2.26 (2H, br m), 2.14-2.07 (2H, br m), 1.73-1.54 (4H, m). MS: m/z 401 (M+H$^+$).

Example 1.70

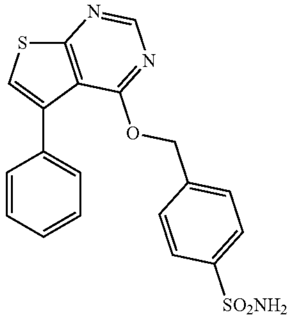 [SMILES: NS(=O)(=O)c1ccc(COc2ncnc3scc(-c4ccccc4)c23)cc1]

4-((5-Phenylthieno[2,3-d]pyrimidin-4-yl)oxymethyl) benzenesulfonamide

To a solution of 4-(hydroxymethyl)benzenesulfonamide (67.1 mg) in N,N-dimethylformamide (1 mL) was added sodium hydride (60%, dispersion in Paraffin Liquid, 31.4 mg) at 0° C. After stirring for 30 min at 0° C., 4-chloro-5-phenylthieno[2,3-d]pyrimidine (88.2 mg) was added to the reaction mixture. The resulting mixture was stirred for 3 hours at room temperature, and quenched by adding saturated ammonium chloride solution and ethyl acetate. The Organic layer was washed with water and brine, then dried over anhydrous sodium sulfate. After the resulting solid was filtered off, the filtrate was concentrated under reduced pressure. The residue was washed with 80% ethyl acetate in hexane then dried under reduced pressure, to give the title compound as a beige solid (39.3 mg, yield 28%). $^1$H-NMR (DMSO-$D_6$) δ: 8.76 (1H, s), 7.79 (1H, s), 7.70 (2H, d, J=8.0 Hz), 7.55-7.52 (2H, m), 7.45-7.13 (7H, m), 5.54 (2H, s). MS: m/z 398.1 (M+H$^+$).

Example 2

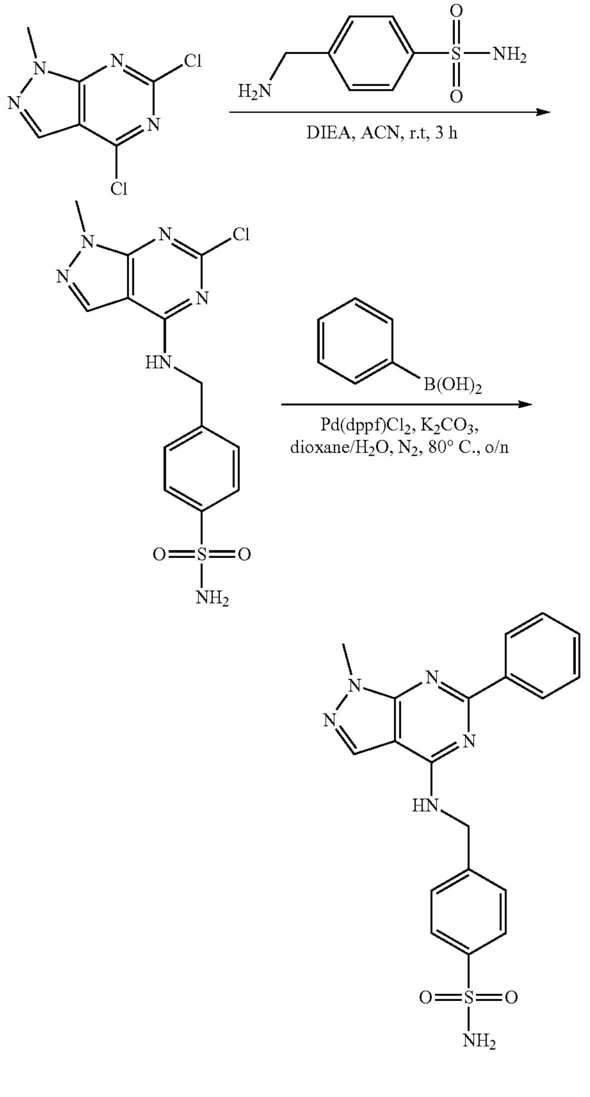

4-(((1-Methyl-6-phenyl-1H-pyrazolo[3,4-d]pyrimidin-4-yl)amino)methyl)-benzenesulfonamide Step 1: To a solution of 4,6-dichloro-1-methyl-1H-pyrazolo[3,4-d]pyrimidine (200 mg, 1 mmol) in ACN (30 mL)

was added 4-(aminomethyl)benzenesulfonamide (2.4 g, 10.8 mmol) and DIEA (258 mg, 2 mmol). The mixture was stirred at room temperature for 3 hrs. The resulting solution was filtered. The cake was washed with ACN to give 4-(((6-chloro-1-methyl-1H-pyrazolo[3,4-d]pyrimidin-4-yl) amino)methyl)benzenesulfonamide (240 mg, yield: δ8%) as a yellow solid. $^{1}$HNMR (400 MHz, DMSO-d6): δ=9.27 (t, J=6.0 Hz, 1H), 8.14 (s, 1H), 7.79 (d, J=8.4 Hz, 2H), 7.52 (d, J=8.0 Hz, 2H), 7.32 (s, 2H), 4.70 (d, J=5.6 Hz, 2H), 3.86 (s, 3H).

Step 2: A mixture of 4-(((6-chloro-1-methyl-1H-pyrazolo [3,4-d]pyrimidin-4-yl)amino)methyl)benzenesulfonamide (100 mg, 0.28 mmol), $K_2CO_3$ (97 mg, 0.7 mmol) and Pd(dppf)$Cl_2$ (22 mg, 0.03 mmol) in dioxane/$H_2O$ (24 mL/6 mL) was stirred at 100° C. overnight under $N_2$ atmosphere (balloon). The mixture was concentrated and purified by prep-HPLC to give 4-(((1-methyl-6-phenyl-1H-pyrazolo[3,4-d]pyrimidin-4-yl)amino)methyl)benzenesulfonamide (14 mg, yield: 13%) as a white solids. $^{1}$HNMR (400 MHz, DMSO-$d_6$): δ=8.90 (t, J=5.6 Hz, 1H), 8.41 (d, J=3.6 Hz, 2H), 8.14 (s, 1H), 7.78 (d, J=8.4 Hz, 2H), 7.60 (d, J=8.0 Hz, 2H), 7.46 (t, J=3.2 Hz, 3H), 7.28 (s, 2H), 4.94 (d, J=5.6 Hz, 2H), 3.98 (s, 3H). MS: m/z 395.1 (M+H$^+$).

Example 2.1

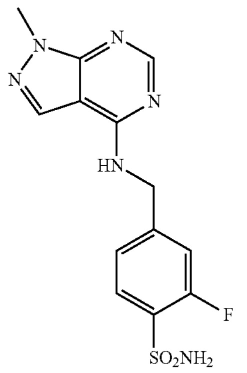 [SMILES: Cn1ncc2c(NCc3ccc(S(N)(=O)=O)c(F)c3)ncnc21]

2-Fluoro-4-(((1-methyl-1H-pyrazolo[3,4-d]pyrimidin-4-yl)amino)methyl)-benzenesulfonamide The title compound was prepared using general procedure of 2-chloro-4-(((1-methyl-1H-pyrazolo[3,4-d]pyrimidin-4-yl)amino)methyl)benzenesulfonamide (Example 2.4). $^{1}$HNMR (400 MHz, $CDCl_3$): δ=8.87 (s, 1H), 8.26 (s, 1H), 8.14 (s, 1H), 7.76-7.72 (m, 1H), 7.60 (s, 2H), 7.37-7.29 (m, 2H), 4.80 (d, J=5.6 Hz, 2H), 3.91 (s, 3H). MS: m/z 337.0 (M+H$^+$).

Example 2.2

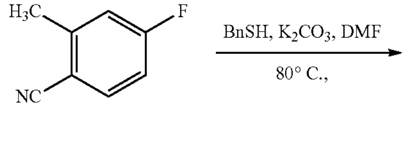

-continued

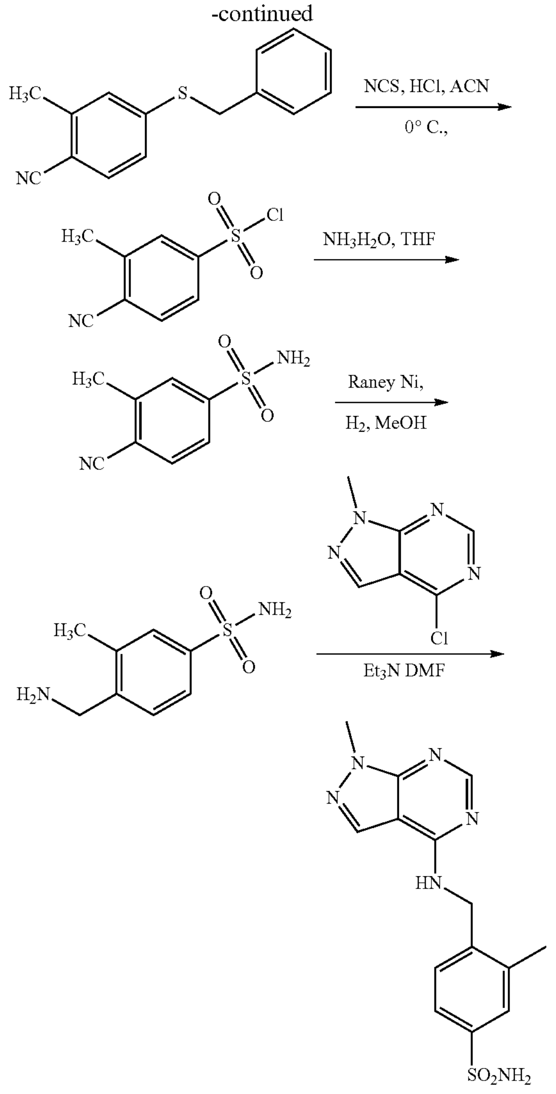

3-Methyl-4-(((1-methyl-1H-pyrazolo[3,4-d]pyrimidin-4-yl)amino)methyl)-benzenesulfonamide Step 1: To a solution of 4-fluoro-2-methylbenzonitrile (1 g, 7.4 mmol) in DMF (5 mL) was added BnSH (1.01 g, 8.1 mmol) and $K_2CO_3$ (2.0 g, 14.8 mmol). The mixture was stirred at 100° C. overnight. Then the reaction mixture was diluted with EA (40 mL). The organic layer was washed with water (100 mL×2), brine (100 mL), dried over $Na_2SO_4$ and concentrated. The residue was purified by silica gel column (EA/PE=1/10) to give 4-(benzylthio)-2-methylbenzonitrile (1.6 g, yield: 90.3%) as a white solid. $^{1}$HNMR (400 MHz, DMSO-$d_6$): δ=7.65 (d, J=8.4 Hz, 1H), 7.43-7.37 (m, 3H), 7.34-7.23 (m, 4H), 4.36 (s, 2H), 2.42 (s, 3H).

Step 2: To a solution of NCS (3.3 g, 25.1 mmol) and 2 M HCl (1.67 mL) in ACN (20 mL) was added 4-(benzylthio)-2-methylbenzonitrile (1.5 g, 6.2 mmol). The mixture was stirred at 0° C. for 1 hr. Then the reaction mixture was concentrated and the residue was partitioned with EA (20 mL) and water (20 mL). The organic layer was dried over $Na_2SO_4$ and concentrated to give 4-cyano-3-methylbenzene-1-sulfonyl chloride (1.1 g, yield: 82%) as a white solid.

Step 3: To a solution of 4-cyano-3-methylbenzene-1-sulfonyl chloride (1.1 g, 5.1 mmol) in THF (10 mL) was added $NH_3H_2O$ (0.5 mL). The mixture was stirred at 0° C. for 30 mins. Then the reaction mixture was concentrated and the residue was purified by silica gel column (EA/PE=1/1) to give 4-cyano-3-methylbenzenesulfonamide (800 mg, yield: 80%) as a white solid. $^1$HNMR (400 MHz, DMSO-$d_6$): δ=8.01 (d, J=8.0 Hz, 1H), 7.88 (s, 1H), 7.93 (d, J=8.0 Hz, 1H), 7.60 (s, 2H), 2.57 (s, 3H).

Step 4: To a solution of 4-cyano-3-methylbenzenesulfonamide (700 mg, 3.58 mmol) in MeOH (10 mL) was added Raney Ni (140 mg). The mixture was stirred at room temperature for 3 hrs under $H_2$ atmosphere (balloon). Then the reaction mixture was filtered and the filtrate was concentrated to give 4-(aminomethyl)-3-methylbenzenesulfonamide (420 mg, yield: δ9%) as a white solid.

Step 5: To a solution of 4-chloro-1-methyl-1H-pyrazolo[3,4-d]pyrimidine (50 mg, 0.29 mmol) in DMF (2 mL) was added 4-(aminomethyl)-3-methylbenzenesulfonamide (71 mg, 0.35 mmol) and $Et_3N$ (53 mg, 0.53 mmol). The mixture was stirred at 80° C. for 3 hrs. Then the reaction mixture was concentrated and the residue was purified by prep-HPLC to give 3-methyl-4-(((1-methyl-1H-pyrazolo[3,4-d]pyrimidin-4-yl)amino)methyl)benzenesulfonamide (25 mg, yield: 25.3%) as a white solid. $^1$HNMR (400 MHz, DMSO-$d_6$): δ=8.71 (s, 1H), 8.25 (s, 1H), 8.16 (s, 1H), 7.65-7.57 (m, 2H), 7.40 (d, J=7.6 Hz, 1H), 7.25 (s, 2H), 4.76-4.74 (m, 2H), 3.90 (s, 3H), 2.41 (s, 3H). MS: m/z 333.1 (M+H$^+$).

Example 2.3

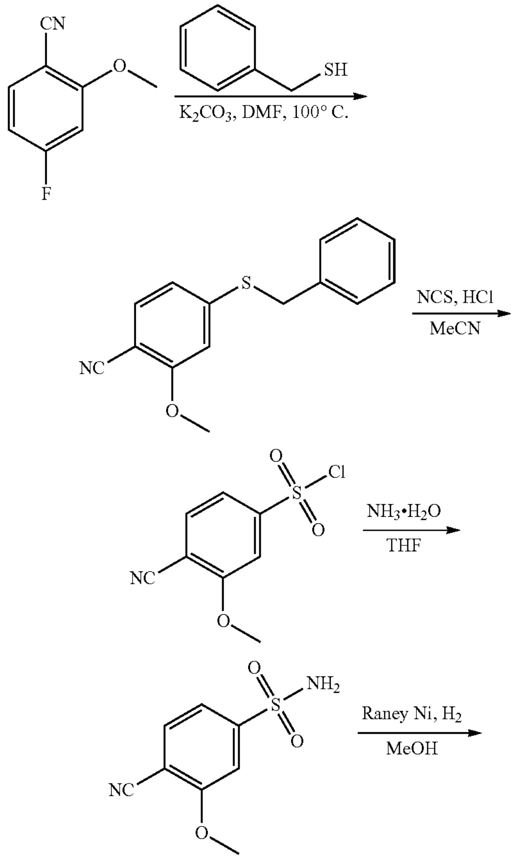

-continued

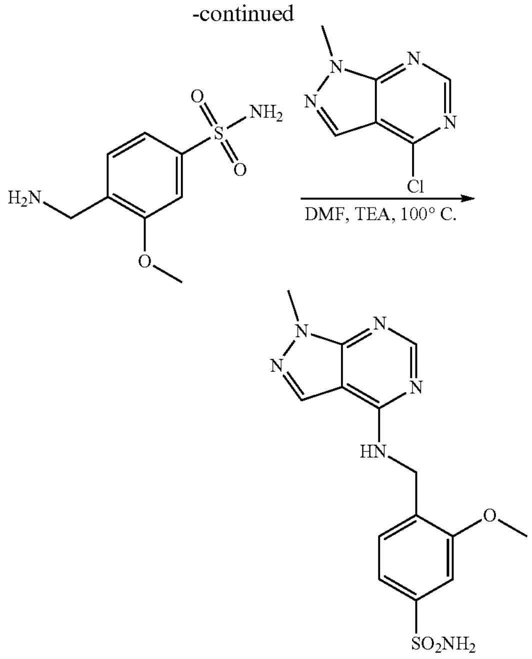

3-Methoxy-4-(((1-methyl-1H-pyrazolo[3,4-d]pyrimidin-4-yl)amino)methyl)-benzenesulfonamide The title compound was prepared using general procedure of 3-methyl-4-(((1-methyl-1H-pyrazolo[3,4-d]pyrimidin-4-yl)amino)methyl)benzenesulfonamide (Example 2.2). $^1$HNMR (400 MHz, DMSO-$d_6$): δ=8.7 (t, J=5.69 Hz, 1H), 8.23 (s, 1H), 8.13 (s, 1H), 7.44 (s, 1H), 7.36-7.30 (m, 4H), 4.72 (d, J=6.0 Hz, 2H), 3.90 (d, J=3.6 Hz, 6H). MS: m/z 349.1 (M+H$^+$).

Example 2.4

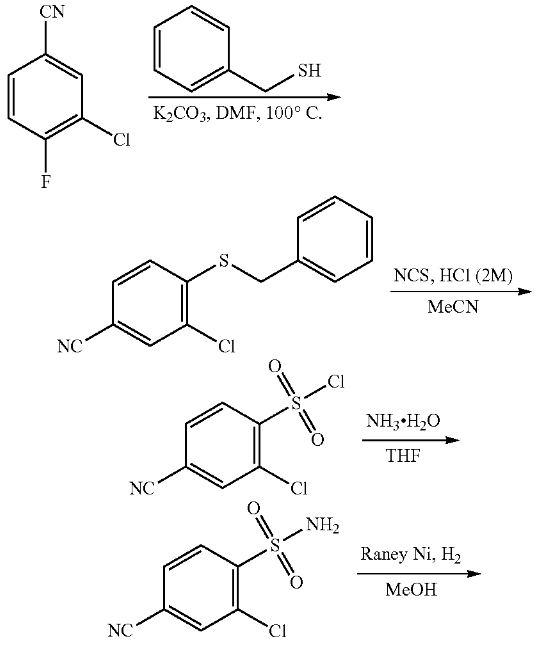

-continued

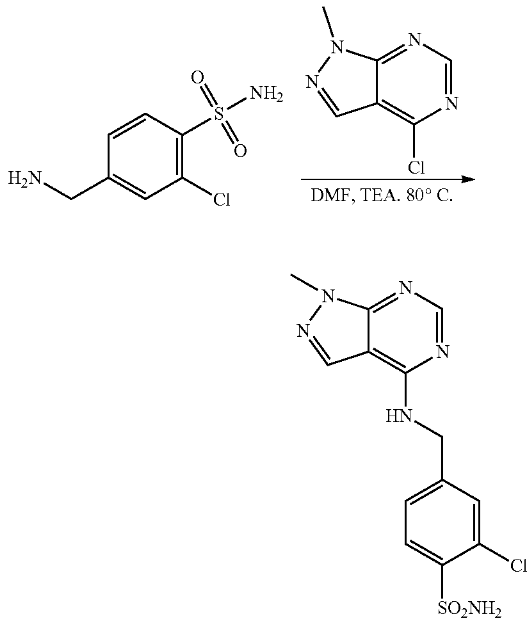

2-Chloro-4-(((1-methyl-1H-pyrazolo[3,4-d]pyrimidin-4-yl)amino)methyl)-benzenesulfonamide The title compound was prepared using general procedure of 3-methyl-4-(((1-methyl-1H-pyrazolo[3,4-d]pyrimidin-4-yl)amino)methyl)benzenesulfonamide (Example 2.2). $^1$HNMR (400 MHz, DMSO-$d_6$): δ=8.84 (s, 1H), 8.26 (s, 1H), 8.14 (s, 1H), 7.92 (d, J=8.0 Hz, 1H), 7.58 (s, 1H), 7.55 (s, 2H), 7.45 (d, J=8.0 Hz, 1H), 4.80 (d, J=6.0 Hz, 2H), 3.91 (s, 3H). MS: m/z 353.0 (M+H$^+$).

Example 2.5

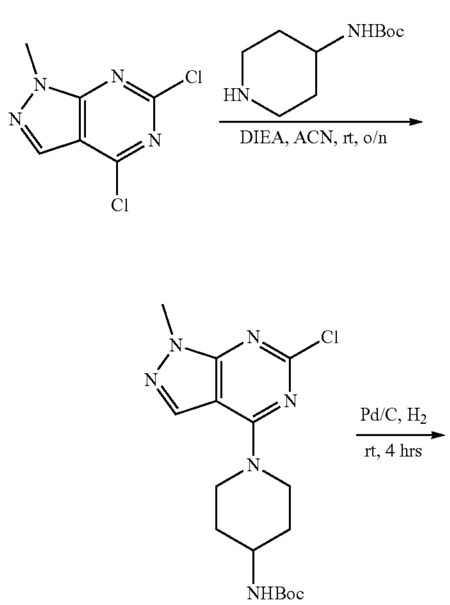

-continued

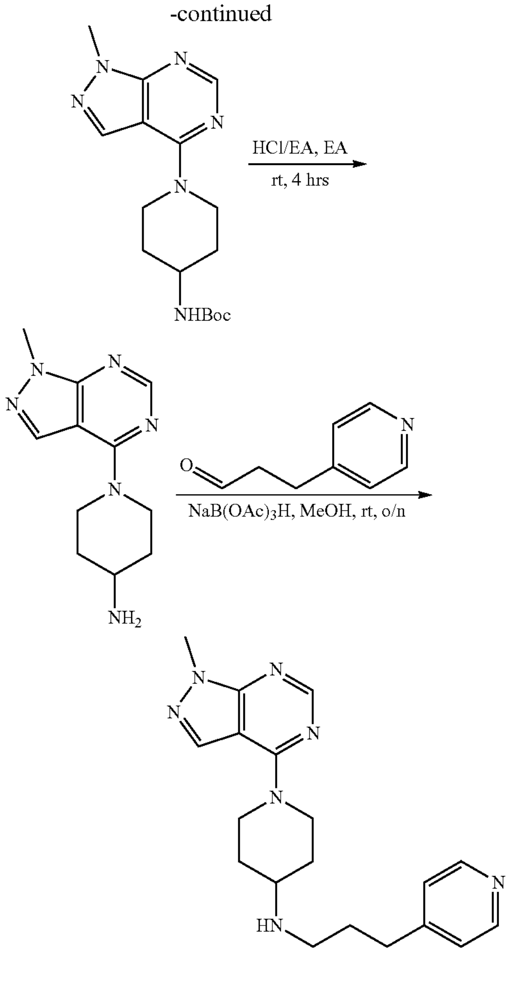

1-(1-Methyl-1H-pyrazolo[3,4-d]pyrimidin-4-yl)-N-(3-(pyridin-4-yl)propyl)piperidin-4-amine Step 1: To a mixture of 4,6-dichloro-1-methyl-1H-pyrazolo[3,4-d]pyrimidine (768 mg, 3.78 mmol) in ACN (40 mL) was added tert-butyl piperidin-4-ylcarbamate (758 mg, 3.78 mmol), followed by DIEA (1.47 g, 11.34 mmol). The resulting mixture was stirred at room temperature overnight. The solid precipitated form the mixture was collected by filtration. The cake was dried in air to afford tert-butyl (1-(6-chloro-1-methyl-1H-pyrazolo[3,4-d]pyrimidin-4-yl)piperidin-4-yl)carbamate (1.31 g, yield: 94%) as a yellow solid.

Step 2: To a mixture of tert-butyl (1-(6-chloro-1-methyl-1H-pyrazolo[3,4-d]pyrimidin-4-yl)piperidin-4-yl)carbamate (100 mg, 0.27 mmol) in MeOH (10 mL) was added Pd/C (20 mg, 20% wt). The resulting mixture was stirred at room temperature for 4 hrs. The reaction was monitored by LCMS. Then Pd/C was removed by filtration. The filtrate was concentrated in vacuum to afford tert-butyl (1-(1-methyl-1H-pyrazolo[3,4-d]pyrimidin-4-yl)piperidin-4-yl)carbamate (86.8 mg, yield: 96%) as a white solid. $^1$HNMR (400 MHz, DMSO-$d_6$): δ=8.27 (d, J=9.2 Hz, 2H), 6.91 (d, J=7.2 Hz, 1H), 4.59-4.55 (m, 2H), 3.90 (m, 3H), 3.63-3.62 (m, 1H), 3.30 (overlap, 2H), 1.89-1.86 (m, 2H), 1.39 (s, 9H), 1.35-1.31 (m, 2H).

Step 3: To a mixture of tert-butyl (1-(1-methyl-1H-pyrazolo[3,4-d]pyrimidin-4-yl)piperidin-4-yl)carbamate (86.8 mg, 0.26 mmol) in dioxane (10 mL) was added HCl/dioxane (5 mL, >4 M). The resulting mixture was stirred at room temperature for 4 hrs. The reaction was monitored by LCMS. The mixture was concentrated in vacuum to afford 1-(1-methyl-1H-pyrazolo[3,4-d]pyrimidin-4-yl)piperidin-4-amine (70.2 mg, yield: 100%) as a white solid.

Step 4: To a mixture of 1-(1-methyl-1H-pyrazolo[3,4-d]pyrimidin-4-yl)piperidin-4-amine (70.2 mg, 0.26 mmol) in MeOH (10 mL) was added 3-(pyridin-4-yl)propanal (42 mg, 0.31 mmol). The resulting mixture was stirred at room temperature overnight. Then $NaBH(OAc)_3$ (165 mg, 0.78 mmol) was added and the mixture was stirred at room temperature for another 1 hr. The reaction was monitored by LCMS. The mixture was concentrated in vacuum to give a residue, which was purified by prep-HPLC with $NH_4HCO_3$ as additive to afford 1-(1-methyl-1H-pyrazolo[3,4-d]pyrimidin-4-yl)-N-(3-(pyridin-4-yl)propyl)piperidin-4-amine (10.6 mg, yield: 12%) as a yellow solid. $^1$HNMR (400 MHz, DMSO-$d_6$): δ=8.44 (d, J=4.8 Hz, 2H), 8.28 (s, 1H), 8.21 (s, 1H), 7.34 (d, J=5.2 Hz, 2H), 4.89 (s, 2H), 3.97 (s, 3H), 3.26-3.24 (m, 3H), 3.94 (t, J=7.6 Hz, 2H), 2.78 (t, J=7.6 Hz, 2H), 2.22-2.19 (m, 2H), 1.99-1.96 (m, 2H), 1.55-1.54 (m, 2H). MS: m/z 351.9 (M+H$^+$).

Example 2.6

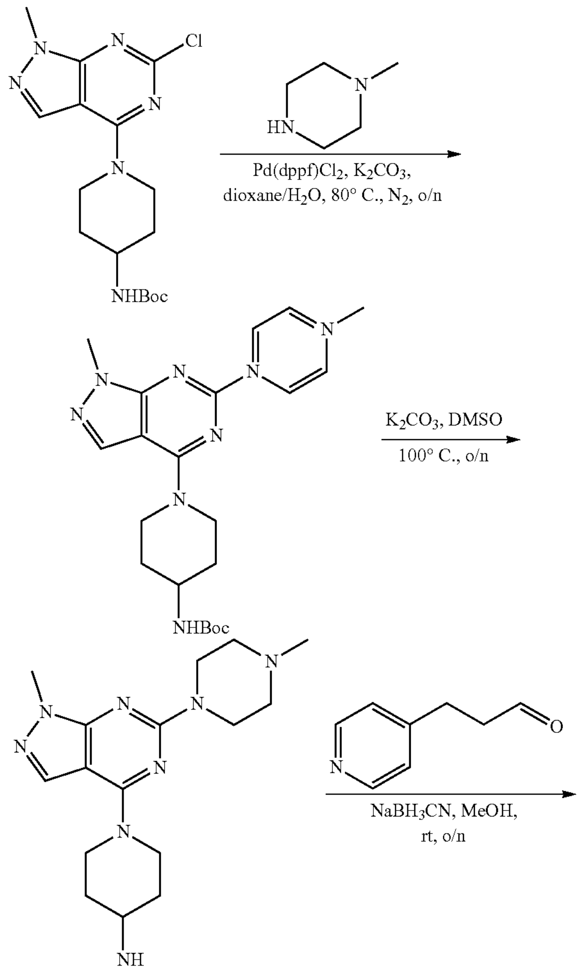

-continued

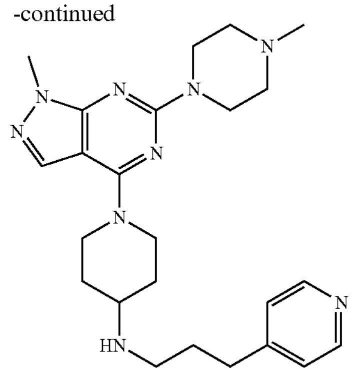

1-(1-Methyl-6-(4-methylpiperazin-1-yl)-1H-pyrazolo[3,4-d]pyrimidin-4-yl)-N-(3-(pyridin-4-yl)propyl)piperidin-4-amine Step 1: To a solution of tert-butyl (1-(6-chloro-1-methyl-1H-pyrazolo[3,4-d]pyrimidin-4-yl)piperidin-4-yl)carbamate (183 mg, 0.50 mmol) and 1-methylpiperazine (150 mg, 1.50 mmol) in DMSO (5 mL) was added $K_2CO_3$ (207 mg, 1.50 mmol). Then the resulting mixture was stirred at 100° C. overnight. The reaction was monitored by LCMS. Then $K_2CO_3$ was filtered off, and the filtrate was concentrated in vacuum to give a residue, which was purified by silica gel column (DCM/MeOH=100/1 to 30/1) to afford tert-butyl (1-(1-methyl-6-(4-methylpiperazin-1-yl)-1H-pyrazolo[3,4-d]pyrimidin-4-yl)piperidin-4-yl)carbamate (174 mg, yield: 81%) as a yellow solid. $^1$HNMR (400 MHz, $CDCl_3$): δ=7.71 (s, 1H), 4.58-4.55 (m, 2H), 4.50-4.49 (m, 1H), 3.88 (s, 4H), 3.85 (s, 3H), 3.79-3.77 (m, 1H), 3.20 (t, J=11.8 Hz, 2H), 2.50 (t, J=4.6 Hz, 4H), 2.36 (s, 3H), 2.80 (d, J=10.8 Hz, 2H), 1.46 (s, 9H), 1.41-1.37 (m, 2H).

Step 2: To a solution of tert-butyl (1-(1-methyl-6-(4-methylpiperazin-1-yl)-1H-pyrazolo[3,4-d]pyrimidin-4-yl)piperidin-4-yl)carbamate (174 mg, 0.40 mmol) in EA (10 mL) was added HCl/dioxane (10 mL). The resulting mixture was stirred at room temperature overnight. The reaction was monitored by LCMS. Then the mixture was concentrated in vacuum to afford 1-(1-methyl-6-(4-methylpiperazin-1-yl)-1H-pyrazolo[3,4-d]pyrimidin-4-yl)piperidin-4-amine (132 mg, yield: 89%) as a yellow solid.

Step 3: To a solution of 1-(1-methyl-6-(4-methylpiperazin-1-yl)-1H-pyrazolo[3,4-d]pyrimidin-4-yl)piperidin-4-amine (132 mg, 0.36 mmol) in MeOH (10 mL) was added 3-(pyridin-4-yl)propanal (58 mg, 0.43 mmol). The resulting mixture was stirred at room temperature overnight. Then $NaBH_3CN$ (68 mg, 1.08 mmol) was added in to the mixture and the mixture was stirred for another 1 hr. The reaction was monitored by LCMS. Then the mixture was concentrated in vacuum to give a residue, which was purified by prep-HPLC with TFA as additive to afford 1-(1-methyl-6-(4-methylpiperazin-1-yl)-1H-pyrazolo[3,4-d]pyrimidin-4-yl)-N-(3-(pyridin-4-yl)propyl)piperidin-4-amine (21.1 mg, yield: 13%) as a yellow solid. $^1$HNMR (400 MHz, DMSO-$d_6$): δ=8.79 (d, J=6.4 Hz, 2H), 8.23 (brs, 1H), 8.08 (d, J=6.0 Hz, 2H), 4.90 (s, 4H), 3.98 (s, 3H), 3.64 (d, J=12.0 Hz, 3H), 3.53 (t, J=12.8 Hz, 2H), 3.39 (s, 2H), 3.26-3.21 (m, 4H), 3.13 (t, J=7.8 Hz, 2H), 2.98 (s, 3H), 2.37 (d, J=11.2 Hz, 2H), 2.21 (m, 2H), 1.84-1.80 (m, 2H). MS: m/z 449.9 (M+H$^+$).

Example 2.7

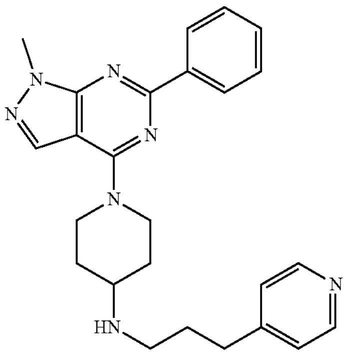 [SMILES: Cn1ncc2c(N3CCC(NCCCc4ccncc4)CC3)nc(-c3ccccc3)nc21]

1-(1-Methyl-6-phenyl-1H-pyrazolo[3,4-d]pyrimidin-4-yl)-N-(3-(pyridin-4-yl)propyl)piperidin-4-amine The title compound was prepared using general procedure of 1-(1,6-dimethyl-1H-pyrazolo[3,4-d]pyrimidin-4-yl)-N-(3-(pyridin-4-yl)propyl)piperidin-4-amine (Example 2.51). $^{1}$HNMR (400 MHz, $CD_3OD$): δ=8.45 (d, J=5.6 Hz, 4H), 8.29 (s, 1H), 7.50-7.49 (s, 3H), 7.24 (d, J=5.2 Hz, 2H), 4.66 (brs, 1H), 3.99 (s, 3H), 3.38-3.35 (m, 4H), 2.78-2.81 (m, 1H), 2.68-2.60 (m, 4H), 2.01-1.98 (m, 2H), 1.78-1.71 (m, 2H), 1.38-1.31 (m, 2H). MS: m/z 427.9 ($M+H^+$).

Example 2.8

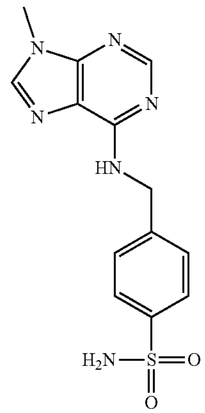 [SMILES: Cn1cnc2c(NCc3ccc(S(N)(=O)=O)cc3)ncnc21]

4-(((9-Methyl-9H-purin-6-yl)amino)methyl)benzenesulfonamide

The title compound was prepared using general procedure of 5-(((5-phenylthieno[2,3-d]pyrimidin-4-yl)amino)methyl)thiophene-2-sulfonamide (Example 1.28). $^{1}$HNMR (400 MHz, DMSO-d): δ=8.39 (brs, 1H), 8.20 (s, 1H), 8.13 (s, 1H), 7.74 (d, J=8 Hz, 2H), 7.48 (d, J=8 Hz, 2H), 7.27 (s, 2H), 4.75 (brs, 2H), 3.72 (s, 3H). MS: m/z 319.1 ($M+H^+$).

Example 2.9

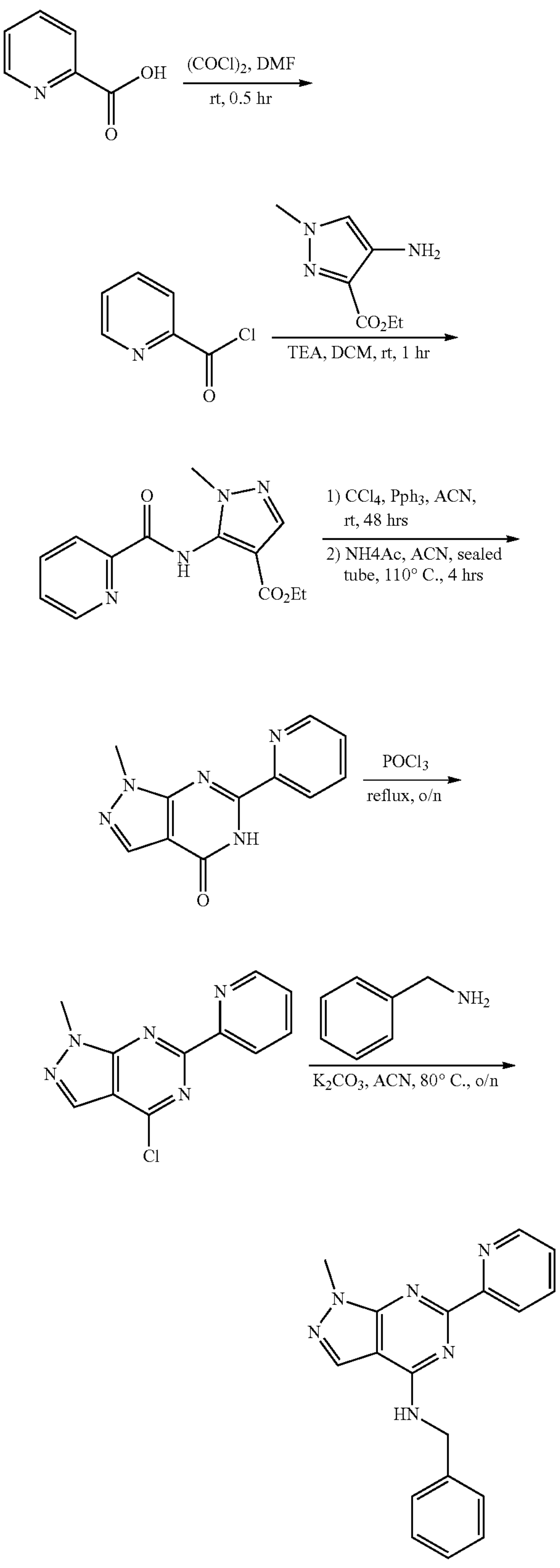

N-Benzyl-1-methyl-6-(pyridin-2-yl)-1H-pyrazolo[3,4-d]pyrimidin-4-amine

Step 1 and Step 2: To a solution of picolinic acid (246 mg, 2.0 mmol) in $(COCl)_2$ (3 mL) was added 1 drop of DMF. The resulting mixture was stirred at room temperature for 0.5 hr. Then the mixture was concentrated in vacuum to give picolinoyl chloride as a white solid, which was dissolved in dry DCM (20 mL). Then ethyl 4-amino-1-methyl-1H-pyrazole-3-carboxylate (676 mg, 4.0 mmol) was added, followed by TEA (607 mg, 6.0 mmol). The resulting mixture was stirred at room temperature for 1 hr. The reaction was monitored by LCMS and TLC. Then the reaction mixture was concentrated in vacuum to give a residue, which was purified by silica gel column (DMC/MeOH=100/1 to 50/1) to afford ethyl 1-methyl-5-(picolinamido)-1H-pyrazole-4-carboxylate (482 mg, yield: 88%) as a white solid. $^1$HNMR (400 MHz, DMSO-d): δ=10.74 (s, 1H), 8.77 (d, J=4.4 Hz, 1H), 8.16-8.07 (m, 2H), 7.87 (s, 1H), 7.75-7.72 (m, 1H), 4.11 (q, J=7.2 Hz, 2H), 3.73 (s, 3H), 1.11 (t, J=7.2 Hz, 3H).

Step 3: To a mixture of ethyl 1-methyl-5-(picolinamido)-1H-pyrazole-4-carboxylate (274 mg, 1.0 mmol) and triphenylphosphine (787 mg, 3.0 mmol) in ACN (20 mL) was added $CCl_4$ (462 mg, 3.0 mmol). The resulting mixture was stirred at room temperature for 48 hrs. Then the reaction was treated with NH4Ac (excess) and heated at 110° C. overnight in a sealed tube vial. The reaction was monitored by LCMS. Then the reaction mixture was concentrated in vacuum to give a residue, which was purified by reverse phase column (5-95% ACN in $H_2O$, 60 mins) to afford 1-methyl-6-(pyridin-2-yl)-1H-pyrazolo[3,4-d]pyrimidin-4(5H)-one (82 mg, yield: 36%) as a white solid. $^1$HNMR (400 MHz, DMSO-d6): δ=11.59 (s, 1H), 8.77 (d, J=5.6 Hz, 1H), 8.46 (d, J=8.0 Hz, 1H), 8.13-8.08 (m, 2H), 7.70-7.67 (m, 1H), 4.02 (s, 3H).

Step 4: A mixture of 1-methyl-6-(pyridin-2-yl)-1H-pyrazolo[3,4-d]pyrimidin-4(5H)-one (1.12 g, 4.93 mmol) in $POCl_3$ (10 mL) was stirred at 110° C. overnight. The reaction was monitored by LCMS and TLC. Then the reaction mixture was concentrated in vacuum to give a residue, which was purified by silica gel column (DCM/MeOH=20/1) to afford 4-chloro-1-methyl-6-(pyridin-2-yl)-1H-pyrazolo[3,4-d]pyrimidine (1.11 g, yield: 92%) as a yellow solid.

Step 5: To a solution of 4-chloro-1-methyl-6-(pyridin-2-yl)-1H-pyrazolo[3,4-d]pyrimidine (100 mg, 0.41 mmol) in ACN (20 mL) was added phenylmethanamine (52.3 mg, 0.49 mmol), followed by $K_2CO_3$ (168 mg, 1.22 mmol). Then the resulting mixture was stirred at 80° C. overnight. The reaction was monitored by LCMS. Then $K_2CO_3$ was filtered off, and the filtrate was concentrated in vacuum to give a residue, which was purified by prep-HPLC with $NH_4OH$ as additive to afford N-benzyl-1-methyl-6-(pyridin-2-yl)-1H-pyrazolo[3,4-d]pyrimidin-4-amine (60.0 mg, yield: 47%) as a yellow solid. $^1$HNMR (400 MHz, DMSO-$d_6$): δ=8.86-8.83 (m, 1H), 8.72 (d, J=8.0 Hz, 1H), 8.39 (d, J=8.0 Hz, 1H), 8.17 (s, 1H), 7.94-7.89 (m, 1H), 7.48-7.43 (m, 3H), 7.36-7.32 (t, J=8 Hz, 2H), 7.25 (t, J=8 Hz, 1H), 4.88 (d, J=4 Hz, 2H), 3.98 (s, 3H). MS: m/z 317.1 (M+H$^+$).

Example 2.10

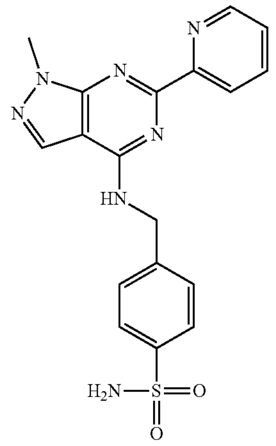 [SMILES: Cn1ncc2c(NCc3ccc(S(N)(=O)=O)cc3)nc(-c3ccccn3)nc21]

4-(((1-Methyl-6-(pyridin-2-yl)-1H-pyrazolo[3,4-d]pyrimidin-4-yl)amino)methyl)-benzenesulfonamide The title compound was prepared using general procedure of N-benzyl-1-methyl-6-(pyridin-2-yl)-1H-pyrazolo[3,4-d]pyrimidin-4-amine (Example 2.9). $^1$HNMR (400 MHz, DMSO-$d_6$): δ=8.69-8.67 (m, 1H), 8.16-8.14 (d, J=8.0 Hz, 1H), 8.03 (d, J=8.4 Hz, 2H), 7.92-7.90 (m, 1H), 7.89-7.86 (m, 1H), 7.44-7.40 (m, 3H), 4.01 (s, 2H), 3.90 (s, 3H). MS: m/z 396.1 (M+H$^+$).

Example 2.11

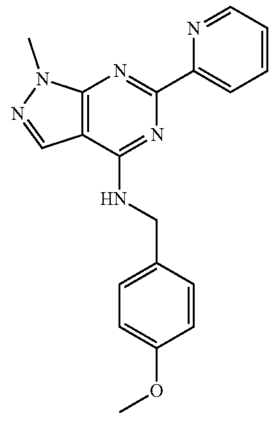 [SMILES: COc1ccc(CNc2nc(-c3ccccn3)nc3c2cnn3C)cc1]

N-(4-Methoxybenzyl)-1-methyl-6-(pyridin-2-yl)-1H-pyrazolo[3,4-d]pyrimidin-4-amine The title compound was prepared using general procedure of N-benzyl-1-methyl-6-(pyridin-2-yl)-1H-pyrazolo[3,4-d]pyrimidin-4-amine (Example 2.9). $^1$HNMR (400 MHz, DMSO-$d_6$): δ=8.78-8.75 (m, 1H), 8.73-8.71 (m, 1H), 8.42 (d, J=8.0 Hz, 1H), 8.15 (s, 1H), 7.95-7.91 (m, 1H), 7.49-7.46 (m, 1H), 7.37 (d, J=8 Hz, 2H), 6.90 (d, J=8 Hz, 2H), 4.81 (d, J=4 Hz, 2H), 3.98 (s, 3H), 3.72 (s, 3H). MS: m/z 347.1 (M+H$^+$).

Example 2.12

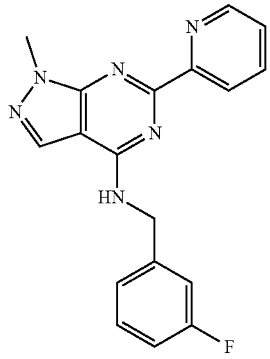 [SMILES: Cn1ncc2c(NCc3cccc(F)c3)nc(-c3ccccn3)nc21]

N-(3-Fluorobenzyl)-1-methyl-6-(pyridin-2-yl)-1H-pyrazolo[3,4-d]pyrimidin-4-amine The title compound was prepared using general procedure of N-benzyl-1-methyl-6-(pyridin-2-yl)-1H-pyrazolo[3,4-d]pyrimidin-4-amine (Example 2.9). $^1$HNMR (400 MHz, DMSO-$d_6$): δ=8.90-8.87 (m, 1H), 8.73-8.71 (m, 1H), 8.38 (d, J=8 Hz, 1H), 8.17 (s, 1H), 7.93-7.89 (m, 1H), 7.49-7.46 (m, 1H), 7.41-7.36 (m, 1H), 7.28 (d, J=8 Hz, 2H), 7.11-7.06 (m, 1H), 4.89 (d, J=8 Hz, 2H), 3.99 (s, 3H). MS: m/z 335.1 (M+H$^+$).

Example 2.13

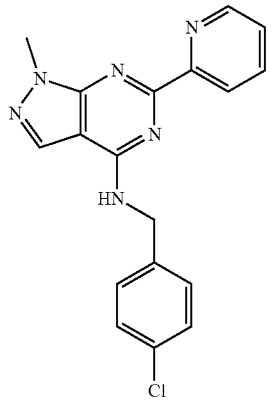 [SMILES: Cn1ncc2c(NCc3ccc(Cl)cc3)nc(-c3ccccn3)nc21]

N-(4-Chlorobenzyl)-1-methyl-6-(pyridin-2-yl)-1H-pyrazolo[3,4-d]pyrimidin-4-amine The title compound was prepared using general procedure of N-benzyl-1-methyl-6-(pyridin-2-yl)-1H-pyrazolo[3,4-d]pyrimidin-4-amine (Example 2.9). $^1$HNMR (400 MHz, DMSO-$d_6$): δ=8.92-8.90 (m, 1H), 8.74-8.70 (m, 2H), 8.48-8.46 (m, 1H), 8.38 (d, J=8 Hz, 1H), 8.16 (s, 1H), 7.95-7.86 (m, 2H), 7.49-7.46 (m, 1H), 7.37-7.34 (m, 1H), 4.88 (d, J=8 Hz, 2H), 3.98 (s, 3H). MS: m/z 318.1 (M+H$^+$).

Example 2.14

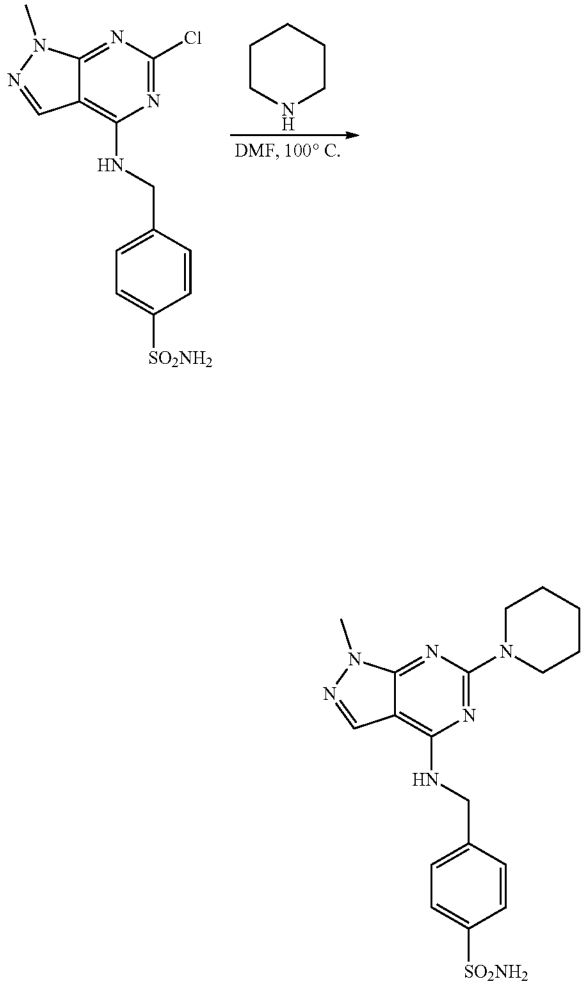

4-(((1-Methyl-6-(piperidin-1-yl)-1H-pyrazolo[3,4-d]pyrimidin-4-yl)amino)methyl)-benzenesulfonamide A solution of 4-(((6-chloro-1-methyl-1H-pyrazolo[3,4-d]pyrimidin-4-yl)amino)methyl)benzenesulfonamide (130 mg, 0.36 mmol) and piperidine (62 mg, 0.73 mol) in DMF (2 mL) was stirred at 110° C. for 3 hrs. The reaction mixture was concentrated and the residue was purified by prep-HPLC to give 4-(((1-methyl-6-(piperidin-1-yl)-1H-pyrazolo[3,4-d]pyrimidin-4-yl)amino)methyl)benzenesulfonamide (35 mg, yield: 23.5%) as a white solid. $^1$HNMR (400 MHz, DMSO-$d_6$): δ=8.42 (brs, 1H), 7.81 (s, 1H), 7.77 (d, J=8.4 Hz, 2H), 7.52 (t, J=8.0 Hz, 2H), 7.29 (s, 2H), 4.69-4.68 (m, 2H), 3.70-3.68 (m, 7H), 1.57-1.56 (m, 2H), 1.42-1.44 (m, 4H). MS: m/z 401.8 (M+H$^+$).

Example 2.15

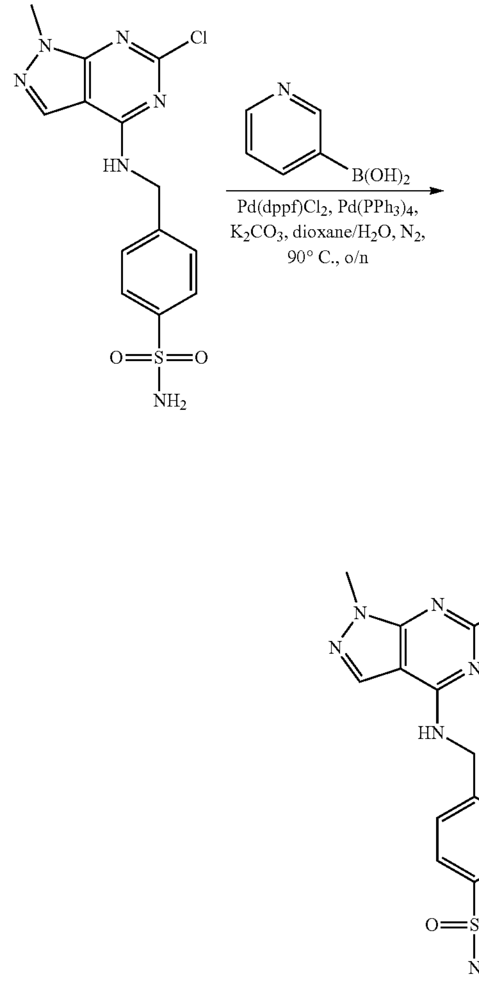

4-(((1-Methyl-6-(pyridin-3-yl)-1H-pyrazolo[3,4-d]pyrimidin-4-yl)amino)methyl)-benzenesulfonamide A mixture of 4-(((6-chloro-1-methyl-1H-pyrazolo[3,4-d]pyrimidin-4-yl)amino)methyl)benzenesulfonamide (100 mg, 0.28 mmol), pyridin-3-ylboronic acid (107 mg, 0.84 mmol), $K_2CO_3$ (120 mg, 0.8 mmol), Pd(dppf)$Cl_2$ (44 mg, 0.05 mmol) and Pd($PPh_3$)$_4$ (47 mg, 0.05 mmol) in dioxane/$H_2O$ (24 mL/6 mL) was stirred at 90° C. overnight under $N_2$ atmosphere (balloon). The reaction solution was concentrated and the residue was purified by prep-HPLC to give 4-(((1-methyl-6-(pyridin-3-yl)-1H-pyrazolo[3,4-d]pyrimidin-4-yl)amino)methyl)benzenesulfonamide (66.9 mg, yield: δ1%) as a white solid. $^1$HNMR (400 MHz, DMSO-$d_6$): δ=9.52 (s, 1H), 9.03 (t, J=5.6 Hz, 1H), 8.70-8.62 (m, 2H), 8.17 (s, 1H), 7.79 (d, J=8.4 Hz, 2H), 7.60 (d, J=8.4 Hz, 2H), 7.54-7.47 (m, 1H), 7.29 (s, 2H), 4.94 (d, J=5.6 Hz, 2H), 3.99 (s, 3H). MS: m/z 396.1 (M+H$^+$).

Example 2.16

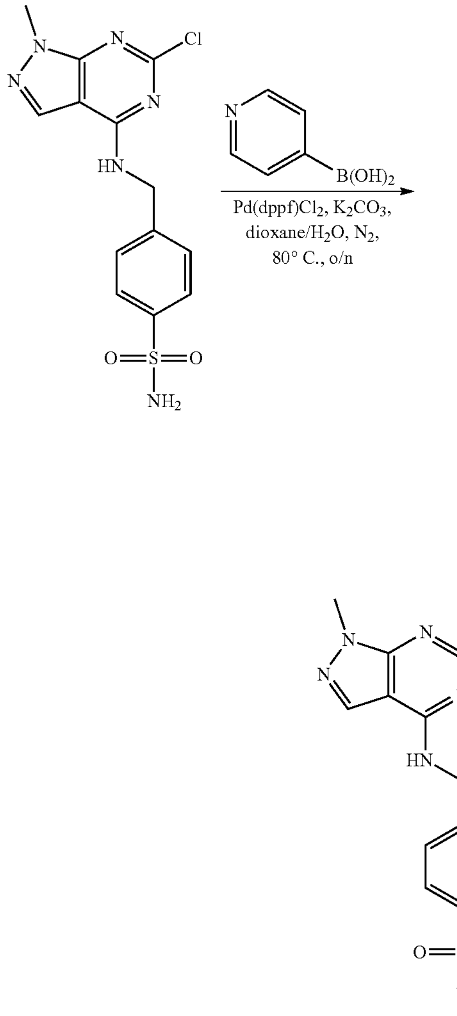

4-(((1-Methyl-6-(pyridin-4-yl)-1H-pyrazolo[3,4-d]pyrimidin-4-yl)amino)methyl)-benzenesulfonamide The title compound (40 mg, yield: 28%, yellow, solid) was prepared using general procedure of 4-(((1-methyl-6-(pyridin-3-yl)-1H-pyrazolo[3,4-d]pyrimidin-4-yl)amino)methyl)benzenesulfonamide. $^1$HNMR (400 MHz, DMSO-$d_6$): δ=9.18 (t, J=5.6 Hz, 1H), 8.81 (d, J=4.4 Hz, 2H), 8.45 (d, J=6.0 Hz, 2H), 8.22 (s, 1H), 7.79 (d, J=8.4 Hz, 2H), 7.61 (d, J=8.0 Hz, 2H), 7.30 (s, 2H), 4.95 (d, J=6.0 Hz, 2H), 4.02 (s, 3H). MS: m/z 396.1 (M+H$^+$).

Example 2.17

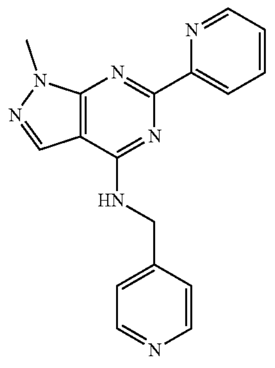 [SMILES: Cn1ncc2c(NCc3ccncc3)nc(-c3ccccn3)nc21]

1-Methyl-6-(pyridin-2-yl)-N-(pyridin-4-ylmethyl)-1H-pyrazolo[3,4-d]pyrimidin-4-amine The title compound was prepared using general procedure of N-benzyl-1-methyl-6-(pyridin-2-yl)-1H-pyrazolo[3,4-d]pyrimidin-4-amine (Example 2.9). $^1$HNMR (400 MHz, DMSO-$d_6$): δ=8.99-8.97 (m, 1H), 8.72-8.71 (m, 1H), 8.52-8.50 (m, 2H), 8.30-8.29 (m, 1H), 8.20 (s, 1H), 7.91-7.90 (m, 1H), 7.48-7.42 (m, 3H), 4.90 (d, J=4 Hz, 2H), 4.01 (s, 3H). MS: m/z 318.1 (M+H$^+$).

Example 2.18

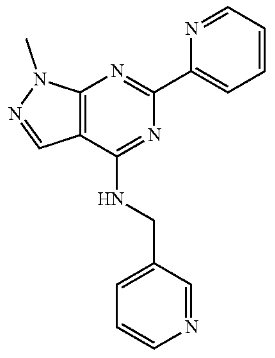 [SMILES: Cn1ncc2c(NCc3cccnc3)nc(-c3ccccn3)nc21]

1-Methyl-6-(pyridin-2-yl)-N-(pyridin-3-ylmethyl)-1H-pyrazolo[3,4-d]pyrimidin-4-amine The title compound was prepared using general procedure of N-benzyl-1-methyl-6-(pyridin-2-yl)-1H-pyrazolo[3,4-d]pyrimidin-4-amine (Example 2.9). $^1$HNMR (400 MHz, DMSO-$d_6$): δ=8.89-8.87 (m, 1H), 8.73-8.71 (m, 1H), 8.37 (d, J=8.0 Hz, 1H), 8.16 (s, 1H), 7.93-7.89 (m, 1H), 7.48-7.45 (m, 3H), 7.40-7.38 (d, J=8 Hz, 2H), 4.86 (d, J=6.0 Hz, 2H), 3.98 (s, 3H). MS: m/z 318.1 (M+H$^+$).

Example 2.19

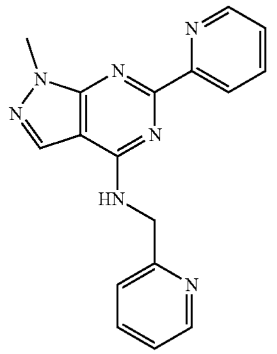 [SMILES: Cn1ncc2c(NCc3ccccn3)nc(-c3ccccn3)nc21]

1-Methyl-6-(pyridin-2-yl)-N-(pyridin-2-ylmethyl)-1H-pyrazolo[3,4-d]pyrimidin-4-amine The title compound was prepared using general procedure of N-benzyl-1-methyl-6-(pyridin-2-yl)-1H-pyrazolo[3,4-d]pyrimidin-4-amine (Example 2.9). $^1$HNMR (400 MHz, DMSO-$d_6$): δ=9.01-8.97 (m, 1H), 8.70 (m, 1H), 8.55 (m, 1H), 8.31-8.29 (d, J=8 Hz, 1H), 8.21 (s, 1H), 7.91-8.87 (m, 1H), 7.76-7.72 (m, 1H), 7.47-7.44 (m, 2H), 7.29-7.25 (m, 1H), 4.96 (d, J=6.4 Hz, 2H), 3.98 (s, 3H). MS: m/z 318.1 (M+H$^+$).

Example 2.20

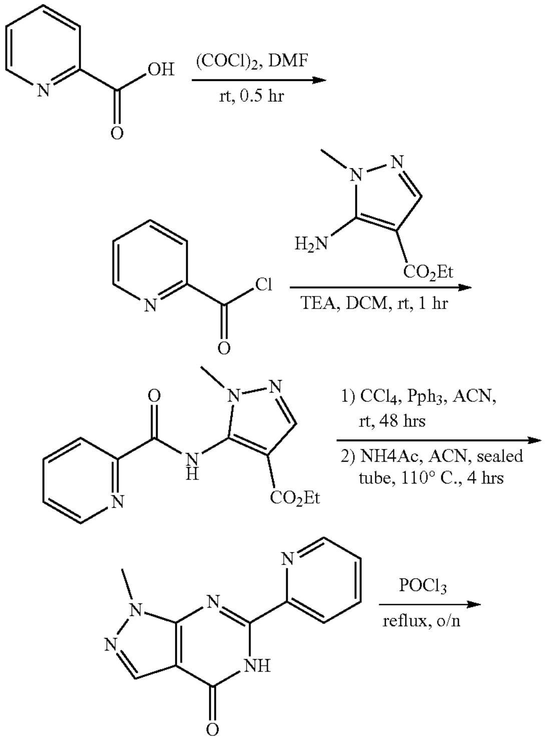

-continued

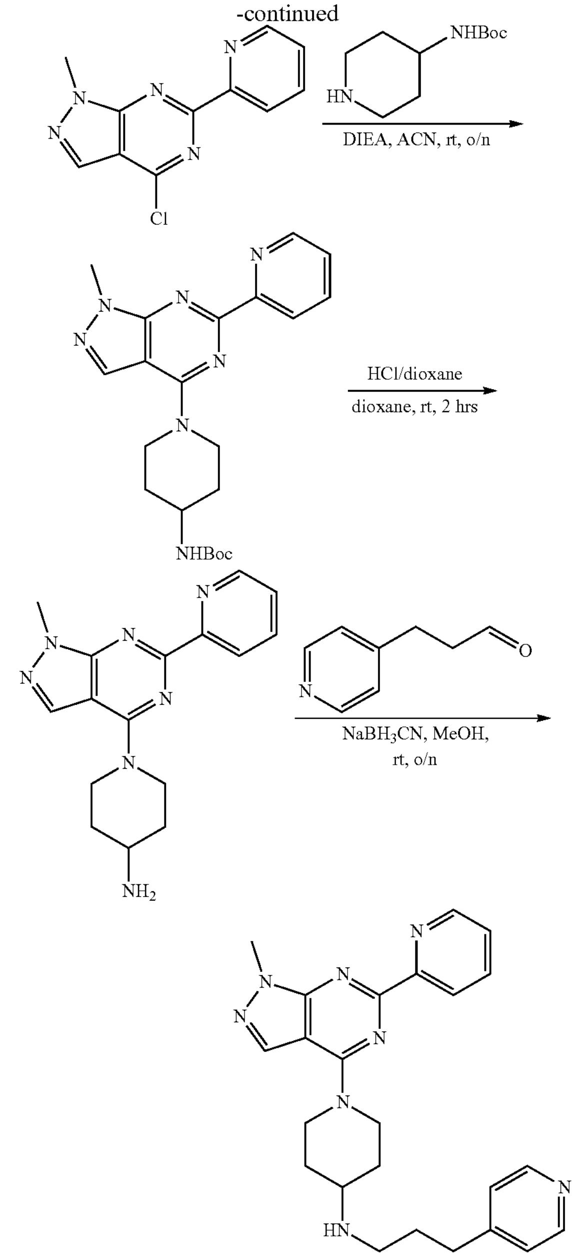

1-(1-Methyl-6-(pyridin-2-yl)-1H-pyrazolo[3,4-d] pyrimidin-4-yl)-N-(3-(pyridin-4-yl)propyl)piperidin-4-amine Step 1 and Step 2: To a solution of picolinic acid (1.23 g, 10.0 mmol) in $(COCl)_2$ (10 mL) was added 2 drops of DMF. The resulting mixture was stirred at room temperature for 0.5 hr. Then the mixture was concentrated in vacuum to give picolinoyl chloride as a white solid, which was dissolved in dry DCM (20 mL). Then ethyl 5-amino-1-methyl-1H-pyrazole-4-carboxylate (3.38 g, 20.0 mmol) was added, followed by TEA (3.03 g, 30.0 mmol). The resulting mixture was stirred at room temperature for 1 hr. The reaction was monitored by LCMS and TLC. Then the reaction mixture was concentrated in vacuum to give a residue, which was purified by silica gel column (DCM/MeOH=50/1) to afford ethyl 1-methyl-5-(picolinamido)-1H-pyrazole-4-carboxylate (2.36 g, yield: 86%) as a white solid.

Step 3: To a mixture of ethyl 1-methyl-5-(picolinamido)-1H-pyrazole-4-carboxylate (2.36 g, 8.60 mmol) and triphenylphosphine (6.77 g, 25.8 mmol) in ACN (40 mL) was added $CCl_4$ (3.97 g, 25.8 mmol). The resulting mixture was stirred at room temperature for 48 hrs. Then the reaction was treated with $NH_4Ac$ (excess) and heated at 110° C. overnight in a sealed tube vial. The reaction was monitored by LCMS. Then the reaction mixture was concentrated in vacuum to give a residue, which was purified by reverse phase column (5-95% ACN in $H_2O$, 60 mins) to afford 1-methyl-6-(pyridin-2-yl)-1H-pyrazolo[3,4-d]pyrimidin-4(5H)-one (946 mg, yield: 48%) as a white solid.

Step 4: A mixture of 1-methyl-6-(pyridin-2-yl)-1H-pyrazolo[3,4-d]pyrimidin-4(5H)-one (946 mg, 4.16 mmol) in $POCl_3$ (10 mL) was stirred at 110° C. overnight. The reaction was monitored by LCMS and TLC. Then the reaction mixture was concentrated in vacuum to give a residue, which was purified by silica gel column (DCM/MeOH=50/1) to afford 4-chloro-1-methyl-6-(pyridin-2-yl)-1H-pyrazolo[3,4-d]pyrimidine (824 mg, yield: 81%) as a yellow solid.

Step 5: To a solution of 4-chloro-1-methyl-6-(pyridin-2-yl)-1H-pyrazolo[3,4-d]pyrimidine (491 mg, 2.0 mmol) in ACN (30 mL) was added tert-butyl piperidin-4-ylcarbamate (801 mg, 4.0 mmol), followed by DIEA (774 mg, 6.0 mmol). The resulting mixture was stirred at room temperature overnight. The reaction was monitored by LCMS. Then the mixture was concentrated in vacuum to give a residue, which was purified by silica gel column (DCM/MeOH=50/1) to afford tert-butyl (1-(1-methyl-6-(pyridin-2-yl)-1H-pyrazolo[3,4-d]pyrimidin-4-yl)piperidin-4-yl)carbamate (455 mg, yield: 56%) as a yellow solid. $^1$HNMR (400 MHz, DMSO-$d_6$): δ=8.74-8.73 (m, 1H), 8.41 (d, J=8.0 Hz, 1H), 8.34 (brs, 1H), 7.96-7.92 (m, 1H), 7.51-7.48 (m, 1H), 6.93 (d, J=12.0 Hz, 1H), 4.72 (s, 2H), 4.00 (s, 3H), 3.68-3.65 (m, 1H), 3.41-3.40 (m, 2H), 1.95-1.91 (m, 2H), 1.44-1.40 (m, 2H), 1.40 (s, 9H).

Step 6: To a mixture of tert-butyl (1-(1-methyl-6-(pyridin-2-yl)-1H-pyrazolo[3,4-d]pyrimidin-4-yl)piperidin-4-yl)carbamate (455 mg, 1.10 mmol) in dioxane (20 mL) was added HCl/dioxane (10 mL, >4 M). The resulting mixture was stirred at room temperature for 4 hrs. The reaction was monitored by LCMS. The mixture was concentrated in vacuum to afford 1-(1-methyl-6-(pyridin-2-yl)-1H-pyrazolo[3,4-d]pyrimidin-4-yl)piperidin-4-amine (quantitative) as a yellow solid.

Step 7: To a mixture of 1-(1-methyl-6-(pyridin-2-yl)-1H-pyrazolo[3,4-d]pyrimidin-4-yl)piperidin-4-amine (100 mg, 0.29 mmol) in MeOH (10 mL) was added 3-(pyridin-4-yl)propanal (78 mg, 0.58 mmol). The resulting mixture was stirred at room temperature overnight. Then $NaBCNH_3$ (55 mg, 0.87 mmol) was added and the mixture was stirred at room temperature for another 1 hr. The reaction was monitored by LCMS. The mixture was concentrated in vacuum to give a residue, which was purified by prep-HPLC with $NH_4HCO_3$ as additive to afford 1-(1-methyl-6-(pyridin-2-yl)-1H-pyrazolo[3,4-d]pyrimidin-4-yl)-N-(3-(pyridin-4-yl)propyl)piperidin-4-amine (22.8 mg, yield: 18%) as a yellow solid. $^1$HNMR (400 MHz, DMSO-$d_6$): δ=8.74-8.73 (m, 1H), 8.45-8.44 (m, 2H), 8.41 (d, J=8.0 Hz, 1H), 8.33 (brs, 1H), 7.96-7.92 (m, 1H), 7.48-7.51 (m, 1H), 7.24 (d, J=6.0 Hz, 2H), 4.65 (s, 1H), 4.00 (s, 3H), 3.21 (m, 4H), 2.77 (m, 1H), 2.65 (t, J=7.6 Hz, 2H), 2.58 (t, J=7.6 Hz, 2H), 1.99-1.96 (m, 2H), 1.75-1.71 (m, 2H), 1.33-1.30 (m, 2H). MS: m/z 428.9 $(M+H^+)$.

Example 2.21

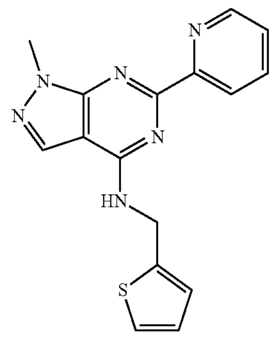 [SMILES: Cn1ncc2c(NCc3cccs3)nc(-c3ccccn3)nc21]

1-Methyl-6-(pyridin-2-yl)-N-(thiophen-2-ylmethyl)-1H-pyrazolo[3,4-d]pyrimidin-4-amine The title compound was prepared using general procedure of N-benzyl-1-methyl-6-(pyridin-2-yl)-1H-pyrazolo[3,4-d]pyrimidin-4-amine (Example 2.9). $^{1}$HNMR (400 MHz, DMSO-$d_6$): δ=8.96-8.94 (m, 1H), 8.75-8.73 (m, 1H), 8.51 (d, J=8 Hz, 1H), 8.14 (s, 1H), 7.97-7.93 (m, 1H), 7.50-7.47 (m, 1H), 7.39-7.37 (m, 1H), 7.16 (s, 1H), 6.98-6.96 (m, 1H), 5.03 (d, J=6.0 Hz, 2H), 3.99 (s, 3H). MS: m/z 323.0 (M+H$^+$).

Example 2.22

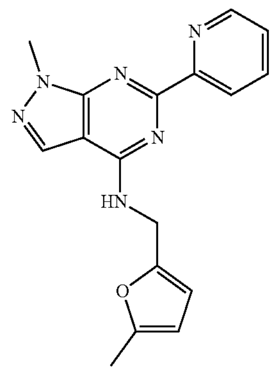 [SMILES: Cc1ccc(CNc2nc(-c3ccccn3)nc3c2cnn3C)o1]

1-Methyl-N-((5-methylfuran-2-yl)methyl)-6-(pyridin-2-yl)-1H-pyrazolo[3,4-d]pyrimidin-4-amine The title compound was prepared using general procedure of N-benzyl-1-methyl-6-(pyridin-2-yl)-1H-pyrazolo[3,4-d]pyrimidin-4-amine (Example 2.9). $^{1}$HNMR (400 MHz, DMSO-$d_6$): δ=8.79-8.76 (m, 1H), 8.75-8.73 (m, 1H), 8.47 (d, J=6.0 Hz, 1H), 8.18 (s, 1H), 7.97-7.93 (m, 1H), 7.50-7.47 (m, 1H), 6.31-6.29 (m, 1H), 6.01-6.00 (m, 1H), 4.81-4.79 (m, 2H), 3.97 (s, 3H), 2.23 (s, 3H). MS: m/z 321.1 (M+H$^+$).

Example 2.23

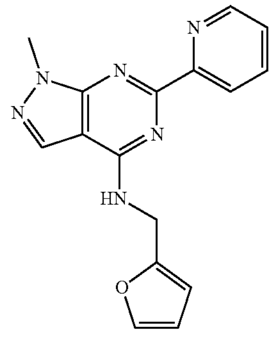 [SMILES: Cn1ncc2c(NCc3ccco3)nc(-c3ccccn3)nc21]

N-(Furan-2-ylmethyl)-1-methyl-6-(pyridin-2-yl)-1H-pyrazolo[3,4-d]pyrimidin-4-amine The title compound was prepared using general procedure of N-benzyl-1-methyl-6-(pyridin-2-yl)-1H-pyrazolo[3,4-d]pyrimidin-4-amine (Example 2.9). $^{1}$HNMR (400 MHz, DMSO-$d_6$): δ=8.81-8.78 (m, 1H), 8.74-8.72 (m, 1H), 8.47-8.45 (m, 1H), 8.17 (s, 1H), 7.96-7.92 (m, 1H), 7.62-7.61 (m, 1H), 7.50-7.47 (m, 1H), 6.44-6.41 (m, 2H), 4.86 (d, J=9.2 Hz, 1H), 3.98 (s, 3H). MS: m/z 307.1 (M+H$^+$).

Example 2.24

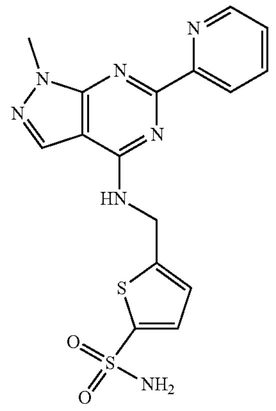 [SMILES: Cn1ncc2c(NCc3ccc(S(N)(=O)=O)s3)nc(-c3ccccn3)nc21]

5-(((1-Methyl-6-(pyridin-2-yl)-1H-pyrazolo[3,4-d]pyrimidin-4-yl)amino)methyl)thiophene-2-sulfonamide The title compound was prepared using general procedure of N-benzyl-1-methyl-6-(pyridin-2-yl)-1H-pyrazolo[3,4-d]pyrimidin-4-amine (Example 2.9). $^{1}$HNMR (400 MHz, DMSO-$d_6$): δ=9.08-9.04 (m, 1H), 8.74 (m, 1H), 8.50 (d, J=8 Hz, 1H), 8.14 (s, 1H), 7.97-7.92 (m, 1H), 7.53-7.48 (m, 3H), 7.38 (d, J=3.6 Hz, 1H), 7.16 (d, J=3.6 Hz, 1H), 5.05 (d, J=6.0 Hz, 2H), 4.00 (s, 3H). MS: m/z 402.0 (M+H$^+$).

Example 2.25

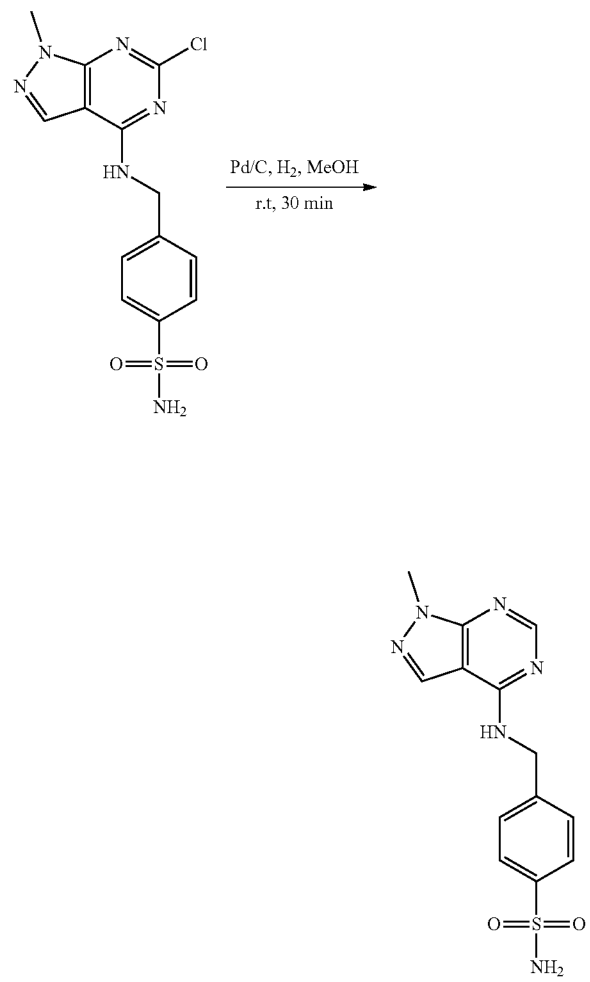

4-(((1-Methyl-1H-pyrazolo[3,4-d]pyrimidin-4-yl) amino)methyl)benzenesulfonamide

A mixture of 4-(((6-chloro-1-methyl-1H-pyrazolo[3,4-d] pyrimidin-4-yl)amino)methyl)benzenesulfonamide (50 mg, 0.14 mmol) and Pd/C (15 mg, 0.1 mmol) in MeOH (50 mL) was stirred at room temperature for 30 mins under $H_2$ atmosphere (balloon). The reaction solution was filtered and the filtrate was concentrated. The residue was purified by prep-HPLC to give 4-(((1-methyl-1H-pyrazolo[3,4-d]pyrimidin-4-yl)amino)methyl)benzenesulfonamide (4.4 mg, yield: 10%) as a white solid. $^1$HNMR (400 MHz, DMSO-$d_6$): δ=8.85 (t, J=5.2 Hz, 1H), 8.25 (s, 1H), 8.14 (s, 1H), 7.77 (d, J=8.4 Hz, 2H), 7.50 (d, J=8.0 Hz, 2H), 7.31 (s, 2H), 4.81 (d, J=6.0 Hz, 2H), 3.90 (s, 3H). MS: m/z 319.1 (M+H$^+$).

Example 2.26

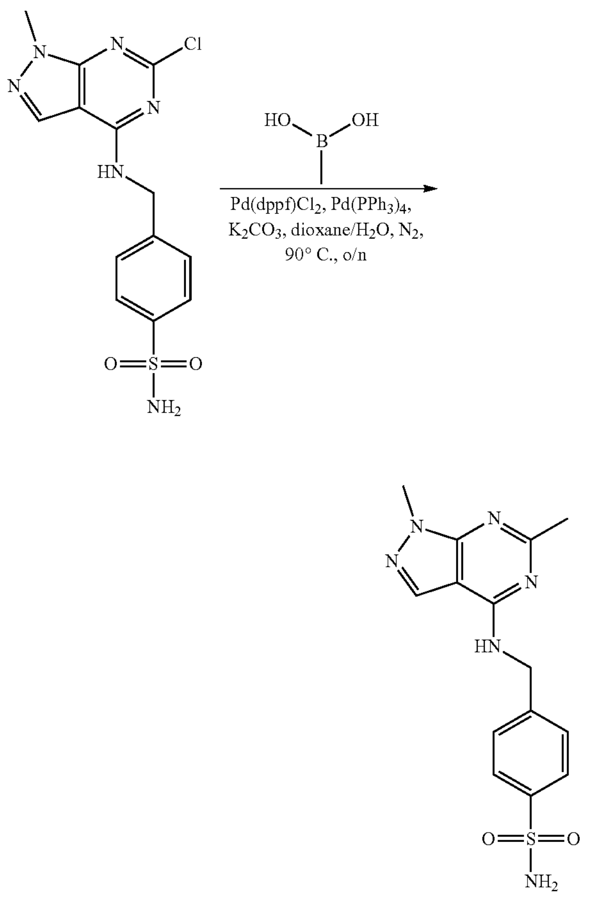

4-(((1,6-Dimethyl-1H-pyrazolo[3,4-d]pyrimidin-4-yl)amino)methyl)benzenesulfonamide The title compound (200 mg, yield: 43%, white, solid) was prepared using general procedure of 4-(((1-methyl-6-(pyridin-3-yl)-1H-pyrazolo[3,4-d]pyrimidin-4-yl)amino) methyl) benzenesulfonamide (Example 2.15). $^1$HNMR (400 MHz, DMSO-$d_6$): δ=8.67 (t, J=4.8 Hz, 1H), 8.05 (s, 1H), 7.78 (d, J=8.4 Hz, 2H), 7.52 (d, J=8.4 Hz, 2H), 7.31 (s, 2H), 4.80 (d, J=6.0 Hz, 2H), 3.86 (s, 3H), 2.42 (s, 3H). MS: m/z 333.1 (M+H$^+$).

Example 2.27 and Example 2.28

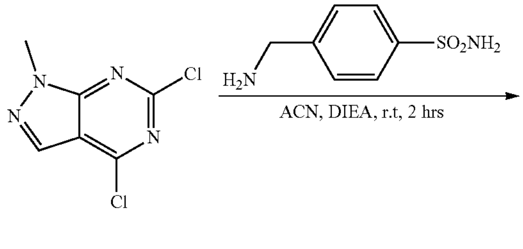

-continued

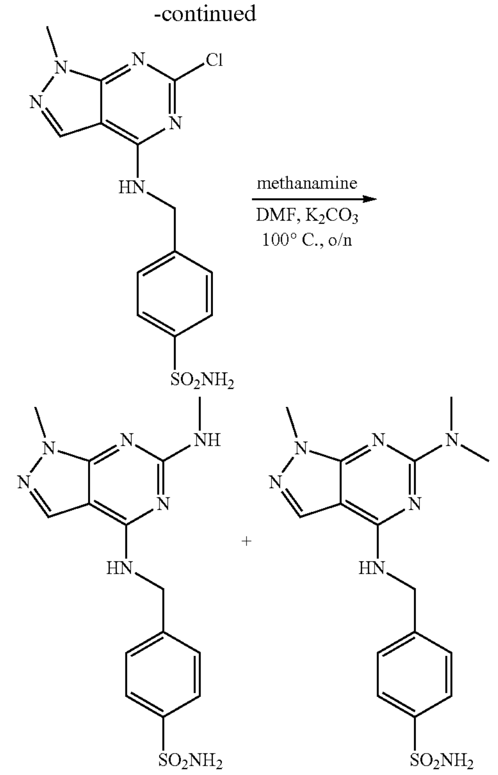

4-(((1-Methyl-6-(methylamino)-1H-pyrazolo[3,4-d]pyrimidin-4-yl)amino)methyl)-benzenesulfonamide (Example 2.27) and 4-(((6-(Dimethylamino)-1-methyl-1H-pyrazolo[3,4-d]pyrimidin-4-yl)amino)methyl)-benzenesulfonamide (Example 2.28)

Step 1: To a solution of 4,6-dichloro-1-methyl-1H-pyrazolo[3,4-d]pyrimidine (2 g, 9.9 mmol) in ACN (100 mL) was added 4-(aminomethyl)benzenesulfonamide (2.4 g, 10.8 mmol) and DIEA (2.5 g, 19.4 mmol). The mixture was stirred at room temperature for 2 hrs. The resulting solution was filtered. The cake washed with ACN to give 4-(((6-chloro-1-methyl-1H-pyrazolo[3,4-d]pyrimidin-4-yl)amino)methyl)benzenesulfonamide (2.3 g, yield: δ6%) as a yellow solid.

Step 2: A mixture of 4-(((6-chloro-1-methyl-1H-pyrazolo[3,4-d]pyrimidin-4-yl)amino)methyl)benzenesulfonamide (100 mg, 0.28 mmol), $K_2CO_3$ (77.3 mg, 0.56 mmol) and methanamine (22.8 mg, 0.34 mmol) in DMF (15 mL) was stirred at 100° C. overnight. The resulting solution was concentrated and the residue was purified by prep-HPLC to give 4-(((1-methyl-6-(methylamino)-1H-pyrazolo[3,4-d]pyrimidin-4-yl)amino)methyl)benzenesulfonamide (2.4 mg) and 4-(((6-(dimethylamino)-1-methyl-1H-pyrazolo[3,4-d]pyrimidin-4-yl)amino)methyl)benzenesulfonamide (30.6 mg) as both white solids.

$^1$HNMR (400 MHz, DMSO-$d_6$): δ=8.32 (s, 1H), 7.81 (s, 1H), 7.67 (d, J=8.4 Hz, 2H), 7.51 (d, J=8.4 Hz, 2H), 7.30 (s, 2H), 6.59 (d, J=4.8 Hz, 1H), 4.71 (d, J=5.6 Hz, 2H), 3.70 (s, 3H), 2.76 (d, J=4.8 Hz, 3H). MS: m/z 348.1 ($M+H^+$). $^1$HNMR (400 MHz, DMSO-$d_6$): δ=8.44 (t, J=5.6 Hz 1H), 7.82 (s, 1H), 7.76 (d, J=8.0 Hz, 2H), 7.51 (d, J=8.0 Hz, 2H), 7.30 (s, 2H), 4.71 (d, J=6.0 Hz, 2H), 3.70 (s, 3H), 3.01 (s, 6H). MS: m/z 362.1 ($M+H^+$).

Example 2.29

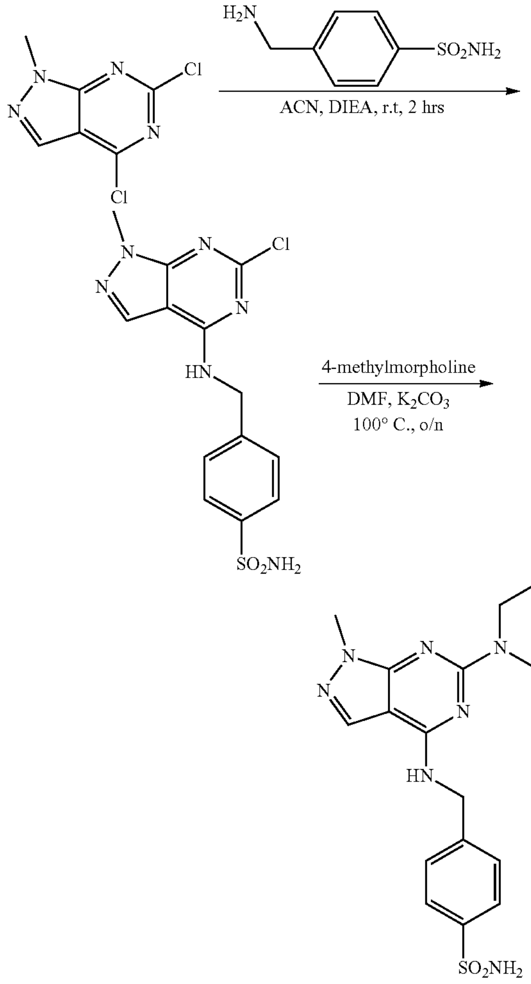

4-(((1-Methyl-6-morpholino-1H-pyrazolo[3,4-d]pyrimidin-4-yl)amino)methyl)-benzenesulfonamide The title compound (63.4 mg, yield: 57%, white, solid) was prepared using general procedure of 4-(((1-methyl-6-(methylamino)-1H-pyrazolo[3,4-d]pyrimidin-4-yl)amino)methyl)benzenesulfonamide (Example 2.27). $^1$HNMR (400 MHz, DMSO-$d_6$): δ=8.55 (t, J=5.2 Hz, 1H), 7.86 (s, 1H), 7.76 (d, J=8.0 Hz, 2H), 7.51 (d, J=8.0 Hz, 2H), 7.31 (s, 2H), 4.70 (d, J=5.6 Hz, 2H), 3.71 (s, 3H), 3.66-3.65 (m, 4H), 3.59-3.58 (m, 4H). MS: m/z 403.8 ($M+H^+$).

Example 2.30

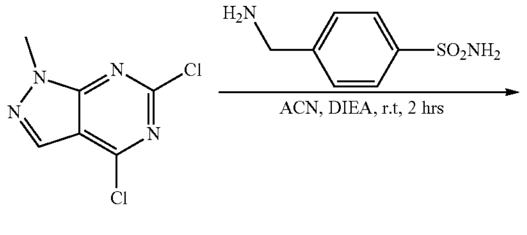

-continued

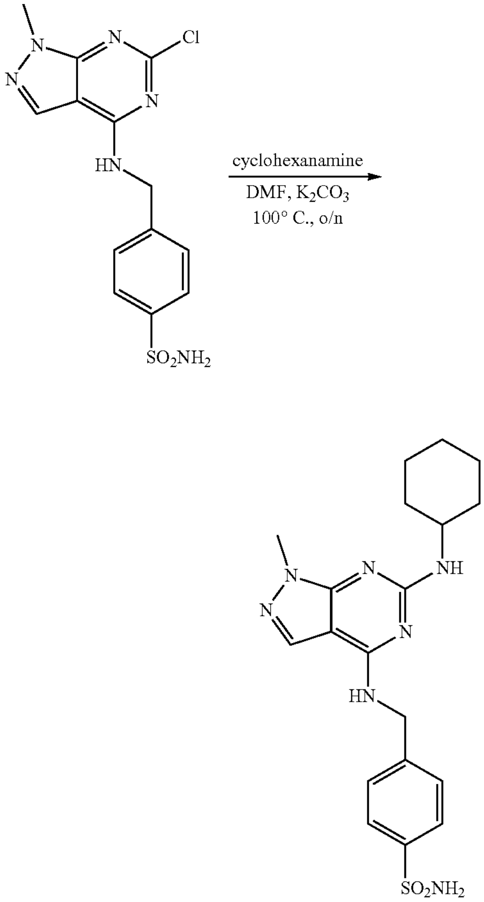

4-(((6-(Cyclohexylamino)-1-methyl-1H-pyrazolo[3,4-d]pyrimidin-4-yl)amino)methyl)-benzenesulfonamide The title compound (32.2 mg, yield: 28%, yellow, solid) was prepared using general procedure of 4-(((1-methyl-6-(methylamino)-1H-pyrazolo[3,4-d]pyrimidin-4-yl)amino)methyl)-benzenesulfonamide (Example 2.27). $^1$HNMR (400 MHz, DMSO-$d_6$): δ=8.44 (brs, 1H), 7.80 (s, 1H), 7.76 (d, J=8.0 Hz, 2H), 7.49 (d, J=8.0 Hz, 2H), 7.29 (s, 2H), 6.45 (d, J=4.8 Hz, 1H), 4.70 (d, J=2.8 Hz, 2H), 3.67 (s, 4H), 1.67-1.55 (m, 5H), 1.20-1.07 (m, 5H). MS: m/z 415.8 ($M+H^+$).

Example 2.31

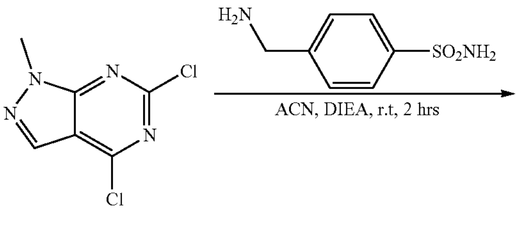

-continued

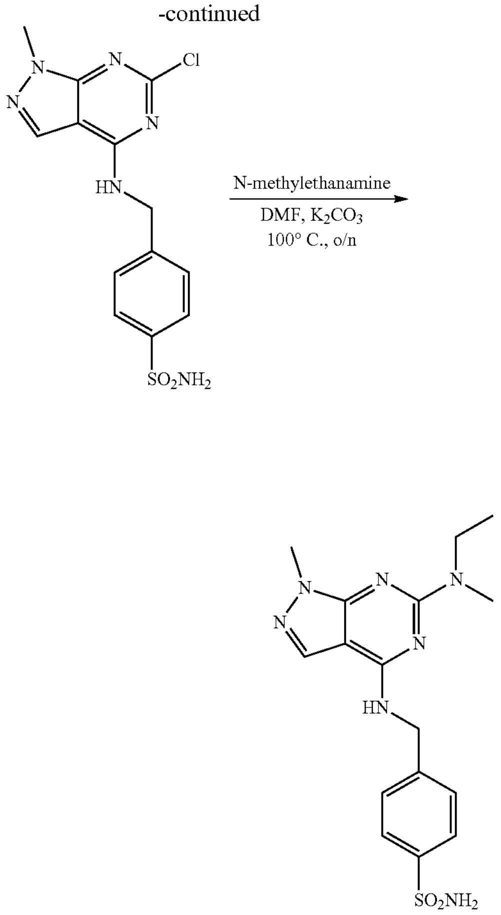

4-(((6-(Ethyl(methyl)amino)-1-methyl-1H-pyrazolo[3,4-d]pyrimidin-4-yl)amino)methyl)-benzenesulfonamide The title compound (66.2 mg, yield: δ3%, white, solid) was prepared using general procedure of 4-(((1-methyl-6-(methylamino)-1H-pyrazolo[3,4-d]pyrimidin-4-yl)amino)methyl)benzenesulfonamide (Example 2.27). $^1$HNMR (400 MHz, DMSO-$d_6$): δ=8.43 (t, J=6.0 Hz, 1H), 7.82 (s, 1H), 7.76 (d, J=8.4 Hz, 2H), 7.50 (d, J=8.0 Hz, 2H), 7.29 (s, 2H), 4.69 (d, J=6.0 Hz, 2H), 3.70 (s, 3H), 3.59-3.53 (m, 2H), 3.02 (s, 3H), 0.98 (t, J=5.2 Hz, 3H). MS: m/z 376.1 ($M+H^+$).

Example 2.32

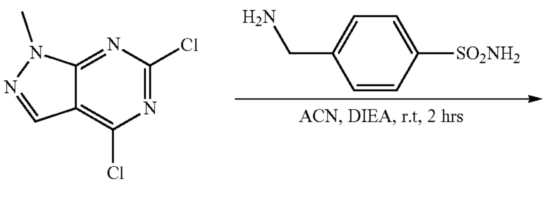

-continued

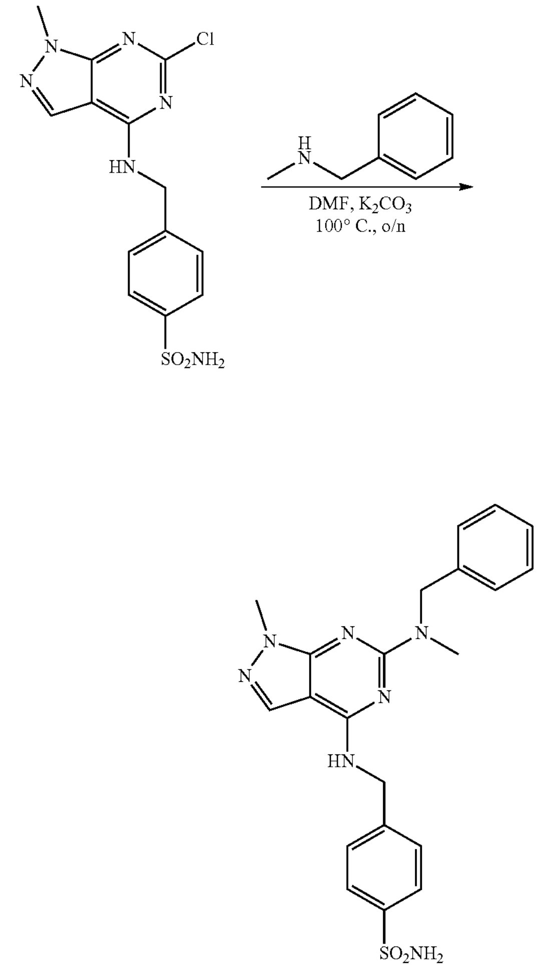

4-(((6-(Benzyl(methyl)amino)-1-methyl-1H-pyrazolo[3,4-d]pyrimidin-4-yl)amino)methyl)-benzenesulfonamide The title compound (79.9 mg, yield: δ6%, white, solid) was prepared using general procedure of 4-(((1-methyl-6-(methylamino)-1H-pyrazolo[3,4-d]pyrimidin-4-yl)amino)methyl)benzenesulfonamide (Example 2.27). $^1$HNMR (400 MHz, DMSO-$d_6$): δ=8.48 (t, J=6.0 Hz, 1H), 7.85 (s, 1H), 7.71 (d, J=8.0 Hz, 2H), 7.50-7.38 (m, 2H), 7.34-7.13 (m, 7H), 4.81 (s, 2H), 4.67 (d, J=5.6 Hz, 2H), 3.71 (s, 3H), 3.04 (s, 3H). MS: m/z 438.1 (M+H$^+$).

Example 2.33

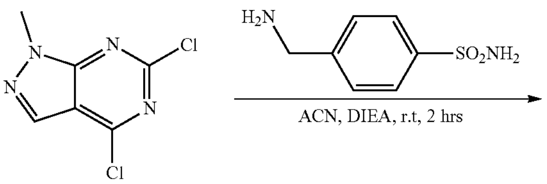

-continued

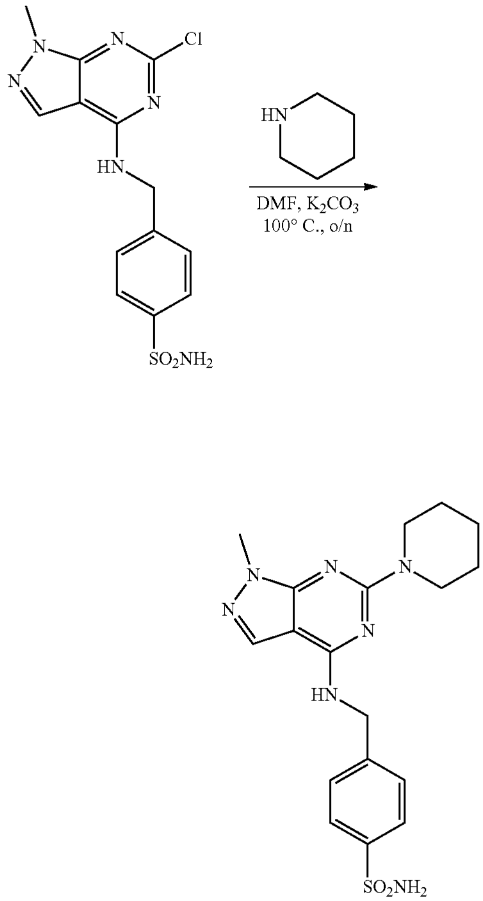

4-(((1-Methyl-6-(piperidin-1-yl)-1H-pyrazolo[3,4-d]pyrimidin-4-yl)amino)methyl)-benzenesulfonamide The title compound (38.9 mg, yield: 35%, yellow, solid) was prepared using general procedure of 4-(((1-methyl-6-(methylamino)-1H-pyrazolo[3,4-d]pyrimidin-4-yl)amino)methyl)benzenesulfonamide (Example 2.27). $^1$HNMR (400 MHz, DMSO-$d_6$): δ=8.44 (t, J=6.0 Hz, 1H), 7.81 (s, 1H), 7.76 (d, J=8.4 Hz, 2H), 7.50 (d, J=8.0 Hz, 2H), 7.30 (s, 2H), 4.68 (d, J=5.6 Hz, 2H), 3.76-3.64 (m, 7H), 1.62-1.52 (m, 2H), 1.48-1.38 (m, 4H). MS: m/z 402.2 (M+H$^+$).

Example 2.34

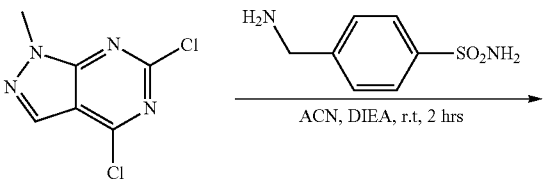

-continued

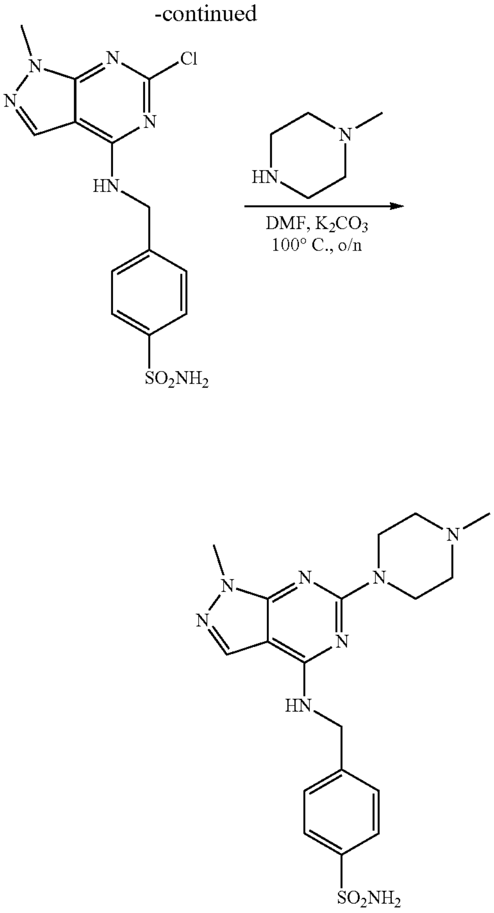

4-(((1-Methyl-6-(4-methylpiperazin-1-yl)-1H-pyrazolo[3,4-d]pyrimidin-4-yl)amino)methyl)-benzenesulfonamide The title compound (71.5 mg, yield: δ2%, yellow, solid) was prepared using general procedure of 4-(((1-methyl-6-(methylamino)-1H-pyrazolo[3,4-d]pyrimidin-4-yl)amino)methyl)benzenesulfonamide (Example 2.27). $^1$HNMR (400 MHz, DMSO-$d_6$): δ=8.49 (t, J=6.0 Hz, 1H), 7.84 (s, 1H), 7.76 (d, J=8.4 Hz, 2H), 7.51 (d, J=8.4 Hz, 2H), 7.30 (s, 2H), 4.69 (d, J=5.6 Hz, 2H), 3.75-3.63 (m, 7H), 2.36-2.23 (m, 4H), 2.18 (s, 3H). MS: m/z 416.9 (M+H$^+$).

Example 2.35

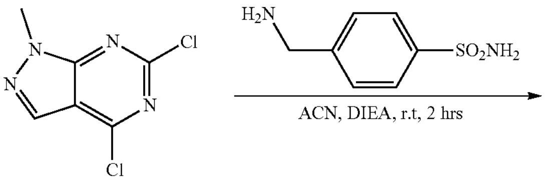

-continued

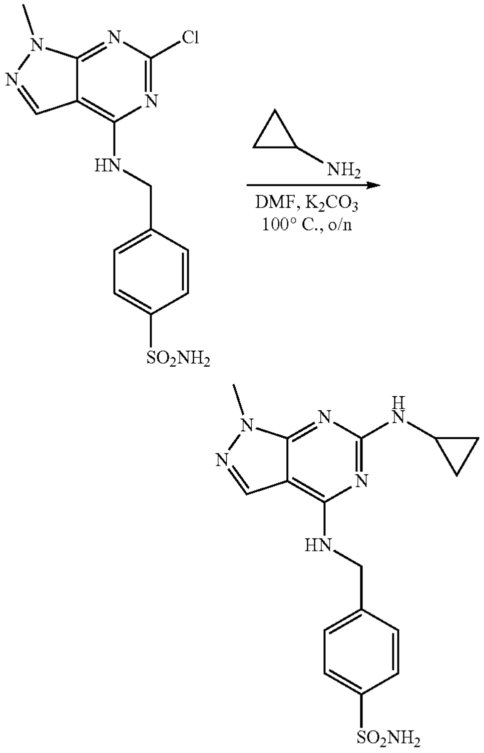

4-(((6-(Cyclopropylamino)-1-methyl-1H-pyrazolo[3,4-d]pyrimidin-4-yl)amino)methyl)-benzenesulfonamide The title compound (36.2 mg, yield: 35%, white, solid) was prepared using general procedure of 4-(((1-methyl-6-(methylamino)-1H-pyrazolo[3,4-d]pyrimidin-4-yl)amino)methyl)benzenesulfonamide (Example 2.27). $^1$HNMR (400 MHz, DMSO-$d_6$): δ=8.43-8.30 (m, 1H), 7.82 (s, 1H), 7.76 (d, J=8.4 Hz, 2H), 7.52 (d, J=8.0 Hz, 2H), 7.30 (s, 2H), 6.89-6.79 (m, 1H), 4.71 (d, J=5.6 Hz, 2H), 3.70 (s, 3H), 2.80-2.70 (m, 1H), 0.65-0.54 (m, 2H), 0.48-0.36 (m, 2H). MS: m/z 374.1 (M+H$^+$).

Example 2.36

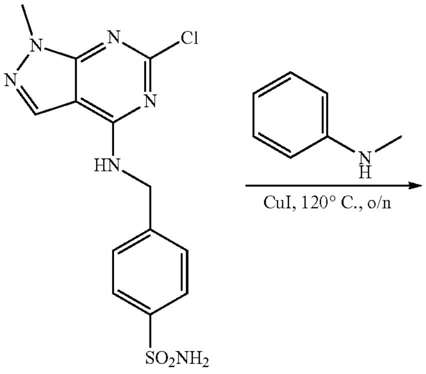

-continued

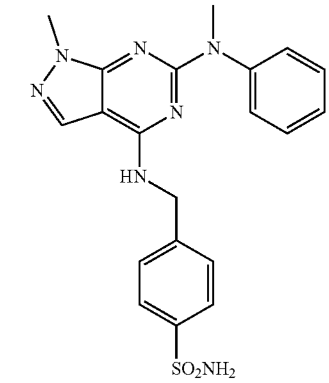

4-(((1-Methyl-6-(methyl(phenyl)amino)-1H-pyrazolo[3,4-d]pyrimidin-4-yl)amino)methyl)-benzenesulfonamide A mixture of 4-(((6-chloro-1-methyl-1H-pyrazolo[3,4-d]pyrimidin-4-yl)amino)methyl)benzenesulfonamide (100 mg, 0.28 mmol) in N-methylaniline (6 mL) was added CuI (106 mg, 0.56 mmol). The mixture was stirred at 120° C. overnight. The resulting solution was concentrated and the residue was purified by prep-HPLC to give 4-(((1-methyl-6-(methyl(phenyl)amino)-1H-pyrazolo [3,4-d]pyrimidin-4-yl)amino)methyl)benzenesulfonamide (12.5 mg, yield: 11%) as a purple solid. $^1$HNMR (400 MHz, DMSO-$d_6$): δ=8.53 (t, J=5.6 Hz, 1H), 7.85 (s, 1H), 7.68 (d, J=8.0 Hz, 2H), 7.36-7.26 (m, 6H), 7.22 (d, J=8.0 Hz, 2H), 7.18-7.11 (m, 1H), 4.46 (d, J=6.0 Hz, 2H), 3.72 (s, 3H), 3.45 (s, 3H). MS: m/z 423.8 (M+$H^+$).

Example 2.37

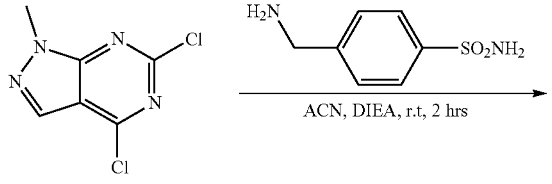

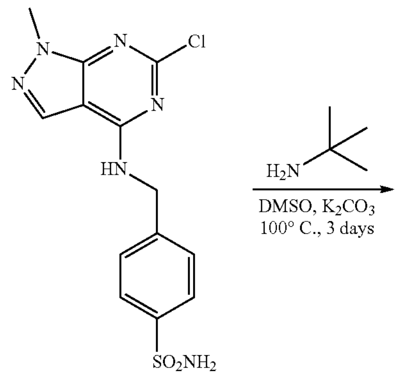

-continued

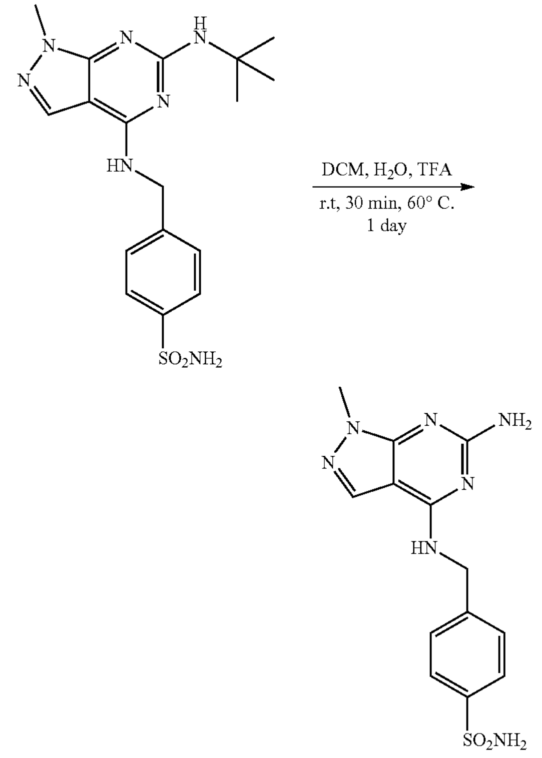

4-(((6-Amino-1-methyl-1H-pyrazolo[3,4-d]pyrimidin-4-yl)amino)methyl)-benzenesulfonamide Step 1 and 2: The step 1 and step 2 were prepared using general procedure of 4-(((6-(cyclopropylamino)-1-methyl-1H-pyrazolo[3,4-d]pyrimidin-4-yl)amino)methyl)benzenesulfonamide (Example 2.35).

Step 3: A mixture of 4-(((6-(tert-butylamino)-1-methyl-1H-pyrazolo[3,4-d]pyrimidin-4-yl)amino)methyl)benzenesulfonamide (62 mg, 0.16 mmol) and TFA (0.5 ml) in DCM/$H_2O$ (10 mL/0.5 mL) was stirred at 100° C. for 1 day. The resulting solution was concentrated and the residue was purified by prep-HPLC to give 4-(((6-amino-1-methyl-1H-pyrazolo[3,4-d]pyrimidin-4-yl)amino)methyl)benzenesulfonamide (4.8 mg, yield: 9%) as a white solid. $^1$HNMR (400 MHz, DMSO-$d_6$): δ=7.85 (d, J=8.4 Hz, 2H), 7.80 (s, 1H), 7.53 (d, J=8.4 Hz, 2H), 4.80 (s, 2H), 3.78 (s, 3H). MS: m/z 334.1 (M+$H^+$).

Example 2.38

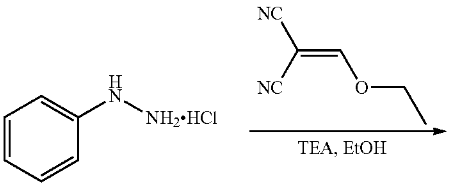

-continued

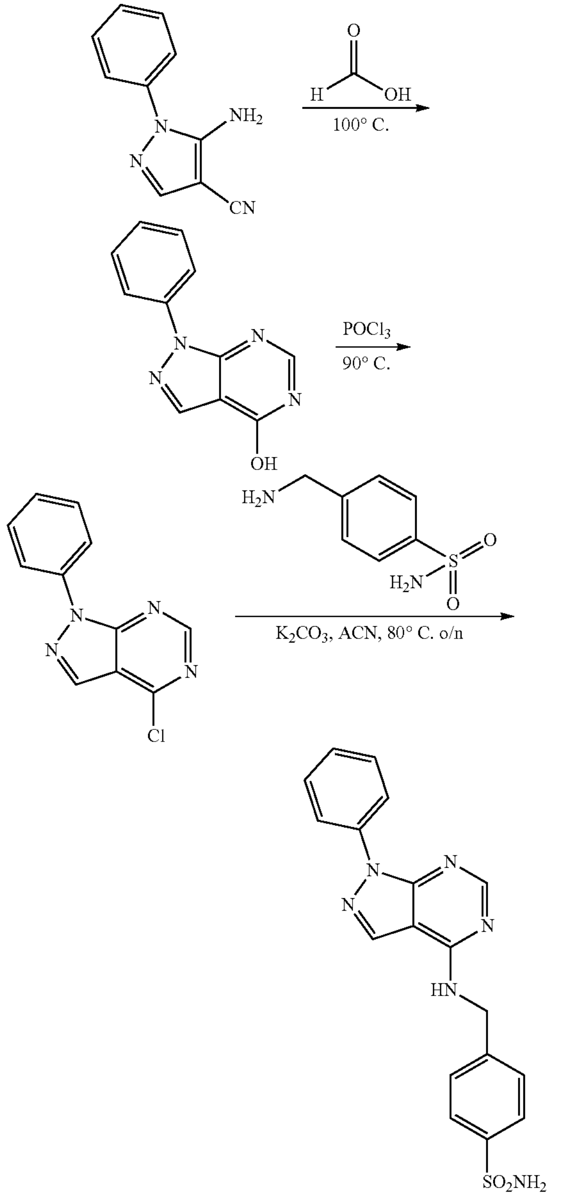

4-(((1-Phenyl-1H-pyrazolo[3,4-d]pyrimidin-4-yl)amino)methyl)benzenesulfonamide

Step 1: A solution of phenylhydrazine hydrochloride (1 g, 6.9 mmol), 2-(ethoxymethylene)malononitrile (0.8 g, 6.9 mmol) and TEA (2 g, 20.7 mmol) in EtOH (15 mL) was stirred at 50° C. for 5 hrs. The reaction mixture was concentrated and the residue was purified by silica gel column (PE/EA=10/1) to give 5-amino-1-phenyl-1H-pyrazole-4-carbonitrile (1 g, yield: 78.7%) as a yellow solid. MS: m/z 185.4 $(M+H^+)$.

Step 2: A solution of 5-amino-1-phenyl-1H-pyrazole-4-carbonitrile (1 g, 5.4 mmol) in formic acid (10 mL) was stirred at 100° C. overnight. The reaction was concentrated and the residue was purified by slurry with DCM to give 1-phenyl-1H-pyrazolo[3,4-d]pyrimidin-4-ol (0.8 g, yield: 72%) as a yellow solid. MS: m/z 213.3 $(M+H^+)$.

Step 3: A solution of 1-phenyl-1H-pyrazolo[3,4-d]pyrimidin-4-ol (200 mg, 0.9 mmol) in $POCl_3$ (5 mL) was stirred at 120° C. for 3 hrs. The $POCl_3$ was removed under reduced pressure. The mixture was quenched with hot water and neutralized with saturated aqueous $NaHCO_3$ solution (100 mL). The water phase was extracted with EA (100 mL×3). The combined organic layers were dried and concentrated. The residue was purified by silica gel column (PE/EA=10/1) to give 4-chloro-1-phenyl-1H-pyrazolo[3,4-d]pyrimidine (0.11 g, yield: 51%) as a white solid. $^1$HNMR (400 MHz, DMSO-d6): δ=9.00 (s, 1H), 8.78 (s, 1H), 8.17-8.15 (m, 2H), 7.65-7.61 (m, 2H), 7.48-7.44 (m, 1H). MS: m/z 231.0 $(M+H^+)$.

Step 4: A solution of 4-chloro-1-phenyl-1H-pyrazolo[3,4-d]pyrimidine (100 mg, 0.4 mmol), 4-(aminomethyl)benzenesulfonamide (145.2 mg, 0.6 mmol) and $K_2CO_3$ (180 mg, 1.3 mmol) in ACN (5 mL) was stirred at 80° C. overnight. The reaction mixture was neutralized to pH=7 and filtered. The filtrate was concentrated and purified by prep-HPLC ($NH_4HCO_3$) to give 4-(((1-phenyl-1H-pyrazolo[3,4-d]pyrimidin-4-yl)amino)methyl)benzenesulfonamide (89.3 mg, yield: 54%) as a white solid. $^1$HNMR (400 MHz, DMSO-$d_6$): δ=9.09-9.06 (m, 1H), 8.45 (s, 1H), 8.45 (s, 1H), 8.19 (d, J=8 Hz, 2H), 7.79 (d, J=8.4 Hz, 2H), 7.57-7.54 (m, 4H), 7.37-7.32 (m, 3H), 4.85 (d, J=6 Hz, 2H). MS: m/z 381.0 $(M+H^+)$.

Example 2.39 and Example 2.40

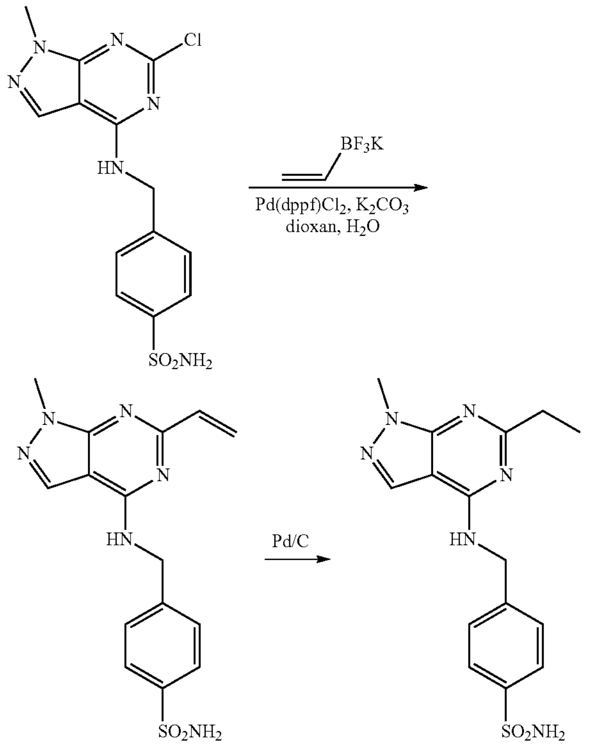

4-(((1-Methyl-6-vinyl-1H-pyrazolo[3,4-d]pyrimidin-4-yl)amino)methyl)benzenesulfonamide (Example 2.39) and 4-(((6-Ethyl-1-methyl-1H-pyrazolo[3,4-d]pyrimidin-4-yl)amino)methyl)benzenesulfonamide (Example 2.40)

Step 1: A solution of 4-(((6-chloro-1-methyl-1H-pyrazolo[3,4-d]pyrimidin-4-yl)amino)methyl)benzenesulfonamide (300 mg, 0.85 mmol), potassium vinyltrifluoroborate (228 mg, 1.70 mmol) and $K_2CO_3$ (352 mg, 2.55 mmol) and Pd(dppf)$Cl_2$ (62 mg, 0.08 mmol) in dioxane/$H_2O$ (3 mL/0.5 mL) was stirred at 100° C. overnight. Then the reaction was concentrated and the residue was purified by prep-HPLC to give 4-(((1-methyl-6-vinyl-1H-pyrazolo[3,4-d]pyrimidin-4-yl)amino)methyl)benzenesulfonamide (114 mg, yield: 38.9%) as a white solid. $^1$HNMR (400 MHz, DMSO-$d_6$): δ=8.81 (s, 1H), 8.09 (s, 1H), 7.78 (d, J=8.0 Hz, 2H), 7.56 (d, J=8.4 Hz, 2H), 7.30 (s, 2H), 6.66-6.59 (m, 1H), 6.48-6.44 (m, 1H), 5.62-5.59 (m, 1H), 4.84-4.82 (m, 2H), 3.89 (s, 3H). MS: m/z 345.1 (M+H$^+$).

Step 2: A solution of 4-(((1-methyl-6-vinyl-1H-pyrazolo[3,4-d]pyrimidin-4-yl)amino)methyl)benzenesulfonamide (110 mg, 0.319 mmol) and Pd/C (11 mg) in MeOH (10 mL) was stirred at room temperature for 3 hrs. Then the reaction mixture was filtered and the filtrate was concentrated. The residue was purified by prep-HPLC to give 4-(((6-ethyl-1-methyl-1H-pyrazolo[3,4-d]pyrimidin-4-yl)amino)methyl)benzenesulfonamide (22 mg, yield: 20%) as a white solid. $^1$HNMR (400 MHz, DMSO-$d_6$): δ=8.70 (s, 1H), 8.05 (s, 1H), 7.78 (d, J=8.4 Hz, 2H), 7.53 (d, J=8.0 Hz, 2H), 7.30 (s, 2H), 4.80-4.79 (m, 2H), 3.86 (s, 3H), 2.67 (q, J=7.6 Hz, 2H), 1.21 (t, J=8.0 Hz, 3H). MS: m/z 347.1 (M+H$^+$).

Example 2.41

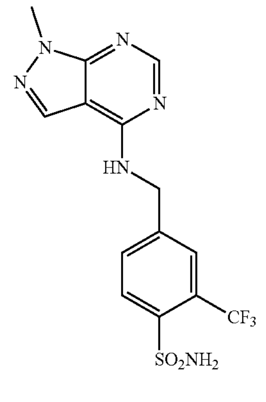

4-(((1-Methyl-1H-pyrazolo[3,4-d]pyrimidin-4-yl)amino)methyl)-2-(trifluoromethyl)-benzenesulfonamide The title compound was prepared using general procedure of 3-methyl-4-(((1-methyl-1H-pyrazolo[3,4-d]pyrimidin-4-yl)amino)methyl)benzenesulfonamide (Example 2.2). $^1$HNMR (400 MHz, DMSO-$d_6$): δ=8.71 (s, 1H), 8.25 (s, 1H), 8.13-8.09 (m, 2H), 7.90 (s, 1H), 7.82 (s, 1H), 7.65 (s, 2H), 4.87-4.86 (m, 2H), 3.90 (s, 3H). MS: m/z 387.1 (M+H$^+$).

Example 2.42

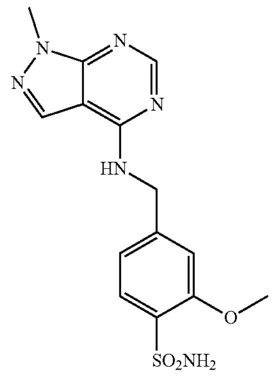 [SMILES: COc1cc(CNc2ncnc3c2cnn3C)ccc1S(N)(=O)=O]

2-Methoxy-4-(((1-methyl-1H-pyrazolo[34-d]pyrimidin-4-yl)amino)methyl)-benzenesulfonamide The title compound was prepared using general procedure of 3-methyl-4-(((1-methyl-1H-pyrazolo[3,4-d]pyrimidin-4-yl)amino)methyl)benzenesulfonamide (Example 2.2). $^1$HNMR (400 MHz, DMSO-$d_6$): δ=8.81 (s, 1H), 8.26 (s, 1H), 8.14 (s, 1H), 7.67 (d, J=8.0 Hz, 1H), 7.20 (s, 1H), 7.00-6.98 (m, 3H), 4.79-4.78 (m, 2H), 3.96 (s, 3H), 3.90 (s, 3H). MS: m/z 349.1 (M+H$^+$).

Example 2.43

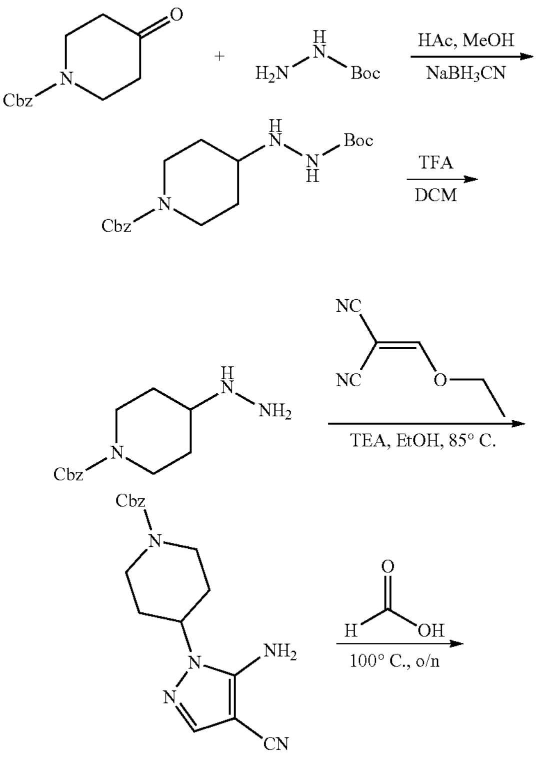

-continued

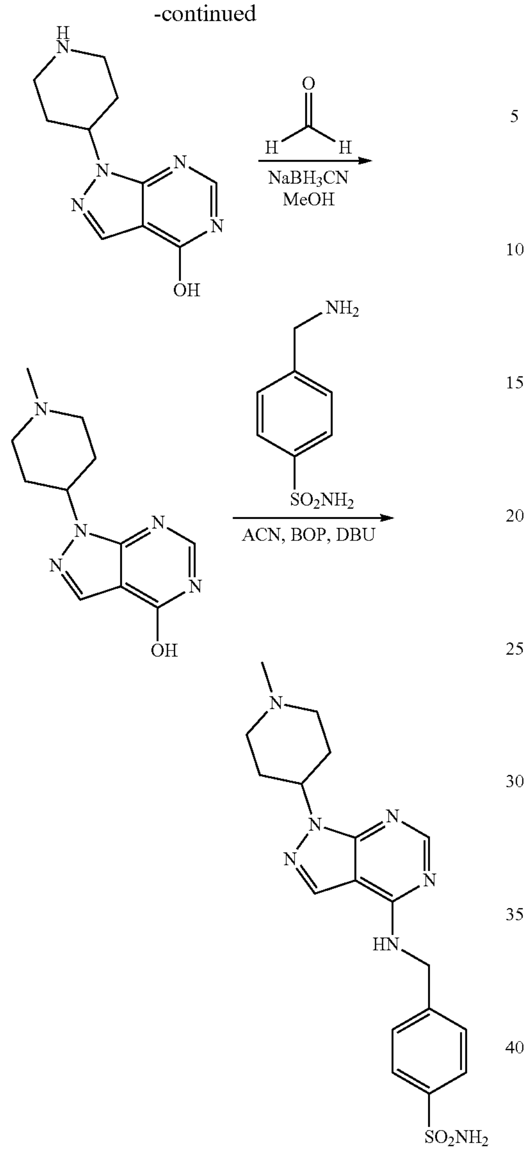

4-(((1-(1-Methylpiperidin-4-yl)-1H-pyrazolo[3,4-d]pyrimidin-4-yl)amino)methyl)-benzenesulfonamide Step 1: To a solution of benzyl 4-oxopiperidine-1-carboxylate (2.0 g, 8.6 mmol) in MeOH (10 mL) was added tert-butyl hydrazinecarboxylate (1.14 g, 8.6 mmol) and HOAc (1.04 g, 17.2 mmol). The mixture was stirred at room temperature for 1 hr. Then the mixture was added $NaBH_3CN$ (1.08 g, 17.2 mmol). The new mixture was stirred at room temperature overnight. The reaction was quenched with saturated aqueous $NH_4Cl$ solution and extracted with DCM (10 mL×3). The combined organic layers were concentrated in vacuum to give benzyl 4-(2-(tert-butoxycarbonyl)hydrazinyl) piperidine-1-carboxylate (2.6 g, yield: 86.7%) as a yellow oil. MS: m/z 350.5 ($M+H^+$).

Step 2: To a solution of benzyl 4-(2-(tert-butoxycarbonyl) hydrazinyl)piperidine-1-carboxylate (2.60 g, 7.4 mmol) in DCM (40 mL) was added TFA (10 mL) dropwise. The reaction mixture was stirred at room temperature overnight. The reaction was evaporated to remove solvent to give benzyl 4-hydrazinylpiperidine-1-carboxylate (2.19 g, yield: 70.4%) as a yellow oil. MS: m/z 250.4 ($M+H^+$).

Step 3: To a solution of benzyl 4-hydrazinylpiperidine-1-carboxylate (2.19 g, 6.04 mmol) in EtOH (20 mL) was added 2-(ethoxymethylene)malononitrile (670 mg, 5.49 mmol) and TEA (1.67 g, 16.47 mmol). The mixture was heated to 85° C. and stirred overnight. The reaction mixture was evaporated to remove solvent. The residue was purified by silica flash column (EA/PE=0-40%) to give benzyl 4-(5-amino-4-cyano-1H-pyrazol-1-yl)piperidine-1-carboxylate (1.52 g, yield: 77.6%) as a yellow oil. $^1$HNMR (300 MHz, DMSO-$d_6$): δ=7.51 (s, 1H), 7.37-7.26 (m, 5H), 6.59 (s, 2H), 5.06 (s, 2H), 4.28-4.21 (m, 1H), 4.01 (d, J=13.8 Hz, 2H), 2.91-2.85 (m, 2H), 1.75-1.64 (m, 4H). MS: m/z 326.5 ($M+H^+$).

Step 4: A solution of benzyl 4-(5-amino-4-cyano-1H-pyrazol-1-yl)piperidine-1-carboxylate (500 mg, 1.54 mmol) in formic acid (20 mL) was stirred at 100° C. overnight. The reaction mixture was evaporated to remove solvent. The residue was purified by prep-TLC (DCM/MeOH=10/1) to give 1-(piperidin-4-yl)-1H-pyrazolo[3,4-d]pyrimidin-4-ol (302 mg, yield: 89.6%) as a white solid. MS: m/z 220.1 ($M+H^+$).

Step 5: A solution of 1-(piperidin-4-yl)-1H-pyrazolo[3,4-d]pyrimidin-4-ol (300 mg, 1.37 mmol) in formaldehyde (20 mL) was stirred at room temperature for 1 hr. Then added $NaBH_3CN$ (173 mg, 2.74 mmol) into the above mixture and stirred at room temperature overnight. The reaction mixture was quenched with saturated aqueous $NH_4Cl$ solution and extracted with DCM (10 mL×3). The combined organic layers were concentrated in vacuum. The residue was purified by prep-TLC (DCM/MeOH=10/1) to give 1-(1-methylpiperidin-4-yl)-1H-pyrazolo[3,4-d]pyrimidin-4-ol (57 mg, yield: 18.0%) as a white solid. $^1$HNMR (400 MHz, DMSO-$d_6$): δ=12.27 (brs, 1H), 8.04 (s, 2H), 4.71-4.51 (m, 1H), 3.02-2.98 (m, 2H), 2.36 (s, 3H), 2.36-2.16 (m, 4H), 1.90-1.85 (m, 2H). MS: m/z 234.1 ($M+H^+$).

Step 6: To a solution of 4-(aminomethyl)benzenesulfonamide (65 mg, 0.29 mmol) in ACN (5 mL) was added BOP (128 mg, 0.29 mmol) and DBU (38 mg, 0.25 mmol) under $N_2$ atmosphere (balloon). The reaction mixture was stirred at room temperature for 1 hr. Then 1-(1-methylpiperidin-4-yl)-1H-pyrazolo[3,4-d]pyrimidin-4-ol (45 mg, 0.19 mmol) was added into the mixture and the new mixture was stirred overnight. The reaction mixture was evaporated to remove solvent. The residue was poured into $H_2O$ (10 mL) and extracted with DCM (10 mL×3). The combined organic layers were concentrated in vacuum. The residue was purified by prep-HPLC to give 4-(((1-(1-methylpiperidin-4-yl)-1H-pyrazolo[3,4-d]pyrimidin-4-yl) amino)methyl)benzenesulfonamide (10.6 mg, yield: 13.8%) as a colorless oil. $^1$HNMR (400 MHz, DMSO-$d_6$): δ=8.87 (t, J=5.8 Hz, 1H), 8.23 (s, 1H), 8.17 (s, 1H), 7.77 (d, J=8.4 Hz, 2H), 7.51 (d, J=8.0 Hz, 2H), 7.31 (s, 2H), 4.80 (d, J=5.6 Hz, 2H), 4.61-4.55 (m, 1H), 2.91 (d, J=8.8 Hz, 2H), 2.24 (s, 3H), 2.21-2.08 (m, 4H), 1.85-1.82 (m, 2H). MS: m/z 401.8 ($M+H^+$).

Example 2.44

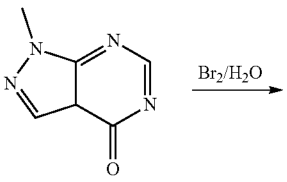

-continued

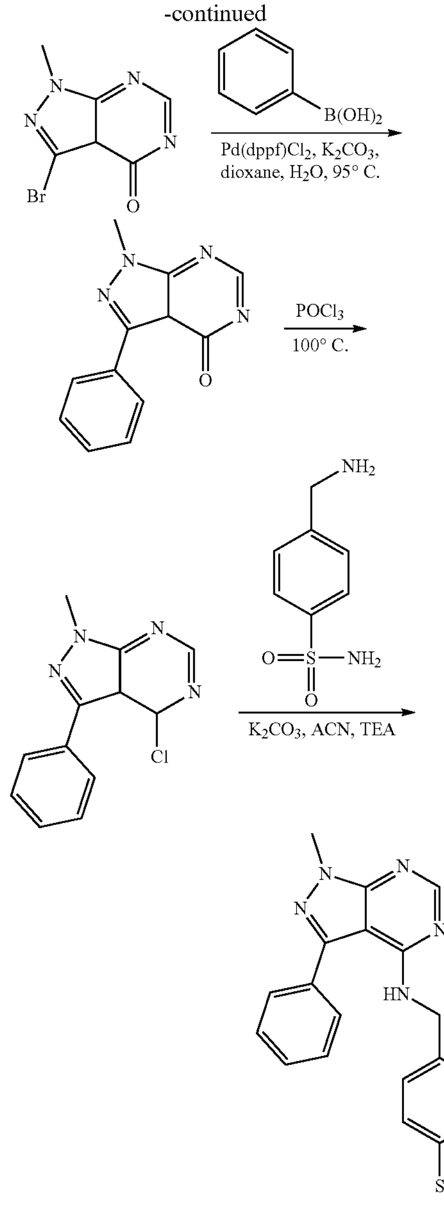

4-(((1-Methyl-3-phenyl-1H-pyrazolo[3,4-d]pyrimidin-4-yl)amino)methyl)-benzenesulfonamide Step 1: A mixture of 1-methyl-1H-pyrazolo[3,4-d]pyrimidin-4(3aH)-one (500 mg, 0.33 mmol) in $Br_2/H_2O$ (10 mL/3 mL) was stirred at room temperature for two days. The mixture was concentrated to give 3-bromo-1-methyl-1H-pyrazolo[3,4-d]pyrimidin-4(3aH)-one (650 mg, yield: 80%) as a yellow solid. MS: m/z 228.0 ($M+H^+$).

Step 2: A mixture of 3-bromo-1-methyl-1H-pyrazolo[3,4-d]pyrimidin-4(3aH)-one (600 mg, 2.6 mmol), phenyl boric acid (470 mg, 3.9 mmol), $K_2CO_3$ (1.07 g, 7.8 mmol) and $Pd(dppf)Cl_2$ (190 mg, 0.03 mmol) in dioxane/$H_2O$ was stirred at 95° C. overnight under $N_2$ atmosphere (balloon). The mixture was filtered and the filtrate was concentrated. The residue was purified by silica flash column (PE/EA=0/1) to give 1-methyl-3-phenyl-1H-pyrazolo [3,4-d]pyrimidin-4 (3aH)-one (170 mg, yield: 28.9%) as a brown solid. MS: m/z 227.0 ($M+H^+$).

Step 3: A mixture of 1-methyl-3-phenyl-1H-pyrazolo[3,4-d]pyrimidin-4(3aH)-one (129 mg, 0.57 mmol) in $POCl_3$ (5 mL) was stirred at 100° C. for 4 hrs. The mixture was concentrated to give 4-chloro-1-methyl-3-phenyl-3a,4-dihydro-1H-pyrazolo[3,4-d]pyrimidine (85 mg, yield: δ1%) as a yellow solid. MS: m/z 247.0 ($M+H^+$).

Step 4: To a mixture of 4-chloro-1-methyl-3-phenyl-3a,4-dihydro-1H-pyrazolo[3,4-d]pyrimidine (85 mg, 0.35 mmol) and $K_2CO_3$ (241 mg, 1.75 mmol) in ACN (5 mL) was added 4-(aminomethyl)benzenesulfonamide (231 mg, 1.04 mmol). The mixture was stirred at 80° C. overnight. The mixture was filtered and the filtrate was purified by prep-HPLC to give 4-(((1-methyl-3-phenyl-1H-pyrazolo[3,4-d]pyrimidin-4-yl)amino)methyl)benzenesulfonamide (3 mg) as a white solid. $^1$HNMR (400 MHz, DMSO-$d_6$): δ=8.31 (s, 1H), 7.76-7.70 (m, 4H), 7.57-7.48 (m, 5H), 7.03 (s, 2H), 7.09 (t, J=4.4 Hz, 1H), 4.18 (d, J=6.4 Hz, 2H), 3.97 (s, 2H). MS: m/z 395.1 ($M+H^+$).

Example 2.45

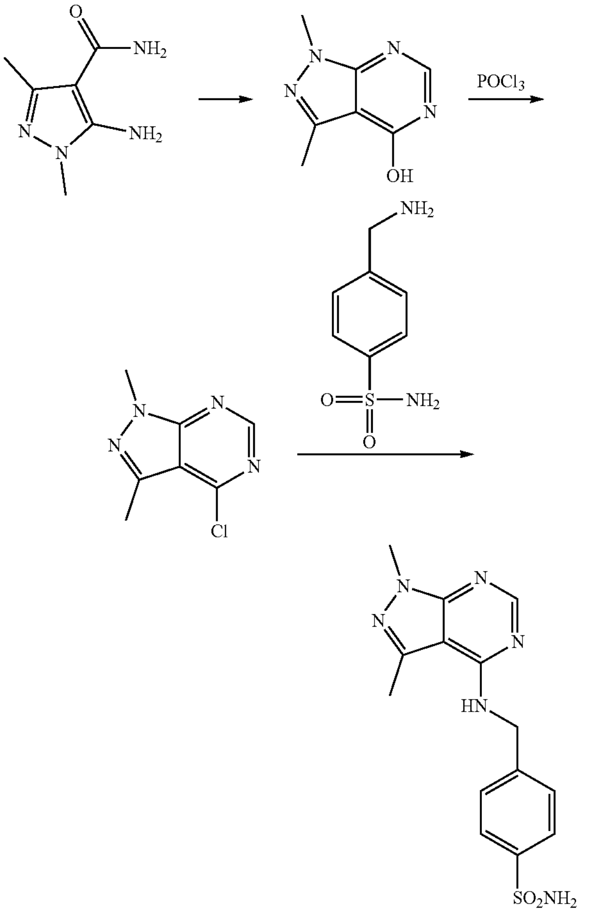

4-(((1,3-Dimethyl-1H-pyrazolo[3,4-d]pyrimidin-4-yl)amino)methyl)benzenesulfonamide Step 1: A mixture of 5-amino-1,3-dimethyl-1H-pyrazole-4-carboxamide (400 mg, 2.5 mmol) in triethoxymethane (20 mL) was stirred at 140° C. for two days. The mixture was concentrated to give 1,3-dimethyl-1H-pyrazolo[3,4-d]pyrimidin-4-ol (300 mg, yield: 73%) as a yellow solid. MS: m/z 165.0 ($M+H^+$).

Step 2: A mixture of 1,3-dimethyl-1H-pyrazolo[3,4-d]pyrimidin-4-ol (200 mg, 1.2 mmol) in $POCl_3$ (5 mL) was stirred at 95° C. for 4 hrs. The mixture was concentrated to give 4-chloro-1,3-dimethyl-1H-pyrazolo[3,4-d]pyrimidine (200 mg, yield: 89%) as a yellow solid. MS: m/z 182.9 ($M+H^+$).

Step 3: A mixture of 4-chloro-1,3-dimethyl-1H-pyrazolo[3,4-d]pyrimidine (200 mg, 1.09 mmol), $K_2CO_3$ (451 mg, 3.27 mmol) and 4-(aminomethyl)benzenesulfonamide (489 mg, 2.19 mmol) in ACN (10 mL) was stirred at 80° C. overnight. The mixture was filtered and the filtrate was purified by prep-HPLC to give 4-(((1,3-dimethyl-1H-pyrazolo[3,4-d]pyrimidin-4-yl)amino)methyl)-benzenesulfonamide (2.1 mg) as a white solid. $^1$HNMR (400 MHz, DMSO-$d_6$): δ=8.17 (s, 1H), 7.87 (t, J=6.0 Hz, 1H), 7.75 (d, J=8.0 Hz, 2H), 7.50 (d, J=6.8 Hz, 2H), 7.29 (s, 2H), 4.80 (d, J=4.0 Hz, 2H), 3.81 (s, 3H), 2.59 (s, 3H). MS: m/z 332.9 ($M+H^+$).

Example 2.46

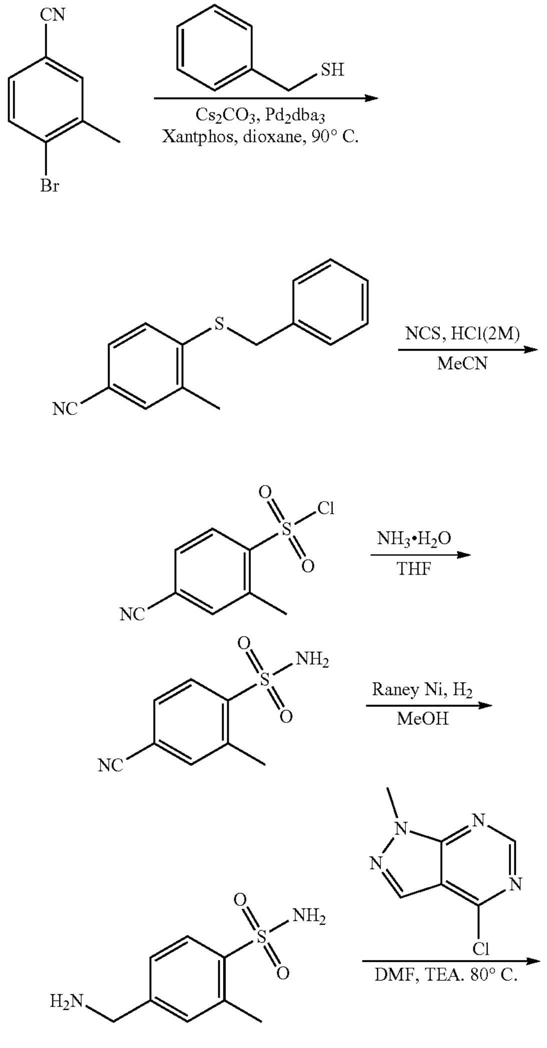

-continued

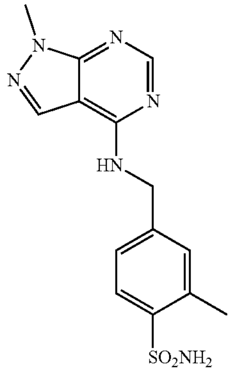

2-Methyl-4-(((1-methyl-1H-pyrazolo[3,4-d]pyrimidin-4-yl)amino)methyl)-benzenesulfonamide Step 1: A solution of 4-bromo-3-methylbenzonitrile (2 g, 10.2 mmol), $Cs_2CO_3$ (6.6 g, 20.4 mmol), $Pd_2(dba)_3$ (467 mg, 0.51 mmol), Xantphos (295 mg, 0.51 mmol) and phenylmethanethiol (1.5 g, 12.24 mmol) in dioxane (20 mL) was stirred at 100° C. overnight under $N_2$ atmosphere (balloon). The dioxane was removed under reduced pressure. The residue was purified by silica gel column (PE/EA=1/1) to give 4-(benzylthio)-3-methylbenzonitrile (1 g, yield: 36%) as a yellow solid.

Step 2 through Step 5: The title compound was prepared using general procedure of 2-chloro-4-(((1-methyl-1H-pyrazolo[3,4-d]pyrimidin-4-yl)amino)methyl)benzenesulfonamide (Example 2.4). $^1$HNMR (400 MHz, DMSO-$d_6$): δ=8.79 (t, J=5.2 Hz, 1H), 8.25 (s, 1H), 8.14 (s, 1H), 7.79 (d, J=8.0 Hz, 1H), 7.37-7.29 (m, 2H), 4.76 (d, J=6.0 Hz, 2H), 3.90 (s, 3H), 2.56 (s, 3H). MS: m/z 333.1 ($M+H^+$).

Example 2.47

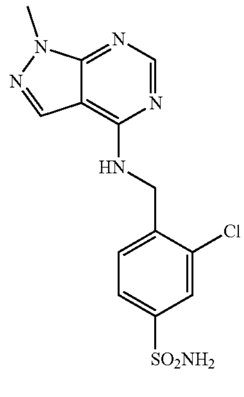 [SMILES: Cn1ncc2c(NCc3ccc(S(N)(=O)=O)cc3Cl)ncnc21]

3-Chloro-4-(((1-methyl-1H-pyrazolo[3,4-d]pyrimidin-4-yl)amino)methyl)-benzenesulfonamide The title compound was prepared using general procedure of 2-chloro-4-(((1-methyl-1H-pyrazolo[3,4-d]pyrimidin-4-yl)amino)methyl)benzenesulfonamide (Example 2.4). $^1$HNMR (400 MHz, DMSO-$d_6$): δ=8.86 (s, 1H), 8.25 (s, 1H), 8.18 (s, 1H), 7.88 (s, 1H), 7.73-7.71 (m, 1H), 7.53 (d, J=8.0 Hz, 1H), 7.47 (s, 2H), 4.84 (d, J=6.0 Hz, 2H), 3.91 (s, 3H). MS: m/z 353.0 (M+H+).

Example 2.48

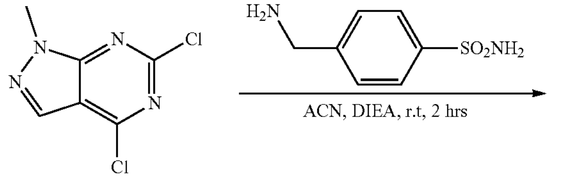

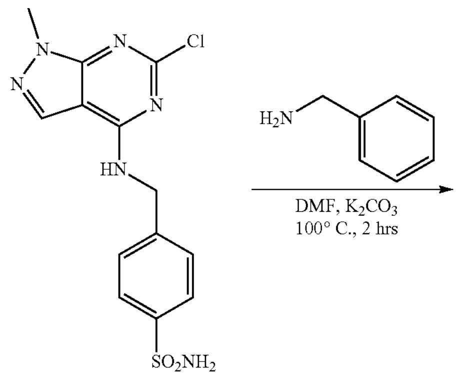

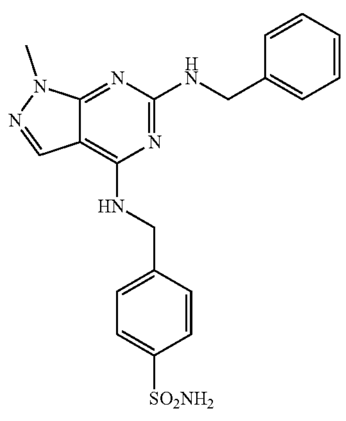

4-(((6-(Benzylamino)-1-methyl-1H-pyrazolo[3,4-d]pyrimidin-4-yl)amino)methyl)-benzenesulfonamide Step 1: To a solution of 4,6-dichloro-1-methyl-1H-pyrazolo[3,4-d]pyrimidine (500 mg, 2.46 mmol) in ACN (40 mL) was added 4-(aminomethyl)benzenesulfonamide (604 mg, 2.7 mmol) and DIEA (635 mg, 4.92 mmol). The mixture was stirred at room temperature for 2 hrs. After completion, the reaction mixture was filtered and the filtrate was concentrated in vacuum to give 4-(((6-chloro-1-methyl-1H-pyrazolo[3,4-d]pyrimidin-4-yl)amino)methyl)benzenesulfonamide (735 mg, yield: 85%) as a yellow solid.

Step 2: To a solution of 4-(((6-chloro-1-methyl-1H-pyrazolo[3,4-d]pyrimidin-4-yl)amino)methyl)benzenesulf (50 mg, 0.14 mmol) in DMF (3 mL) was added phenylmethanamine (76 mg, 0.71 mmol) and potassium carbonate (39 mg, 0.28 mmol). After stirring at 100° C. for 2 hrs by microwave, the reaction mixture was filtered and the filtrate was concentrated in vacuum to give a crude product, which was purified by prep-HPLC give 4-(((6-(benzylamino)-1-methyl-1H-pyrazolo[3,4-d]pyrimidin-4-yl)amino)methyl) benzenesulfonamide (5.6 mg, yield: 9.5%) as a white solid. $^1$HNMR (400 MHz, DMSO-$d_6$): δ=8.36 (brs, 1H), 7.80 (s, 1H), 7.74 (d, J=3.2 Hz, 2H), 7.45 (brs, 2H), 7.31-7.17 (m, 8H), 4.69 (s, 2H), 4.44 (s, 2H), 3.68 (s, 3H). MS: m/z 423.8 (M+H+).

Example 2.49

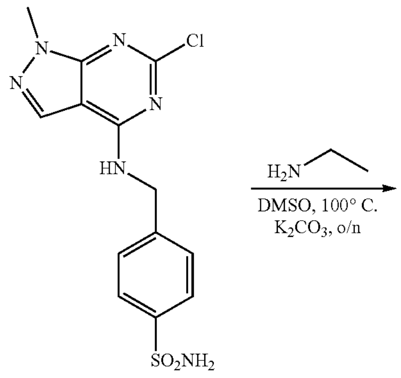

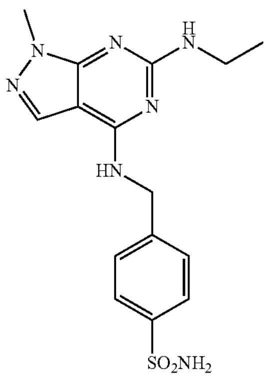

4-(((6-(Ethylamino)-1-methyl-1H-pyrazolo[3,4-d]pyrimidin-4-yl)amino)methyl)-benzenesulfonamide A solution of 4-(((6-chloro-1-methyl-1H-pyrazolo[3,4-d]pyrimidin-4-yl)amino)methyl)benzenesulfonamide (50 mg, 0.14 mmol), ethanamine (25.2 mg, 0.56 mmol) and potassium carbonate (39 mg, 0.28 mmol) in DMSO (5 mL) was stirred at 100° C. for 2 hrs under sealed-tube, the reaction mixture was filtered and the filtrate was concentrated in vacuum to give a crude product, which was purified by prep-HPLC to give 4-(((6-(ethylamino)-1-methyl-1H-pyrazolo[3,4-d]pyrimidin-4-yl)amino)methyl)benzenesulfonamide (9.8 mg, yield: 19.2%) as a white solid. $^1$HNMR (400 MHz, DMSO-$d_6$): δ=8.31 (brs, 1H), 7.80 (s, 1H), 7.77 (d, J=4.2 Hz, 2H), 7.50 (d, J=4.2 Hz, 2H), 7.30 (s, 2H), 6.60 (s, 1H), 4.71 (d, J=3.0 Hz, 2H), 3.68 (s, 3H), 3.26 (brs, 2H), 1.06 (s, 3H). MS: m/z 361.9 (M+H+).

Example 2.50

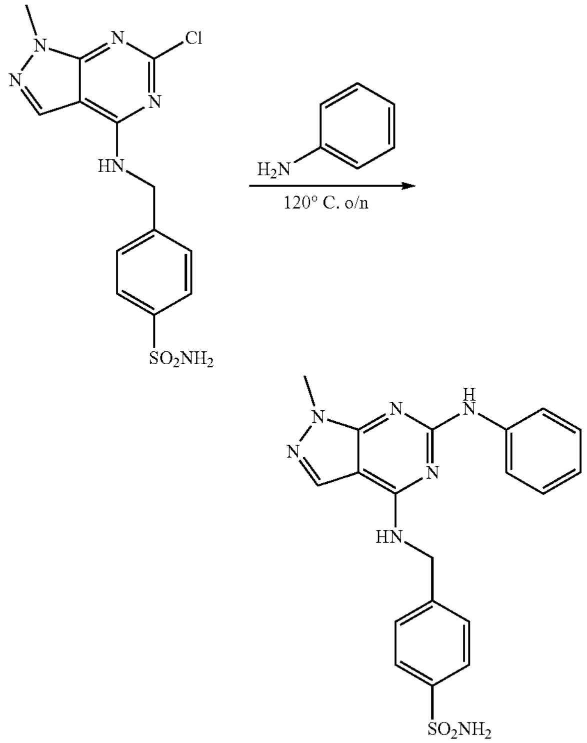

4-(((1-Methyl-6-(phenylamino)-1H-pyrazolo[3,4-d]pyrimidin-4-yl)amino)methyl)-benzenesulfonamide Step 1: A solution of 4-(((6-chloro-1-methyl-1H-pyrazolo[3,4-d]pyrimidin-4-yl)amino)methyl)benzenesulf (50 mg, 0.14 mmol) in aniline (3 mL) was stirred at 120° C. overnight. The reaction mixture was concentrated in vacuum to give a crude product, which was purified by prep-HPLC to give 4-(((1-methyl-6-(phenylamino)-1H-pyrazolo[3,4-d]pyrimidin-4-yl)amino)methyl)benzenesulfonamide (2.0 mg, yield: 0.9%) as a white solid. $^1$HNMR (400 MHz, DMSO-$d_6$): δ=9.14 (brs, 1H), 8.66 (t, J=5.2 Hz, 1H), 7.95 (s, 1H), 7.79 (d, J=4.0 Hz, 2H), 7.75 (d, J=3.8 Hz, 2H), 7.55 (d, J=4.2 Hz, 2H), 7.30 (s, 2H), 7.19 (t, J=8.0 Hz, 2H), 6.86 (t, J=7.6 Hz, 1H), 4.80 (d, J=2.8 Hz, 2H), 3.81 (s, 3H). MS: m/z 409.8 $(M+H^+)$.

Example 2.51

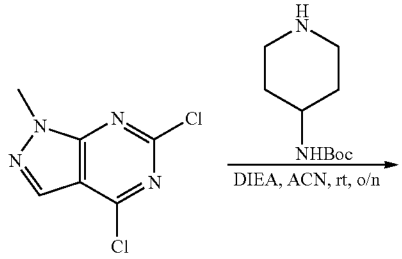

-continued

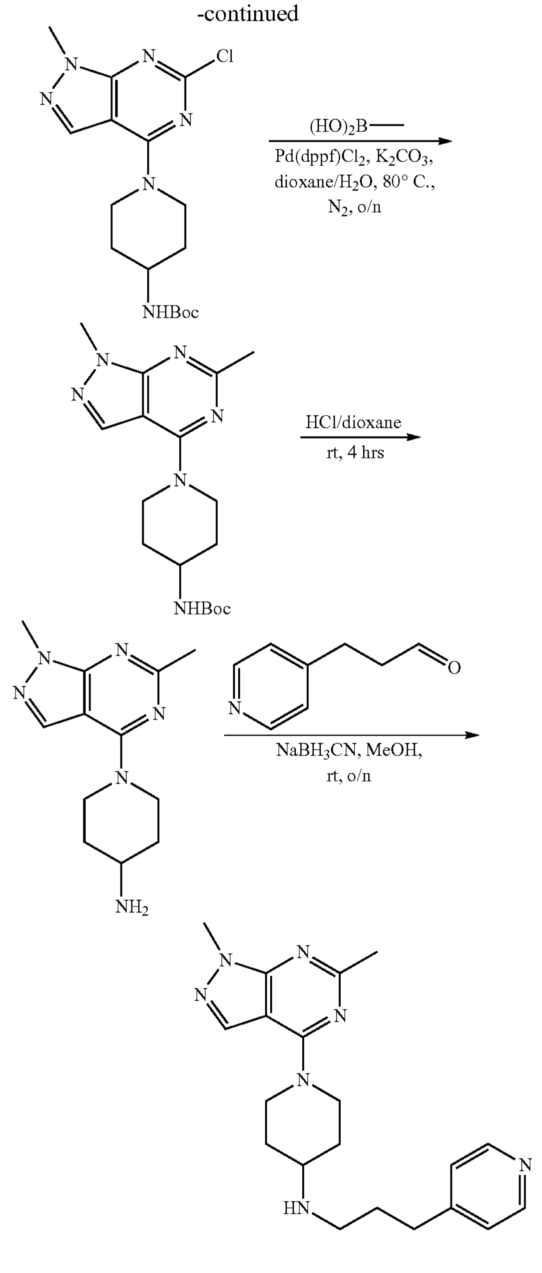

1-(1,6-Dimethyl-1H-pyrazolo[3,4-d]pyrimidin-4-yl)-N-(3-(pyridin-4-yl)propyl)piperidin-4-amine Step 1: To a solution of 4,6-dichloro-1-methyl-1H-pyrazolo[3,4-d]pyrimidine (768 mg, 1.21 mmol) in ACN (40 mL) was added tert-butyl piperidin-4-ylcarbamate (758 mg, 3.78 mmol), followed by DIEA (1.47 g, 11.34 mmol). The resulting mixture was stirred at room temperature overnight. The reaction was monitored by LCMS. Then the solid precipitated from the mixture was filtered and dried in air to afford tert-butyl (1-(6-chloro-1-methyl-1H-pyrazolo[3,4-d]pyrimidin-4-yl)piperidin-4-yl)carbamate (1.31 g, yield: 94%) as a yellow solid.

Step 2: To a solution of tert-butyl (1-(6-chloro-1-methyl-1H-pyrazolo[3,4-d]pyrimidin-4-yl)piperidin-4-yl)carbamate (366 mg, 1.0 mmol) and methylboronic acid (600 mg, 10.0 mmol) in dioxane/$H_2O$ (30 mL/10 mL) was added $K_2CO_3$ (414 mg, 3.0 mmol), followed by $Pd(dppf)Cl_2$ (73 mg, 0.1 mmol). Then the resulting mixture was stirred at 80° C. overnight under $N_2$ atmosphere (balloon). The reaction was monitored by LCMS and TLC. Then the mixture was concentrated in vacuum to give a residue, which was purified by silica gel column (DCM/MeOH=100/1 to 30/1) to afford tert-butyl (1-(1,6-dimethyl-1H-pyrazolo[3,4-d]pyrimidin-4-yl)piperidin-4-yl)carbamate (186 mg, yield: 54%) as a yellow solid. $^1$HNMR (400 MHz, DMSO-$d_6$): δ=8.20 (s, 1H), 6.91 (d, J=7.6 Hz, 1H), 4.57-4.56 (m, 2H), 3.86 (s, 3H), 3.63-3.61 (m, 1H), 3.23-3.18 (m, 2H), 2.42 (s, 3H), 1.88-1.85 (m, 2H), 1.39 (s, 9H), 1.36-1.30 (m, 2H).

Step 3: To a solution of tert-butyl (1-(1,6-dimethyl-1H-pyrazolo[3,4-d]pyrimidin-4-yl)piperidin-4-yl)carbamate (186 mg, 0.53 mmol) in EA (10 mL) was added HCl/dioxane (6 mL). The resulting mixture was stirred at room temperature overnight. The reaction was monitored by LCMS. Then the mixture was concentrated in vacuum to afford 1-(1,6-dimethyl-1H-pyrazolo[3,4-d]pyrimidin-4-yl)piperidin-4-amine (118 mg, yield: 89%) as a brown solid.

Step 4: To a solution of 1-(1,6-dimethyl-1H-pyrazolo[3,4-d]pyrimidin-4-yl)piperidin-4-amine (118 mg, 0.42 mmol) in MeOH (10 mL) was added 3-(pyridin-4-yl)propanal (57 mg, 0.42 mmol). The resulting mixture was stirred at room temperature overnight. Then $NaBH_3CN$ (80 mg, 1.26 mmol) was added in to the mixture and the mixture was stirred for another 1 hr. The reaction was monitored by LCMS. Then the mixture was concentrated in vacuum to give a residue, which was purified by prep-HPLC with $NH_4HCO_3$ as additive to afford 1-(1,6-dimethyl-1H-pyrazolo[3,4-d]pyrimidin-4-yl)-N-(3-(pyridin-4-yl)propyl)piperidin-4-amine (27.2 mg, yield: 18%) as a yellow solid. $^1$HNMR (400 MHz, $CD_3OD$): δ=8.42 (d, J=6.0 Hz, 2H), 8.12 (s, 1H), 7.33 (d, J=5.6 Hz, 2H), 4.90 (overlap, 2H), 3.93 (s, 3H), 3.21 (t, J=12.0 Hz, 2H), 3.07 (t, J=9.6 Hz, 1H), 2.83 (t, J=7.2 Hz, 2H), 2.76 (d, J=7.6 Hz, 2H), 2.50 (s, 3H), 2.15-2.12 (m, 2H), 1.96-1.88 (m, 2H), 1.50-1.40 (m, 2H). MS: m/z 366.7 (M+H$^+$).

Example 2.52

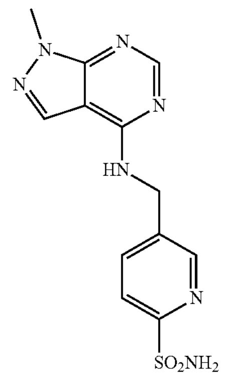 [SMILES: Cn1ncc2c(NCc3ccc(S(N)(=O)=O)nc3)ncnc21]

5-(((1-Methyl-1H-pyrazolo[3,4-d]pyrimidin-4-yl)amino)methyl)pyridine-2-sulfonamide The title compound was prepared using general procedure of 3-methyl-4-(((1-methyl-1H-pyrazolo[3,4-d]pyrimidin-4-yl)amino)methyl)benzenesulfonamide (Example 2.2). $^1$HNMR (400 MHz, DMSO-$d_6$): δ=8.88 (s, 1H), 8.71 (s, 1H), 8.27 (s, 1H), 8.12 (s, 1H), 7.98 (d, J=8.0 Hz, 1H), 7.89 (d, J=8.4 Hz, 1H), 7.43 (s, 2H), 4.85-4.83 (m, 2H), 3.90 (s, 3H). MS: m/z 320.1 (M+H$^+$).

Example 2.53

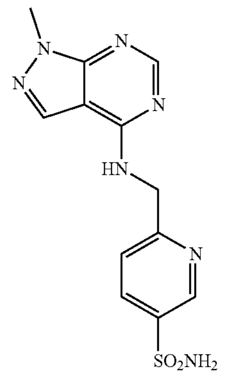 [SMILES: Cn1ncc2c(NCc3ccc(S(N)(=O)=O)cn3)ncnc21]

6-(((1-Methyl-1H-pyrazolo[3,4-d]pyrimidin-4-yl)amino)methyl)pyridine-3-sulfonamide The title compound was prepared using general procedure of 3-methyl-4-(((1-methyl-1H-pyrazolo[3,4-d]pyrimidin-4-yl)amino)methyl)benzenesulfonamide (Example 2.2). $^1$HNMR (400 MHz, DMSO-$d_6$): δ=9.00 (s, 1H), 8.90 (s, 1H), 8.22-8.10 (m, 3H), 7.52 (d, J=8.4 Hz, 1H), 6.29 (brs, 2H), 4.89-4.88 (m, 2H), 3.90 (s, 3H). MS: m/z 320.1 (M+H$^+$).

Example 2.54

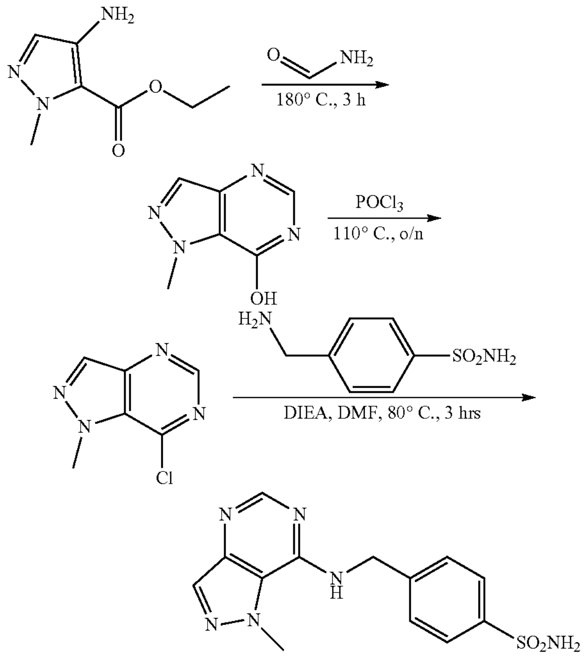

4-[(1-Methyl-1H-pyrazolo[4,3-d]pyrimidin-7-ylamino)-methyl]-benzenesulfonamide

Step 1: A solution of 4-amino-2-methyl-2H-pyrazole-3-carboxylic acid ethyl ester (1 g, 5.92 mmol) in formamide (10 mL) was stirred at 180° C. for 3 hrs. Cooled to room temperature, the reaction mixture was filtered and the pad was rinsed with THF to give 1-methyl-1H-pyrazolo[4,3-d]pyrimidin-7-ol (500 mg, yield: 56%) as a brow solid. MS: m/z 151.1 (M+H$^+$).

Step 2: A mixture of 1-methyl-1H-pyrazolo[4,3-d]pyrimidin-7-ol (500 mg, 3.33 mmol) in $POCl_3$ (8 mL) was stirred at 120° C. for 16 hrs. The $POCl_3$ was removed under reduced pressure. The residue was neutralized with saturated aqueous $NaHCO_3$ solution (100 mL) and extracted with EA (100 mL×3). The combined organic layers were dried over $Na_2SO_4$ and concentrated to give 7-chloro-1-methyl-1H-pyrazolo[4,3-d]pyrimidine (600 mg, crude) as a yellow solid.

Step 3: A mixture of 7-chloro-1-methyl-1H-pyrazolo[4,3-d]pyrimidine (220 mg, 1.31 mmol), 4-(aminomethyl)benzenesulfonamide (366 mg, 1.96 mmol) and $K_2CO_3$ (728 mg, 5.24 mmol) in ACN (30 mL) was stirred at 80° C. overnight. The mixture was acidified with 2 M HCl to pH=7. Then the suspension was filtered and the pad was purified by prep-HPLC ($NH_4HCO_3$) to give 4-[(1-methyl-1H-pyrazolo[4,3-d]pyrimidin-7-ylamino)-methyl]-benzenesulfonamide (86 mg, yield: 21%) as a white solid. $^1$HNMR (400 MHz, DMSO-$d_6$): δ=8.16 (s, 1H), 7.99 (s, 2H), 7.75 (d, J=8.8 Hz, 2H), 7.56 (d, J=8.4 Hz, 2H), 4.81 (d, J=6.4 Hz, 2H), 4.32 (s, 3H). MS: m/z 319.1 (M+H$^+$).

Example 2.55

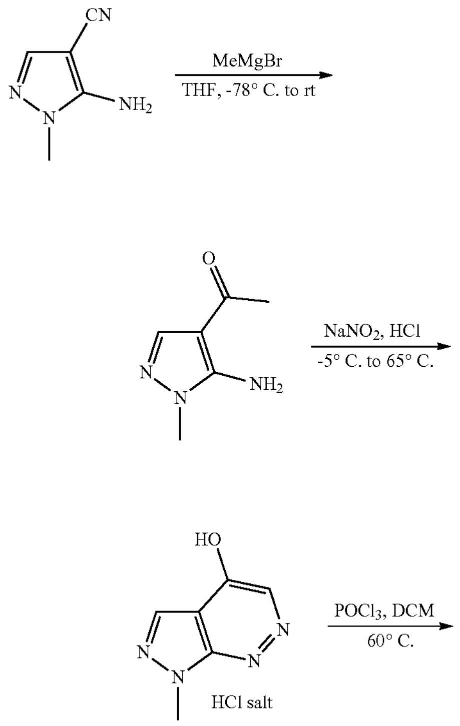

-continued

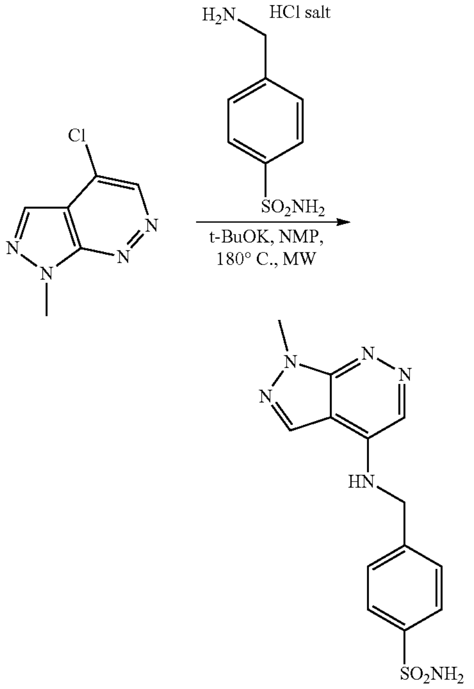

4-(((1-Methyl-1H-pyrazolo[3,4-c]pyridazin-4-yl)amino)methyl)benzenesulfonamide

Step 1: To a suspension of 5-amino-1-methyl-1H-pyrazole-4-carbonitrile (1.0 g, 8.19 mmol) in THF (20 mL) was added MeMgBr (27 mL, 81.9 mmol) dropwise at 0° C. Then the mixture was stirred at 70° C. for 2 hrs. The reaction mixture was poured into saturated aqueous $NH_4Cl$ solution (100 mL) and extracted with EA (50 mL×3). The organic layer was washed with brine (100 mL), dried over $Na_2SO_4$ and concentrated. The residue was purified by silica gel column (PE/EA=3/1 to 1/1) to give 1-(5-amino-1-methyl-1H-pyrazol-4-yl)ethanone (591 mg, yield: 52%) as a yellow solid. $^1$HNMR (400 MHz, DMSO-$d_6$): δ=7.65 (s, 1H), 6.63 (s, 2H), 3.51 (s, 3H), 2.21 (s, 3H).

Step 2: To a suspension of 4,7-dibromobenzo[c][1,2,5]thiadiazole (129 mg, 0.93 mmol) in $H_2O$ (1 mL) and concentrated HCl (4 mL) was added a solution of $NaNO_2$ (128 mg, 1.86 mmol) in $H_2O$ (0.5 mL) dropwise at 0° C. The mixture was stirred at −5° C. for 20 mins. Then the mixture was warmed to room temperature and stirred for 10 mins. The mixture was stirred at 65° C. for 30 mins. The reaction mixture was cooled with ice-bath, then filtered. The filtrate was freeze-dried to give 1-methyl-1H-pyrazolo[3,4-c]pyridazin-4-ol (198 mg, crude) as a yellow solid.

Step 3: A suspension of 1-methyl-1H-pyrazolo[3,4-c]pyridazin-4-ol (198 mg, crude) and $POCl_3$ (8 mL) in DCM (4 mL) was stirred at 65° C. for 2.5 hrs. LCMS showed 1-methyl-1H-pyrazolo[3,4-c]pyridazin-4-ol reacted totally. The mixture was concentrated. The residue was neutralized with saturated aqueous $NaHCO_3$ solution (10 mL) and extracted with EA (30 mL), The organic layer was dried over $Na_2SO_4$ and concentrated. The residue was purified by silica gel column (PE/EA=8/1 to 6/1) to give 4-chloro-1-methyl-1H-pyrazolo[3,4-c]pyridazine (40 mg, yield: 18%) as a white solid. MS: m/z 168.9 (M+H$^+$)

Step 4: A suspension of 4-chloro-1-methyl-1H-pyrazolo[3,4-c]pyridazine (40 mg, 0.24 mmol), 4-(aminomethyl)benzenesulfonamide (177 mg, 0.95 mmol) and t-BuOK (1.6 mg, 0.014 mmol) in NMP (15 mL) was stirred at 180° C. for 4 hrs by microwave. The reaction mixture was concentrated to remove NMP. The residue was purified by prep-HPLC to give 4-(((1-methyl-1H-pyrazolo[3,4-c]pyridazin-4-yl)amino)methyl)benzenesulfonamide (36 mg, yield: 48%) as a yellow solid. $^1$HNMR (400 MHz, DMSO-$d_6$): δ=8.44 (s, 1H), 8.36 (s, 1H), 8.17 (s, 1H), 7.80 (d, J=8.4 Hz, 2H), 7.57 (d, J=8.0 Hz, 2H), 7.31 (s, 2H), 4.77 (d, J=5.6 Hz, 2H), 4.04 (s, 3H). MS: m/z 319.0 (M+$H^+$).

Example 2.56

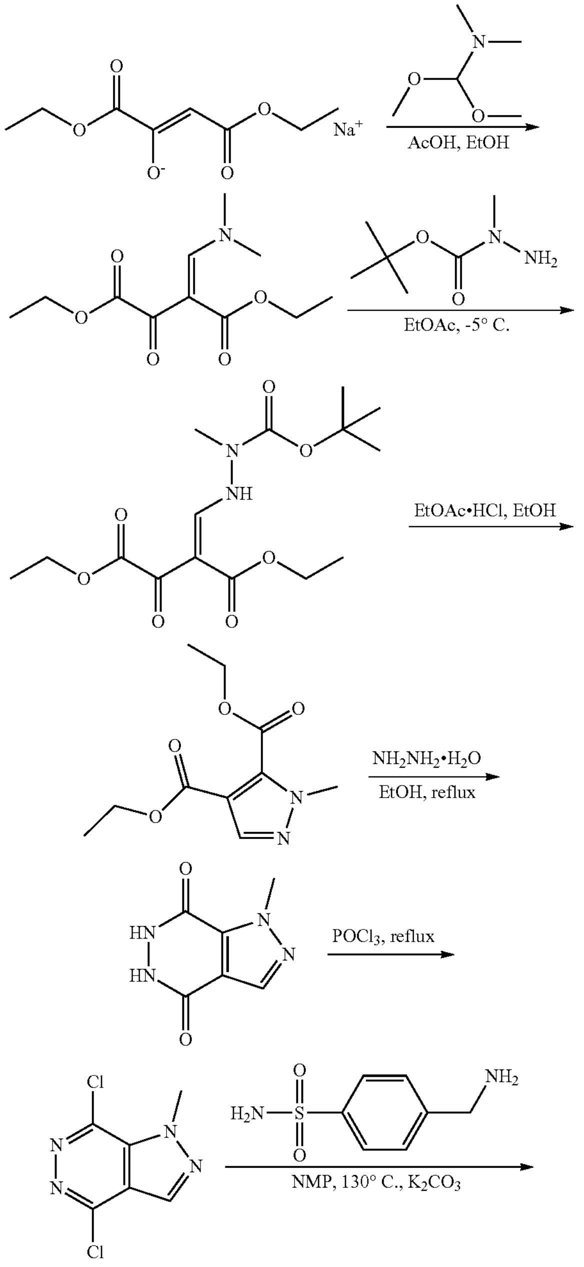

-continued

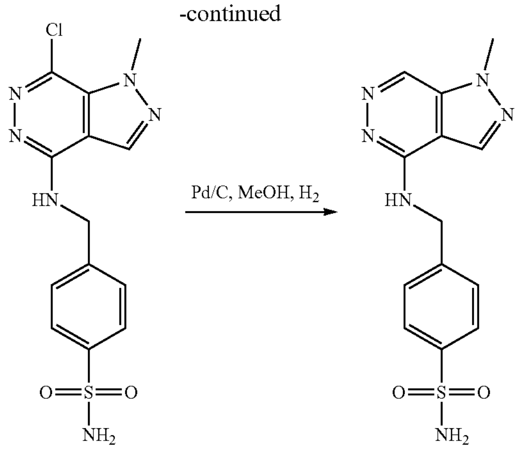

4-(((1-Methyl-1H-pyrazolo[3,4-d]pyridazin-4-yl)amino)methyl)benzenesulfonamide

Step 1: A suspension of sodium (Z)-1,4-diethoxy-1,4-dioxobut-2-en-2-olate (4.2 g, 20 mmol) and 1,1-dimethoxy-N,N-dimethylmethanamine (5.4 mL, 40 mmol) in EtOH (10 mL) was stirred at room temperature for 30 mins. AcOH (2.4 mL, 40 mmol) was added into the mixture. The new mixture was stirred at room temperature for 24 hrs. The mixture was concentrated. The residue was purified by silica gel column (PE/EA=1/1) to give (Z)-diethyl 2-((dimethylamino)methylene)-3-oxosuccinate (2.4 g, yield: 49%) as a yellow oil. MS: m/z 244.1 (M+$H^+$).

Step 2: To a suspension of (Z)-diethyl 2-((dimethylamino)methylene)-3-oxosuccinate (930 mg, 3.8 mmol) in EA (20 mL) was added tert-butyl 1-methylhydrazinecarboxylate (788 mg, 5.4 mmol) at −5° C. The mixture was stirred at −5° C. for 2 hrs. The mixture was concentrated. The residue was purified by silica gel column (PE/EA=2/1) to give (Z)-diethyl 2-((2-(tert-butoxycarbonyl)-2-methylhydrazinyl)methylene)-3-oxosuccinate (980 mg, yield: 75%) as a white solid. MS: m/z 345.2 (M+$H^+$).

Step 3: To a suspension of (Z)-diethyl 2-((2-(tert-butoxycarbonyl)-2-methylhydrazinyl)methylene)-3-oxosuccinate (300 mg, 0.87 mmol) in EtOH (8 mL) was added HCl/EA (8 mL). The mixture was stirred at room temperature for 16 hrs. The mixture was concentrated to give diethyl 1-methyl-1H-pyrazole-4,5-dicarboxylate (280 mg, crude) as a yellow solid. MS: m/z 227.1 (M+$H^+$).

Step 4: To a suspension of diethyl 1-methyl-1H-pyrazole-4,5-dicarboxylate (280 mg, 1.2 mmol) in EtOH (50 mL) was added $NH_2NH_2 \cdot H_2O$ (10 mL). The mixture was stirred at 90° C. for 16 hrs. The mixture was concentrated. The residue was purified by reverse phase column to give 1-methyl-5,6-dihydro-1H-pyrazolo[3,4-d]pyridazine-4,7-dione (350 mg, crude) as a yellow solid. MS: m/z 167.1 (M+$H^+$).

Step 5: To a suspension of 1-methyl-5,6-dihydro-1H-pyrazolo[3,4-d]pyridazine-4,7-dione (161 mg, crude) was added $POCl_3$ (5 mL). The mixture was stirred at 100° C. for 1 hr. The mixture was concentrated. The residue was neutralized with saturated aqueous $NaHCO_3$ solution (20 mL) and extracted with EA (20 mL). The organic layer was dried by $Na_2SO_4$ and concentrated. The residue was purified by reverse phase column to give 4,7-dichloro-1-methyl-1H-pyrazolo[3,4-d]pyridazine (23 mg, yield: 11%) as a yellow solid. MS: m/z 203.2 (M+$H^+$).

Step 6: A suspension of 4,7-dichloro-1-methyl-1H-pyrazolo[3,4-d]pyridazine (23 mg, 0.11 mmol), $K_2CO_3$ (47 mg, 0.34 mmol) and 4-(aminomethyl)benzenesulfonamide (76 mg, 0.34 mmol) in NMP (2 mL) was stirred at 130° C. for 2 hrs. The mixture was purified by prep-HPLC to give 4-(((7-chloro-1-methyl-1H-pyrazolo[3,4-d]pyridazin-4-yl)amino)methyl)benzenesulfonamide (5 mg, yield: 12%) as a yellow solid.

Step 7: A suspension of 4-(((7-chloro-1-methyl-1H-pyrazolo[3,4-d]pyridazin-4-yl)amino)methyl)benzenesulfonamide (5 mg, 0.0142 mmol) and Pd/C (3 mg) in MeOH (3 mL) was stirred at room temperature for 16 hrs under $H_2$ atmosphere (balloon). The mixture was filtered. The filtrate was purified by prep-HPLC to give 4-(((1-methyl-1H-pyrazolo[3,4-d]pyridazin-4-yl)amino)methyl)benzenesulfonamide (3.3 mg, yield: 73%) as a white solid.

$^1$HNMR (400 MHz, $CD_3OD$): δ=8.82 (d, J=0.4 Hz, 1H), 8.09 (d, J=0.4 Hz, 1H), 7.74 (d, J=8.4 Hz, 2H), 7.47 (d, J=8.4 Hz, 2H), 4.79 (s, 2H), 4.04 (s, 3H). MS: m/z 319.1 (M+H$^+$).

Example 2.57

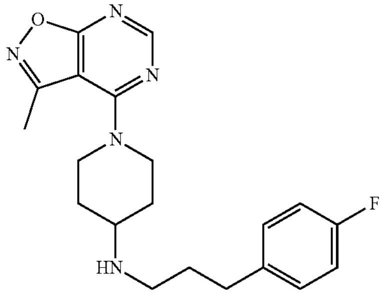 [SMILES: Cc1noc2ncnc(N3CCC(NCCCc4ccc(F)cc4)CC3)c12]

N-(3-(4-Fluorophenyl)propyl)-1-(3-methylisoxazolo[5,4-d]pyrimidin-4-yl)piperidin-4-amine The title compound was prepared using general procedure of 1-(1-methyl-1H-pyrazolo[3,4-d]pyrimidin-4-yl)-N-(3-(pyridin-4-yl)propyl)piperidin-4-amine (Example 2.5). $^1$HNMR (400 MHz, $CD_3OD$): δ=8.38 (s, 1H), 7.26-7.23 (m, 2H), 7.02 (t, J=9.2 Hz, 2H), 4.59-4.56 (m, 2H), 3.33-3.27 (m, 2H), 3.06 (t, J=7.6 Hz, 1H), 2.82 (t, J=7.6 Hz, 2H), 2.71 (t, J=7.6 Hz, 2H), 2.66 (s, 3H), 2.16-2.13 (m, 2H), 1.94-1.89 (m, 2H), 1.56-1.51 (m, 2H). MS: m/z 370.1 (M+H$^+$).

Example 2.58

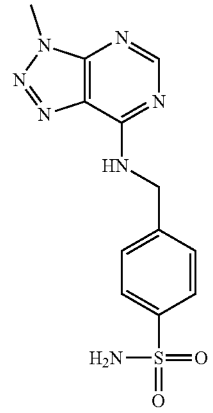 [SMILES: Cn1nnc2c(NCc3ccc(S(N)(=O)=O)cc3)ncnc21]

4-(((3-Methyl-3H-[1,2,3]triazolo[4,5-d]pyrimidin-7-yl)amino)methyl)benzenesulfonamide The title compound was prepared using general procedure of 5-(((5-phenylthieno[2,3-d]pyrimidin-4-yl)amino)methyl)thiophene-2-sulfonamide (Example 1.28). $^1$HNMR (400 MHz, DMSO-$d_6$): δ=9.53-9.50 (m, 1H), 8.38 (s, 1H), 7.77 (d, J=8 Hz, 2H), 7.50 (d, J=4 Hz, 2H), 7.28 (brs, 2H), 4.83 (d, J=4 Hz, 2H), 4.14 (s, 3H). MS: m/z 320.1 (M+H$^+$).

Example 2.59

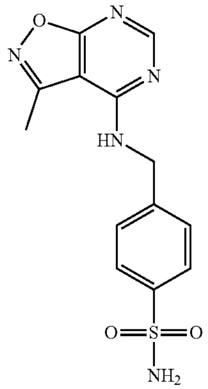 [SMILES: Cc1noc2ncnc(NCc3ccc(S(N)(=O)=O)cc3)c12]

4-(((3-Methylisoxazolo[5,4-d]pyrimidin-4-yl)amino)methyl)benzenesulfonamide

The title compound was prepared using general procedure of 5-(((5-phenylthieno[2,3-d]pyrimidin-4-yl)amino)methyl)thiophene-2-sulfonamide (Example 1.28). $^1$HNMR (400 MHz, DMSO-$d_6$): δ=8.37 (brs, 1H), 8.35-8.32 (m, 1H), 7.76 (d, J=8 Hz, 2H), 7.54 (d, J=8 Hz, 2H), 7.23 (s, 2H), 4.82 (d, J=4 Hz, 2H), 2.65 (s, 3H). MS: m/z 320.0 (M+H$^+$).

Example 2.60

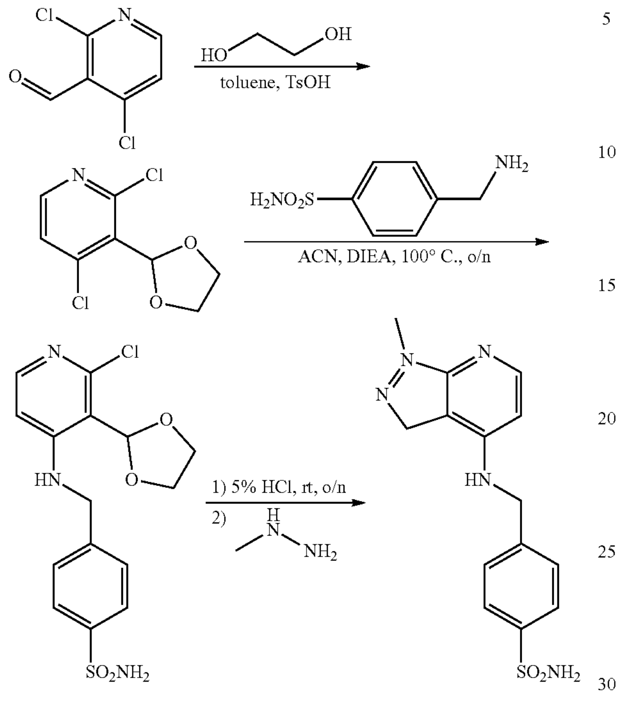

4-(((1-Methyl-1H-pyrazolo[3,4-b]pyridin-4-yl)amino)methyl)benzenesulfonamide

Step 1: A solution of 2,4-dichloronicotinaldehyde (1.0 g, 5.7 mmol), ethane-1,2-diol (709 mg, 11.4 mmol) and TsOH (980 mg, 5.7 mmol) in toluene (30 mL) was stirred at 130° C. overnight. After completion, the reaction mixture was concentrated to give a crude product, which was purified by silica gel column chromatography (PE/EA=2/1) to give 2,4-dichloro-3-(1,3-dioxolan-2-yl)pyridine (1.1 g, yield: 88%) as a yellow oil.

Step 2: To a solution of 2,4-dichloro-3-(1,3-dioxolan-2-yl)pyridine (150 mg, 0.86 mmol) in ACN (15 mL) was added 4-(aminomethyl)benzenesulfonamide (573 mg, 2.57 mmol) and DIEA (332 mg, 2.57 mmol). The reaction mixture was stirred at 100° C. overnight. The mixture was concentrated in vacuum to give a crude product, which was purified by silica gel column (DCM/MeOH=10/1) to give 4-(((2-chloro-3-(1,3-dioxolan-2-yl)pyridin-4-yl)amino)methyl)benzenesulfonamide (70 mg, yield: 22%) as a yellow solid.

Step 3: To a solution of 4-(((2-chloro-3-(1,3-dioxolan-2-yl)pyridin-4-yl)amino)methyl)benzenesulfonamide (50 mg, 0.14 mmol) in THF (10 mL) was added 5% HCl (1 mL). The mixture was stirred at room temperature overnight. The reaction mixture was poured into water (20 mL) and extracted with EA (20 mL×3). The combined EA layers were dried over $Na_2SO_4$, filtered and concentrated. Then the residue was dissolved in DMSO (5 mL) and added methylhydrazine and DIEA (55 mg, 0.42 mmol). The mixture was stirred at 120° C. overnight. The mixture was concentrated in vacuum to give a crude product, which was purified by prep-HPLC to give 4-(((1-methyl-1H-pyrazolo[3,4-b]pyridin-4-yl)amino)methyl)benzenesulfonamide (9.0 mg, yield: 20%) as a white solid. $^1$HNMR (400 MHz, DMSO-$d_6$): δ=8.13 (s, 1H), 8.04 (t, J=6.0 Hz, 1H), 7.97 (d, J=2.8 Hz, 1H), 7.78 (d, J=4.2 Hz, 2H), 7.53 (d, J=4.2 Hz, 2H), 7.30 (s, 2H), 6.07 (d, J=2.8 Hz, 1H), 4.61 (d, J=3.0 Hz, 2H), 3.90 (s, 3H). MS: m/z 318.0 (M+H$^+$).

Example 2.61

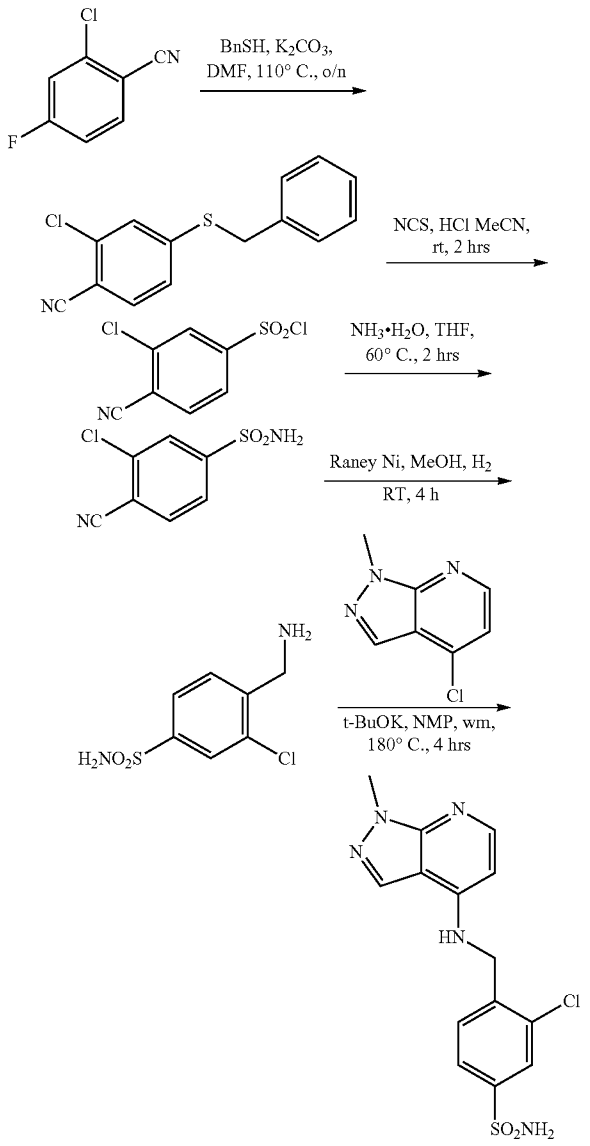

3-Chloro-4-(((1-methyl-1H-pyrazolo[3,4-b]pyridin-4-yl)amino)methyl)benzenesulfonamide Step 1: A solution of 2-chloro-4-fluorobenzonitrile (3 g, 19 mmoL), BnSH (2.3 mL, 19.7 mmoL) and $K_2CO_3$ (5.3 g, 38.4 mmoL) in DMF (35 mL) was stirred at 110° C. overnight. The reaction mixture was poured into $H_2O$ (150 mL) and extracted with EA (150 mL). The EA layer was washed with brine (150 mL×2), dried over $Na_2SO_4$ and concentrated to dryness in vacuum. The residue was purified by silica gel column (PE/EA=20/1) and silica flash column (2% EA in PE) to give 4-(benzylthio)-2-chlorobenzonitrile (1.5 g, yield: 30%) as a yellow solid. $^1$HNMR (400 MHz, DMSO-$d_6$): δ=7.83 (d, J=8.4 Hz, 1H), 7.68 (d, J=1.6 Hz, 1H), 7.46-7.42 (m, 3H), 7.36-7.32 (m, 2H), 7.29-7.25 (m, 1H), 4.43 (s, 2H).

Step 2: A solution of NCS (206 mg, 1.54 mmoL) and HCl (0.3 mL, 3.6 mmoL) in MeCN (4 mL) was stirred at room temperature for 30 mins. Then a solution of 4-(benzylthio)-2-chlorobenzonitrile (100 mg, 0.39 mmoL) in MeCN (3 mL) was added into the reaction mixture. The new mixture was stirred at room temperature for 2 hrs. The reaction mixture was poured into $H_2O$ (40 mL) and extracted with EA (40 mL). The EA layer was washed with brine (40 mL), dried over $Na_2SO_4$ and concentrated to give 3-chloro-4-cyanobenzene-1-sulfonyl chloride (150 mg, yield: crude) as a colorless oil.

Step 3: To a solution of 3-chloro-4-cyanobenzene-1-sulfonyl chloride (150 mg, 0.6 mmoL) in THF (3 mL) was added $NH_3·H_2O$ (1.5 mL) at room temperature. The mixture was stirred at 60° C. for 2 hrs. The reaction mixture was concentrated and the residue was purified with silica flash column (25% EA in PE) to give 3-chloro-4-cyanobenzenesulfonamide (65 mg, yield: 50%) as a white solid. $^1$HNMR (400 MHz, DMSO-$d_6$): δ=8.21 (d, J=8.0 Hz, 1H), 8.09 (d, J=1.6 Hz, 1H), 7.94-7.91 (m, 1H), 7.77 (s, 2H).

Step 4: A solution of 3-chloro-4-cyanobenzenesulfonamide (300 mg, 1.4 mmoL), Raney-Ni and $NH_4OH$ (1.5 mL) in MeOH (10 mL) was stirred at room temperature for 3.5 hrs under $H_2$ atmosphere (balloon). The reaction mixture was filtered and the filtrate was concentrated to dryness in vacuum. The residue was purified with reverse phase column (22% MeCN in $H_2O$) to give 4-(aminomethyl)-3-chlorobenzenesulfonamide (165 mg, yield: 54%) as a white solid.

Step 5: A solution of 4-chloro-1-methyl-1H-pyrazolo[3,4-b]pyridine (30 mg, 0.18 mmoL), 4-(aminomethyl)-3-chlorobenzenesulfonamide (160 mg, 0.73 mmoL) and t-BuOK (1.2 mg, 0.01 mmoL) in NMP (2 mL) was stirred at 180° C. for 4 hrs under microwave atmosphere. The reaction mixture was concentrated and the residue was purified with prep-HPLC ($NH_4CO_3$) to give 3-chloro-4-(((1-methyl-1H-pyrazolo[3,4-b]pyridin-4-yl)amino)methyl)benzenesulfonamide (4.5 mg, yield: 7%) as a yellow solid. $^1$HNMR (400 MHz, DMSO-$d_6$): δ=8.12 (s, 1H), 8.00 (d, J=5.2 Hz, 2H), 7.89 (d, J=1.2 Hz, 1H), 7.72 (d, J=8.0 Hz, 1H), 7.52 (d, J=8.0 Hz, 1H), 6.01 (d, J=5.2 Hz, 1H), 4.64 (d, J=5.6 Hz, 2H), 3.92 (s, 3H). MS: m/z 352.0 (M+H$^+$).

Example 2.62

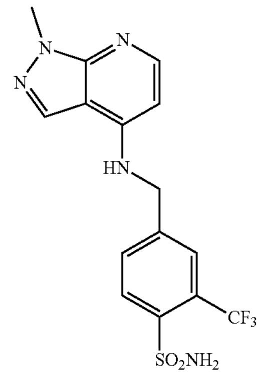 [SMILES: Cn1ncc2c(NCc3ccc(S(N)(=O)=O)c(C(F)(F)F)c3)ccnc21]

4-(((1-Methyl-1H-pyrazolo[3,4-b]pyridin-4-yl)amino)methyl)-2-(trifluoromethyl)-benzenesulfonamide The title compound was prepared using general procedure of 3-chloro-4-(((1-methyl-1H-pyrazolo[3,4-b]pyridin-4-yl)amino)methyl)benzenesulfonamide (Example 2.61). $^1$HNMR (400 MHz, DMSO-$d_6$): δ=8.12 (s, 1H), 8.11 (s, 1H), 8.04 (t, J=6.0 Hz, 1H), 7.99 (d, J=5.6 Hz, 1H), 7.93 (s, 1H), 7.81 (d, J=8.4 Hz, 1H), 7.66 (s, 2H), 6.10 (d, J=5.6 Hz, 1H), 4.70 (d, J=6.0 Hz, 2H), 3.91 (s, 3H). MS: m/z 386.0 (M+H$^+$).

Example 2.63

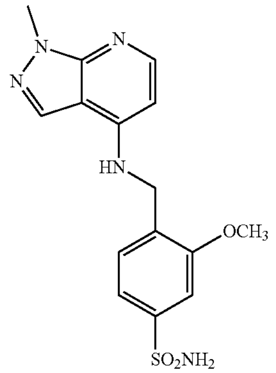 [SMILES: COc1cc(S(N)(=O)=O)ccc1CNc1ccnc2c1cnn2C]

3-Methoxy-4-(((1-methyl-1H-pyrazolo[3,4-b]pyridin-4-yl)amino)methyl)benzenesulfonamide The title compound was prepared using general procedure of 3-chloro-4-(((1-methyl-1H-pyrazolo[3,4-b]pyridin-4-yl)amino)methyl)benzenesulfonamide (Example 2.61). $^1$HNMR (400 MHz, DMSO-$d_6$): δ=8.10 (s, 1H), 7.97 (d, J=5.6 Hz, 1H), 7.86 (t, J=6.0 Hz, 1 H), 7.46 (d, J=1.2 Hz, 1H), 7.37-7.30 (m, 4H), 6.0 (d, J=5.2 Hz, 1H), 4.50 (d, J=6.0 Hz, 2H), 3.93 (s, 3H), 3.90 (s, 3H). MS: m/z 348.1 (M+H$^+$).

Example 2.64

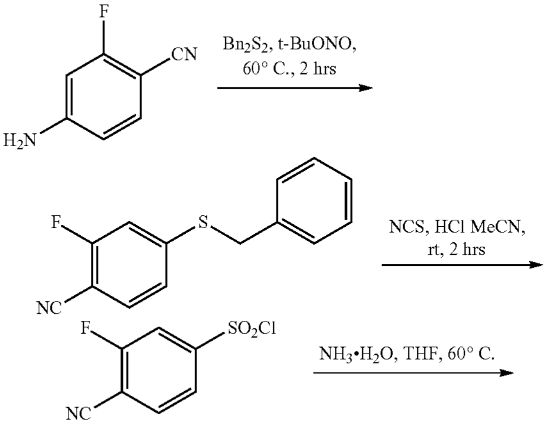

-continued

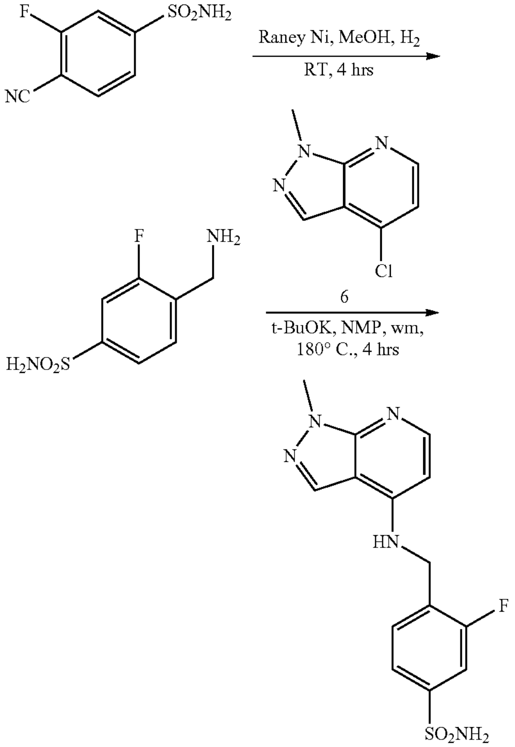

3-Fluoro-4-(((1-methyl-1H-pyrazolo[3,4-b]pyridin-4-yl)amino)methyl)benzenesulfonamide Step 1: To a solution of 4-amino-2-fluorobenzonitrile (4 g, 29.4 mmoL) in MeCN (100 mL) was added $Bn_2S_2$ and t-BuONO (2.1 g) at room temperature. Then the mixture was stirred at 60° C. for 2 hrs. The reaction mixture was poured into saturated aqueous $NaHCO_3$ solution (300 mL) and extracted with EA (250 mL). The EA layer was washed with brine (200 mL), dried over $Na_2SO_4$ and concentrated to dryness in vacuum. The residue was purified by silica gel column (PE/EA=100/1) to give 4-(benzylthio)-2-fluorobenzonitrile (2.7 g, yield: 38%) as a yellow solid. $^1$HNMR (400 MHz, $CDCl_3$): δ=7.45-7.43 (m, 1H), 7.42-7.28 (m, 5H), 7.08-7.02 (m, 2H), 4.20 (s, 2H).

Step 2: A solution of NCS (440 mg, 3.3 mmoL) and HCl (0.7 mL, 8.4 mmoL) in MeCN (3 mL) was stirred at room temperature for 30 mins. Then a solution of 4-(benzylthio)-2-fluorobenzonitrile (200 mg, 0.8 mmoL) in MeCN (2 mL) was added into the reaction mixture. The new mixture was stirred at room temperature for 2 hrs. The reaction mixture was poured into $H_2O$ (50 mL) and extracted with EA (50 mL). The EA layer was washed with brine (50 mL), dried over $Na_2SO_4$ and concentrated to give 4-cyano-3-fluorobenzene-1-sulfonyl chloride (180 mg, yield: crude) as a colorless oil.

Step 3: To a solution of 4-cyano-3-fluorobenzene-1-sulfonyl chloride (180 mg, 0.8 mmoL) in THF (3 mL) was added $NH_3 \cdot H_2O$ (2 mL) at room temperature. The mixture was stirred at 60° C. for 2 hrs. The reaction mixture was concentrated and the residue was purified by silica flash column (28% EA in PE) to give 4-cyano-3-fluorobenzenesulfonamide (150 mg, yield: 91%) as a white solid.

Step 4: A solution of 4-cyano-3-fluorobenzenesulfonamide (550 mg, 2.75 mmoL), Raney-Ni and $NH_4OH$ (4 mL) in MeOH (35 mL) was stirred at room temperature for 6 hrs under $H_2$ atmosphere (balloon). The reaction mixture was filtered and the filtrate was concentrated to dryness in vacuum. The residue was purified with reverse phase column (14% MeCN in $H_2O$) to give 4-(aminomethyl)-3-fluorobenzenesulfonamide (370 mg, yield: δ6%) as a yellow solid.

Step 5: A solution of 4-chloro-1-methyl-1H-pyrazolo[3,4-b]pyridine (75 mg, 0.45 mmoL), 4-(aminomethyl)-3-fluorobenzenesulfonamide (370 mg, 1.81 mmoL) and t-BuOK (3 mg, 0.03 mmoL) in NMP (4 mL) was stirred at 180° C. for 4 hrs under microwave atmosphere. The reaction mixture was concentrated and the residue was purified by prep-HPLC ($NH_4CO_3$) to give 3-fluoro-4-(((1-methyl-1H-pyrazolo[3,4-b]pyridin-4-yl)amino)methyl)benzenesulfonamide (22.8 mg, yield: 15%) as a white solid. $^1$HNMR (400 MHz, DMSO-$d_6$): δ=8.13 (s, 1H), 8.01 (d, J=5.6 Hz, 1H), 7.95 (t, J=6.0 Hz, 1H), 7.64-7.60 (m, 2H), 7.56-7.52 (m, 1H), 7.46 (s, 2H), 6.11 (d, J=5.6 Hz, 1H), 4.63 (d, J=6.0 Hz, 2H), 3.91 (s, 3H). MS: m/z 336.0 (M+H$^+$).

Example 2.65

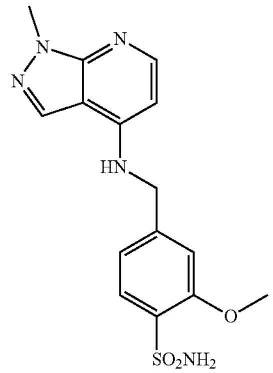 [SMILES: COc1cc(CNc2ccnc3c2cnn3C)ccc1S(N)(=O)=O]

2-Methoxy-4-(((1-methyl-1H-pyrazolo[3,4-b]pyridin-4-yl)amino)methyl)-benzenesulfonamide The title compound was prepared using general procedure of 3-chloro-4-(((1-methyl-1H-pyrazolo[3,4-b]pyridin-4-yl)amino)methyl)benzenesulfonamide (Example 2.61). $^1$HNMR (400 MHz, $CD_3OD$): δ=8.11 (s, 1H), 8.02 (d, J=5.6 Hz, 1H), 7.81 (d, J=8.0 Hz, 1H), 7.24 (s, 1H), 7.11-7.08 (m, 1H), 6.19 (d, J=5.6 Hz, 1H), 4.69 (s, 2H), 4.00 (s, 3H), 3.96 (s, 3H). MS: m/z 348.1 (M+H$^+$).

Example 2.66

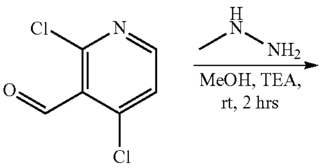

-continued

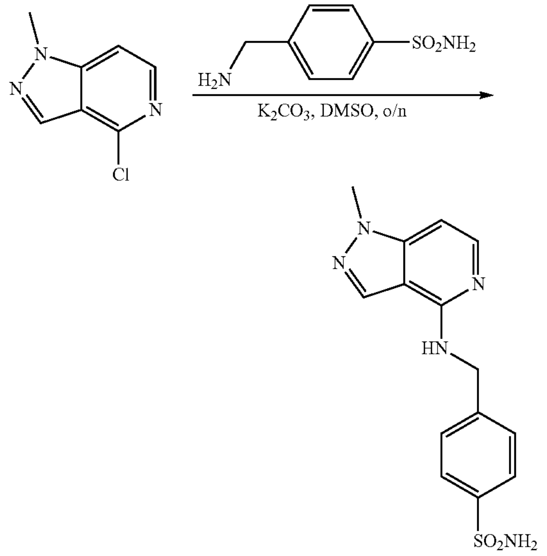

4-(((1-Methyl-1H-pyrazolo[4,3-c]pyridin-4-yl) amino)methyl)benzenesulfonamide

Step 1: To a solution of 2,4-dichloronicotinaldehyde (100 mg, 0.57 mmol) in MeOH (20 mL) was added methylhydrazine (29 mg, 0.63 mmol) and TEA (0.5 ml). The mixture was stirred at room temperature for 2 hrs. The resulting solution was filtered. The cake was purified by prep-TLC (DCM/MeOH=30/1) to give 4-chloro-1-methyl-1H-pyrazolo[4,3-c]pyridine (80 mg, yield: 83%) as a white solid. $^1$HNMR (400 MHz, DMSO-$d_6$): δ=8.30 (s, 1H), 8.15 (d, J=6.0 Hz, 1H), 7.74 (d, J=6.0 Hz, 1H), 4.10 (s, 3H).

Step 2: The title compound (13.8 mg, yield: 15%, white, solid) was prepared using general procedure of 4-(((1-methyl-6-(methylamino)-1H-pyrazolo[3,4-d]pyrimidin-4-yl)amino)methyl)benzenesulfonamide (Example 2.27). $^1$HNMR (400 MHz, DMSO-$d_6$): δ=8.19 (s, 1H), 7.94 (t, J=6.0 Hz, 1H), 7.74 (d, J=8.4 Hz, 2H), 7.70 (d, J=6.0 Hz, 1H), 7.49 (d, J=8.0 Hz, 2H), 7.26 (s, 2H), 6.76 (dd, J=6.4, 0.8 Hz, 1H), 4.75 (d, J=6.0 Hz, 2H), 3.93 (s, 3H). MS: m/z 318.0 (M+H$^+$).

Example 2.67

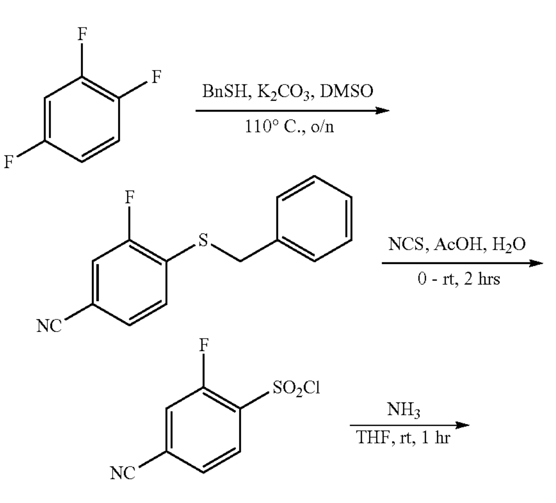

-continued

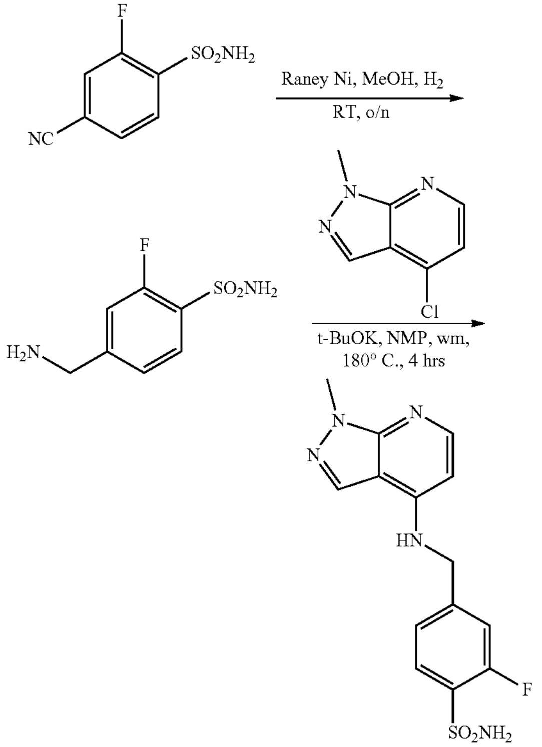

2-Fluoro-4-(((1-methyl-1H-pyrazolo[3,4-b]pyridin-4-yl)amino)methyl)benzenesulfonamide Step 1: A solution of 3,4-difluorobenzonitrile (5 g, 35.97 mmol), phenylmethanethiol (4.2 mL, 35.97 mmol) and $K_2CO_3$ (10 g, 71.94 mmol) in DMSO (20 mL) was stirred at 110° C. overnight. The reaction mixture was diluted with water (120 mL) and extracted with EA (100 mL×2). The combined organic layers were washed with brine (200 mL), dried over $Na_2SO_4$ and concentrated. The residue was purified by silica gel column (PE/EA=20/1) to afford 4-(benzylthio)-3-fluorobenzonitrile (5.89 g, yield: δ7%) as a white solid.

Step 2: A solution of 4-(benzylthio)-3-fluorobenzonitrile (5.89 g, 24.24 mmol) and NCS (13 g, 96.95 mmol) in AcOH (20 mL) was stirred at 0° C. for 1 hr. The reaction mixture was diluted with water (100 mL) and extracted with EA (100 mL×2). The combined organic layers were washed with brine (200 mL), dried over $Na_2SO_4$ and concentrated to afford 4-cyano-2-fluorobenzene-1-sulfonyl chloride (5 g, crude) as a colorless oil.

Step 3: A solution of 4-cyano-2-fluorobenzene-1-sulfonyl chloride (5 g, 22.83 mmol) and $NH_3$—$H_2O$ (2 mL) in THF (10 mL) was stirred at room temperature for 2 hrs. The reaction mixture was concentrated. The residue was purified by silica gel column (PE/EA=2/1) to afford 4-cyano-2-fluorobenzenesulfonamide (2.5 g, yield: 54%) as a white solid.

Step 4: A solution of 4-cyano-2-fluorobenzenesulfonamide (500 mg, 2.5 mmol), Reany.Ni (500 mg, 2.5 mmol) and $NH_3$—$H_2O$ (1 mL) in MeOH (5 mL) was stirred at room temperature overnight under $H_2$ atmosphere (balloon). The reaction mixture was filtered and the filtrate was concentrated. The residue was purified by reverse phase column to afford 4-(aminomethyl)-2-fluorobenzenesulfonamide (300 g, yield: 59%) as a white solid.

Step 5: A solution of 4-chloro-1-methyl-1H-pyrazolo[3,4-b]pyridine (30 mg, 0.18 mmol), 4-(aminomethyl)-2-fluorobenzenesulfonamide (146 mg, 0.718 mmol) and t-BuOK (1.2 mg, 0.01 mmol) in NMP (2 mL) was stirred at 180° C. for 4 hrs by microwave. The reaction mixture was concentrated and the residue was purified by prep-HPLC to afford 2-fluoro-4-(((1-methyl-1H-pyrazolo[3,4-b]pyridin-4-yl)amino)methyl)benzenesulfonamide (8 mg, yield: 13%) as a white solid. $^{1}$HNMR (400 MHz, DMSO-$d_6$): δ=8.11 (s, 1H), 8.00 (dd, J=12.0, 6.0 Hz, 2H), 7.75 (t, J=8.0 Hz, 1H), 7.60 (s, 2H), 7.35 (q, 2H), 6.08 (d, J=5.6 Hz, 1H), 4.61 (d, J=6.0 Hz, 2H), 3.90 (s, 3H). MS: m/z 336.0 (M+H$^{+}$).

Example 2.68

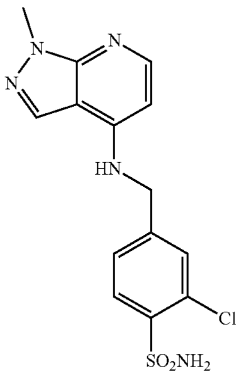 [SMILES: Cn1ncc2c(NCc3ccc(S(N)(=O)=O)c(Cl)c3)ccnc21]

2-Chloro-4-(((1-methyl-1H-pyrazolo[3,4-b]pyridin-4-yl)amino)methyl)-benzenesulfonamide The title compound was prepared using general procedure of 2-fluoro-4-(((1-methyl-1H-pyrazolo[3,4-b]pyridin-4-yl)amino)methyl)benzenesulfonamide (Example 2.67). $^{1}$HNMR (400 MHz, $CD_3OD$): δ=8.08 (s, 1H), 8.02 (q, 2H), 7.58 (d, J=1.6 Hz, 1H), 7.47-7.44 (m, 1H), 6.15 (d, J=5.6 Hz, 1H), 4.66 (s, 2H), 3.98 (s, 3H). MS: m/z 351.9 (M+H$^{+}$).

Example 2.69

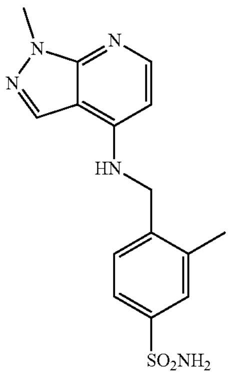 [SMILES: Cc1cc(S(N)(=O)=O)ccc1CNc1ccnc2c1cnn2C]

3-Methyl-4-(((1-methyl-1H-pyrazolo[3,4-b]pyridin-4-yl)amino)methyl)-benzenesulfonamide The title compound was prepared using general procedure of 2-fluoro-4-(((1-methyl-1H-pyrazolo[3,4-b]pyridin-4-yl)amino)methyl)benzenesulfonamide (Example 2.67). $^{1}$HNMR (400 MHz, DMSO-$d_6$): δ=8.13 (s, 1H), 7.98 (d, J=5.2 Hz, 1H), 7.86 (t, J=5.2 Hz, 1H), 7.66 (s, 1H), 7.57 (d, J=8.0 Hz, 1H), 7.36 (d, J=8.0 Hz, 1H), 7.25 (s, 2H), 6.04 (d, J=5.2 Hz, 1H), 4.54 (d, J=5.6 Hz, 2H), 3.91 (s, 3H), 2.43 (s, 3H). MS: m/z 332.1 (M+H$^{+}$).

Example 2.70

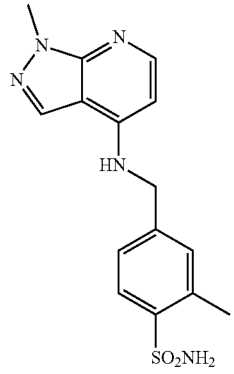 [SMILES: Cc1cc(CNc2ccnc3c2cnn3C)ccc1S(N)(=O)=O]

2-Methyl-4-(((1-methyl-1H-pyrazolo[3,4-b]pyridin-4-yl)amino)methyl)-benzenesulfonamide The title compound was prepared using general procedure of 2-fluoro-4-(((1-methyl-1H-pyrazolo[3,4-b]pyridin-4-yl)amino)methyl)benzenesulfonamide (Example 2.67). $^{1}$HNMR (400 MHz, DMSO-$d_6$): δ=8.12 (s, 1H), 7.98 (dd, J=14.8, 5.2 Hz, 2H), 7.79 (d, J=8.0 Hz, 1H), 7.33 (t, J=6.8 Hz, 4H), 6.07 (d, J=5.2 Hz, 1H), 4.55 (d, J=5.2 Hz, 1H), 3.90 (s, 3H), 2.55 (s, 3H). MS: m/z 332.1 (M+H$^{+}$).

Example 2.71

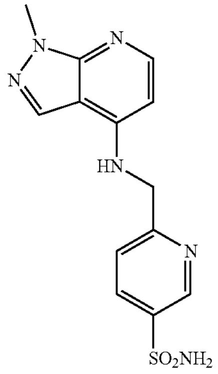 [SMILES: Cn1ncc2c(NCc3ccc(S(N)(=O)=O)cn3)ccnc21]

6-(((1-Methyl-1H-pyrazolo[3,4-b]pyridin-4-yl)amino)methyl)pyridine-3-sulfonamide The title compound was prepared using general procedure of 2-fluoro-4-(((1-methyl-1H-pyrazolo[3,4-b]pyridin-4-yl)

amino)methyl)benzenesulfonamide (Example 2.67). $^{1}$HNMR (400 MHz, DMSO-$d_6$): δ=8.93 (d, J=1.6 Hz, 1H), 8.15-8.09 (m, 3H), 7.97 (d, J=5.6 Hz, 1H), 7.54 (d, J=8.0 Hz, 3H), 6.06 (d, J=5.2 Hz, 1H), 4.70 (d, J=6.0 Hz, 2H), 3.90 (s, 3H). MS: m/z 319.0 (M+$H^+$).

Example 2.72

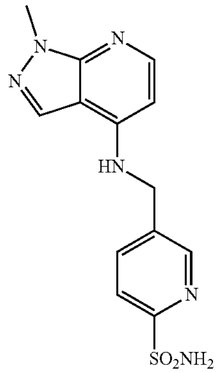 [SMILES: Cn1ncc2c(NCc3ccc(S(N)(=O)=O)nc3)ccnc21]

5-(((1-Methyl-1H-pyrazolo[3,4-b]pyridin-4-yl)amino)methyl)pyridine-2-sulfonamide The title compound was prepared using general procedure of 2-fluoro-4-(((1-methyl-1H-pyrazolo[3,4-b]pyridin-4-yl)amino)methyl)benzenesulfonamide (Example 2.67). $^{1}$HNMR (400 MHz, $CD_3OD$): δ=8.61 (s, 1H), 7.99 (s, 1H), 7.92 (d, J=5.6 Hz, 2H), 7.87 (d, J=8.0 Hz, 1H), 6.11 (d, J=6.0 Hz, 1H), 5.24 (t, J=4.8 Hz, 1H), 4.64 (s, 2H), 3.89 (s, 3H). MS: m/z 319.1 (M+$H^+$).

Example 2.73

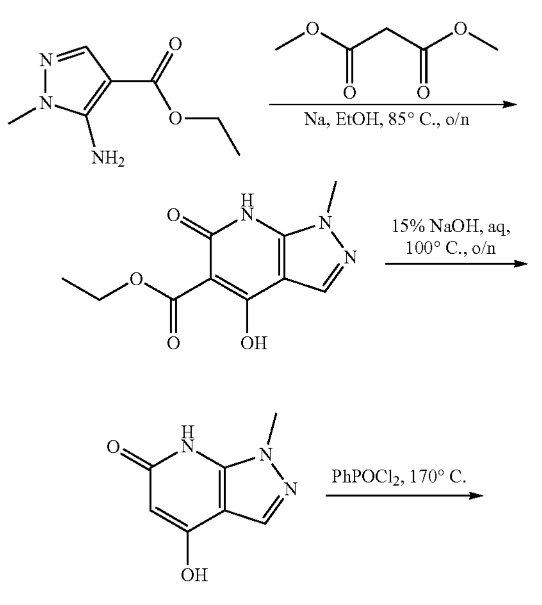

-continued

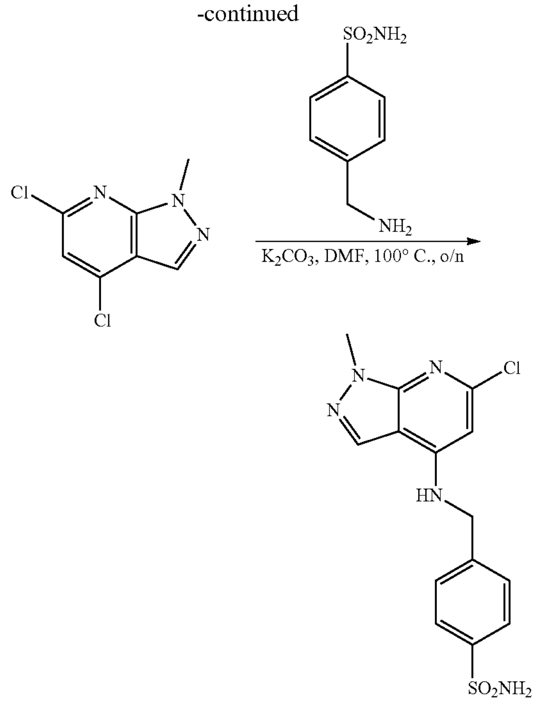

4-(((6-Chloro-1-methyl-1H-pyrazolo[3,4-b]pyridin-4-yl)amino)methyl)benzenesulfonamide Step 1: Na (7 g, 304 mmoL) was added into EtOH at room temperature and the mixture was stirred for 1 hr under $N_2$ atmosphere (balloon). Then ethyl 5-amino-1-methyl-1H-pyrazole-4-carboxylate (12 g, 71 mmoL) was added into the mixture and the new mixture was stirred at room temperature for 0.5 hr, followed by adding dimethyl malonate dropwise into the reaction mixture. The new reaction mixture was stirred at 85° C. overnight under $N_2$ atmosphere (balloon). The reaction mixture was concentrated and the residue was dissolved with $H_2O$ which was about 200 mL. The suspension was filtered and the pad was dissolved with $H_2O$ (120 mL). The solution was acidified with concentrated HCl to pH=3.0. The new suspension was filtered and the pad was dried to give part of ethyl 4-hydroxy-1-methyl-6-oxo-6,7-dihydro-1H-pyrazolo[3,4-b]pyridine-5-carboxylate. Then the filtrate was acidified with concentrated HCl again. The suspension was filtered and the pad was triturated with EA/$H_2O$ (60 mL/15 mL) to give another part of ethyl 4-hydroxy-1-methyl-6-oxo-6,7-dihydro-1H-pyrazolo[3,4-b]pyridine-5-carboxylate. The combined target material was pale-yellow solid which was about 18 g.

Step 2: A solution of ethyl 4-hydroxy-1-methyl-6-oxo-6,7-dihydro-1H-pyrazolo[3,4-b]pyridine-5-carboxylate (5.8 g, 24.5 mmoL) and NaOH (7 g) in $H_2O$ (40 mL) was stirred at 100° C. overnight. The reaction mixture was acidified with concentrated HCl to pH=3.0. The suspension was filtered and rinsed with $H_2O$ and EA to give 4-hydroxy-1-methyl-1H-pyrazolo[3,4-b]pyridin-6(7H)-one (1.5 g, yield: 37%) as a white solid. $^{1}$HNMR (400 MHz, DMSO-$d_6$): δ=11.36 (brs, 1H), 11.18 (s, 1H), 7.73 (s, 1H), 5.48 (s, 1H), 3.84 (s, 3H).

Step 3: A solution of 4-hydroxy-1-methyl-1H-pyrazolo[3,4-b]pyridin-6(7H)-one (7.6 g, 46 mmoL) in $PhPOCl_2$ (38 mL) was stirred at 170° C. for 8 hrs. The reaction mixture was cooled to room temperature and added hot water (150 mL, about 50° C.). Then the mixture was neutralized with $NaHCO_3$ slowly. The $H_2O$ phase was extracted with EA (150 mL). The EA phase was washed with brine (150 mL), dried and concentrated to give 4,6-dichloro-1-methyl-1H-pyrazolo[3,4-b]pyridine (8.2 g, yield: 89%) as a grey solid. $^1$HNMR (400 MHz, DMSO-$d_6$): δ=8.30 (s, 1H), 7.58 (s, 1H), 4.04 (s, 3H).

Step 4: A solution of 4,6-dichloro-1-methyl-1H-pyrazolo [3,4-b]pyridine (4 g, 20 mmoL), 4-(aminomethyl)benzenesulfonamide (4 g, 21.5 mmoL) and $K_2CO_3$ (6.8 g, 49 mmoL) in DMF (30 mL) was stirred at 100° C. overnight. The reaction mixture was poured into $H_2O$ (100 mL) and extracted with EA (160 mL). The suspension was filtered and the pad was rinsed with $H_2O$ and EA to give 4-(((6-chloro-1-methyl-1H-pyrazolo[3,4-b]pyridin-4-yl)amino) methyl)benzenesulfonamide (2.49 g, yield: 36%) as a off-white solid. $^1$HNMR (400 MHz, DMSO-$d_6$): δ=8.37-8.36 (m, 1H), 8.14 (s, 1H), 7.81 (d, J=8.4 Hz, 2H), 7.54 (d, J=8 Hz, 2H), 7.32 (s, 2H), 6.14 (s, 1H), 4.64 (d, J=8 Hz, 2H), 3.87 (s, 3H). MS: m/z 352.0 (M+H$^+$).

Example 2.74

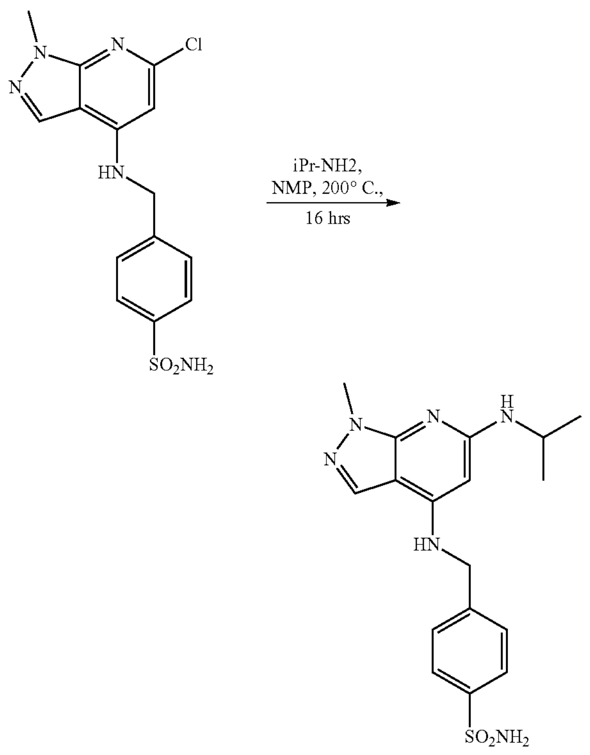

4-(((6-(Isopropylamino)-1-methyl-1H-pyrazolo[3,4-b]pyridin-4-yl)amino)methyl)benzenesulfonamide A solution of 4-(((6-chloro-1-methyl-1H-pyrazolo[3,4-b] pyridin-4-yl)amino)methyl)benzenesulfonamide (60 mg, 0.17 mmoL) and iPr-$NH_2$ (2 mL) in NMP (0.5 mL) was stirred at 200° C. for 16 hrs. The reaction mixture was concentrated and the residue was purified by prep-HPLC ($NH_4CO_3$) to give 4-(((6-(isopropylamino)-1-methyl-1H-pyrazolo[3,4-b]pyridin-4-yl)amino)methyl)benzenesulfonamide (5 mg, yield: 8%) as a white solid. $^1$HNMR (400 MHz, $CD_3OD$): δ=7.77-7.75 (m, 2H), 7.69 (s, 1H), 7.43 (d, J=8.4 Hz, 2H), 5.13 (s, 1H), 4.46 (s, 2H), 3.90-3.80 (m, 1H), 3.71 (s, 3H), 1.04 (s, 3H), 1.03 (s, 3H). MS: m/z 375.1 (M+H$^+$).

Example 2.75

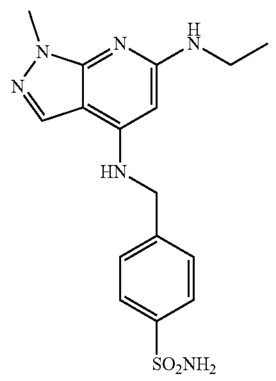 [SMILES: CCNc1cc(NCc2ccc(S(N)(=O)=O)cc2)c2cnn(C)c2n1]

4-(((6-(Ethylamino)-1-methyl-1H-pyrazolo[3,4-b] pyridin-4-yl)amino)methyl)-benzenesulfonamide The title compound was prepared using general procedure of 4-(((6-(isopropylamino)-1-methyl-1H-pyrazolo[3,4-b] pyridin-4-yl)amino)methyl)benzenesulfonamide (Example 2.74). $^1$HNMR (400 MHz, $CD_3OD$): δ=7.67 (d, J=8.0 Hz, 2H), 7.60 (s, 1H), 7.34 (d, J=8.0 Hz, 2H), 5.05 (s, 1H), 4.37 (s, 2H), 3.63 (s, 3H), 3.10 (overlap, 2H), 0.95 (t, J=7.2 Hz, 3H). MS: m/z 361.1 (M+H$^+$).

Example 2.76

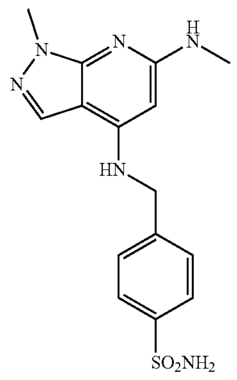 [SMILES: CNc1cc(NCc2ccc(S(N)(=O)=O)cc2)c2cnn(C)c2n1]

4-(((1-Methyl-6-(methylamino)-1H-pyrazolo[3,4-b] pyridin-4-yl)amino)methyl)-benzenesulfonamide The title compound was prepared using general procedure of 4-(((6-(isopropylamino)-1-methyl-1H-pyrazolo[3,4-b] pyridin-4-yl)amino)methyl)benzenesulfonamide (Example 2.74). $^1$HNMR (400 MHz, DMSO-$d_6$): δ=7.80-7.77 (m, 3H), 7.50 (d, J=8.0 Hz, 2H), 7.44 (s, 1H), 7.29 (s, 2H), 6.32 (s, 1H), 5.17 (s, 1H), 4.46 (d, J=6.0 Hz, 2H), 3.74 (s, 3H), 2.73 (d, J=4.4 Hz, 3H). MS: m/z 347.1 (M+H$^+$).

Example 2.77

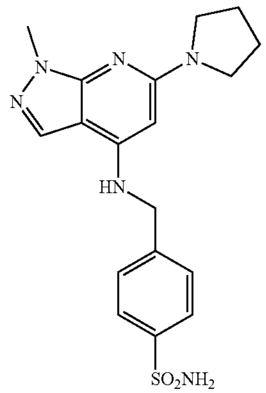 [SMILES: Cn1ncc2c(NCc3ccc(S(N)(=O)=O)cc3)cc(N3CCCC3)nc21]

4-(((1-Methyl-6-(pyrrolidin-1-yl)-1H-pyrazolo[3,4-b]pyridin-4-yl)amino)methyl)-benzenesulfonamide The title compound was prepared using general procedure of 4-(((6-(isopropylamino)-1-methyl-1H-pyrazolo[3,4-b]pyridin-4-yl)amino)methyl)benzenesulfonamide (Example 2.74). $^1$HNMR (400 MHz, DMSO-$d_6$): δ=7.82-7.77 (m, 3H), 7.55-7.48 (m, 3H), 7.28 (s, 2H), 5.19 (s, 1H), 4.53 (d, J=6.0 Hz, 2H), 3.73 (s, 3H), 3.32-3.31 (m, 4H), 1.87 (t, J=6.4 Hz, 4H). MS: m/z 387.1 (M+$H^+$).

Example 2.78

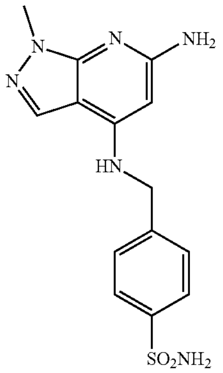 [SMILES: Cn1ncc2c(NCc3ccc(S(N)(=O)=O)cc3)cc(N)nc21]

4-(((6-Amino-1-methyl-1H-pyrazolo[3,4-b]pyridin-4-yl)amino)methyl)-benzenesulfonamide The title compound was prepared using general procedure of 4-(((6-(isopropylamino)-1-methyl-1H-pyrazolo[3,4-b]pyridin-4-yl)amino)methyl)benzenesulfonamide (Example 2.74). $^1$HNMR (400 MHz, DMSO-$d_6$): δ=7.79-7.77 (m, 3H), 7.50-7.44 (m, 3H), 7.30 (s, 2H), 5.77 (s, 2H), 5.20 (s, 1H), 4.46 (d, J=6.0 Hz, 2H), 3.70 (s, 3H). MS: m/z 333.0 (M+$H^+$).

Example 2.79

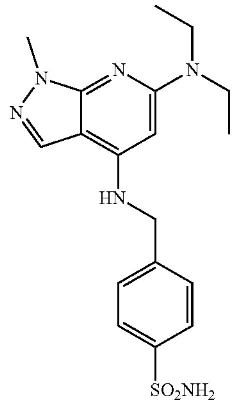 [SMILES: CCN(CC)c1cc(NCc2ccc(S(N)(=O)=O)cc2)c2cnn(C)c2n1]

4-(((6-(Diethylamino)-1-methyl-1H-pyrazolo[3,4-b]pyridin-4-yl)amino)methyl)-benzenesulfonamide The title compound was prepared using general procedure of 4-(((6-(isopropylamino)-1-methyl-1H-pyrazolo[3,4-b]pyridin-4-yl)amino)methyl)benzenesulfonamide (Example 2.74). $^1$HNMR (400 MHz, DMSO-$d_6$): δ=7.79-7.76 (m, 3H), 7.55-7.49 (m, 3H), 7.29 (s, 2H), 5.23 (s, 1H), 4.52 (d, J=6.0 Hz, 2H), 3.71 (s, 3H), 3.40 (q, J=6.8 Hz, 4H), 0.99 (t, J=6.8 Hz, 6H). MS: m/z 389.1 (M+$H^+$).

Example 2.80

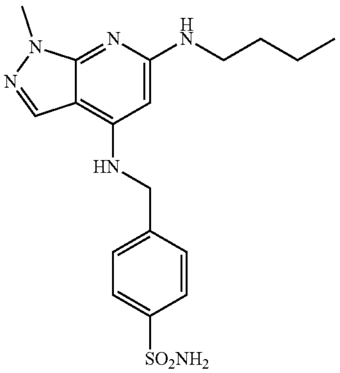 [SMILES: CCCCNc1cc(NCc2ccc(S(N)(=O)=O)cc2)c2cnn(C)c2n1]

4-(((6-(Butylamino)-1-methyl-1H-pyrazolo[3,4-b]pyridin-4-yl)amino)methyl)-benzenesulfonamide The title compound was prepared using general procedure of 4-(((6-(isopropylamino)-1-methyl-1H-pyrazolo[3,4-b]pyridin-4-yl)amino)methyl)benzenesulfonamide (Example 2.74). $^1$HNMR (400 MHz, DMSO-$d_6$): δ=7.79-7.77 (m, 3H), 7.49 (d, J=8.0 Hz, 2H), 7.37 (d, J=5.6 Hz, 1H), 7.29 (s, 2H), 6.29 (t, J=5.2 Hz, 1H), 5.19 (s, 1H), 4.45 (d, J=6.0 Hz, 2H), 3.72 (s, 3H), 3.21 (q, J=6.8 Hz, 2H), 1.47-1.42 (m, 2H), 1.33-1.28 (m, 2H), 0.88 (t, J=7.2 Hz, 3H). MS: m/z 389.1 (M+$H^+$).

Example 2.81

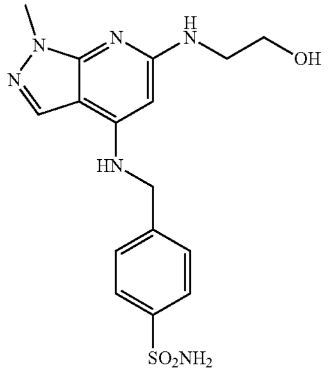

4-(((6-((2-Hydroxyethyl)amino)-1-methyl-1H-pyrazolo[3,4-b]pyridin-4-yl)amino)methyl)-benzenesulfonamide The title compound was prepared using general procedure of 4-(((6-(isopropylamino)-1-methyl-1H-pyrazolo[3,4-b]pyridin-4-yl)amino)methyl)benzenesulfonamide (Example 2.74). $^1$HNMR (400 MHz, DMSO-$d_6$): δ=7.79-7.77 (m, 3H), 7.50 (d, J=8.4 Hz, 2H), 7.43 (t, J=5.6 Hz, 1H), 7.29 (s, 2H), 6.34 (t, J=5.6 Hz, 1H), 5.23 (s, 1H), 4.76 (s, 1H), 4.45 (d, J=6.0 Hz, 2H), 3.72 (s, 3H), 3.49 (d, J=4.8 Hz, 2H), 3.31 (overlap, 2H). MS: m/z 377.1 (M+H$^+$).

Example 2.82

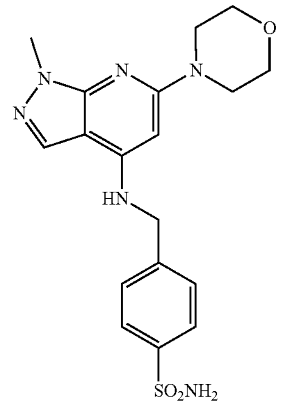

4-(((1-Methyl-6-morpholino-1H-pyrazolo[3,4-b]pyridin-4-yl)amino)methyl)-benzenesulfonamide The title compound was prepared using general procedure of 4-(((6-(isopropylamino)-1-methyl-1H-pyrazolo[3,4-b]pyridin-4-yl)amino)methyl)benzenesulfonamide (Example 2.74). $^1$HNMR (400 MHz, DMSO-$d_6$): δ=7.86 (s, 1H), 7.78 (m, J=8.0 Hz, 2H), 7.60 (t, J=6.0 Hz, 1H), 7.54 (d, J=8.4 Hz, 2H), 7.29 (s, 2H), 5.59 (s, 1H), 4.56 (d, J=6.0 Hz, 2H), 3.75 (s, 3H), 3.65 (t, J=4.4 Hz, 4H), 3.41 (t, J=4.8 Hz, 4H). MS: m/z 403.1 (M+H$^+$).

Example 2.83

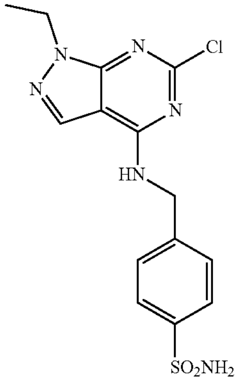 [SMILES: CCn1ncc2c(NCc3ccc(S(N)(=O)=O)cc3)nc(Cl)nc21]

4-((6-Chloro-1-ethyl-1H-pyrazolo[3,4-d]pyrimidin-4-yl)aminomethyl)benzenesulfonamide To a suspension of 2,4,6-trichloro-5-pyrimidinecarboxaldehyde (3.12 g) in ethanol (30 mL) were added ethylhydrazine (1.09 mL) and triethylamine (6.2 mL) dropwise at −78° C. The resulting mixture was stirred at −78° C. for 1 hour then room temperature for 3 hours. To the mixture were added homosulfamine hydrochloride (3.64 g) and triethylamine (4.2 mL), then the mixture was stirred at 80° C. for 4 hours. After the reaction, the reaction mixture was evaporated under reduced pressure. To the residue were added ethyl acetate and saturated ammonium chloride solution, then the mixture was stirred at room temperature for 1 hour. The precipitate was collected and washed with water, ethyl acetate and 2-propanol successively, then dried under reduced pressure, to give the title compound as a yellow solid (2.37 g, yield 44%). $^1$H-NMR (DMSO-$D_6$) δ: 9.12 (1H, br m), 8.14 (1H, s), 7.80 (2H, d, J=8.6 Hz), 7.53 (2H, d, J=8.6 Hz), 7.19 (2H, s), 4.77 (2H, d, J=5.5 Hz), 4.26 (2H, q, J=7.2 Hz), 1.37 (3H, t, J=7.2 Hz). MS: m/z 367 (M+H$^+$).

Example 2.84

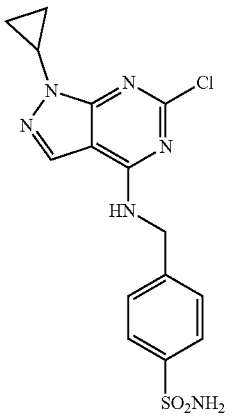 [SMILES: NS(=O)(=O)c1ccc(CNc2nc(Cl)nc3c2cnn3C2CC2)cc1]

4-((6-Chloro-1-cyclopropyl-1H-pyrazolo[3,4-d]pyrimidin-4-yl)aminomethyl)-benzenesulfonamide The title compound was prepared according to the general procedure of Example 2.83 using cyclopropylhydrazine hydrochloride. $^1$H-NMR (DMSO-$D_6$) δ: 9.14-9.07 (1H, br m), 8.08 (1H, s), 7.79 (2H, d, J=8.6 Hz), 7.52 (2H, d, J=8.6 Hz), 7.19 (2H, s), 4.76 (2H, d, J=5.5 Hz), 3.79-3.72 (1H, m), 1.16-1.01 (4H, m). MS: m/z 379.1 (M+H$^+$).

Example 2.85

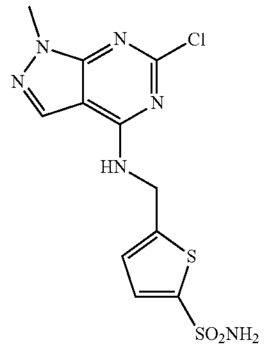 [SMILES: Cn1ncc2c(NCc3ccc(S(N)(=O)=O)s3)nc(Cl)nc21]

5-((6-Chloro-1-methyl-1H-pyrazolo[3,4-d]pyrimidin-4-yl)aminomethyl)thiophene-2-sulfonamide To a suspension of 4,6-dichloro-1-methylpyrazolo[3,4-d]pyrimidine (77.4 mg) and 5-(aminomethyl)thiophene-2-sulfonamide (88.0 mg) in 2-propanol (2 mL) were added N,N-diisopropylethylamine (0.146 mL) at room temperature. The resulting mixture was stirred at 85° C. for 7 hours and evaporated under reduced pressure. To the residue were added ethyl acetate and saturated ammonium chloride solution, then the mixture was stirred at room temperature. The precipitate was collected and washed with water, ethyl acetate successively, then dried under reduced pressure, to give the title compound as a yellow solid (60.0 mg, yield 44%). $^1$H-NMR (DMSO-$D_6$) δ: 9.44 (1H, t, J=6.1 Hz), 8.11 (1H, s), 7.60 (2H, s), 7.40 (1H, d, J=3.7 Hz), 7.11 (1H, d, J=3.7 Hz), 4.87 (2H, d, J=6.1 Hz), 3.87 (3H, s). MS: m/z 359 (M+H$^+$).

Example 2.86

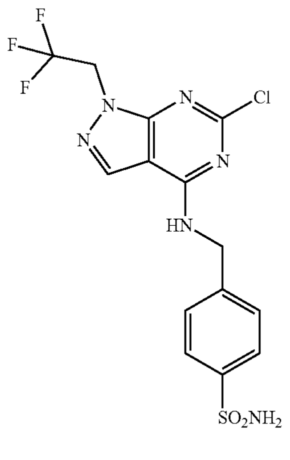 [SMILES: NS(=O)(=O)c1ccc(CNc2nc(Cl)nc3c2cnn3CC(F)(F)F)cc1]

4-((6-Chloro-1-(2,2,2-trifluoroethyl)-1H-pyrazolo[3,4-d]pyrimidin-4-yl)aminomethyl)-benzenesulfonamide Step 1: To a suspension of 2,4,6-trichloro-5-pyrimidinecarboxaldehyde (797 mg) in ethanol (12 mL) were added 2,2,2-trifluoroethylhydrazine (70 wt. % in water, 612 mg) and triethylamine (1.60 mL) dropwise at −78° C. The resulting mixture was stirred at −78° C. for 30 min and 0° C. to room temperature for 1.5 hours. The reaction mixture was evaporated under reduced pressure. To the residue were added ethyl acetate and washed with saturated ammonium chloride solution, brine successively, then dried over anhydrous sodium sulfate. After the resulting solid was filtered off, the filtrate was concentrated under reduced pressure. The residue was purified by automated flash chromatography using 0-25% ethyl acetate in hexane, to give 4,6-dichloro-1-(2,2,2-trifluoroethyl)-1H-pyrazolo[3,4-d]pyrimidine as a colorless solid (260 mg, yield 25%). MS: m/z 271.0 (M+H$^+$).

Step 2: The title compound was prepared according to the general procedure of Example 2.85 using 4,6-dichloro-1-(2,2,2-trifluoroethyl)-1H-pyrazolo[3,4-d]pyrimidine obtained above and homosulfamine hydrochloride $^1$H-NMR (DMSO-$D_6$) δ: 9.31-9.29 (1H, br m), 8.28 (1H, s), 7.80 (2H, d, J=8.6 Hz), 7.54 (2H, d, J=8.6 Hz), 7.19 (2H, s), 5.15 (2H, q, J=9.0 Hz), 4.78 (2H, d, J=5.5 Hz). MS: m/z 421.1 (M+H$^+$).

Example 2.87

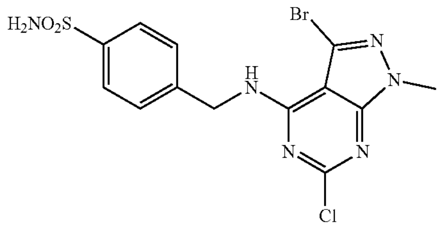 [SMILES: Cn1nc(Br)c2c(NCc3ccc(S(N)(=O)=O)cc3)nc(Cl)nc21]

4-((3-Bromo-6-chloro-1-methyl-1H-pyrazolo[3,4-d]pyrimidin-4-yl)aminomethyl)-benzenesulfonamide Step 1: To a solution of 3-bromo-4,6-dichloro-1H-pyrazolo[3,4-d]pyrimidine (50.6 mg), triphenylphosphine (98.2 mg) in methanol (0.2 mL) and tetrahydrofuran (2.0 mL) was added 1,1'-(azodicarbonyl)dipiperidine (94.8 mg) at room temperature. The reaction mixture was stirred at room temperature for 6 hours, then quenched by adding water, and extracted with ethyl acetate. The combined organic layer was washed with water and brine, then dried over anhydrous sodium sulfate. After the resulting solid was filtered off, the filtrate was concentrated under reduced pressure. The residue was purified by automated flash chromatography using 10-75% ethyl acetate in dichloromethane followed by 9% methanol in dichloromethane as eluent, to give 3-bromo-4,6-dichloro-1-methyl-1H-pyrazolo[3,4-d]pyrimidine as a colorless solid (31.5 mg, yield 59.2%).

Step 2: The title compound was prepared according to the general procedure of Example 2.85 using 3-bromo-4,6-dichloro-1-methyl-1H-pyrazolo[3,4-d]pyrimidine obtained above and homosulfamine hydrochloride. $^1$H-NMR (DMSO-$D_6$) δ: 8.25 (1H, t, J=6.1 Hz), 7.75-7.80 (2H, m), 7.50-7.53 (2H, m), 7.32 (2H, s), 4.80 (2H, d, J=6.1 Hz), 3.84 (3H, s). MS: m/z 430.9 (M+H$^+$).

Example 2.88

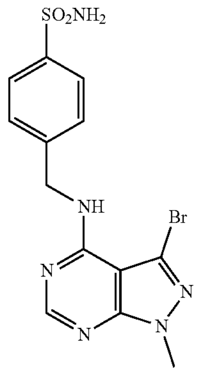 [SMILES: Cn1nc(Br)c2c(NCc3ccc(S(N)(=O)=O)cc3)ncnc21]

4-((3-Bromo-1-methyl-1H-pyrazolo[3,4-d]pyrimidin-4-yl)aminomethyl)-benzenesulfonamide The title compound was prepared according to the general procedure of Example 2.85 using 3-bromo-4-chloro-1-methyl-1H-pyrazolo[3,4-d]pyrimidine and homosulfamine hydrochloride. MS: m/z 397 (M+H$^+$).

Example 2.89

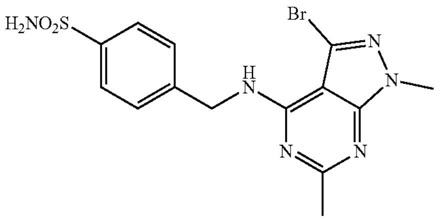 [SMILES: Cc1nc(NCc2ccc(S(N)(=O)=O)cc2)c2c(Br)nn(C)c2n1]

4-((3-Bromo-1,6-dimethyl-1H-pyrazolo[3,4-d]pyrimidin-4-yl)aminomethyl)-benzenesulfonamide The title compound was prepared according to the general procedure of Example 2.85 using 3-bromo-4-chloro-1,6-dimethyl-1H-pyrazolo[3,4-d]pyrimidine and homosulfamine hydrochloride. $^1$H-NMR (DMSO-D$_6$) δ: 7.74-7.78 (2H, m), 7.72 (1H, t, J=6.4 Hz), 7.50-7.55 (2H, m), 7.31 (2H, s), 4.83 (2H, d, J=6.1 Hz), 3.84 (3H, s), 2.40 (3H, s). MS: m/z 411.0 (M+H$^+$).

Example 2.90

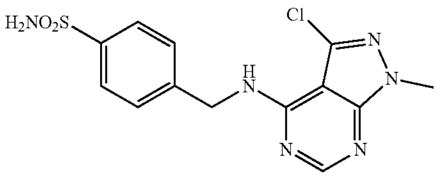 [SMILES: Cn1nc(Cl)c2c(NCc3ccc(S(N)(=O)=O)cc3)ncnc21]

4-((3-Chloro-1-methyl-1H-pyrazolo[3,4-d]pyrimidin-4-yl)aminomethyl)-benzenesulfonamide Step 1: To a suspension of 3,4-dichloro-1H-pyrazolo[3,4-d]pyrimidine (66.8 mg) and potassium carbonate (111 mg) in N,N-dimethylformamide (2.0 mL) was added iodomethane (0.048 mL). The mixture was stirred at room temperature overnight, then quenched by adding water and extracted with ethyl acetate. The combined organic layer was washed with brine and dried over anhydrous sodium sulfate. After the resulting solid was filtered off, the filtrate was concentrated under reduced pressure. The residue was purified by automated flash chromatography using 0-60% ethyl acetate in dichloromethane as eluent, to give 3,4-dichloro-1-methyl-1H-pyrazolo[3,4-d]pyrimidine as a colorless solid (55.1 mg, yield 76.8%). $^1$H-NMR (DMSO-D$_6$) δ: 8.92 (1H, s), 4.04 (3H, s). MS: m/z 203.0 (M+H$^+$).

Step 2: The title compound was prepared according to the general procedure of Example 2.85 using 3,4-dichloro-1-methyl-1H-pyrazolo[3,4-d]pyrimidine obtained above and homosulfamine hydrochloride. $^1$H-NMR (DMSO-D$_6$) δ: 8.27 (1H, s), 8.11 (1H, t, J=6.1 Hz), 7.73-7.78 (2H, m), 7.47-7.52 (2H, m), 7.30 (2H, s), 4.82 (2H, d, J=6.1 Hz), 3.87 (3H, s). MS: m/z 353.1 (M+H$^+$).

Example 2.91

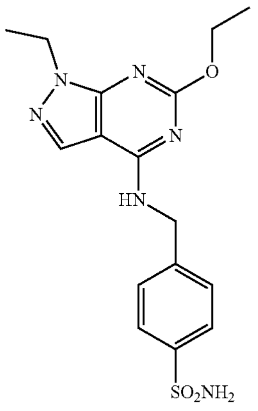 [SMILES: CCOc1nc(NCc2ccc(S(N)(=O)=O)cc2)c2cnn(CC)c2n1]

4-((6-Ethoxy-1-ethyl-1H-pyrazolo[3,4-d]pyrimidin-4-yl)aminomethyl)benzenesulfonamide To 4-((6-chloro-1-ethyl-1H-pyrazolo[3,4-d]pyrimidin-4-yl)aminomethyl)benzenesulfonamide (40.9 mg) obtained in Example 2.83 was added 20% sodium ethoxide ethanol solution (1 mL), and the mixture was stirred at 80° C. for 6 hours. The resulting mixture was diluted with DMSO and water, and purified by preparative HPLC using 0.1 volume/volume percent (v/v %) formic acid-distilled water and 0.1 v/v % formic acid-acetonitrile as eluent, to give the title compound as a colorless amorphous (22.4 mg, yield 53%). $^1$H-NMR (CD$_3$OD) δ: 8.37 (1H, br s), 7.92 (1H, s), 7.86 (2H, d, J=8.0 Hz), 7.53 (2H, d, J=8.0 Hz), 4.50-4.54 (4H, m), 4.38 (2H, q, J=7.0 Hz), 4.26 (2H, q, J=7.2 Hz), 1.40 (3H, t, J=7.4 Hz), 1.33 (3H, t, J=7.1 Hz). MS: m/z 377.1 (M+H$^+$).

Example 2.92

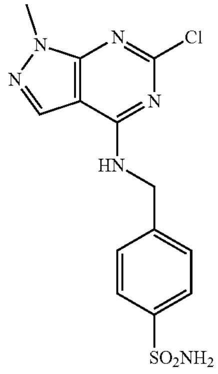 [SMILES: Cn1ncc2c(NCc3ccc(S(N)(=O)=O)cc3)nc(Cl)nc21]

4-((6-Chloro-1-methyl-1H-pyrazolo[3,4-d]pyrimidin-4-yl)aminomethyl)-benzenesulfonamide The title compound was prepared according to the general procedure of Example 2.85 using 4,6-dichloro-1-methyl-1H-pyrazolo[3,4-d]pyrimidine and homosulfamine hydrochloride. MS: m/z 353.0 (M+H$^+$).

Example 2.93

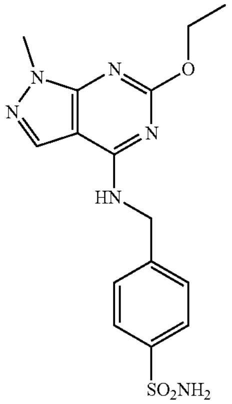

4-((6-Ethoxy-1-methyl-1H-pyrazolo[3,4-d]pyrimidin-4-yl)aminomethyl)-benzenesulfonamide The title compound was prepared according to the general procedure of Example 2.91 using 4-((6-chloro-1-methyl-1H-pyrazolo[3,4-d]pyrimidin-4-yl)aminomethyl)benzenesulfonamide obtained above. $^1$H-NMR (DMSO-$D_6$) δ: 8.84 (1H, t, J=5.8 Hz), 8.00 (1H, s), 7.78 (2H, d, J=8.6 Hz), 7.50 (2H, d, J=8.6 Hz), 7.31 (2H, br s), 4.74 (2H, d, J=5.5 Hz), 4.27 (2H, q, J=7.0 Hz), 3.78 (3H, s), 1.25 (3H, t, J=7.1 Hz). MS: m/z 363.1 (M+H$^+$).

Example 2.94

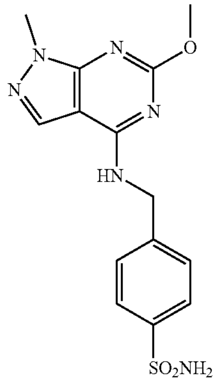 [SMILES: COc1nc(NCc2ccc(S(N)(=O)=O)cc2)c2cnn(C)c2n1]

4-((6-Methoxy-1-methyl-1H-pyrazolo[3,4-d]pyrimidin-4-yl)aminomethyl)-benzenesulfonamide The title compound was prepared according to the general procedure of Example 2.91 using 4-((6-chloro-1-methyl-1H-pyrazolo[3,4-d]pyrimidin-4-yl)aminomethyl)benzenesulfonamide obtained in Example 2.92 and 1 mol/1 sodium methoxide solution. $^1$H-NMR (DMSO-$D_6$) δ: 8.86 (1H, t, J=5.5 Hz), 8.00 (1H, s), 7.78 (2H, d, J=8.5 Hz), 7.51 (2H, d, J=8.5 Hz), 7.32 (2H, s), 4.74 (2H, d, J=5.5 Hz), 3.82 (3H, s), 3.80 (3H, s). MS: m/z 349.1 (M+H$^+$).

Example 2.95

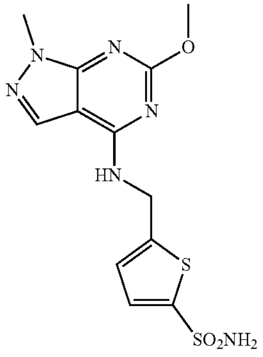 [SMILES: COc1nc(NCc2ccc(S(N)(=O)=O)s2)c2cnn(C)c2n1]

5-((6-Methoxy-1-methyl-1H-pyrazolo[3,4-d]pyrimidin-4-yl)aminomethyl)thiophene-2-sulfonamide The title compound was prepared according to the general procedure of Example 2.91 using 5-((6-chloro-1-methyl-1H-pyrazolo[3,4-d]pyrimidin-4-yl)aminomethyl)thiophene-2-sulfonamide obtained in Example 2.85 and 1 mol/1 sodium methoxide solution. $^1$H-NMR ($CD_3OD$) δ: 7.88 (1H, s), 7.44 (1H, d, J=3.7 Hz), 7.05 (1H, d, J=3.7 Hz), 4.93 (2H, s), 4.00 (3H, s), 3.85 (3H, s). MS: m/z 365 (M+H$^+$).

Example 2.96

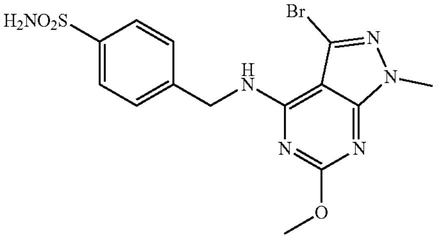 [SMILES: COc1nc(NCc2ccc(S(N)(=O)=O)cc2)c2c(Br)nn(C)c2n1]

4-((3-Bromo-6-methoxy-1-methyl-1H-pyrazolo[3,4-d]pyrimidin-4-yl)aminomethyl)-benzenesulfonamide The title compound was prepared according to the general procedure of Example 2.91 using 4-((3-bromo-6-chloro-1-methyl-1H-pyrazolo[3,4-d]pyrimidin-4-yl)aminomethyl) benzenesulfonamide obtained in Example 2.87 and 1 mol/1 sodium methoxide solution. $^1$H-NMR (DMSO-$D_6$) δ: 7.86 (1H, t, J=6.1 Hz), 7.76 (2H, d, J=8.0 Hz), 7.51 (2H, d, J=8.0 Hz), 7.31 (2H, s), 4.78 (2H, d, J=6.1 Hz), 3.80 (3H, s), 3.77 (3H, s). MS: m/z 427.0 (M+$H^+$).

Example 2.97

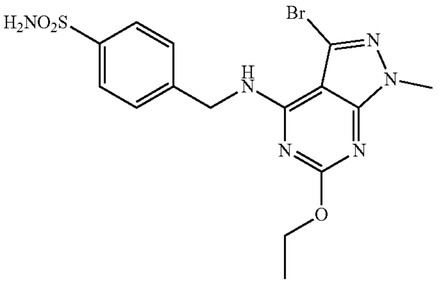 [SMILES: CCOc1nc(NCc2ccc(S(N)(=O)=O)cc2)c2c(Br)nn(C)c2n1]

4-((3-Bromo-6-ethoxy-1-methyl-1H-pyrazolo[3,4-d]pyrimidin-4-yl)aminomethyl)-benzenesulfonamide The title compound was prepared according to the general procedure of Example 2.91 using 4-((3-bromo-6-chloro-1-methyl-1H-pyrazolo[3,4-d]pyrimidin-4-yl)aminomethyl) benzenesulfonamide obtained in Example 2.87. $^1$H-NMR (DMSO-$D_6$) δ: 7.83 (1H, t, J=6.1 Hz), 7.74-7.79 (2H, m), 7.47-7.52 (2H, m), 7.31 (2H, s), 4.78 (2H, d, J=6.1 Hz), 4.24 (2H, q, J=7.2 Hz), 3.76 (3H, s), 1.22 (3H, t, J=7.1 Hz). MS: m/z 440.0 (M+$H^+$).

Example 2.98

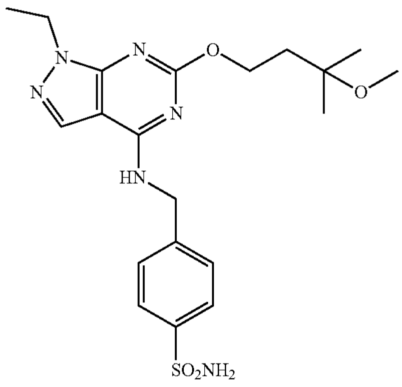 [SMILES: CCn1ncc2c(NCc3ccc(S(N)(=O)=O)cc3)nc(OCCC(C)(C)OC)nc21]

4-((1-Ethyl-6-(3-methoxy-3-methylbutoxy)-1H-pyrazolo[3,4-d]pyrimidin-4-yl)aminomethyl)-benzenesulfonamide To 3-methoxy-3-methylbutanol (1 mL) was added potassium tert-butoxide (147 mg) at room temperature. After stirring at the same temperature for 20 min, 4-((6-chloro-1-ethyl-1H-pyrazolo[3,4-d]pyrimidin-4-yl)aminomethyl)benzenesulfonamide (109 mg) obtained in Example 2.83 was added to the mixture. The resulting mixture was stirred at 70° C. for 10 hours, and diluted with dimethyl sulfoxide, and purified by preparative HPLC using 0.1 v/v % formic acid-distilled water and 0.1 v/v % formic acid-acetonitrile as eluent, to give the title compound as a colorless solid (102 mg, yield 76%). $^1$H-NMR (DMSO-$D_6$) δ: 8.83 (1H, t, J=6.0 Hz), 8.00 (1H, s), 7.78 (2H, d, J=8.0 Hz), 7.50 (2H, d, J=8.0 Hz), 7.31 (2H, s), 4.74 (2H, d, J=6.0 Hz), 4.28 (2H, t, J=7.7 Hz), 4.19 (2H, q, J=7.3 Hz), 3.10 (3H, s), 1.85 (2H, t, J=7.7 Hz), 1.34 (3H, t, J=7.3 Hz), 1.13 (6H, s). MS: m/z 449.1 (M+$H^+$).

Example 2.99

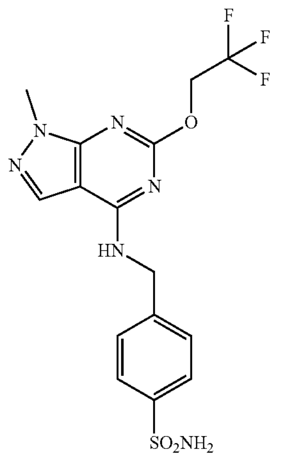 [SMILES: Cn1ncc2c(NCc3ccc(S(N)(=O)=O)cc3)nc(OCC(F)(F)F)nc21]

4-((6-(2,2,2-Trifluoroethoxy)-1-methyl-1H-pyrazolo[3,4-d]pyrimidin-4-yl)aminomethyl)-benzenesulfonamide The title compound was prepared according to the general procedure of Example 2.98 using 4-((6-chloro-1-methyl-1H-pyrazolo[3,4-d]pyrimidin-4-yl)aminomethyl)benzenesulfonamide obtained in Example 2.92 and 2,2,2-trifluoroethanol in dimethyl sulfoxide. $^1$H-NMR (DMSO-$D_6$) δ: 9.06 (1H, t, J=5.8 Hz), 8.06 (1H, s), 7.79 (2H, d, J=8.5 Hz), 7.52 (2H, d, J=8.5 Hz), 7.33 (2H, s), 5.00-4.92 (2H, m), 4.78 (2H, d, J=6.1 Hz), 3.82 (3H, s). MS: m/z 417.1 ($M+H^+$).

Example 2.100

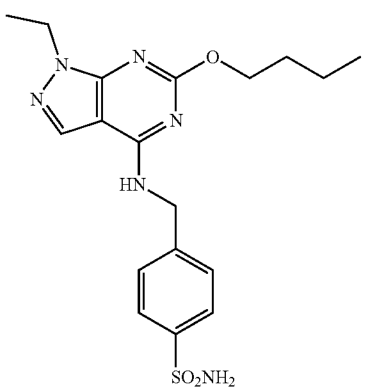 [SMILES: CCCCOc1nc(NCc2ccc(S(N)(=O)=O)cc2)c2cnn(CC)c2n1]

4-((6-Butoxy-1-ethyl-1H-pyrazolo[3,4-d]pyrimidin-4-yl)aminomethyl)benzenesulfonamide The title compound was prepared according to the general procedure of Example 2.98 using 4-((6-chloro-1-ethyl-1H-pyrazolo[3,4-d]pyrimidin-4-yl)aminomethyl)benzenesulfonamide obtained in Example 2.83 and 1-butanol. $^1$H-NMR (DMSO-$D_6$) δ: 8.82 (1H, t, J=5.8 Hz), 8.00 (1H, s), 7.78 (2H, d, J=8.6 Hz), 7.50 (2H, d, J=8.6 Hz), 7.31 (2H, s), 4.74 (2H, d, J=5.5 Hz), 4.24-4.15 (4H, m), 1.67-1.59 (2H, m), 1.42-1.30 (5H, m), 0.90 (3H, t, J=7.4 Hz). MS: m/z 405.1 ($M+H^+$).

Example 2.101

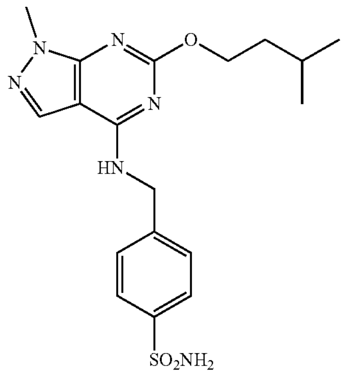 [SMILES: CC(C)CCOc1nc(NCc2ccc(S(N)(=O)=O)cc2)c2cnn(C)c2n1]

4-((1-Methyl-6-(3-methylbutoxy)-1H-pyrazolo[3,4-d]pyrimidin-4-yl)aminomethyl)-benzenesulfonamide The title compound was prepared according to the general procedure of Example 2.98 using 4-((6-chloro-1-methyl-1H-pyrazolo[3,4-d]pyrimidin-4-yl)aminomethyl)benzenesulfonamide obtained in Example 2.92 and 3-methyl-1-butanol. $^1$H-NMR (DMSO-$D_6$) δ: 8.83 (1H, t, J=5.5 Hz), 7.99 (1H, s), 7.78 (2H, d, J=7.9 Hz), 7.50 (2H, d, J=7.9 Hz), 7.32 (2H, s), 4.75 (2H, d, J=5.5 Hz), 4.26 (2H, t, J=6.7 Hz), 3.78 (3H, s), 1.75-1.64 (1H, m), 1.55 (2H, q, J=6.7 Hz), 0.90 (6H, d, J=6.7 Hz). MS: m/z 405.1 ($M+H^+$).

Example 2.102

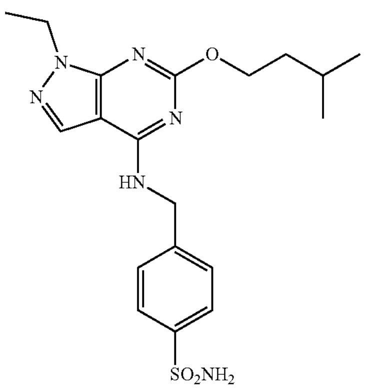 [SMILES: CCn1ncc2c(NCc3ccc(S(N)(=O)=O)cc3)nc(OCCC(C)C)nc21]

4-((1-Ethyl-6-(3-methylbutoxy)-1H-pyrazolo[3,4-d]pyrimidin-4-yl)aminomethyl)-benzenesulfonamide The title compound was prepared according to the general procedure of Example 2.98 using 4-((6-chloro-1-ethyl-1H-pyrazolo[3,4-d]pyrimidin-4-yl)aminomethyl)benzenesulfonamide obtained in Example 2.83 and 3-methyl-1-butanol. $^1$H-NMR (DMSO-$D_6$) δ: 8.63 (1H, br m), 7.97 (1H, br s), 7.78 (2H, d, J=8.6 Hz), 7.50 (2H, d, J=8.6 Hz), 7.16 (2H, s), 4.75 (2H, d, J=6.1 Hz), 4.28 (2H, t, J=6.7 Hz), 4.19 (2H, q, J=7.2 Hz), 1.76-1.65 (1H, m), 1.56 (2H, q, J=6.7 Hz), 1.34 (3H, t, J=7.2 Hz), 0.91 (6H, d, J=6.1 Hz). MS: m/z 419.2 ($M+H^+$).

Example 2.103

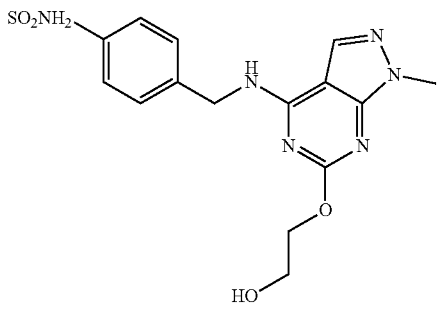 [SMILES: Cn1ncc2c(NCc3ccc(S(N)(=O)=O)cc3)nc(OCCO)nc21]

4-((6-(2-Hydroxyethoxy)-1-methyl-1H-pyrazolo[3,4-d]pyrimidin-4-yl)aminomethyl)-benzenesulfonamide The title compound was prepared according to the general procedure of Example 2.98 using 4-((6-chloro-1-methyl-1H-pyrazolo[3,4-d]pyrimidin-4-yl)aminomethyl)benzenesulfonamide obtained in Example 2.92, 2-(tert-butyldimethylsilyloxy)ethanol and sodium tert-butoxide. $^1$H-NMR (DMSO-D$_6$) δ: 8.85 (1H, t, J=5.8 Hz), 8.00 (1H, s), 7.78 (2H, d, J=8.0 Hz), 7.50 (2H, d, J=8.6 Hz), 7.32 (2H, s), 4.75 (2H, d, J=5.5 Hz), 4.24 (2H, t, J=5.2 Hz), 3.79 (3H, s), 3.66 (2H, t, J=5.2 Hz), 3.54-3.35 (1H, br m). MS: m/z 379.1 (M+H$^+$).

Example 2.104

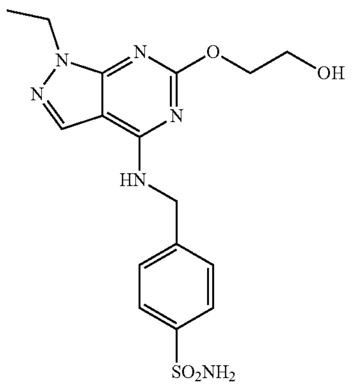 [SMILES: CCn1ncc2c(NCc3ccc(S(N)(=O)=O)cc3)nc(OCCO)nc21]

4-((1-Ethyl-6-(2-hydroxyethoxy)-1H-pyrazolo[3,4-d]pyrimidin-4-yl)aminomethyl)-benzenesulfonamide The title compound was prepared according to the general procedure of Example 2.98 using 4-((6-chloro-1-ethyl-1H-pyrazolo[3,4-d]pyrimidin-4-yl)aminomethyl)benzenesulfonamide obtained in Example 2.83 and ethylene glycol. $^1$H-NMR (DMSO-D$_6$) δ: 8.83 (1H, t, J=5.6 Hz), 8.01 (1H, s), 7.78 (2H, d, J=8.3 Hz), 7.51 (2H, d, J=8.3 Hz), 7.31 (2H, s), 4.83-4.81 (1H, br m), 4.75 (2H, d, J=5.4 Hz), 4.26-4.16 (4H, m), 3.68-3.63 (2H, m), 1.34 (3H, t, J=7.3 Hz). MS: m/z 393 (M+H$^+$).

Example 2.105

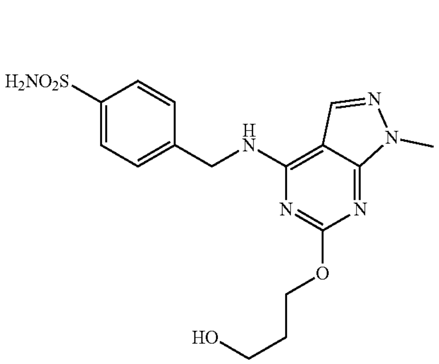 [SMILES: Cn1ncc2c(NCc3ccc(S(N)(=O)=O)cc3)nc(OCCCO)nc21]

4-((6-(3-Hydroxypropoxy)-1-methyl-1H-pyrazolo[3,4-d]pyrimidin-4-yl)aminomethyl)-benzenesulfonamide The title compound was prepared according to the general procedure of Example 2.98 using 4-((6-chloro-1-methyl-1H-pyrazolo[3,4-d]pyrimidin-4-yl)aminomethyl)benzenesulfonamide obtained in Example 2.92, 1,3-propanediol and sodium tert-butoxide. $^1$H-NMR (DMSO-D$_6$) δ: 8.82 (1H, t, J=5.8 Hz), 7.99 (1H, s), 7.76-7.80 (2H, m), 7.48-7.53 (2H, m), 7.32 (2H, s), 4.75 (2H, d, J=5.5 Hz), 4.29 (2H, t, J=6.4 Hz), 3.79 (3H, s), 3.51 (2H, t, J=6.1 Hz), 3.33-3.43 (1H, br m), 1.77-1.84 (2H, m). MS: m/z 393.1 (M+H$^+$).

Example 2.106

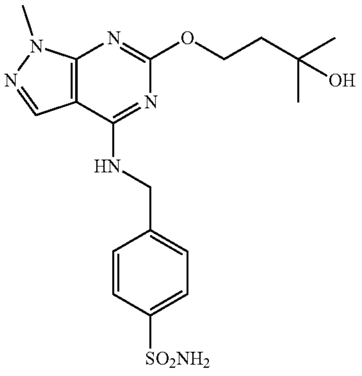 [SMILES: Cn1ncc2c(NCc3ccc(S(N)(=O)=O)cc3)nc(OCCC(C)(C)O)nc21]

4-((6-(3-Hydroxy-3-methylbutoxy)-1-methyl-1H-pyrazolo[3,4-d]pyrimidin-4-yl)aminomethyl)-benzenesulfonamide The title compound was prepared according to the general procedure of Example 2.98 using 4-((6-chloro-1-methyl-1H-pyrazolo[3,4-d]pyrimidin-4-yl)aminomethyl)benzenesulfonamide obtained in Example 2.92 and 3-methyl-1,3-butanediol. $^1$H-NMR (DMSO-D$_6$) δ: 8.64-8.62 (1H, br m), 7.96 (1H, br s), 7.77 (2H, d, J=8.6 Hz), 7.50 (2H, d, J=8.0 Hz), 7.16 (2H, s), 4.75 (2H, d, J=6.1 Hz), 4.37 (2H, t, J=7.4 Hz), 4.15 (1H, s), 3.78 (3H, s), 1.80 (2H, t, J=7.4 Hz), 1.15 (6H, s). MS: m/z 421 (M+H$^+$).

Example 2.107

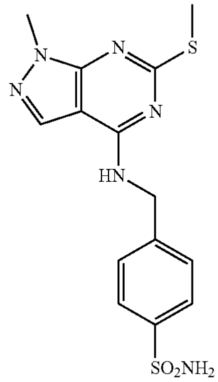

4-((1-Methyl-6-(methylsulfanyl)-1H-pyrazolo[3,4-d]pyrimidin-4-yl)aminomethyl)-benzenesulfonamide To a mixture of 4-((6-chloro-1-methyl-1H-pyrazolo[3,4-d]pyrimidin-4-yl)aminomethyl)benzenesulfonamide (30.2 mg) obtained in Example 2.92 in dimethyl sulfoxide (1 mL) was added sodium thiomethoxide (11.0 mg), then the mixture was stirred at 80° C. for 11 hours. The resulting mixture was quenched by adding ethyl acetate and saturated ammonium chloride. The organic layer was separated and washed with water and brine successively, then dried over anhydrous sodium sulfate. After the resulting solid was filtered off, the filtrate was concentrated under reduced pressure. The residue was purified by preparative HPLC using 0.1 v/v % formic acid-distilled water and 0.1 v/v % formic acid-acetonitrile as eluent, to give the title compound as a colorless solid (11.5 mg, yield 37%). $^1$H-NMR (DMSO-$D_6$) δ: 8.92 (1H, t, J=5.5 Hz), 8.03 (1H, s), 7.78 (2H, d, J=8.6 Hz), 7.51 (2H, d, J=8.6 Hz), 7.32 (2H, s), 4.77 (2H, d, J=5.5 Hz), 3.83 (3H, s), 2.43 (3H, s). MS: m/z 365.1 (M+H$^+$).

Example 2.108

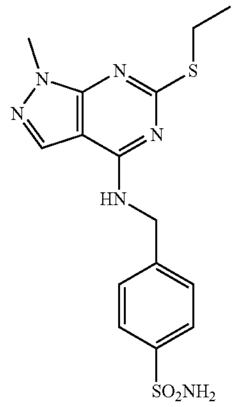 [SMILES: CCSc1nc(NCc2ccc(S(N)(=O)=O)cc2)c2cnn(C)c2n1]

4-((6-(Ethylsulfanyl)-1-methyl-1H-pyrazolo[3,4-d]pyrimidin-4-yl)aminomethyl)-benzenesulfonamide The title compound was prepared according to the general procedure of Example 2.107 using 4-((6-chloro-1-methyl-1H-pyrazolo[3,4-d]pyrimidin-4-yl)aminomethyl)benzenesulfonamide obtained in Example 2.92 and sodium ethanethiolate. $^1$H-NMR (DMSO-$D_6$) δ: 8.93 (1H, t, J=5.8 Hz), 8.03 (1H, s), 7.78 (2H, d, J=8.6 Hz), 7.50 (2H, d, J=8.6 Hz), 7.32 (2H, s), 4.76 (2H, d, J=5.5 Hz), 3.83 (3H, s), 3.01 (2H, q, J=7.4 Hz), 1.23 (3H, t, J=7.4 Hz). MS: m/z 379.1 (M+H$^+$).

Example 2.109

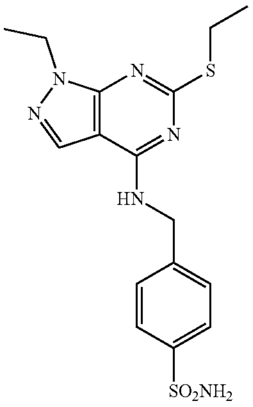

4-((1-Ethyl-6-(ethylsulfanyl)-1H-pyrazolo[3,4-d]pyrimidin-4-yl)aminomethyl)-benzenesulfonamide The title compound was prepared according to the general procedure of Example 2.107 using 4-((6-chloro-1-ethyl-1H-pyrazolo[3,4-d]pyrimidin-4-yl)aminomethyl)benzenesulfonamide obtained in Example 2.83 and sodium ethanethiolate. $^1$H-NMR (DMSO-$D_6$) δ: 8.76-8.69 (1H, br m), 8.01 (1H, s), 7.78 (2H, d, J=8.0 Hz), 7.50 (2H, d, J=8.0 Hz), 7.17 (2H, s), 4.76 (2H, d, J=6.1 Hz), 4.24 (2H, q, J=7.4 Hz), 3.03 (2H, q, J=7.4 Hz), 1.36 (3H, t, J=7.4 Hz), 1.26 (3H, t, J=7.4 Hz). MS: m/z 393 (M+H$^+$).

Example 2.110

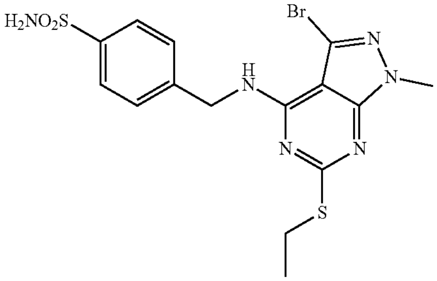

4-((3-Bromo-6-(ethylsulfanyl)-1-methyl-1H-pyrazolo[3,4-d]pyrimidin-4-yl)aminomethyl)-benzenesulfonamide The title compound was prepared according to the general procedure of Example 2.107 using 4-((3-bromo-6-chloro-1-methyl-1H-pyrazolo[3,4-d]pyrimidin-4-yl)aminomethyl)benzenesulfonamide obtained in Example 2.85 and sodium ethanethiolate. $^1$H-NMR (DMSO-$D_6$) δ: 7.93 (1H, t, J=6.1 Hz), 7.74-7.79 (2H, m), 7.47-7.52 (2H, m), 7.31 (2H, s), 4.79 (2H, d, J=6.1 Hz), 3.80 (3H, s), 2.96 (2H, q, J=7.4 Hz), 1.18 (3H, t, J=7.4 Hz). MS: m/z 457.0 (M+H$^+$).

Example 2.111

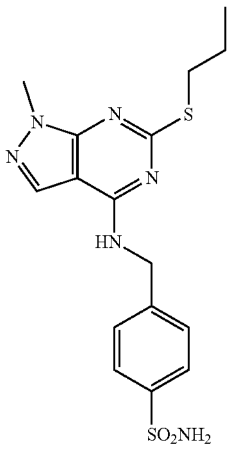 [SMILES: CCCSc1nc(NCc2ccc(S(N)(=O)=O)cc2)c2cnn(C)c2n1]

4-((1-Methyl-6-(propylsulfanyl)-1H-pyrazolo[3,4-d]pyrimidin-4-yl)aminomethyl)-benzenesulfonamide The title compound was prepared according to the general procedure of Example 2.107 using 4-((6-chloro-1-methyl-1H-pyrazolo[3,4-d]pyrimidin-4-yl)aminomethyl)benzenesulfonamide obtained in Example 2.92 and sodium 1-propanethiolate. $^1$H-NMR (DMSO-$D_6$) δ: 8.92 (1H, t, J=6.1 Hz), 8.03 (1H, s), 7.78 (2H, d, J=8.6 Hz), 7.49 (2H, d, J=8.6 Hz), 7.32 (2H, s), 4.77 (2H, d, J=6.1 Hz), 3.82 (3H, s), 2.99 (2H, t, J=7.4 Hz), 1.65-1.54 (2H, m), 0.90 (3H, t, J=7.4 Hz). MS: m/z 393.2 (M+H$^+$).

Example 2.112

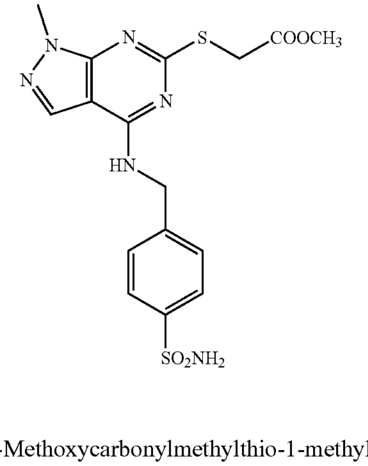

4-((6-Methoxycarbonylmethylthio-1-methyl-1H-pyrazolo[3,4-d]pyrimidin-4-yl)aminomethyl)benzenesulfonamide The title compound was prepared according to the general procedure of Example 2.107 using 4-((6-chloro-1-methyl-1H-pyrazolo[3,4-d]pyrimidin-4-yl)aminomethyl)benzenesulfonamide obtained in Example 2.92, methyl thioglycolate and potassium tert-butoxide. $^1$H-NMR (DMSO-$D_6$) δ: 8.98 (1H, t, J=6.1 Hz), 8.04 (1H, s), 7.79 (2H, d, J=8.6 Hz), 7.50 (2H, d, J=8.6 Hz), 7.33 (2H, s), 4.76 (2H, d, J=6.1 Hz), 3.92 (2H, s), 3.81 (3H, s), 3.57 (3H, s). MS: m/z 423.1 (M+H$^+$).

Example 2.113

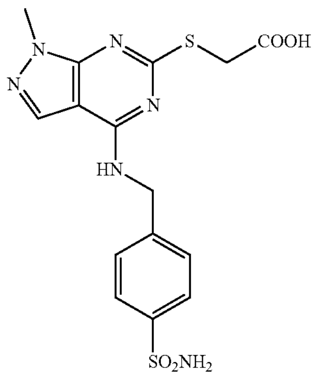 [SMILES: Cn1ncc2c(NCc3ccc(S(N)(=O)=O)cc3)nc(SCC(=O)O)nc21]

4-((6-Carboxymethylthio-1-methyl-1H-pyrazolo[3,4-d]pyrimidin-4-yl)aminomethyl)-benzenesulfonamide To a solution of 4-((6-methoxycarbonylmethylthio-1-methyl-1H-pyrazolo[3,4-d]pyrimidin-4-yl)aminomethyl)benzenesulfonamide (43.4 mg) obtained in Example 2.112 in tetrahydrofuran (1 mL) and methanol (1 mL) was added 1 mol/1 sodium hydroxide solution (1 mL) at room temperature. The mixture was stirred at room temperature overnight, then 1 mol/1 hydrochloric acid solution (1 mL) was added to the mixture. The resulting mixture was evaporated under reduced pressure. The residue was washed with water, and dried under reduced pressure, to give the title compound as a colorless solid (31.1 mg, yield 74%). $^1$H-NMR (DMSO-$D_6$) δ: 8.77 (1H, br s), 8.01 (1H, br s), 7.79 (2H, d, J=8.0 Hz), 7.52 (2H, d, J=8.0 Hz), 7.17 (2H, s), 4.77 (2H, d, J=6.1 Hz), 3.85 (2H, s), 3.81 (3H, s). MS: m/z 409 (M+H$^+$).

Example 2.114

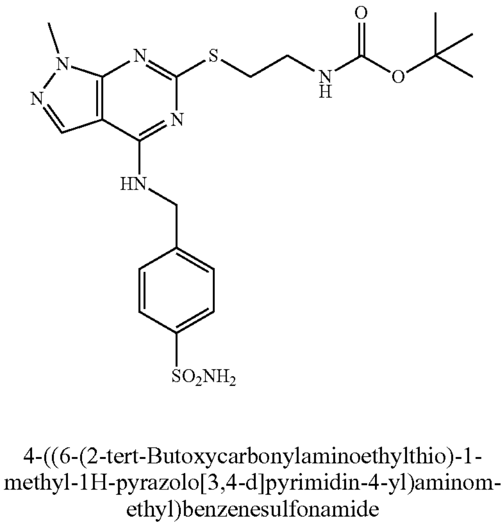

4-((6-(2-tert-Butoxycarbonylaminoethylthio)-1-methyl-1H-pyrazolo[3,4-d]pyrimidin-4-yl)aminomethyl)benzenesulfonamide The title compound was prepared according to the general procedure of Example 2.107 using 4-((6-chloro-1-methyl- 1H-pyrazolo[3,4-d]pyrimidin-4-yl)aminomethyl)benzenesulfonamide obtained in Example 2.92, tert-butyl (2-sulfanylethyl)carbamate and potassium tert-butoxide. $^{1}$H-NMR (DMSO-$D_6$) δ: 8.93 (1H, t, J=5.8 Hz), 8.04 (1H, s), 7.78 (2H, d, J=8.6 Hz), 7.51 (2H, d, J=8.6 Hz), 7.31 (2H, s), 7.08 (1H, t, J=5.5 Hz), 4.79 (2H, d, J=6.1 Hz), 3.84 (3H, s), 3.27-3.19 (2H, m), 3.07 (2H, t, J=6.7 Hz), 1.37 (9H, s). MS: m/z 494.1 (M+H$^+$).

Example 2.115

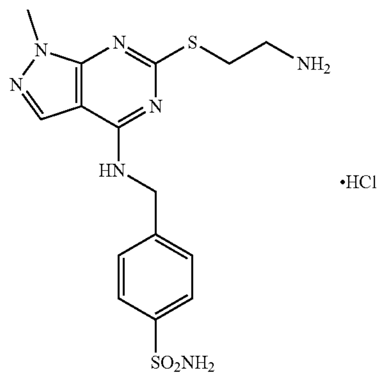 [SMILES: Cn1ncc2c(NCc3ccc(S(N)(=O)=O)cc3)nc(SCCN)nc21 ; Cl]

4-((6-(2-Aminoethylthio)-1-methyl-1H-pyrazolo[3,4-d]pyrimidin-4-yl)aminomethyl)-benzenesulfonamide hydrochloride To a mixture of 4-((6-(2-tert-butoxycarbonylamino)ethylthio-1-methyl-1H-pyrazolo[3,4-d]pyrimidin-4-yl)aminomethyl)benzenesulfonamid (28.3 mg) obtained in Example 2.114 in methanol (1 mL) was added 4 M hydrogen chloride in dioxane (1 mL) at room temperature. The resulting mixture was stirred at the same temperature for 2 hours. The reaction mixture was evaporated under reduced pressure and then dried under reduced pressure, to give the title compound as a yellow solid (23.0 mg, yield 93%). $^{1}$H-NMR (DMSO-$D_6$) δ: 9.07 (1H, br m), 8.15-7.92 (4H, m), 7.86-7.75 (2H, m), 7.60-7.28 (4H, m), 4.82-4.73 (2H, m), 3.87 (3H, br s), 3.36-3.07 (4H, m). MS: m/z 394 (M+H$^+$).

Example 2.116

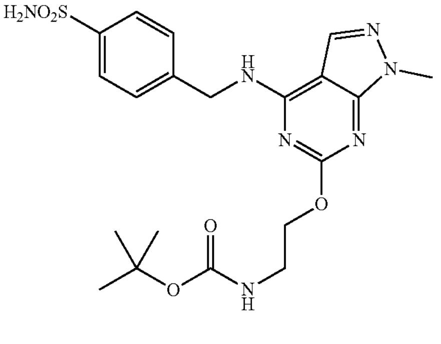 [SMILES: Cn1ncc2c(NCc3ccc(S(N)(=O)=O)cc3)nc(OCCNC(=O)OC(C)(C)C)nc21]

4-((6-(2-tert-Butoxycarbonylaminoethoxy)-1-methyl-1H-pyrazolo[3,4-d]pyrimidin-4-yl)aminomethyl)benzenesulfonamide The title compound was prepared according to the general procedure of Example 2.98 using 4-((6-chloro-1-methyl-1H-pyrazolo[3,4-d]pyrimidin-4-yl)aminomethyl)benzenesulfonamide obtained in Example 2.92, tert-butyl (2-hydroxyethyl)carbamate and sodium tert-butoxide.

Example 2.117

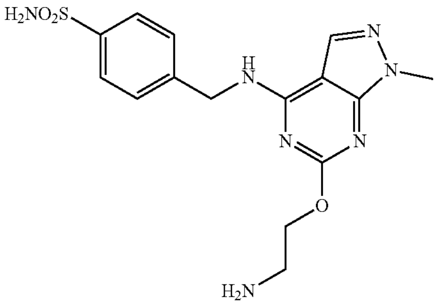 [SMILES: Cn1ncc2c(NCc3ccc(S(N)(=O)=O)cc3)nc(OCCN)nc21]

4-((6-(2-Aminoethoxy)-1-methyl-1H-pyrazolo[3,4-d]pyrimidin-4-yl)aminomethyl)benzenesulfonamide The title compound was prepared according to the general procedure of Example 2.115 using 4-((6-(2-tert-butoxycarbonylaminoethoxy)-1-methyl-1H-pyrazolo[3,4-d]pyrimidin-4-yl)aminomethyl)benzenesulfonamide obtained above. MS: m/z 378.1 (M+H$^+$).

Example 2.118

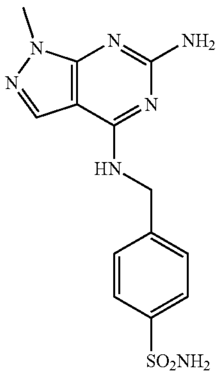 [SMILES: Cn1ncc2c(NCc3ccc(S(N)(=O)=O)cc3)nc(N)nc21]

4-((6-Amino-1-methyl-1H-pyrazolo[3,4-d]pyrimidin-4-yl)aminomethyl)benzenesulfonamide To a mixture of 4-((6-chloro-1-methyl-1H-pyrazolo[3,4-d]pyrimidin-4-yl)aminomethyl)-benzenesulfonamide (42.8 mg) obtained in Example 2.92 in isopropanol (0.6 mL) was added 28% ammonia solution (0.6 mL). The mixture was stirred at 120 to 140° C. under microwave irradiation until starting material was disappeared (for about 18 h). The reaction mixture was concentrated under reduced pressure.

The residue was washed with ethyl acetate and then purified by automated flash chromatography using 0-12% methanol in dichloromethane as eluent, to give the title compound as a colorless solid (21.0 mg, yield 51.9%). $^1$H-NMR ($CD_3OD$) δ: 7.85 (2H, d, J=8.6 Hz), 7.80 (1H, s), 7.53 (2H, d, J=8.6 Hz), 4.80 (2H, s), 3.78 (3H, s). MS: m/z 334.1 ($M+H^+$).

Example 2.119

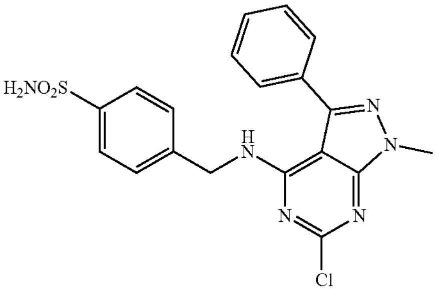

4-((6-Chloro-1-methyl-3-phenyl-1H-pyrazolo[3,4-d]pyrimidin-4-yl)aminomethyl)benzenesulfonamide To a mixture of 4-((3-bromo-6-chloro-1-methyl-1H-pyrazolo[3,4-d]pyrimidin-4-yl)aminomethyl)benzenesulfonamide (251 mg) obtained in Example 2.87 Step 2, phenylboronic acid (72.0 mg), tripotassium phosphate (187 mg) in 1,4-dioxane (6.0 mL) and water (1.5 mL) was added [1,1'-bis(diphenylphosphino)ferrocene]palladium(II) dichloride dichloromethane adduct (49.8 mg). After stirring at 100° C. for 1 hour under microwave irradiation, the resulting mixture was quenched by adding water and extracted with ethyl acetate. The combined organic layer was washed with water and brine successively, and dried over anhydrous sodium sulfate. After the resulting solid was filtered off, the filtrate was concentrated under reduced pressure. The residue was purified by preparative HPLC using 0.1 v/v % formic acid-distilled water and 0.1 v/v % formic acid-acetonitrile as eluent, to give the title compound as a pale brown solid (118 mg, yield 47.3%). $^1$H-NMR (DMSO-$D_6$) δ: 7.75-7.79 (2H, m), 7.66-7.70 (2H, m), 7.47-7.57 (6H, m), 7.32 (2H, s), 4.74 (2H, d, J=6.1 Hz), 3.92 (3H, s). MS: m/z 429.1 ($M+H^+$).

Example 2.120

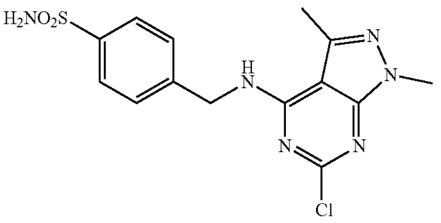 [SMILES: Cc1nn(C)c2nc(Cl)nc(NCc3ccc(S(N)(=O)=O)cc3)c12]

4-((6-Chloro-1,3-dimethyl-1H-pyrazolo[3,4-d]pyrimidin-4-yl)aminomethyl)-benzenesulfonamide The title compound was prepared according to the general procedure of Example 2.119 using 4-((3-bromo-6-chloro-1-methyl-1H-pyrazolo[3,4-d]pyrimidin-4-yl)aminomethyl)benzenesulfonamide obtained in Example 2.87 Step 2 and trimethylboroxine (3.5 M solution in THF). $^1$H-NMR (DMSO-$D_6$) δ: 8.25 (1H, t, J=6.1 Hz), 7.74-7.79 (2H, m), 7.49-7.54 (2H, m), 7.32 (2H, s), 4.75 (2H, d, J=6.1 Hz), 3.77 (3H, s), 2.57 (3H, s). MS: m/z 367.1 ($M+H^+$).

Example 2.121

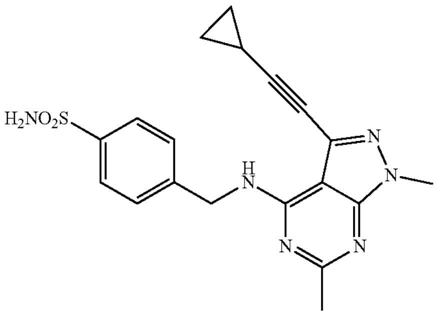 [SMILES: Cc1nc(NCc2ccc(S(N)(=O)=O)cc2)c2c(C#CC3CC3)nn(C)c2n1]

4-((3-(Cyclopropylethynyl)-1,6-dimethyl-1H-pyrazolo[3,4-d]pyrimidin-4-yl)aminomethyl)benzenesulfonamide To a mixture of 4-((3-bromo-1,6-dimethyl-1H-pyrazolo[3,4-d]pyrimidin-4-yl)aminomethyl)benzene-1-sulfonamide (50.7 mg) obtained in Example 2.89 N,N-diisopropylethylamine (0.11 mL), copper(I) iodide (8.7 mg) and cyclopropylacetylene (0.030 mL) in N,N-dimethylformamide (1.25 mL) was added bis(triphenylphosphine)palladium(II) dichloride (49.8 mg) under nitrogen atmosphere. After stirring at 100° C. for 2.5 hours by microwave, the resulting mixture was diluted with ethyl acetate and water, and filtered on a Celite pad. The organic layer was separated from aqueous layer, washed with brine, and dried over anhydrous sodium sulfate. After the resulting solid was filtered off, the filtrate was concentrated under reduced pressure. The residue was purified by automated flash chromatography using 20-100% ethyl acetate in dichloromethane as eluent, followed by preparative HPLC using 0.1 v/v % formic acid-distilled water and 0.1 v/v % formic acid-acetonitrile as eluent, to give the title compound as a pale brown solid (24.7 mg, yield 50.5%). $^1$H-NMR (DMSO-$D_6$) δ: 7.76-7.81 (2H, m), 7.50-7.54 (2H, m), 7.33 (2H, s), 7.15-7.22 (1H, m), 4.86 (2H, d, J=6.1 Hz), 3.83 (3H, s), 2.40 (3H, s), 1.60-1.67 (1H, m), 0.89-0.93 (2H, m), 0.75-0.81 (2H, m).

Example 2.122

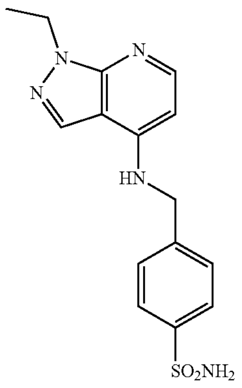 [SMILES: CCn1ncc2c(NCc3ccc(S(N)(=O)=O)cc3)ccnc21]

4-((1-Ethyl-1H-pyrazolo[3,4-b]pyridin-4-yl)aminomethyl)benzenesulfonamide

Step 1: To a mixture of 4-chloro-1H-pyrazolo[3,4-b]pyridine (5 g) and potassium carbonate (5.40 g) in acetonitrile (20 mL) was added iodoethane (5.08 g). After stirring at 80° C. for 8 hours, the resulting mixture was diluted with water, and extracted with ethyl acetate. The combined organic layers were washed with brine, and then dried over anhydrous sodium sulfate. After the resulting solid was filtered off, the filtrate was concentrated under reduced pressure. The residue was purified by column chromatography using 5-17% ethyl acetate in petroleum ether as eluent, to give 4-chloro-1-ethyl-1H-pyrazolo[3,4-b]pyridine as a colorless oil (2.4 g, yield 40.6%). $^1$H-NMR (DMSO-$D_6$) δ: 8.52 (1H, d, J=5.2 Hz), 8.26 (1H, s), 7.38 (1H, d, J=4.8 Hz), 4.51 (2H, q, J=7.2 Hz), 1.43 (3H, t, J=7.2 Hz).

Step 2: To a mixture of 4-chloro-1-ethyl-1H-pyrazolo[3,4-b]pyridine (2.2 g) obtained above and diphenylmethanimine (2.20 g) in 1,4-dioxane (20 mL) were added 4,5-bis(diphenylphosphino)-9,9-dimethylxanthene (701 mg), cesium carbonate (4.34 g) and bis(dibenzylideneacetone)palladium(0) (697 mg). The reaction mixture was stirred at 120° C. for 16 hours under nitrogen atmosphere. The resulting mixture was quenched with water, and extracted with ethyl acetate. 4 M HCl in water (12.11 mL) was added to the organic layer, and the mixture was stirred at 20° C. for 3 hours. The reaction mixture was neutralized with saturated sodium hydrogen carbonate solution and extracted with ethyl acetate. The combined organic layers were dried over sodium sulfate. After the resulting solid was filtered off, the filtrate was concentrated under reduced pressure. The residue was purified by column chromatography using 17-33% ethyl acetate in petroleum ether as eluent, and purified by column chromatography using 2-5% methanol in dichloromethane as eluent, to give 4-amino-1-ethyl-1H-pyrazolo[3,4-b]pyridine as a colorless oil (850 mg, yield 43.3%). $^1$H-NMR ($CDCl_3$) δ: 8.16 (1H, d, J=5.2 Hz), 7.90 (1H, s), 6.25 (1H, d, J=5.2 Hz), 4.68 (2H, br s), 4.50 (2H, q, J=7.2 Hz), 1.51 (3H, t, J=7.2 Hz).

Step 3: To a mixture of 4-amino-1-ethyl-1H-pyrazolo[3,4-b]pyridine (202 mg) obtained above and 4-formylbenzenesulfonamide (254 mg) in tetrahydrofuran (4 mL) was added sodium triacetoxyborohydride (530 mg). After stirring at room temperature for 24 hours and then at 40° C. for 2 hours, sodium triacetoxyborohydride (263 mg) was added to the mixture. After stirring at 40° C. for 1 hour, 4-formylbenzenesulfonamide (219 mg) was added to the reaction mixture. The resulting mixture was stirred for at 40° C. for 2.5 hours and added sodium triacetoxyborohydride (535 mg). After stirring at 40° C. overnight, the reaction mixture was quenched with saturated sodium hydrogen carbonate solution and extracted with methanol and dichloromethane. The combined organic layers were dried over sodium sulfate. After the resulting solid was filtered off, the filtrate was concentrated under reduced pressure. The residue was purified by column chromatography using 17-33% ethyl acetate in petroleum ether as eluent, and purified by column chromatography using 0-10% methanol in dichloromethane as eluent, to give the title compound as a colorless oil (70.7 mg, yield 17%). $^1$H-NMR (DMSO-$D_6$) δ: 8.13 (1H, s), 8.02 (1H, t, J=6.1 Hz), 7.96 (1H, d, J=5.5 Hz), 7.78 (2H, d, J=8.5 Hz), 7.54 (2H, d, J=8.5 Hz), 7.30 (2H, s), 6.06 (1H, d, J=5.5 Hz), 4.61 (2H, d, J=6.1 Hz), 4.33 (2H, q, J=7.1 Hz), 1.35 (3H, t, J=7.3 Hz). MS: m/z 332.1 (M+H$^+$).

Example 2.123

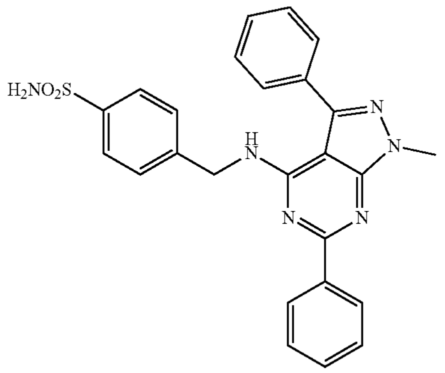 [SMILES: Cn1nc(-c2ccccc2)c2c(NCc3ccc(S(N)(=O)=O)cc3)nc(-c3ccccc3)nc21]

4-((1-Methyl-3,6-diphenyl-1H-pyrazolo[3,4-d]pyrimidin-4-yl)aminomethyl)-benzenesulfonamide The title compound was prepared according to the general procedure of Example 2.119 using 4-((3-bromo-6-chloro-1-methyl-1H-pyrazolo[3,4-d]pyrimidin-4-yl)aminomethyl)benzenesulfonamide obtained in Example 2.87 step 2, phenylboronic acid and tetrakis(triphenylphosphine)palladium (O). $^1$H-NMR (DMSO-$D_6$) δ: 8.35-8.41 (2H, m), 7.72-7.80 (4H, m), 7.54-7.63 (4H, m), 7.45-7.53 (4H, m), 7.29 (2H, s), 7.20 (1H, t, J=6.1 Hz), 4.91 (2H, d, J=5.5 Hz), 4.05 (3H, s). MS: m/z 471.2 (M+H$^+$).

Example 2.124

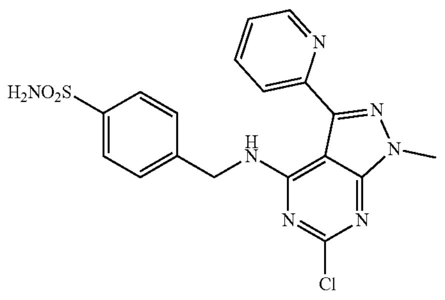

4-((6-Chloro-1-methyl-3-(2-pyridyl)-1H-pyrazolo[3,4-d]pyrimidin-4-yl)aminomethyl)benzenesulfonamide The title compound was prepared according to the general procedure of Example 2.119 using 4-((3-bromo-6-chloro-1-methyl-1H-pyrazolo[3,4-d]pyrimidin-4-yl)aminomethyl) benzenesulfonamide obtained in Example 2.87 Step 2, copper(I) iodide, (2-pyridine)cyclic-triolborate lithium salt and [1,1'-bis(diphenylphosphino)ferrocene]dichloropalladium (II) in DMF. $^1$H-NMR (DMSO-$D_6$) δ: 11.62 (1H, t, J=5.5 Hz), 8.52-8.56 (1H, m), 8.24-8.28 (1H, m), 8.03 (1H, td, J=7.7, 1.8 Hz), 7.81-7.86 (2H, m), 7.60-7.64 (2H, m), 7.50 (1H, td, J=6.4, 1.4 Hz), 7.35 (2H, s), 4.90 (2H, d, J=6.1 Hz), 3.96 (3H, s). MS: m/z 430.1 (M+H$^+$).

Example 2.125

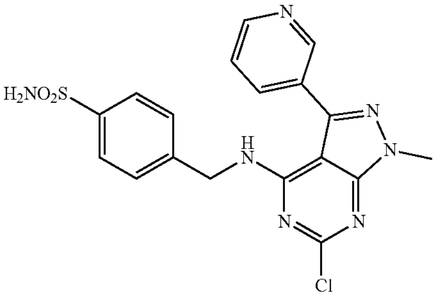 [SMILES: Cn1nc(-c2cccnc2)c2c(NCc3ccc(S(N)(=O)=O)cc3)nc(Cl)nc21]

4-((6-Chloro-1-methyl-3-(3-pyridyl)-1H-pyrazolo[3,4-d]pyrimidin-4-yl)aminomethyl)benzenesulfonamide The title compound was prepared according to the general procedure of Example 2.119 using 4-((3-bromo-6-chloro-1-methyl-1H-pyrazolo[3,4-d]pyrimidin-4-yl)aminomethyl) benzenesulfonamide obtained in Example 2.87 Step 2 and 3-pyridylboronic acid. $^1$H-NMR (DMSO-$D_6$) δ: 8.86 (1H, d, J=1.8 Hz), 8.69 (1H, dd, J=4.9, 1.2 Hz), 8.07 (1H, d, J=8.0 Hz), 7.90 (1H, t, J=6.1 Hz), 7.74-7.79 (2H, m), 7.58 (1H, dd, J=8.0, 4.9 Hz), 7.48-7.54 (2H, m), 7.32 (2H, s), 4.72 (2H, d, J=6.1 Hz), 3.95 (3H, s). MS: m/z 430.1 (M+H$^+$).

Example 2.126

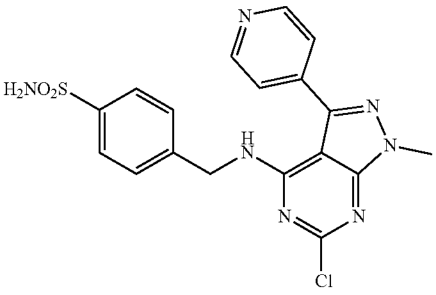

4-((6-Chloro-1-methyl-3-(4-pyridyl)-1H-pyrazolo[3,4-d]pyrimidin-4-yl)aminomethyl)benzenesulfonamide The title compound was prepared according to the general procedure of Example 2.119 using 4-((3-bromo-6-chloro-1-methyl-1H-pyrazolo[3,4-d]pyrimidin-4-yl)aminomethyl) benzenesulfonamide obtained in Example 2.87 Step 2 and 4-pyridylboronic acid. $^1$H-NMR (DMSO-$D_6$) δ: 8.69-8.75 (2H, m), 7.88 (1H, t, J=5.8 Hz), 7.75-7.81 (2H, m), 7.64-7.68 (2H, m), 7.50-7.57 (2H, m), 7.32 (2H, s), 4.74 (2H, d, J=5.5 Hz), 3.95 (3H, s). MS: m/z 430.1 (M+H$^+$).

Example 2.127

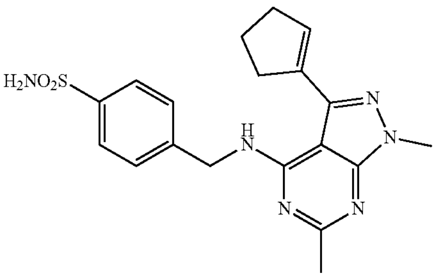 [SMILES: Cc1nc(NCc2ccc(S(N)(=O)=O)cc2)c2c(C3=CCCC3)nn(C)c2n1]

4-((3-(1-Cyclopenten-1-yl)-1,6-dimethyl-1H-pyrazolo[3,4-d]pyrimidin-4-yl)aminomethyl)benzenesulfonamide The title compound was prepared according to the general procedure of Example 2.119 using 4-((3-bromo-1,6-dimethyl-1H-pyrazolo[3,4-d]pyrimidin-4-yl)aminomethyl)benzenesulfonamide obtained in Example 2.89, chloro(2-dicyclohexylphosphino-2',4',6'-triisopropyl-1,1'-biphenyl)[2-(2-aminoethyl)phenyl]palladium(II) and 2-(1-cyclopenten-1-yl)-4,4,5,5-tetramethyl-1,3,2-dioxaborolane. $^1$H-NMR (DMSO-$D_6$) δ: 7.74-7.79 (2H, m), 7.49-7.54 (2H, m), 7.30 (2H, s), 7.14-7.19 (1H, m), 6.16-6.20 (1H, m), 4.82 (2H, d, J=5.5 Hz), 3.84 (3H, s), 2.75-2.83 (2H, m), 2.54-2.61 (2H, m), 2.39 (3H, s), 1.93-2.02 (2H, m). MS: m/z 399.1 (M+H$^+$).

Example 2.128

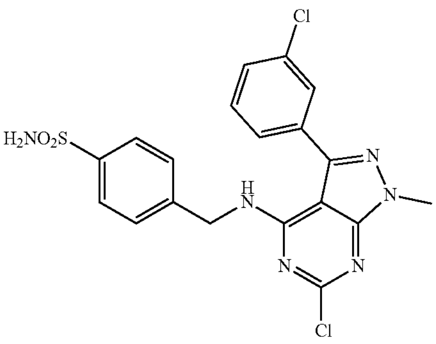 [SMILES: Cn1nc(-c2cccc(Cl)c2)c2c(NCc3ccc(S(N)(=O)=O)cc3)nc(Cl)nc21]

4-((6-Chloro-3-(3-chlorophenyl)-1-methyl-1H-pyrazolo[3,4-d]pyrimidin-4-yl)aminomethyl)benzenesulfonamide The title compound was prepared according to the general procedure of Example 2.119 using 4-((3-bromo-6-chloro-1-methyl-1H-pyrazolo[3,4-d]pyrimidin-4-yl)aminomethyl) benzenesulfonamide obtained in Example 2.87 Step 2 and 3-chlorophenylboronic acid. $^1$H-NMR (DMSO-$D_6$) δ: 7.75-7.81 (3H, m), 7.68-7.70 (1H, br m), 7.51-7.58 (5H, m), 7.33 (2H, s), 4.73 (2H, d, J=5.5 Hz), 3.93 (3H, s). MS: m/z 463.0 (M+H$^+$).

Example 2.129

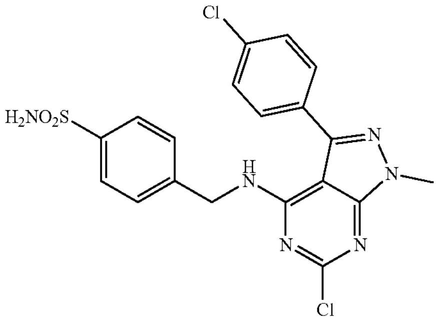 [SMILES: Cn1nc(-c2ccc(Cl)cc2)c2c(NCc3ccc(S(N)(=O)=O)cc3)nc(Cl)nc21]

4-((6-Chloro-3-(4-chlorophenyl)-1-methyl-1H-pyrazolo[3,4-d]pyrimidin-4-yl)aminomethyl)benzenesulfonamide The title compound was prepared according to the general procedure of Example 2.119 using 4-((3-bromo-6-chloro-1-methyl-1H-pyrazolo[3,4-d]pyrimidin-4-yl)aminomethyl) benzenesulfonamide obtained in Example 2.87 Step 2 and 4-chlorophenylboronic acid. $^1$H-NMR (DMSO-$D_6$) δ: 7.75-7.80 (2H, m), 7.66-7.73 (3H, m), 7.59-7.63 (2H, m), 7.48-7.53 (2H, m), 7.32 (2H, s), 4.72 (2H, d, J=5.5 Hz), 3.92 (3H, s). MS: m/z 463.0 (M+H$^+$).

Example 2.130

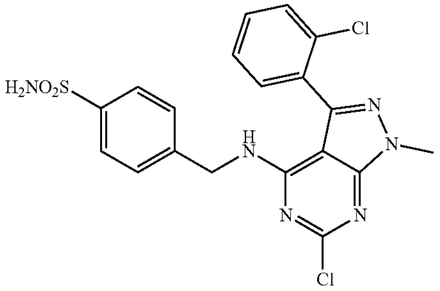 [SMILES: Cn1nc(-c2ccccc2Cl)c2c(NCc3ccc(S(N)(=O)=O)cc3)nc(Cl)nc21]

4-((6-Chloro-3-(2-chlorophenyl)-1-methyl-1H-pyrazolo[3,4-d]pyrimidin-4-yl)aminomethyl)benzenesulfonamide The title compound was prepared according to the general procedure of Example 2.119 using 4-((3-bromo-6-chloro-1-methyl-1H-pyrazolo[3,4-d]pyrimidin-4-yl)aminomethyl) benzenesulfonamide obtained in Example 2.87 Step 2 and 2-chlorophenylboronic acid. $^1$H-NMR (DMSO-$D_6$) δ: 7.73-7.77 (2H, m), 7.62-7.65 (1H, m), 7.41-7.57 (6H, m), 7.30 (2H, s), 4.68 (2H, d, J=5.5 Hz), 3.93 (3H, s). MS: m/z 463.0 (M+H$^+$).

Example 2.131

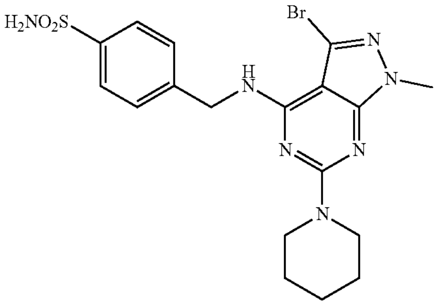 [SMILES: Cn1nc(Br)c2c(NCc3ccc(S(N)(=O)=O)cc3)nc(N3CCCCC3)nc21]

4-((3-Bromo-1-methyl-6-piperidino-1H-pyrazolo[3,4-d]pyrimidin-4-yl)aminomethyl)benzenesulfonamide The title compound was prepared according to the general procedure of Example 2.118 using 4-((3-bromo-6-chloro-1-methyl-1H-pyrazolo[3,4-d]pyrimidin-4-yl)aminomethyl) benzenesulfonamide obtained in Example 2.87 Step 2, piperidine and potassium carbonate in dimethyl sulfoxide. $^1$H-NMR (DMSO-$D_6$) δ: 7.72-7.77 (2H, m), 7.49-7.53 (2H, m), 7.46 (1H, t, J=6.1 Hz), 7.29 (2H, s), 4.71 (2H, d, J=6.1 Hz), 3.63-3.69 (7H, m), 1.52-1.60 (2H, m), 1.34-1.44 (4H, m). MS: m/z 480.1 (M+H$^+$).

Example 2.132

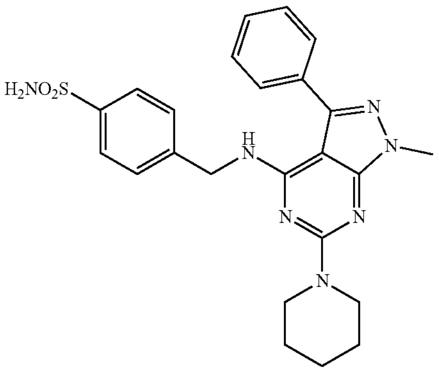 [SMILES: Cn1nc(-c2ccccc2)c2c(NCc3ccc(S(N)(=O)=O)cc3)nc(N3CCCCC3)nc21]

4-((1-Methyl-3-phenyl-6-piperidino-1H-pyrazolo[3,4-d]pyrimidin-4-yl)aminomethyl)benzenesulfonamide The title compound was prepared according to the general procedure of Example 2.118 using 4-((6-chloro-1-methyl-3-phenyl-1H-pyrazolo[3,4-d]pyrimidin-4-yl)aminomethyl) benzenesulfonamide obtained in Example 2.119, piperidine and potassium carbonate in dimethyl sulfoxide. $^1$H-NMR ($DMSO-D_6$) δ: 7.72-7.76 (2H, m), 7.64-7.69 (2H, m), 7.41-7.55 (5H, m), 7.29 (2H, s), 6.71 (1H, t, J=5.8 Hz), 4.66 (2H, d, J=6.1 Hz), 3.76 (3H, s), 3.65-3.71 (4H, m), 1.52-1.61 (2H, m), 1.35-1.45 (4H, m). MS: m/z 478.2 (M+H$^+$).

Example 2.133

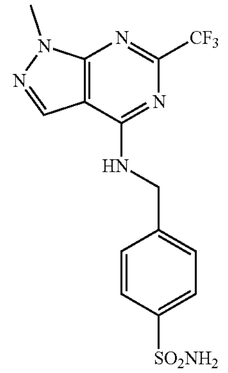 [SMILES: Cn1ncc2c(NCc3ccc(S(N)(=O)=O)cc3)nc(C(F)(F)F)nc21]

4-((1-Methyl-6-trifluoromethyl-1H-pyrazolo[3,4-d]pyrimidin-4-yl)aminomethyl)-benzenesulfonamide Step 1: Sodium hydride (428 mg) was added to a solution of 5-amino-1-methyl-1H-pyrazole-4-carboxamide (0.5 g) in ethanol (10 mL). The mixture was stirred at 10° C. for 0.5 hour. Then ethyl 2,2,2-trifluoroacetate (760 mg) was added to the mixture. The resulting mixture was stirred at 80° C. for 8 hours. After removal of ethanol, the mixture was quenched by addition of saturated aqueous ammonium chloride (30 mL), and then extracted with ethyl actetate 3 times. The combined organic layers were washed with brine 3 times, dried over anhydrous sodium sulfate, filtered and concentrated under reduced pressure to give 1-methyl-6-trifluoromethyl-1H-pyrazolo[3,4-d]pyrimidin-4-ol as a yellow solid (0.5 g, 64% yield). MS: m/z 219.0 (M+H$^+$).

Step 2: A solution of 1-methyl-6-trifluoromethyl-1H-pyrazolo[3,4-d]pyrimidin-4-ol (1.7 g) obtained above in $POCl_3$ (13.0 mL) was stirred at 110° C. for 5 hours. After concentration under reduced pressure, 50 mL of dichloromethane was added to the mixture which was quenched by addition of saturated aqueous sodium hydrogen carbonate (60 mL) at 0° C., and then extracted with dichloromethane (30 mL, 3 times). The combined organic layers were washed with brine (30 mL, 3 times), dried over sodium sulfate, filtered and concentrated under reduced pressure. The residue was purified by chromatography using 2-10% ethyl acetate in petroleum ether, to give 4-chloro-1-methyl-6-trifluoromethyl-1H-pyrazolo[3,4-d]pyrimidine as a colorless solid (1.02 g, yield 55%). $^1$H NMR (400 MHz, $CDCl_3$) δ 8.20 (1H, s), 4.15 (3H, s). MS: m/z 237.0 (M+H$^+$).

Step 3: The title compound was prepared according to the general procedure of Example 2.85 using 4-chloro-1-methyl-6-trifluoromethyl-1H-pyrazolo[3,4-d]pyrimidine obtained above and homosulfamine hydrochloride. $^1$H-NMR ($DMSO-D_6$) δ: 9.42 (1H, t, J=6.1 Hz), 8.25 (1H, s), 7.79 (2H, d, J=8.6 Hz), 7.55 (2H, d, J=8.6 Hz), 7.33 (2H, br s), 4.82 (2H, d, J=6.1 Hz), 3.96 (3H, s). MS: m/z 387.1 (M+H$^+$).

Example 2.134

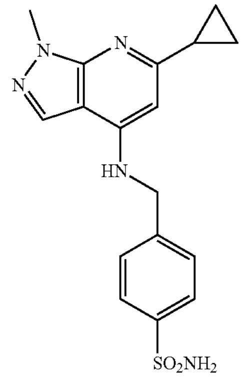 [SMILES: Cn1ncc2c(NCc3ccc(S(N)(=O)=O)cc3)cc(C3CC3)nc21]

4-((6-Cyclopropyl-1-methyl-1H-pyrazolo[3,4-b]pyridin-4-yl)aminomethyl)-benzenesulfonamide Step 1: A mixture of 5-amino-1-methylpyrazole (1 g) and ethyl 4-cyclopropyl-2,4-dioxo-butanoate (1.90 g) in toluene (20 mL) was stirred at 70° C. for 5 hours under nitrogen atmosphere. The reaction mixture was concentrated in vacuo. The residue was purified by chromatography using 25% ethyl acetate in petroleum ether, to give ethyl 6-cyclopropyl-1-methyl-1H-pyrazolo[3,4-b]pyridine-4-carboxylate as a colorless solid (900 mg, yield 36%). $^1$H NMR (400 MHz, $CDCl_3$) δ 8.19 (1H, s), 7.51 (1H, s), 4.42 (2H, q, J=7.2 Hz), 4.02 (3H, s), 2.17-2.19 (1H, m), 1.41 (3H, t, J=7.2 Hz), 1.11-1.13 (2H, m), 1.01-1.04 (2H, m).

Step 2: To a mixture of ethyl 6-cyclopropyl-1-methyl-1H-pyrazolo[3,4-b]pyridine-4-carboxylate obtained above (900 mg) in water (2 mL) and tetrahydrofuran (8 mL) was added lithium hydroxide monohydrate (770 mg) at 20° C. The mixture was stirred at 20° C. for 12 hours. The reaction mixture was poured into water (10 mL) and acidified to pH about 6 with 2 M hydrochloric acid. Then the mixture was filtered and the filter cake was concentrated in vacuo, to give cyclopropyl-1-methyl-pyrazolo[3,4-b]pyridine-4-carboxylic acid as a colorless solid (600 mg, 75% yield). $^1$H NMR (400 MHz, $DMSO-d_6$) δ8.18 (1H, s), 7.57 (1H, s), 3.98 (3H, s), 2.34-2.38 (1H, m), 1.05-1.08 (4H, m). MS: m/z 218.1 (M+H$^+$). To a mixture of 6-cyclopropyl-1-methyl-pyrazolo[3,4-b]pyridine-4-carboxylic acid obtained above (100 mg) and trimethylamine (0.096 mL) in DMF (1 mL) was added diphenylphosphoryl azide (190 mg) at 20° C. The mixture was stirred at 20° C. for 3 hours, then water (0.5 mL) was added. The reaction mixture was heated to 100° C. for 12 hours. The residue was purified by preparative HPLC using 0.1 vol % trifluoroacetic acid-distilled water and acetonitrile as eluent, to give 4-amino-6-cyclopropyl-1-methyl-1H-pyrazolo[3,4-b]pyridine as a colorless solid (10 mg, yield 53%). $^1$H NMR (400 MHz, $DMSO-d_6$) δ 8.21 (1H, s), 6.00 (1H, s), 4.00 (3H, s), 2.15-2.19 (1H, m), 1.18-1.21 (2H, m), 0.93-0.98 (2H, m).

Step 3: The title compound was prepared according to the general procedure of Example 2.122 using 4-amino-6-cyclopropyl-1-methyl-1H-pyrazolo[3,4-b]pyridine obtained above. MS: m/z 358 (M+H$^+$).

Example 2.135

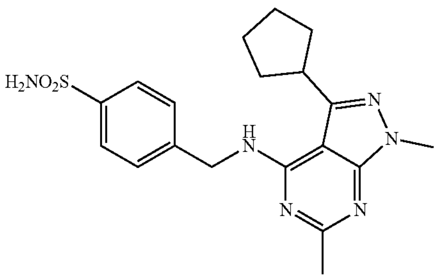 [SMILES: Cc1nc(NCc2ccc(S(N)(=O)=O)cc2)c2c(C3CCCC3)nn(C)c2n1]

4-((3-Cyclopentyl-1,6-dimethyl-1H-pyrazolo[3,4-d]pyrimidin-4-yl)aminomethyl)benzenesulfonamide The mixture of 4-((3-(1-cyclopenten-1-yl)-1,6-dimethyl-1H-pyrazolo[3,4-d]pyrimidin-4-yl)aminomethyl)benzenesulfonamide obtained in Example 2.127 (33.5 mg), 5% Pd—C(W) (31.2 mg) in methanol (2.5 mL) was stirred at room temperature for 6 hours under hydrogen atmosphere, using a balloon. The reaction mixture was filtered and the filtrate was concentrated under reduced pressure. The residue was purified by preparative HPLC using 0.1 vol % formic acid-distilled water and 0.1 vol % formic acid-acetonitrile as eluent, to give the title compound as a colorless solid (21.8 mg, yield 65%). $^1$H-NMR (DMSO-$D_6$) δ: 7.76 (2H, d, J=8.6 Hz), 7.49-7.57 (3H, m), 7.29 (2H, s), 4.81 (2H, d, J=5.5 Hz), 3.77 (3H, s), 3.63 (1H, t, J=8.0 Hz), 2.36 (3H, s), 1.98-2.09 (2H, m), 1.61-1.85 (6H, m). MS: m/z 401.2 (M+H$^+$).

Example 2.136

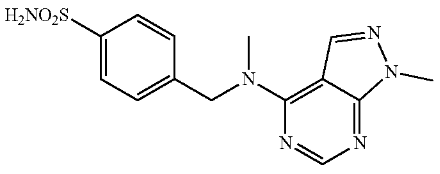 [SMILES: CN(Cc1ccc(S(N)(=O)=O)cc1)c1ncnc2c1cnn2C]

4-(N-methyl-N-(1-methyl-1H-pyrazolo[3,4-d]pyrimidin-4-yl)aminomethyl)-benzenesulfonamide The title compound was prepared according to the general procedure of Example 2.85 using 4-chloro-1-methyl-1H-pyrazolo[3,4-d]pyrimidine and 4-(methylaminomethyl)-benzenesulfonamide. $^1$H-NMR (DMSO-$D_6$) δ: 8.14-8.40 (2H, br m), 7.74-7.80 (2H, m), 7.39-7.45 (2H, m), 7.33 (2H, s), 5.13 (2H, s), 3.91 (3H, s), 3.40 (3H, s). MS: m/z 333.1 (M+H$^+$).

Example 2.137

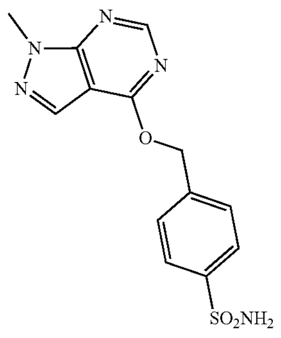 [SMILES: Cn1ncc2c(OCc3ccc(S(N)(=O)=O)cc3)ncnc21]

4-((1-Methyl-1H-pyrazolo[3,4-d]pyrimidin-4-yl)oxymethyl)benzenesulfonamide

To a solution of 4-(hydroxymethyl)benzenesulfonamide (50.6 mg) in N,N-dimethylformamide (1 mL) was added sodium hydride (60%, dispersion in Paraffin Liquid, 30.7 mg) at 0° C. After stirring for 40 min at 0° C., 4-chloro-1-methyl-1H-pyrazolo[3,4-d]pyrimidine (59.3 mg) was added to the reaction mixture. The resulting mixture was stirred for 5 hours at room temperature, and quenched by adding saturated ammonium chloride solution and with ethyl acetate. The organic layer was washed with water and brine, then dried over anhydrous sodium sulfate. After the resulting solid was filtered off, the filtrate was concentrated under reduced pressure. The residue was purified by automated flash chromatography using 0-80% ethyl acetate in hexane as eluent, to give the title compound as a colorless solid (32.8 mg, yield 29.5%). $^1$H-NMR (DMSO-$D_6$) δ: 8.62 (1H, s), 8.30 (1H, s), 7.85 (2H, d, J=8.5 Hz), 7.70 (2H, d, J=8.5 Hz), 7.41 (2H, s), 5.72 (2H, s), 4.03 (3H, s). MS: m/z 320.1 (M+H$^+$).

Example 2.139

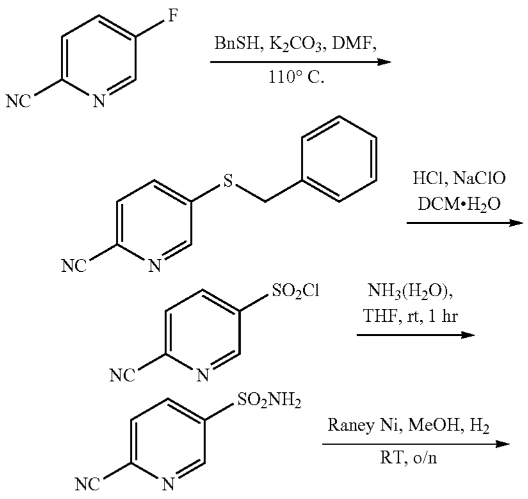

-continued

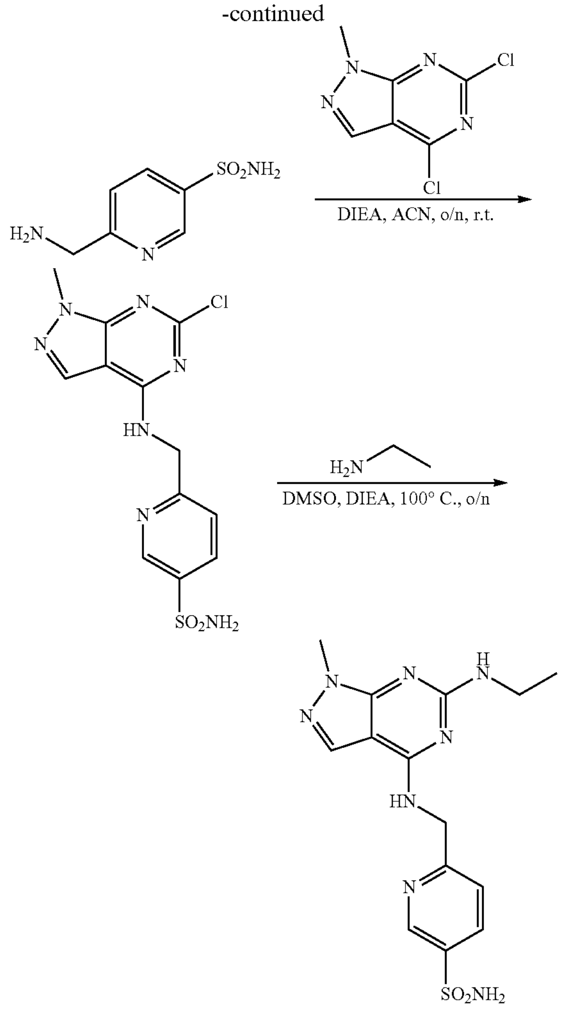

6-(((6-(Ethylamino)-1-methyl-1H-pyrazolo[3,4-d]pyrimidin-4-yl)amino)methyl)pyridine-3-sulfonamide (Example 2.139)

Step 1: A solution of 5-fluoropicolinonitrile (3 g, 25 mmoL), BnSH (3.7 g, 30 mmoL) and $K_2CO_3$ (6.9 g, 50 mmoL) in DMF (50 mL) was stirred at 80° C. overnight. The reaction mixture was poured into $H_2O$ (150 mL) and extracted with EA (150 mL). The EA layer was washed with brine (150 mL×2), dried over $Na_2SO_4$ and concentrated under reduced pressure to dryness in vacuum. The residue was purified by silica gel column (PE/EA=10/1) to give 5-(benzylthio)picolinonitrile (4.35 g, yield: 77%) as a yellow solid.

Step 2: To a solution of 5-(benzylthio)picolinonitrile (1.5 g, 6.6 mmoL) in DCM/$H_2O$ (45 mL/22.5 mL) was added HCl (9 mL) and NaClO (45 mL) slowly at 0° C. The mixture was stirred at room temperature for 4 hrs. The reaction mixture was poured into $H_2O$ (40 mL) and extracted with EA (40 mL). The EA layer was washed with brine (40 mL), dried over $Na_2SO_4$ and concentrated under reduced pressure to give 6-cyanopyridine-3-sulfonyl chloride (crude) as yellow oil.

Step 3: To a solution of 6-cyanopyridine-3-sulfonyl chloride (1.3 g, 6.4 mmoL) in THF (50 mL) was added $NH_3 \cdot H_2O$ (10 mL). The mixture was stirred at at room temperature for 4 hrs. The reaction mixture was concentrated under reduced pressure and the residue was purified by flash column to give 6-cyanopyridine-3-sulfonamide (690 mg, yield: δ3%) as a white solid. $^1$HNMR (400 MHz, DMSO-$d_6$): δ=9.11-9.10 (m, 1H), 8.43-8.40 (m, 1H), 8.28-8.26 (m, 1H), 7.87 (brs, 2H).

Step 4: A solution of 6-cyanopyridine-3-sulfonamide (690 mg, 3.8 mmoL), Raney-Ni and $NH_4OH$ (1.5 mL) in MeOH (50 mL) was stirred at room temperature overnight under $H_2$ atmosphere (balloon). The reaction mixture was filtered and the filtrate was concentrated under reduced pressure to give 6-(aminomethyl)pyridine-3-sulfonamide (crude) as a white solid.

Step 5: A solution of 6-(aminomethyl)pyridine-3-sulfonamide (690 mg, 3.7 mmoL), 4,6-dichloro-1-methyl-1H-pyrazolo[3,4-d]pyrimidine (751 mg, 3.7 mmoL) and DIEA (0.5 mL) in ACN (30 mL) was stirred at room temperature overnight. The reaction mixture was concentrated under reduced pressure and the residue was purified with prep-HPLC to give 6-(((6-chloro-1-methyl-1H-pyrazolo[3,4-d]pyrimidin-4-yl)amino)methyl)pyridine-3-sulfonamide (136 mg, yield: 10%) as a white solid. $^1$HNMR (400 MHz, DMSO-$d_6$): δ=9.41 (t, J=5.2 Hz, 1H), 8.92 (s, 1H), 8.19 (s, 1H), 8.15 (dd, J=8.4, 2.4 Hz, 1H), 7.57-7.56 (m, 3H), 4.86 (d, J=5.6 Hz, 2H), 3.87 (s, 3H). MS: m/z 354.0 ($M+H^+$).

Step 6: A solution of 6-(((6-chloro-1-methyl-1H-pyrazolo[3,4-d]pyrimidin-4-yl)amino)methyl)pyridine-3-sulfonamide (60 mg, 0.17 mmoL), ethanamine (9 mg, 0.2 mmoL) and $K_2CO_3$ (70 mg, 0.51 mmol) in DMSO (5 mL) was stirred at 100° C. overnight. The reaction mixture was concentrated under reduced pressure and the residue was purified by prep-HPLC to give 6-(((6-(ethylamino)-1-methyl-1H-pyrazolo[3,4-d]pyrimidin-4-yl)amino)methyl)pyridine-3-sulfonamide (136 mg, yield: 10%) as a white solid. $^1$HNMR (400 MHz, DMSO-$d_6$): δ=10.32 (brs, 1H), 8.91 (s, 1H), 8.21-8.18 (m, 2H), 7.63-7.61 (m, 3H), 4.91-4.90 (m, 2H), 3.86 (s, 3H), 3.34-3.32 (m, 2H), 1.23-1.00 (m, 3H). MS: m/z 363.1 ($M+H^+$).

Example 2.140 And Example 2.141

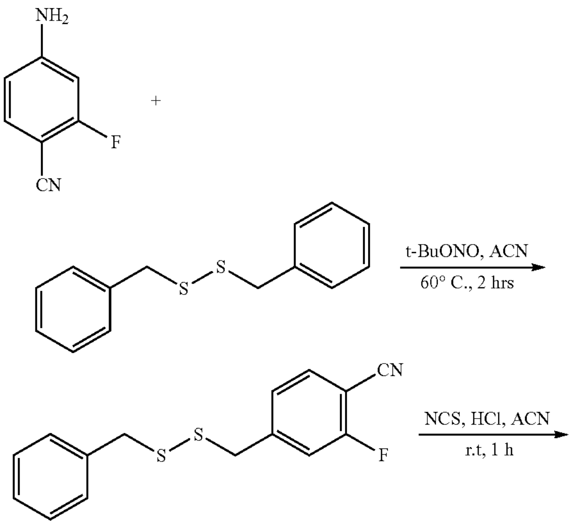

-continued

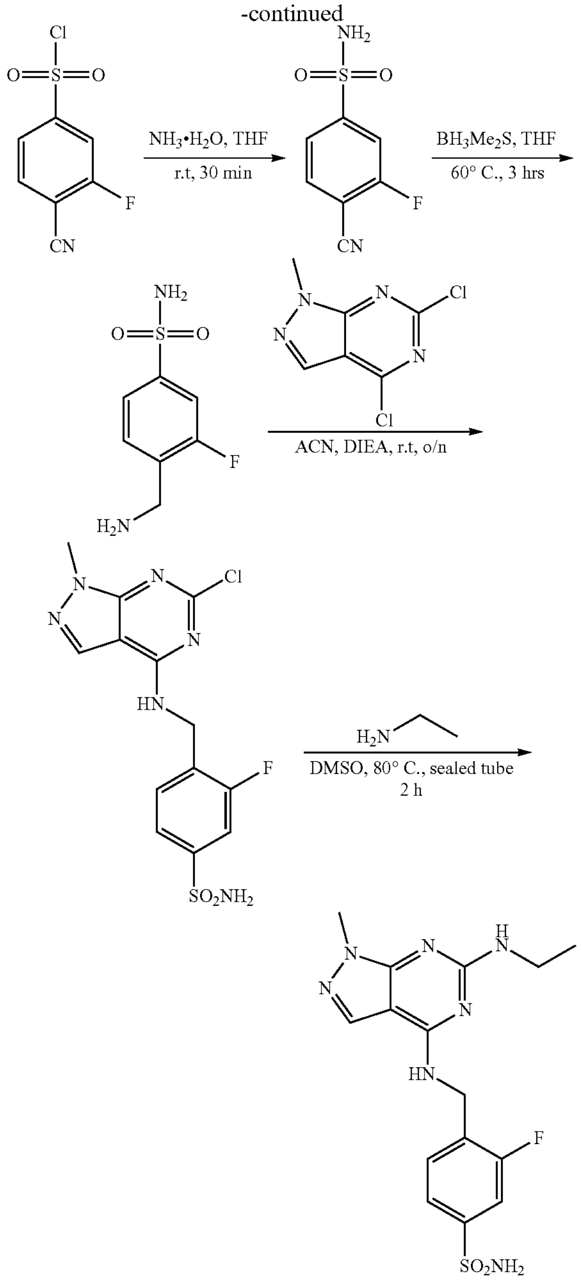

4-(((6-Chloro-1-methyl-1H-pyrazolo[3,4-d]pyrimidin-4-yl)amino)methyl)-3-fluorobenzenesulfonamide (Example 2.140) and 4-(((6-(Ethylamino)-1-methyl-1H-pyrazolo[3,4-d]pyrimidin-4-yl)amino)methyl)-3-fluorobenzenesulfonamide (Example 2.141)

Step 1: A solution of 4-amino-2-fluorobenzonitrile (5 g, 37 mmoL), 1,2-dibenzyldisulfane (7.2 g, 29 mmoL) and t-BuONO (2.7 g, 26 mmoL) in ACN (100 mL) was stirred at 60° C. for 2 hrs. The reaction mixture was concentrated and the residue was purified by silica gel column (PE/EA=100/5) to give 4-(benzylthio)-2-fluorobenzonitrile (4.0 g, yield: 45%) as a white solid.

Step 2: To a solution of 4-(benzylthio)-2-fluorobenzonitrile (4.0 g, 16.5 mmoL) in ACN (200 mL) was added NCS (8.8 g, 65.8 mmol) and HCl (4.1 mL). The mixture was stirred at 0° C. for 1 hr. The reaction mixture was poured into $H_2O$ (40 mL) and extracted with EA (40 mL). The EA layer was washed with brine (40 mL), dried over $Na_2SO_4$ and concentrated under reduced pressure to give 4-cyano-3-fluorobenzene-1-sulfonyl chloride (crude) as a yellow solid.

Step 3: To a solution of 4-cyano-3-fluorobenzene-1-sulfonyl chloride (3.6 g, 16.5 mmoL) in THF (50 mL) was added $NH_3 \cdot H_2O$ (10 mL). The mixture was stirred at at room temperature for 30 mins. The reaction mixture was concentrated under reduced pressure and the residue was purified by flash column to give 4-cyano-3-fluorobenzenesulfonamide (2.8 g, yield: 85%) as a brown solid.

Step 4: A solution of 4-cyano-3-fluorobenzenesulfonamide (500 mg, 2.5 mmoL) and $BH_3Me_2S$ (2 mL) in THF (30 mL) was stirred at 45° C. for 4 hrs. Then added MeOH (10 mL) and HCl (5 d). The solution was stirred at 45° C. for 1 hr and purified by silica flash column to give 4-(aminomethyl)-3-fluorobenzenesulfonamide (480 mg, yield: 94%) as a white solid.

Step 5: A solution of 4-(aminomethyl)-3-fluorobenzenesulfonamide (100 mg, 0.49 mmoL), 4,6-dichloro-1-methyl-1H-pyrazolo[3,4-d]pyrimidine (100 mg, 0.49 mmoL) and DIEA (0.5 mL) in ACN (20 mL) was stirred at room temperature overnight. The reaction mixture was concentrated under reduced pressure and the residue was purified by prep-HPLC to give 4-(((6-chloro-1-methyl-1H-pyrazolo[3,4-d]pyrimidin-4-yl)amino)methyl)-3-fluorobenzenesulfonamide (60 mg, yield: 33%) as a white solid. $^1$HNMR (400 MHz, DMSO-$d_6$): δ=9.27 (t, J=5.6 Hz, 1H), 8.15 (s, 1H), 7.65-7.58 (m, 3H), 7.48 (s, 2H), 4.77 (d, J=5.6 Hz, 2H), 3.86 (s, 3H). MS: m/z 371.0 (M+H$^+$).

Step 6: A solution of 4-(((6-chloro-1-methyl-1H-pyrazolo[3,4-d]pyrimidin-4-yl)amino)methyl)-3-fluorobenzenesulfonamide (30 mg, 0.08 mmoL) and ethanamine (2 mL) in DMSO (5 mL) was stirred at 80° C. for 2 hrs. The reaction mixture was concentrated under reduced pressure and the residue was purified with prep-HPLC to give 4-(((6-(ethylamino)-1-methyl-1H-pyrazolo[3,4-d]pyrimidin-4-yl)amino)methyl)-3-fluorobenzenesulfonamide (11.3 mg, yield: 38%) as a white solid. $^1$HNMR (400 MHz, DMSO-$d_6$): δ=9.91 (brs, 1H), 8.09 (s, 1H), 7.63-7.61 (m, 3H), 7.53-7.50 (m, 3H), 4.83 (brs, 2H), 3.83 (s, 3H), 3.39-3.35 (m, 2H), 1.08 (s, 3H). MS: m/z 380.1 (M+H$^+$).

Example 2.142

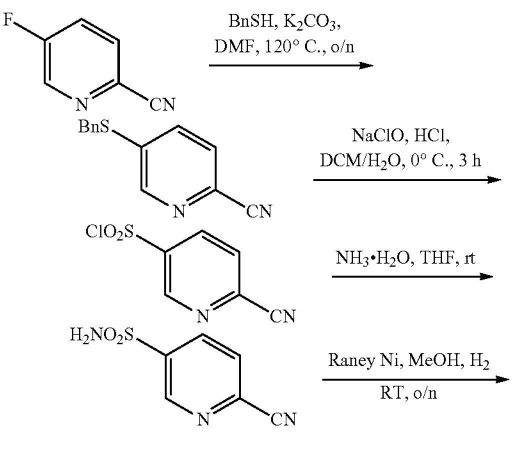

-continued

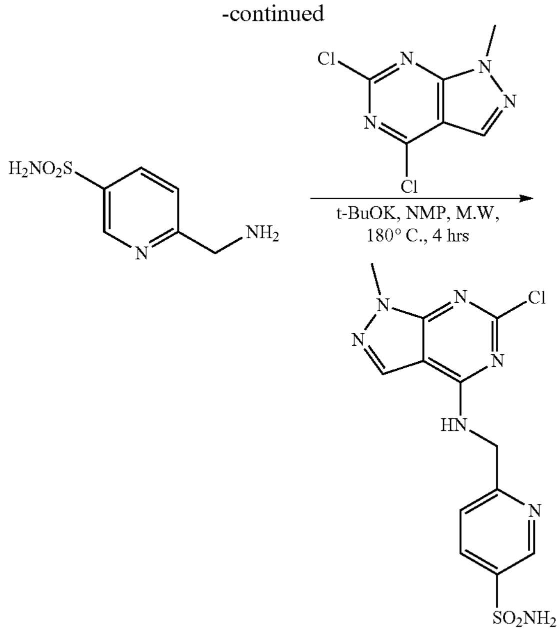

6-(((6-Chloro-1-methyl-1H-pyrazolo[3,4-b]pyridin-4-yl)amino)methyl)pyridine-3-sulfonamide The title compound was prepared using general procedure of 6-(((6-(ethylamino)-1-methyl-1H-pyrazolo[3,4-d]pyrimidin-4-yl)amino)methyl)pyridine-3-sulfonamide. $^1$HNMR (400 MHz, DMSO-$d_6$): δ=8.94 (d, J=2.0 Hz, 1H), 8.45 (t, J=5.6 Hz, 1H), 8.17-8.15 (m, 2H), 8.59-8.57 (m, 3H), 6.15 (brs, 1H), 4.73 (d, J=5.2 Hz, 2H), 3.87 (s, 3H). MS: m/z 353.0 (M+H$^+$).

Example 2.143

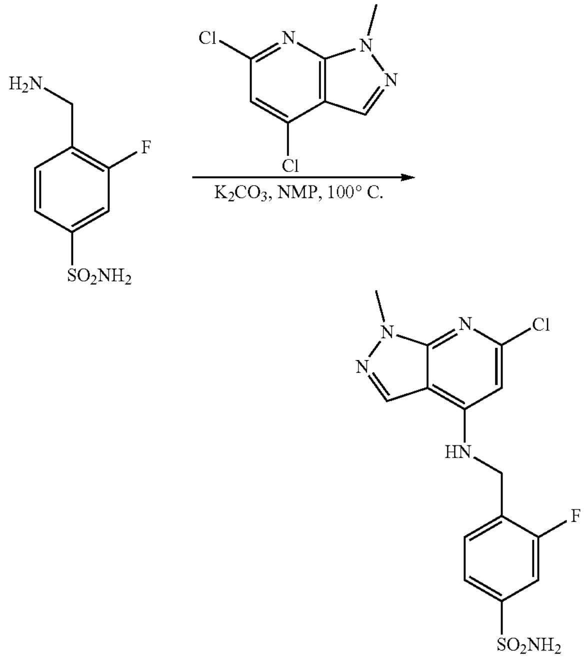

4-(((6-Chloro-1-methyl-1H-pyrazolo[3,4-b]pyridin-4-yl)amino)methyl)-3-fluorobenzenesulfonamide A solution of 4,6-dichloro-1-methyl-1H-pyrazolo[3,4-b]pyridine (200 mg, 0.99 mmoL), 4-(aminomethyl)-3-fluorobenzenesulfonamide (210 mg, 1.03 mmoL) and $K_2CO_3$ (560 mg, 4.06 mmoL) in NMP (4 mL) was stirred at 100° C. overnight. The reaction mixture was poured into $H_2O$ (30 mL) and extracted with EA (30 mL). The EA phase was concentrated and the residue was purified with reverse phase column to give 4-(((6-chloro-1-methyl-1H-pyrazolo[3,4-b]pyridin-4-yl)amino)methyl)-3-fluorobenzenesulfonamide (28 mg, yield: 8%) as a yellow solid. $^1$HNMR (400 MHz, $CD_3OD$): δ=8.04 (s, 1H), 7.70-7.66 (m, 2H), 7.55 (t, J=7.6 Hz, 1H), 6.19 (s, 1H), 4.68 (s, 2H), 3.94 (s, 3H). MS: m/z 370.0 (M+H$^+$).

Example 2.144

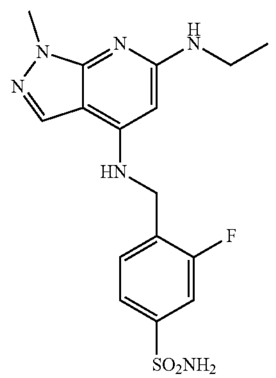 [SMILES: CCNc1cc(NCc2ccc(S(N)(=O)=O)cc2F)c2cnn(C)c2n1]

4-(((6-(Ethylamino)-1-methyl-1H-pyrazolo[3,4-b]pyridin-4-yl)amino)methyl)-3-fluorobenzenesulfonamide The title compound was prepared using general procedure of 4-(((6-(Isopropylamino)-1-methyl-1H-pyrazolo[3,4-b]pyridin-4-yl)amino)methyl)benzenesulfonamide (Example 2.74). $^1$HNMR (400 MHz, DMSO-$d_6$): δ=7.79 (s, 1H), 7.61 (d, J=9.2 Hz, 2H), 7.52-7.44 (m, 3H), 7.34 (d, J=6.0 Hz, 1H), 6.33 (t, J=5.6 Hz, 1H), 5.17 (s, 1H), 4.47 (d, J=6.0 Hz, 2H), 3.73 (s, 3H), 3.25-3.21 (m, 2H), 1.08 (t, J=7.2 Hz, 3H). MS: m/z 379.1 (M+H$^+$).

Example 3

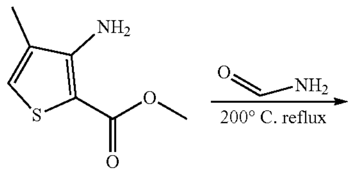

-continued

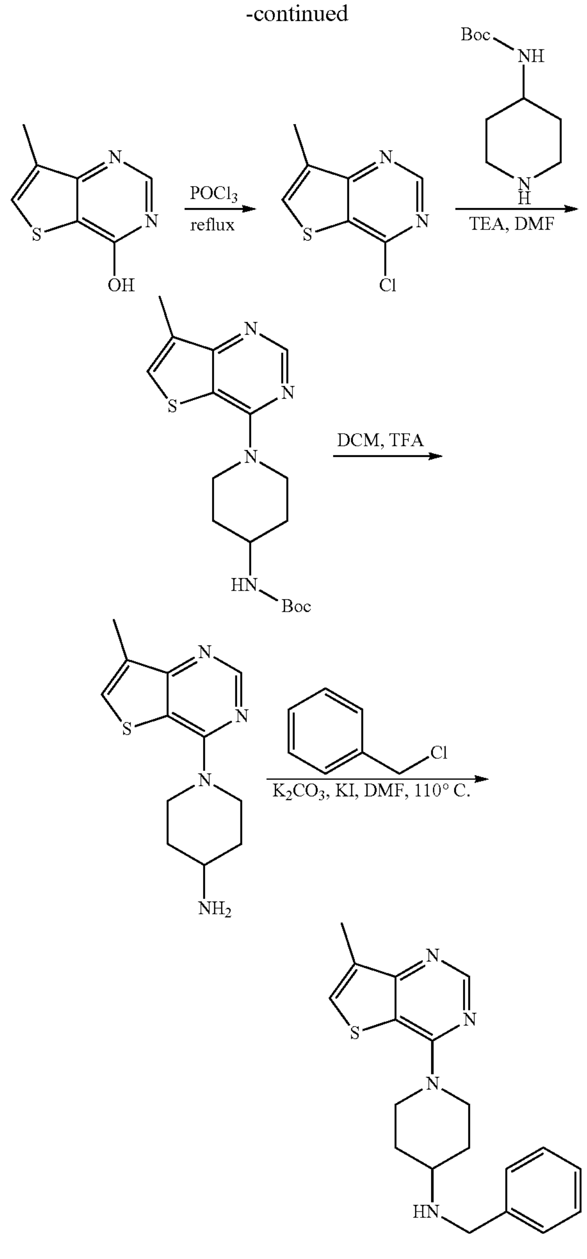

N-Benzyl-1-(7-methylthieno[3,2-d]pyrimidin-4-yl)piperidin-4-amine

Step 1: A solution of methyl 3-amino-4-methylthiophene-2-carboxylate (3 g, 17.5 mmol) in formamide (20 mL) was stirred at 200° C. for 8 hrs. The reaction was cooled to room temperature and filtered. The pad was rinsed with THF to give 7-methyl thieno [3,2-d]pyrimidin-4-ol (2 g, yield: δ88.9%) as a gray solid. $^1$HNMR (400 MHz, DMSO-d6): δ=12.14-12.11 (m, 1H), 8.18 (s, 1H), 7.83 (s, 1H), 2.32 (s, 3H). MS: m/z 167.9 (M+H$^+$).

Step 2: A solution of 7-methylthieno[3,2-d]pyrimidin-4-ol (500 mg, 3.0 mmol) in $POCl_3$ (5 mL) was stirred at 120° C. for 2 hrs. The $POCl_3$ was removed under reduced pressure. The residue was neutralized with saturated aqueous $NaHCO_3$ solution (100 mL) and extracted with EA (200 mL×3). The combined organic layers were dried over $Na_2SO_4$ and concentrated to give 4-chloro-7-methylthieno[3,2-d]pyrimidine (0.66 g, crude) as a yellow solid.

Step 3: A solution of 4-chloro-7-methylthieno[3,2-d]pyrimidine (560 mg, 3.0 mmol), TEA (0.6 g, 6.0 mmol) and tert-butyl piperidin-4-ylcarbamate (1.2 g, 6.0 mmol) in DMF (5 mL) was stirred at 80° C. for 4 hrs. The DMF was removed under reduced pressure. The residue was purified by silica gel column (PE/EA=1/1) to give tert-butyl (1-(7-methylthieno[3,2-d]pyrimidin-4-yl)piperidin-4-yl)carbamate (0.75 g, yield: 71%) as a white solid. MS: m/z 349.2 (M+H$^+$).

Step 4: A solution of tert-butyl (1-(7-methylthieno[3,2-d]pyrimidin-4-yl)piperidin-4-yl)carbamate (0.75 g, 2.1 mmol) and TFA (2 mL) in DCM (10 mL) was stirred at room temperature for 4 hrs. The DCM and TFA was removed under reduced pressure. The residue was washed with saturated aqueous $NaHCO_3$ solution and concentrated. The residue was dissolved in MeOH and filtered. The filtrate was concentrated to give 1-(7-methyl thieno [3,2-d]pyrimidin-4-yl)piperidin-4-amine (740 mg, crude) as a colorless oil.

Step 5: A solution of 1-(7-methylthieno[3,2-d]pyrimidin-4-yl)piperidin-4-amine (100 mg, 0.4 mmol), (chloromethyl)benzene (40 mg, 0.3 mmol), $K_2CO_3$ (110 mg, 0.8 mmol) and KI (2 mg) in DMF (3 mL) was stirred at 110° C. for 5 hrs. The DMF was removed under reduced pressure. The residue was purified by prep-HPLC ($NH_4HCO_3$) to give N-benzyl-1-(7-methylthieno[3,2-d]pyrimidin-4-yl)piperidin-4-amine (14.8 mg, yield: 11.6%) as a colorless oil. $^1$HNMR (400 MHz, $CDCl_3$): δ=8.56 (s, 1H), 7.21-7.18 (m, 6H), 4.62 (d, J=13.2 Hz, 2H), 3.79 (s, 2H), 3.26-3.19 (m, 2H), 2.85-2.80 (m, 1H), 2.38 (s, 3H), 2.10-1.97 (m, 2H), 1.48-1.40 (m, 2H). MS: m/z 339.1 (M+H$^+$).

Example 3.1

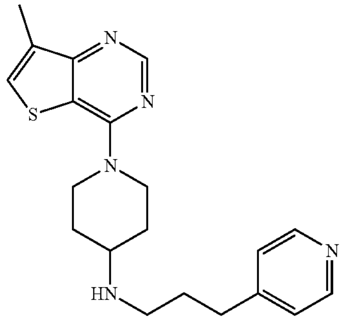 [SMILES: Cc1csc2c(N3CCC(NCCCc4ccncc4)CC3)ncnc12]

1-(7-Methyl thieno[3,2-d]pyrimidin-4-yl)-N-(3-(pyridin-4-yl)propyl)piperidin-4-amine The title compound was prepared using general procedure of 1-(7-methyl thieno[3,2-d]pyrimidin-4-yl)-N-(3-(pyridin-2-yl)propyl)piperidin-4-amine (Example 3.3). $^1$HNMR (400 MHz, DMSO-d$_6$): δ=8.54-8.47 (m, 3H), 7.86 (s, 1H), 7.26 (d, J=4.8 Hz, 2H), 4.69 (d, J=12.8 Hz, 2H), 3.34-3.15 (m, 2H), 2.84-2.81 (m, 2H), 2.71-2.67 (m, 2H), 2.35 (s, 3H), 2.14-2.11 (m, 2H), 1.93-1.90 (m, 2H), 1.56-1.54 (m, 2H), 1.23 (s, 1H). MS: m/z 368.1 (M+H$^+$).

Example 3.2

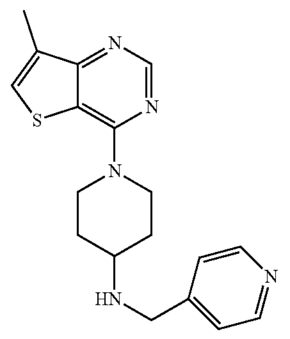 [SMILES: Cc1csc2c(N3CCC(NCc4ccncc4)CC3)ncnc12]

1-(7-Methylthieno[3,2-d]pyrimidin-4-yl)-N-(pyridin-4-ylmethyl)piperidin-4-amine

The title compound was prepared using general procedure of N-benzyl-1-(7-methylthieno[3,2-d]pyrimidin-4-yl)piperidin-4-amine (Example 3). $^1$HNMR (400 MHz, $CDCl_3$): δ=8.50-8.48 (m, 3H), 7.82 (s, 1H), 7.37 (d, J=5.6 Hz, 2H), 4.55-4.52 (m, 2H), 3.79 (s, 2H), 3.31-3.28 (m, 2H), 2.75-2.73 (m, 1H), 2.33 (s, 3H), 1.98-1.95 (m, 2H), 1.37-1.32 (m, 2H). MS: m/z 339.9 (M+H$^+$).

Example 3.3

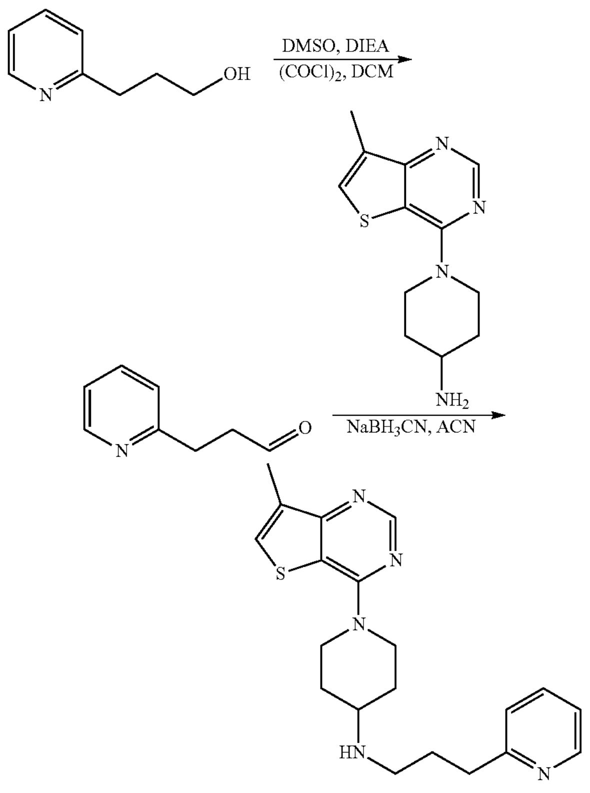

1-(7-Methylthieno[3,2-d]pyrimidin-4-yl)-N-(3-(pyridin-2-yl)propyl)piperidin-4-amine Step 1: To a solution of $(COCl)_2$ (370 mg, 2.9 mmol) in DCM (10 mL) was added DMSO (456 mg, 5.8 mmol) dropwise under $N_2$ atmosphere (balloon). The mixture was stirred at −78° C. for 1 hr. Then 3-(pyridin-2-yl) propan-1-ol (200 mg, 1.4 mmol) was added into the mixture slowly and the new mixture was stirred at −78° C. for a further 1 hr. Then the reaction mixture was added DIEA (1.1 g, 8.8 mmol). The reaction mixture was warmed to room temperature and stirred at room temperature overnight. The reaction mixture was concentrated and the residue was purified by silica gel column (DCM/MeOH=10/1) to give 3-(pyridin-2-yl)propanal (166 mg, yield: 84%) as a yellow solid.

Step 2: A solution of 1-(7-methylthieno[3,2-d]pyrimidin-4-yl)piperidin-4-amine (277 mg, 1.1 mmol) and 3-(pyridin-2-yl)propanal (166 mg, 1.2 mmol) in ACN (10 mL) was stirred at room temperature for 0.5 hr. Then the mixture was cooled to 0° C. and added $NaBH_3CN$ (232 mg, 3.7 mmol). The reaction mixture was stirred at room temperature overnight. The ACN was removed under reduced pressure. The residue was purified by prep-HPLC ($NH_4HCO_3$) to give 1-(7-methylthieno[3,2-d]pyrimidin-4-yl)-N-(3-(pyridin-2-yl)propyl)piperidin-4-amine (25.8 mg, yield: 5%) as a white solid. $^1$HNMR (400 MHz, $CDCl_3$): δ=8.65 (s, 1H), 8.40-8.39 (m, 1H), 7.68-7.63 (m, 1H), 7.37 (s, 1H), 7.22 (d, J=8 Hz, 1H), 7.18-7.15 (m, 1H), 4.92 (d, J=13.2 Hz, 2H), 3.37-3.33 (m, 1H), 3.20-3.13 (m, 2H), 3.12-3.10 (m, 2H), 3.04-3.00 (m, 2H), 2.46 (s, 3H), 2.41-2.35 (m, 2H), 2.33-2.28 (m, 2H), 1.97-1.87 (m, 2H). MS: m/z 368.2 (M+H$^+$).

Example 3.4

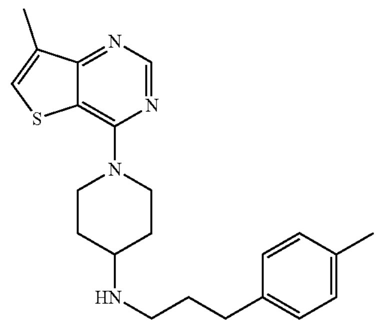 [SMILES: Cc1ccc(CCCNC2CCN(c3ncnc4c(C)csc34)CC2)cc1]

1-(7-Methylthieno[3,2-d]pyrimidin-4-yl)-N-(3-(p-tolyl)propyl)piperidin-4-amine

The title compound was prepared using general procedure of 1-(7-methylthieno[3,2-d]pyrimidin-4-yl)-N-(3-(pyridin-2-yl)propyl)piperidin-4-amine (Example 3.3). $^1$HNMR (400 MHz, $CDCl_3$): δ=8.64 (s, 1H), 7.34 (s, 1H), 7.08-7.04 (m, 4H), 4.87 (d, J=13.2 Hz, 2H), 3.28-3.22 (m, 1H), 3.07-3.01 (m, 2H), 2.93-2.89 (m, 2H), 2.65-2.62 (m, 2H), 2.44 (s, 3H), 2.32-2.30 (m, 2H), 2.27 (s, 3H), 2.24-2.20 (m, 2H), 1.98-1.88 (m, 2H). MS: m/z 381.2 (M+H$^+$).

Example 3.5

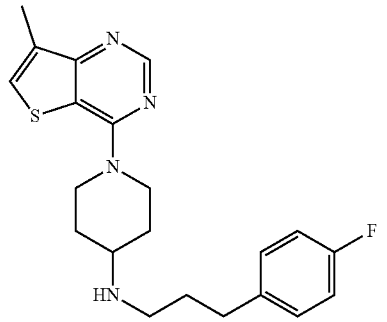 [SMILES: Cc1csc2c(N3CCC(NCCCc4ccc(F)cc4)CC3)ncnc12]

N-(3-(4-Fluorophenyl)propyl)-1-(7-methylthieno[3,2-d]pyrimidin-4-yl)piperidin-4-amine The title compound was prepared using general procedure of 1-(7-methylthieno[3,2-d]pyrimidin-4-yl)-N-(3-(pyridin-2-yl)propyl)piperidin-4-amine (Example 3.3). $^1$HNMR (400 MHz, $CD_3OD$): δ=8.64 (s, 1H), 7.35 (s, 1H), 7.16-7.12 (m, 2H), 6.98-6.93 (m, 2H), 4.85 (d, J=12.8 Hz, 2H), 3.16-3.07 (m, 3H), 2.89-2.86 (m, 2H), 2.67-2.64 (m, 2H), 2.45 (s, 3H), 2.28-2.25 (m, 2H), 2.18-2.10 (m, 2H), 1.88-1.80 (m, 2H). MS: m/z 385.1 (M+H$^+$).

Example 3.6

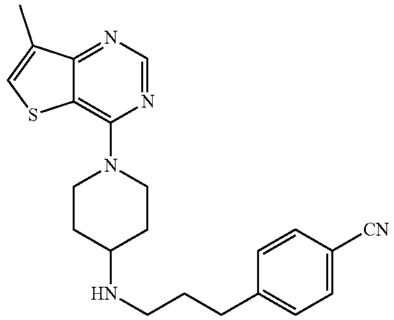 [SMILES: Cc1csc2c(N3CCC(NCCCc4ccc(C#N)cc4)CC3)ncnc12]

4-(3-((1-(7-Methylthieno[3,2-d]pyrimidin-4-yl)piperidin-4-yl)amino)propyl)benzonitrile The title compound was prepared using general procedure of 1-(7-methylthieno[3,2-d]pyrimidin-4-yl)-N-(3-(pyridin-2-yl)propyl)piperidin-4-amine (Example 3.3). $^1$HNMR (400 MHz, $CD_3OD$): δ=8.49 (s, 1H), 7.66 (d, J=8 Hz, 3H), 7.42 (d, J=8.4 Hz, 2H), 4.92 (s, 2H), 3.31-3.20 (m, 2H), 3.15-3.09 (m, 1H), 2.87-2.83 (m, 2H), 2.81-2.77 (m, 2H), 2.40 (s, 3H), 2.15-2.12 (m, 2H), 1.95-1.87 (m, 2H), 1.54-1.45 (m, 2H). MS: m/z 391.9 (M+H$^+$).

Example 3.7

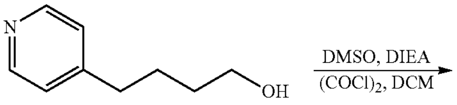

-continued

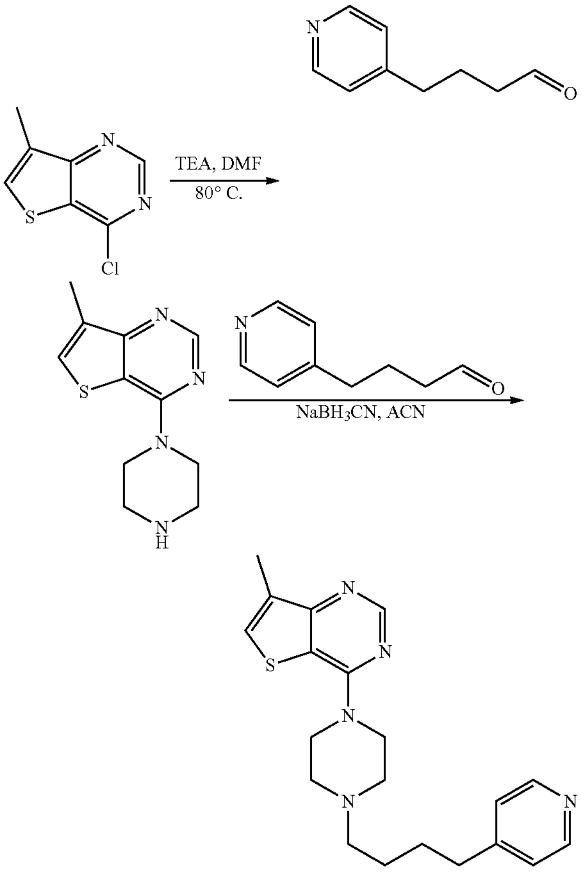

7-Methyl-4-(4-(4-(pyridin-4-yl)butyl)piperazin-1-yl)thieno[3,2-d]pyrimidine

Step 1: The step 1 was as same as the step 1 of 1-(7-methylthieno[3,2-d]pyrimidin-4-yl)-N-(3-(pyridin-2-yl)propyl)piperidin-4-amine (Example 3.3)

Step 2: The step 2 was as same as the step 3 of N-benzyl-1-(7-methylthieno[3,2-d]pyrimidin-4-yl)piperidin-4-amine (Example 3.0)

Step 3: The step 3 was as same as the step 2 of 1-(7-methylthieno[3,2-d]pyrimidin-4-yl)-N-(3-(pyridin-2-yl)propyl)piperidin-4-amine (Example 3.3). $^1$HNMR (400 MHz, $CDCl_3$): δ=8.64 (s, 1H), 8.49 (d, J=5.6 Hz, 2H), 7.36 (s, 1H), 7.11 (d, J=6 Hz, 2H), 4.02-4.00 (m, 4H), 2.65 (t, J=7.6 Hz, 2H), 2.65 (t, J=4.8 Hz, 4H), 2.45 (s, 3H), 2.43-2.40 (m, 2H), 1.70-1.68 (m, 2H), 1.57-1.25 (m, 2H). MS: m/z 367.9 (M+H$^+$).

Example 3.8

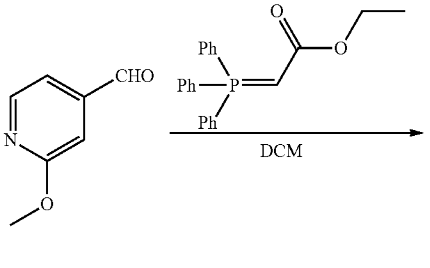

-continued

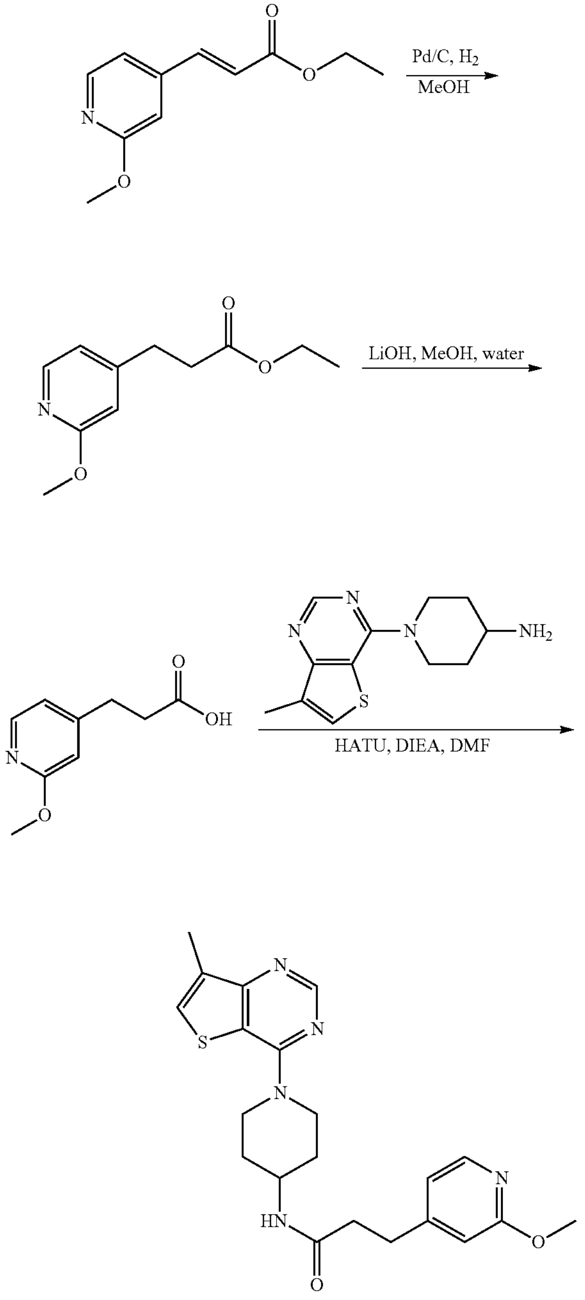

3-(2-Methoxypyridin-4-yl)-N-(1-(7-methylthieno[3,2-d]pyrimidin-4-yl)piperidin-4-yl)propenamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.64 (s, 1H), 8.05 (d, J=5.2 Hz, 1H), 6.73-6.71 (m, 1H), 6.57 (s, 1H), 5.23 (d, J=7.6 Hz, 1H), 5.40 (d, J=7.6 Hz, 1H), 4.74 (d, J=13.2 Hz, 2H), 4.14-4.10 (m, 1H), 3.91 (s, 3H), 3.28-3.21 (m, 2H), 2.92 (t, J=7.8 Hz, 2H), 2.46-2.42 (m, 5H), 2.07-2.03 (m, 2H), 1.45-1.35 (m, 2H). MS: m/z 412.2 ($M+H^+$).

Example 3.9

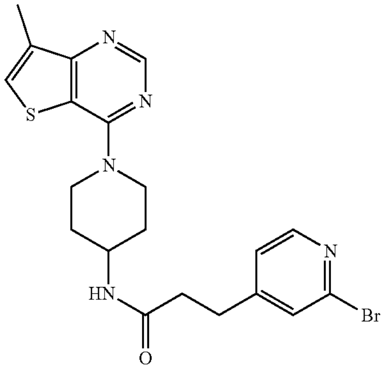 [SMILES: Cc1csc2c(N3CCC(NC(=O)CCc4ccnc(Br)c4)CC3)ncnc12]

3-(2-Bromopyridin-4-yl)-N-(1-(7-methylthieno[3,2-d]pyrimidin-4-yl)piperidin-4-yl)propenamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.61 (s, 1H), 8.31 (d, J=4.2 Hz, 1H), 7.69 (s, 1H), 7.43 (s, 1H), 7.21 (d, J=4.4 Hz, 1H), 6.59 (d, J=7.6 Hz, 1H), 4.91-4.87 (m, 2H), 4.23-4.19 (m, 1H), 3.52-3.49 (m, 2H), 3.01-2.97 (m, 2H), 2.58-2.55 (m, 2H), 2.51 (s, 3H), 2.18-2.13 (m, 2H), 1.60-1.50 (m, 2H). MS: m/z 459.7 ($M+H^+$).

Example 3.10

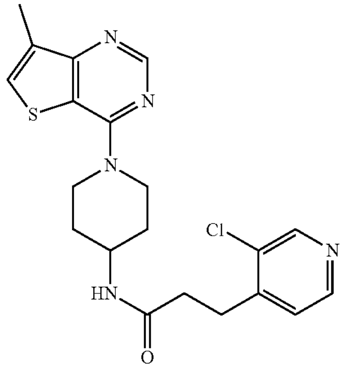 [SMILES: Cc1csc2c(N3CCC(NC(=O)CCc4ccncc4Cl)CC3)ncnc12]

3-(3-Chloropyridin-4-yl)-N-(1-(7-methylthieno[3,2-d]pyrimidin-4-yl)piperidin-4-yl)propenamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.64 (s, 1H), 8.53 (s, 1H), 8.38 (d, J=5.2 Hz, 1H), 7.37 (s, 1H), 7.21 (d, J=5.2 Hz, 1H), 5.28-5.26 (m, 1H), 4.78-4.75 (m, 2H), 4.12-4.11 (m, 1H), 3.27-3.20 (m, 2H), 3.10 (t, J=7.2 Hz, 2H), 2.50 (t, J=7.6 Hz, 2H), 2.45 (s, 3H), 2.07-2.04 (m, 2H), 1.46-1.39 (m, 2H). MS: m/z 415.8 ($M+H^+$).

Example 3.11

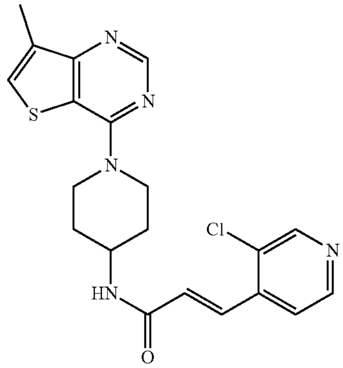 [SMILES: Cc1csc2c(N3CCC(NC(=O)/C=C/c4ccncc4Cl)CC3)ncnc12]

(E)-3-(3-Chloropyridin-4-yl)-N-(1-(7-methylthieno[3,2-d]pyrimidin-4-yl)piperidin-4-yl)acrylamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.64 (d, J=7.2 Hz, 2H), 8.47 (d, J=5.2 Hz, 1H), 7.91-7.87 (m, 1H), 7.40-7.39 (m, 2H), 6.56-6.52 (m, 1H), 5.70-5.68 (m, 1H), 4.85-4.81 (m, 2H), 4.32-4.29 (m, 1H), 3.35-3.29 (m, 2H), 2.46 (s, 3H), 2.22-2.18 (m, 2H), 1.58-1.51 (m, 2H). MS: m/z 413.8 ($M+H^+$).

Example 3.12

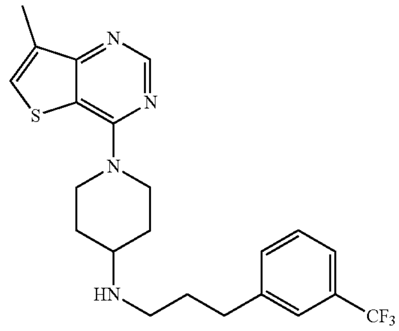 [SMILES: Cc1csc2c(N3CCC(NCCCc4cccc(C(F)(F)F)c4)CC3)ncnc12]

1-(7-Methylthieno[3,2-d]pyrimidin-4-yl)-N-(3-(3-(trifluoromethyl)phenyl)propyl)piperidin-4-amine The title compound was prepared using general procedure of 1-(7-methylthieno[3,2-d]pyrimidin-4-yl)-N-(3-(pyridin-2-yl)propyl)piperidin-4-amine (Example 3.3). $^1$HNMR (400 MHz, $CDCl_3$): δ=8.63 (s, 1H), 7.46-7.42 (m, 2H), 7.40-7.36 (m, 3H), 4.72 (d, J=13.2 Hz, 2H), 3.29-3.22 (m, 2H), 2.84-2.80 (m, 1H), 2.79-2.68 (m, 4H), 2.45 (s, 3H), 2.04-2.00 (m, 2H), 1.88-1.80 (m, 2H), 1.46-1.38 (m, 2H). MS: m/z 435.2 ($M+H^+$).

Example 3.13

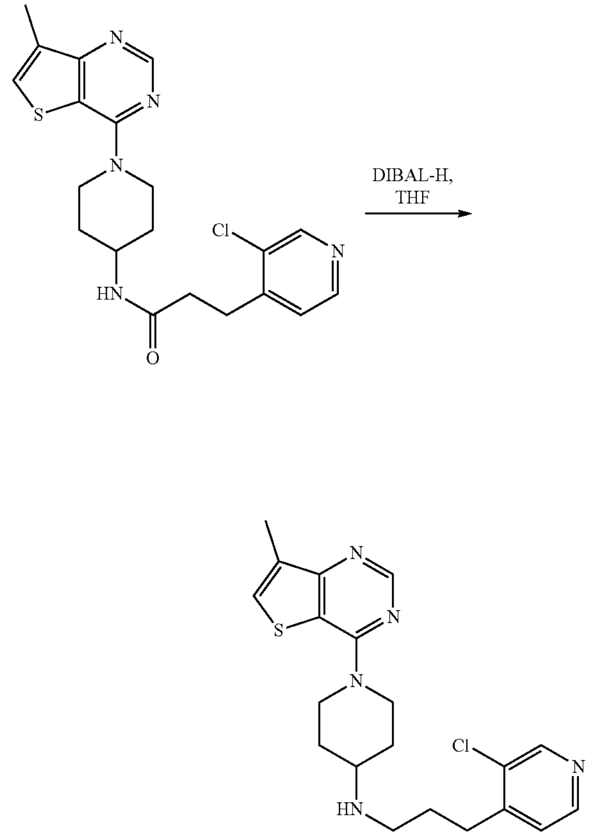

N-(3-(3-Chloropyridin-4-yl)propyl)-1-(7-methylthieno[3,2-d]pyrimidin-4-yl)piperidin-4-amine To a solution of 3-(3-chloropyridin-4-yl)-N-(1-(7-methylthieno[3,2-d]pyrimidin-4-yl)piperidin-4-yl)propanamide (150 mg, 0.36 mmol) in THF (3 mL) was added DIBAL-H (1.5 M, 4 mL) at −78° C. The mixture was stirred at −78° C. for 6 hrs under $H_2$ atmosphere (balloon). Then it was quenched by $H_2O$ slowly at −65° C. The mixture was concentrated and purified by prep-HPLC ($NH_4HCO_3$) to give N-(3-(3-chloropyridin-4-yl)propyl)-1-(7-methylthieno[3,2-d]pyrimidin-4-yl)piperidin-4-amine (13.5 mg, yield: 9.3%) as a yellow oil. $^1$HNMR (400 MHz, $CDCl_3$): δ=8.63 (s, 1H), 8.53 (s, 1H), 8.38 (d, J=5.2 Hz, 1H), 7.36 (s, 1H), 7.17 (d, J=4.8 Hz, 1H), 4.75-4.70 (m, 2H), 3.31-3.24 (m, 2H), 2.86-2.79 (m, 3H), 2.75-2.72 (m, 2H), 2.45 (s, 3H), 2.06-2.02 (m, 2H), 1.87-1.79 (m, 2H), 1.48-1.28 (m, 2H). MS: m/z 401.8 ($M+H^+$).

Example 3.14

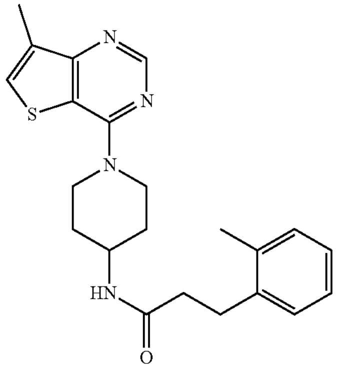 [SMILES: Cc1ccccc1CCC(=O)NC1CCN(c2ncnc3c(C)csc23)CC1]

N-(1-(7-Methylthieno[3,2-d]pyrimidin-4-yl)piperidin-4-yl)-3-(o-tolyl)propanamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.63 (s, 1H), 7.37 (s, 1H), 7.15-7.11 (m, 4H), 5.17 (d, J=7.6 Hz, 1H), 4.73-4.70 (m, 2H), 4.12-4.10 (m, 1H), 3.29-3.22 (m, 2H), 2.98-2.95 (m, 2H), 2.45 (s, 3H), 2.43-2.40 (m, 2H), 2.32 (s, 3H), 2.05-2.02 (m, 2H), 1.42-1.35 (m, 2H). MS: m/z 395.1 (M+H$^+$).

Example 3.15

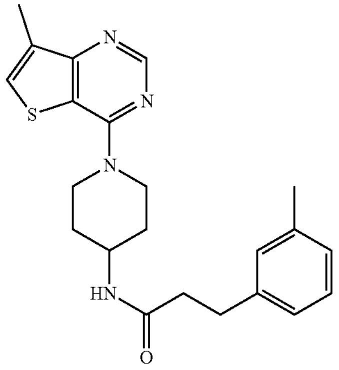 [SMILES: Cc1cccc(CCC(=O)NC2CCN(c3ncnc4c(C)csc34)CC2)c1]

N-(1-(7-Methylthieno[3,2-d]pyrimidin-4-yl)piperidin-4-yl)-3-(m-tolyl)propanamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.63 (s, 1H), 7.35 (s, 1H), 7.25-7.15 (m, 1H), 7.02-6.98 (m, 3H), 5.18 (d, J=8 Hz, 1H), 4.69 (d, J=13.2 Hz, 2H), 4.12-4.08 (m, 1H), 3.29-3.22 (m, 2H), 2.92 (t, J=7.6 Hz, 2H), 2.47-2.43 (m, 5H), 2.31 (s, 3H), 2.03-1.99 (m, 2H), 1.40-1.30 (m, 2H). MS: m/z 395.1 (M+H$^+$).

Example 3.16

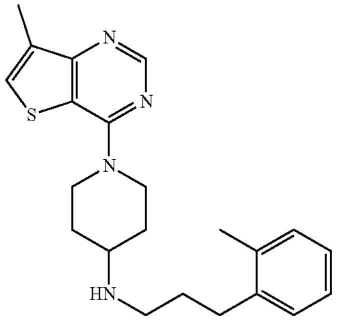 [SMILES: Cc1ccccc1CCCNC1CCN(c2ncnc3c(C)csc23)CC1]

1-(7-Methylthieno[3,2-d]pyrimidin-4-yl)-N-(3-(o-tolyl)propyl)piperidin-4-amine

The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=8.63 (s, 1H), 7.35 (s, 1H), 7.15-7.11 (m, 4H), 4.72 (d, J=13.2 Hz, 2H), 3.28-3.21 (m, 2H), 2.85-2.80 (m, 1H), 2.74 (t, J=7.2 Hz, 2H), 2.66 (t, J=8 Hz, 2H), 2.45 (s, 3H), 2.31 (s, 3H), 2.06-2.02 (m, 2H), 1.83-1.75 (m, 2H), 1.49-1.40 (m, 2H). MS: m/z 381.2 (M+H$^+$).

Example 3.17

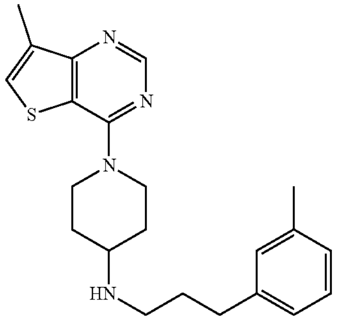 [SMILES: Cc1cccc(CCCNC2CCN(c3ncnc4c(C)csc34)CC2)c1]

1-(7-Methylthieno[3,2-d]pyrimidin-4-yl)-N-(3-(m-tolyl)propyl)piperidin-4-amine

The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=8.63 (s, 1H), 7.36 (s, 1H), 7.20-7.16 (m, 1H), 7.01-6.98 (m, 3H), 4.73 (d, J=13.2 Hz, 2H), 3.28-3.21 (m, 2H), 2.85-2.80 (m, 1H), 2.71 (t, J=7.6 Hz, 2H), 2.64 (t, J=7.6 Hz, 2H), 2.45 (s, 3H), 2.33 (s, 3H), 2.05-2.01 (m, 2H), 1.86-1.82 (m, 2H), 1.45-1.43 (m, 2H). MS: m/z 381.2 (M+H$^+$).

Example 3.18

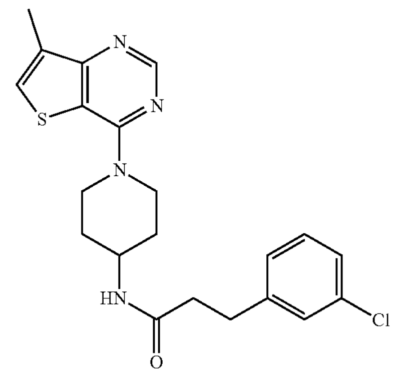 [SMILES: Cc1csc2c(N3CCC(NC(=O)CCc4cccc(Cl)c4)CC3)ncnc12]

3-(3-Chlorophenyl)-N-(1-(7-methylthieno[3,2-d]pyrimidin-4-Y)piperidin-4-yl)propanamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.63 (s, 1H), 7.37 (s, 1H), 7.23-7.15 (m, 3H), 7.07 (d, J=7.2 Hz, 1H), 5.29 (d, J=7.6 Hz, 1H), 4.73 (d, J=13.6 Hz, 2H), 4.15-4.08 (m, 1H), 3.28-3.21 (m, 2H), 2.95 (t, J=7.2 Hz, 2H), 2.45-2.42 (m, 5H), 2.05-2.02 (m, 2H), 1.42-1.32 (m, 2H). MS: m/z 414.8 (M+H$^+$).

Example 3.19

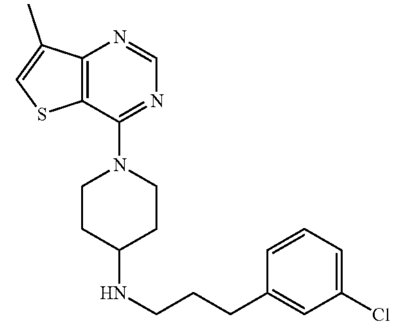 [SMILES: Cc1csc2c(N3CCC(NCCCc4cccc(Cl)c4)CC3)ncnc12]

N-(3-(3-Chlorophenyl)propyl)-1-(7-methylthieno[3,2-d]pyrimidin-4-yl)piperidin-4-amine The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=8.63 (s, 1H), 7.36 (s, 1H), 7.23-7.16 (m, 3H), 7.06 (d, J=7.6 Hz, 1H), 4.73 (d, J=13.2 Hz, 2H), 3.26-3.20 (m, 2H), 2.86-2.84 (m, 1H), 2.72-2.64 (m, 4H), 2.45 (s, 3H), 2.06-2.02 (m, 2H), 1.88-1.82 (m, 2H), 1.47-1.45 (m, 2H). MS: m/z 400.9 (M+H$^+$).

Example 3.20

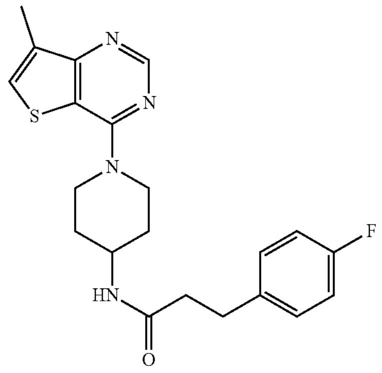 [SMILES: Cc1csc2c(N3CCC(NC(=O)CCc4ccc(F)cc4)CC3)ncnc12]

3-(4-Fluorophenyl)-N-(1-(7-methylthieno[3,2-d]pyrimidin-4-yl)piperidin-4-yl)propanamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.63 (s, 1H), 7.37 (s, 1H), 7.17-7.12 (m, 2H), 6.99-6.94 (m, 2H), 5.21 (d, J=8 Hz, 1H), 4.73 (d, J=13.2 Hz, 2H), 4.13-4.07 (m, 1H), 3.27-3.20 (m, 2H), 2.94 (d, J=7.6 Hz, 2H), 2.45-2.41 (m, 5H), 2.04-2.00 (m, 2H), 1.42-1.32 (m, 2H). MS: m/z 398.9 (M+H$^+$).

Example 3.21

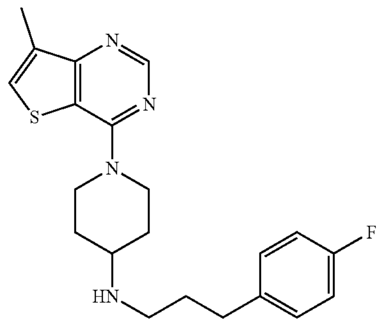 [SMILES: Cc1csc2c(N3CCC(NCCCc4ccc(F)cc4)CC3)ncnc12]

N-(3-(4-Fluorophenyl)propyl)-1-(7-methylthieno[3,2-d]pyrimidin-4-yl)piperidin-4-amine The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=8.65 (s, 1H), 7.35 (s, 1H), 7.16-7.12 (m, 2H), 7.00-6.94 (m, 2H), 4.88 (d, J=14.4 Hz, 2H), 3.24-3.20 (m, 1H), 3.10-3.04 (m, 2H), 2.93-2.89 (m, 2H), 2.67-2.63 (m, 2H), 2.45 (s, 3H), 2.33-2.30 (m, 2H), 2.23-2.18 (m, 2H), 1.96-1.87 (m, 2H). MS: m/z 384.9 (M+H$^+$).

Example 3.22

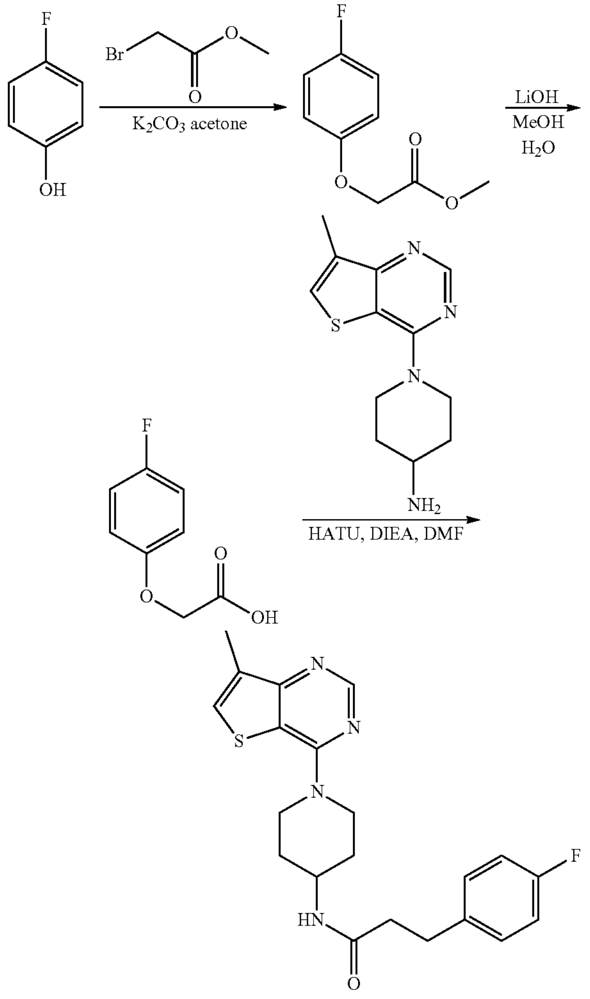

2-(4-Fluorophenoxy)-N-(1-(7-methylthieno[3,2-d]pyrimidin-4-yl)piperidin-4-yl)acetamide Step 1: A solution of 4-fluorophenol (2 g, 17.8 mmol) and $K_2CO_3$ (7.4 g, 53.5 mmol) in acetone (20 mL) was stirred at room temperature for 2 hrs. Then added methyl 2-bromoacetate (5.4 g, 35.6 mmol) to the solution. The mixture was stirred at room temperature for 0.5 hr and 60° C. overnight. The reaction mixture was filtered and the filtrate was concentrated. The residue was purified by silica gel column (PE/EA=10/1) to give methyl 2-(4-fluorophenoxy)acetate (3.2 g, yield: 96.7%) as a white solid. $^1$HNMR (400 MHz, $CDCl_3$): δ=7.01-6.96 (m, 2H), 6.88-6.85 (m, 2H), 4.61 (s, 2H), 3.81 (s, 3H).

Step 2: A solution of methyl 2-(4-fluorophenoxy)acetate (1 g, 5.4 mmol) and LiOH (0.4 g, 10.8 mmol) in MeOH/water (9 mL/3 mL) was stirred at room temperature for 2 hrs. The MeOH was removed under reduced pressure. The aqueous was acidified with 1 N HCl. The solid formed was collected by filtration to give 2-(4-fluorophenoxy)acetic acid (700 mg, yield: 75.8%) as a white solid.

Step 3: A solution of 2-(4-fluorophenoxy)acetic acid (100 mg, 0.6 mmol), HATU (268.2 mg, 0.7 mmol) and DIEA (227.6 mg, 1.8 mmol) in DCM (5 mL) was stirred at room temperature for 10 mins. Then added 1-(7-methylthieno[3,2-d]pyrimidin-4-yl)piperidin-4-amine (167.3 mg, 0.6 mmol) and the new mixture was stirred at room temperature overnight. The DCM was removed under reduced pressure. The residue was purified by slurry in DMF to give 2-(4-fluorophenoxy)-N-(1-(7-methylthieno[3,2-d]pyrimidin-4-yl)piperidin-4-yl)acetamide (28.3 mg, yield: 12%) as a white solid. $^1$HNMR (400 MHz, $CDCl_3$): δ=8.65 (s, 1H), 7.38 (s, 1H), 7.02-6.98 (m, 2H), 6.86-6.83 (m, 2H), 6.46 (d, J=8.4 Hz, 1H), 4.80 (d, J=13.6 Hz, 2H), 4.45 (s, 2H), 4.28-4.23 (m, 1H), 3.33-3.26 (m, 2H), 2.46 (s, 3H), 2.15-2.11 (m, 2H), 1.59-1.55 (m, 2H). MS: m/z 401.1 (M+H$^+$).

Example 3.23

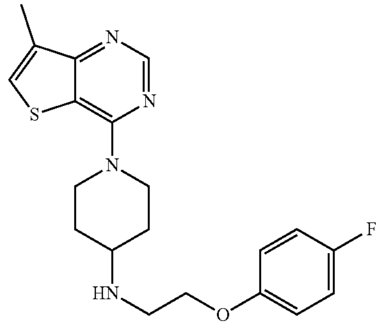 [SMILES: Cc1csc2c(N3CCC(NCCOc4ccc(F)cc4)CC3)ncnc12]

N-(2-(4-Fluorophenoxy)ethyl)-1-(7-methylthieno[3,2-d]pyrimidin-4-yl)piperidin-4-amine The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=8.64 (s, 1H), 7.36 (s, 1H), 6.99-6.95 (m, 2H), 6.86-6.82 (m, 2H), 4.76-4.72 (m, 2H), 4.06-4.04 (m, 2H), 3.32-3.26 (m, 2H), 3.06 (t, J=5.2 Hz, 2H), 2.94-2.89 (m, 2H), 2.45 (s, 3H), 2.10-2.06 (m, 2H), 1.54-1.48 (m, 2H). MS: m/z 387.2 (M+H$^+$).

Example 3.24

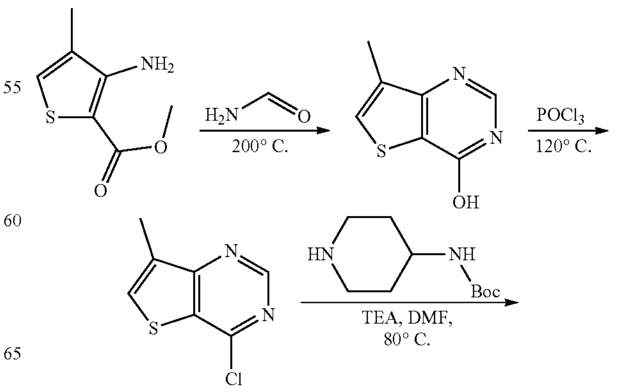

-continued

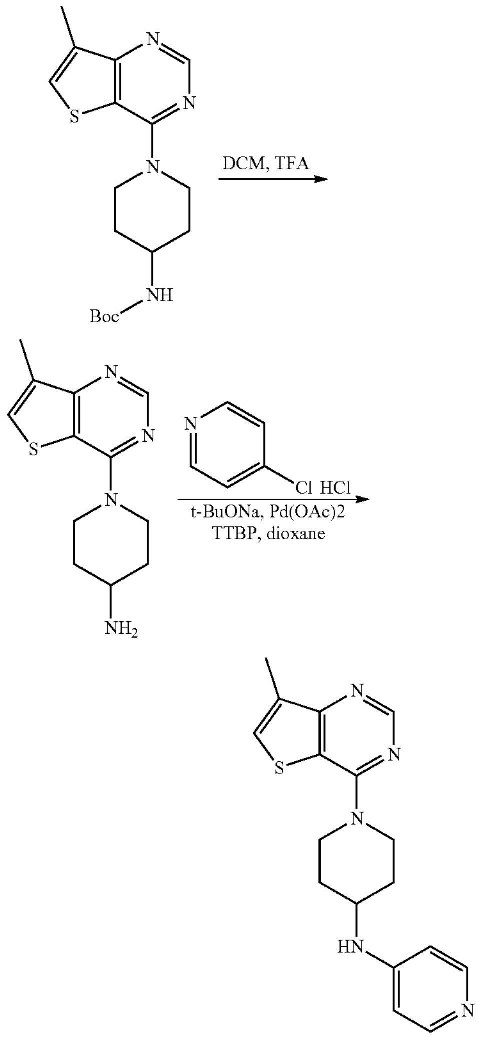

N-(1-(7-Methylthieno[3,2-d]pyrimidin-4-yl)piperidin-4-yl)pyridin-4-amine

Step 1 through Step 4: The title compound was prepared using general procedure of 1-(7-methylthieno[3,2-d]pyrimidin-4-yl)-N-(3-(pyridin-3-yl)propyl)piperidin-4-amine (Example 3.26).

Step 5: A solution of 1-(7-methylthieno[3,2-d]pyrimidin-4-yl)piperidin-4-amine (200 mg, 0.81 mmol), 4-chloropyridine (133 mg, 0.89 mmol), t-BuONa (432 mg, 3.22 mmol), $Pd(OAc)_2$ (18 mg, 0.08 mmol) and TTBP (23 mg, 0.08 mmol) in dioxane (10 mL) was stirred at 100° C. overnight under $N_2$ atmosphere (balloon). The reaction mixture was filtered. The filtrate was concentrated and the residue was purified by prep-HPLC ($NH_4OAc$) to give N-(1-(7-methylthieno[3,2-d]pyrimidin-4-yl)piperidin-4-yl)pyridin-4-amine (3.5 mg, yield: 1.3%) as a white solid. $^1$HNMR (400 MHz, $CDCl_3$): δ=8.66 (s, 1H), 8.21 (d, J=6.4 Hz, 2H), 7.39 (s, 1H), 6.47 (d, J=6.4 Hz, 2H), 4.78 (d, J=13.2 Hz, 2H), 4.11 (d, J=7.2 Hz, 1H), 3.72-3.70 (m, 1H), 3.38 (t, J=11.6 Hz, 2H), 2.46 (s, 3H), 2.26-2.22 (m, 2H), 1.61-1.52 (m, 2H). MS: m/z 325.9. (M+H$^+$).

Example 3.25

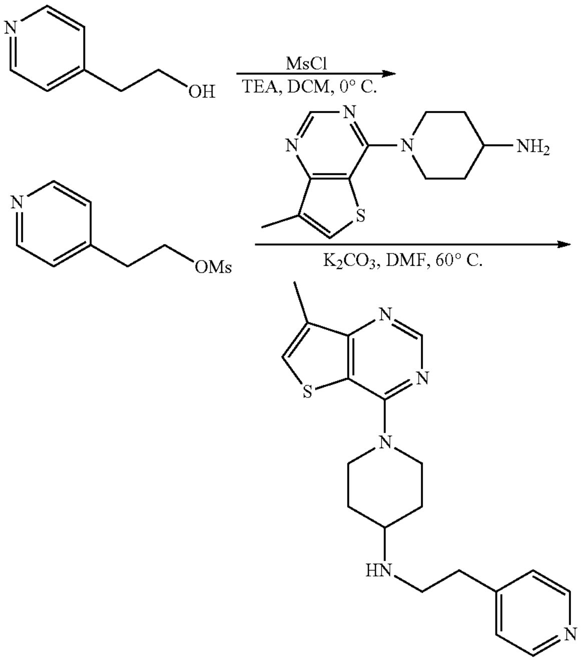

1-(7-Methylthieno[3,2-d]pyrimidin-4-yl)-N-(2-(pyridin-4-yl)ethyl)piperidin-4-amine Step 1: To a solution of 2-(pyridin-4-yl)ethanol (200 mg, 1.6 mmol) and TEA (323 mg, 3.2 mmol) in DCM (15 mL) was added MsCl (217 mg, 1.9 mmol) at 0° C. The mixture was stirred at 0° C. for 1 hr under $N_2$ atmosphere (balloon). The mixture was washed with saturated aqueous $NaHCO_3$ solution (15 mL), dried over $Na_2SO_4$ and concentrated to give 2-(pyridin-4-yl)ethyl methanesulfonate (321 mg, yield: 100%) as a yellow oil.

Step 2: A solution of 1-(7-methylthieno[3,2-d]pyrimidin-4-yl)piperidin-4-amine (360 mg, 1.45 mmol), 2-(pyridin-4-yl)ethyl methanesulfonate (321 mg, 1.6 mmol) and $K_2CO_3$ (600 mg, 4.35 mmol) in DMF (10 mL) was stirred at 60° C. overnight. The DMF was removed under reduced pressure. The residue was purified by prep-HPLC ($NH_4HCO_3$) to give 1-(7-methylthieno[3,2-d]pyrimidin-4-yl)-N-(2-(pyridin-4-yl)ethyl)piperidin-4-amine (1.1 mg, yield: 0.2%) as a yellow oil. $^1$HNMR (400 MHz, $CDCl_3$): δ=8.63 (s, 1H), 8.52 (d, J=6.0 Hz, 2H), 7.36 (s, 1H), 7.16 (d, J=6.0 Hz, 2H), 4.73 (d, J=13.6 Hz, 2H), 3.25 (t, J=11.2 Hz, 2H), 2.99 (t, J=7.2 Hz, 2H), 2.91-2.82 (m, 3H), 2.45 (s, 3H), 2.06-2.03 (m, 2H), 1.50-1.38 (m, 2H). MS: m/z 353.9 (M+H$^+$).

Example 3.26

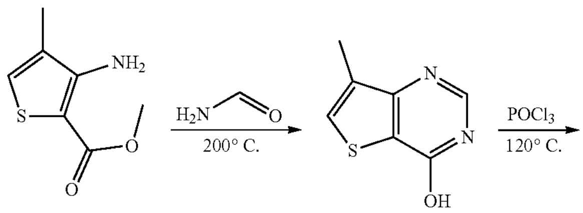

-continued

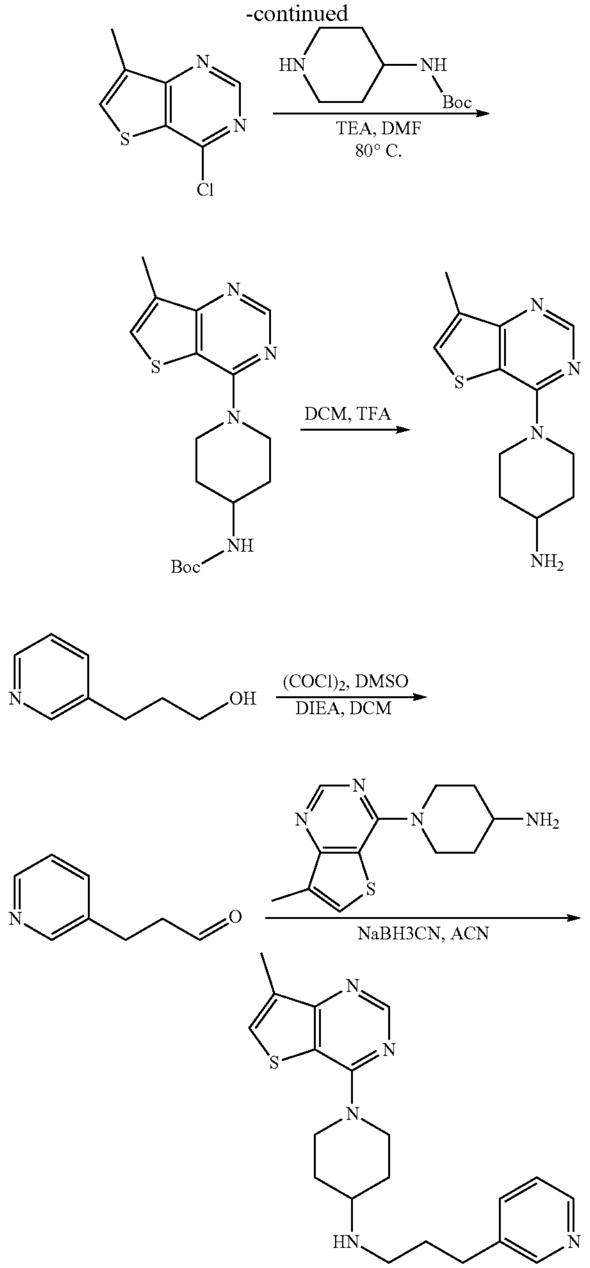

1-(7-Methylthieno[3,2-d]pyrimidin-4-yl)-N-(3-(pyridin-3-yl)propyl)piperidin-4-amine Step 1: A solution of methyl 3-amino-4-methylthiophene-2-carboxylate (10 g, 0.058 mol) in formamide (100 mL) was stirred at 200° C. for 8 hrs. The reaction was cooled to room temperature and filtered. The pad was rinsed with THF to give 7-methylthieno[3,2-d]pyrimidin-4-ol (5.3 g, yield: 55%) as a gray solid.

Step 2: A solution of 7-methylthieno[3,2-d]pyrimidin-4-ol (4.8 g, 0.03 mol) in $POCl_3$ (40 mL) was stirred at 120° C. for 2 hrs. The $POCl_3$ was removed under reduced pressure. The residue was neutralized with saturated aqueous $NaHCO_3$ solution (150 mL) and extracted with EA (200 mL×3). The combined organic layers were dried over $Na_2SO_4$ and concentrated. The residue was purified by silica gel column (PE/EA=10/1) to give 4-chloro-7-methylthieno[3,2-d]pyrimidine (4.3 g, yield: 81%) as a white solid. $^1$HNMR (300 MHz, $CDCl_3$): δ=9.02 (s, 1H), 7.68 (s, 1H), 2.50 (s, 3H). MS: m/z 185.2 (M+$H^+$).

Step 3: To a solution of 4-chloro-7-methylthieno[3,2-d]pyrimidine (3.5 g, 19 mmol) and tert-butyl piperidin-4-ylcarbamate (7.6 g, 38 mmol) in DMF (50 mL) was added TEA (3.8 g, 38 mmol). The mixture was stirred at 80° C. for 2 hrs. The DMF was removed under reduced pressure. The residue was purified by silica gel column (PE/EA=10/1) to give tert-butyl (1-(7-methylthieno[3,2-d]pyrimidin-4-yl)piperidin-4-yl)carbamate (5.8 g, yield: 87.9%) as a white solid. MS: m/z 349.5 (M+$H^+$).

Step 4: A solution of tert-butyl (1-(7-methylthieno[3,2-d]pyrimidin-4-yl)piperidin-4-yl)carbamate (2 g, 5.7 mmol) and TFA (4 mL) in DCM (20 mL) was stirred at room temperature overnight. The DCM and TFA was removed under reduced pressure. The residue was treated with saturated aqueous $NaHCO_3$ solution and concentrated. The residue was dissolved in MeOH and the mixture was filtered. The filtrate was concentrated to give 1-(7-methylthieno[3,2-d]pyrimidin-4-yl)piperidin-4-amine (2 g, crude) as a yellow oil. MS: m/z 249.4 (M+$H^+$).

Step 5: The step 5 was as same as the step 1 of 1-(7-methylthieno[3,2-d]pyrimidin-4-yl)-N-(3-(pyridin-2-yl)propyl)piperidin-4-amine (Example 3.3).

Step 6: A solution of 1-(7-methylthieno[3,2-d]pyrimidin-4-yl)piperidin-4-amine (330 mg, 1.35 mmol) and 3-(pyridin-3-yl)propanal (200 mg, 1.48 mmol) in ACN (15 mL) was stirred at room temperature for 0.5 hr. Then the reaction was cooled to 0° C. and added $NaBH_3CN$ (254 mg, 4.05 mmol). The reaction was stirred at room temperature overnight. The ACN was removed under reduced pressure. The residue was purified by prep-HPLC ($NH_4HCO_3$) to give 1-(7-methylthieno[3,2-d]pyrimidin-4-yl)-N-(3-(pyridin-3-yl)propyl)piperidin-4-amine (88.4 mg, yield: 17.8%) as a yellow oil. $^1$HNMR (400 MHz, DMSO-$d_6$): δ=8.50 (s, 1H), 8.43 (s, 1H), 8.43-8.38 (m, 1H), 7.82 (d, J=1.2 Hz, 1H), 7.64-7.62 (m, 1H), 7.32-7.28 (m, 1H), 4.53 (d, J=13.2 Hz, 2H), 3.34-3.28 (m, 2H), 2.77-2.72 (m, 1H), 2.64 (t, J=8.0 Hz, 2H), 2.58-2.51 (m, 2H), 2.33 (s, 3H), 1.95-1.91 (m, 2H), 1.74-1.68 (m, 2H), 1.32-1.23 (m, 2H). MS: m/z 367.9 (M+$H^+$).

Example 3.27

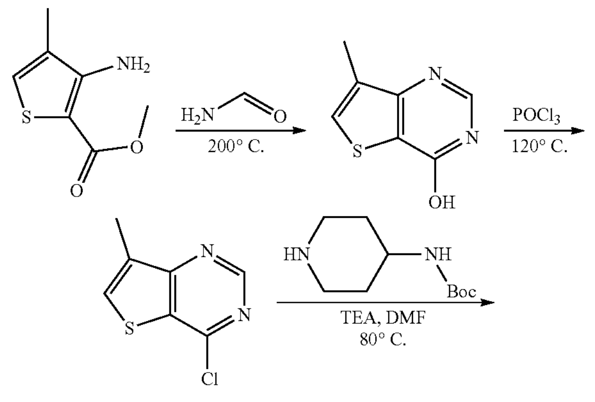

-continued

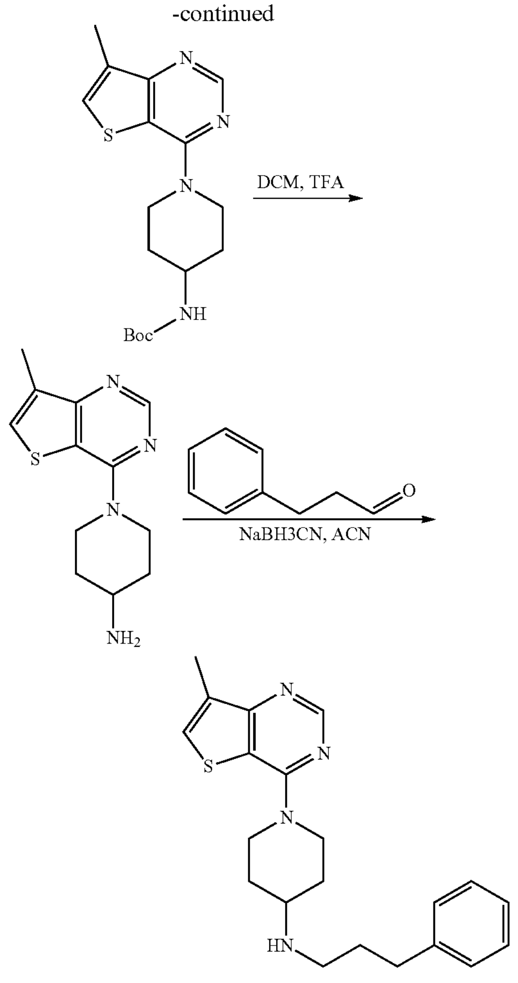

1-(7-Methylthieno[3,2-d]pyrimidin-4-yl)-N-(3-phenylpropyl)piperidin-4-amine

The title compound was prepared using general procedure of 1-(7-methylthieno[3,2-d]pyrimidin-4-yl)-N-(3-(pyridin-3-yl)propyl)piperidin-4-amine (Example 3.26). $^1$HNMR (400 MHz, $CDCl_3$): δ=8.64 (s, 1H), 7.34 (s, 1H), 7.29-7.25 (m, 2H), 7.19-7.15 (m, 3H), 4.85 (d, J=13.6 Hz, 2H), 3.19-3.17 (m, 1H), 3.07 (t, J=12.0 Hz, 2H), 2.89 (t, J=8.0 Hz, 2H), 2.66 (t, J=7.2 Hz, 2H), 2.45 (s, 3H), 2.25 (d, J=10.8 Hz, 2H), 2.20-2.14 (m, 2H), 1.89-1.83 (m, 2H). MS: m/z 367.2 $(M+H^+)$.

Example 3.28

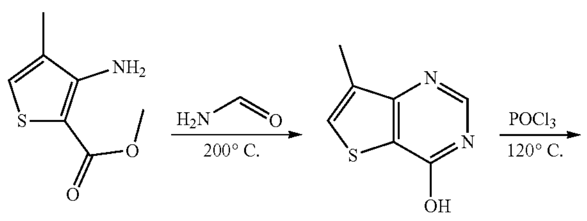

-continued

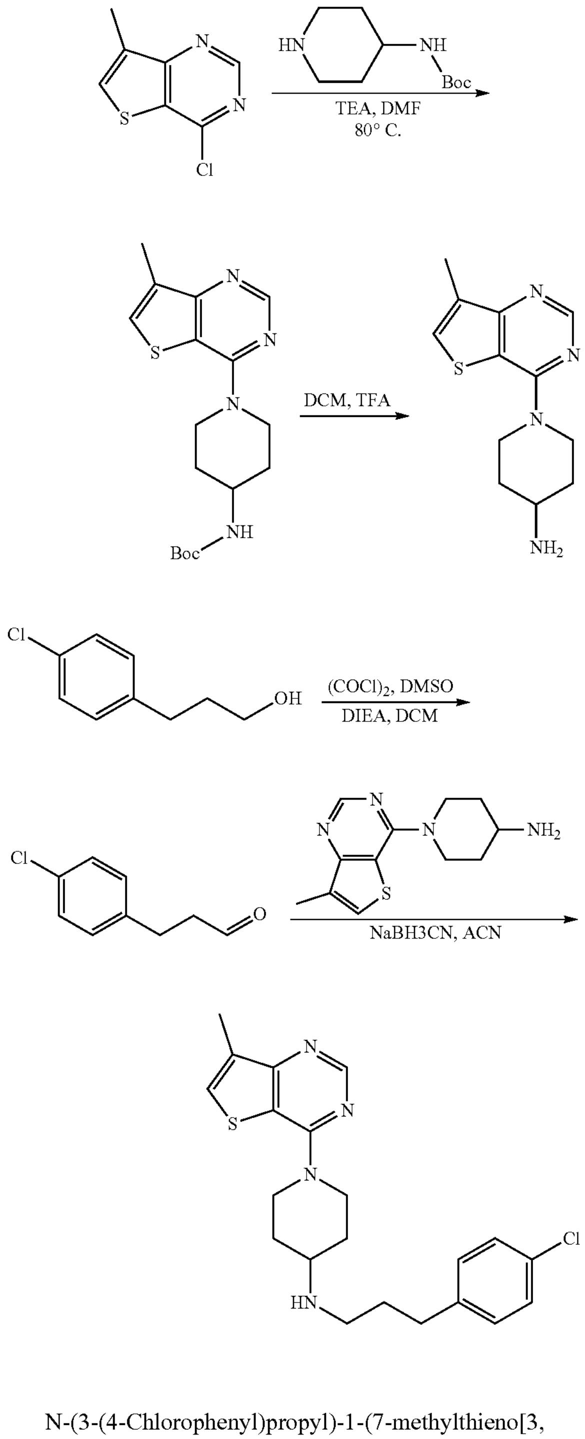

N-(3-(4-Chlorophenyl)propyl)-1-(7-methylthieno[3,2-d]pyrimidin-4-yl)piperidin-4-amine The title compound was prepared using general procedure of 1-(7-methylthieno[3,2-d]pyrimidin-4-yl)-N-(3-(pyridin-3-yl)propyl)piperidin-4-amine (Example 3.26). $^1$HNMR (400 MHz, $CDCl_3$): δ=8.65 (s, 1H), 7.35 (s, 1H), 7.24 (d, J=8.0 Hz, 2H), 7.11 (d, J=8.4 Hz, 2H), 4.88 (d, J=13.6 Hz, 2H), 3.27-3.07 (m, 1H), 3.07 (t, J=12.4 Hz, 2H), 2.92 (t, J=8.0 Hz, 2H), 2.65 (t, J=8.0 Hz, 2H), 2.45 (s, 3H), 2.32 (d, J=10.8 Hz, 2H), 2.23-2.20 (m, 2H), 1.94-1.91 (m, 2H). MS: m/z 401.1 $(M+H^+)$.

Example 3.29

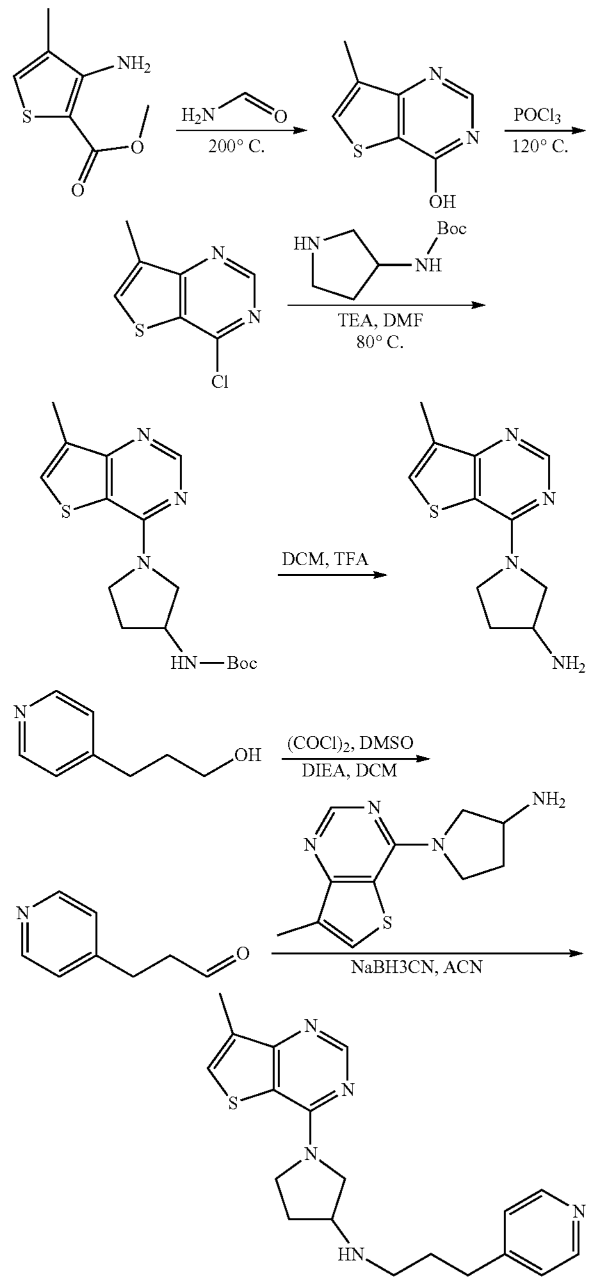

1-(7-Methylthieno[3,2-d]pyrimidin-4-yl)-N-(3-(pyridin-4-yl)propyl)pyrrolidin-3-amine The title compound was prepared using general procedure of 1-(7-methylthieno[3,2-d]pyrimidin-4-yl)-N-(3-(pyridin-3-yl)propyl)piperidin-4-amine (Example 3.26). $^1$HNMR (400 MHz, $CDCl_3$): δ=8.58 (s, 1H), 8.48 (d, J=5.2 Hz, 2H), 7.38 (s, 1H), 7.11 (d, J=5.2 Hz, 2H), 4.05 (s, 2H), 3.95 (s, 1H), 3.69-3.66 (m, 1H), 3.5 (t, J=5.2 Hz, 2H), 2.73-2.67 (m, 4H), 2.44 (s, 3H), 2.25-2.21 (m, 1H), 1.62-1.59 (m, 3H). MS: m/z 354.1 ($M+H^+$).

Example 3.30

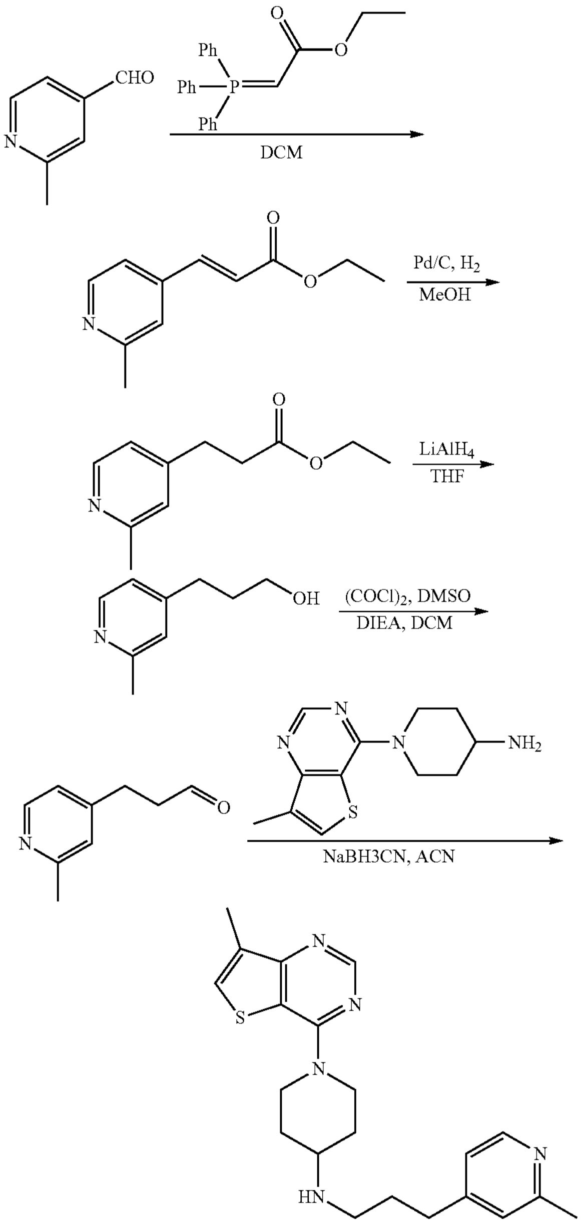

N-(3-(2-Methylpyridin-4-yl)propyl)-1-(7-methylthieno[3,2-d]pyrimidin-4-yl)piperidin-4-amine Step 1 through Step 2: The title compound was prepared using general procedure of 3-(3-fluoropyridin-4-yl)-N-(1-(7-methylthieno[3,2-d]pyrimidin-4-yl)piperidin-4-yl)propanamide (Example 3.38).

Step 3: To a solution of ethyl 3-(2-methylpyridin-4-yl) propanoate (340 mg, 1.76 mmol) in THF (10 mL) was added $LiAlH_4$ (200 mg, 5.28 mmol) slowly at 0° C. The mixture was stirred at 0° C. for 0.5 hr. The reaction was added 1 mL water, 1 mL NaOH (a.q, 15%) and 3 mL water slowly at 0° C. The mixture was filtered and the filtrate was concentrated under reduced pressure. The residue was purified by silica gel column (PE/EA=5/1) to give 3-(2-methylpyridin-4-yl) propan-1-ol (220 mg, yield: 83%) as a colorless oil.

Step 4 through Step 5: The title compound was prepared using general procedure of 1-(7-methylthieno[3,2-d]pyrimidin-4-yl)-N-(3-(pyridin-3-yl)propyl)piperidin-4-amine (Example 3.26). $^1$HNMR (400 MHz, $CDCl_3$): δ=8.63 (s, 1H), 8.37 (d, J=5.2 Hz, 1H), 7.36 (s, 1H), 6.99 (s, 1H), 6.93 (d, J=5.6 Hz, 1H), 4.74 (d, J=13.2 Hz, 2H), 3.24 (t, J=11.2 Hz, 2H), 2.90-2.85 (m, 1H), 2.73 (t, J=7.2 Hz, 2H), 2.64 (t, J=7.2 Hz, 2H), 2.52 (s, 3H), 2.45 (s, 3H), 2.08-2.03 (m, 2H), 1.90-1.78 (m, 2H), 1.49-1.46 (m, 2H). MS: m/z 381.9 ($M+H^+$).

Example 3.31

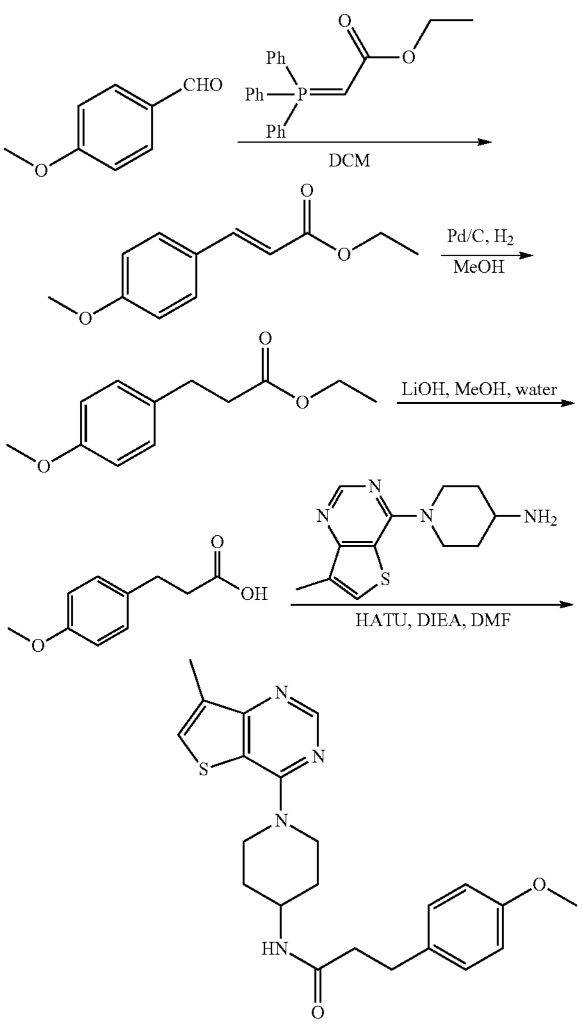

3-(4-Methoxyphenyl)-N-(1-(7-methylthieno[3,2-d]pyrimidin-4-yl)piperidin-4-yl)propanamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.63 (s, 1H), 7.37 (s, 1H), 7.11 (d, J=8.8 Hz, 2H), 6.82 (d, J=8.4 Hz, 2H), 5.17 (d, J=8.4 Hz, 1H), 4.70 (d, J=14.0 Hz, 2H), 4.12-4.08 (m, 1H), 3.77 (s, 3H), 3.25 (t, J=13.6 Hz, 2H), 2.91 (t, J=7.2 Hz, 2H), 2.45 (s, 3H), 2.43 (t, J=7.6 Hz, 2H), 2.02 (d, J=10.0 Hz, 2H), 1.43-1.25 (m, 2H). MS: m/z 411.2 ($M+H^+$).

Example 3.32

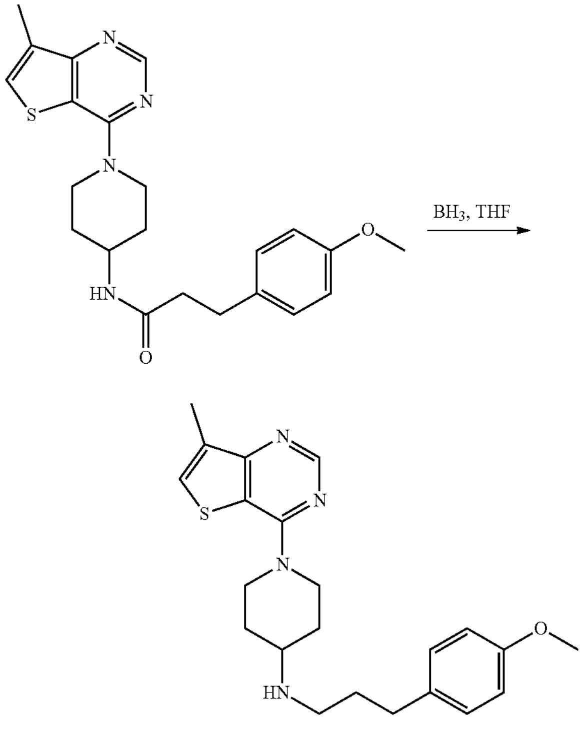

N-(3-(4-Methoxyphenyl)propyl)-1-(7-methylthieno[3,2-d]pyrimidin-4-yl)piperidin-4-amine The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=9.22 (s, 1H), 8.64 (s, 1H), 7.69 (s, 1H), 7.03 (d, J=8.8 Hz, 2H), 6.79 (d, J=8.8 Hz, 2H), 5.00 (d, J=10.4 Hz, 2H), 3.79 (s, 3H), 3.50-3.47 (m, 1H), 3.35 (t, J=12.0 Hz, 2H), 3.02-2.98 (m, 2H), 2.56 (t, J=7.2 Hz, 2H), 2.49 (s, 3H), 2.31 (d, J=10.8 Hz, 2H), 2.00-1.90 (m, 4H). MS: m/z 396.9 ($M+H^+$).

Example 3.33

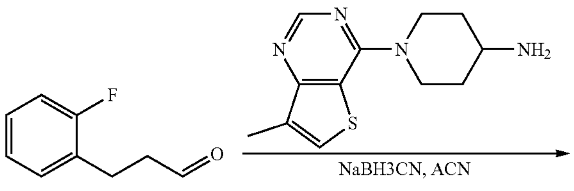

-continued

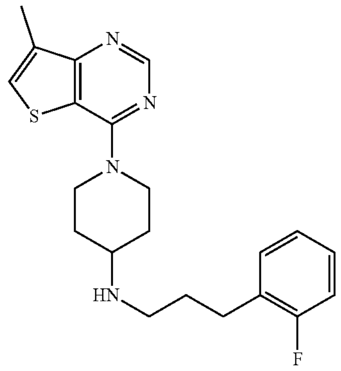

N-(3-(2-Fluorophenyl)propyl)-1-(7-methylthieno[3,2-d]pyrimidin-4-yl)piperidin-4-amine The title compound was prepared using general procedure of 1-(7-methylthieno[3,2-d]pyrimidin-4-yl)-N-(3-(pyridin-3-yl)propyl)piperidin-4-amine (Example 3.26). $^1$HNMR (400 MHz, $CDCl_3$): δ=8.63 (s, 1H), 7.35 (s, 1H), 7.27-7.14 (m, 2H), 7.08-6.98 (m, 2H), 4.71 (d, J=13.6 Hz, 2H), 3.25 (t, J=11.2 Hz, 2H), 2.84-2.78 (m, 1H), 2.72-2.69 (m, 4H), 2.45 (s, 3H), 2.02 (d, J=10.0 Hz, 2H), 1.82 (t, J=7.2 Hz, 2H), 1.47-1.38 (m, 2H). MS: m/z 384.9 ($M+H^+$).

Example 3.34

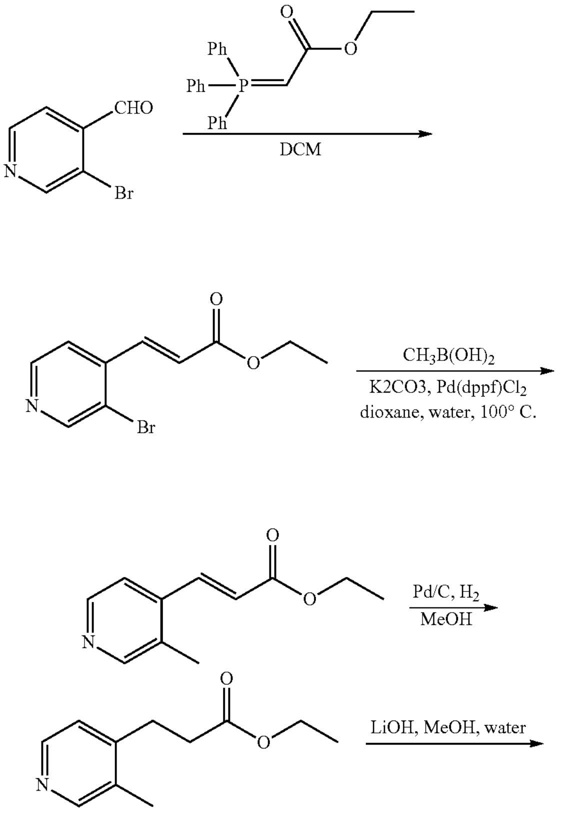

-continued

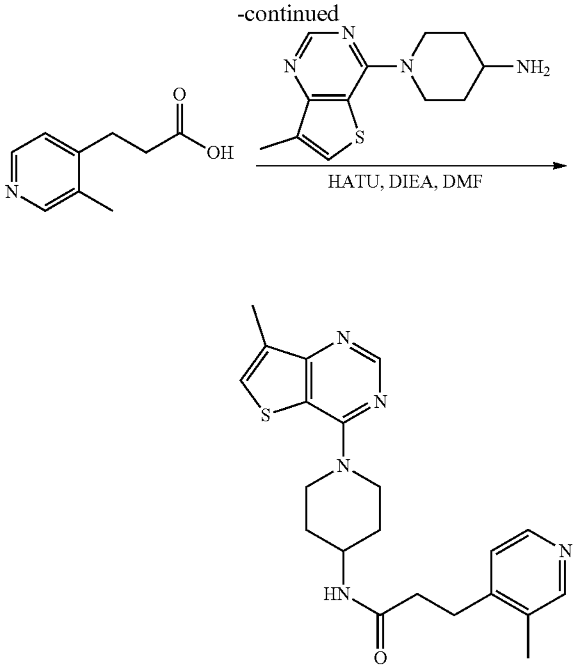

3-(3-Methylpyridin-4-yl)-N-(1-(7-methylthieno[3,2-d]pyrimidin-4-yl)piperidin-4-yl)propanamide Step 1: To a solution of 3-bromoisonicotinaldehyde (2 g, 10.7 mmol) in DCM (30 mL) was added a solution of ethyl 2-(triphenylphosphoranylidene)acetate (3.7 g, 10.7 mmol) in DCM (20 mL). The mixture was stirred at room temperature for 2 hrs under $N_2$ atmosphere. The DCM was removed under reduced pressure. The residue was purified by silica gel column (PE/EA=1/1) to give (E)-ethyl 3-(3-bromopyridin-4-yl)acrylate (2.3 g, yield: 85%) as a yellow oil. MS: m/z 258.2 ($M+H^+$).

Step 2: A solution of (E)-ethyl 3-(3-bromopyridin-4-yl) acrylate (1.5 g, 5.88 mmol), methylboronic acid (704 mg, 11.76 mol), $K_2CO_3$ (2.4 g, 17.64 mmol) and $Pd(dppf)Cl_2$ (430 mg, 0.588 mmol) in dioxane/water (40 mL/8 mL) was stirred at 100° C. overnight under $N_2$ atmosphere (balloon). The dioxane and water was removed under reduced pressure. The residue was purified by silica gel column (PE/EA=1/1) to give (E)-ethyl 3-(3-methylpyridin-4-yl)acrylate (600 mg, yield: 54.5%) as a yellow oil. $^1$HNMR (400 MHz, CDCl3): δ=8.47 (d, J=7.2 Hz, 2H), 7.85 (d, J=16.0 Hz, 1H), 7.35 (d, J=4.8 Hz, 1H), 6.50 (d, J=16.0 Hz, 1H), 4.30 (q, J=7.2 Hz, 2H), 2.41 (s, 3H), 1.36 (t, J=7.2 Hz, 3H). MS: m/z 192.3 ($M+H^+$).

Step 3 through Step 5: The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.61 (s, 1H), 8.32-8.30 (m, 2H), 7.37 (s, 1H), 7.03 (d, J=4.8 Hz, 1H), 5.62 (d, J=8.0 Hz, 1H), 4.81-4.74 (m, 4H), 4.15-4.09 (m, 1H), 3.24 (t, J=12.0 Hz, 2H), 2.95 (t, J=7.2 Hz, 2H), 2.45 (s, 3H), 2.29 (s, 3H), 2.29-2.03 (m, 2H), 1.46-1.36 (m, 2H). MS: m/z 396.2 ($M+H^+$).

Example 3.35

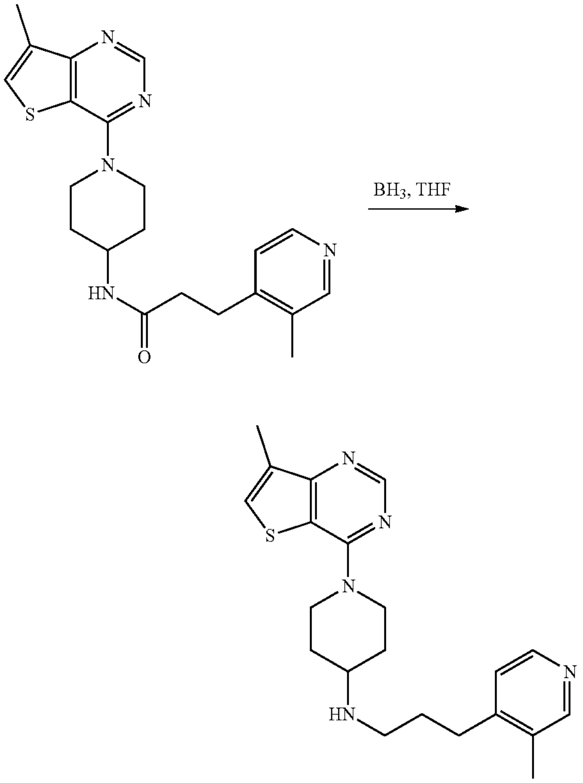 [SMILES: Cc1cnccc1CCC(=O)NC1CCN(c2ncnc3c(C)csc23)CC1 ; Cc1cnccc1CCCNC1CCN(c2ncnc3c(C)csc23)CC1]

N-(3-(3-Methylpyridin-4-yl)propyl)-1-(7-methylthieno[3,2-d]pyrimidin-4-yl)piperidin-4-amine The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=8.63 (s, 1H), 8.34-8.33 (m, 2H), 7.36 (s, 1H), 7.05 (d, J=4.8 Hz, 1H), 4.73 (d, J=10.8 Hz, 2H), 3.26 (t, J=10.8 Hz, 2H), 2.85-2.80 (m, 1H), 2.73 (t, J=7.2 Hz, 2H), 2.66 (t, J=7.6 Hz, 2H), 2.45 (s, 3H), 2.29 (s, 3H), 2.06-2.02 (m, 2H), 1.83-1.75 (m, 2H), 1.48-1.42 (m, 2H). MS: m/z 381.9 (M+H$^+$).

Example 3.36

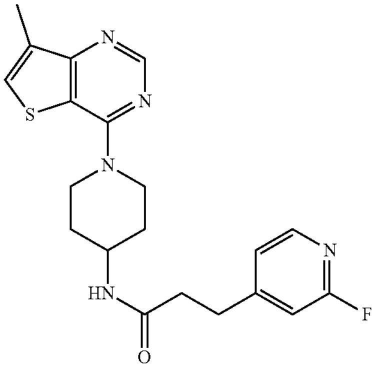 [SMILES: Cc1csc2c(N3CCC(NC(=O)CCc4ccnc(F)c4)CC3)ncnc12]

3-(2-Fluoropyridin-4-yl)-N-(1-(7-methylthieno[3,2-d]pyrimidin-4-yl)piperidin-4-yl)propanamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.63 (s, 1H), 8.11 (d, J=5.2 Hz, 1H), 7.38 (s, 1H), 7.03 (d, J=5.2 Hz, 1H), 6.77 (s, 1H), 5.37 (d, J=7.6 Hz, 1H), 4.77 (d, J=13.2 Hz, 2H), 4.15-4.11 (m, 1H), 3.24 (t, J=12.0 Hz, 2H), 3.02 (t, J=7.2 Hz, 2H), 2.48 (t, J=7.6 Hz, 2H), 2.45 (s, 3H), 2.08-2.04 (m, 2H), 1.46-1.37 (m, 2H). MS: m/z 400.2 (M+H$^+$).

Example 3.37

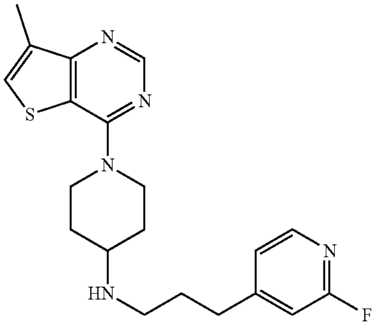 [SMILES: Cc1csc2c(N3CCC(NCCCc4ccnc(F)c4)CC3)ncnc12]

N-(3-(2-Fluoropyridin-4-yl)propyl)-1-(7-methylthieno[3,2-d]pyrimidin-4-yl)piperidin-4-amine The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=8.63 (s, 1H), 8.10 (d, J=4.8 Hz, 1H), 7.36 (s, 1H), 7.01 (d, J=5.2 Hz, 1H), 6.76 (s, 1H), 4.72 (d, J=13.2 Hz, 2H), 3.26 (t, J=11.2 Hz, 2H), 2.84-2.79 (m, 1H), 2.74-2.68 (m, 4H), 2.45 (s, 3H), 2.05-2.01 (m, 2H), 1.87-1.79 (m, 2H), 1.47-1.38 (m, 2H). MS: m/z 386.2 (M+H$^+$).

Example 3.38

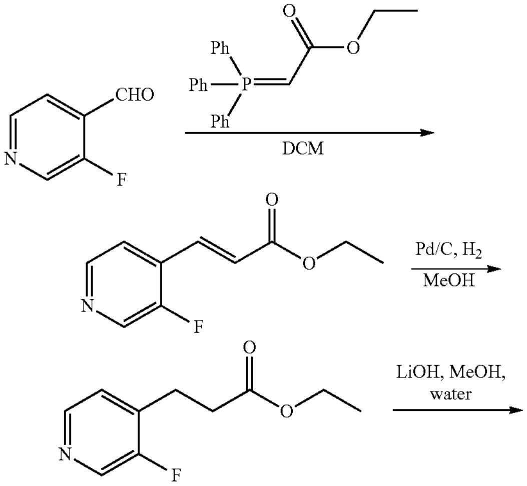

-continued

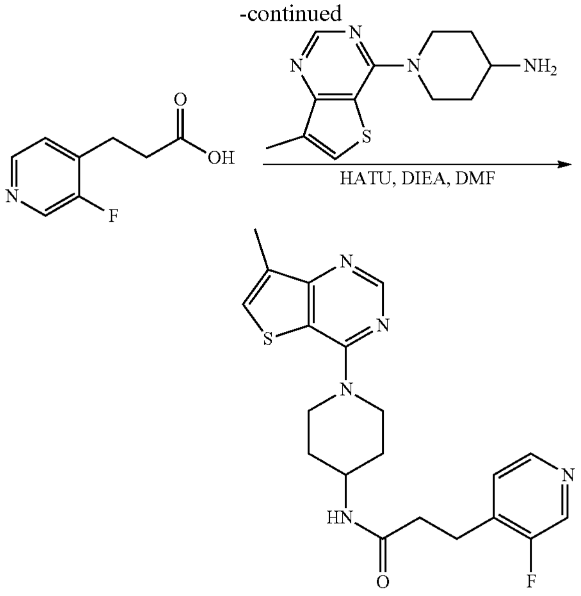

3-(3-Fluoropyridin-4-yl)-N-(1-(7-methylthieno[3,2-d]pyrimidin-4-yl)piperidin-4-yl)propanamide Step 1: To a solution of 3-fluoroisonicotinaldehyde (500 mg, 4 mmol) in DCM (20 mL) was added a solution of ethyl 2-(triphenylphosphoranylidene)acetate (1.39 g, 4 mmol) in DCM (10 mL). The mixture was stirred at room temperature for 2 hrs under $N_2$ atmosphere (balloon). The DCM was removed under reduced pressure. The residue was purified by silica gel column (PE/EA=1/1) to give (E)-ethyl 3-(3-fluoropyridin-4-yl)acrylate (700 mg, yield: 89.7%) as a yellow oil. MS: m/z 196.3 ($M+H^+$).

Step 2: A solution of (E)-ethyl 3-(3-fluoropyridin-4-yl) acrylate (650 mg, 3.3 mmol) and Pd/C (130 mg) in MeOH (20 mL) was stirred at room temperature overnight under $H_2$ atmosphere (balloon). The reaction mixture was filtered and the filtrate was concentrated to give ethyl 3-(3-fluoropyridin-4-yl)propanoate (600 mg, yield: 91.5%) as a colorless oil. MS: m/z 198.3 ($M+H^+$).

Step 3: A solution of ethyl 3-(3-fluoropyridin-4-yl)propanoate (500 mg, 2.54 mmol) and LiOH (120 mg, 5 mmol) in MeOH/water (9 mL/3 mL) was stirred at room temperature for 1 hr. The MeOH was removed under reduced pressure. The aqueous was acidified with 1 N hydrochloric acid. The suspension was filtered and the pad was rinsed with water to give 3-(3-fluoropyridin-4-yl)propanoic acid (280 mg, yield: $\delta$5.3%) as a white solid.

Step 4: A solution of 3-(3-fluoropyridin-4-yl)propanoic acid (560 mg, 3.3 mmol), HATU (1.5 g, 3.96 mmol) and DIEA (638 mg, 4.95 mmol) in DMF (10 mL) was stirred at room temperature for 10 mins. Then added 1-(7-methylthieno[3,2-d]pyrimidin-4-yl)piperidin-4-amine (821 mg, 3.3 mmol) and the mixture was stirred at room temperature overnight. The DMF was removed under reduced pressure. The residue was purified by silica gel column (DCM/MeOH=10/1) to give 3-(3-fluoropyridin-4-yl)-N-(1-(7-methylthieno[3,2-d]pyrimidin-4-yl)piperidin-4-yl)propanamide (650 mg, yield: 50%) as a white solid. $^1$HNMR (400 MHz, $CDCl_3$): $\delta$=8.63 (s, 1H), 8.38 (d, J=1.6 Hz, 1H), 8.31 (d, J=4.8 Hz, 1H), 7.37 (s, 1H), 7.20 (t, J=5.6 Hz, 1H), 5.40 (d, J=7.6 Hz, 1H), 4.76 (d, J=13.6 Hz, 2H), 4.13-4.10 (m, 1H), 3.23 (t, J=12.0 Hz, 2H), 3.04 (t, J=8.0 Hz, 2H), 2.50 (t, J=7.2 Hz, 2H), 2.45 (s, 3H), 2.07-2.03 (m, 2H), 1.46-1.36 (m, 2H). MS: m/z 399.8 ($M+H^+$).

Example 3.39

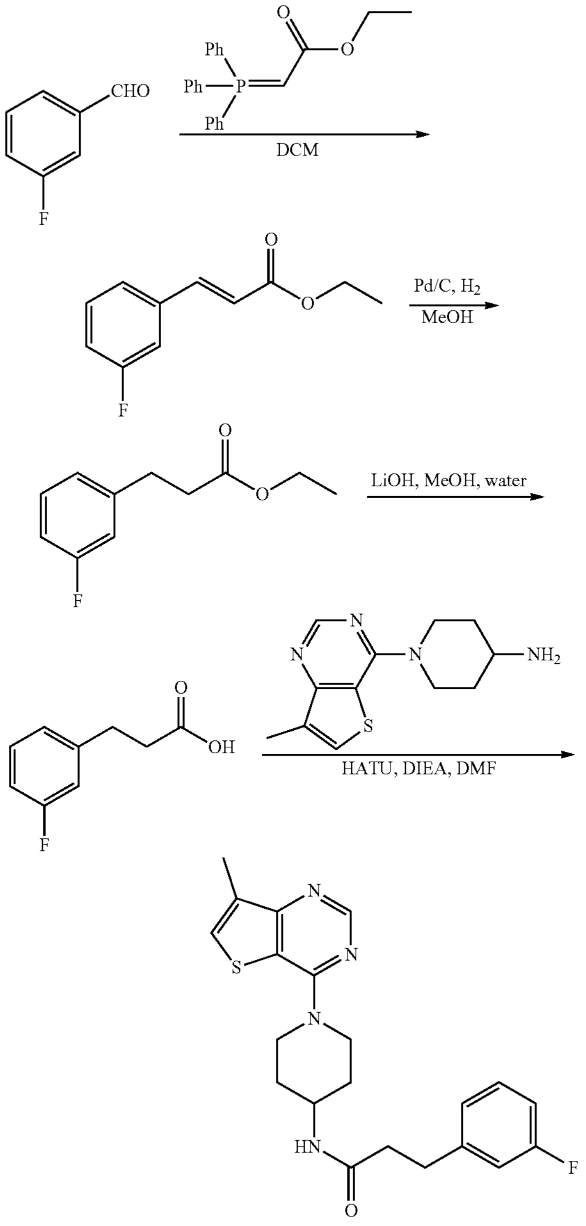

3-(3-Fluorophenyl)-N-(1-(7-methylthieno[3,2-d]pyrimidin-4-yl)piperidin-4-yl)propanamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): $\delta$=8.63 (s, 1H), 7.37 (s, 1H), 7.25-7.21 (m, 1H), 6.97 (d, J=8.0 Hz, 1H), 6.91-6.87 (m, 2H), 5.23 (d, J=8.0 Hz, 1H), 4.72 (d, J=13.2 Hz, 2H), 4.13-4.09 (m, 1H), 3.24 (t, J=11.6 Hz, 2H), 2.97 (t, J=7.6 Hz, 2H), 2.46-2.43 (m, 5H), 2.05-2.01 (m, 2H), 1.42-1.32 (m, 2H). MS: m/z 399.1 ($M+H^+$).

Example 3.40

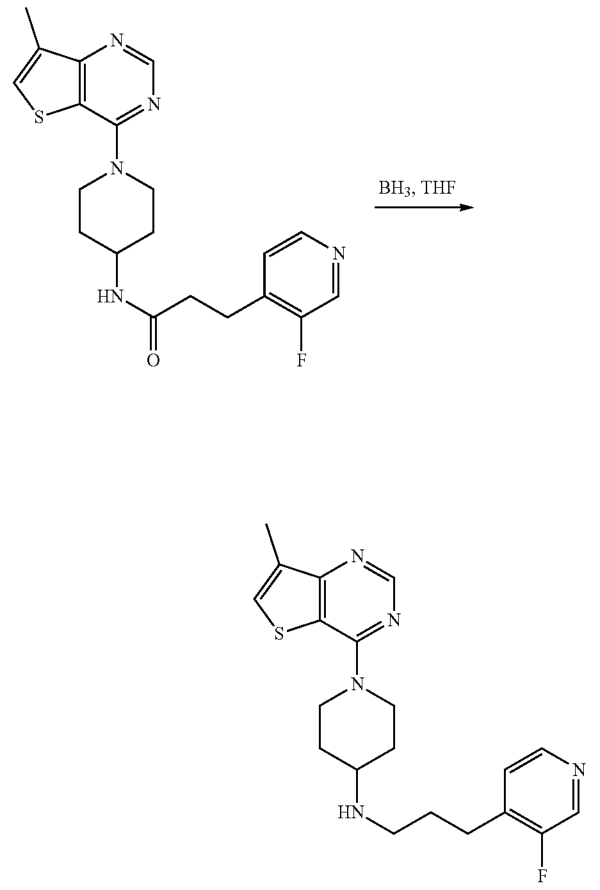

N-(3-(3-Fluoropyridin-4-yl)propyl)-1-(7-methylthieno[3,2-d]pyrimidin-4-yl)piperidin-4-amine To a solution of 3-(3-fluoropyridin-4-yl)-N-(1-(7-methylthieno[3,2-d]pyrimidin-4-yl)piperidin-4-yl)propanamide (200 mg, 0.5 mmol) in THF (3 mL) was added $BH_3$ (10 M, 2 mL) at 0° C. The reaction was stirred at room temperature overnight. The $BH_3$ was quenched by MeOH slowly at 0° C. and added 1 N hydrochloric acid refluxed for 1 hr. The MeOH was removed under reduced pressure. The aqueous was neutralized by saturated aqueous $NaHCO_3$ solution (50 mL) and extracted with DCM (50 mL×2). The combined organic layers were concentrated and the residue was purified by prep-HPLC ($NH_4HCO_3$) to give N-(3-(3-fluoropyridin-4-yl)propyl)-1-(7-methylthieno[3,2-d]pyrimidin-4-yl)piperidin-4-amine (17 mg, yield: 8.8%) as a yellow oil. $^1$HNMR (400 MHz, $CDCl_3$): δ=8.63 (s, 1H), 8.38 (d, J=1.6 Hz, 1H), 8.31 (d, J=4.8 Hz, 1H), 7.36 (s, 1H), 7.16 (t, J=6.4 Hz, 1H), 4.72 (d, J=13.2 Hz, 2H), 3.27 (t, J=11.6 Hz, 2H), 2.84-2.79 (m, 1H), 2.77-2.70 (m, 4H), 2.45 (s, 3H), 2.05-2.01 (m, 2H), 1.87-1.80 (m, 2H), 1.51-1.38 (m, 2H). MS: m/z 385.9 (M+H$^+$).

Example 3.41

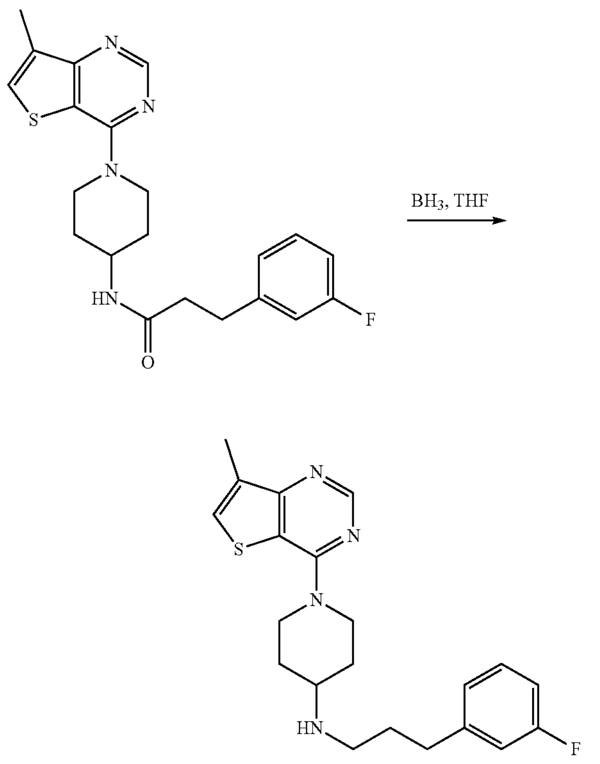 [SMILES: Cc1csc2c(N3CCC(NC(=O)CCc4cccc(F)c4)CC3)ncnc12 ; Cc1csc2c(N3CCC(NCCCc4cccc(F)c4)CC3)ncnc12]

N-(3-(3-Fluorophenyl)propyl)-1-(7-methylthieno[3,2-d]pyrimidin-4-yl)piperidin-4-amine The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=8.63 (s, 1H), 7.36 (s, 1H), 7.36-7.21 (m, 1H), 6.96 (d, J=7.2 Hz, 1H), 6.91-6.87 (m, 2H), 4.73 (d, J=13.2 Hz, 2H), 3.24 (t, J=11.6 Hz, 2H), 2.83-2.79 (m, 1H), 2.71-2.67 (m, 4H), 2.45 (s, 3H), 2.03 (d, J=10.0 Hz, 2H), 1.86-1.78 (m, 2H), 1.47-1.37 (m, 2H). MS: m/z 384.9 (M+H$^+$).

Example 3.42

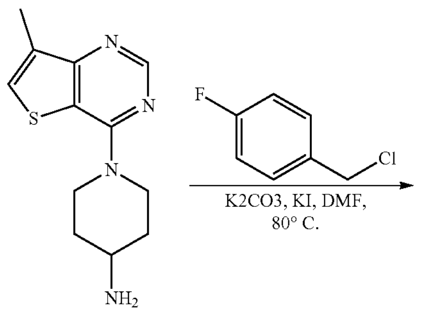

-continued

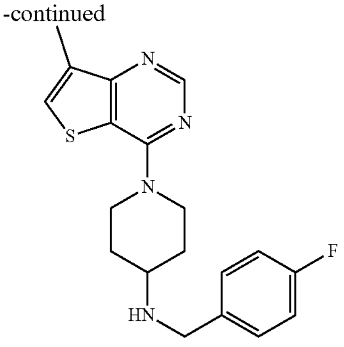

N-(4-Fluorobenzyl)-1-(7-methylthieno[3,2-d]pyrimidin-4-yl)piperidin-4-amine

A solution of 1-(7-methylthieno[3,2-d]pyrimidin-4-yl)piperidin-4-amine (108 mg, 0.38 mmol), 1-(chloromethyl)-4-fluorobenzene (50 mg, 0.346 mmol), $K_2CO_3$ (143 mg, 1.038 mmol) and KI (2 mg) in DMF (3 mL) was stirred at 80° C. for 1 hr. The DMF was removed under reduced pressure. The residue was purified by prep-HPLC ($NH_4HCO_3$) to give N-(4-fluorobenzyl)-1-(7-methylthieno[3,2-d]pyrimidin-4-yl)piperidin-4-amine (14.3 mg, yield: 11.6%) as a white solid. $^1$HNMR (400 MHz, $CDCl_3$): δ=8.64 (s, 1H), 7.39-7.36 (m, 3H), 7.04 (t, J=8.8 Hz, 2H), 4.75 (d, J=13.6 Hz, 2H), 3.87 (s, 2H), 3.23 (t, J=11.6 Hz, 2H), 2.95-2.90 (m, 1H), 2.45 (s, 3H), 2.11 (d, J=10.4 Hz, 2H), 1.64-1.55 (m, 2H). MS: m/z 356.9 (M+H$^+$).

Example 3.43

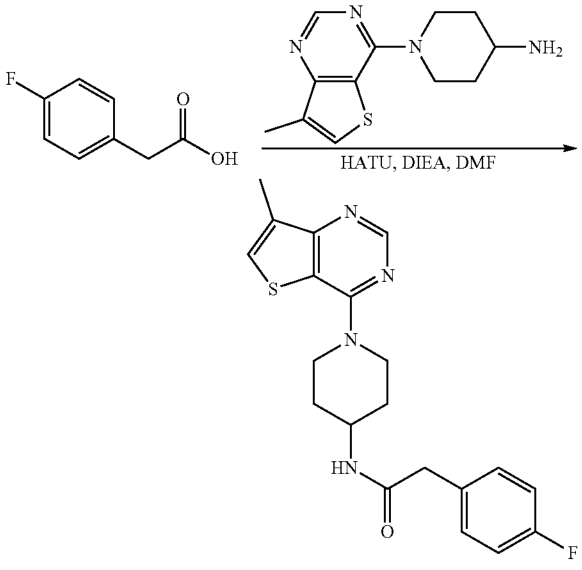

2-(4-Fluorophenyl)-N-(1-(7-methylthieno[3,2-d]pyrimidin-4-yl)piperidin-4-yl)acetamide The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.61 (s, 1H), 7.36 (s, 1H), 7.22-7.19 (m, 2H), 7.03 (t, J=8.8 Hz, 2H), 5.26 (d, J=7.6 Hz, 1H), 4.72 (d, J=13.2 Hz, 2H), 4.15-4.10 (m, 1H), 3.53 (s, 2H), 3.23 (t, J=12.0 Hz, 2H), 2.44 (s, 3H), 2.05 (d, J=9.6 Hz, 2H), 1.42-1.33 (m, 2H). MS: m/z 385.1 (M+H$^+$).

Example 3.44

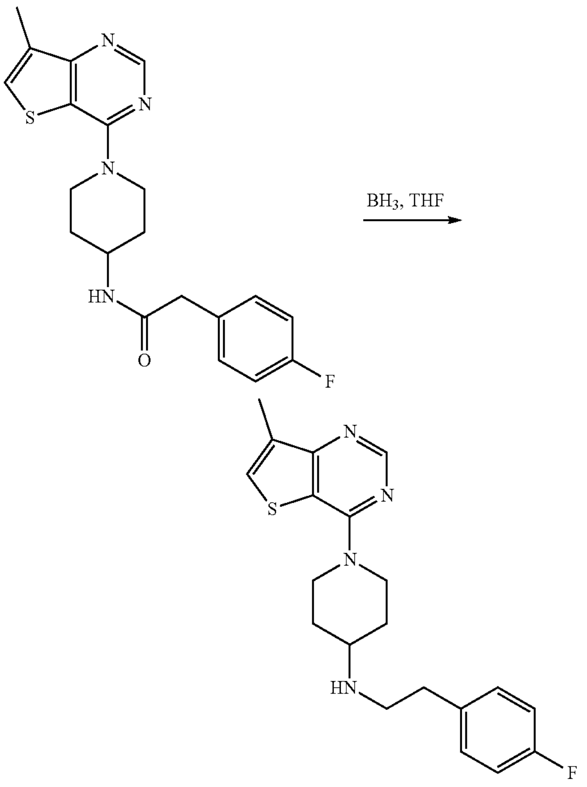

N-(4-Fluorophenethyl)-1-(7-methylthieno[3,2-d]pyrimidin-4-yl)piperidin-4-amine

The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=8.63 (s, 1H), 7.35 (s, 1H), 7.19-7.15 (m, 2H), 6.99 (t, J=8.8 Hz, 2H), 4.72 (d, J=13.2 Hz, 2H), 3.24 (t, J=11.2 Hz, 2H), 2.93 (t, J=7.2 Hz, 2H), 2.87-2.84 (m, 1H), 2.81-2.77 (m, 2H), 2.45 (s, 3H), 2.03 (d, J=10.4 Hz, 2H), 1.47-1.38 (m, 2H). MS: m/z 370.9 (M+H$^+$).

Example 3.45

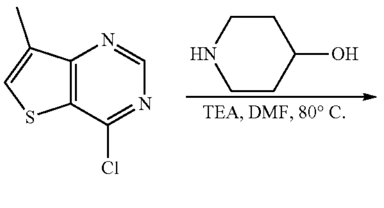

-continued

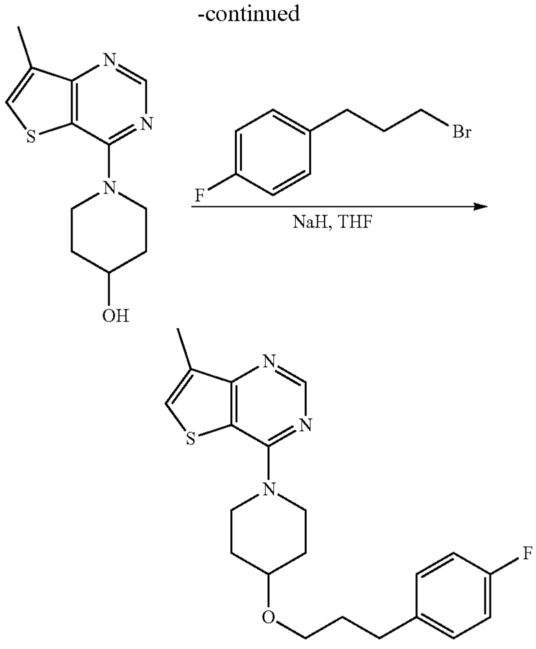

4-(4-(3-(4-Fluorophenyl)propoxy)piperidin-1-yl)-7-methylthieno[3,2-d]pyrimidine

Step 1: A solution of 4-chloro-7-methylthieno[3,2-d]pyrimidine (300 mg, 1.6 mmol), TEA (323 mg, 3.2 mmol) and piperidin-4-ol (164 mg, 1.6 mmol) in DMF (10 mL) was stirred at 80° C. for 2 hrs. The DMF was removed under reduced pressure. The residue was purified by silica gel column (DCM/MeOH=10/1) to give 1-(7-methylthieno[3,2-d]pyrimidin-4-yl)piperidin-4-ol (400 mg, yield: 98.5%) as a white solid. MS: m/z 250.2 (M+H$^+$).

Step 2: To a solution of 1-(7-methylthieno[3,2-d]pyrimidin-4-yl)piperidin-4-ol (200 mg, 0.8 mmol) in THF (5 mL) was added NaH (96 mg, 2.4 mmol) at 0° C. The mixture was stirred at 0° C. for 30 mins and added 1-(3-bromopropyl)-4-fluorobenzene (210 mg, 0.96 mmol). The mixture was stirred at 60° C. overnight. The NaH was quenched with saturated aqueous $NH_4Cl$ solution (1 mL) and the mixture was partitioned between DCM (20 mL) and water (20 mL). The organic layer was dried over $Na_2SO_4$ and concentrated in vacuum. The residue was purified by prep-HPLC ($NH_4HCO_3$) to give 4-(4-(3-(4-fluorophenyl)propoxy)piperidin-1-yl)-7-methylthieno[3,2-d]pyrimidine (35.7 mg, yield: 11.6%) as a yellow oil. $^1$HNMR (400 MHz, $CDCl_3$): δ=8.64 (s, 1H), 7.36 (s, 1H), 7.16-7.13 (m, 2H), 6.99-6.94 (m, 2H), 4.33-4.27 (m, 2H), 3.75-3.69 (m, 2H), 3.61-3.58 (m, 1H), 3.48 (t, J=6.4 Hz, 2H), 2.69 (t, J=7.6 Hz, 2H), 2.45 (s, 3H), 2.00-1.93 (m, 2H), 1.91-1.76 (m, 2H), 1.75-1.73 (m, 2H). MS: m/z 386.2 (M+H$^+$).

Example 3.46

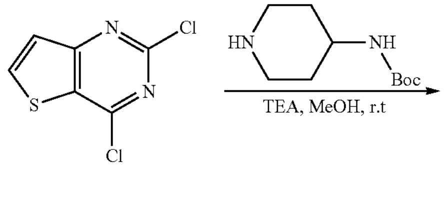

-continued

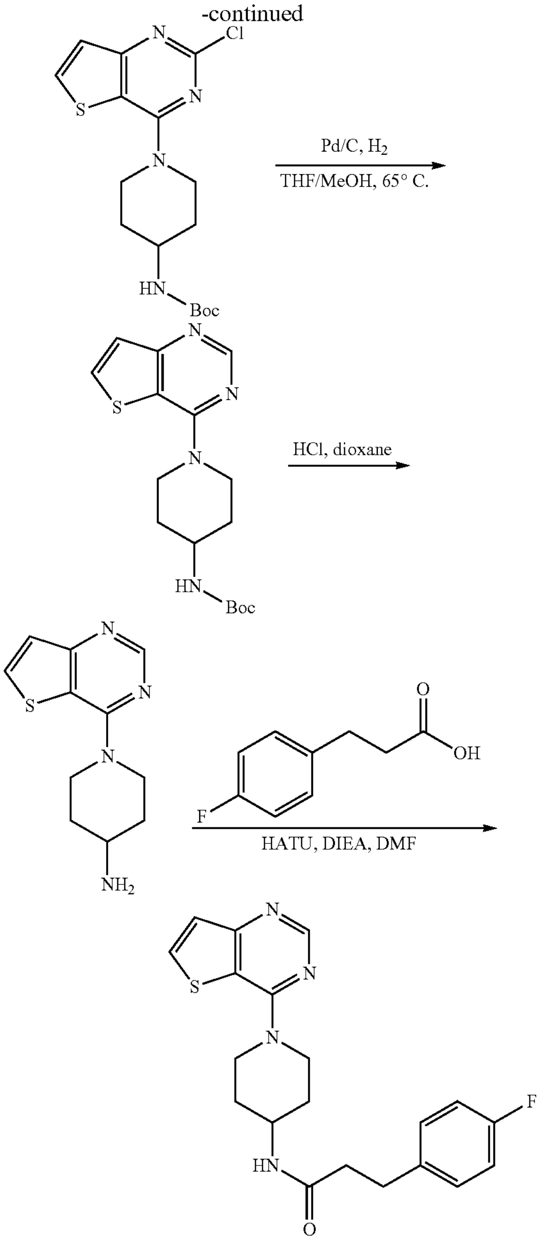

3-(4-Fluorophenyl)-N-(1-(thieno[3,2-d]pyrimidin-4-yl)piperidin-4-yl)propanamide

Step 1: A solution of 2,4-dichlorothieno[3,2-d]pyrimidine (2 g, 9.76 mmol), TEA (1.5 g, 14.64 mmol) and tert-butyl piperidin-4-ylcarbamate (1.95 g, 9.76 mmol) in MeOH (30 mL) was stirred at room temperature for 4 hrs. The formed solid was collected by filtration to give tert-butyl (1-(2-chlorothieno[3,2-d]pyrimidin-4-yl)piperidin-4-yl)carbamate (2.8 g, yield: 78%) as a yellow solid. MS: m/z 369.3 (M+H$^+$).

Step 2: A solution of tert-butyl (1-(2-chlorothieno[3,2-d]pyrimidin-4-yl)piperidin-4-yl)carbamate (800 mg, 2.17 mmol) and Pd/C (160 mg) in MeOH/THF (20 mL/4 mL) was stirred at 65° C. overnight under $H_2$ atmosphere (balloon). The reaction mixture was filtered and the filtrate was concentrated to give tert-butyl (1-(thieno[3,2-d]pyrimidin- 4-yl)piperidin-4-yl)carbamate (726 mg, yield: 100%) as a white solid. MS: m/z 335.3 (M+H+).

Step 3: A solution of tert-butyl (1-(thieno[3,2-d]pyrimidin-4-yl)piperidin-4-yl)carbamate (500 mg, 1.5 mmol) in HCl/dioxane was stirred at room temperature for 1 hr. The formed solid was collected by filtration to give 1-(thieno[3,2-d]pyrimidin-4-yl)piperidin-4-amine (360 mg, yield: 89%) as a white solid.

Step 4: The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, DMSO-$d_6$): δ=8.49 (s, 1H), 8.21 (d, J=5.6 Hz, 1H), 7.81 (d, J=7.6 Hz, 1H), 7.44 (d, J=5.6 Hz, 1H), 7.24-7.20 (m, 2H), 7.11-7.06 (m, 2H), 4.53 (d, J=13.6 Hz, 2H), 3.96-3.93 (m, 1H), 3.40-3.32 (m, 2H), 2.80 (t, J=7.6 Hz, 2H), 2.34 (t, J=8.0 Hz, 2H), 1.87-1.83 (m, 2H), 1.41-1.31 (m, 2H). MS: m/z 385.1 (M+H+).

Example 3.47

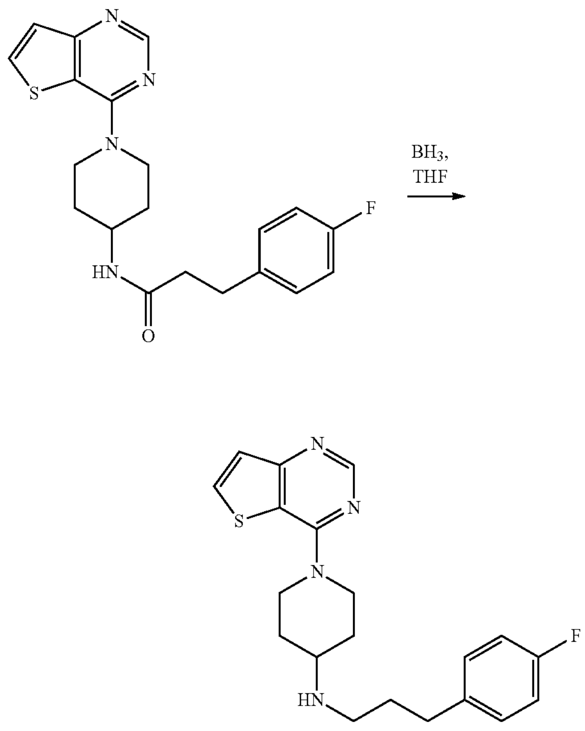

N-(3-(4-Fluorophenyl)propyl)-1-(thieno[3,2-d]pyrimidin-4-yl)piperidin-4-amine

The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=8.57 (s, 1H), 7.71 (d, J=5.6 Hz, 1H), 7.42 (d, J=5.6 Hz, 1H), 7.14-7.10 (m, 2H), 6.98-6.93 (m, 2H), 4.73 (d, J=13.6 Hz, 2H), 3.25 (t, J=11.2 Hz, 2H), 2.92-2.75 (m, 1H), 2.73 (t, J=7.2 Hz, 2H), 2.64 (t, J=7.6 Hz, 2H), 2.07 (d, J=10.0 Hz, 2H), 1.87-1.77 (m, 2H), 1.70-1.50 (m, 2H). MS: m/z 371.1 (M+H+).

Example 3.48

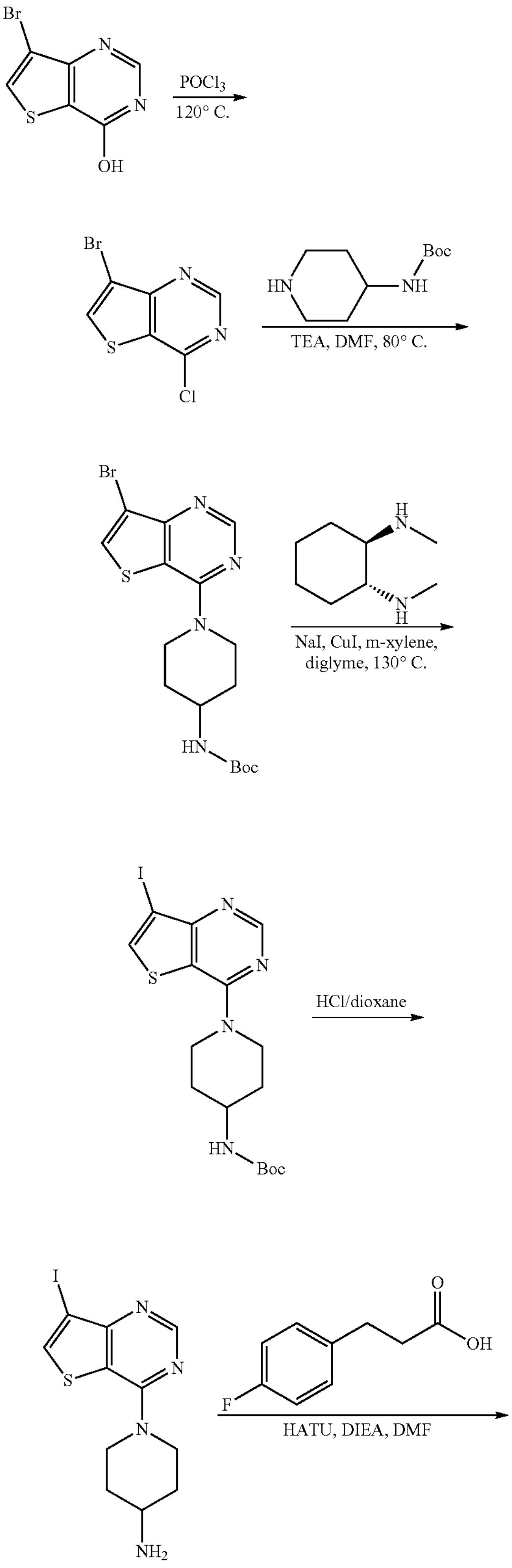

-continued

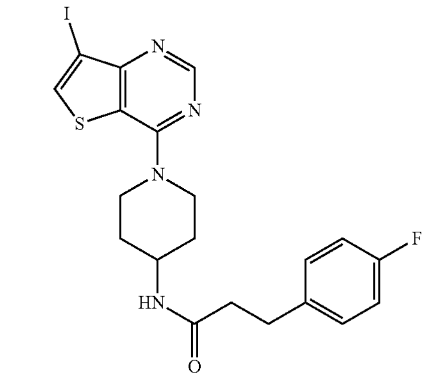

3-(4-Fluorophenyl)-N-(1-(7-iodothieno[3,2-d]pyrimidin-4-yl)piperidin-4-yl)propanamide Step 1 through Step 2: The title compound was prepared using general procedure of 3-(4-fluorophenyl)-N-(1-(7-phenylthieno[3,2-d]pyrimidin-4-yl)piperidin-4-yl)propanamide (Example 3.57)

Step 3: A solution of tert-butyl (1-(7-bromothieno[3,2-d]pyrimidin-4-yl)piperidin-4-yl)carbamate (450 mg, 1.1 mmol), NaI (327 mg, 2.2 mmol), CuI (10.4 mg, 0.055 mmol) and (1R,2R)—N1,N2-dimethylcyclohexane-1,2-diamine (16 mg, 0.11 mmol) in m-xylene/diglyme (8 mL/2 mL) was stirred at 130° C. overnight under $N_2$ atmosphere (balloon). The m-xylene and diglyme were removed under reduced pressure. The residue was purified by silica gel column (PE/EA=1/1) to give tert-butyl (1-(7-iodothieno[3,2-d]pyrimidin-4-yl)piperidin-4-yl)carbamate (470 mg, 93%) as a yellow solid. MS: m/z 461.2 ($M+H^+$).

Step 4 through Step 5: The title compound was prepared using general procedure of 3-(4-fluorophenyl)-N-(1-(7-phenylthieno[3,2-d]pyrimidin-4-yl)piperidin-4-yl)propanamide (Example 3.57). $^1$HNMR (400 MHz, $CDCl_3$): δ=8.7 (s, 1H), 7.9 (s, 1H), 7.17-7.15 (m, 2H), 7.00-6.94 (m, 2H), 5.17 (d, J=6.8 Hz, 1H), 4.71 (d, J=13.6 Hz, 2H), 4.12-4.11 (m, 1H), 3.27 (t, J=12.0 Hz, 2H), 2.94 (t, J=8.0 Hz, 2H), 2.43 (t, J=7.6 Hz, 2H), 2.06-2.02 (m, 2H), 1.41-1.32 (m, 2H). MS: m/z 511.0 ($M+H^+$).

Example 3.49

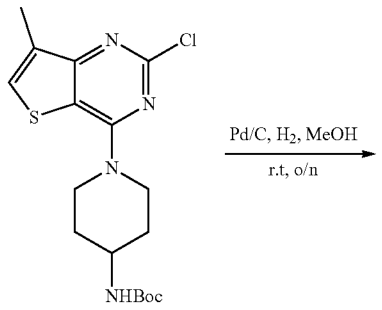

-continued

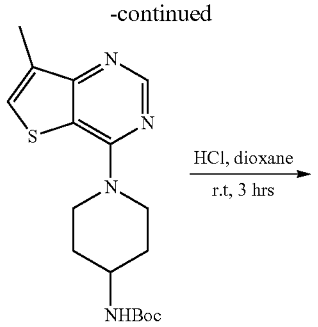

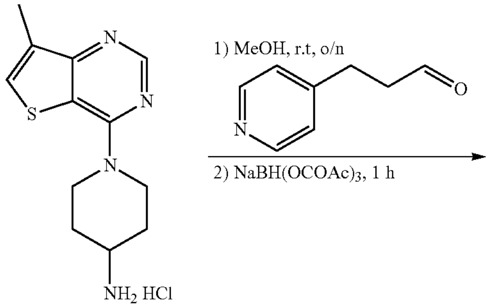

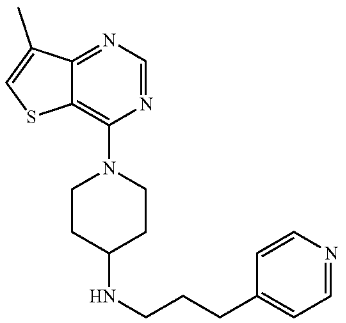

1-(7-Methylthieno[3,2-d]pyrimidin-4-yl)-N-(3-(pyridin-4-yl)propyl)piperidin-4-amine Step 1: A mixture of tert-butyl (1-(2-chloro-7-methylthieno[3,2-d]pyrimidin-4-yl)piperidin-4-yl)carbamate (130 mg, 0.34 mmol) and Pd/C (3.2 mg, 0.03 mmol) in MeOH (80 mL) was stirred at room temperature overnight under $H_2$ atmosphere (balloon). The reaction mixture was filtered and the filtrate was concentrated to give tert-butyl (1-(7-methylthieno[3,2-d]pyrimidin-4-yl)piperidin-4-yl)carbamate.

Step 2 through 3: The step 2 and step 3 was used general procedure of the step 2 and step 3 of 1-(7-methyl-2-phenylthieno[3,2-d]pyrimidin-4-yl)-N-(3-(pyridin-4-yl)propyl) piperidin-4-amine (Example 3.61). $^1$HNMR (400 MHz, DMSO-d6): δ=8.52 (s, 1H), 8.45 (d, J=6.4 Hz, 2H), 7.68 (d, J=1.2 Hz, 1H), 7.35 (d, J=6.0 Hz, 2H), 5.03-4.93 (m, 2H), 3.47-3.37 (m, 1H), 3.29-3.20 (m, 2H), 3.05 (t, J=7.6 Hz, 2H), 2.79 (t, J=8.0 Hz, 2H), 2.41 (s, 3H), 2.23 (d, J=6.4 Hz, 2H) 2.03-1.92 (m, 2H), 1.68-1.53 (m, 2H). MS: m/z 368.2 ($M+H^+$).

Example 3.50

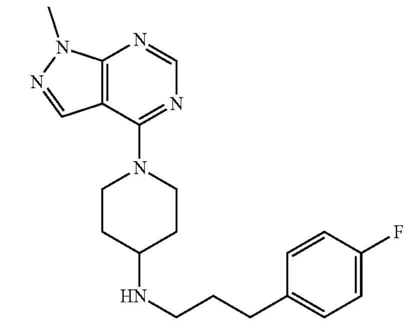 [SMILES: Cn1ncc2c(N3CCC(NCCCc4ccc(F)cc4)CC3)ncnc21]

N-(3-(4-Fluorophenyl)propyl)-1-(1-methyl-1H-pyrazolo[3,4-d]pyrimidin-4-yl)piperidin-4-amine The title compound was prepared using general procedure of 1-(1-methyl-1H-pyrazolo[3,4-d]pyrimidin-4-yl)-N-(3-(pyridin-4-yl)propyl)piperidin-4-amine (Example 2.5). $^1$HNMR (400 MHz, DMSO-$d_6$): δ=8.55 (s, 1H), 8.46 (s, 1H), 7.29-7.26 (m, 2H), 7.03 (t, J=8.4 Hz, 2H), 4.76 (d, J=10.0 Hz, 2H), 4.09 (s, 3H), 3.68-3.63 (m, 3H), 3.12 (t, J=8.0 Hz, 2H), 2.75 (t, J=7.6 Hz, 2H), 2.44-2.41 (m, 2H), 2.08-2.00 (m, 2H), 1.95-1.87 (m, 2H). MS: m/z 368.9 (M+H$^+$).

Example 3.51

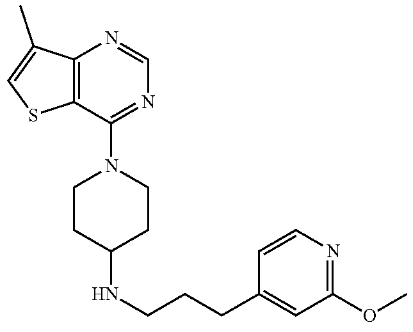 [SMILES: COc1cc(CCCNC2CCN(c3ncnc4c(C)csc34)CC2)ccn1]

N-(3-(2-Methoxypyridin-4-yl)propyl)-1-(7-methylthieno[3,2-d]pyrimidin-4-yl)piperidin-4-amine The title compound was prepared using general procedure of 1-(1-methyl-1H-pyrazolo[3,4-d]pyrimidin-4-yl)-N-(3-(pyridin-4-yl)propyl)piperidin-4-amine (Example 2.5). $^1$HNMR (400 MHz, $CD_3OD$): δ=8.48 (s, 1H), 8.00 (d, J=5.2 Hz, 1H), 7.65 (s, 1H), 6.85 (d, J=4.8 Hz, 1H), 6.68 (s, 1H), 4.86 (overlap, 2H), 3.88 (s, 3H), 3.23 (t, J=12.0 Hz, 2H), 3.04-2.99 (m, 1H), 2.77 (t, J=7.2 Hz, 2H), 2.67 (t, J=7.6 Hz, 2H), 2.40 (s, 3H), 2.12-2.10 (m, 2H), 1.91-1.84 (m, 2H), 1.50-1.40 (m, 2H). MS: m/z 398.2 (M+H$^+$).

Example 3.52

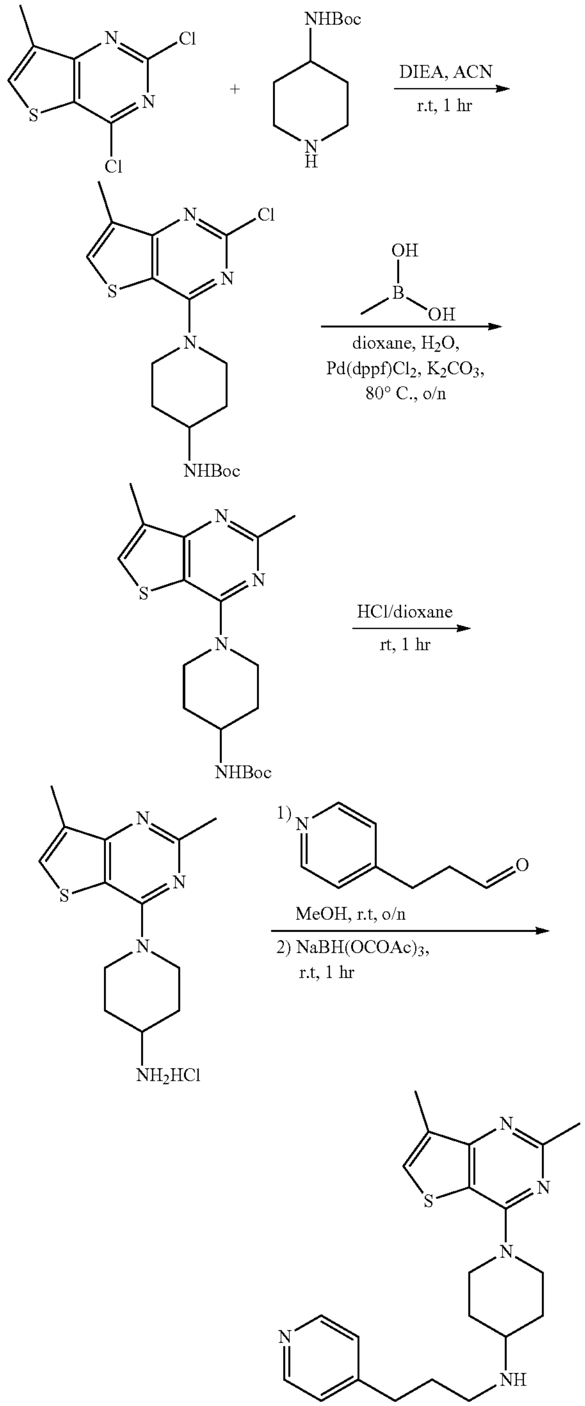

1-(2,7-Dimethylthieno[3,2-d]pyrimidin-4-yl)-N-(3-(pyridin-4-yl)propyl)piperidin-4-amine The title compound (20 mg, yield: 13%, yellow, oil) was prepared using general procedure of 1-(7-methyl-2-phenylthieno[3,2-d]pyrimidin-4-yl)-N-(3-(pyridin-4-yl)propyl) piperidin-4-amine (Example 3.61). $^1$HNMR (400 MHz, DMSO-$d_6$): δ=8.44 (dd, J=4.4, 1.6 Hz, 2H), 7.75 (d, J=1.2

Hz, 1H), 7.23 (dd, J=4.4, 1.6 Hz, 2H), 4.56-4.48 (m, 2H), 3.39-3.21 (m, 2H), 2.75-2.67 (m, 1H), 2.64 (d, J=7.6 Hz, 2H), 2.55 (d, J=7.2 Hz, 2H), 2.48 (s, 3H), 2.30 (d, J=0.8 Hz, 3H), 1.96-1.87 (m, 2H), 1.75-1.66 (m, 2H), 1.31-1.18 (m, 2H). MS: m/z 382.1 (M+H$^+$).

Example 3.53

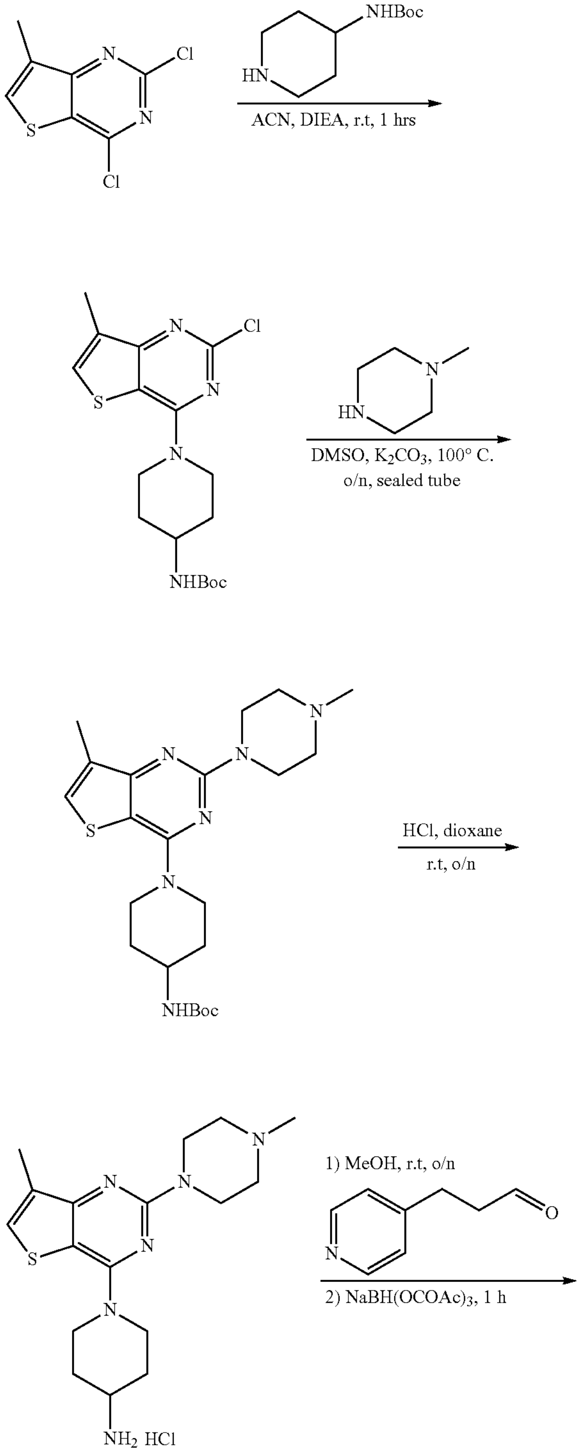

-continued

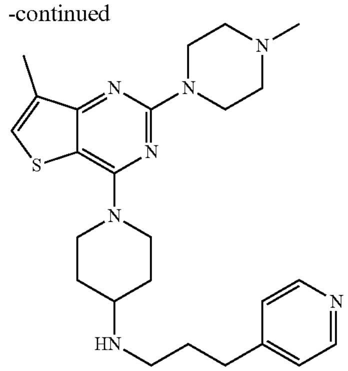

1-(7-Methyl-2-(4-methylpiperazin-1-yl)thieno[3,2-d]pyrimidin-4-yl)-N-(3-(pyridin-4-yl)propyl)piperidin-4-amine The title compound (5.8 mg, yield: 3%, yellow, oil) was prepared using general procedure of 1-(7-methyl-2-phenylthieno[3,2-d]pyrimidin-4-yl)-N-(3-(pyridin-4-yl)propyl)piperidin-4-amine (Example 3.61). $^1$HNMR (400 MHz, DMSO-d4): δ=8.48 (d, J=6.0 Hz, 2H), 7.67 (s, 1H), 7.17 (d, J=6.0 Hz, 2H), 4.69-4.57 (m, 2H), 3.77 (brs, 4H), 3.33 (overlap, 4H), 3.18-3.07 (m, 2H), 2.91 (t, J=7.2 Hz, 2H), 2.70 (t, J=7.6 Hz, 2H), 2.50 (overlap, 1H), 2.32 (brs, 3H), 2.23 (s, 3H), 2.20-2.12 (m, 2H), 2.03-1.92 (m, 2H), 1.68-1.53 (m, 2H). MS: m/z 465.9 (M+H$^+$).

Example 3.54

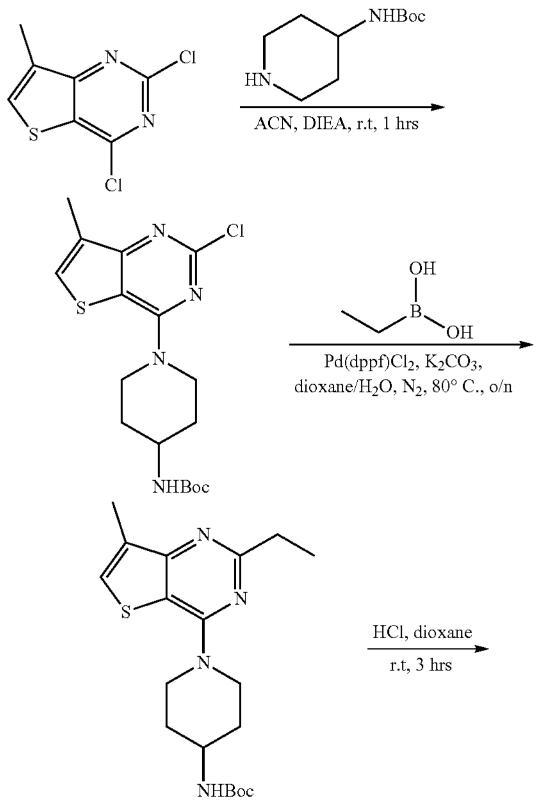

-continued

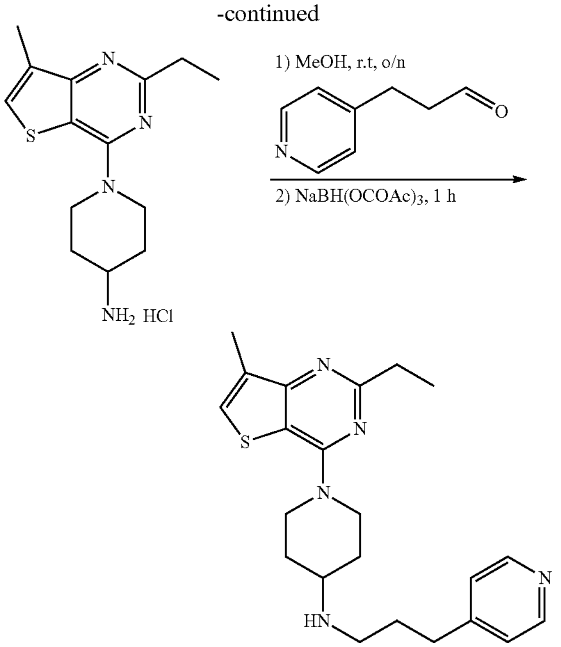

1-(2-Ethyl-7-methylthieno[3,2-d]pyrimidin-4-yl)-N-(3-(pyridin-4-yl)propyl)piperidin-4-amine The title compound (40 mg, yield:26%, brown, oil) was prepared using general procedure of 1-(7-methyl-2-phenylthieno[3,2-d]pyrimidin-4-yl)-N-(3-(pyridin-4-yl)propyl)piperidin-4-amine (Example 3.61). $^1$HNMR (400 MHz, DMSO-$d_6$): δ=8.44 (dd, J=4.4, 1.6 Hz, 2H), 7.76 (d, J=1.2 Hz, 1H), 7.23 (d, J=6.0 Hz, 2H), 4.58-4.50 (m, 2H), 3.32-3.22 (m, 2H), 2.78-2.70 (m, 2H), 2.71-2.66 (m, 1H), 2.64 (t, J=7.6 Hz, 2H), 2.55 (d, J=7.2 Hz, 2H), 2.31 (s, 3H), 1.96-1.88 (m, 2H), 1.75-1.66 (m, 2H), 1.27 (t, J=7.6 Hz, 3H), 1.25-1.19 (m, 2H). MS: m/z 396.2 (M+H$^+$).

Example 3.55

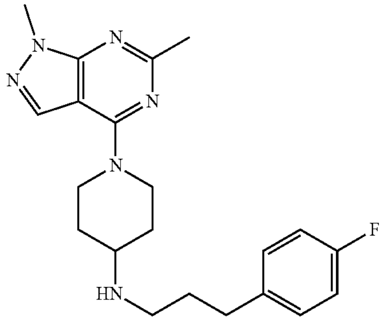 [SMILES: Cc1nc(N2CCC(NCCCc3ccc(F)cc3)CC2)c2cnn(C)c2n1]

1-(1,6-Dimethyl-1H-pyrazolo[3,4-d]pyrimidin-4-yl)-N-(3-(4-fluorophenyl)propyl)piperidin-4-amine The title compound was prepared using general procedure of 1-(1,6-dimethyl-1H-pyrazolo[3,4-d]pyrimidin-4-yl)-N-(3-(pyridin-4-yl)propyl)piperidin-4-amine (Example 2.51). $^1$HNMR (400 MHz, $CD_3OD$): δ=8.46 (s, 1H), 7.29-7.26 (m, 2H), 7.03 (t, J=8.4 Hz, 2H), 4.90 (s, 2H), 4.07 (s, 3H), 3.69-3.60 (m, 3H), 3.11 (t, J=7.6 Hz, 2H), 2.75 (t, J=7.6 Hz, 2H), 2.71 (s, 3H), 2.41-2.38 (m, 2H), 2.06-2.02 (m, 2H), 1.87-1.84 (m, 2H). MS: m/z 382.9 (M+H$^+$).

Example 3.56

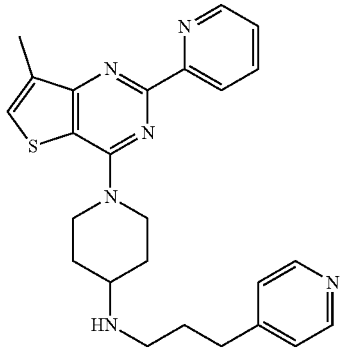 [SMILES: Cc1csc2c(N3CCC(NCCCc4ccncc4)CC3)nc(-c3ccccn3)nc12]

1-(7-Methyl-2-(pyridin-2-yl)thieno[3,2-d]pyrimidin-4-yl)-N-(3-(pyridin-4-yl)propyl)piperidin-4-amine The title compound was prepared using general procedure of 1-(1-methyl-6-(pyridin-2-yl)-1H-pyrazolo[3,4-d]pyrimidin-4-yl)-N-(3-(pyridin-4-yl)propyl)piperidin-4-amine (Example 2.20). $^1$HNMR (400 MHz, DMSO-$d_6$): δ=8.70 (d, 1H), 8.52 (d, J=8.0 Hz, 1H), 8.42-8.40 (m, 2H), 8.00-7.96 (m, 1H), 7.65 (brs, 1H), 7.53-7.50 (m, 1H), 7.32 (d, J=6.4 Hz, 2H), 4.99 (m, J=13.6 Hz, 2H), 3.30-3.24 (m, 2H), 2.90-2.85 (m, 1H), 2.75-2.68 (m, 4H), 2.58 (s, 3H), 2.10 (d, J=12.0 Hz, 2H), 1.90-1.83 (m, 2H), 1.50-1.40 (m, 2H). MS: m/z 444.9 (M+H$^+$).

Example 3.57

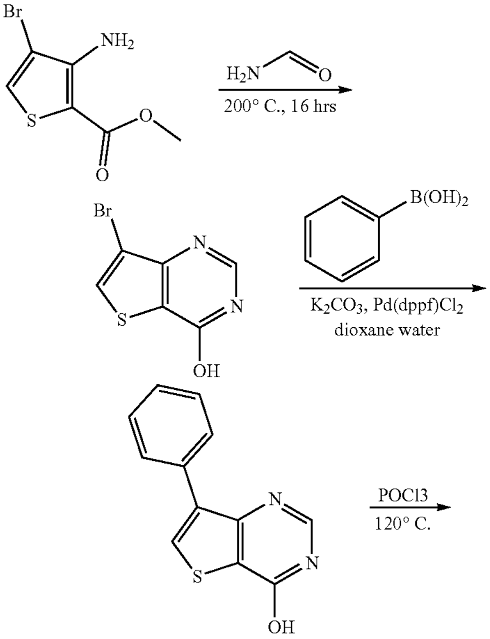

-continued

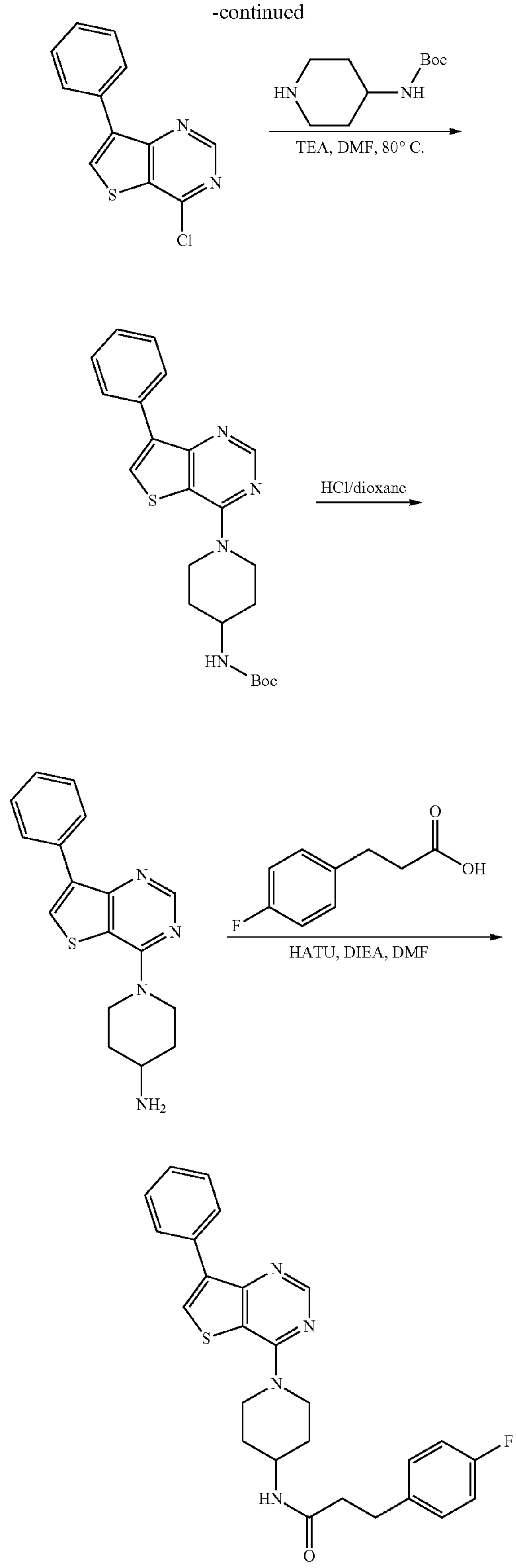

3-(4-Fluorophenyl)-N-(1-(7-phenylthieno[3,2-d]pyrimidin-4-yl)piperidin-4-yl)propanamide Step 1: A solution of methyl 3-amino-4-bromothiophene-2-carboxylate (3 g, 12.76 mmol) in formamide (30 mL) was stirred at 200° C. for 16 hrs. The reaction was cooled to room temperature. The formed solid was collected by filtration to give 7-bromothieno[3,2-d]pyrimidin-4-ol (1.7 g, yield: 58%) as a gray solid.

Step 2: A solution 7-bromothieno[3,2-d]pyrimidin-4-ol (700 mg, 3.04 mmol), phenylboronic acid (743 mg, 6.08 mmol), $K_2CO_3$ (1.26 g, 9.12 mmol) and Pd(dppf)$Cl_2$ (222 mg, 0.304 mmol) in dioxane/water (15 mL/3 mL) was stirred at 90° C. overnight under $N_2$ atmosphere (balloon). The dioxane and water was removed under reduced pressure. The residue was purified by silica gel column (DCM/MeOH=10/1) to give 7-phenylthieno[3,2-d]pyrimidin-4-ol (600 mg, yield: 86%) as a yellow solid. MS: m/z 229.2 ($M+H^+$).

Step 3: A solution of 7-phenylthieno[3,2-d]pyrimidin-4-ol (550 mg, 2.4 mmol) in $POCl_3$ (15 mL) was stirred at 120° C. for 2 hrs. The $POCl_3$ was removed under reduced pressure. The residue was neutralized with saturated aqueous $NaHCO_3$ solution (100 mL) and extracted with EA (200 mL×3). The combined organic layers were dried over $Na_2SO_4$ and concentrated. The residue was purified by silica gel column (PE/EA=3/1) to give 4-chloro-7-phenylthieno[3,2-d]pyrimidine (400 mg, yield: δ7.8%) as a white solid.

Step 4: A solution of 4-chloro-7-phenylthieno[3,2-d]pyrimidine (400 mg, 1.6 mmol), TEA (323 mg, 3.2 mmol) and tert-butyl piperidin-4-ylcarbamate (325 mg, 1.6 mmol) in DMF (15 mL) was stirred at 80° C. for 2 hrs. The DMF was removed under reduced pressure. The residue was purified by silica gel column (PE/EA=3/1) to give tert-butyl (1-(7-phenylthieno[3,2-d]pyrimidin-4-yl)piperidin-4-yl)carbamate (450 mg, yield: δ7.6%) as a white solid. MS: m/z 411.4 ($M+H^+$).

Step 5: A solution of tert-butyl (1-(7-phenylthieno[3,2-d]pyrimidin-4-yl)piperidin-4-yl)carbamate (450 mg, 1.1 mmol) in HCl/dioxane was stirred at room temperature for 1 hr. The formed solid was collected by filtration to give 1-(7-phenylthieno[3,2-d]pyrimidin-4-yl)piperidin-4-amine (450 mg, yield: >99%) as a white solid. MS: m/z 311.4 ($M+H^+$).

Step 6: The title compound was prepared using general procedure of 3-(3-fluoropyridin-4-yl)-N-(1-(7-methylthieno[3,2-d]pyrimidin-4-yl)piperidin-4-yl)propanamide (Example 3.38). $^1$HNMR (400 MHz, $CDCl_3$): δ=8.68 (s, 1H), 7.86 (d, J=8.4 Hz, 2H), 7.77 (s, 1H), 7.48 (t, J=7.2 Hz, 2H), 7.38 (t, J=7.6 Hz, 1H), 7.17-7.14 (m, 2H), 6.70-6.95 (m, 2H), 5.20 (d, J=7.6 Hz, 1H), 4.76 (d, J=13.6 Hz, 2H), 4.15-4.11 (m, 1H), 3.29 (t, J=11.6 Hz, 2H), 2.95 (t, J=7.6 Hz, 2H), 2.44 (t, J=7.6 Hz, 2H), 2.05 (d, J=9.6 Hz, 2H), 1.46-1.36 (m, 2H). MS: m/z 461.2 ($M+H^+$).

Example 3.58

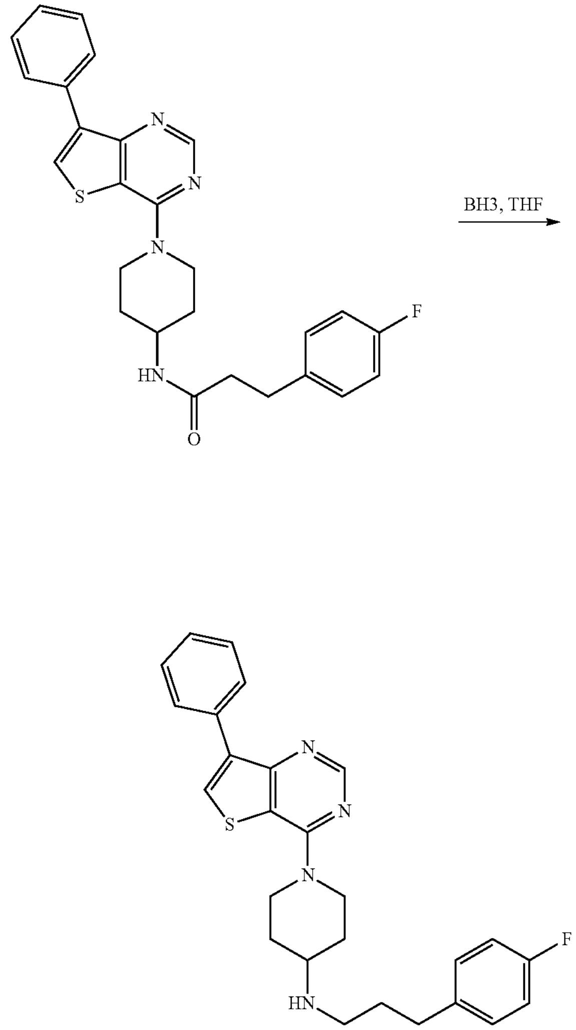

N-(3-(4-Fluorophenyl)propyl)-1-(7-phenylthieno[3,2-d]pyrimidin-4-yl)piperidin-4-amine The title compound was prepared using general procedure of N-(3-(3-fluoropyridin-4-yl)propyl)-1-(7-methylthieno[3,2-d]pyrimidin-4-yl)piperidin-4-amine (Example 3.40). $^1$HNMR (400 MHz, $CDCl_3$): δ=8.68 (s, 1H), 7.86 (d, J=8.4 Hz, 2H), 7.76 (s, 1H), 7.48 (t, J=7.2 Hz, 2H), 7.38 (t, J=7.6 Hz, 1H), 7.17-7.14 (m, 2H), 6.70-6.95 (m, 2H), 4.76 (d, J=13.6 Hz, 2H), 3.30 (t, J=11.6 Hz, 2H), 2.86-2.80 (m, 1H), 2.72-2.64 (m, 4H), 2.07-2.00 (m, 2H), 1.85-1.78 (m, 2H), 1.56-1.48 (m, 2H). MS: m/z 447.2 ($M+H^+$).

Example 3.59

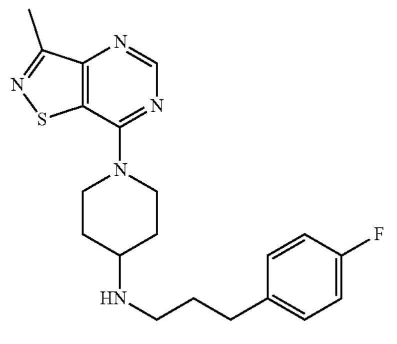 [SMILES: Cc1nsc2c(N3CCC(NCCCc4ccc(F)cc4)CC3)ncnc12]

N-(3-(4-Fluorophenyl)propyl)-1-(3-methylisothiazolo[4,5-d]pyrimidin-7-yl)piperidin-4-amine The title compound was prepared using general procedure of 1-(1-methyl-1H-pyrazolo[3,4-d]pyrimidin-4-yl)-N-(3-(pyridin-4-yl)propyl)piperidin-4-amine (Example 2.5). $^1$HNMR (400 MHz, $CD_3OD$): δ=8.50 (s, 1H), 7.22-7.19 (m, 2H), 7.00-6.96 (m, 2H), 4.65-4.61 (m, 2H), 3.31-3.27 (m, 2H), 2.90-2.85 (m, 1H), 2.67-2.64 (m, 7H), 2.11-2.08 (m, 2H), 1.86-1.78 (m, 2H), 1.43-1.33 (m, 2H). MS: m/z 386.1 ($M+H^+$).

Example 3.60

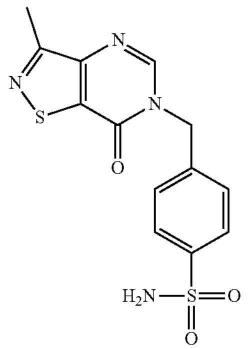 [SMILES: Cc1nsc2c(=O)n(Cc3ccc(S(N)(=O)=O)cc3)cnc12]

4-((3-Methyl-7-oxoisothiazolo[4,5-d]pyrimidin-6(7H)-yl)methyl)benzenesulfonamide The title compound was prepared using general procedure of 5-(((5-phenylthieno[2,3-d]pyrimidin-4-yl)amino)methyl)thiophene-2-sulfonamide (Example 1.28). $^1$HNMR (400 MHz, DMSO-$d_6$): δ=8.78 (s, 1H), 7.79 (d, J=8 Hz, 2H), 7.52 (d, J=4 Hz, 2H), 7.32 (brs, 2H), 5.34 (s, 2H), 2.62 (s, 3H). MS: m/z 337.0 ($M+H^+$).

Example 3.61

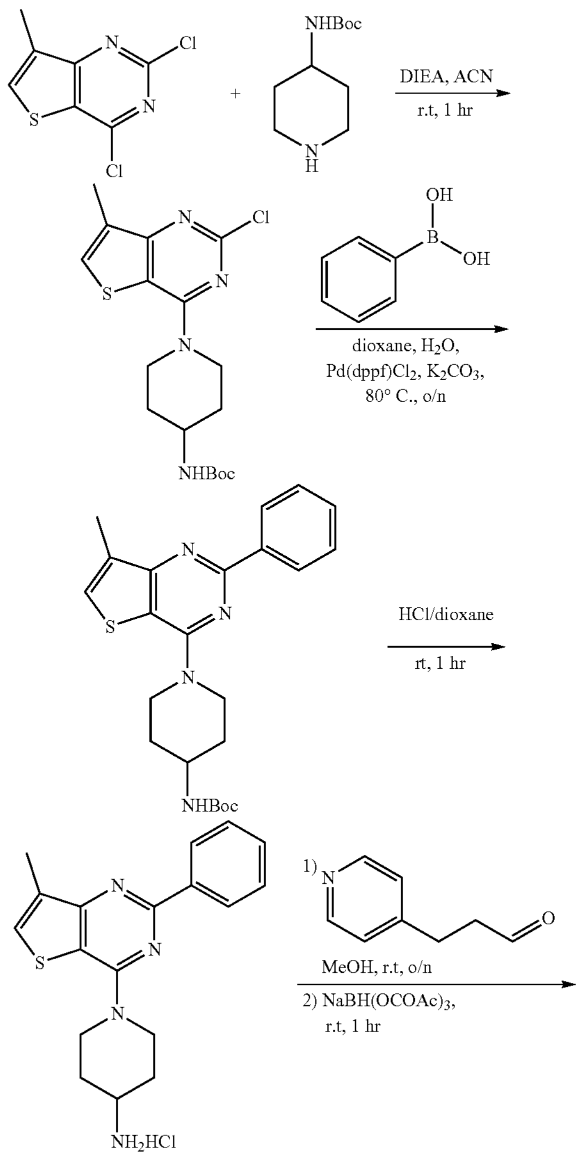

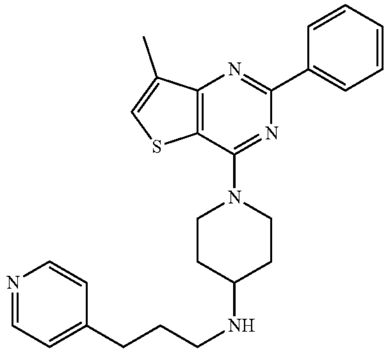

1-(7-Methyl-2-phenylthieno[3,2-d]pyrimidin-4-yl)-N-(3-(pyridin-4-yl)propyl)piperidin-4-amine Step 1: A solution of 2,4-dichloro-7-methylthieno[3,2-d]pyrimidine (450 mg, 2.1 mmol), tert-butyl piperidin-4-ylcarbamate (411 mg, 2.1 mmol) and DIEA (542 mg, 4.2 mmol) in ACN (20 mL) was stirred at room temperature for 1 hr. The resulting solution was filtered. The cake was washed with ACN to give tert-butyl (1-(2-chloro-7-methylthieno[3,2-d]pyrimidin-4-yl)piperidin-4-yl)carbamate (530 mg, yield: δ6%) as a white solid. $^1$HNMR (400 MHz, DMSO-$d_6$): δ=7.92 (d, J=1.2 Hz, 1H), 6.93 (d, J=8.0 Hz, 2H), 3.66-3.64 (m, 1H), 3.41-3.30 (m, 4H), 2.29 (s, 3H), 1.95-1.85 (m, 2H), 1.46-1.33 (m, 9H).

Step 2: A mixture of tert-butyl (1-(2-chloro-7-methylthieno[3,2-d]pyrimidin-4-yl)piperidin-4-yl)carbamate (100 mg, 0.26 mmol), phenylboronic acid (63 mg, 0.52 mmol), $K_2CO_3$ (90 mg, 0.65 mmol) and Pd(dppf)$Cl_2$ (22 mg, 0.03 mmol) in dioxane/$H_2O$ (16 mL/4 mL) was stirred at 80° C. overnight under $N_2$ atmosphere (balloon). The solution was concentrated and purified by prep-TLC (DCM/MeOH=30/1) to give tert-butyl (1-(7-methyl-2-phenylthieno[3,2-d]pyrimidin-4-yl)piperidin-4-yl)carbamate (30 mg, yield: 27%) as a white solid.

Step 3: To a mixture of tert-butyl (1-(7-methyl-2-phenylthieno[3,2-d]pyrimidin-4-yl)piperidin-4-yl)carbamate (30 mg, 0.07 mmol) in dioxane (20 mL) was added HCl (4 ml). The mixture was stirred at room temperature for 3 hrs. The solution was concentrated to give 1-(7-methyl-2-phenylthieno[3,2-d]pyrimidin-4-yl)piperidin-4-amine hydrochloride (crude) as a white solid.

Step 4: A mixture of 1-(7-methyl-2-phenylthieno[3,2-d]pyrimidin-4-yl)piperidin-4-amine hydrochloride (23 mg, 0.07 mmol) and 3-(pyridin-4-yl)propanal (10 mg, 0.08 mmol) in MeOH (20 mL) was stirred at room temperature overnight. Then NaBH(OCOAc)$_3$ (30 mg, 0.14 mmol) was added into the mixture. The mixture was keep stirring at room temperature for 1 hr. The solution was concentrated and the residue was purified by prep-HPLC to give 1-(7-methyl-2-phenylthieno[3,2-d]pyrimidin-4-yl)-N-(3-(pyridin-4-yl)propyl)piperidin-4-amine (2 mg, yield: 7%) as a white solid. $^1$HNMR (400 MHz, DMSO-$d_6$): δ=8.47-8.44 (m, 4H), 7.86 (s, 1H), 7.53-7.48 (m, 3H), 7.23 (d, J=6.0 Hz, 2H), 4.69-4.66 (m, 2H), 3.37 (overlap, 2H), 2.82 (t, J=7.2 Hz, 1H), 2.66-2.59 (m, 4H), 2.43 (s, 3H), 2.01-1.98 (m, 2H), 1.75-1.71 (m, 2H), 1.36-1.33 (m, 2H). MS: m/z 443.9 (M+H$^+$).

Example 3.62 and 3.63

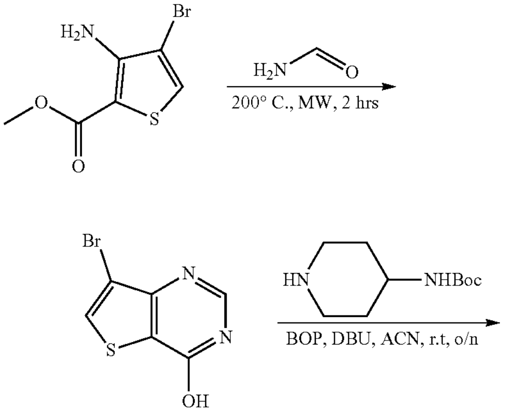

-continued

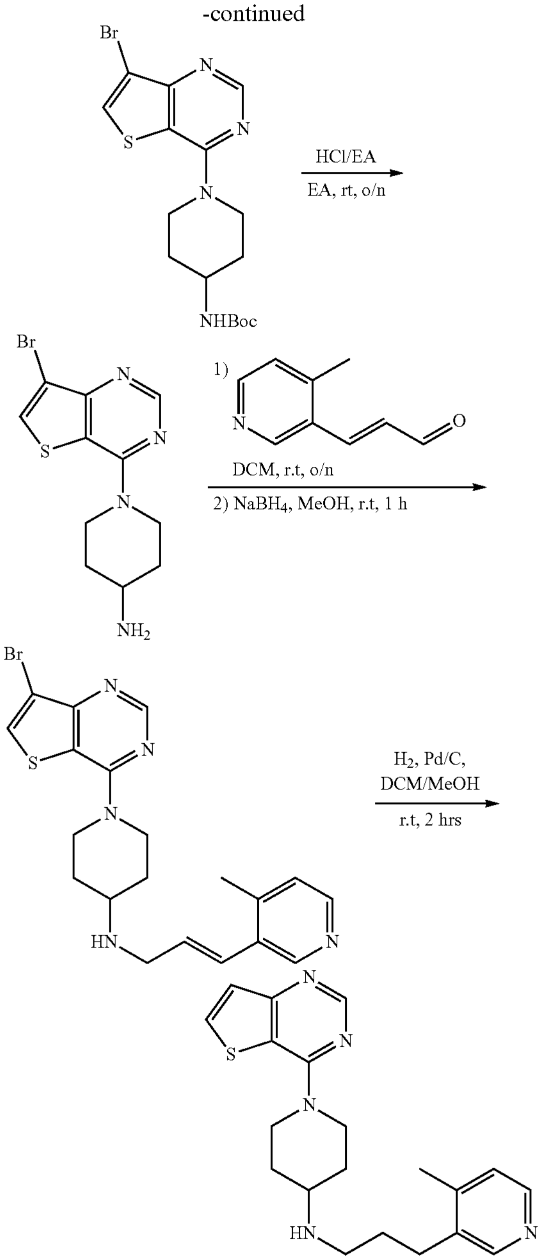

(E)-1-(7-Bromothieno[3,2-d]pyrimidin-4-yl)-N-(3-(4-methylpyridin-3-yl)allyl)piperidin-4-amine (Example 3.62) and N-(3-(4-Methylpyridin-3-yl)propyl)-1-(thieno[3,2-d]pyrimidin-4-yl)piperidin-4-amine (Example 3.63)

Step 1: A solution of methyl 3-amino-4-bromothiophene-2-carboxylate (400 mg, 1.7 mmol) in formamide (5 mL) was stirred at 200° C. for 2 hrs. The reaction mixture was filtered and the cake was dried under reduced pressure to give 7-bromothieno[3,2-d]pyrimidin-4-ol (195 mg, yield: 50%) as yellow solid.

Step 2: To a solution of 7-bromothieno[3,2-d]pyrimidin-4-ol (195 mg, 0.85 mmol) in ACN (15 mL) was added BOP (751 mg, 1.70 mmol), DBU (258 mg, 1.70 mmol) and tert-butyl piperidin-4-ylcarbamate (339 mg, 1.70 mmol). The reaction was stirred at room temperature overnight. The reaction mixture was concentrated. The residue was purified by silica gel column (DCM/MeOH=30/1) to give tert-butyl (1-(7-bromothieno[3,2-d]pyrimidin-4-yl)piperidin-4-yl)carbamate (100 mg, crude) as a white solid.

Step 3: To a solution of tert-butyl (1-(7-bromothieno[3,2-d]pyrimidin-4-yl)piperidin-4-yl)carbamate (100 mg, 0.24 mmol) in EA (10 mL) was added HCl (3 mL, 2 M in EA). The mixture was stirred at room temperature overnight. The resulting solution was filtered. The cake was dried under reduced pressure to give 1-(7-bromothieno[3,2-d]pyrimidin-4-yl)piperidin-4-amine (45 mg, yield: 80%) as a white solid.

Step 4: To a solution of 1-(7-bromothieno[3,2-d]pyrimidin-4-yl)piperidin-4-amine (40 mg, 0.13 mmol) in DCM/MeOH (5 mL/5 mL) was added (E)-3-(4-methylpyridin-3-yl)acrylaldehyde (23 mg, 0.15 mmol) and $CH_3COOH$ (2 d). The mixture was stirred at room temperature overnight. Then added $NaBH_4$ (10 mg, 0.26 mmol). The new mixture was stirred at room temperature for 1 hr. The resulting solution was concentrated under reduced pressure and purified by prep-HPLC to give (E)-1-(7-bromothieno[3,2-d]pyrimidin-4-yl)-N-(3-(4-methylpyridin-3-yl)allyl)piperidin-4-amine (45 mg, yield: 80%) as a white solid. $^1$HNMR (400 MHz, DMSO-$d_6$): δ=8.58 (s, 1H), 8.55 (s, 1H), 8.43 (s, 1H), 8.27 (d, J=4.4 Hz, 1H), 7.17 (d, J=4.4 Hz, 1H), 6.73-6.69 (m, 1H), 6.33-6.26 (m, 1H), 4.54-4.51 (m, 2H), 3.42-3.40 (m, 4H), 2.88-2.84 (m, 1H), 2.31 (s, 3H), 2.02-1.99 (m, 2H), 1.40-1.31 (m, 2H). MS: m/z 444.0 (M+H$^+$).

Step 5: To a solution of (E)-1-(7-bromothieno[3,2-d]pyrimidin-4-yl)-N-(3-(4-methylpyridin-3-yl)allyl)piperidin-4-amine (20 mg, 0.05 mmol) in DCM/MeOH (5 mL/5 mL) was added Pd/C (10 mg). The mixture was stirred at room temperature overnight under $H_2$ atmosphere (balloon). The resulting solution was concentrated under reduced pressure and purified by prep-TLC (DCM/MeOH=10/1) to give N-(3-(4-methylpyridin-3-yl)propyl)-1-(thieno[3,2-d]pyrimidin-4-yl)piperidin-4-amine (4.2 mg, yield: 19%) as a yellow solid. $^1$HNMR (400 MHz, DMSO-$d_6$): δ=8.50 (s, 1H), 8.32 (s, 1H), 8.26 (d, J=4.8 Hz, 1H), 8.22 (d, J=5.6 Hz, 1H), 7.44 (d, J=5.6 Hz, 1H), 7.15 (d, J=4.8 Hz, 1H), 4.67-4.64 (m, 2H), 3.28 (overlap, 2H), 2.79 (m, 2H), 2.67 (t, J=7.6 Hz, 2H), 2.30 (s, 3H), 2.10-2.08 (m, 2H), 2.01-1.99 (m, 1H), 1.79 (m, 2H), 1.49-1.47 (m, 2H). MS: m/z 368.1 (M+H$^+$).

Example 3.64

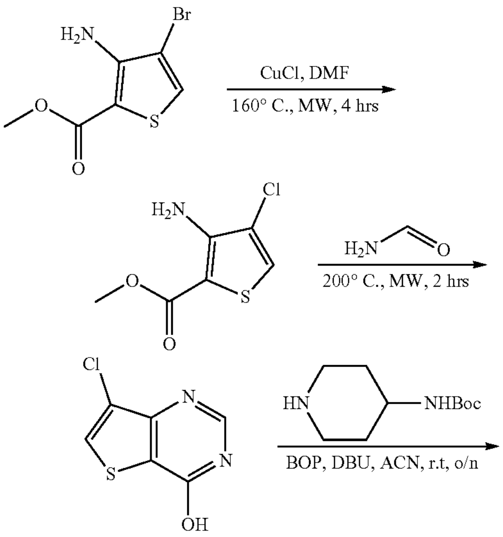

-continued

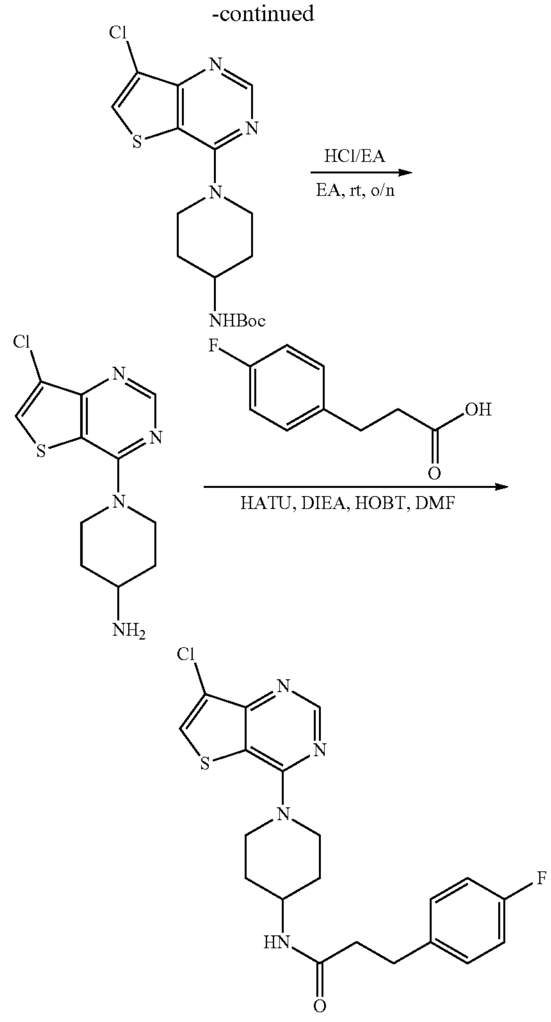

N-(1-(7-Chlorothieno[3,2-d]pyrimidin-4-yl)piperidin-4-yl)-3-(4-fluorophenyl)propanamide Step 1: To a solution of methyl 3-amino-4-bromothiophene-2-carboxylate (500 mg, 2.1 mmol) in DMF (5 mL) was added CuCl (1.05 g, 10.5 mmol). The mixture was stirred at 160° C. for 4 hrs, the reaction was purified by silica gel column (PE/EA=10/1) to give methyl 3-amino-4-chlorothiophene-2-carboxylate (230 mg, yield: 57%) as a white solid.

Step 2: A solution of methyl 3-amino-4-chlorothiophene-2-carboxylate (230 mg, 1.2 mmol) in formamide (3 mL) was stirred at 200° C. for 2 hrs. The reaction mixture was filtered and the cake was dried under reduced pressure to give 7-chlorothieno[3,2-d]pyrimidin-4-ol (93 mg, yield: 41%) as a yellow solid.

Step 3: To a solution of 7-chlorothieno[3,2-d]pyrimidin-4-ol (93 mg, 0.5 mmol) in ACN (15 mL) was added BOP (442 mg, 1 mmol), DBU (152 mg, 1 mmol) and tert-butyl piperidin-4-ylcarbamate (120 mg, 0.6 mmol). The reaction was stirred at room temperature overnight. The reaction mixture was concentrated and the residue was purified by silica gel column (DCM) to give tert-butyl (1-(7-chlorothieno[3,2-d]pyrimidin-4-yl)piperidin-4-yl)carbamate (92 mg, crude) as a white solid.

Step 4: A solution of tert-butyl (1-(7-chlorothieno[3,2-d]pyrimidin-4-yl)piperidin-4-yl)carbamate (92 mg, 0.25 mmol) and HCl (12 mL, 3 M in EA) in EA (10 mL) was stirred at room temperature overnight. The resulting solution was filtered. The cake was dried under reduced pressure to give 1-(7-chlorothieno[3,2-d]pyrimidin-4-yl)piperidin-4-amine (50 mg, yield: 75%) as a white solid.

Step 5: To a solution of 1-(7-chlorothieno[3,2-d]pyrimidin-4-yl)piperidin-4-amine (20 mg, 0.07 mmol) in DMF (15 mL) was added 3-(4-fluorophenyl)propanoic acid (15 mg, 0.09 mmol), HATU (80 mg, 0.21 mmol), HOBT (28 mg, 0.21 mmol) and DIEA (0.2 mL). The mixture was stirred at room temperature for 5 hrs. The resulting solution was concentrated under reduced pressure and the residue was purified by prep-HPLC to give N-(1-(7-chlorothieno[3,2-d]pyrimidin-4-yl)piperidin-4-yl)-3-(4-fluorophenyl)propanamide (18 mg, yield: δ2%) as a white solid. $^1$HNMR (400 MHz, DMSO-$d_6$): δ=8.56 (s, 1H), 8.34 (s, 1H), 7.80 (d, J=7.6 Hz, 1H), 7.24-7.20 (m, 2H), 7.10-7.06 (m, 2H), 4.51-4.48 (m, 2H), 3.99-3.87 (m, 1H), 3.44-3.37 (m, 2H), 2.80 (t, J=7.6 Hz, 2H), 2.34 (t, J=7.6 Hz, 2H), 1.88-1.84 (m, 2H), 1.38-1.37 (m, 2H). MS: m/z 418.9 (M+H$^+$).

Example 3.65

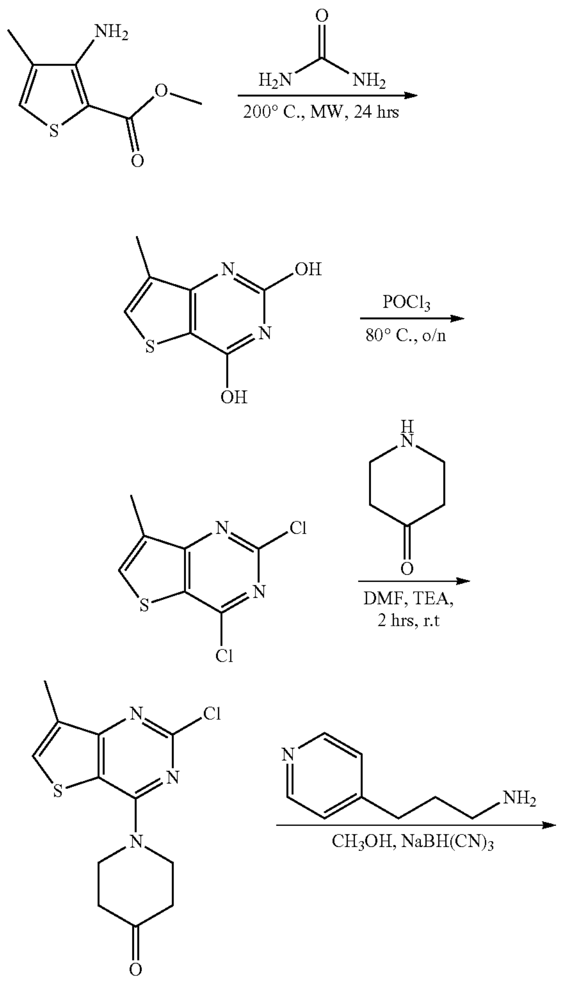

-continued

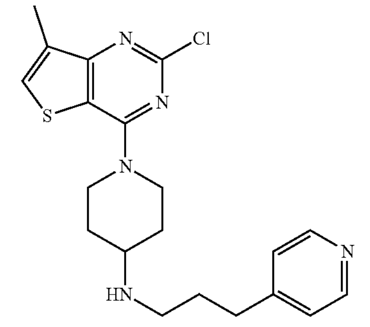

1-(2-Chloro-7-methylthieno[3,2-d]pyrimidin-4-yl)-N-(3-(pyridin-4-yl)propyl)piperidin-4-amine Step 1: To a solution of methyl 3-amino-4-methylthiophene-2-carboxylate (855 mg, 5 mmol) in tetrahydrothiophene 1,1-dioxide (3 mL) was added urea (600 mg, 10 mmol). After stirred at 200° C. microwave overnight, the reaction mixture was evaporated in vacuum. The residue was purified by silica flash column (ACN %=30%-60%, 30 mins) to give 7-methylthieno[3,2-d]pyrimidine-2,4-diol (322 mg, yield: 35.4%) as a yellow solid.

Step 2: A solution of methyl 7-methylthieno[3,2-d]pyrimidine-2,4-diol (322 mg, 1.77 mmol) in $POCl_3$ (10 mL) was stirred at 80° C. overnight. The reaction mixture was evaporated in vacuum. The residue was purified by silica flash column (ACN %=50%-100%, 30 mins) to give 2,4-dichloro-7-methylthieno[3,2-d]pyrimidine (218 mg, yield: 55.5%) as a white solid.

Step 3: To a solution of 2,4-dichloro-7-methylthieno[3,2-d]pyrimidine (218 mg, 1 mmol) in DMF (10 mL) was added piperidin-4-one (135 mg, 11 mmol) and $K_2CO_3$ (276 mg, 2 mmol). After stirred at room temperature overnight, the reaction mixture was evaporated in vacuum. The residue was purified by silica gel column (PE/EA=10/1) to give 1-(2-chloro-7-methylthieno[3,2-d]pyrimidin-4-yl)piperidin-4-one (113 mg, yield: 40.1%) as a yellow solid. $^1$HNMR (400 MHz, DMSO-$d_6$): δ=7.96 (d, J=0.6 Hz, 1H), 5.76 (s, 1H), 4.21 (t, J=6.4 Hz, 4H), 2.60 (t, J=6.4 Hz, 4H), 2.31 (s, 3H).

Step 4: To a solution of 1-(2-chloro-7-methylthieno[3,2-d]pyrimidin-4-yl)piperidin-4-one (28 mg, 0.1 mmol) in toluene (10 mL) was added 3-(pyridin-4-yl)propan-1-amine (20.4 mg, 0.15 mmol). The mixture was stirred at room temperature overnight. This reaction was monitored by LCMS. Then added $NaBH(CN)_3$ (22.4 mg, 0.2 mmol) and $CH_3OH$ (10 mL). The mixture was stirred at 0° C. for 1 hr. This reaction was monitored by LC-MS. The reaction mixture was evaporated in vacuum. The residue was purified by prep-HPLC to give 1-(2-chloro-7-methylthieno[3,2-d]pyrimidin-4-yl)-N-(3-(pyridin-4-yl)propyl)piperidin-4-amine (2.0 mg, yield: 5.0%) as a white oil. $^1$HNMR (400 MHz, DMSO-$d_6$): δ=8.42-8.40 (m, 2H), 7.66 (d, J=1.2 Hz, 1H), 7.32 (d, J=6.0 Hz, 2H), 4.78 (d, J=13.2 Hz, 2H), 3.29-3.21 (m, 2H), 2.89-2.84 (m, 1H), 2.75-2.67 (m, 4H), 2.35 (s, 3H), 2.09 (d, J=12.4 Hz, 2H), 1.89-1.85 (m, 2H), 1.42-1.38 (m, 2H). MS: m/z 402.1 (M+H$^+$).

Example 3.66

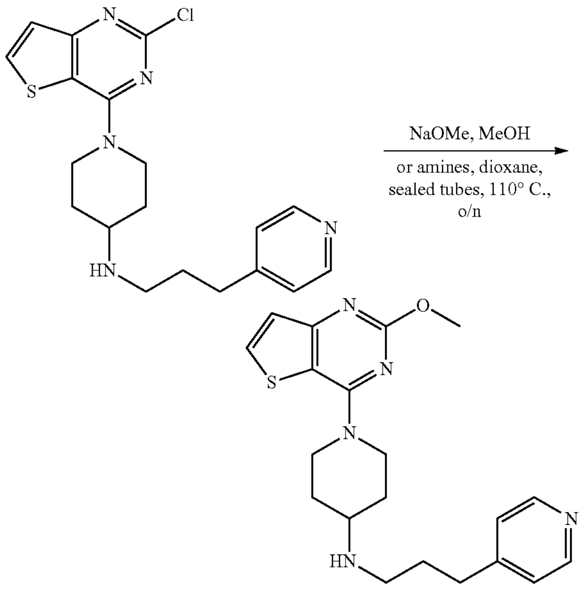

1-(2-Methoxy-7-methylthieno[3,2-d]pyrimidin-4-yl)-N-(3-(pyridin-4-yl)propyl)piperidin-4-amine To a solution of 1-(2-chloro-7-methylthieno[3,2-d]pyrimidin-4-yl)-N-(3-(pyridin-4-yl)propyl)piperidin-4-amine (Example 3.65, 50 mg, 0.125 mmol) in MeOH (10 mL) was added sodium methanolate (67.5 mg, 1.25 mmol). The resulting mixture was stirred at room temperature overnight. The reaction was monitored by LC-MS. Then the mixture was concentrated in vacuum to give a residue, which was purified by prep-HPLC to afford 1-(2-methoxy-7-methylthieno[3,2-d]pyrimidin-4-yl)-N-(3-(pyridin-4-yl)propyl)piperidin-4-amine (28.6 mg, yield: 58%) as colorless oil. $^1$HNMR (400 MHz, DMSO-$d_6$): δ=8.44 (d, J=5.2 Hz, 2H), 7.76 (s, 1H), 7.23 (d, J=5.2 Hz, 2H), 4.48 (d, J=13.2 Hz, 2H), 3.87 (s, 3H), 3.33-3.20 (m, 2H), 2.78-2.68 (m, 1H), 2.64 (t, J=7.6 Hz, 2H), 2.55 (t, J=7.2 Hz, 2H), 2.27 (s, 3H), 1.97-1.86 (m, 2H), 1.76-1.64 (m, 2H), 1.33-1.18 (m, 2H). MS: m/z 398.0 (M+H$^+$).

Example 3.67

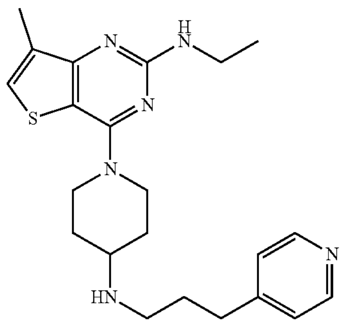 [SMILES: CCNc1nc(N2CCC(NCCCc3ccncc3)CC2)c2scc(C)c2n1]

N-Ethyl-7-methyl-4-(4-((3-(pyridin-4-yl)propyl)amino)piperidin-1-yl)thieno[3,2-d]pyrimidin-2-amine The title compound was prepared using general procedure of 1-(2-Methoxy-7-methylthieno[3,2-d]pyrimidin-4-yl)-N-(3-(pyridin-4-yl)propyl)piperidin-4-amine (Example 3.66). $^1$HNMR (400 MHz, DMSO-$d_6$): δ=9.64 (brs, 2H), 8.85 (d, J=6.4 Hz, 2H), 8.07-8.06 (m, 1H), 8.04 (s, 1H), 7.98 (d, J=6.4 Hz, 2H), 4.72 (brs, 2H), 3.50-3.44 (m, 5H), 3.05-3.01 (m, 2H), 2.97-2.96 (m, 2H), 2.33-2.29 (m, 5H), 2.12-2.08 (m, 2H), 1.80-1.77 (m, 2H), 1.23-1.17 (m, 3H). MS: m/z 411.1 (M+H$^+$).

Example 3.68 and Example 3.69

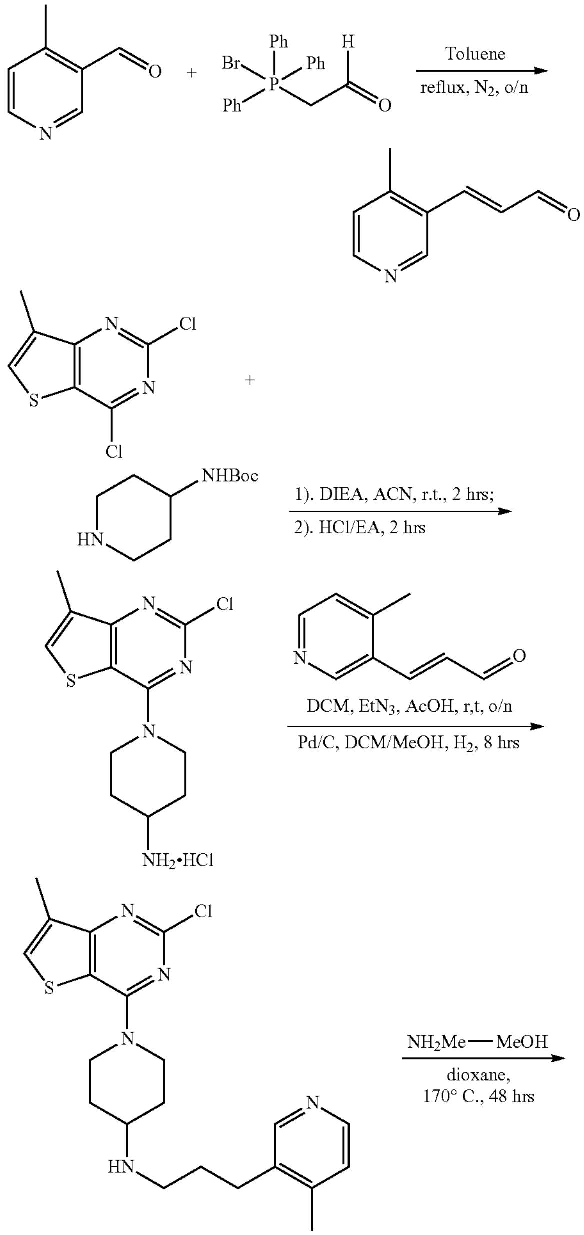

-continued

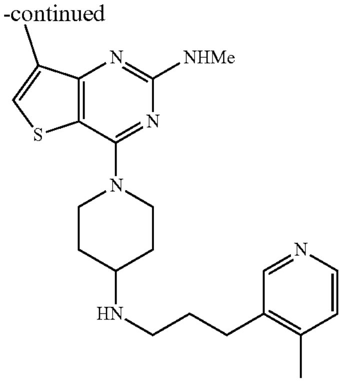

1-(2-Chloro-7-methylthieno[3,2-d]pyrimidin-4-yl)-N-(3-(4-methylpyridin-3-yl)propyl)piperidin-4-amine (Example 3.68) and N,7-Dimethyl-4-(4-((3-(4-methylpyridin-3-yl)propyl)amino)piperidin-1-yl)thieno[3,2-d]pyrimidin-2-amine (Example 3.69)

Step 1: To a solution of 4-methylnicotinaldehyde (2 g, 8.1 mmol) in toluene (100 mL) was added 2-(bromotriphenyl-15-phosphanyl)acetaldehyde (1.32 g, 9.7 mmol) under $N_2$ atmosphere (balloon). The mixture was stirred at 110° C. for 8 hrs. The reaction was monitored by LC-MS and TLC. Then the reaction mixture was concentrated in vacuum to give the crude product, which was purified by reverse-phase column (5-95% ACN in $H_2O$) to afford 3-(4-methylpyridin-3-yl)acrylaldehyde as a brown solid.

Step 2: To a solution of 2,4-dichloro-7-methylthieno[3,2-d]pyrimidine (12 g, 100 mmol) and tert-butyl piperidin-4-ylcarbamate (24.8 g, 220 mmol) in ACN (200 mL) was added DIEA (13.1 g, 150 mmol). The resulting mixture was stirred at room temperature for 2 hrs. The solid precipitated from the mixture was collected by filtration. The cake was dried in air which can be used directly without any further operation. To a mixture of last produce (86.8 mg, 0.26 mmol) in EA (10 mL) was added HCl/EA (5 mL). The resulting mixture was stirred at room temperature for 3 hrs. The solid precipitated form the mixture was collected by filtration. The cake was dried in air which can be used directly without any further operation to afford 1-(2-chloro-7-methylthieno[3,2-d]pyrimidin-4-yl)piperidin-4-amine hydrochloride as a white solid.

Step 3: To a mixture of 3-(4-methylpyridin-3-yl)acrylaldehyde (70.2 mg, 0.26 mmol) and 1-(2-chloro-7-methylthieno[3,2-d]pyrimidin-4-yl)piperidin-4-amine in DCM (10 mL) was added $Et_3N$ (42 mg, 0.31 mmol) with some drops of AcOH. The resulting mixture was stirred at room temperature overnight. Under $H_2$, Pd/C (165 mg, 0.78 mmol)(10 mol %) and MeOH (10 mL) were added and the mixture was stirred at room temperature for another 8~10 hr. The reaction was monitored by LC-MS. The mixture was concentrated in vacuum to give a residue, which was purified by prep-HPLC with $NH_4HCO_3$ as additive to afford 1-(2-chloro-7-methylthieno[3,2-d]pyrimidin-4-yl)-N-(3-(4-methylpyridin-3-yl)propyl)piperidin-4-amine as yellow oil (218 mg, yield: 28%). $^1$HNMR (400 MHz, $CD_3OD$) δ 8.30 (s, 1H), 8.23 (d, J=4.8 Hz, 1H), 7.68 (s, 1H), 7.23 (d, J=4.8 Hz, 1H), 4.81 (d, J=13.6 Hz, 2H), 3.37 (s, 1H), 3.27 (t, J=12.1 Hz, 2H), 2.90 (m, 1H), 2.75 (t, J=7.9 Hz, 4H), 2.40 (s, 3H), 2.37 (s, 3H), 2.11 (d, J=10.8 Hz, 2H), 1.81 (dd, J=15.2, 7.6 Hz, 2H), 1.49-1.36 (m, 2H). MS: m/z 416.1 (M+H$^+$).

Step 4: To a solution of 1-(2-chloro-7-methylthieno[3,2-d]pyrimidin-4-yl)-N-(3-(4-methylpyridin-3-yl)propyl)piperidin-4-amine in dioxane (5 mL) was added $NH_2Me$-MeOH (1 mL) by using a pressure bomb and heated the reaction to 170° C. about 48 hrs. The reaction was monitored by LC-MS. The mixture was concentrated in vacuum to give a residue, which was purified by prep-HPLC with $NH_4HCO_3$ as additive to afford N,7-dimethyl-4-(4-((3-(4-methylpyridin-3-yl)propyl)amino)piperidin-1-yl)thieno[3,2-d]pyrimidin-2-amine as yellow oil (13.8 mg, yield: 28%). $^1$HNMR (400 MHz, $CDCl_3$): δ=8.33 (s, 1H), 8.31 (d, J=4.9 Hz, 1H), 7.20 (d, J=1.1 Hz, 1H), 7.04 (d, J=4.9 Hz, 1H), 4.79 (s, 1H), 4.67 (d, J=13.3 Hz, 2H), 3.19-3.10 (m, 2H), 3.01 (d, J=5.0 Hz, 3H), 2.81-2.74 (m, 1H), 2.73-2.63 (m, 4H), 2.32 (d, J=1.3 Hz, 6H), 1.99 (d, J=10.4 Hz, 2H), 1.75 (dd, J=14.7, 7.5 Hz, 2H), 1.40 (td, J=13.5, 3.8 Hz, 2H). MS: m/z 411.0 (M+H$^+$).

Example 3.70

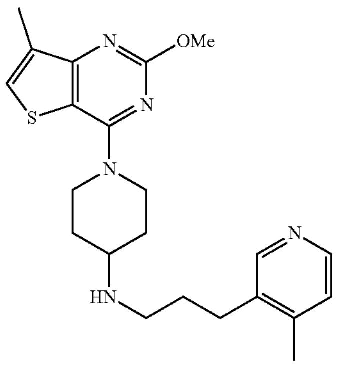 [SMILES: COc1nc(N2CCC(NCCCc3cnccc3C)CC2)c2scc(C)c2n1]

1-(2-Methoxy-7-methylthieno[3,2-d]pyrimidin-4-yl)-N-(3-(4-methylpyridin-3-yl)propyl)piperidin-4-amine To a solution of (2-chloro-7-methylthieno[3,2-d]pyrimidin-4-yl)-N-(3-(4-methylpyridin-3-yl)allyl)piperidin-4-amine in MeOH (10 mL) was added MeONa (13 mg, 0.24 mmol) by using a pressure bomb and refluxed the reaction to 70° C. about 48 hrs. The reaction was monitored by LC-MS. Then, the mixture was concentrated in vacuum to give a residue, which was purified by prep-HPLC with $NH_4HCO_3$ as additive to afford 1-(2-methoxy-7-methylthieno[3,2-d]pyrimidin-4-yl)-N-(3-(4-methylpyridin-3-yl)propyl)piperidin-4-amine as colorless oil (9.8 mg, yield: 19%). $^1$HNMR (400 MHz, $CD_3OD$): δ=8.18 (s, 1H), 8.12 (d, J=4.9 Hz, 1H), 7.45 (s, 1H), 7.12 (d, J=5.0 Hz, 1H), 4.72-4.68 (m, 2H), 3.88 (s, 3H), 3.13 (t, J=12.1 Hz, 2H), 2.77 (dd, J=12.5, 8.8 Hz, 1H), 2.63 (t, J=7.4 Hz, 4H), 2.29 (s, 3H), 2.21 (s, 3H), 1.97 (d, J=12.8 Hz, 2H), 1.74-1.65 (m, 2H), 1.31 (dd, J=23.2, 8.9 Hz, 2H). MS: m/z 412.0 (M+H$^+$).

Example 3.71

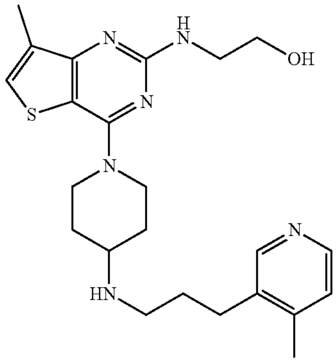 [SMILES: Cc1ccncc1CCCNC1CCN(c2nc(NCCO)nc3c(C)csc23)CC1]

2-((7-Methyl-4-(4-((3-(4-methylpyridin-3-yl)propyl)amino)piperidin-1-yl)thieno[3,2-d]pyrimidin-2-yl)amino)ethanol The title compound was prepared using general procedure of N,7-dimethyl-4-(4-((3-(4-methylpyridin-3-yl)propyl)amino)piperidin-1-yl)thieno[3,2-d]pyrimidin-2-amine (Example 3.69). $^1$HNMR (400 MHz, $CDCl_3$): δ=8.32 (s, 1H), 8.30 (d, J=5.0 Hz, 1H), 7.22 (d, J=1.1 Hz, 1H), 7.05 (d, J=4.9 Hz, 1H), 5.26 (t, J=5.3 Hz, 1H), 4.62 (d, J=13.3 Hz, 2H), 3.87-3.82 (m, 2H), 3.58 (dd, J=9.2, 5.5 Hz, 2H), 3.22-3.12 (m, 2H), 2.78 (ddd, J=14.1, 10.0, 3.9 Hz, 1H), 2.73-2.64 (m, 4H), 2.31 (s, 6H), 1.99 (dd, J=13.1, 3.0 Hz, 2H), 1.76 (dt, J=14.6, 7.4 Hz, 2H), 1.39 (td, J=13.6, 3.8 Hz, 2H). MS: m/z 441.0 (M+H$^+$).

Example 3.72

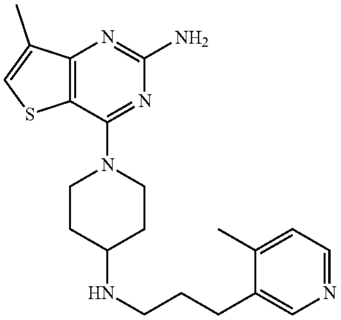 [SMILES: Cc1ccncc1CCCNC1CCN(c2nc(N)nc3c(C)csc23)CC1]

7-Methyl-4-(4-((3-(4-methylpyridin-3-yl)propyl)amino)piperidin-1-yl)thieno[3,2-d]pyrimidin-2-amine The title compound was prepared using general procedure of N,7-dimethyl-4-(4-((3-(4-methylpyridin-3-yl)propyl)amino)piperidin-1-yl)thieno[3,2-d]pyrimidin-2-amine (Example 3.69). $^1$HNMR (400 MHz, $CD_3OD$): δ=8.56 (s, 1H), 8.49 (d, J=4.6 Hz, 1H), 7.80 (d, J=5.5 Hz, 1H), 7.74 (d, J=1.0 Hz, 1H), 4.92 (s, 2H), 3.57-3.45 (m, 1H), 3.27 (d, J=14.5 Hz, 2H), 3.19-3.10 (m, 2H), 2.92-2.83 (m, 2H), 2.56 (s, 3H), 2.27 (d, J=0.7 Hz, 5H), 1.98 (dt, J=16.0, 8.1 Hz, 2H), 1.72-1.62 (m, 2H). MS: m/z 397.0 (M+H$^+$).

Examples 3.73, 3.74 and 3.75

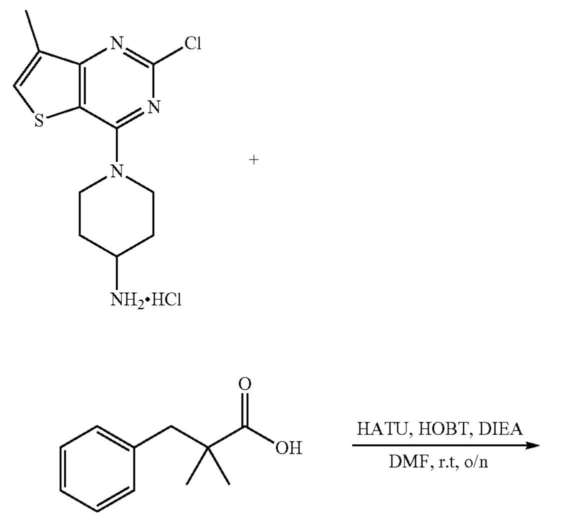

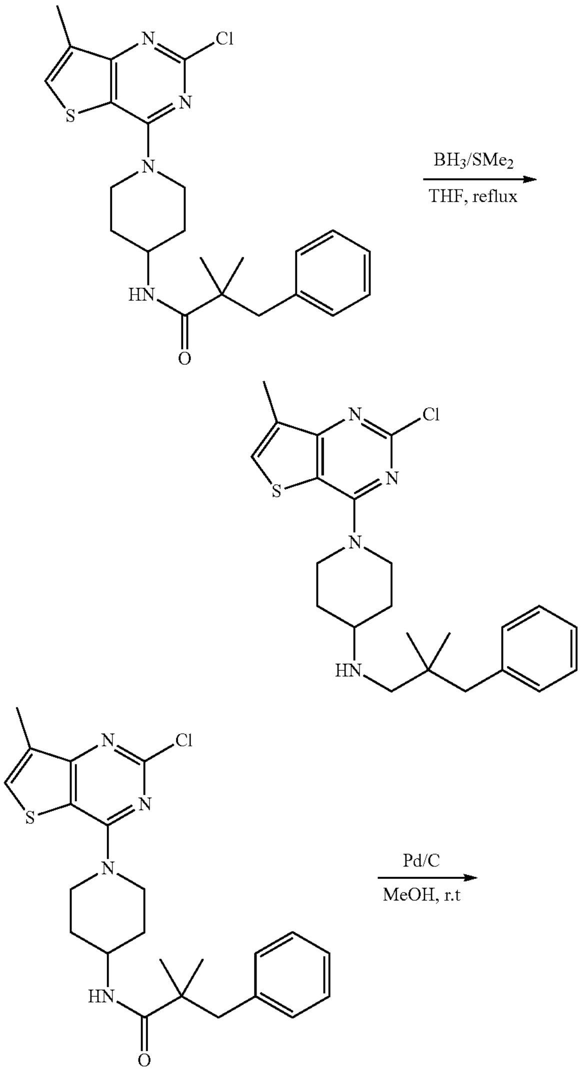

-continued

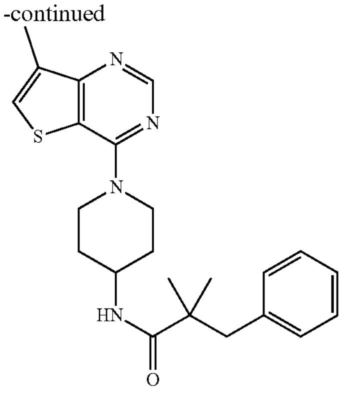

N-(1-(2-Chloro-7-methylthieno[3,2-d]pyrimidin-4-yl)piperidin-4-yl)-2,2-dimethyl-3-phenylpropanamide (Example 3.73) and 1-(2-Chloro-7-methylthieno[3,2-d]pyrimidin-4-yl)-N-(2,2-dimethyl-3-phenylpropyl)piperidin-4-amine (Example 3.74) and 2,2-Dimethyl-N-(1-(7-methylthieno[3,2-d]pyrimidin-4-yl)piperidin-4-yl)-3-phenylpropanamide (Example 3.75)

Step 1: To a solution of 1-(2-chloro-7-methylthieno[3,2-d]pyrimidin-4-yl)piperidin-4-amine hydrochloride (200 mg, 0.7 mmol) in DMF (6 mL) was added 2,2-dimethyl-3-phenylpropanoic acid (163 mg, 0.91 mmol). Then, HATU (798 mg), HOBT (283 mg) and DIEA (1.2 mL) were added to the reaction mixture. The resulting mixture was stirred at room temperature overnight. The reaction was monitored by LC-MS and TLC. The reaction was added water (20 mL) and extracted with EA(15 mL×3). The combined EA phases were dried over $Na_2SO_4$ and concentrated. The desired product was purified by prep-HPLC with $NH_4HCO_3$ as additive to afford N-(1-(2-chloro-7-methylthieno[3,2-d]pyrimidin-4-yl)piperidin-4-yl)-2,2-dimethyl-3-phenylpropanamide (201 mg, yield: δ5%) as yellow solid. $^1$HNMR (400 MHz, $CD_3OD$): δ=7.57 (d, J=1.1 Hz, 1H), 7.16-7.01 (m, 5H), 4.68 (d, J=13.6 Hz, 2H), 4.02-3.92 (m, 1H), 3.15 (d, J=12.2 Hz, 2H), 2.71 (s, 2H), 2.25 (d, J=1.0 Hz, 3H), 1.80 (d, J=9.7 Hz, 2H), 1.47-1.36 (m, 2H), 1.05 (s, 6H). MS: m/z 444.0 (M+H$^+$).

Step 2: To a solution of N-(1-(2-chloro-7-methylthieno[3,2-d]pyrimidin-4-yl)piperidin-4-yl)-2,2-dimethyl-3-phenylpropanamide (120 mg, 0.27 mmol) in dried THF (5 mL) was added $BH_3$/$SMe_2$ (0.12 mL) under $N_2$ atmosphere (balloon). Then, refluxed the reaction mixture overnight. Cooling the reaction mixture to 0° C., 5 mL of MeOH was added to the reaction very slowly and carefully. Then, 1 mL of conc. HCl was added to the reaction and refluxed 1 hr. The reaction was monitored by LC-MS and TLC. The reaction was evaporated in vacuo and prep-TLC with TFA as additive to afford 1-(2-chloro-7-methylthieno[3,2-d]pyrimidin-4-yl)-N-(2,2-dimethyl-3-phenylpropyl)piperidin-4-amine(5.8 mg, yield: 5%) as a white solid. $^1$HNMR (400 MHz, DMSO-d$_6$): 6=8.14 (s, 2H), 7.99 (s, 1H), 7.41-7.14 (m, 5H), 4.72 (d, J=12.6 Hz, 2H), 3.52 (s, 1H), 3.27 (s, 2H), 2.88 (s, 2H), 2.61 (s, 2H), 2.31 (s, 3H), 2.27-2.09 (m, 2H), 1.67 (d, J=8.5 Hz, 2H), 0.91 (s, 6H). MS: m/z 429.1 (M+H$^+$).

Step 3: A solution of N-(1-(2-chloro-7-methylthieno[3,2-d]pyrimidin-4-yl)piperidin-4-yl)-2,2-dimethyl-3-phenylpropanamide (140 mg, 0.32 mmol) and Pd/C (40 mg) in MeOH (10 mL) was stirred at room temperature overnight under $H_2$ atmosphere (balloon). The reaction was monitored by LC-MS and TLC. The reaction was filtered and the filtrate was concentrated. The residue was purified by prep-TLC with TFA as additive to afford 2,2-Dimethyl-N-(1-(7-methylthieno[3,2-d]pyrimidin-4-yl)piperidin-4-yl)-3-phenylpropanamide (9.3 mg, yield: 7.4%) as a white solid. $^1$HNMR (400 MHz, MeOD): δ=8.36 (s, 1H), 7.53 (d, J=1.1 Hz, 1H), 7.14 (dd, J=11.2, 4.5 Hz, 2H), 7.10-7.07 (m, 1H), 7.05-7.01 (m, 2H), 4.72 (d, J=13.6 Hz, 2H), 4.01-3.92 (m, 1H), 3.16 (dd, J=18.9, 7.1 Hz, 2H), 2.71 (s, 2H), 2.29 (d, J=0.9 Hz, 3H), 1.84-1.75 (m, 2H), 1.41 (qd, J=12.5, 3.9 Hz, 2H), 1.05 (s, 6H). MS: m/z 409.0 (M+H$^+$).

Example 3.76

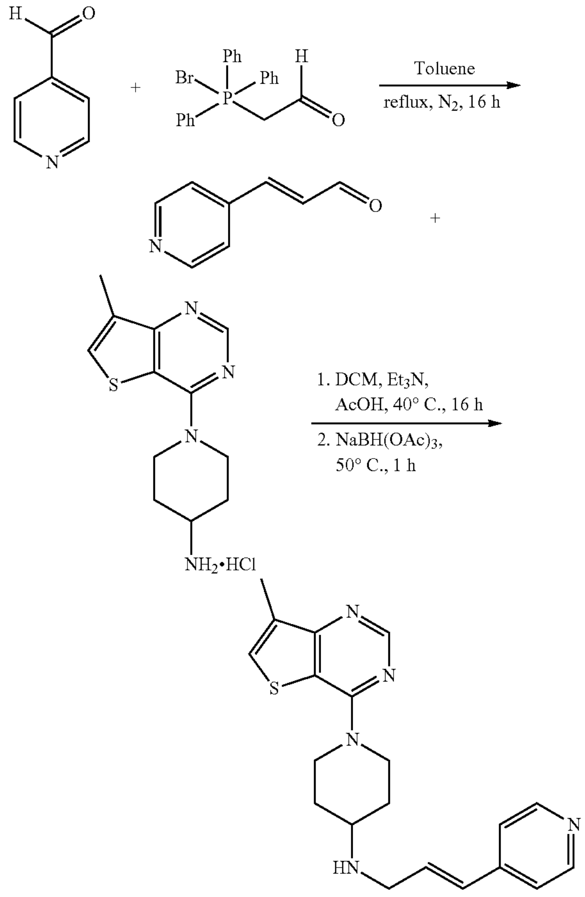

(E)-1-(7-methylthieno[3,2-d]pyrimidin-4-yl)-N-(3-(pyridin-4-yl)allyl)piperidin-4-amine Step 1: A solution of isonicotinaldehyde (500 mg, 0.44 mmol) and 2-(bromotriphenylphosphoranyl)acetaldehyde (1.85 g, 6.10 mmol) in toluene (230 mL) was heated to reflux for 16 hrs under $N_2$ (atmosphere). Concentrated and purified by flash to afford (E)-3-(pyridin-4-yl)acrylaldehyde (385 mg, yield: δ1.8%) as a yellow solid.

Step 2: A solution of (E)-3-(pyridin-4-yl)acrylaldehyde (200 mg, 0.71 mmol), 1-(7-methylthieno[3,2-d]pyrimidin-4-yl)piperidin-4-amine hydrochloride (113 mg, 0.85 mmol), triethylamine (215 mg, 2.13 mmol) and 3 drops of AcOH in DCM (10 mL) was stirred at 40° C. for 16 hrs. Then Sodium triacetoxyborohyride (302 mg, 1.42 mmol) was added in and the reaction mixture was stirred at 50° C. for 1 hr. The reaction mixture was filtered and the filtrate was concentrated. The residue was dissolved with EA (30 mL). The EA phase was washed with brine (30 mL), dried over anhydrous sodium sulfate and concentrated. The residue was purified by flash to afford (E)-1-(7-methylthieno[3,2-d]pyrimidin-4-yl)-N-(3-(pyridin-4-yl)allyl)piperidin-4-amine (25 mg, yield: 9.6%) as a white solid. $^1$HNMR (400 MHz, $CD_3OD$-$d_6$): δ=8.45 (s, 1H), 8.47 (d, J=6.4 Hz, 2H), 7.67 (s, 1H), 7.46 (d, J=6.4 Hz, 2H), 6.68 (d, J=5.6 Hz, 2H), 3.55 (d, J=4.8 Hz, 2H), 3.25-3.33 (m, 4H), 2.98 (s, 1H), 2.42 (s, 3H), 2.15 (d, J=6.4 Hz, 2H), 1.49 (dd, J=11.2, 2.8 Hz, 2H). MS: m/z 366.1 (M+H$^+$).

Example 3.77

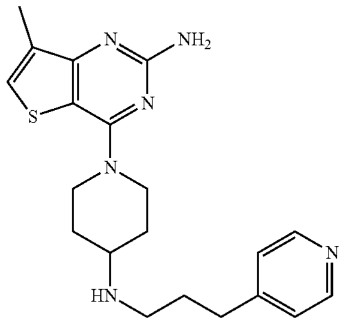 [SMILES: Cc1csc2c(N3CCC(NCCCc4ccncc4)CC3)nc(N)nc12]

7-Methyl-4-(4-((3-(pyridin-4-yl)propyl)amino)piperidin-1-yl)thieno[3,2-d]pyrimidin-2-amine The title compound was prepared using general procedure of 1-(2-Methoxy-7-methylthieno[3,2-d]pyrimidin-4-yl)-N-(3-(pyridin-4-yl)propyl)piperidin-4-amine (Example 3.66). $^1$HNMR (400 MHz, DMSO-$d_6$): δ=8.32-8.31 (m, 2H), 7.32 (s, 1H), 7.22 (d, J=5.2 Hz, 2H), 4.69-4.66 (m, 2H), 3.05-2.98 (m, 2H), 2.74-2.69 (m, 1H), 2.65-2.56 (m, 4H), 2.17 (s, 3H), 1.93-1.90 (m, 2H), 1.80-1.72 (m, 2H), 1.31-1.20 (m, 2H). MS: m/z 383.1 (M+H$^+$).

Example 3.78

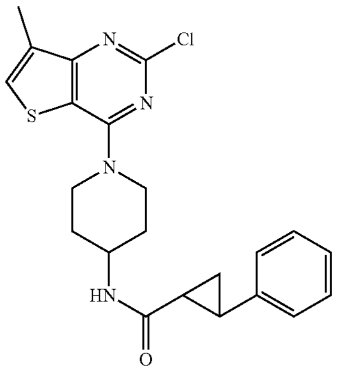 [SMILES: Cc1csc2c(N3CCC(NC(=O)C4CC4c4ccccc4)CC3)nc(Cl)nc12]

N-(1-(2-Chloro-7-methylthieno[3,2-d]pyrimidin-4-yl)piperidin-4-yl)-2-phenylcyclopropanecarboxamide The title compound was prepared using general procedure of N-(1-(2-chloro-7-methylthieno[3,2-d]pyrimidin-4-yl)piperidin-4-yl)-2,2-dimethyl-3-phenylpropanamide (Example 3.73). $^1$HNMR (400 MHz, DMSO-$d_6$): δ=8.14 (d, J=7.6 Hz, 1H), 7.92 (d, J=5.2 Hz, 1H), 7.28-7.24 (m, 2H), 7.18-7.14 (m, 1H), 7.13-7.10 (m, 2H), 4.49-4.46 (m, 2H), 4.00-3.97 (m, 1H), 3.46-3.40 (m, 2H), 2.51 (s, 3H), 2.50-2.49 (m, 1H), 2.29-2.25 (m, 2H), 1.85-1.81 (m, 1H), 1.48-1.42 (m, 2H), 1.37-1.34 (m, 1H), 1.23-1.17 (m, 1H). MS: m/z 426.9 ($M+H^+$).

Example 3.79

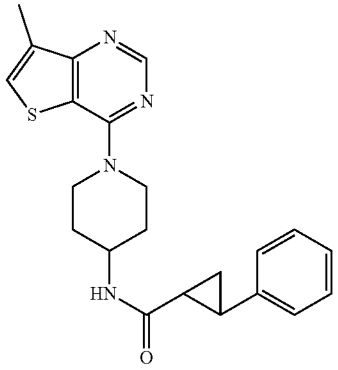 [SMILES: Cc1csc2c(N3CCC(NC(=O)C4CC4c4ccccc4)CC3)ncnc12]

N-(1-(7-Methylthieno[3,2-d]pyrimidin-4-yl)piperidin-4-yl)-2-phenylcyclopropanecarboxamide The title compound was prepared using general procedure of 2,2-dimethyl-N-(1-(7-methylthieno[3,2-d]pyrimidin-4-yl)piperidin-4-yl)-3-phenylpropanamide (Example 3.75). $^1$HNMR (400 MHz, DMSO-$d_6$): δ=8.52 (s, 1H), 8.12 (d, J=7.2 Hz, 1H), 7.83 (s, 1H), 7.28-7.24 (m, 2H), 7.18-7.10 (m, 3H), 4.57-4.53 (m, 2H), 3.98-3.97 (m, 1H), 3.41-3.38 (m, 2H), 3.34 (s, 3H), 2.25-2.24 (m, 1H), 1.92-1.90 (m, 2H), 1.83-1.81 (m, 1H), 1.45-1.35 (m, 3H), 1.24-1.19 (m, 1H). MS: m/z 393.0 ($M+H^+$).

Example 3.80

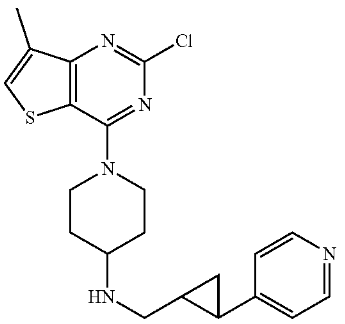 [SMILES: Cc1csc2c(N3CCC(NCC4CC4c4ccncc4)CC3)nc(Cl)nc12]

1-(2-Chloro-7-methylthieno[3,2-d]pyrimidin-4-yl)-N-((2-(pyridin-4-yl)cyclopropyl)methyl)piperidin-4-amine The title compound was prepared using general procedure of 1-(2-chloro-7-methylthieno[3,2-d]pyrimidin-4-yl)-N-(2,2-dimethyl-3-phenylpropyl)piperidin-4-amine (Example 3.74). $^1$HNMR (400 MHz, DMSO-$d_6$): δ=7.91 (s, 1H), 7.24-7.21 (m, 2H), 7.12-7.11 (m, 1H), 7.09-7.05 (m, 2H), 4.46-4.43 (m, 2H), 3.33 (overlap, 2H), 2.85-2.81 (m, 1H), 2.67-2.63 (m, 1H), 2.60-2.56 (m, 1H), 2.29 (s, 3H), 1.98-1.95 (m, 2H), 1.78-1.73 (m, 1H), 1.36-1.31 (m, 2H), 1.23-1.16 (m, 1H), 0.87-0.83 (m, 2H). MS: m/z 412.9 ($M+H^+$).

Example 3.81

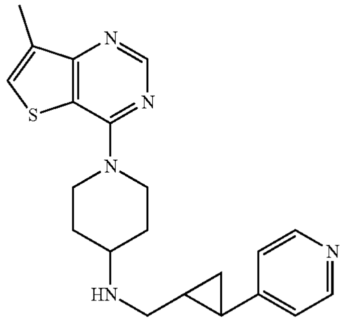 [SMILES: Cc1csc2c(N3CCC(NCC4CC4c4ccncc4)CC3)ncnc12]

1-(7-Methylthieno[3,2-d]pyrimidin-4-yl)-N-((2-(pyridin-4-yl)cyclopropyl)methyl)piperidin-4-amine The title compound was prepared using general procedure of 2,2-dimethyl-N-(1-(7-methylthieno[3,2-d]pyrimidin-4-yl)piperidin-4-yl)-3-phenylpropanamide (Example 3.75). $^1$HNMR (400 MHz, DMSO-$d_6$): δ=8.50 (s, 1H), 7.81 (s, 1H), 7.25-7.21 (m, 2H), 7.1-7.05 (m, 3H), 4.56-4.53 (m, 2H), 3.33-3.27 (m, 2H), 2.83-2.78 (m, 1H), 2.66-2.54 (m, 2H), 2.34 (s, 3H), 1.96-1.93 (m, 2H), 1.77-1.73 (m, 1H), 1.32-1.1.17 (m, 3H), 0.87-0.83 (m, 2H). MS: m/z 379.0 ($M+H^+$).

Example 3.82

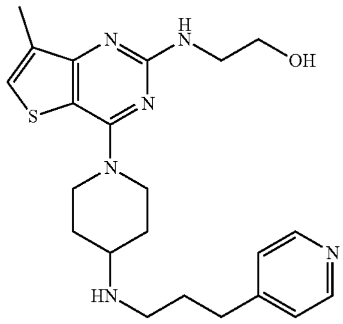 [SMILES: Cc1csc2c(N3CCC(NCCCc4ccncc4)CC3)nc(NCCO)nc12]

2-((7-Methyl-4-(4-((3-(pyridin-4-yl)propyl)amino)piperidin-1-yl)thieno[3,2-d]pyrimidin-2-yl)amino)ethanol The title compound was prepared using general procedure of 1-(2-methoxy-7-methylthieno[3,2-d]pyrimidin-4-yl)-N-

(3-(pyridin-4-yl)propyl)piperidin-4-amine (Example 3.66). $^1$HNMR (400 MHz, $CD_3OD$): δ=8.31 (d, J=8.0 Hz, 2H), 7.29 (s, 1H), 7.20 (d, J=8.0 Hz, 2H), 4.66 (d, J=16.0 Hz, 2H), 3.65-3.62 (m, 2H), 3.45-3.42 (m, 2H), 3.00 (t, J=24.0 Hz, 2H), 2.83-2.74 (m, 1H), 2.64-2.60 (m, 4H), 2.15 (s, 3H), 1.94 (d, J=4.0 Hz, 2H), 1.81-1.75 (m, 2H), 1.34-1.25 (m, 2H). MS: m/z 427.2 ($M+H^+$).

Example 3.83

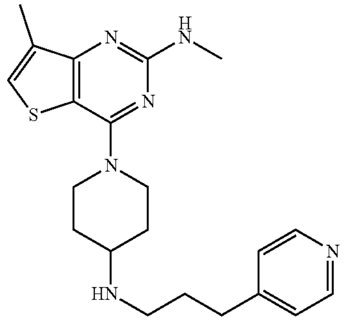 [SMILES: CNc1nc(N2CCC(NCCCc3ccncc3)CC2)c2scc(C)c2n1]

N,7-Dimethyl-4-(4-((3-(pyridin-4-yl)propyl)amino) piperidin-1-yl)thieno[3,2-d]pyrimidin-2-amine The title compound was prepared using general procedure of 1-(2-methoxy-7-methylthieno[3,2-d]pyrimidin-4-yl)-N-(3-(pyridin-4-yl)propyl)piperidin-4-amine (Example 3.66). $^1$HNMR (400 MHz, $CD_3OD$): δ=8.43 (d, J=4.0 Hz, 2H), 7.40 (s, 1H), 7.33 (d, J=8.0 Hz, 2H), 4.81 (d, J=12.0 Hz, 2H), 3.12 (t, J=24.0 Hz, 2H), 2.97 (s, 3H), 2.84-2.83 (m, 1H), 2.76-2.69 (m, 4H), 2.28 (s, 3H), 2.04 (d, J=12.0 Hz, 2H), 1.90-1.87 (m, 2H), 1.42-1.39 (m, 2H). MS: m/z 397.1 ($M+H^+$).

Example 3.84

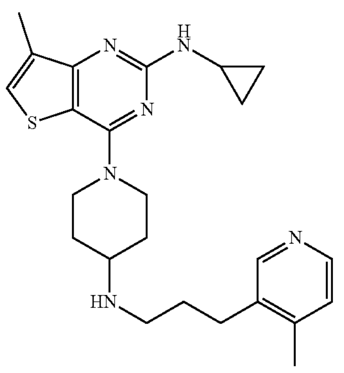 [SMILES: Cc1ccncc1CCCNC1CCN(c2nc(NC3CC3)nc3c(C)csc23)CC1]

N-Cyclopropyl-7-methyl-4-(4-((3-(4-methylpyridin-3-yl)propyl)amino)piperidin-1-yl)thieno[3,2-d]pyrimidin-2-amine The title compound was prepared using general procedure of N,7-dimethyl-4-(4-((3-(4-methylpyridin-3-yl)propyl) amino)piperidin-1-yl)thieno[3,2-d]pyrimidin-2-amine (Example 3.69). $^1$HNMR (400 MHz, $CD_3OD$) δ 8.56 (s, 1H), 8.49 (d, J=5.9 Hz, 1H), 7.80 (d, J=6.0 Hz, 1H), 7.74 (s, 1H), 4.91 (d, J=40.0 Hz, 2H), 3.57-3.49 (m, 1H), 3.37 (d, J=27.2 Hz, 2H), 3.25 (s, 1H), 3.19-3.13 (m, 2H), 2.89 (dd, J=16.5, 8.7 Hz, 2H), 2.79 (dt, J=7.0, 3.5 Hz, 1H), 2.56 (s, 3H), 2.29 (d, J=12.8 Hz, 5H), 1.99 (dt, J=15.9, 8.1 Hz, 2H), 1.71 (ddd, J=24.3, 12.2, 3.8 Hz, 2H), 0.80 (q, J=6.6 Hz, 2H), 0.61-0.55 (m, 2H). MS: m/z 437.2 ($M+H^+$).

Example 3.85

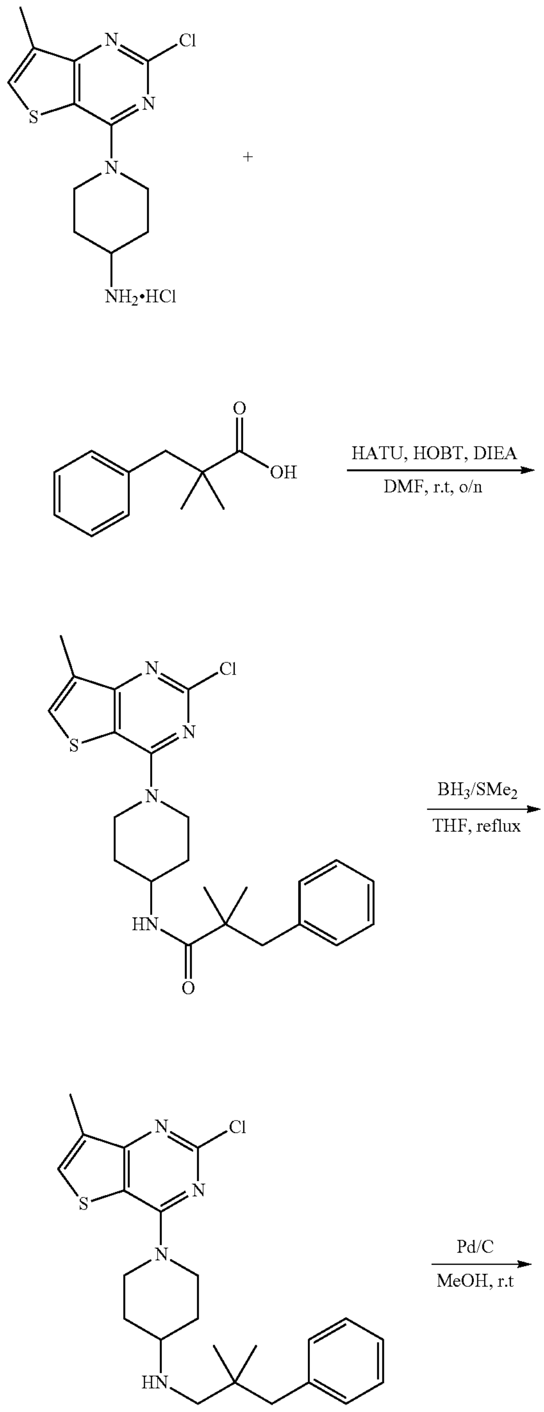

-continued

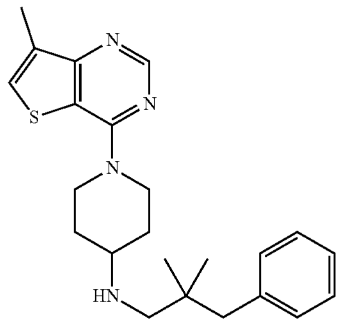

N-(2,2-Dimethyl-3-phenylpropyl)-1-(7-methylthieno[3,2-d]pyrimidin-4-yl)piperidin-4-amine The title compound was prepared using general procedure of 2,2-dimethyl-N-(1-(7-methylthieno[3,2-d]pyrimidin-4-yl)piperidin-4-yl)-3-phenylpropanamide (Example 3.75). $^1$HNMR (400 MHz, $CD_3OD$): δ=8.38 (s, 1H), 7.55 (d, J=1.1 Hz, 1H), 7.16 (t, J=7.2 Hz, 2H), 7.08 (dt, J=8.2, 6.4 Hz, 3H), 4.77 (d, J=3.1 Hz, 2H), 3.19-3.12 (m, 2H), 2.90 (ddd, J=14.8, 10.7, 3.9 Hz, 1H), 2.51 (s, 4H), 2.30 (d, J=1.0 Hz, 3H), 2.03 (d, J=10.3 Hz, 2H), 1.47-1.38 (m, 2H), 0.83 (s, 6H). MS: m/z 395.0 ($M+H^+$).

Example 3.87 and Example 3.86

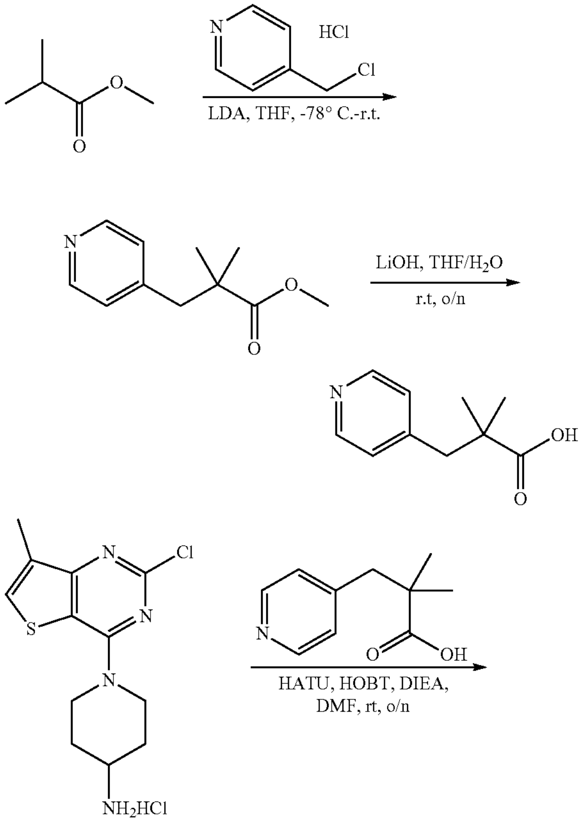

-continued

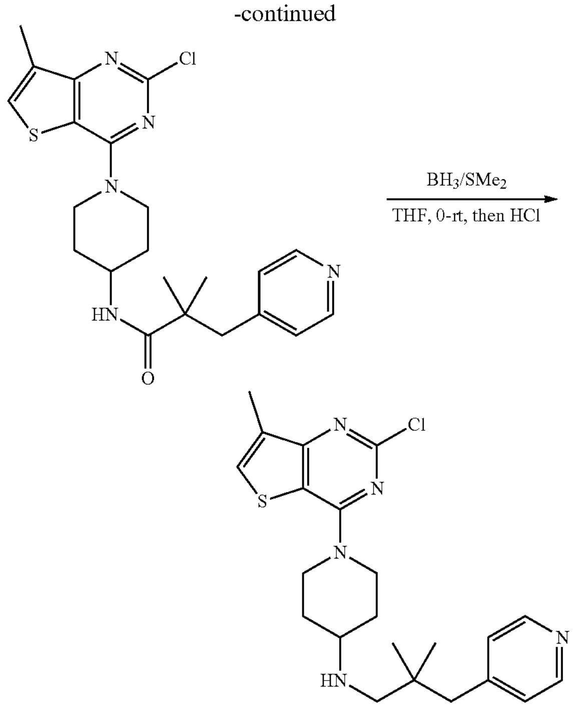

N-(1-(2-Chloro-7-methylthieno[3,2-d]pyrimidin-4-yl)piperidin-4-yl)-2,2-dimethyl-3-(pyridin-4-yl)propanamide (Example 3.86)

1-(2-Chloro-7-methylthieno[3,2-d]pyrimidin-4-yl)-N-(2,2-dimethyl-3-(pyridin-4-yl)propyl)piperidin-4-amine (Example 3.87)

Step 1: A solution of methyl isobutyrate (150 mg, 1.47 mmol) was cooled to −72° C. After 15 mins, 4-(chloromethyl)pyridine hydrochloride (361 mg, 2.21 mmol) was added very carefully. The reaction was keeping −72° C. for 1.5 hrs and slowly warmed to room temperature. The reaction was monitored by LC-MS and TLC. The reaction mixture was quenched with saturated $NH_4C_1$, extracted with EA (15 mL×3). The combined organic layers were dried over $Na_2SO_4$ and concentrated. The crude mixture was purified by silica gel column (PE/EA=5:1) to afford methyl 2,2-dimethyl-3-(pyridin-4-yl)propanoate (207 mg, yield: 73%) as brown oil.

Step 2: A solution of methyl 2,2-dimethyl-3-(pyridin-4-yl)propanoate (207 mg) and LiOH in THF/$H_2O$ (1/1, 5 mL) was stirred at room temperature overnight. The reaction was monitored by LC-MS and TLC. The reaction was poured into water (20 mL) and extracted with EA (15 mL×3). The combined EA phases were dried over $Na_2SO_4$ and concentrated to afford 2,2-dimethyl-3-(pyridin-4-yl)propanoic acid (41 mg, yield: 22%) as yellow oil.

Step 3: To a solution of 1-(2-chloro-7-methylthieno[3,2-d]pyrimidin-4-yl)piperidin-4-amine (200 mg, 0.7 mmol) in DMF (6 mL) was added 2,2-dimethyl-3-(pyridin-4-yl)propanoic acid (163 mg, 0.85 mmol). Then, HATU (798 mg), HOBT (283 mg) and DIEA (1.2 mL) were added into the reaction mixture. The resulting mixture was stirred at room temperature overnight. The reaction was monitored by LC-MS and TLC. The reaction was poured into water (20 mL) and extracted with EA (15 mL×3). The combined EA phases were dried over $Na_2SO_4$ and concentrated. The desired product was purified by prep-HPLC with $NH_4HCO_3$ as additive to afford N-(1-(2-chloro-7-methylthieno[3,2-d]pyrimidin-4-yl)piperidin-4-yl)-2,2-dimethyl-3-(pyridin-4-yl) propanamide (14.8 mg, yield: 4.7%) as a white solid. $^1$HNMR (400 MHz, $CD_3OD$): δ=8.43 (d, J=5.2 Hz, 2H), 7.68 (d, J=1.0 Hz, 1H), 7.25 (d, J=5.9 Hz, 2H), 4.81 (d, J=13.5 Hz, 2H), 4.11 (td, J=11.2, 5.7 Hz, 1H), 3.29 (t, J=13.0 Hz, 2H), 2.90 (s, 2H), 2.37 (s, 3H), 1.94 (d, J=10.1 Hz, 2H), 1.60-1.50 (m, 2H), 1.20 (d, J=10.9 Hz, 6H). MS: m/z 444.0 ($M+H^+$).

Step 4: To a solution of N-(1-(2-chloro-7-methylthieno [3,2-d]pyrimidin-4-yl)piperidin-4-yl)-2,2-dimethyl-3-(pyridin-4-yl)propanamide (100 mg, 0.22 mmol) in dry of THF (5 mL) was added $BH_3/SMe_2$ (0.7 mL) under $N_2$ atmosphere (balloon). Then, refluxed the reaction mixture overnight. Cooling the reaction mixture to 0° C., 2 mL of MeOH was added to the reaction very slowly and carefully. Then, 0.5 mL of conc.HCl was added to the reaction and reflux for 1 hr. The reaction was monitored by LC-MS and TLC. The reaction was evaporated in vacuo and prep-TLC (TFA) as additive to afford 1-(2-chloro-7-methylthieno[3,2-d]pyrimidin-4-yl)-N-(2,2-dimethyl-3-(pyridin-4-yl)propyl)piperidin-4-amine (3.5 mg, yield: 3.7%) as yellow oil. $^1$HNMR (400 MHz, $CD_3OD$): δ=8.67 (d, J=5.8 Hz, 2H), 7.85 (d, J=6.2 Hz, 2H), 7.64 (s, 1H), 4.89 (d, J=13.8 Hz, 2H), 3.56-3.49 (m, 1H), 3.17 (d, J=12.9 Hz, 2H), 3.04 (s, 2H), 2.96 (s, 2H), 2.29 (d, J=13.1 Hz, 5H), 1.71 (dt, J=12.4, 8.6 Hz, 2H), 0.99 (s, 6H). MS: m/z 430.0 ($M+H^+$).

Example 3.88

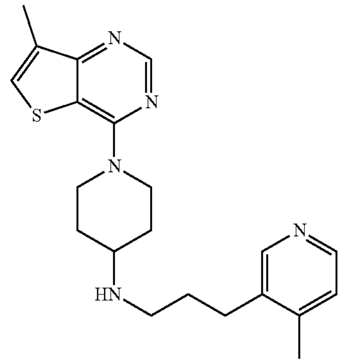 [SMILES: Cc1ccncc1CCCNC1CCN(c2ncnc3c(C)csc23)CC1]

N-[3-(4-Methylpyridin-3-yl)propyl]-1-(7-methylthieno[3,2-d]pyrimidin-4-yl)-4-piperidylamine Step 1: To a mixture of 4-chloro-7-methylthieno[3,2-d] pyrimidine (1.00 g) in ethanol (27 mL) was added 4-(tert-butoxycarbonylamino)piperidine (1.19 g) and N,N-diisopropylethylamine (2.83 mL). The reaction mixture was allowed to stir at room temperature for 22.5 hours. After the reaction, the reaction mixture was evaporated under reduced pressure. The residue was diluted with ethyl acetate, washed with water and brine, and then dried over anhydrous sodium sulfate. After the resulting solid was filtered off, the filtrate was concentrated under reduced pressure to N-(tert-butoxycarbonyl)-1-(7-methylthieno[3,2-d]pyrimidin-4-yl)-4-piperidylamine (1.88 g) as a white solid.

Step 2: To a mixture of N-(tert-butoxycarbonyl)-1-(7-methylthieno[3,2-d]pyrimidin-4-yl)-4-piperidylamine obtained above in dichloromethane (27 mL) was added trifluoroacetic acid (3 mL), then the mixture was stirred at room temperature for 10 hours. After the reaction, the reaction mixture was evaporated under reduced pressure. The residue was purified by automated flash chromatography using 0-7% methanol in dichloromethane as eluent, to give 1-(7-methylthieno[3,2-d]pyrimidin-4-yl)-4-piperidylamine as a white solid.

Step 3: To a mixture of 1-(7-methylthieno[3,2-d]pyrimidin-4-yl)-4-piperidylamine (150 mg) obtained above and dichloromethane (3 mL) was added 3-(4-methylpyridin-3-yl)propanal (100 mg) and sodium triacetoxyborohydride (192 mg), then the mixture was stirred at room temperature for 5 hours. The reaction mixture was applied directly onto a silica gel column, then eluted with 0-7% methanol in dichloromethane to give the title compound (140 mg, yield 61%) as a yellow oil. 1H-NMR (400 MHz, $CDCl_3$) δ: 8.63 (1H, s), 8.33 (1H, s), 8.31 (1H, d, J=5.1 Hz), 7.27 (1H, s), 7.05 (1H, d, J=5.1 Hz), 4.74-4.69 (2H, m), 3.30-3.23 (2H, m), 2.81-2.70 (6H, m), 2.45 (3H, s), 2.30 (3H, s), 2.05-2.01 (2H, m), 1.80-1.73 (2H, m), 1.47-1.38 (2H, m).

Example 3.89

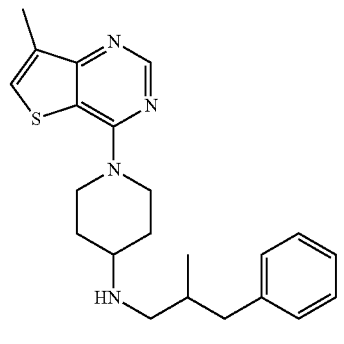 [SMILES: Cc1csc2c(N3CCC(NCC(C)Cc4ccccc4)CC3)ncnc12]

N-(2-Methyl-3-phenylpropyl)-1-(7-methylthieno[3,2-d]pyrimidin-4-yl)-4-piperidylamine The title compound was prepared according to the general procedure of Example 3.88 Step 3 using 2-methyl-3-phenyl-1-propanal. $^1$H-NMR ($CDCl_3$) δ: 8.63 (1H, s), 7.35-7.15 (6H, m), 4.68-4.65 (2H, m), 3.30-3.23 (2H, m), 2.76-2.40 (8H, m), 2.00-1.89 (3H, m), 1.42-1.39 (2H, m), 0.91 (3H, d, J=6.7 Hz), 1.05-0.85 (1H, br s).

Example 3.90

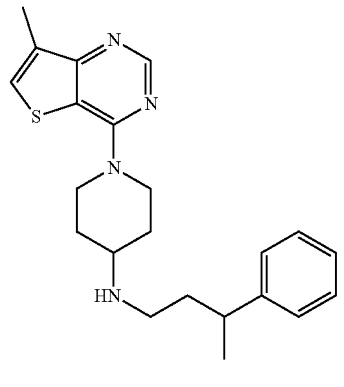 [SMILES: Cc1csc2c(N3CCC(NCCC(C)c4ccccc4)CC3)ncnc12]

N-[1-(7-Methylthieno[3,2-d]pyrimidin-4-yl)-4-piperidyl]-3-phenylbutylamine

The title compound was prepared according to the general procedure of Example 3.88 Step 3using 3-phenylbutyraldehyde. $^1$H-NMR ($CDCl_3$) δ: 8.62 (1H, s), 7.34 (1H, d, J=1.2 Hz), 7.29 (2H, tt, J=7.4, 2.7 Hz), 7.21-7.17 (3H, m), 4.69-4.64 (2H, m), 3.25-3.17 (2H, m), 2.81-2.65 (2H, m), 2.62-2.44 (5H, m), 2.05-1.93 (2H, m), 1.77 (2H, tt, J=11.0, 3.6 Hz), 1.58-1.50 (1H, br s), 1.41-1.30 (2H, m), 1.27-1.19 (3H, m).

Example 3.91

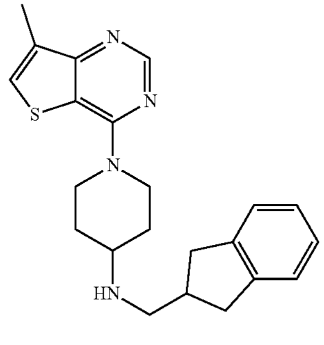 [SMILES: Cc1csc2c(N3CCC(NCC4Cc5ccccc5C4)CC3)ncnc12]

N-[(2,3-Dihydro-1H-inden-2-yl)methyl]-1-(7-methylthieno[3,2-d]pyrimidin-4-yl)-4-piperidylamine The title compound was prepared according to the general procedure of Example 3.88 Step 3 using 2,3-dihydro-1H-indene-2-carbaldehyde. $^1$H-NMR (400 MHz, $CDCl_3$) δ: 8.63 (1H, s), 7.35 (1H, d, J=1.2 Hz), 7.20-7.17 (2H, m), 7.15-7.12 (2H, m), 4.70 (2H, dt, J=13.6, 3.3 Hz), 3.29 (2H, dt, J=17.2, 6.4 Hz), 3.09 (2H, dd, J=14.9, 7.4 Hz), 2.86-2.59 (6H, m), 2.45 (3H, s), 2.06-2.02 (2H, m), 1.46 (2H, dt, J=19.2, 8.0 Hz), 0.95-1.00 (1H, br s).

Example 3.92

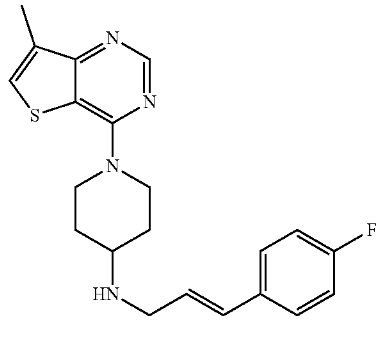 [SMILES: Cc1csc2c(N3CCC(NC/C=C/c4ccc(F)cc4)CC3)ncnc12]

N-[(2E)-3-(4-Fluorophenyl)-2-propenyl]-1-(7-methylthieno[3,2-d]pyrimidin-4-yl)-4-piperidylamine The title compound was prepared according to the general procedure of Example 3.88 Step 3 using 4-fluorocinnamaldehyde. $^1$H-NMR (400 MHz, $CDCl_3$) δ: 8.63 (1H, s), 7.31 (3H, m), 7.00 (2H, dt, J=10.8, 3.8 Hz), 6.51 (1H, d, J=15.7 Hz), 6.22 (1H, dt, J=15.8, 6.4 Hz), 4.75-4.71 (2H, m), 3.48 (2H, dd, J=6.3, 1.2 Hz), 3.31-3.24 (2H, m), 2.93-2.88 (1H, m), 2.45 (3H, d, J=0.8 Hz), 2.07 (2H, td, J=9.2, 4.8 Hz), 1.52-1.42 (3H, m).

Example 3.93

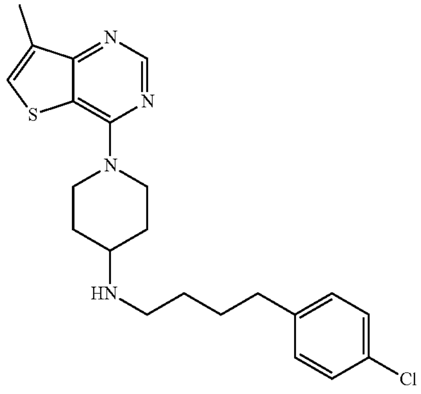 [SMILES: Cc1csc2c(N3CCC(NCCCCc4ccc(Cl)cc4)CC3)ncnc12]

N-[4-(4-Chlorophenyl)butyl]-1-(7-methylthieno[3,2-d]pyrimidin-4-yl)-4-piperidylamine The title compound was prepared according to the general procedure of Example 3.88 Step 3 using 4-(4-chlorophenyl) butanal. $^1$H-NMR (400 MHz, $CDCl_3$) δ: 8.63 (1H, s), 7.35 (1H, d, J=1.2 Hz), 7.23 (2H, dt, J=8.9, 2.2 Hz), 7.09 (2H, dt, J=8.7, 2.2 Hz), 4.73-4.68 (2H, m), 3.28-3.21 (2H, m), 2.82-2.75 (1H, m), 2.63-2.57 (4H, m), 2.44 (3H, d, J=1.2 Hz), 2.04-2.00 (2H, m), 1.68-1.36 (7H, m).

Example 3.94

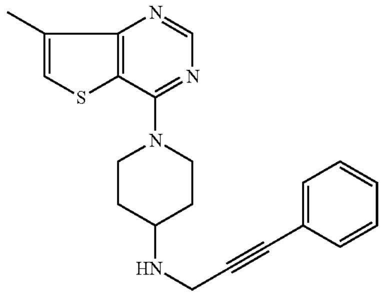 [SMILES: Cc1csc2c(N3CCC(NCC#Cc4ccccc4)CC3)ncnc12]

N-[1-(7-Methylthieno[3,2-d]pyrimidin-4-yl)-4-piperidyl]-3-phenyl-2-propynylamine The title compound was prepared according to the general procedure of Example 3.88 Step 3 using phenylpropargylaldehyde. $^1$H-NMR ($CDCl_3$) δ: 8.61 (1H, s), 7.43-7.37 (2H, m), 7.33 (1H, d, J=1.2 Hz), 7.31-7.26 (3H, m), 4.68 (2H, dt, J=13.6, 3.3 Hz), 3.70 (2H, s), 3.38-3.29 (2H, m), 3.16-3.08 (1H, m), 2.43 (3H, d, J=1.2 Hz), 2.09-1.99 (2H, m), 1.54-1.42 (2H, m), 1.28 (1H, br s).

Example 3.95

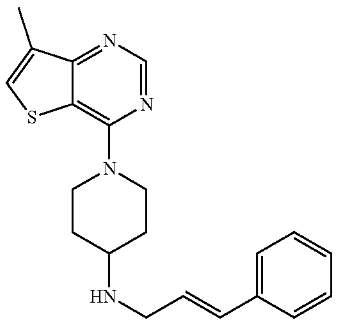 [SMILES: Cc1csc2c(N3CCC(NC/C=C/c4ccccc4)CC3)ncnc12]

N-[1-(7-Methylthieno[3,2-d]pyrimidin-4-yl)-4-piperidyl]-(2E)-3-phenyl-2-propenylamine The title compound was prepared according to the general procedure of Example 3.88 Step 3 using trans-cinnamaldehyde. $^1$H-NMR ($CDCl_3$) δ: 8.64 (1H, s), 7.40-7.35 (3H, m), 7.34-7.29 (2H, m), 7.27-7.21 (1H, m), 6.55 (1H, d, J=15.7 Hz), 6.31 (1H, dt, J=15.9, 6.4 Hz), 4.74 (2H, dt, J=13.4, 3.1 Hz), 3.50 (2H, dd, J=6.4, 1.6 Hz), 3.32-3.24 (2H, m), 2.97-2.87 (1H, m), 2.45 (3H, d, J=1.2 Hz), 2.12-2.05 (2H, m), 1.53-1.41 (2H, m), 1.06 (1H, br s).

Example 3.96

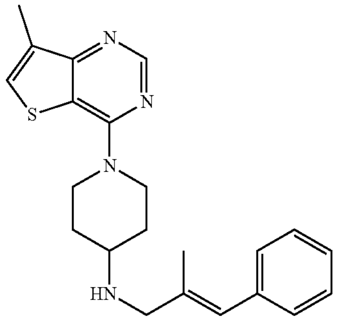 [SMILES: C/C(=C\c1ccccc1)CNC1CCN(c2ncnc3c(C)csc23)CC1]

N-[(2E)-2-Methyl-3-phenyl-2-propenyl]-1-(7-methylthieno[3,2-d]pyrimidin-4-yl)-4-piperidylamine The title compound was prepared according to the general procedure of Example 3.88 Step 3 using (2E)-2-methyl-3-phenylprop-2-enal. $^1$H-NMR ($CDCl_3$) δ: 8.61 (1H, s), 7.34-7.28 (3H, m), 7.26-7.22 (2H, m), 7.21-7.15 (1H, m), 6.44 (1H, s), 4.68 (2H, dt, J=13.4, 3.1 Hz), 3.37 (2H, s), 3.33-3.24 (2H, m), 2.90-2.81 (1H, m), 2.42 (3H, d, J=1.2 Hz), 2.09-2.01 (2H, m), 1.89 (3H, d, J=1.6 Hz), 1.52-1.41 (2H, m), 1.08 (1H, br s).

Example 3.97

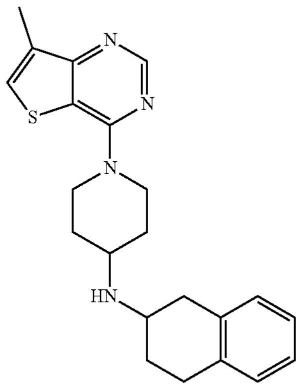 [SMILES: Cc1csc2c(N3CCC(NC4CCc5ccccc5C4)CC3)ncnc12]

N-[1-(7-Methylthieno[3,2-d]pyrimidin-4-yl)-4-piperidyl]-1,2,3,4-tetrahydro-2-naphthylamine The title compound was prepared according to the general procedure of Example 3.88 Step 3 using 3,4-dihydronaphthalen-2(1H)-one in 1,2-dichloroethane. $^1$H-NMR ($CDCl_3$) δ: 8.64 (1H, s), 7.36 (1H, d, J=1.2 Hz), 7.14-7.05 (4H, m), 4.80-4.71 (2H, m), 3.33-3.23 (2H, m), 3.19-2.99 (3H, m), 2.96-2.80 (2H, m), 2.59 (1H, dd, J=16.0, 9.4 Hz), 2.45 (3H, d, J=1.2 Hz), 2.12-2.01 (3H, m), 1.67-1.55 (1H, m), 1.51-1.39 (2H, m), 0.95 (1H, br s).

Example 3.98

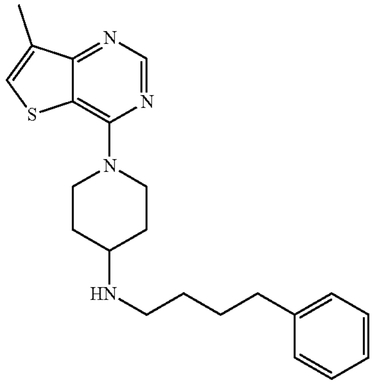 [SMILES: Cc1csc2c(N3CCC(NCCCCc4ccccc4)CC3)ncnc12]

N-[1-(7-Methylthieno[3,2-d]pyrimidin-4-yl)-4-piperidyl]-4-phenylbutylamine

The title compound was prepared according to the general procedure of Example 3.88 Step 3 using 4-phenylbutanal. $^1$H-NMR ($CDCl_3$) δ: 8.63 (1H, s), 7.35 (1H, d, J=1.2 Hz), 7.30-7.25 (2H, m), 7.20-7.15 (3H, m), 4.71 (2H, dt, J=13.6, 2.9 Hz), 3.30-3.21 (2H, m), 2.83-2.75 (1H, m), 2.70-2.60 (4H, m), 2.45 (3H, d, J=1.2 Hz), 2.06-1.98 (2H, m), 1.71-1.62 (2H, m), 1.57-1.49 (2H, m), 1.47-1.36 (2H, m), 0.88 (1H, br s).

Example 3.99

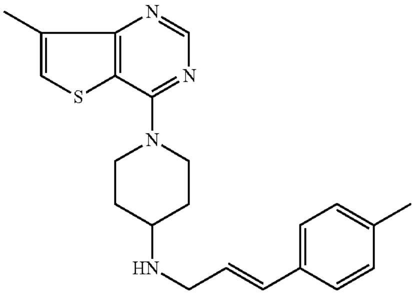

N-[(2E)-3-(4-Methylphenyl)-2-propenyl]-1-(7-methylthieno[3,2-d]pyrimidin-4-yl)-4-piperidylamine The title compound was prepared according to the general procedure of Example 3.88 Step 3 using (2E)-3-(4-methylphenyl)prop-2-enal. $^1$H-NMR ($CDCl_3$) δ: 8.64 (1H, s), 7.36 (1H, d, J=1.2 Hz), 7.28 (2H, d, J=8.2 Hz), 7.12 (2H, d, J=8.2 Hz), 6.51 (1H, d, J=15.7 Hz), 6.25 (1H, dt, J=15.7, 6.4 Hz), 4.74 (2H, dt, J=13.7, 3.0 Hz), 3.48 (2H, dd, J=6.4, 1.2 Hz), 3.31-3.23 (2H, m), 2.95-2.87 (1H, m), 2.45 (3H, d, J=1.2 Hz), 2.33 (3H, s), 2.12-2.04 (2H, m), 1.53-1.41 (2H, m), 1.12 (1H, br s).

Example 3.100

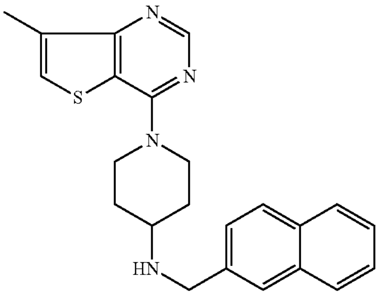 [SMILES: Cc1csc2c(N3CCC(NCc4ccc5ccccc5c4)CC3)ncnc12]

N-[1-(7-Methylthieno[3,2-d]pyrimidin-4-yl)-4-piperidyl]-2-naphthylmethylamine

The title compound was prepared according to the general procedure of Example 3.88 Step 3 using naphthalene-2-carbaldehyde. $^1$H-NMR ($CDCl_3$) δ: 8.64 (1H, s), 7.86-7.79 (3H, m), 7.77 (1H, br s), 7.50-7.43 (3H, m), 7.35 (1H, d, J=1.2 Hz), 4.71 (2H, dt, J=13.7, 3.2 Hz), 4.03 (2H, s), 3.33-3.25 (2H, m), 2.97-2.89 (1H, m), 2.45 (3H, d, J=1.2 Hz), 2.13-2.05 (2H, m), 1.59-1.47 (2H, m), 1.37 (1H, br s).

Example 3.101

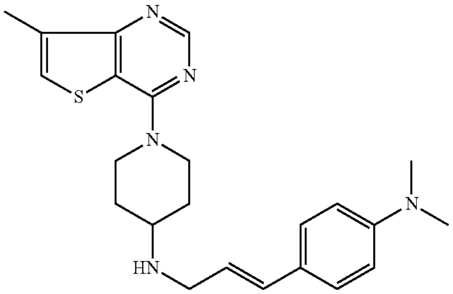

N-[(2E)-3-(4-Dimethylaminophenyl)-2-propenyl]-1-(7-methylthieno[3,2-d]pyrimidin-4-yl)-4-piperidylamine The title compound was prepared according to the general procedure of Example 3.88 Step 3 using 4-dimethylaminocinnamaldehyde. $^1$H-NMR ($CDCl_3$) δ: 8.63 (1H, s), 7.35 (1H, d, J=1.2 Hz), 7.30-7.25 (2H, m), 6.70-6.65 (2H, m), 6.45 (1H, d, J=15.7 Hz), 6.09 (1H, dt, J=15.7, 6.6 Hz), 4.73 (2H, dt, J=13.6, 2.9 Hz), 3.45 (2H, dd, J=6.6, 1.4 Hz), 3.31-3.22 (2H, m), 2.97-2.87 (1H, m), 2.95 (6H, s), 2.45 (3H, d, J=1.2 Hz), 2.12-2.04 (2H, m), 1.52-1.40 (2H, m), 1.08 (1H, br s).

Example 3.102

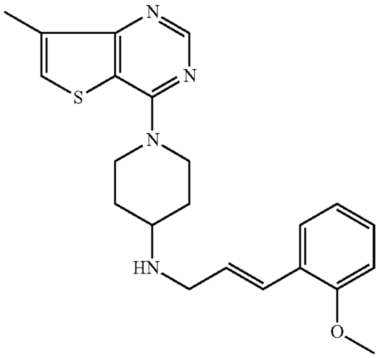

N-[(2E)-3-(2-Methoxyphenyl)-2-propenyl]-1-(7-methylthieno[3,2-d]pyrimidin-4-yl)-4-piperidylamine The title compound was prepared according to the general procedure of Example 3.88 Step 3 using (2E)-3-(2-methoxyphenyl)prop-2-enal. $^1$H-NMR ($CDCl_3$) δ: 8.64 (1H, s), 7.44 (1H, dd, J=7.6, 1.8 Hz), 7.36 (1H, d, J=1.2 Hz), 7.25-7.19 (1H, m), 6.95-6.84 (3H, m), 6.31 (1H, dt, J=15.9, 6.4 Hz), 4.74 (2H, dt, J=13.6, 3.1 Hz), 3.85 (3H, s), 3.50 (2H, dd, J=6.4, 1.4 Hz), 3.33-3.23 (2H, m), 2.96-2.88 (1H, m), 2.45 (3H, d, J=1.2 Hz), 2.13-2.05 (2H, m), 1.53-1.41 (2H, m), 1.20 (1H, br s).

Example 3.103

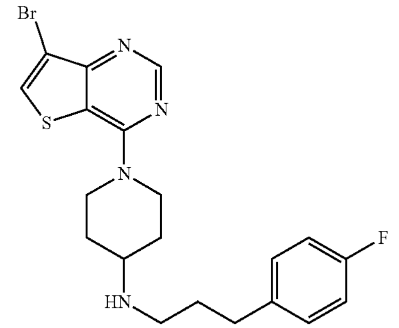 [SMILES: Fc1ccc(CCCNC2CCN(c3ncnc4c(Br)csc34)CC2)cc1]

N-[1-(7-Bromothieno[3,2-d]pyrimidin-4-yl)-4-piperidyl]-3-(4-fluorophenyl)propylamine Step 1: N-(tert-Butoxycarbonyl)-1-(7-bromothieno[3,2-d]pyrimidin-4-yl)-4-piperidylamine was prepared according to the general procedure of Example 3.88 Step 1 using 7-bromo-4-chlorothieno[3,2-d]pyrimidine in N,N-dimethylformamide Step 2: 1-(7-Bromothieno[3,2-d]pyrimidin-4-yl)-4-piperidylamine was prepared according to the general procedure of Example 3.88 Step 2 using N-(tert-butoxycarbonyl)-1-(7-bromothieno[3,2-d]pyrimidin-4-yl)-4-piperidylamine obtained above.

Step 3: The title compound was prepared according to the general procedure of Example 3.88 Step 3 using 1-(7-bromothieno[3,2-d]pyrimidin-4-yl)-4-piperidylamine obtained above and 3-(4-fluorophenyl)propanal. $^1$H-NMR ($CDCl_3$) δ: 8.68 (1H, s), 7.74 (1H, s), 7.27-6.94 (4H, m), 4.67 (2H, dt, J=13.7, 3.2 Hz), 3.35-3.28 (2H, m), 2.84-2.79 (1H, m), 2.66 (4H, dt, J=13.3, 5.2 Hz), 2.05-2.00 (2H, m), 1.83-1.76 (2H, m), 1.43 (2H, tt, J=15.3, 5.5 Hz), 1.05-0.85 (1H, br s).

Example 3.104

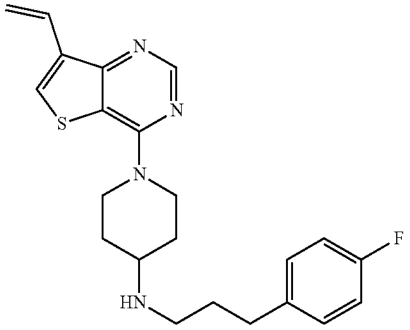 [SMILES: C=Cc1csc2c(N3CCC(NCCCc4ccc(F)cc4)CC3)ncnc12]

N-[3-(4-Fluorophenyl)propyl]-1-(7-vinylthieno[3,2-d]pyrimidin-4-yl)-4-piperidylamine Step 1: A mixture of N-(tert-butoxycarbonyl)-1-(7-bromothieno[3,2-d]pyrimidin-4-yl)-4-piperidylamine (500 mg, 1.21 mmol) obtained in Example 3.103 Step 1, 4,4,5,5-tetramethyl-2-vinyl-1,3,2-dioxaborolane (0.414 mL, 2.42 mmol), tetrakis(triphenylphosphine)palladium(0) (140 mg, 0.121 mmol) in 2 M sodium carbonate aqueous solution (3 mL) and 1,2-dimethoxyethane (6 mL) was refluxed for 6 hours under a nitrogen atmosphere, using a balloon. The resulting mixture was diluted with ethyl acetate, washed with water and brine, and then dried over anhydrous sodium sulfate. After the resulting solid was filtered off, the filtrate was concentrated under reduced pressure. The residue was purified by automated flash chromatography using 0-100% ethyl acetate in hexane as eluent, to give N-(tert-butoxycarbonyl)-1-(7-vinylthieno[3,2-d]pyrimidin-4-yl)-4-piperidylamine as a colorless solid.

Step 2: 1-(7-Vinylthieno[3,2-d]pyrimidin-4-yl)-4-piperidylamine was prepared according to the general procedure of Example 3.88 Step 2 using N-(tert-butoxycarbonyl)-1-(7-vinylthieno[3,2-d]pyrimidin-4-yl)-4-piperidylamine obtained above.

Step 3: The title compound was prepared according to the general procedure of Example 3.88 Step 3 using 1-(7-vinylthieno[3,2-d]pyrimidin-4-yl)-4-piperidylamine and 3-(4-fluorophenyl)propanal obtained above. $^1$H-NMR ($CDCl_3$) δ: 8.60 (1H, s), 7.65 (1H, s), 7.12-6.91 (5H, m), 6.10 (1H, dd, J=18.0, 1.6 Hz), 5.41 (1H, dd, J=11.0, 1.6 Hz), 4.67 (2H, dt, J=13.4, 3.1 Hz), 3.28-3.21 (2H, m), 2.80-2.75 (1H, m), 2.66-2.60 (4H, m), 2.01-1.97 (2H, m), 1.80-1.73 (2H, m), 1.44-1.35 (2H, m), 1.05-0.85 (1H, br s).

Example 3.105

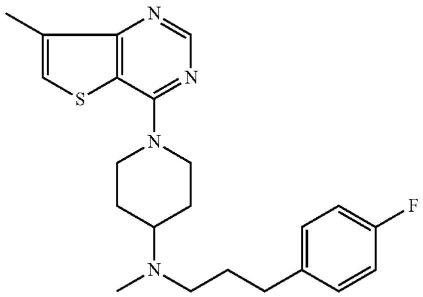 [SMILES: Cc1csc2c(N3CCC(N(C)CCCc4ccc(F)cc4)CC3)ncnc12]

N-[3-(4-Fluorophenyl)propyl]-N-methyl-1-(7-methylthieno[3,2-d]pyrimidin-4-yl)-4-piperidylamine Step 1: N-[3-(4-Fluorophenyl)propyl]-N-methyl-1-(tert-butoxycarbonyl)-4-piperidylamine was prepared according to the general procedure of Example 3.88 Step 3 using 1-tert-butoxycarbonyl-4-(methylamino)piperidine and 3-(4-fluorophenyl)propanal.

Step 2: N-[3-(4-Fluorophenyl)propyl]-N-methyl-4-piperidylamine was prepared according to the general procedure of Example 3.88 Step 2 using N-[3-(4-fluorophenyl)propyl]-N-methyl-1-(tert-butoxycarbonyl)-4-piperidylamine obtained above.

Step 3: The title compound was prepared according to the general procedure of Example 3.88 Step 1 using N-[3-(4-fluorophenyl)propyl]-N-methyl-4-piperidylamine obtained above. $^1$H-NMR (400 MHz, $CDCl_3$) δ: 8.64 (1H, s), 7.36 (1H, d, J=1.2 Hz), 7.16-6.92 (4H, m), 4.92-4.85 (2H, m), 3.11-3.04 (2H, m), 2.71 (1H, tt, J=11.3, 3.8 Hz), 2.60 (2H, t, J=7.7 Hz), 2.49-2.43 (5H, m), 2.25 (3H, s), 1.93-1.72 (4H, m), 1.64-1.52 (2H, m). MS: m/z 399 ($M+H^+$).

Example 3.106

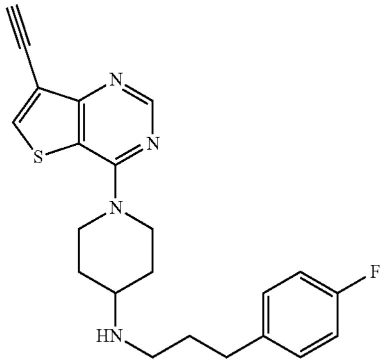 [SMILES: C#Cc1csc2c(N3CCC(NCCCc4ccc(F)cc4)CC3)ncnc12]

N-[1-(7-Ethynylthieno[3,2-d]pyrimidin-4-yl)-4-piperidyl]-3-(4-fluorophenyl)propylamine Step 1: A mixture of N-(tert-butoxycarbonyl)-1-(7-bromothieno[3,2-d]pyrimidin-4-yl)-4-piperidylamine (500 mg, 1.21 mmol) obtained in Example 3.103 Step 1, trimethylsilylacetylene (0.335 mL, 2.32 mmol), bis(triphenylphosphine)palladium(II) dichloride (212 mg, 0.302 mmol), copper(I) iodide (0.0922 mg, 0.484 mmol) and N,N-diisopropylethylamine (0.316 mL, 1.82 mmol) in acetonitrile (6 mL) was refluxed for 5 hours under a nitrogen atmosphere, using a balloon. The resulting mixture was diluted with ethyl acetate, washed with water and brine, then dried over anhydrous sodium sulfate. After the resulting solid was filtered off, the filtrate was concentrated under reduced pressure. The residue was purified by automated flash chromatography using 0-100% ethyl acetate in hexane as eluent, to give N-(tert-butoxycarbonyl)-1-[7-(2-trimethylsilylethynyl)thieno[3,2-d]pyrimidin-4-yl]-4-piperidylamine (331 mg, yield 64%) as a colorless solid.

Step 2: 1-[7-(2-Trimethylsilylethynyl)thieno[3,2-d]pyrimidin-4-yl]-4-piperidylamine was prepared according to the general procedure of Example 3.88 Step 2 using N-(tert-butoxycarbonyl)-1-[7-(2-trimethylsilylethynyl)thieno[3,2-d]pyrimidin-4-yl]-4-piperidylamine obtained above.

Step 3: The N-[3-(4-Fluorophenyl)propyl]-1-[7-(2-trimethylsilylethynyl)thieno[3,2-d]pyrimidin-4-yl]-4-piperidylamine was prepared according to the general procedure of Example 3.88 Step 3 using 1-[7-(2-trimethylsilylethynyl)thieno[3,2-d]pyrimidin-4-yl]-4-piperidylamine and 3-(4-fluorophenyl)propanal obtained above.

Step 4: To a solution of N-[3-(4-fluorophenyl)propyl]-1-[7-(2-trimethylsilylethynyl)thieno[3,2-d]pyrimidin-4-yl]-4-piperidylamine (263 mg, 0.564 mmol) obtained above in THF (2 mL) was added tetrabutylammonium fluoride (1 mol/L in tetrahydrofuran, 0.8 mL) at room temperature. The resulting mixture was stirred at room temperature for 1.5 hours and quenched by adding ethyl acetate and water. Organic layer was separated and washed with brine, then dried over anhydrous sodium sulfate. After the resulting solid was filtered off, the filtrate was concentrated under reduced pressure. The residue was purified by automated flash chromatography using 10% methanol in dichloromethane as eluent, to give the title compound (115 mg, yield 52%) as a light-brown solid. $^1$H-NMR (400 MHz, $CDCl_3$) δ: 8.68 (1H, s), 7.92 (1H, s), 7.17-6.93 (4H, m), 4.68 (2H, dt, J=13.7, 3.2 Hz), 3.41 (1H, s), 3.33-3.26 (2H, m), 2.87-2.80 (1H, m), 2.70-2.63 (4H, m), 2.08-1.99 (2H, m), 1.85-1.77 (2H, m), 1.60-1.30 (3H, br m).

Example 3.107

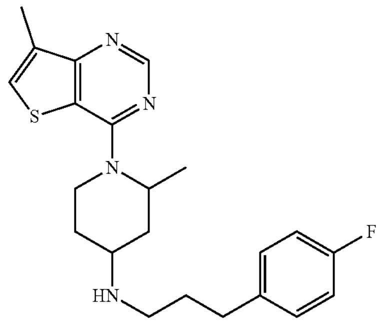 [SMILES: Cc1csc2c(N3CCC(NCCCc4ccc(F)cc4)CC3C)ncnc12]

N-[3-(4-Fluorophenyl)propyl]-2-methyl-1-(7-methylthieno[3,2-d]pyrimidin-4-yl)-4-piperidylamine Step 1: N-(tert-Butoxycarbonyl)-2-methyl-1-(7-methylthieno[3,2-d]pyrimidin-4-yl)-4-piperidylamine was prepared according to the general procedure of Example 3.88 Step 1 using 4-(tert-butoxycarbonylamino)-2-methylpiperidine.

Step 2: 2-Methyl-1-(7-methylthieno[3,2-d]pyrimidin-4-yl)-4-piperidylamine was prepared according to the general procedure of Example 3.88 Step 2 using N-(tert-butoxycarbonyl)-2-methyl-1-(7-methylthieno[3,2-d]pyrimidin-4-yl)-4-piperidylamine obtained above.

Step 3: The title compound was prepared according to the general procedure of Example 3.88 Step 3 using 2-methyl-1-(7-methylthieno[3,2-d]pyrimidin-4-yl)-4-piperidylamine obtained above and 3-(4-fluorophenyl)propanal as a mixture of isomers.

More polar isomer: $^1$H-NMR (400 MHz, $CDCl_3$) δ: 8.62 (1H, s), 7.34 (1H, t, J=1.2 Hz), 7.13 (2H, td, J=6.0, 2.5 Hz), 6.99-6.93 (2H, m), 4.85-4.78 (1H, m), 4.51-4.45 (1H, m), 3.58-3.47 (1H, m), 2.92-2.87 (1H, m), 2.67-2.60 (4H, m), 2.44 (3H, s), 2.08-1.99 (2H, m), 1.83-1.75 (2H, m), 1.63-1.56 (3H, m), 1.46 (3H, d, J=7.0 Hz). MS: m/z 399 ($M+H^+$).

Less polar isomer: $^1$H-NMR ($CDCl_3$) δ: 8.61 (1H, s), 7.34 (1H, d, J=1.2 Hz), 7.16-6.92 (4H, m), 4.87-4.77 (1H, m), 4.52-4.45 (1H, m), 3.60-3.50 (1H, m), 2.93-2.87 (1H, m), 2.68-2.60 (4H, m), 2.44 (3H, d, J=1.2 Hz), 2.08-1.99 (2H, m), 1.83-1.75 (2H, m), 1.63-1.56 (3H, m), 1.46 (3H, d, J=7.0 Hz). MS: m/z 399 ($M+H^+$).

Example 3.108

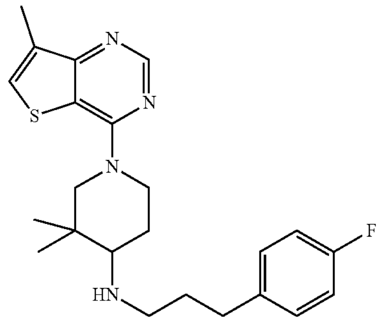 [SMILES: Cc1csc2c(N3CCC(NCCCc4ccc(F)cc4)C(C)(C)C3)ncnc12]

N-[3-(4-Fluorophenyl)propyl]-3-methyl-1-(7-methylthieno[3,2-d]pyrimidin-4-yl)-4-piperidylamine Step 1: N-(tert-Butoxycarbonyl)-3-methyl-1-(7-methylthieno[3,2-d]pyrimidin-4-yl)-4-piperidylamine was prepared according to the general procedure of Example 3.88 Step 1 using tert-butyl N-(3-methylpiperidin-4-yl)carbamate.

Step 2: 3-Methyl-1-(7-methylthieno[3,2-d]pyrimidin-4-yl)-4-piperidylamine was prepared according to the general procedure of Example 3.88 Step 2 using N-(tert-butoxycarbonyl)-3-methyl-1-(7-methylthieno[3,2-d]pyrimidin-4-yl)-4-piperidylamine obtained above, Step 3: The title compound was prepared according to the general procedure of Example 3.88 Step 3 using 3-methyl-1-(7-methylthieno[3,2-d]pyrimidin-4-yl)-4-piperidylamine obtained above and 3-(4-fluorophenyl)propanal. MS: m/z 399 (M+H$^+$).

Example 3.109

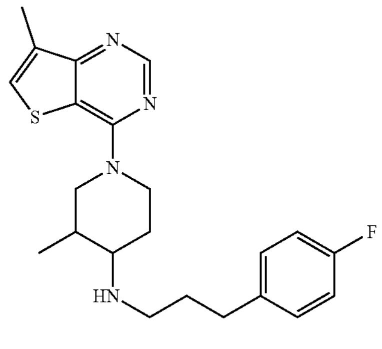 [SMILES: Cc1csc2c(N3CCC(NCCCc4ccc(F)cc4)C(C)C3)ncnc12]

N-[3-(4-Fluorophenyl)propyl]-3-methyl-1-(7-methylthieno[3,2-d]pyrimidin-4-yl)-4-piperidylamine Step 1: N-(tert-Butoxycarbonyl)-3-methyl-1-(7-methylthieno[3,2-d]pyrimidin-4-yl)-4-piperidylamine was prepared according to the general procedure of Example 3.88 Step 1 using tert-butyl N-(3-methylpiperidin-4-yl)carbamate.

Step 2: 3-Methyl-1-(7-methylthieno[3,2-d]pyrimidin-4-yl)-4-piperidylamine was prepared according to the general procedure of Example 3.88 Step 2 using N-(tert-butoxycarbonyl)-3-methyl-1-(7-methylthieno[3,2-d]pyrimidin-4-yl)-4-piperidylamine obtained above, Step 3: The title compound was prepared according to the general procedure of Example 3.88 Step 3 using 3-methyl-1-(7-methylthieno[3,2-d]pyrimidin-4-yl)-4-piperidylamine obtained above and 3-(4-fluorophenyl)propanal. MS: m/z 399 (M+H$^+$).

Example 3.110

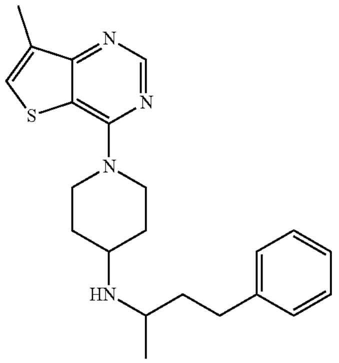 [SMILES: Cc1csc2c(N3CCC(NC(C)CCc4ccccc4)CC3)ncnc12]

N-(4-Phenylbutan-2-yl)-1-(7-methylthieno[3,2-d]pyrimidin-4-yl)-4-piperidylamine

The mixture of 1-(7-methylthieno[3,2-d]pyrimidin-4-yl)-4-piperidylamine (200 mg, 0.805 mmol) obtained in Example 3.88 Step 2, 3-bromobutylbenzene (200 mg, 0.939 mmol) and potassium bicarbonate (120 mg, 1.20 mmol) in DMF (1.5 mL) was stirred at room temperature for 24 hours. The resulting mixture was quenched by adding ethyl acetate and water. The organic layer was separated and washed with water and brine successively, then dried over anhydrous sodium sulfate. After the resulting solid was filtered off, the filtrate was concentrated under reduced pressure. The residue was purified by automated flash chromatography using 0-7% methanol in dichloromethane as eluent, to give the title compound (12.0 mg, yield 4%) as a colorless oil. $^1$H-NMR ($CDCl_3$) δ: 8.63 (1H, s), 7.36 (1H, d, J=1.2 Hz), 7.31-7.16 (5H, m), 4.75-4.64 (2H, m), 3.34-3.19 (2H, m), 2.95-2.81 (2H, m), 2.73-2.61 (2H, m), 2.45 (3H, d, J=1.2 Hz), 2.03-1.93 (2H, m), 1.81-1.18 (5H, m), 1.12 (3H, d, J=6.3 Hz).

Example 3.111

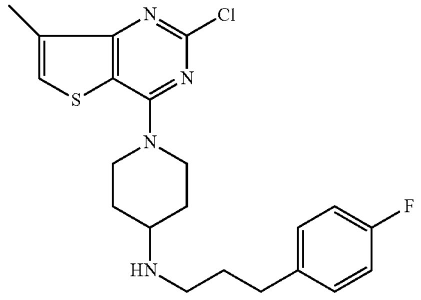

•HCl

N-[1-(2-Chloro-7-methylthieno[3,2-d]pyrimidin-4-yl)-4-piperidyl]-3-(4-fluorophenyl)propylamine hydrochloride Step 1: N-[1-(Benzyloxycarbonyl)-4-piperidyl]-3-(4-fluorophenyl)propylamine was prepared according to the general procedure of Example 3.110 using benzyl 4-aminopiperidine-1-carboxylate and 1-(3-bromopropyl)-4-fluorobenzene.

Step 2: The mixture of N-[1-(benzyloxycarbonyl)-4-piperidyl]-3-(4-fluorophenyl)propylamine (1.70 g, 4.60 mmol) obtained above, di-tert-butyl dicarbonate (2.01 g, 9.20 mmol) and N,N-diisopropylethylamine (2.40 mL, 13.8 mmol) in dichloromethane (23 mL) was stirred at room temperature for 4 days then concentrated under reduced pressure. The residue was purified by automated flash chromatography using 50-75% ethyl acetate in hexane as eluent, to give the N-[1-(benzyloxycarbonyl)-4-piperidyl]-N-(tert-butoxycarbonyl)-3-(4-fluorophenyl)propylamine (2.2 g, yield 100%) as a colorless oil.

Step 3: The mixture of N-[1-(benzyloxycarbonyl)-4-piperidyl]-N-(tert-butoxycarbonyl)-3-(4-fluorophenyl)propylamine (2.2 g, 4.60 mmol) obtained above, 10% Pd—C (W) (0.1 g) in THF (15 mL) and ethanol (10 mL) was stirred at room temperature for 4 hours under a hydrogen atmosphere, using a balloon. The reaction mixture was filtered and the filtrate was concentrated under reduced pressure. The residue was purified by automated flash chromatography using 10% methanol in dichloromethane as eluent, to give N-(tert-butoxycarbonyl)-N-[3-(4-fluorophenyl)propyl]-4-piperidylamine (1.13 g, yield 73%) as a colorless oil.

Step 4: N-(tert-Butoxycarbonyl)-N-[1-(2-chloro-7-methylthieno[3,2-d]pyrimidin-4-yl)-4-piperidyl]-3-(4-fluorophenyl)propylamine was prepared according to the general procedure of Example 3.88 Step 1 using N-(tert-butoxycarbonyl)-N-[3-(4-fluorophenyl)propyl]-4-piperidylamine.

Step 5: The title compound was prepared according to the general procedure of Example 3.88 Step 2 using N-(tert-butoxycarbonyl)-N-[1-(2-chloro-7-methylthieno[3,2-d]pyrimidin-4-yl)-4-piperidyl]-3-(4-fluorophenyl)propylamine obtained above and 4 M hydrochloric acid in 1,4-dioxane. $^1$H-NMR (DMSO-$D_6$) δ: 9.23 (2H, br s), 7.97 (1H, d, J=1.2 Hz), 7.31-7.25 (2H, m), 7.17-7.10 (2H, m), 4.68 (2H, d, J=13.3 Hz), 3.49-3.38 (1H, m), 3.26 (2H, t, J=12.1 Hz), 2.96-2.87 (2H, m), 2.67 (2H, t, J=7.6 Hz), 2.30 (3H, d, J=1.2 Hz), 2.26-2.19 (2H, m), 1.99-1.91 (2H, m), 1.72-1.60 (2H, m).

Example 3.112

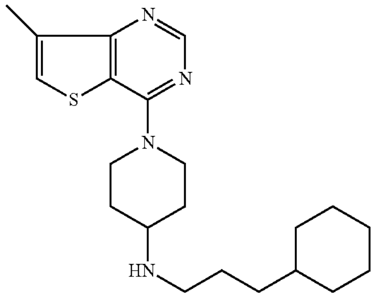 [SMILES: Cc1csc2c(N3CCC(NCCCC4CCCCC4)CC3)ncnc12]

N-(3-Cyclohexylpropyl)-1-(7-methylthieno[3,2-d]pyrimidin-4-yl)-4-piperidylamine

Step 1: The mixture of 4-amino-1-tert-butoxycarbonylpiperidine (1.00 g, 4.99 mmol), 2,4-dinitrobenzenesulfonyl chloride (1.33 g, 4.99 mmol) in saturated sodium bicarbonate (25 mL) and dichloromethane (25 mL) was stirred at room temperature for 20 hours. The resulting mixture was diluted with dichloromethane and the organic layer was separated and washed with brine, then dried over anhydrous sodium sulfate. After the resulting solid was filtered off, the filtrate was concentrated under reduced pressure. The residue was purified by automated flash chromatography using 25-50% ethyl acetate in hexane as eluent then triturated with ethyl acetate and hexane, to give N-[1-(tert-butoxycarbonyl)-4-piperidyl]-2,4-dinitrobenzenesulfonamide (1.70 g, yield 79%) as a pale-yellow solid.

Step 2: The mixture of N-[1-(tert-butoxycarbonyl)-4-piperidyl]-2,4-dinitrobenzenesulfonamide (500 mg, 1.16 mmol) obtained above, 3-cyclohexyl-1-propanol (0.212 mL, 1.39 mmol), triphenylphosphine (366 mg, 1.39 mmol) and diisopropyl azodicarboxylate (0.199 mL, 1.39 mmol) in THF (5.8 mL) was stirred at room temperature for 19 hours and concentrated under reduced pressure. The residue was purified by automated flash chromatography using 50-100% ethyl acetate in hexane as eluent, to give N-[1-(tert-butoxycarbonyl)-4-piperidyl]-N-(3-cyclohexylpropyl)-2,4-dinitrobenzenesulfonamide (581 mg, yield 90%) as a colorless oil.

Step 3: To a solution of N-[1-(tert-butoxycarbonyl)-4-piperidyl]-N-(3-cyclohexylpropyl)-2,4-dinitrobenzenesulfonamide (500 mg, 1.16 mmol) obtained above in dichloromethane (5 mL) was added hydrogen chloride, 4N solution in ethyl acetate (1.5 mL) at room temperature. The resulting mixture was stirred at room temperature for 1.5 hours and concentrated under reduced pressure. The residue was triturated with diethyl ether to give N-(3-cyclohexylpropyl)-N-(4-piperidyl)-2,4-dinitrobenzenesulfonamide hydrochloride (473 mg, yield 92%) as a colorless solid.

Step 4: N-(3-Cyclohexylpropyl)-N-[1-(7-methylthieno[3,2-d]pyrimidin-4-yl)-4-piperidyl]-2,4-dinitrobenzenesulfonamide was prepared according to the general procedure of Example 3.88 Step 1 using N-(3-cyclohexylpropyl)-N-(4-piperidyl)-2,4-dinitrobenzenesulfonamide hydrochloride obtained above.

Step 5: The mixture of N-(3-cyclohexylpropyl)-N-[1-(7-methylthieno[3,2-d]pyrimidin-4-yl)-4-piperidyl]-2,4-dinitrobenzenesulfonamide (519 mg, 0.861 mmol) obtained above, thioglycolic acid (0.0897 mL, 1.29 mmol) and trimethylamine (0.239 mL, 1.72 mmol) in dichloromethane (5 mL) was stirred at room temperature for 2.5 hours. The resulting mixture was quenched by adding ethyl acetate and water. The organic layer was separated and washed with brine, then dried over anhydrous sodium sulfate. After the resulting solid was filtered off, the filtrate was concentrated under reduced pressure. The residue was purified by automated flash chromatography using 0-50% ethyl acetate in hexane as eluent, to give the title compound (237 mg, yield 74%) as a colorless oil. $^1$H-NMR ($CDCl_3$) δ: 8.63 (1H, s), 7.35 (1H, d, J=1.2 Hz), 4.73 (2H, dt, J=13.7, 3.0 Hz), 3.30-3.22 (2H, m), 2.86-2.77 (1H, m), 2.63 (2H, t, J=7.2 Hz), 2.45 (3H, d, J=1.2 Hz), 2.08-2.00 (2H, m), 1.74-1.60 (5H, m), 1.53-1.37 (4H, m), 1.28-1.06 (6H, m), 0.95-0.80 (3H, m).

Example 3.113

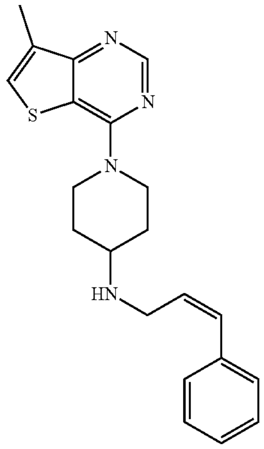 [SMILES: Cc1csc2c(N3CCC(NC/C=C\c4ccccc4)CC3)ncnc12]

N-[1-(7-Methylthieno[3,2-d]pyrimidin-4-yl)-4-piperidyl]-(2Z)-3-phenyl-2-propenylamine Step 1: N-[1-(7-Methylthieno[3,2-d]pyrimidin-4-yl)-4-piperidyl]-2,4-dinitrobenzenesulfonamide was prepared according to the general procedure of Example 3.112 Step 1 using 1-(7-methylthieno[3,2-d]pyrimidin-4-yl)-4-piperidylamine obtained in Example 3.88 Step 2.

Step 2: N-[1-(7-Methylthieno[3,2-d]pyrimidin-4-yl)-4-piperidyl]-N-[(2Z)-3-phenyl-2-propenyl]-2,4-dinitrobenzenesulfonamide was prepared according to the general procedure of Example 3.112 Step 2 using N-[1-(7-methylthieno[3,2-d]pyrimidin-4-yl)-4-piperidyl]-2,4-dinitrobenzenesulfonamide obtained above and (Z)-3-phenylprop-2-en-1-ol.

Step 3: The title compound was prepared according to the general procedure of Example 3.112 Step 5 using N-[1-(7-methylthieno[3,2-d]pyrimidin-4-yl)-4-piperidyl]-N-[(2Z)-3-phenyl-2-propenyl]-2,4-dinitrobenzenesulfonamide obtained above. $^1$H-NMR ($CDCl_3$) δ: 8.63 (1H, s), 7.40-7.31 (3H, m), 7.29-7.23 (3H, m), 6.55 (1H, d, J=11.7 Hz), 5.76 (1H, dt, J=11.7, 6.5 Hz), 4.69 (2H, dt, J=13.7, 3.2 Hz), 3.60 (2H, dd, J=6.5, 1.8 Hz), 3.29-3.21 (2H, m), 2.90-2.82 (1H, m), 2.45 (3H, d, J=1.2 Hz), 2.02-1.95 (2H, m), 1.48-1.36 (2H, m), 1.05 (1H, br s).

Example 3.114

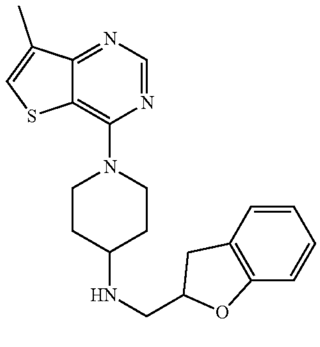 [SMILES: Cc1csc2c(N3CCC(NCC4Cc5ccccc5O4)CC3)ncnc12]

N-[(2,3-Dihydro-1-benzofuran-2-yl)methyl]-1-(7-methylthieno[3,2-d]pyrimidin-4-yl)-4-piperidylamine Step 1: N-[(2,3-Dihydro-1-benzofuran-2-yl)methyl]-N-[1-(7-methylthieno[3,2-d]pyrimidin-4-yl)-4-piperidyl]-2,4-dinitrobenzenesulfonamide was prepared according to the general procedure of Example 3.113 Step 2 using (2,3-dihydro-1-benzofuran-2-yl)methanol.

Step 2: The title compound was prepared according to the general procedure of Example 3.112 Step 5 using N-[(2,3-dihydro-1-benzofuran-2-yl)methyl]-N-[1-(7-methylthieno[3,2-d]pyrimidin-4-yl)-4-piperidyl]-2,4-dinitrobenzenesulfonamide obtained above. $^1$H-NMR ($CDCl_3$) δ: 8.63 (1H, s), 7.35 (1H, d, J=1.2 Hz), 7.18-7.08 (2H, m), 6.84 (1H, td, J=7.4, 0.8 Hz), 6.77 (1H, d, J=7.8 Hz), 4.95-4.87 (1H, m), 4.73-4.66 (2H, m), 3.35-3.24 (3H, m), 3.02-2.83 (4H, m), 2.45 (3H, d, J=1.2 Hz), 2.10-2.00 (2H, m), 1.54-1.42 (2H, m), 1.36 (1H, br s).

Example 3.115

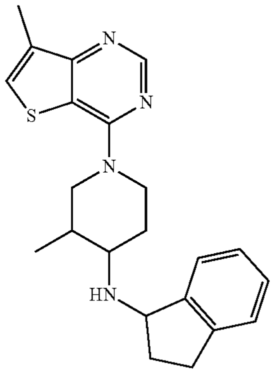 [SMILES: Cc1csc2c(N3CCC(NC4CCc5ccccc54)C(C)C3)ncnc12]

N-(2,3-Dihydro-1H-inden-1-yl)-1-(7-methylthieno[3,2-d]pyrimidin-4-yl)-4-piperidylamine Step 1: N-(2,3-Dihydro-H-inden-1-yl)-N-[1-(7-methythieno[3,2-d]pyrimidin-4-yl)-4-piperidyl]-2,4-dinitrobenzenesulfonamide was prepared according to the general procedure of Example 3.113 Step 2 using 2,3-dihydro-1H-inden-1-ol.

Step 2: The title compound was prepared according to the general procedure of Example 3.112 Step 5 using N-(2,3-Dihydro-1H-inden-1-yl)-N-[1-(7-methylthieno[3,2-d]pyrimidin-4-yl)-4-piperidyl]-2,4-dinitrobenzenesulfonamide obtained above. $^1$H-NMR ($CDCl_3$) δ: 8.64 (1H, s), 7.37-7.31 (2H, m), 7.27-7.17 (3H, m), 4.76-4.67 (2H, m), 4.38 (1H, t, J=6.8 Hz), 3.42-3.31 (2H, m), 3.15-2.96 (2H, m), 2.87-2.77 (1H, m), 2.52-2.43 (4H, m), 2.17-2.01 (2H, m), 1.84-1.74 (1H, m), 1.61-1.49 (2H, m), 1.15 (1H, br s).

Example 3.116

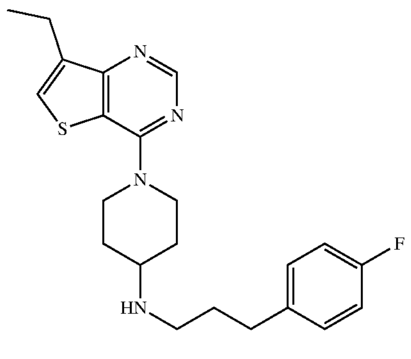 [SMILES: CCc1csc2c(N3CCC(NCCCc4ccc(F)cc4)CC3)ncnc12]

N-[1-(7-Ethylthieno[3,2-d]pyrimidin-4-yl)-4-piperidyl]-3-(4-fluorophenyl)propylamine The title compound was prepared according to the general procedure of Example 3.111 Step 3 using N-[1-(7-ethynylthieno[3,2-d]pyrimidin-4-yl)-4-piperidyl]-3-(4-fluorophenyl) propylamine obtained in Example 3.107 Step 4. $^1$H-NMR ($CDCl_3$) δ: 8.62 (1H, s), 7.35 (1H, t, J=1.2 Hz), 7.17-7.10 (2H, m), 7.00-6.92 (2H, m), 4.76-4.68 (2H, m), 3.29-3.19 (2H, m), 2.94-2.78 (3H, m), 2.72-2.61 (4H, m), 2.07-1.99 (2H, m), 1.87-1.77 (2H, m), 1.52-1.31 (3H, m), 1.35 (3H, t, J=7.4 Hz.

BIOLOGY EXAMPLES

Example B1: ENPP1 Assay with ATP Substrate

Ectonucleotide pyrophosphatase/phosphodiesterase 1 (ENPP1) hydrolyzes ATP, breaking it down into 5'-AMP and pyrophosphate. The 5'-AMP formed from the reaction is detected by Transcreener® AMP2/GMP2 TR-FRET Assay (Bellbrook), containing AMP-tracer (HiLyte 647) and anti-AMP Terbium (Tb) donor. 5'-AMP generated in the reaction competes with AMP-tracer for binding with Anti-AMP Tb donor, and decreases TR-FRET signal.

Different concentrations of ENPP1 inhibitors are added to dry assay plate, followed by 2 μl 300 nM ATP. The reaction is initiated with the addition of 2 μl 8.5 μM human ENPP1 (generated by SBP Protein group). The assay reaction mixture contains a buffer of 50 mM Tris, pH 7.5, 1 mM TCEP, 2 mM MgCl2, 0.005% Tween 20, and 1% DMSO. The reaction is stopped after 1 hour at room temperature by adding 2 μL of 2 nM AMP-tracer and 2 μl of 2 nM Anti-AMP Tb donor in the 50 mM Tris, pH 7.5, buffer containing 20 mM EDTA and 0.1% Prionex. After 2 hour additional incubation at room temperature, the generated signal is measured using BMG Lab PHERASTAR instrument. 100% activity control samples (containing enzyme, substrate, buffer: MAX) and no enzyme control samples (containing substrate and buffer: MIN) are utilized to calculate percent inhibition (%) for each compound concentration well (COMPOUND) as follows.

$$\%\ \text{inhibition} = 100\% * \frac{\text{MAX} - \text{COMPOUND}}{\text{MAX} - \text{MIN}}$$

The $IC_{50}$ values are determined by fitting the inhibition curves with 2-parameter variable slope model in Graphpad Prism software using percent inhibition vs compound concentration data:

$$\%\ \text{inhibition} = \frac{100\% * [\text{compound}]^{Hill\ slope}}{IC_{50}^{Hill\ slope} + [\text{compound}]_{50}^{Hill\ slope}}$$

Representative in vitro biochemical data is presented in Table 4.

TABLE 4

In vitro potency data.

| Compound | Compd No. | ENPP1 TR-FRET ($IC_{50}$ μM) | ENPP3 Km ATP ($IC_{50}$ μM) |
|---|---|---|---|
| 5-Phenyl-2-(pyridin-2-yl)-N-(pyridin-4-ylmethyl)thieno[2,3-d]pyrimidin-4-amine | 1 | B | D |
| 5-Phenyl-2-(pyridin-2-yl)-N-(pyridin-3-ylmethyl)thieno[2,3-d]pyrimidin-4-amine | 1.1 | C | D |
| (5-Phenyl-2-pyridin-2-yl-thieno[2,3-d]pyrimidin-4-yl)-pyridin-2-ylmethyl-amine | 1.2 | D | — |
| N-(4-Methoxybenzyl)-5-phenyl-2-(pyridin-2-yl)thieno[2,3-d]pyrimidin-4-amine | 1.3 | D | D |
| N-(4-Fluorobenzyl)-5-phenyl-2-(pyridin-2-yl)thieno[2,3-d]pyrimidin-4-amine | 1.4 | D | D |
| N-Benzyl-5-phenyl-2-(pyridin-2-yl)thieno[2,3-d]pyrimidin-4-amine | 1.5 | D | D |
| 4-(((5-Phenyl-2-(pyridin-2-yl)thieno[2,3-d]pyrimidin-4-yl)amino)methyl)benzenesulfonamide | 1.6 | A | A |
| (4-Methyl-benzyl)-(5-phenyl-2-pyridin-2-yl-thieno[2,3-d]pyrimidin-4-yl)-amine | 1.7 | D | D |
| (2-Fluoro-benzyl)-(5-phenyl-2-pyridin-2-yl-thieno[2,3-d]pyrimidin-4-yl)-amine | 1.8 | D | D |
| (3-Fluoro-benzyl)-(5-phenyl-2-pyridin-2-yl-thieno[2,3-d]pyrimidin-4-yl)-amine | 1.9 | D | D |
| (4-Chloro-benzyl)-(5-phenyl-2-pyridin-2-yl-thieno[2,3-d]pyrimidin-4-yl)-amine | 1.10 | D | D |
| 4-[(5-Phenyl-2-pyridin-2-yl-thieno[2,3-d]pyrimidin-4-ylamino)-methyl]-benzonitrile | 1.11 | D | D |

TABLE 4-continued

In vitro potency data.

| Compound | Compd No. | ENPP1 TR-FRET ($IC_{50}$ μM) | ENPP3 Km ATP ($IC_{50}$ μM) |
|---|---|---|---|
| 3-(((5-phenyl-2-(pyridin-2-yl)thieno[2,3-d]pyrimidin-4-yl)amino)methyl)benzenesulfonamide | 1.12 | C | — |
| 2-Fluoro-4-(((5-phenyl-2-(pyridin-2-yl)thieno[2,3-d]pyrimidin-4-yl)amino)methyl)benzenesulfonamide | 1.13 | A | B |
| 4-(((5-Phenyl-2-(pyridin-2-yl)thieno[2,3-d]pyrimidin-4-yl)amino)methyl)-2-(trifluoromethyl)benzenesulfonamide | 1.14 | A | B |
| 3-Methyl-4-(((5-phenyl-2-(pyridin-2-yl)thieno[2,3-d]pyrimidin-4-yl)amino)methyl)benzenesulfonamide | 1.15 | B | B |
| 2-Methoxy-4-(((5-phenyl-2-(pyridin-2-yl)thieno[2,3-d]pyrimidin-4-yl)amino)methyl)benzenesulfonamide | 1.16 | B | C |
| 3-Methoxy-4-(((5-phenyl-2-(pyridin-2-yl)thieno[2,3-d]pyrimidin-4-yl)amino)methyl)benzenesulfonamide | 1.17 | A | C |
| 2-Chloro-4-(((5-phenyl-2-(pyridin-2-yl)thieno[2,3-d]pyrimidin-4-yl)amino)methyl)benzenesulfonamide | 1.18 | A | B |
| 2-Methyl-4-(((5-phenyl-2-(pyridin-2-yl)thieno[2,3-d]pyrimidin-4-yl)amino)methyl)benzenesulfonamide | 1.19 | A | B |
| 4-(((2-(Pyridin-2-yl)-5-(pyridin-4-yl)thieno[2,3-d]pyrimidin-4-yl)amino)methyl)benzenesulfonamide | 1.20 | C | D |
| 3-Chloro-4-(((5-phenyl-2-(pyridin-2-yl)thieno[2,3-d]pyrimidin-4-yl)amino)methyl)benzenesulfonamide | 1.21 | A | B |
| 4-(((2-(Pyridin-2-yl)-5-(pyridin-3-yl)thieno[2,3-d]pyrimidin-4-yl)amino)methyl)benzenesulfonamide | 1.22 | A | C |
| 4-(((2,5-Di(pyridin-2-yl)thieno[2,3-d]pyrimidin-4-yl)amino)methyl)benzenesulfonamide | 1.23 | B | C |
| 4-(((2,5-Diphenylthieno[2,3-d]pyrimidin-4-yl)amino)methyl)benzenesulfonamide | 1.24 | D | D |
| 4-(((2-(4-Methylpiperazin-1-yl)-5-phenylthieno[2,3-d]pyrimidin-4-yl)amino)methyl)benzenesulfonamide | 1.25 | A | A |
| 4-(((2-(Cyclopropylamino)-5-phenylthieno[2,3-d]pyrimidin-4-yl)amino)methyl)benzenesulfonamide | 1.26 | A | A |
| 5-(((2,5-Diphenylthieno[2,3-d]pyrimidin-4-yl)amino)methyl)thiophene-2-sulfonamide | 1.27 | C | D |
| 5-(((5-Phenylthieno[2,3-d]pyrimidin-4-yl)amino)methyl)thiophene-2-sulfonamide | 1.28 | C | D |
| 5-(((5-Phenyl-2-(pyridin-4-yl)thieno[2,3-d]pyrimidin-4-yl)amino)methyl)thiophene-2-sulfonamide | 1.29 | D | D |
| 5-(((5-Phenyl-2-(pyridin-3-yl)thieno[2,3-d]pyrimidin-4-yl)amino)methyl)thiophene-2-sulfonamide | 1.30 | C | D |
| 5-(((5-Phenyl-2-(pyridin-2-yl)thieno[2,3-d]pyrimidin-4-yl)amino)methyl)thiophene-2-sulfonamide | 1.31 | A | B |
| N-((5-methylfuran-2-yl)methyl)-5-phenyl-2-(pyridin-2-yl)thieno[2,3-d]pyrimidin-4-amine | 1.32 | C | D |
| (5-Phenyl-2-pyridin-2-yl-thieno[2,3-d]pyrimidin-4-yl)-thiophen-2-ylmethyl-amine | 1.33 | B | C |
| N-((5-amino-1-methyl-1H-pyrazol-4-yl)methyl)-5-phenyl-2-(pyridin-2-yl)thieno[2,3-d]pyrimidin-4-amine | 1.34 | C | — |
| N-(furan-2-ylmethyl)-5-phenyl-2-(pyridin-2-yl)thieno[2,3-d]pyrimidin-4-amine | 1.35 | C | — |
| N-cyclopentyl-N-methyl-5-phenyl-2-(pyridin-2-yl)thieno [2,3-d]pyrimidin-4-amine | 1.36 | D | — |
| 5-(((5-methyl-2-(pyridin-2-yl)thieno[2,3-d]pyrimidin-4-yl)amino)methyl)thiophene-2-sulfonamide | 1.37 | D | — |
| 4-(((2-Morpholino-5-phenylthieno[2,3-d]pyrimidin-4-yl)amino)methyl)benzenesulfonamide | 1.38 | A | A |
| 4-(((5-Phenyl-2-(piperidin-1-yl)thieno[2,3-d]pyrimidin-4-yl)amino)methyl)benzenesulfonamide | 1.39 | B | B |
| 4-(((2-(Cyclohexylamino)-5-phenylthieno[2,3-d]pyrimidin-4-yl)amino)methyl)benzenesulfonamide | 1.40 | B | C |
| 4-(((2-(Benzylamino)-5-phenylthieno[2,3-d]pyrimidin-4-yl)amino)methyl)benzenesulfonamide | 1.41 | A | B |
| 4-(((2-(Methylamino)-5-phenylthieno[2,3-d]pyrimidin-4-yl)amino)methyl)benzenesulfonamide | 1.42 | A | A |
| 4-(((2-(Dimethylamino)-5-phenylthieno[2,3-d]pyrimidin-4-yl)amino)methyl)benzenesulfonamide | 1.43 | A | B |
| 4-(((2-Methyl-5-phenylthieno[2,3-d]pyrimidin-4-yl)amino)methyl)benzenesulfonamide | 1.44 | A | A |
| 5-(((2-Methyl-5-phenylthieno[2,3-d]pyrimidin-4-yl)amino)methyl)thiophene-2-sulfonamide | 1.45 | D | D |
| 4-(((5-Phenylthieno[2,3-d]pyrimidin-4-yl)amino)methyl)benzenesulfonamide | 1.46 | A | A |
| 4-(((3-Phenyl-6-(pyridin-2-yl)thieno[2,3-b]pyridin-4-yl)amino)methyl)benzenesulfonamide | 1.47 | A | C |

TABLE 4-continued

In vitro potency data.

| Compound | Compd No. | ENPP1 TR-FRET ($IC_{50}$ μM) | ENPP3 Km ATP ($IC_{50}$ μM) |
|---|---|---|---|
| 4-((5-Bromothieno[2,3-d]pyrimidin-4-yl)aminomethyl)benzenesulfonamide | 1.49 | B | A |
| 4-((2-(2-Hydroxyethylamino)-5-phenylthieno[2,3-d]pyrimidin-4-yl)aminomethyl)benzenesulfonamide | 1.50 | A | A |
| 4-((2-(3-Hydroxypropyl)amino-5-phenylthieno[2,3-d]pyrimidin-4-yl)aminomethyl)benzenesulfonamide | 1.51 | A | A |
| 4-((2-(N-Ethyl-N-(2-hydroxyethyl)amino)-5-phenylthieno[2,3-d]pyrimidin-4-yl)aminomethyl)benzenesulfonamide | 1.52 | A | B |
| 4-((2-(N-Ethyl-N-(1-hydroxy-2-methylpropan-2-yl)amino)-5-phenylthieno[2,3-d]pyrimidin-4-yl)aminomethyl)benzenesulfonamide | 1.53 | B | B |
| 4-((2-(2-Methoxyethyl)amino-5-phenylthieno[2,3-d]pyrimidin-4-yl)aminomethyl)benzenesulfonamide | 1.54 | A | A |
| 4-((2-(N-Methyl-N-(2-methoxyethyl)amino)-5-phenylthieno[2,3-d]pyrimidin-4-yl)aminomethyl)benzenesulfonamide | 1.55 | A | B |
| 4-((2-(3-Methoxypropyl)amino-5-phenylthieno[2,3-d]pyrimidin-4-yl)aminomethyl)benzenesulfonamide | 1.56 | A | A |
| 4-((2-Amino-5-phenylthieno[2,3-d]pyrimidin-4-yl)aminomethyl)benzenesulfonamide | 1.57 | A | B |
| 4-((2-((N-2-(Dimethylamino)ethyl)-N-methylamino)-5-phenylthieno[2,3-d]pyrimidin-4-yl)aminomethyl)benzenesulfonamide | 1.58 | A | A |
| 4-((2-(3-Dimethylaminopropyl)amino-5-phenylthieno[2,3-d]pyrimidin-4-yl)aminomethyl)benzenesulfonamide | 1.59 | A | A |
| 4-((2-(2-Dimethylamino)ethylamino-5-phenylthieno[2,3-d]pyrimidin-4-yl)aminomethyl)benzenesulfonamide | 1.60 | A | A |
| 4-((2-Methyl-5,6,7,8-tetrahydro[1]benzothieno[2,3-d]pyrimidin-4-yl)aminomethyl)benzenesulfonamide | 1.64 | D | C |
| 4-(1-(5-Phenylthieno[2,3-d]pyrimidin-4-yl)aminoethyl)benzenesulfonamide | 1.65 | C | C |
| 4-(5-Phenylthieno[2,3-d]pyrimidin-4-yl)aminomethyl-1-piperidinesulfonamide | 1.66 | B | C |
| 4-((5-Phenyl-2-(2-pyridyl)thieno[2,3-d]pyrimidin-4-yl)aminomethyl)-1-piperidinesulfonamide | 1.67 | B | C |
| 4-((5-(1-Cyclohexenyl)thieno[2,3-d]pyrimidin-4-yl)aminomethyl)benzenesulfonamide | 1.69 | D | B |
| 4-((5-Phenylthieno[2,3-d]pyrimidin-4-yl)oxymethyl)benzenesulfonamide | 1.70 | B | C |
| 4-(((1-methyl-6-phenyl-1H-pyrazolo[3,4-d]pyrimidin-4-yl)amino)methyl)benzenesulfonamide | 2 | C | — |
| 2-Fluoro-4-(((1-methyl-1H-pyrazolo[3,4-d]pyrimidin-4-yl)amino)methyl)benzenesulfonamide | 2.1 | A | C |
| 3-Methyl-4-(((1-methyl-1H-pyrazolo[3,4-d]pyrimidin-4-yl)amino)methyl)benzenesulfonamide | 2.2 | B | C |
| 3-Methoxy-4-(((1-methyl-1H-pyrazolo[3,4-d]pyrimidin-4-yl)amino)methyl)benzenesulfonamide | 2.3 | B | C |
| 2-Chloro-4-(((1-methyl-1H-pyrazolo[3,4-d]pyrimidin-4-yl)amino)methyl)benzenesulfonamide | 2.4 | B | C |
| 1-(1-Methyl-1H-pyrazolo[3,4-d]pyrimidin-4-yl)-N-(3-(pyridin-4-yl)propyl)piperidin-4-amine | 2.5 | D | D |
| 1-(1-Methyl-6-(4-methylpiperazin-1-yl)-1H-pyrazolo[3,4-d]pyrimidin-4-yl)-N-(3-(pyridin-4-yl)propyl)piperidin-4-amine | 2.6 | D | D |
| 1-(1-Methyl-6-phenyl-1H-pyrazolo[3,4-d]pyrimidin-4-yl)-N-(3-(pyridin-4-yl)propyl)piperidin-4-amine | 2.7 | D | D |
| 4-(((9-Methyl-9H-purin-6-yl)amino)methyl)benzenesulfonamide | 2.8 | D | C |
| N-benzyl-1-methyl-6-(pyridin-2-yl)-1H-pyrazolo[3,4-d]pyrimidin-4-amine | 2.9 | D | — |
| 4-(((1-Methyl-6-(pyridin-2-yl)-1H-pyrazolo[3,4-d]pyrimidin-4-yl)amino)methyl)benzenesulfonamide | 2.10 | A | C |
| N-(4-methoxybenzyl)-1-methyl-6-(pyridin-2-yl)-1H-pyrazolo[3,4-d]pyrimidin-4-amine | 2.11 | D | — |
| N-(3-fluorobenzyl)-1-methyl-6-(pyridin-2-yl)-1H-pyrazolo[3,4-d]pyrimidin-4-amine | 2.12 | D | — |
| N-(4-chlorobenzyl)-1-methyl-6-(pyridin-2-yl)-1H-pyrazolo[3,4-d]pyrimidin-4-amine | 2.13 | D | — |
| 4-(((1-Methyl-6-(piperidin-1-yl)-1H-pyrazolo[3,4-d]pyrimidin-4-yl)amino)methyl)benzenesulfonamide | 2.14 | C | B |

TABLE 4-continued

| In vitro potency data. | | | |
|---|---|---|---|
| Compound | Compd No. | ENPP1 TR-FRET ($IC_{50}$ μM) | ENPP3 Km ATP ($IC_{50}$ μM) |
| 4-(((1-methyl-6-(pyridin-3-yl)-1H-pyrazolo[3,4-d]pyrimidin-4-yl)amino)methyl)benzenesulfonamide | 2.15 | C | — |
| 4-(((1-methyl-6-(pyridin-4-yl)-1H-pyrazolo[3,4-d]pyrimidin-4-yl)amino)methyl)benzenesulfonamide | 2.16 | D | — |
| 1-methyl-6-(pyridin-2-yl)-N-(pyridin-4-ylmethyl)-1H-pyrazolo[3,4-d]pyrimidin-4-amine | 2.17 | C | — |
| 1-methyl-6-(pyridin-2-yl)-N-(pyridin-3-ylmethyl)-1H-pyrazolo[3,4-d]pyrimidin-4-amine | 2.18 | D | — |
| 1-methyl-6-(pyridin-2-yl)-N-(pyridin-2-ylmethyl)-1H-pyrazolo[3,4-d]pyrimidin-4-amine | 2.19 | D | — |
| 1-(1-Methyl-6-(pyridin-2-yl)-1H-pyrazolo[3,4-d]pyrimidin-4-yl)-N-(3-(pyridin-4-yl)propyl)piperidin-4-amine | 2.20 | D | D |
| 1-methyl-6-(pyridin-2-yl)-N-(thiophen-2-ylmethyl)-1H-pyrazolo [3,4-d]pyrimidin-4-amine | 2.21 | D | — |
| 1-methyl-N-((5-methylfuran-2-yl)methyl)-6-(pyridin-2-yl)-1H-pyrazolo[3,4-d]pyrimidin-4-amine | 2.22 | D | — |
| N-(furan-2-ylmethyl)-1-methyl-6-(pyridin-2-yl)-1H-pyrazolo[3,4-d]pyrimidin-4-amine | 2.23 | D | — |
| 5-(((1-Methyl-6-(pyridin-2-yl)-1H-pyrazolo[3,4-d]pyrimidin-4-yl)amino)methyl)thiophene-2-sulfonamide | 2.24 | B | B |
| 4-(((1-Methyl-1H-pyrazolo[3,4-d]pyrimidin-4-yl)amino)methyl)benzenesulfonamide | 2.25 | A | C |
| 4-(((1,6-Dimethyl-1H-pyrazolo[3,4-d]pyrimidin-4-yl)amino)methyl)benzenesulfonamide | 2.26 | A | B |
| 4-(((1-Methyl-6-(methylamino)-1H-pyrazolo[3,4-d]pyrimidin-4-yl)amino)methyl)benzenesulfonamide | 2.27 | A | B |
| 4-(((6-(Dimethylamino)-1-methyl-1H-pyrazolo[3,4-d]pyrimidin-4-yl)amino)methyl)benzenesulfonamide | 2.28 | C | B |
| 4-(((1-Methyl-6-morpholino-1H-pyrazolo[3,4-d]pyrimidin-4-yl)amino)methyl)benzenesulfonamide | 2.29 | D | B |
| 4-(((6-(Cyclohexylamino)-1-methyl-1H-pyrazolo[3,4-d]pyrimidin-4-yl)amino)methyl)benzenesulfonamide | 2.30 | C | C |
| 4-(((6-(Ethyl(methyl)amino)-1-methyl-1H-pyrazolo[3,4-d]pyrimidin-4-yl)amino)methyl)benzenesulfonamide | 2.31 | C | B |
| 4-(((6-(Benzyl(methyl)amino)-1-methyl-1H-pyrazolo[3,4-d]pyrimidin-4-yl)amino)methyl)benzenesulfonamide | 2.32 | D | B |
| 4-(((1-Methyl-6-(4-methylpiperazin-1-yl)-1H-pyrazolo[3,4-d]pyrimidin-4-yl)amino)methyl)benzenesulfonamide | 2.34 | D | B |
| 4-(((6-(Cyclopropylamino)-1-methyl-1H-pyrazolo[3,4-d]pyrimidin-4-yl)amino)methyl)benzenesulfonamide | 2.35 | B | B |
| 4-(((1-Methyl-6-(methyl(phenyl)amino)-1H-pyrazolo[3,4-d]pyrimidin-4-yl)amino)methyl)benzenesulfonamide | 2.36 | D | B |
| 4-(((6-Amino-1-methyl-1H-pyrazolo[3,4-d]pyrimidin-4-yl)amino)methyl)benzenesulfonamide | 2.37 | B | B |
| 4-(((1-Phenyl-1H-pyrazolo[3,4-d]pyrimidin-4-yl)amino)methyl)benzenesulfonamide | 2.38 | C | C |
| 4-(((1-Methyl-6-vinyl-1H-pyrazolo[3,4-d]pyrimidin-4-yl)amino)methyl)benzenesulfonamide | 2.39 | A | A |
| 4-(((6-Ethyl-1-methyl-1H-pyrazolo[3,4-d]pyrimidin-4-yl)amino)methyl)benzenesulfonamide | 2.40 | A | B |
| 4-(((1-Methyl-1H-pyrazolo[3,4-d]pyrimidin-4-yl)amino)methyl)-2-(trifluoromethyl)benzenesulfonamide | 2.41 | B | C |
| 2-Methoxy-4-(((1-methyl-1H-pyrazolo[3,4-d]pyrimidin-4-yl)amino)methyl)benzenesulfonamide | 2.42 | D | D |
| 4-(((1-(1-Methylpiperidin-4-yl)-1H-pyrazolo[3,4-d]pyrimidin-4-yl)amino)methyl)benzenesulfonamide | 2.43 | D | C |
| 4-(((1-Methyl-3-phenyl-1H-pyrazolo[3,4-d]pyrimidin-4-yl)amino)methyl)benzenesulfonamide | 2.44 | A | A |
| 4-(((1,3-Dimethyl-1H-pyrazolo[3,4-d]pyrimidin-4-yl)amino)methyl)benzenesulfonamide | 2.45 | B | B |
| 2-Methyl-4-(((1-methyl-1H-pyrazolo[3,4-d]pyrimidin-4-yl)amino)methyl)benzenesulfonamide | 2.46 | C | C |
| 3-Chloro-4-(((1-methyl-1H-pyrazolo[3,4-d]pyrimidin-4-yl)amino)methyl)benzenesulfonamide | 2.47 | B | C |

TABLE 4-continued

| In vitro potency data. | | | |
|---|---|---|---|
| Compound | Compd No. | ENPP1 TR-FRET ($IC_{50}$ μM) | ENPP3 Km ATP ($IC_{50}$ μM) |
| 4-(((6-(Benzylamino)-1-methyl-1H-pyrazolo[3,4-d]pyrimidin-4-yl)amino)methyl)benzenesulfonamide | 2.48 | B | B |
| 4-(((6-(Ethylamino)-1-methyl-1H-pyrazolo[3,4-d]pyrimidin-4-yl)amino)methyl)benzenesulfonamide | 2.49 | B | B |
| 4-(((1-Methyl-6-(phenylamino)-1H-pyrazolo[3,4-d]pyrimidin-4-yl)amino)methyl)benzenesulfonamide | 2.50 | A | B |
| 1-(1,6-Dimethyl-1H-pyrazolo[3,4-d]pyrimidin-4-yl)-N-(3-(pyridin-4-yl)propyl)piperidin-4-amine | 2.51 | D | D |
| 5-(((1-Methyl-1H-pyrazolo[3,4-d]pyrimidin-4-yl)amino)methyl)pyridine-2-sulfonamide | 2.52 | A | C |
| 6-(((1-Methyl-1H-pyrazolo[3,4-d]pyrimidin-4-yl)amino)methyl)pyridine-3-sulfonamide | 2.53 | B | D |
| 4-[(1-Methyl-1H-pyrazolo[4,3-d]pyrimidin-7-ylamino)-methyl]-benzenesulfonamide | 2.54 | A | C |
| 4-(((1-Methyl-1H-pyrazolo[3,4-c]pyridazin-4-yl)amino)methyl)benzenesulfonamide | 2.55 | B | C |
| 4-(((1-Methyl-1H-pyrazolo[3,4-d]pyridazin-4-yl)amino)methyl)benzenesulfonamide | 2.56 | D | D |
| N-(3-(4-Fluorophenyl)propyl)-1-(3-methylisoxazolo[5,4-d]pyrimidin-4-yl)piperidin-4-amine | 2.57 | D | D |
| 4-(((3-Methyl-3H-[1,2,3]triazolo[4,5-d]pyrimidin-7-yl)amino)methyl)benzenesulfonamide | 2.58 | C | C |
| 4-(((3-Methylisoxazolo[5,4-d]pyrimidin-4-yl)amino)methyl)benzenesulfonamide | 2.59 | C | C |
| 4-(((1-Methyl-1H-pyrazolo[3,4-b]pyridin-4-yl)amino)methyl)benzenesulfonamide | 2.60 | A | B |
| 3-Chloro-4-(((1-methyl-1H-pyrazolo[3,4-b]pyridin-4-yl)amino)methyl)benzenesulfonamide | 2.61 | B | B |
| 4-(((1-Methyl-1H-pyrazolo[3,4-b]pyridin-4-yl)amino)methyl)-2-(trifluoromethyl)benzenesulfonamide | 2.62 | A | B |
| 3-Methoxy-4-(((1-methyl-1H-pyrazolo[3,4-b]pyridin-4-yl)amino)methyl)benzenesulfonamide | 2.63 | B | C |
| 3-Fluoro-4-(((1-methyl-1H-pyrazolo[3,4-b]pyridin-4-yl)amino)methyl)benzenesulfonamide | 2.64 | A | B |
| 2-Methoxy-4-(((1-methyl-1H-pyrazolo[3,4-b]pyridin-4-yl)amino)methyl)benzenesulfonamide | 2.65 | C | D |
| 4-(((1-Methyl-1H-pyrazolo[4,3-c]pyridin-4-yl)amino)methyl)benzenesulfonamide | 2.66 | C | C |
| 2-Fluoro-4-(((1-methyl-1H-pyrazolo[3,4-b]pyridin-4-yl)amino)methyl)benzenesulfonamide | 2.67 | A | B |
| 2-Chloro-4-(((1-methyl-1H-pyrazolo[3,4-b]pyridin-4-yl)amino)methyl)benzenesulfonamide | 2.68 | B | C |
| 3-Methyl-4-(((1-methyl-1H-pyrazolo[3,4-b]pyridin-4-yl)amino)methyl)benzenesulfonamide | 2.69 | B | C |
| 2-Methyl-4-(((1-methyl-1H-pyrazolo[3,4-b]pyridin-4-yl)amino)methyl)benzenesulfonamide | 2.70 | B | C |
| 6-(((1-Methyl-1H-pyrazolo[3,4-b]pyridin-4-yl)amino)methyl)pyridine-3-sulfonamide | 2.71 | A | B |
| 5-(((1-Methyl-1H-pyrazolo[3,4-b]pyridin-4-yl)amino)methyl)pyridine-2-sulfonamide | 2.72 | A | B |
| 4-(((6-Chloro-1-methyl-1H-pyrazolo[3,4-b]pyridin-4-yl)amino)methyl)benzenesulfonamide | 2.73 | A | A |
| 4-(((6-(Isopropylamino)-1-methyl-1H-pyrazolo[3,4-b]pyridin-4-yl)amino)methyl)benzenesulfonamide | 2.74 | C | C |
| 4-(((6-(Ethylamino)-1-methyl-1H-pyrazolo[3,4-b]pyridin-4-yl)amino)methyl)benzenesulfonamide | 2.75 | B | C |
| 4-(((1-Methyl-6-(methylamino)-1H-pyrazolo[3,4-b]pyridin-4-yl)amino)methyl)benzenesulfonamide | 2.76 | C | B |
| 4-(((1-Methyl-6-(pyrrolidin-1-yl)-1H-pyrazolo[3,4-b]pyridin-4-yl)amino)methyl)benzenesulfonamide | 2.77 | C | B |
| 4-(((6-Amino-1-methyl-1H-pyrazolo[3,4-b]pyridin-4-yl)amino)methyl)benzenesulfonamide | 2.78 | B | B |
| 4-(((6-(Diethylamino)-1-methyl-1H-pyrazolo[3,4-b]pyridin-4-yl)amino)methyl)benzenesulfonamide | 2.79 | D | C |
| 4-(((6-(Butylamino)-1-methyl-1H-pyrazolo[3,4-b]pyridin-4-yl)amino)methyl)benzenesulfonamide | 2.80 | C | C |
| 4-(((6-((2-Hydroxyethyl)amino)-1-methyl-1H-pyrazolo[3,4-b]pyridin-4-yl)amino)methyl)benzenesulfonamide | 2.81 | C | C |
| 4-(((1-Methyl-6-morpholino-1H-pyrazolo[3,4-b]pyridin-4-yl)amino)methyl)benzenesulfonamide | 2.82 | C | C |

TABLE 4-continued

In vitro potency data.

| Compound | Compd No. | ENPP1 TR-FRET ($IC_{50}$ μM) | ENPP3 Km ATP ($IC_{50}$ μM) |
|---|---|---|---|
| 4-((6-Chloro-1-ethyl-1H-pyrazolo[3,4-d]pyrimidin-4-yl)aminomethyl)benzenesulfonamide | 2.83 | A | C |
| 4-((6-Chloro-1-cyclopropyl-1H-pyrazolo[3,4-d]pyrimidin-4-yl)aminomethyl)benzenesulfonamide | 2.84 | A | C |
| 5-((6-Chloro-1-methyl-1H-pyrazolo[3,4-d]pyrimidin-4-yl)aminomethyl)thiophene-2-sulfonamide | 2.85 | B | B |
| 4-((6-Chloro-1-(2,2,2-trifluoroethyl)-1H-pyrazolo[3,4-d]pyrimidin-4-yl)aminomethyl)benzenesulfonamide | 2.86 | C | C |
| 4-((3-Bromo-6-chloro-1-methyl-1H-pyrazolo[3,4-d]pyrimidin-4-yl)aminomethyl)benzenesulfonamide | 2.87 | A | A |
| 4-((3-Bromo-1,6-dimethyl-1H-pyrazolo[3,4-d]pyrimidin-4-yl)aminomethyl)benzenesulfonamide | 2.89 | A | A |
| 3-chloro-1-methyl-N-(4-methylbenzyl)-1H-pyrazolo[3,4-d]pyrimidin-4-amine | 2.90 | B | B |
| 4-((6-Chloro-1-methyl-1H-pyrazolo[3,4-d]pyrimidin-4-yl)aminomethyl)benzenesulfonamide | 2.92 | A | B |
| 4-((6-Ethoxy-1-methyl-1H-pyrazolo[3,4-d]pyrimidin-4-yl)aminomethyl)benzenesulfonamide | 2.93 | A | B |
| 4-((6-Methoxy-1-methyl-1H-pyrazolo[3,4-d]pyrimidin-4-yl)aminomethyl)benzenesulfonamide | 2.94 | A | B |
| 5-((6-Methoxy-1-methyl-1H-pyrazolo[3,4-d]pyrimidin-4-yl)aminomethyl)thiophene-2-sulfonamide | 2.95 | B | B |
| 4-((3-Bromo-6-methoxy-1-methyl-1H-pyrazolo[3,4-d]pyrimidin-4-yl)aminomethyl)benzenesulfonamide | 2.96 | A | A |
| 4-((3-Bromo-6-ethoxy-1-methyl-1H-pyrazolo[3,4-d]pyrimidin-4-yl)aminomethyl)benzenesulfonamide | 2.97 | A | A |
| 4-((1-Ethyl-6-(3-methoxy-3-methylbutoxy)-1H-pyrazolo[3,4-d]pyrimidin-4-yl)aminomethyl)benzenesulfonamide | 2.98 | A | C |
| 4-((6-(2,2,2-Trifluoroethoxy)-1-methyl-1H-pyrazolo[3,4-d]pyrimidin-4-yl)aminomethyl)benzenesulfonamide | 2.99 | B | B |
| 4-((1-Methyl-6-(3-methylbutoxy)-1H-pyrazolo[3,4-d]pyrimidin-4-yl)aminomethyl)benzenesulfonamide | 2.101 | A | B |
| 4-((1-Ethyl-6-(3-methylbutoxy)-1H-pyrazolo[3,4-d]pyrimidin-4-yl)aminomethyl)benzenesulfonamide | 2.102 | A | B |
| 4-((1-Methyl-6-(methylsulfanyl)-1H-pyrazolo[3,4-d]pyrimidin-4-yl)aminomethyl)benzenesulfonamide | 2.107 | A | A |
| 4-((6-(Ethylsulfanyl)-1-methyl-1H-pyrazolo[3,4-d]pyrimidin-4-yl)aminomethyl)benzenesulfonamide | 2.108 | A | A |
| 4-((1-Ethyl-6-(ethylsulfanyl)-1H-pyrazolo[3,4-d]pyrimidin-4-yl)aminomethyl)benzenesulfonamide | 2.109 | A | B |
| 4-((3-Bromo-6-(ethylsulfanyl)-1-methyl-1H-pyrazolo[3,4-d]pyrimidin-4-yl)aminomethyl)benzenesulfonamide | 2.110 | A | A |
| 4-((1-Methyl-6-(propylsulfanyl)-1H-pyrazolo[3,4-d]pyrimidin-4-yl)aminomethyl)benzenesulfonamide | 2.111 | A | B |
| 4-((1-Ethyl-1H-pyrazolo[3,4-b]pyridin-4-yl)aminomethyl)benzenesulfonamide | 2.122 | A | C |
| 4-((6-Chloro-1-methyl-3-(2-pyridyl)-1H-pyrazolo[3,4-d]pyrimidin-4-yl)aminomethyl)benzenesulfonamide | 2.124 | B | B |
| 4-((3-(1-Cyclopenten-1-yl)-1,6-dimethyl-1H-pyrazolo[3,4-d]pyrimidin-4-yl)aminomethyl)benzenesulfonamide | 2.127 | C | B |
| 4-((3-Bromo-1-methyl-6-piperidino-1H-pyrazolo[3,4-d]pyrimidin-4-yl)aminomethyl)benzenesulfonamide | 2.131 | C | A |
| 4-((1-Methyl-3-phenyl-6-piperidino-1H-pyrazolo[3,4-d]pyrimidin-4-yl)aminomethyl)benzenesulfonamide | 2.132 | A | B |
| 4-((1-Methyl-6-trifluoromethyl-1H-pyrazolo[3,4-d]pyrimidin-4-yl)aminomethyl)benzenesulfonamide | 2.133 | C | C |
| 4-((6-Cyclopropyl-1-methyl-1H-pyrazolo[3,4-b]pyridin-4-yl)aminomethyl)benzenesulfonamide | 2.134 | C | C |
| 4-((3-Cyclopentyl-1,6-dimethyl-1H-pyrazolo[3,4-d]pyrimidin-4-yl)aminomethyl)benzenesulfonamide | 2.135 | C | C |
| 4-(N-methyl-N-(1-methyl-1H-pyrazolo[3,4-d]pyrimidin-4-yl)aminomethyl)benzenesulfonamide | 2.136 | C | B |
| 4-((1-Methyl-1H-pyrazolo[3,4-d]pyrimidin-4-yl)oxymethyl)benzenesulfonamide | 2.137 | C | C |
| 4-(((5-Phenyl-2-(piperidin-1-yl)thieno[2,3-d]pyrimidin-4-yl)amino)methyl)-benzenesulfonamide | 2.139 | C | C |

TABLE 4-continued

In vitro potency data.

| Compound | Compd No. | ENPP1 TR-FRET ($IC_{50}$ μM) | ENPP3 Km ATP ($IC_{50}$ μM) |
|---|---|---|---|
| 4-(((2-(Cyclohexylamino)-5-phenylthieno[2,3-d]pyrimidin-4-yl)amino)methyl)-benzenesulfonamide | 2.140 | B | B |
| 4-(((2-(Benzylamino)-5-phenylthieno[2,3-d]pyrimidin-4-yl)amino)methyl)benzenesulfonamide | 2.141 | B | B |
| 4-(((2-(Methylamino)-5-phenylthieno[2,3-d]pyrimidin-4-yl)amino)methyl)-benzenesulfonamide | 2.142 | A | B |
| 4-(((2-(Dimethylamino)-5-phenylthieno[2,3-d]pyrimidin-4-yl)amino)methyl)-benzenesulfonamide | 2.143 | A | A |
| 4-(((2-Methyl-5-phenylthieno[2,3-d]pyrimidin-4-yl)amino)methyl)benzenesulfonamide | 2.144 | B | B |
| N-Bnzyl-1-(7-methylthieno[3,2-d]pyrimidin-4-yl)piperidin-4-amine | 3.0 | B | D |
| 1-(7-Methyl thieno[3,2-d]pyrimidin-4-yl)-N-(3-(pyridin-4-yl)propyl)piperidin-4-amine | 3.1 | B | D |
| 1-(7-Methylthieno[3,2-d]pyrimidin-4-yl)-N-(pyridin-4-ylmethyl)piperidin-4-amine | 3.2 | C | D |
| 1-(7-Methylthieno[3,2-d]pyrimidin-4-yl)-N-(3-(pyridin-2-yl)propyl)piperidin-4-amine | 3.3 | B | D |
| 1-(7-Methylthieno[3,2-d]pyrimidin-4-yl)-N-(3-(p-tolyl)propyl)piperidin-4-amine | 3.4 | B | D |
| N-(3-(4-Fluorophenyl)propyl)-1-(7-methylthieno[3,2-d]pyrimidin-4-yl)piperidin-4-amine | 3.5 | B | D |
| 4-(3-((1-(7-Methylthieno[3,2-d]pyrimidin-4-yl)piperidin-4-yl)amino)propyl)benzonitrile | 3.6 | B | D |
| 7-Methyl-4-(4-(4-(pyridin-4-yl)butyl)piperazin-1-yl)thieno[3,2-d]pyrimidine | 3.7 | C | D |
| 3-(2-Methoxypyridin-4-yl)-N-(1-(7-methylthieno[3,2-d]pyrimidin-4-yl)piperidin-4-yl)propenamide | 3.8 | C | D |
| 3-(2-Bromopyridin-4-yl)-N-(1-(7-methylthieno[3,2-d]pyrimidin-4-yl)piperidin-4-yl)propanamide | 3.9 | C | D |
| 3-(3-Chloropyridin-4-yl)-N-(1-(7-methylthieno[3,2-d]pyrimidin-4-yl)piperidin-4-yl)propanamide | 3.10 | C | D |
| (E)-3-(3-Chloropyridin-4-yl)-N-(1-(7-methylthieno[3,2-d]pyrimidin-4-yl)piperidin-4-yl)acrylamide | 3.11 | C | D |
| 1-(7-Methylthieno[3,2-d]pyrimidin-4-yl)-N-(3-(3-(trifluoromethyl)phenyl)propyl)piperidin-4-amine | 3.12 | B | D |
| N-(3-(3-Chloropyridin-4-yl)propyl)-1-(7-methylthieno[3,2-d]pyrimidin-4-yl)piperidin-4-amine | 3.13 | B | D |
| N-(1-(7-Methylthieno[3,2-d]pyrimidin-4-yl)piperidin-4-yl)-3-(o-tolyl)propanamide | 3.14 | D | D |
| N-(1-(7-Methylthieno[3,2-d]pyrimidin-4-yl)piperidin-4-yl)-3-(m-tolyl)propanamide | 3.15 | D | D |
| 1-(7-Methylthieno[3,2-d]pyrimidin-4-yl)-N-(3-(o-tolyl)propyl)piperidin-4-amine | 3.16 | B | D |
| 1-(7-Methylthieno[3,2-d]pyrimidin-4-yl)-N-(3-(m-tolyl)propyl)piperidin-4-amine | 3.17 | B | C |
| 3-(3-Chlorophenyl)-N-(1-(7-methylthieno[3,2-d]pyrimidin-4-yl)piperidin-4-yl)propanamide | 3.18 | D | D |
| N-(3-(3-Chlorophenyl)propyl)-1-(7-methylthieno[3,2-d]pyrimidin-4-yl)piperidin-4-amine | 3.19 | B | D |
| 3-(4-Fluorophenyl)-N-(1-(7-methylthieno[3,2-d]pyrimidin-4-yl)piperidin-4-yl)propanamide | 3.20 | D | D |
| 2-(4-Fluorophenoxy)-N-(1-(7-methylthieno[3,2-d]pyrimidin-4-yl)piperidin-4-yl)acetamide | 3.22 | C | D |
| N-(2-(4-Fluorophenoxy)ethyl)-1-(7-methylthieno[3,2-d]pyrimidin-4-yl)piperidin-4-amine | 3.23 | D | D |
| N-(1-(7-Methylthieno[3,2-d]pyrimidin-4-yl)piperidin-4-yl)pyridin-4-amine | 3.24 | C | D |
| 1-(7-Methylthieno[3,2-d]pyrimidin-4-yl)-N-(2-(pyridin-4-yl)ethyl)piperidin-4-amine | 3.25 | B | D |
| 1-(7-Methylthieno[3,2-d]pyrimidin-4-yl)-N-(3-(pyridin-3-yl)propyl)piperidin-4-amine | 3.26 | B | D |
| 1-(7-Methylthieno[3,2-d]pyrimidin-4-yl)-N-(3-phenylpropyl)piperidin-4-amine | 3.27 | B | D |
| N-(3-(4-Chlorophenyl)propyl)-1-(7-methylthieno[3,2-d]pyrimidin-4-yl)piperidin-4-amine | 3.28 | A | D |
| 1-(7-Methylthieno[3,2-d]pyrimidin-4-yl)-N-(3-(pyridin-4-yl)propyl)pyrrolidin-3-amine | 3.29 | B | D |
| N-(3-(2-Methylpyridin-4-yl)propyl)-1-(7-methylthieno[3,2-d]pyrimidin-4-yl)piperidin-4-amine | 3.30 | B | D |
| 3-(4-Methoxyphenyl)-N-(1-(7-methylthieno[3,2-d]pyrimidin-4-yl)piperidin-4-yl)propanamide | 3.31 | D | D |

TABLE 4-continued

In vitro potency data.

| Compound | Compd No. | ENPP1 TR-FRET ($IC_{50}$ μM) | ENPP3 Km ATP ($IC_{50}$ μM) |
|---|---|---|---|
| N-(3-(4-Methoxyphenyl)propyl)-1-(7-methylthieno[3,2-d]pyrimidin-4-yl)piperidin-4-amine | 3.32 | B | D |
| N-(3-(2-Fluorophenyl)propyl)-1-(7-methylthieno[3,2-d]pyrimidin-4-yl)piperidin-4-amine | 3.33 | B | D |
| 3-(3-Methylpyridin-4-yl)-N-(1-(7-methylthieno[3,2-d]pyrimidin-4-yl)piperidin-4-yl)propanamide | 3.34 | D | D |
| N-(3-(3-Methylpyridin-4-yl)propyl)-1-(7-methylthieno[3,2-d]pyrimidin-4-yl)piperidin-4-amine | 3.35 | B | D |
| 3-(2-Fluoropyridin-4-yl)-N-(1-(7-methylthieno[3,2-d]pyrimidin-4-yl)piperidin-4-yl)propanamide | 3.36 | C | D |
| N-(3-(2-Fluoropyridin-4-yl)propyl)-1-(7-methylthieno[3,2-d]pyrimidin-4-yl)piperidin-4-amine | 3.37 | B | D |
| 3-(3-Fluoropyridin-4-yl)-N-(1-(7-methylthieno[3,2-d]pyrimidin-4-yl)piperidin-4-yl)propanamide | 3.38 | D | D |
| 3-(3-Fluorophenyl)-N-(1-(7-methylthieno[3,2-d]pyrimidin-4-yl)piperidin-4-yl)propanamide | 3.39 | D | D |
| N-(3-(3-Fluoropyridin-4-yl)propyl)-1-(7-methylthieno[3,2-d]pyrimidin-4-yl)piperidin-4-amine | 3.40 | B | D |
| N-(3-(3-Fluorophenyl)propyl)-1-(7-methylthieno[3,2-d]pyrimidin-4-yl)piperidin-4-amine | 3.41 | B | D |
| N-(4-Fluorobenzyl)-1-(7-methylthieno[3,2-d]pyrimidin-4-yl)piperidin-4-amine | 3.42 | C | D |
| 2-(4-Fluorophenyl)-N-(1-(7-methylthieno[3,2-d]pyrimidin-4-yl)piperidin-4-yl)acetamide | 3.43 | C | D |
| N-(4-Fluorophenethyl)-1-(7-methylthieno[3,2-d]pyrimidin-4-yl)piperidin-4-amine | 3.44 | B | D |
| 4-(4-(3-(4-Fluorophenyl)propoxy)piperidin-1-yl)-7-methylthieno[3,2-d]pyrimidine | 3.45 | D | D |
| 3-(4-Fluorophenyl)-N-(1-(thieno[3,2-d]pyrimidin-4-yl)piperidin-4-yl)propanamide | 3.46 | D | D |
| N-(3-(4-Fluorophenyl)propyl)-1-(thieno[3,2-d]pyrimidin-4-yl)piperidin-4-amine | 3.47 | C | D |
| 3-(4-Fluorophenyl)-N-(1-(7-iodothieno[3,2-d]pyrimidin-4-yl)piperidin-4-yl)propanamide | 3.48 | B | D |
| N-(3-(4-Fluorophenyl)propyl)-1-(1-methyl-1H-pyrazolo[3,4-d]pyrimidin-4-yl)piperidin-4-amine | 3.50 | D | D |
| N-(3-(2-Methoxypyridin-4-yl)propyl)-1-(7-methylthieno[3,2-d]pyrimidin-4-yl)piperidin-4-amine | 3.51 | B | D |
| 1-(2,7-Dimethylthieno[3,2-d]pyrimidin-4-yl)-N-(3-(pyridin-4-yl)propyl)piperidin-4-amine | 3.52 | D | D |
| 1-(7-Methyl-2-(4-methylpiperazin-1-yl)thieno[3,2-d]pyrimidin-4-yl)-N-(3-(pyridin-4-yl)propyl)piperidin-4-amine | 3.53 | D | D |
| 1-(2-Ethyl-7-methylthieno[3,2-d]pyrimidin-4-yl)-N-(3-(pyridin-4-yl)propyl)piperidin-4-amine | 3.54 | D | D |
| 1-(1,6-Dimethyl-1H-pyrazolo[3,4-d]pyrimidin-4-yl)-N-(3-(4-fluorophenyl)propyl)piperidin-4-amine | 3.55 | D | D |
| 1-(7-Methyl-2-(pyridin-2-yl)thieno[3,2-d]pyrimidin-4-yl)-N-(3-(pyridin-4-yl)propyl)piperidin-4-amine | 3.56 | D | D |
| 3-(4-Fluorophenyl)-N-(1-(7-phenylthieno[3,2-d]pyrimidin-4-yl)piperidin-4-yl)propanamide | 3.57 | D | D |
| N-(3-(4-Fluorophenyl)propyl)-1-(7-phenylthieno[3,2-d]pyrimidin-4-yl)piperidin-4-amine | 3.58 | C | D |
| N-(3-(4-Fluorophenyl)propyl)-1-(3-methylisothiazolo[4,5-d]pyrimidin-7-yl)piperidin-4-amine | 3.59 | C | D |
| 4-((3-Methyl-7-oxoisothiazolo[4,5-d]pyrimidin-6(7H)-yl)methyl)benzenesulfonamide | 3.60 | C | C |
| 1-(7-Methyl-2-phenylthieno[3,2-d]pyrimidin-4-yl)-N-(3-(pyridin-4-yl)propyl)piperidin-4-amine | 3.61 | D | D |
| (E)-1-(7-Bromothieno[3,2-d]pyrimidin-4-yl)-N-(3-(4-methylpyridin-3-yl)allyl)piperidin-4-amine | 3.62 | A | — |
| N-(3-(4-Methylpyridin-3-yl)propyl)-1-(thieno[3,2-d]pyrimidin-4-yl)piperidin-4-amine | 3.63 | C | — |
| N-(1-(7-Chlorothieno[3,2-d]pyrimidin-4-yl)piperidin-4-yl)-3-(4-fluorophenyl)propanamide | 3.64 | C | — |
| 1-(2-Chloro-7-methylthieno[3,2-d]pyrimidin-4-yl)-N-(3-(pyridin-4-yl)propyl)piperidin-4-amine | 3.65 | C | — |
| 1-(2-Methoxy-7-methylthieno[3,2-d]pyrimidin-4-yl)-N-(3-(pyridin-4-yl)propyl)piperidin-4-amine | 3.66 | C | — |
| 1-(2-chloro-7-methylthieno[3,2-d]pyrimidin-4-yl)-N-(3-(4-methylpyridin-3-yl)propyl)piperidin-4-amine | 3.68 | C | — |
| N,7-Dimethyl-4-(4-((3-(4-methylpyridin-3-yl)propyl)amino)piperidin-1-yl)thieno[3,2- | 3.69 | C | — |

TABLE 4-continued

In vitro potency data.

| Compound | Compd No. | ENPP1 TR-FRET ($IC_{50}$ μM) | ENPP3 Km ATP ($IC_{50}$ μM) |
|---|---|---|---|
| d]pyrimidin-2-amine | | | |
| 1-(2-Methoxy-7-methylthieno[3,2-d]pyrimidin-4-yl)-N-(3-(4-methylpyridin-3-yl)propyl)piperidin-4-amine | 3.70 | B | — |
| 2-((7-Methyl-4-(4-((3-(4-methylpyridin-3-yl)propyl)amino)piperidin-1-yl)thieno[3,2-d]pyrimidin-2-yl)amino)ethanol | 3.71 | B | — |
| 1-(7-Methylthieno[3,2-d]pyrimidin-4-yl)-N-(3-(pyridin-4-yl)propyl)piperidin-4-amine | 3.76 | B | — |
| N-(1-(7-Methylthieno[3,2-d]pyrimidin-4-yl)piperidin-4-yl)-2-phenylcyclopropanecarboxamide | 3.79 | C | — |
| 1-(2-Chloro-7-methylthieno[3,2-d]pyrimidin-4-yl)-N-((2-(pyridin-4-yl)cyclopropyl)methyl)piperidin-4-amine | 3.80 | C | — |
| 1-(7-Methylthieno[3,2-d]pyrimidin-4-yl)-N-((2-(pyridin-4-yl)cyclopropyl)methyl)piperidin-4-amine | 3.81 | B | — |

A < 0.1 μM, B = 0.1-1.0 μM, C > 1.0 μM-20 μM, D > 20 μM

What is claimed is:

1. A compound of Formula (XI):

Formula (XI)

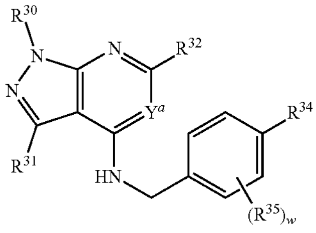

or a pharmaceutically acceptable salt thereof, wherein:

$R^{30}$ is $C_1$-$C_6$ alkyl, $C_3$-$C_6$ cycloalkyl, $C_3$-$C_6$ heterocycloalkyl, phenyl, or monocyclic heteroaryl, wherein the $C_1$-$C_6$ alkyl, phenyl, or monocyclic heteroaryl is optionally substituted with one, two, or three independently selected $R^{37}$ substituents;

each $R^{37}$ is independently halogen, CN, $C_1$-$C_4$ alkyl, $C_1$-$C_4$ fluoroalkyl, $NR^{1A}R^{1A}$, $OR^{1B}$, or $SR^{1B}$;

$R^{31}$ is H, halogen, $C_1$-$C_6$ alkyl, $C_1$-$C_4$ fluoroalkyl, $C_2$-$C_6$ alkenyl, $C_2$-$C_6$ alkynyl, or phenyl, wherein the phenyl is optionally substituted with one, two, or three independently selected $R^{38}$ substituents;

each $R^{38}$ is independently halogen, CN, $C_1$-$C_4$ alkyl, $C_1$-$C_4$ fluoroalkyl, $NR^{1A}R^{1A}$, $OR^{1B}$, or $SR^{1B}$;

$R^{32}$ is H, halogen, CN, $C_1$-$C_6$ alkyl, $C_1$-$C_4$ fluoroalkyl, $C_1$-$C_6$ alkyl-OH, $C_2$-$C_4$ alkenyl, $C_2$-$C_4$ alkynyl, $NR^{1A}R^{1A}$, $OR^{1B}$, $OC_1$-$C_4$ fluoroalkyl, $SR^{1B}$, monocyclic $C_2$-$C_6$ heterocycloalkyl, phenyl, or monocyclic 5- or 6-membered heteroaryl, wherein the $C_1$-$C_6$ alkyl, $C_2$-$C_4$ alkenyl, $C_2$-$C_4$ alkynyl, phenyl, or monocyclic 5- or 6-membered heteroaryl is optionally substituted with one, two, or three independently selected $R^{39}$ substituents;

each $R^{39}$ is independently halogen, CN, $C_1$-$C_4$ alkyl, $C_1$-$C_4$ fluoroalkyl, $NR^{1A}R^{1A}$, $OR^{1B}$, or $SR^{1B}$;

$Y^a$ is CH;

$R^{34}$ is $S(O)_2NR^{1A}R^{1A}$;

w is 0, 1, 2, or 3;

each $R^{35}$ is independently halogen, CN, $C_1$-$C_6$ alkyl, $C_1$-$C_6$ haloalkyl, $C_2$-$C_4$ alkynyl, $OR^{1B}$, or cycloalkyl;

each $R^{1A}$ is independently H, $C_1$-$C_6$ alkyl, $CH_2$-phenyl, cycloalkyl, or aryl; and each $R^{1B}$ is independently H, $C_1$-$C_6$ alkyl, $C_2$-$C_6$ alkenyl, $C_2$-$C_6$ alkynyl, cycloalkyl, heterocycloalkyl, aryl, or heteroaryl.

2. The compound of claim 1, or a pharmaceutically acceptable salt thereof, wherein $R^{32}$ is H, halogen, CN, $C_1$-$C_6$ alkyl, $C_1$-$C_4$ fluoroalkyl, $C_1$-$C_6$ alkyl-OH, $NR^{1A}R^{1A}$, or $OR^{1B}$.

3. The compound of claim 2, or a pharmaceutically acceptable salt thereof, wherein $R^{32}$ is $CH_3$, $CH_2CH_3$, $NH_2$, $NHCH_3$, $NHCH_2CH_3$, $N(CH_3)_2$, or $OCH_3$.

4. The compound of claim 1, or a pharmaceutically acceptable salt thereof, wherein $R^{34}$ is $S(O)_2NH_2$, $S(O)_2NHC_1$-$C_3$ alkyl, or $S(O)_2N(C_1$-$C_3$ alkyl)($C_1$-$C_3$ alkyl).

5. The compound of claim 4, or a pharmaceutically acceptable salt thereof, wherein $R^{34}$ is $S(O)_2NH_2$.

6. The compound of claim 1, or a pharmaceutically acceptable salt thereof, wherein w is 0.

7. The compound of claim 1, or a pharmaceutically acceptable salt thereof, wherein each $R^{35}$ is independently halogen, CN, $C_1$-$C_6$ alkyl, $C_1$-$C_6$ haloalkyl, or $OR^{1B}$.

8. The compound of claim 7, or a pharmaceutically acceptable salt thereof, wherein each $R^{35}$ is independently F, Cl, Br, $CH_3$, or $CF_3$.

9. The compound of claim 1, wherein the compound is selected from the group consisting of:

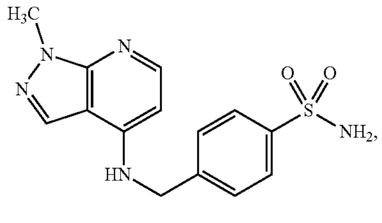

-continued
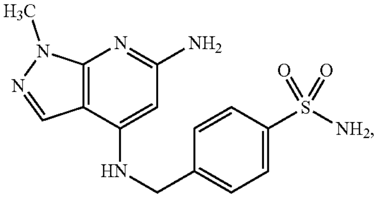
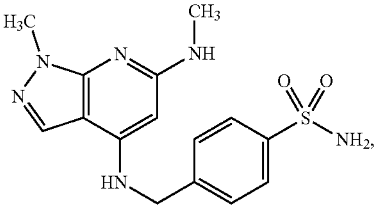
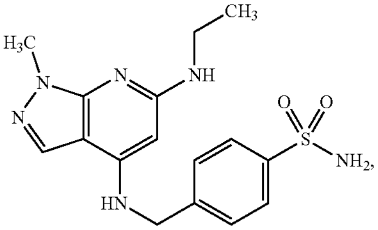
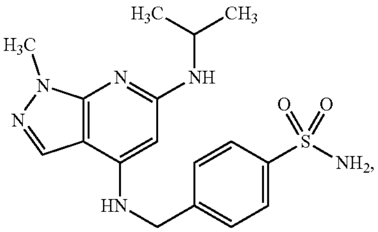
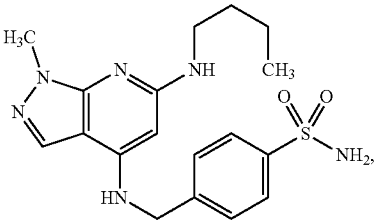
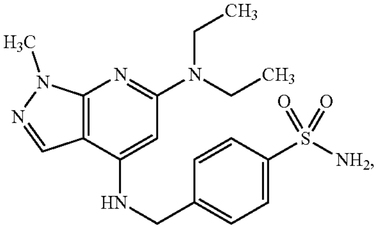
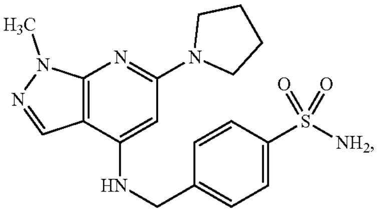
-continued
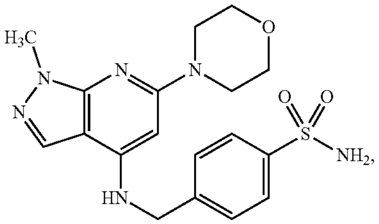
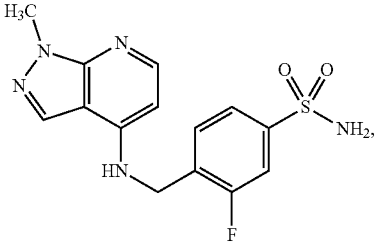
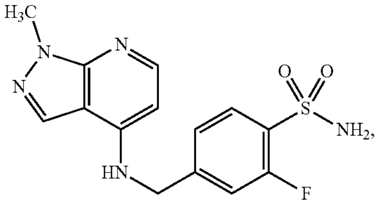
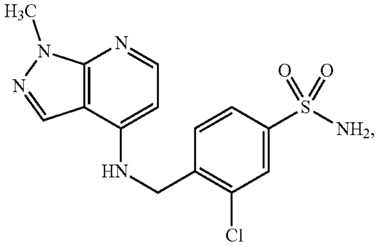
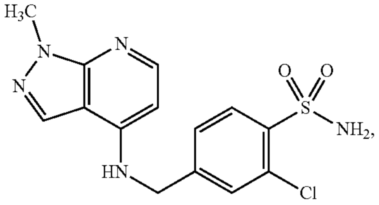
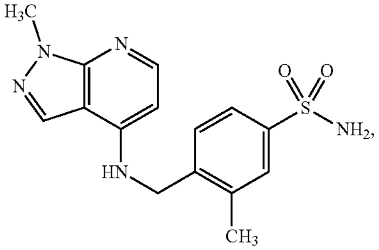
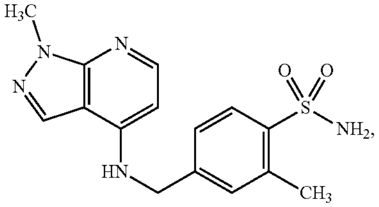

-continued
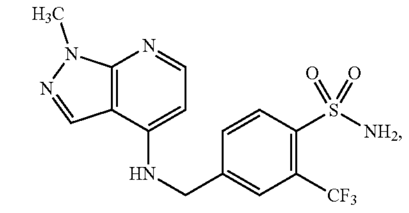
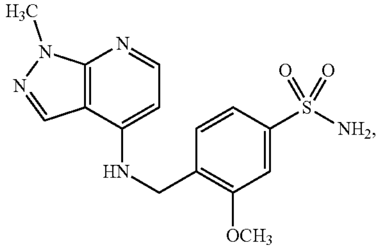
and
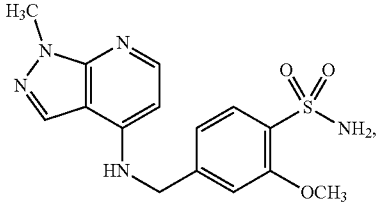
or a pharmaceutically acceptable salt thereof.
10. The compound of claim 1, wherein the compound is selected from the group consisting of:
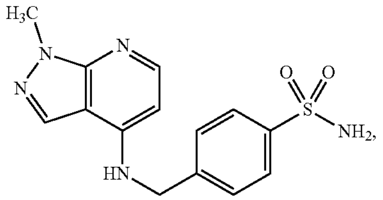
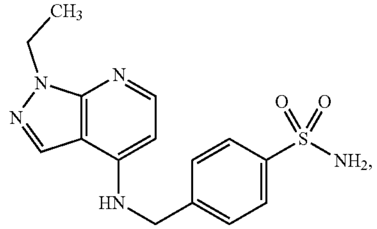
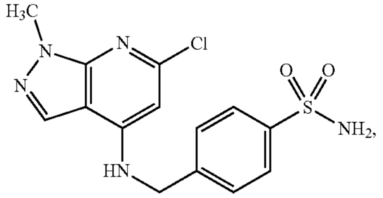
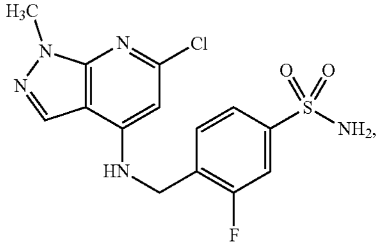
-continued
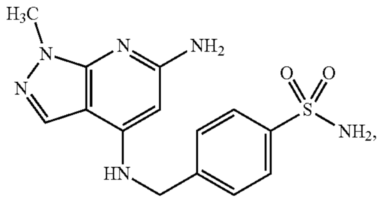
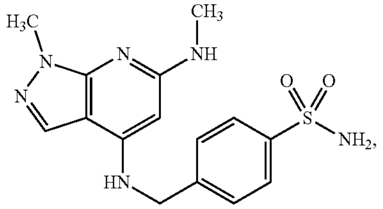
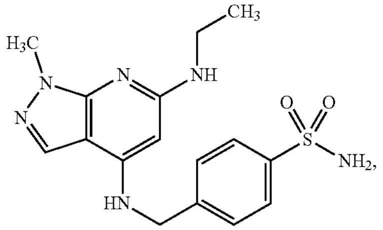
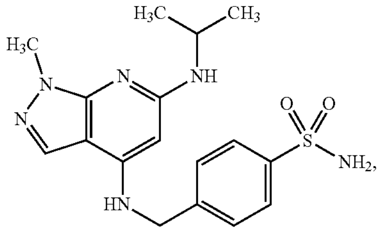
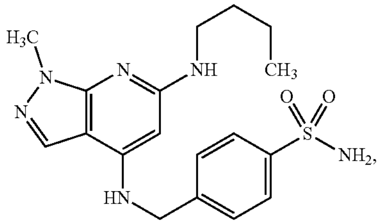
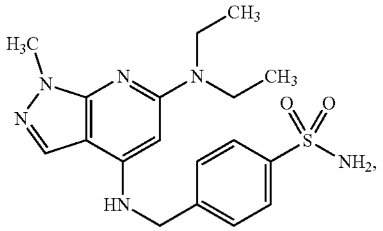
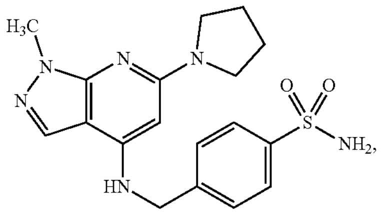

-continued

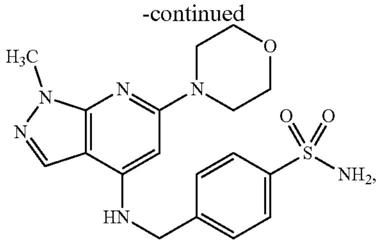

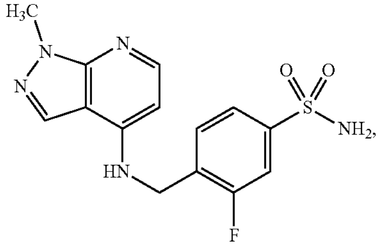

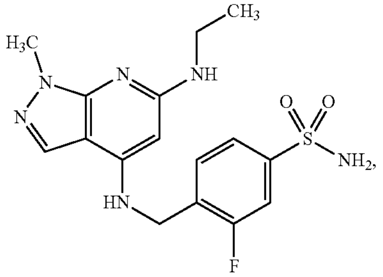

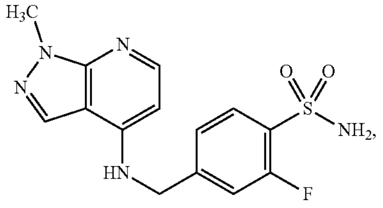

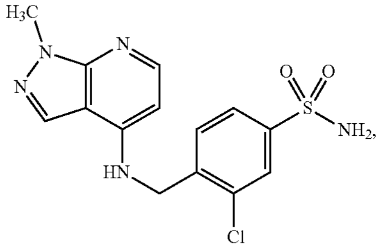

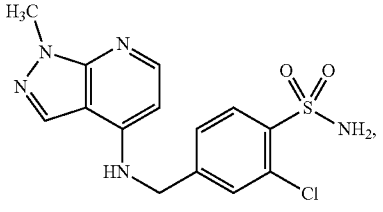

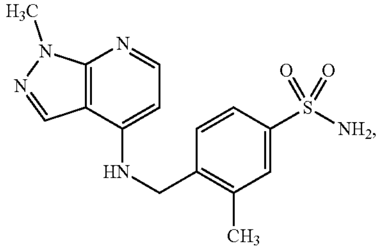

-continued

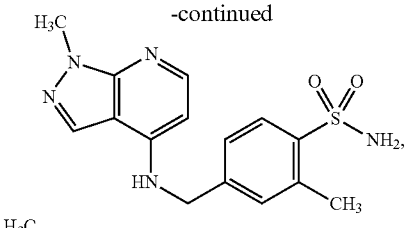

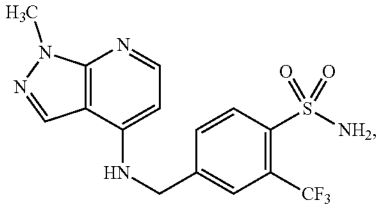

and

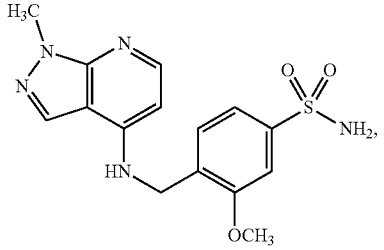

or a pharmaceutically acceptable salt thereof.

11. A pharmaceutical composition comprising at least one pharmaceutically acceptable excipient and a compound of claim 1, or a pharmaceutically acceptable salt thereof.

12. The pharmaceutical composition of claim 11, wherein the pharmaceutical composition is formulated for administration to a mammal by dermal administration, inhalation, intravenous administration, ophthalmic administration, nasal administration, oral administration, or subcutaneous administration.

13. The pharmaceutical composition of claim 11, wherein the pharmaceutical composition is formulated as a capsule, a dispersion, an emulsion, a gel, a liquid, a lotion, an ointment, a pill, a solution, a suspension, or a tablet.

14. A method for treating arthritis in a mammal, wherein the method comprises administering to the mammal in need thereof a therapeutically effective amount of a compound of claim 1, or a pharmaceutically acceptable salt thereof.

15. The method of claim 14, wherein the arthritis is false gout or pseudogout.

16. A compound selected from the group consisting of:

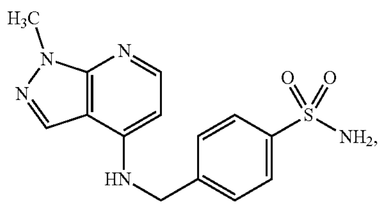

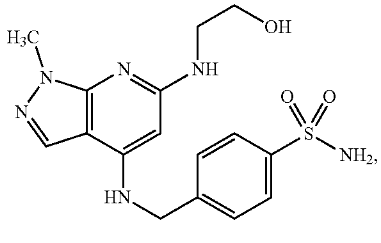

and

-continued
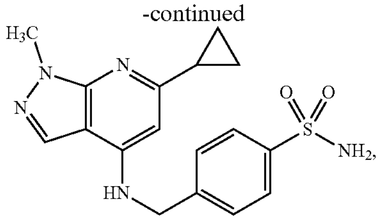
or a pharmaceutically acceptable salt thereof.
* * * * *